(12) United States Patent
Wrobleski et al.

(10) Patent No.: US 8,987,268 B2
(45) Date of Patent: Mar. 24, 2015

(54) PYRROLOPYRIDAZINE JAK3 INHIBITORS AND THEIR USE FOR THE TREATMENT OF INFLAMMATORY AND AUTOIMMUNE DISEASES

(75) Inventors: Stephen T. Wrobleski, Flemington, NJ (US); Jagabandhu Das, Mercerville, NJ (US); Jingwu Duan, Yardley, PA (US); Junqing Guo, Princeton, NJ (US); John Hynes, Washington Crossing, PA (US); Bin Jiang, Norristown, PA (US); James Kempson, Princeton, NJ (US); Shuqun Lin, Newtown, PA (US); Zhonghui Lu, King of Prussia, PA (US); William J. Pitts, Newtown, PA (US); Steven H. Spergel, Warrington, PA (US); Hong Wu, New Hope, PA (US); Bingwei Vera Yang, Belle Mead, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/005,568

(22) PCT Filed: Mar. 16, 2012

(86) PCT No.: PCT/US2012/029366
§ 371 (c)(1),
(2), (4) Date: Sep. 17, 2013

(87) PCT Pub. No.: WO2012/125893
PCT Pub. Date: Sep. 20, 2012

(65) Prior Publication Data
US 2014/0011800 A1    Jan. 9, 2014

Related U.S. Application Data

(60) Provisional application No. 61/453,616, filed on Mar. 17, 2011.

(51) Int. Cl.
C07D 487/04    (2006.01)
C07D 471/04    (2006.01)
A01N 43/58    (2006.01)
A61K 31/50    (2006.01)

(52) U.S. Cl.
USPC .......................... 514/248; 544/235

(58) Field of Classification Search
USPC .......................... 514/248; 544/235
See application file for complete search history.

(56) References Cited

FOREIGN PATENT DOCUMENTS

WO    WO 2004/099204    11/2004
WO    WO 2011/014817    2/2011

OTHER PUBLICATIONS

Coombs, J.H. et al., "Improved pain, physical functioning and health status in patients with rheumatoid arthritis treated with CP-690,550, an orally active Janus kinase (JAK) inhibitor: results from a randomised, double-blind, placebo-controlled trial", Ann. Rheum. Dis., vol. 69, pp. 413-416 (2010).
Ghoreschi, K. et al., "Modulation of Innate and Adaptive Immune Responses by Tofacitinib (CP-690,550)", The Journal of Immunology, vol. 186, pp. 4234-4243 (2011).
Milici, A.J. et al., "Cartilage preservation by inhibition of Janus kinase 3 in two rodent models of rheumatoid arthritis", Arthritis Research & Therapy, vol. 10, R14 (2008).
O'Shea, J.J. et al., A New Modality for Immunosuppression: Targeting the JAK/STAT Pathway, Nature Reviews: Drug Discovery, vol. 3, pp. 555-564 (2004).
Pesu, M. et al., "Jak3, severe combined immunodeficiency, and a new class of immunosuppressive drugs", Immunological Reviews, vol. 203, pp. 127-142 (2005).
Shi, M. et al., "Janus-Kinase-3-Dependent Signals Induce Chromatin Remodeling at the *Ifng* Locus during T Helper 1 Cell Differentiation", Immunity, vol. 28, pp. 763-773 (2008).

*Primary Examiner* — Paul V. Ward
(74) *Attorney, Agent, or Firm* — Mary VanAtten

(57) ABSTRACT

The present invention provides compounds of formula I and pharmaceutically acceptable salts thereof. The formula I compounds inhibit tyrosine kinase activity of JAK3, thereby making them useful for the treatment of inflammatory and autoimmune diseases.

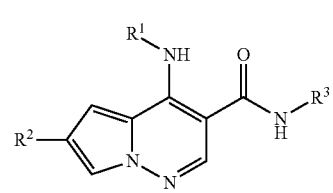

14 Claims, No Drawings

PYRROLOPYRIDAZINE JAK3 INHIBITORS AND THEIR USE FOR THE TREATMENT OF INFLAMMATORY AND AUTOIMMUNE DISEASES

This application is a 371 application of PCT/US2012/029366 filed Mar. 16, 2012 which claims priority from U.S. Provisional Application Ser. No. 61/453,616 filed Mar. 17, 2011 which are incorporated by reference herein in their entirety.

FIELD OF THE INVENTION

This invention relates to novel pyrrolopyridazine compounds that are useful as inhibitors of Janus kinases (JAKs), more particularly JAK3. This invention also relates to a method of using the compounds in the treatment of inflammatory and autoimmune diseases, and to pharmaceutical compositions containing the compounds.

BACKGROUND OF THE INVENTION

The present invention relates to pyrrolopyridazine compounds, the methods of preparation of these compounds, and their use in the treatment of conditions in which selective modulation of the JAK signaling pathway via inhibition of the Janus kinases (JAKs) kinases, particularly JAK3 kinase, may be therapeutically beneficial.

The Janus kinases (JAKs) belong to the non-receptor protein tyrosine kinase family and are known to be critical intracellular regulators of cytokine signaling via modulation of the JAK-STAT pathway (see, Murray, P. J. *Immunity*, 2008, 28, 763). There are four known mammalian JAK isoforms which include JAK1, JAK2, JAK3 and TYK2.

JAK3 has been shown to play a specific role in the signaling of a subset of cytokines known as the gamma common chain cytokine family which includes the interleukins IL-2, IL-4, IL-7, IL-9, IL-15, and IL-21. Deficiency of JAK3 in rodents and humans results in a severe combined immunodeficient (SCID) phenotype (see, Pesu, M. et al *Immunol. Rev.* 2005, 203, 127). Furthermore, JAK3 is known to have limited expression in hematopoeitic cells whereas JAK1, JAK2 and TYK2 have been shown to be more ubiquitously expressed. As a result of its specific role in regulating the immune response and its localized expression in lymphoid cells, inhibition of JAK3 has been recognized as a promising strategy for development of novel and selective immunosuppressive agents useful for transplant rejection prevention and in the treatment of autoimmune and inflammatory diseases such as psoriasis, rheumatoid arthritis, psoriatic arthritis, multiple sclerosis, inflammatory bowel dioesase, and lupus (see, O'Shea J. J. et al, *Nat. Rev. Drug Discov.* 2004, 3(7), 555). Moreover, the reported JAK inhibitor CP-690,550 which potently inhibits JAK3 has been shown to be effective in the treatment arthritis in rodent models as well as in patients with rheumatoid arthritis (see, Milici, A. J. et. al. *Arthritis Res. & Therapy*, 2008, $R^{14}$ and Coombs, J. H. et al *Ann. Rheum. Dis.* 2010, 69, 413). It has been suggested that the clinical efficacy of CP-690,550 (Tofacitinib) may be related to its ability to inhibit other JAK family members (see Ghoreschi, K et al, *J. Immunol.* 2011, 186, 4234). While JAK3 and JAK1 are both capable of modulating gamma common chain induce phosphorylation of STAT signalling, JAK1 inhibition can also decrease non-gamma common chain cytokine signalling (e.g. IL-6 signalling). As such, orally available compounds that inhibit JAK3 and/or JAK1 may be useful for the treatment of inflammatory and autoimmune diseases.

Accordingly, novel compounds which inhibit the JAK/STAT pathway, more particularly via selective inhibition of JAK3 and/or JAK1, may be therapeutically useful. The closely related isoform JAK2 is classically associated with interferon-γ production through the IL-12 pathway, but it also mediates the signaling of important hematopoietic growth factors such as erythropoietin (EPO), thromobopoetin (TPO) and granulocyte macrophage-stimulating factor (GM-CSF). As a result, inhibition of JAK2 may result in adverse hematopoietic effects such as anemia, thrombocytopenia and generalized leukopenia. As such, novel compounds which selectively inhibit JAK3 and/or JAK1 over JAK2 may be especially desirable in the safe treatment of chronic inflammatory and autoimmune diseases.

DETAILED DESCRIPTION OF THE INVENTION

The present invention provides for compounds of formula I, pharmaceutical compositions employing such compounds and for methods of using such compounds.

In accordance with the present invention, there are disclosed compounds of formula I

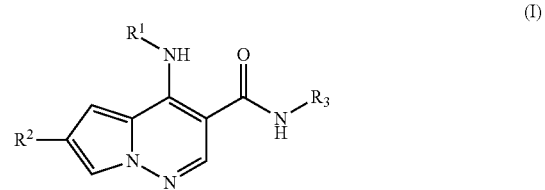

(I)

or a stereoisomer or pharmaceutically acceptable salt thereof, wherein $R^1$ is a 4 to 10 membered saturated or partially saturated heterocycle containing one heteroatom selected from O and $NR^{1b}$, substituted with 0-5 $R^{1a}$;

$R^{1a}$ is independently at each occurrence =O, F, Cl, Br, $OCF_3$, $CF_3$, CN, $NO_2$, $-(CH_2)_rOR^b$, $-(CH_2)_rSR^b$, $-(CH_2)_rC(O)R^{1d}$, $-(CH_2)_rC(O)OR^b$, $-(CH_2)_rOC(O)R^b$, $-(CH_2)_rNR^{11}R^{11}$, $-(CH_2)_rC(O)NR^{11}R^{11}$, $-(CH_2)_rNR^bC(O)R^{1c}$, $-(CH_2)_rNR^bC(O)OR^c$, $-(CH_2)_rNR^bC(O)NR^{11}R^{11}$, $-(CH_2)_rS(O)_2NR^{11}$, $-(CH_2)_rNR^bS(O)_2R^c$, $-(CH_2)_rS(O)R^c$, $-(CH_2)_rS(O)_2R^c$, $C_{1-6}$ alkyl substituted with 0-2 $R^a$, $C_{1-6}$ haloalkyl, $-(CH_2)_r$-3-14 membered carbocycle substituted with 0-2 $R^a$, or $-(CH_2)_r$-5-7 membered heterocycle comprising carbon atoms and 1-4 heteroatoms selected from N, O, and $S(O)_p$ substituted with 0-2 $R^a$;

$R^{1b}$ is hydrogen, $CF_3$, $-(CH_2)_qOR^b$, $-(CH_2)OR^b$, $-(CH_2)_rC(O)R^{1d}$, $(CH_2)_rC(O)OR^b$, $-(CH_2)_qOC(O)R^b$, $-(CH_2)_qNR^{11}R^{11}$, $-(CH_2)_rC(O)NR^{11}R^{11}$, $-(CH_2)_qNR^bC(O)R^{1c}$, $-(CH_2)_qNR^bC(O)OR^c$, $-(CH_2)_qNR^bC(O)NR^{11}R^{11}$, $-(CH_2)_qS(O)_2NR^{11}R^{11}$, $-S(O)_2NR^{11}R^{11}$, $-(CH_2)_qNR^bS(O)_2R^c$, $-(CH_2)_qS(O)R^c$, $-(CH_2)_qS(O)_2R^c$, $C_{1-6}$ alkyl substituted with 0-2 $R^a$, $C_{1-6}$ haloalkyl, $-(CH_2)_r$-3-14 membered carbocycle substituted with 0-1 $R^a$, or $-(CH_2)_r$-5-7 membered heterocycle comprising carbon atoms and 1-4 heteroatoms selected from N, O, and $S(O)_p$ substituted with 0-2 $R^a$;

$R^{1c}$ is independently at each occurrence hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, a 5-10 membered heterocycle containing 1-4 heteroatoms selected from N, O, and S, substituted with 0-3 R$^a$, a 5-10 membered heteroaryl containing 1-4 heteroatoms selected from N, O, and S, substituted with 0-3 R$^a$;

R$^{1d}$ is independently at each occurrence hydrogen, C$_{1-6}$ alkyl substituted with 0-2 R$^d$, C$_{1-6}$ haloalkyl, C(O)NR$^{11}$R$^{11}$, C$_{3-6}$ cycloalkyl substituted with 0-2 R$^d$, or (CH$_2$)$_r$-phenyl substituted with 0-2 R$^a$, a 5-10 membered heterocycle containing 1-4 heteroatoms selected from N, O, and S, substituted with 0-3 R$^a$;

R$^2$ is —NR$^b$C(O)NR$^{11}$R$^{11}$, —NR$^b$C(O)R$^{2b}$, —NR$^b$C(O)OR$^{2d}$, —NR$^b$S(O)$_2$R$^{2b}$, —(—(CH$_2$)$_r$—C6_10 aryl substituted with 0-3 R$^{2a}$, or —(CH$_2$)$_r$-4-10 membered heterocycle containing 1-4 heteroatoms selected from N, O, and S substituted with 0-3 R$^{2a}$;

R$^{2a}$ is independently at each occurrence =O, F, Cl, Br, OCF$_3$, CF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^{2b}$, —(CH$_2$)$_r$NR$^b$C(O)OR$^c$, —NR$^b$C(O)NR$^{11}$R$^{11}$, —S(O)$_2$ NR$^{11}$R$^{11}$, —NR$^b$S(O)$_2$R$^c$, —S(O)R$^c$, —S(O)$_2$R$^c$, (CH$_2$)$_r$NH(C=NCN)NHR$^{11}$, C$_{1-6}$ alkyl substituted with 0-2 R$^a$, C$_{2-6}$ alkenyl, C$_{1-6}$ haloalkyl, —(CH$_2$)$_r$-3-14 membered carbocycle substituted with 0-1 R$^a$, or —(CH$_2$)$_r$-5-10 membered heterocycle comprising carbon atoms and 1-4 heteroatoms selected from N, O, and S(O)$_p$ substituted with 0-1 R$^a$;

R$^{2b}$ is independently at each occurrence hydrogen, C$_{1-6}$ alkyl substituted with 0-2 R$^a$, C$_{1-6}$ haloalkyl, C$_{3-6}$ cycloalkyl substituted with 0-2 R$^a$, or (CH$_2$)$_r$-phenyl substituted with 0-2 R$^a$, or —(CH$_2$)$_r$-5-10 membered heterocycle comprising carbon atoms and 1-4 heteroatoms selected from N, O, and S(O)$_p$ substituted with 0-1 R$^a$;

R$^{2d}$ is independently at each occurrence C$_{1-6}$ alkyl substituted with 0-2 R$^a$, C$_{1-6}$ haloalkyl, C$_{3-6}$ cycloalkyl substituted with 0-2 R$^a$, or (CH$_2$)$_r$-phenyl substituted with 0-2 R$^a$, or —(CH$_2$)$_r$-5-10 membered heterocycle comprising carbon atoms and 1-4 heteroatoms selected from N, O, and S(O)$_p$ substituted with 0-1 R$^a$;

R$^3$ is hydrogen, C$_{1-6}$ alkyl substituted with 0-1 R$^a$, phenyl substituted with 0-1 R$^a$, or C$_{3-6}$ cycloalkyl substituted with 0-1 R$^a$;

R$^{11}$ is independently at each occurrence hydrogen or C$_{1-4}$ alkyl substituted with 0-1 R$^a$, C$_{2-4}$ alkenyl substituted with 0-1 R$^a$, —(CH$_2$)$_r$-5-6 membered carbocycle substituted with 0-1 R$^a$, or —(CH$_2$)$_r$-5-7 membered heterocycle comprising carbon atoms and 1-4 heteroatoms selected from N, O, and S(O)$_p$;

R$^a$ is independently at each occurrence hydrogen, =O, F, Cl, Br, OCF$_3$, CF$_3$, CHF2, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^c$R$^c$, —(CH$_2$)$_r$C(O)NR$^c$R$^c$, —(CH$_2$)$_r$ NR$^b$C(O)R$^c$, —(CH$_2$)$_r$NR$^b$C(O)OR$^c$, —NR$^b$C(O)NR$^c$R$^c$, —S(O)$_2$NR$^c$R$^c$, —NR$^b$S(O)$_2$R$^c$, —S(O)R$^c$, —S(O)$_2$R$^c$, (CH$_2$)$_r$NH(C=NCN)NHR$^c$, C$_{1-6}$ alkyl substituted with 0-1 R$^f$, C$_{1-6}$ haloalkyl, —(CH$_2$)$_r$-3-14 membered carbocycle substituted with 0-1 R$^d$, or —(CH$_2$)$_r$-5-7 membered heterocycle comprising carbon atoms and 1-4 heteroatoms selected from N, O, and S(O)$_p$ substituted with 0-1 R$^d$, alternatively two R$^a$ on adjacent or the same carbon atom form a cyclic acetal of the formula —O—(CH$_2$)$_n$—O—, or —O—CF$_2$—O—, wherein n is selected from 1 or 2;

R$^b$ is independently at each occurrence hydrogen, C$_{1-6}$ alkyl substituted with 0-2 R$^d$, C$_{1-6}$ haloalkyl, C$_{3-6}$ cycloalkyl substituted with 0-2 R$^d$, or (CH$_2$)$_r$-phenyl substituted with 0-2 R$^d$, or —(CH$_2$)$_r$-5-7 membered heterocycle comprising carbon atoms and 1-4 heteroatoms selected from N, O, and S(O)$_p$ substituted with 0-1 R$^d$, R$^c$ is independently at each occurrence hydrogen, C$_{1-6}$ alkyl substituted with 0-1 R$^f$, C$_{3-6}$ cycloalkyl, or (CH$_2$)$_r$-phenyl substituted with 0-1 R$^f$;

R$^d$ is independently at each occurrence hydrogen, F, Cl, Br, OCF$_3$, CF$_3$, CN, NO$_2$, —OR$^e$, —(CH$_2$)$_r$C(O)R$^e$, —NR$^e$R$^e$, —NR$^e$C(O)OR$^e$, —C(O)OR$^e$, —SO$_2$N(R$^e$)$_2$, C$_{1-6}$ alkyl, or (CH$_2$)$_r$-phenyl;

R$^e$ is independently at each occurrence C$_{1-6}$ alkyl, C$_{3-6}$ cycloalkyl, or (CH$_2$)$_r$-phenyl;

R$^f$ is independently at each occurrence hydrogen, halo, CN, SO$_2$-methyl, phenyl, NH$_2$, NHCO-methyl, OH, or OCH$_3$;

q is 2 to 5;
r is 0, 1, 2, 3, or 4; and
p is 0, 1, or 2.

In another embodiment, there are provided compounds of formula (I) wherein:

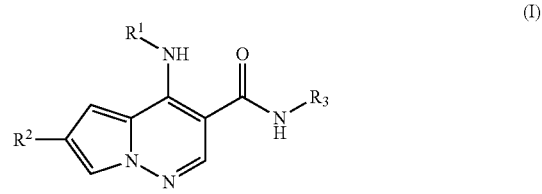

(I)

or a stereoisomer or pharmaceutically acceptable salt thereof, wherein:

R$^1$ is a 5 to 10 membered saturated or partially saturated heterocycle containing one heteroatom selected from O and NR$^{1b}$, substituted with 0-5 R$^{1a}$, R$^{1a}$ is independently at each occurrence =O, F, Cl, Br, OCF$_3$, CF$_3$, CN, NO$_2$, —(CH$_2$)$_r$OR$^b$, —(CH$_2$)$_r$SR$^b$, —(CH$_2$)$_r$C(O)R$^{1d}$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^{1c}$, —(CH$_2$)$_r$NR$^b$C(O)OR$^c$, —(CH$_2$)$_r$NR$^b$C(O)NR$^{11}$R$^{11}$, —(CH$_2$)$_r$S(O)$_2$N$^{11}$R$^{11}$, —(CH$_2$)$_r$NR$^b$S(O)$_2$R$^c$, —(CH$_2$)$_r$S(O)R$^c$, —(CH$_2$)$_r$S(O)$_2$R$^c$, C$_{1-6}$ alkyl substituted with 0-2 R$^a$, C$_{1-6}$ haloalkyl, —(CH$_2$)$_r$-3-14 membered carbocycle substituted with 0-2 R$^a$, or —(CH$_2$)$_r$-5-7 membered heterocycle comprising carbon atoms and 1-4 heteroatoms selected from N, O, and S(O)$_p$ substituted with 0-1 R$^a$;

R$^{1b}$ is hydrogen, CF$_3$, —(CH$_2$)$_q$OR$^b$, —(CH$_2$)$_q$OR$^b$, —(CH$_2$)$_q$C(O)R$^{1d}$, —(CH$_2$)$_q$C(O)OR$^b$, —(CH$_2$)$_q$OC(O)R$^b$, —(CH$_2$)$_q$NR$^{11}$R$^{11}$, —(CH$_2$)$_q$C(O)NR$^{11}$R$^{11}$, —(CH$_2$)$_q$NR$^b$C(O)R$^{1c}$, —(CH$_2$)$_q$NR$^b$C(O)OR$^c$, —(CH$_2$)$_q$NR$^b$C(O)NR$^{11}$R$^{11}$, —(CH$_2$)$_q$(O)$_2$NR$^{11}$R$^{11}$, —S(O)$_q$NR$^{11}$R$^{11}$, —(CH$_2$)$_q$NR$^b$S(O)$_2$R$^d$, —(CH$_2$)$_q$S(O)R$^c$, —(CH$_2$)$_q$S(O)$_2$R$^c$, C$_{1-6}$ alkyl substituted with 0-2 R$^a$, C$_{1-6}$ haloalkyl, —(CH$_2$)$_r$-3-14 membered carbocycle substituted with 0-1 R$^a$, or —(CH$_2$)$_r$-5-7 membered heterocycle comprising carbon atoms and 1-4 heteroatoms selected from N, O, and S(O)$_p$ substituted with 0-1 R$^a$;

R$^{1c}$ is independently at each occurrence C$_{1-6}$ alkyl substituted with 0-3 R$^a$, C$_{2-6}$ alkenyl substituted with 0-3 R$^a$, C$_{3-10}$ cycloalkyl substituted with 0-3 R$^a$, C$_{6-10}$ aryl substituted with 0-3 R$^a$, a 5-10 membered heterocycle containing 1-4 heteroatoms selected from N, O, and S, substituted with 0-3 R$^a$, a 5-10 membered heteroaryl containing 1-4 heteroatoms selected from N, O, and S, substituted with 0-3 R$^a$;

R$^{1d}$ is independently at each occurrence hydrogen, C$_{1-6}$ alkyl substituted with 0-2 R$^d$, C$_{1-6}$haloalkyl, C$_{3-6}$ cycloalkyl substituted with 0-2 R$^d$, or (CH$_2$)$_r$-phenyl substituted with 0-2 R$^a$, a 5-10 membered heterocycle containing 1-4 heteroatoms selected from N, O, and S, substituted with 0-3 R$^a$;

$R^2$ is $-NR^bC(O)NR^{11}R^{11}$, $NR^bC(O)R^{2b}$, $-NR^bC(O)OR^{2d}$, $-NR^bS(O)_2R^{2b}$, $-(-(CH_2)_r-C_{6-10}$ aryl substituted with 0-3 $R^{2a}$, or $-(CH_2)_r$-4-10 membered heterocycle containing 1-4 heteroatoms selected from N, O, and S substituted with 0-3 $R^{2a}$;

$R^{2a}$ is independently at each occurrence =O, F, Cl, Br, $OCF_3$, $CF_3$, CN, $NO_2$, $-(CH_2)_rOR^b$, $-(CH_2)_rSR^b$, $-(CH_2)_r C(O)R^b$, $-(CH_2)_rC(O)OR^b$, $-(CH_2)_rOC(O)R^b$, $-(CH_2)_r NR^{11}R^{11}$, $-(CH_2)_rC(O)NR^{11}R^{11}$, $-(CH_2)_rNR^bC(O)R^{2b}$, $-(CH_2)_rNR^bC(O)OR^c$, $-NR^bC(O)NR^{11}R^{11}$, $-S(O)_2 NR^{11}R^{11}$, $-NR^bS(O)_2R^c$, $-S(O)R^c$, $-S(O)_2R^c$, $(CH_2)_r NH(C=NCN)NHR^{11}$, $C_{1-6}$ alkyl substituted with 0-2 $R^a$, $C_{2-6}$ alkenyl, $C_{1-6}$ haloalkyl, $-(CH_2)_r$-3-14 membered carbocycle substituted with 0-1 $R^a$, or $-(CH_2)_r$-5-10 membered heterocycle comprising carbon atoms and 1-4 heteroatoms selected from N, O, and $S(O)_p$ substituted with 0-1 $R^a$;

$R^{2b}$ is independently at each occurrence hydrogen, $C_{1-6}$ alkyl substituted with 0-2 $R^a$, $C_{1-6}$ haloalkyl, $C_{3-6}$ cycloalkyl substituted with 0-2 $R^a$, or $(CH_2)_r$-phenyl substituted with 0-2 $R^a$, or $-(CH_2)_r$-5-10 membered heterocycle comprising carbon atoms and 1-4 heteroatoms selected from N, O, and $S(O)_p$ substituted with 0-1 $R^a$;

$R^{2d}$ is independently at each occurrence $C_{1-6}$ alkyl substituted with 0-2 $R^a$, $C_{1-6}$ haloalkyl, $C_{3-6}$ cycloalkyl substituted with 0-2 $R^a$, or $(CH_2)_r$-phenyl substituted with 0-2 $R^a$, or $-(CH_2)_r$-5-10 membered heterocycle comprising carbon atoms and 1-4 heteroatoms selected from N, O, and $S(O)_p$ substituted with 0-1 $R^a$;

$R^3$ is hydrogen, $C_{1-6}$ alkyl substituted with 0-1 $R^a$, phenyl substituted with 0-1 $R^a$, or $C_{3-6}$ cycloalkyl substituted with 0-1 $R^a$;

$R^{11}$ is independently at each occurrence hydrogen or $C_{1-4}$ alkyl substituted with 0-1 $R^a$, $C_{2-4}$ alkenyl substituted with 0-1 $R^a$, $-(CH_2)_r$-5-6 membered carbocycle substituted with 0-1 $R^a$, or $-(CH_2)_r$-5-7 membered heterocycle comprising carbon atoms and 1-4 heteroatoms selected from N, O, and $S(O)_p$;

$R^a$ is independently at each occurrence hydrogen, =O, F, Cl, Br, $OCF_3$, $CF_3$, $CHF_2$, CN, $NO_2$, $-(CH_2)_rOR^b$, $-(CH_2)_rSR^b$, $-(CH_2)_rC(O)R^b$, $-(CH_2)_rC(C)OR^b$, $-(CH_2)_rOC(O)R^b$, $-(CH_2)_rNR^cR^c$, $-(CH_2)_rC(O)NR^cR^c$, $-(CH_2)_r NR^bC(O)R^c$, $-(CH_2)_rNR^bC(O)OR^c$, $-NR^bC(O)NR^cR^c$, $-S(O)_2NR^cR^c$, $-NR^bS(O)_2R^c$, $-S(O)R^c$, $-S(O)_2R^c$, $(CH_2)_rNH(C=NCN)NHR^c$, $C_{1-6}$ alkyl substituted with 0-1 $R^f$, $C_{1-6}$ haloalkyl, $-(CH_2)_r$-3-14 membered carbocycle substituted with 0-1 $R^d$, or $-(CH_2)_r$-5-7 membered heterocycle comprising carbon atoms and 1-4 heteroatoms selected from N, O, and $S(O)_p$ substituted with 0-1 $R^d$, alternatively two $R^a$ on adjacent or the same carbon atom form a cyclic acetal of the formula $-O-(CH_2)_n-O-$, or $-O-CF_2-O-$, wherein n is selected from 1 or 2;

$R^b$ is independently at each occurrence hydrogen, $C_{1-6}$ alkyl substituted with 0-2 $R^d$, $C_{1-6}$ haloalkyl, $C_{3-6}$ cycloalkyl substituted with 0-2 $R^d$, or $(CH_2)_r$-phenyl substituted with 0-2 $R^d$, or $-(CH_2)_r$-5-7 membered heterocycle comprising carbon atoms and 1-4 heteroatoms selected from N, O, and $S(O)_p$ substituted with 0-1 $R^d$, $R^c$ is independently at each occurrence $C_{1-6}$ alkyl substituted with 0-1 $R^f$, $C_{3-6}$ cycloalkyl, or $(CH_2)_r$-phenyl substituted with 0-1 $R^f$;

$R^d$ is independently at each occurrence F, Cl, Br, $OCF_3$, $CF_3$, CN, $NO_2$, $-OR^e$, $-(CH_2)_rC(O)R^e$, $-NR^eR^e$, $-NR^eC(O)OR^e$, $-C(O)OR^e$, $-SO_2N(R^e)_2$, $C_{1-6}$ alkyl, or $(CH_2)_r$-phenyl;

$R^e$ is independently at each occurrence hydrogen, $C_{1-6}$ alkyl, $C_{3-6}$ cycloalkyl, or $(CH_2)_r$-phenyl;

$R^f$ is independently at each occurrence hydrogen, halo, CN, $SO_2$-methyl, phenyl, $NH_2$, NHCO-methyl, OH, or $OCH_3$;

q is 2 to 5;

r is 0, 1, 2, 3, or 4; and p is 0, 1, or 2.

In another embodiment, there are provided compounds of formula (I), or a stereoisomer or pharmaceutically acceptable salt thereof, wherein:

$R^1$ is a 5 to 10 membered saturated or partially saturated heterocycle containing one heteroatom selected from O and $NR^{1b}$, substituted with 0-5 $R^{1a}$, $R^{1a}$ is independently at each occurrence =O, F, Cl, Br, $OCF_3$, $CF_3$, CN, $NO_2$, $-(CH_2)_rOR^b$, $-(CH_2)_rSR^b$, $-(CH_2)_r C(o)R^{1d}$, $-(CH_2)_rC(O)OR^b$, $-(CH_2)_rOC(O)R^b$, $-(CH_2)_r NR^{11}R^{11}$, $-(CH_2)_rC(O)NR^{11}R^{11}$, $-(CH_2)_rNR^bC(O)R^{1c}$, $-(CH_2)_rNR^bC(O)OR^c$, $-(CH_2)_rNR^bC(O)NR^{11}R^{11}$, $-(CH_2)_rS(O)_2NR^{11}$, $-(CH_2)_rNR^bS(O)_2R^c$, $-(CH_2)_rS(O)R^c$, $-(CH_2)_rS(O)_2R^c$, $C_{1-6}$ alkyl substituted with 0-2 $R^a$, $C_{1-6}$ haloalkyl, $-(CH_2)_r$-3-14 membered carbocycle substituted with 0-1 $R^a$, or $-(CH_2)_r$-5-7 membered heterocycle comprising carbon atoms and 1-4 heteroatoms selected from N, O, and $S(O)_p$ substituted with 0-1 $R^a$;

$R^{1b}$ is independently at each occurrence hydrogen, $CF_3$, $-(CH_2)_qOR^b$, $-(CH_2)_qSR^b$, $-(CH_2)_qC(O)R^{1d}$, $-(CH_2)_qC(O)OR^b$, $-(CH_2)_qOC(O)R^b$, $-(CH_2)_qNR^{11}R^{11}$, $-(CH_2)_qC(O)NR^{11}R^{11}$, $-(CH_2)_qNR^bC(O)R^{1c}$, $-(CH_2)_qNR^bC(O)OR^c$, $-(CH_2)_qNR^bC(O)NR^{11}R^{11}$, $-(CH_2)_aS(O)_2NR^{11}R^{11}$, $-S(O)_2NR^{11}R^{11}$, $-(CH_2)_qNR^bS(O)_2R^c$, $-(CH_2)_qS(O)R^c$, $-(CH_2)_qS(O)_2R^c$, $C_{1-6}$ alkyl substituted with 0-2 $R^a$, $C_{1-6}$ haloalkyl, $-(CH_2)_r$-3-14 membered carbocycle substituted with 0-1 $R^a$, or $-(CH_2)_r$-5-7 membered heterocycle comprising carbon atoms and 1-4 heteroatoms selected from N, O, and $S(O)_p$ substituted with 0-1 $R^a$;

$R^{1d}$ is independently at each occurrence hydrogen, $C_{1-6}$ alkyl substituted with 0-2 $R^d$, $C_{1-6}$-haloalkyl, $C_{3-6}$ cycloalkyl substituted with 0-2 $R^d$, or $(CH_2)_r$-phenyl substituted with 0-2 $R^a$, a 5-10 membered heterocycle containing 1-4 heteroatoms selected from N, O, and S, substituted with 0-3 $R^a$; and $R^c$ is independently at each occurrence $C_{1-6}$ alkyl substituted with 0-1 $R^f$, $C_{3-6}$ cycloalkyl, or $(CH_2)_r$-phenyl substituted with 0-1 $R^f$.

In another embodiment, there are provided compounds of formula (I) wherein $R^3$ is hydrogen.

In another embodiment, there are provided compounds of formula (I) wherein:

$R^1$ is a 4- to 10-membered saturated or partially saturated heterocycle containing one heteroatom selected from O and $NR^{1b}$, substituted with 0-2 $R^{1a}$, wherein the heterocycle is selected from pyrrolidinyl piperidinyl, octahydrocylopentapyrrolyl, tetrahydrofuranyl, tetrahydropyranyl, oxabicycloheptane, and oxetane;

$R^{1a}$ is independently at each occurrence F, Cl, Br, $-(CH_2)_r OR^b$, $C_{1-6}$ alkyl substituted with 0-2 $R^a$, or $-(CH_2)_r$3-6 membered carbocycle substituted with 0-2 $R^a$;

$R^{1b}$ is hydrogen, $-(CH_2)_rC(O)R^{1d}$, $-(CH_2)_rC(O)OR^b$, $-(CH_2)_qS(O)_2R^c$, $C_{1-6}$ alkyl substituted with 0-2 $R^a$, or $-(CH_2)_r$-5-7 membered heterocycle comprising carbon atoms and 1-4 heteroatoms selected from N, O, and $S(O)_p$ substituted with 0-2 $R^a$;

$R^{1d}$ is independently at each occurrence hydrogen, $C_{1-6}$ alkyl substituted with 0-2 $R^d$, $C_{1-6}$haloalkyl, $C(O)NR^{11}R^{11}$, $C_{3-6}$ cycloalkyl substituted with 0-2 $R^d$, or $(CH_2)_r$ phenyl substituted with 0-2 $R^a$, a 5-10 membered heterocycle containing 1-4 heteroatoms selected from N, O, and S, substituted with 0-3 $R^a$; and r is 0, 1, or 2.

In another embodiment, there are provided compounds of formula (I), or a stereoisomer or pharmaceutically acceptable salt thereof, wherein:

$R^2$ is —$NR^bC(O)R^{2b}$, $C_{6-10}$ aryl substituted with 0-3 $R^{2a}$, or 4-10 membered heterocycle containing 1-4 heteroatoms selected from N, O, and $S(O)_p$ substituted with 0-3 $R^{2a}$;

$R^{2a}$ is independently at each occurrence =O, F, Cl, Br, $CF_3$, CN, —$(CH_2)_rOR^b$, $(CH_2)_rC(O)C(O)R^b$, —$(CH_2)_rC(O)OR^b$, —$(CH_2)_rNR^{11}R^{11}$, —$(CH_2)_rC(O)NR^{11}R^{11}$, —$(CH_2)_rNR^bC(O)R^{2b}$, —$S(O)_2R^c$, $C_{1-6}$ alkyl substituted with 0-2 $R^a$, —$(CH_2)_r$-3-14 membered carbocycle substituted with 0-1 $R^a$, or —$(CH_2)_r$-5-10 membered heterocycle comprising carbon atoms and 1-4 heteroatoms selected from N, O, and $S(O)_p$ substituted with 0-1 $R^a$;

$R^{2b}$ is independently at each occurrence $C_{1-6}$ alkyl substituted with 0-2 $R^a$ or $C_{1-6}$ haloalkyl; and r is 0, 1, or 2.

In another embodiment, there are provided compounds of formula (I), wherein

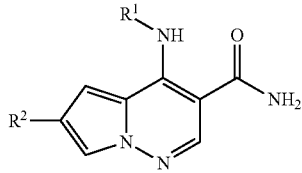

or a stereoisomer or pharmaceutically acceptable salt thereof, wherein:

$R^1$ is a 4- to 10-membered saturated or partially saturated heterocycle containing one heteroatom selected from O and $NR^{1b}$, substituted with 0-2 $R^{1a}$, wherein the heterocycle is selected from piperidinyl, tetrahydrofuranyl, tetrahydropyranyl, oxabicycloheptane, oxetane, octahydrocylopentapyrrolyl and pyrrolidinyl;

$R^{1a}$ is independently at each occurrence F, Cl, Br, —$(CH_2)_rOR^b$, $C_{1-6}$ alkyl substituted with 0-2 $R^a$, —$(CH_2)_r$-3-6 membered carbocycle substituted with 0-2 $R^a$;

$R^{1b}$ is hydrogen, —$(CH_2)_rC(O)R^{1d}$, —$(CH_2)_rC(O)OR^b$, —$(CH_2)_qS(O)_2R^c$, $C_{1-6}$ alkyl substituted with 0-2 $R^a$, or —$(CH_2)_r$-5-7 membered heterocycle comprising carbon atoms and 1-4 heteroatoms selected from N, O, and $S(O)_p$ substituted with 0-2 $R^a$;

$R^{1d}$ is independently at each occurrence hydrogen, $C_{1-6}$ alkyl substituted with 0-2 $R^d$, $C_{1-6}$ haloalkyl, $C(O)NR^{11}R^{11}$, $C_{3-6}$ cycloalkyl substituted with 0-2 $R^d$, or $(CH_2)_r$ phenyl substituted with 0-2 $R^a$, a 5-10 membered heterocycle containing 1-4 heteroatoms selected from N, O, and S, substituted with 0-3 $R^a$;

$R^2$ is —$NR^bC(O)R^{2b}$, $C_{6-10}$ aryl substituted with 0-3 $R^{2a}$, or 4-10 membered heterocycle containing 1-4 heteroatoms selected from N, O, and $S(O)_p$ substituted with 0-3 $R^{2a}$;

$R^{2a}$ is independently at each occurrence =O, F, Cl, Br, $CF_3$, CN, —$(CH_2)_rOR^b$, $(CH_2)_rC(O)R^b$, —$(CH_2)_rC(O)OR^b$, —$(CH_2)_rNR^{11}R^{11}$, —$(CH_2)_rC(O)NR^{11}R^{11}$, —$(CH_2)_rNR^bC(O)R^{2b}$, —$S(O)_2R^c$, $C_{1-6}$ alkyl substituted with 0-2 $R^a$, —$(CH_2)_r$-3-14 membered carbocycle substituted with 0-1 $R^a$, or —$(CH_2)_r$-5-10 membered heterocycle comprising carbon atoms and 1-4 heteroatoms selected from N, O, and $S(O)_p$ substituted with 0-1 $R^a$;

$R^{2b}$ is independently at each occurrence $C_{1-6}$ alkyl substituted with 0-2 $R^a$ or $C_{1-6}$ haloalkyl;

$R^a$ is independently at each occurrence hydrogen, F, Cl, Br, $CF_3$, CN, —$(CH_2)_rOR^b$, —$(CH_2)_rNR^cR^c$, $C_{1-6}$ alkyl substituted with 0-1 $R^f$, haloalkyl;

$R^b$ is independently at each occurrence hydrogen, $C_{1-6}$ alkyl substituted with 0-2 $R^d$, $C_{3-6}$ cycloalkyl substituted with 0-2 $R^d$, or —$(CH_2)_r$-5-7 membered heterocycle comprising carbon atoms and 1-4 heteroatoms selected from N, O, and $S(O)_p$ substituted with 0-1 $R^d$, $R^c$ is independently at each occurrence hydrogen or $C_{1-6}$ alkyl;

$R^d$ is independently at each occurrence hydrogen, F, Cl, Br, $CF_3$, CN, —$OR^e$, or $C_{1-6}$ alkyl;

$R^e$ is independently at each occurrence hydrogen or $C_{1-6}$ alkyl;

q is 2 to 5;

r is 0, 1, 2, 3, or 4; and p is 0, 1, or 2.

r is 0, 1, or 2.

In another embodiment, there are provided compounds of formula (I), or a stereoisomer or pharmaceutically acceptable salt thereof, wherein $R^1$ is a 4- to 10-membered saturated or partially saturated heterocycle containing one heteroatom selected from O and $NR^{1b}$, substituted with 0-2 $R^{1a}$, wherein the heterocycle is selected from piperidinyl, tetrahydrofuranyl, tetrahydropyranyl, oxabicycloheptane, oxetane, octahydrocylopentapyrrolyl and pyrrolidinyl;

$R^{1a}$ is selected independently at each occurrence from fluoro, methyl, ethyl, $OR^b$, $CH_2)_rR^a$, and cyclobutyl;

$R^{1b}$ is selected from hydrogen, methyl, ethyl, $CH_2CH(CH_3)R^a$, $(CH_2)_2R^a$, $CH_2CH(R^a)CH_3$, $SO_2R^c$, $C(O)R^{1d}$ and —$C(O)_2R^b$; or pyridazinyl pyrimidinyl, pyrazinyl, pyridinyl, and thiazolyl, each group substituted by 0-2 $R^a$; and $R^{1d}$ is methyl, $CH(R^d)CH^3$, $CH_2R^d$, $C(O)NH_2$, cyclobutyl($R^d$), cyclopropyl($R^d$), $CH_2R^d$, $C(CH_3)_2(R^d)$, oxabicycloheptane or $CH(R^d)_2$. (More preferably $R^{1d}$ is methyl, $CH(R^d)CH^3$, $CH_2R^d$, cyclobutyl($R^d$), cyclopropyl($R^d$), $CH_2R^d$, $C(CH_3)_2(R^d)$, oxabicycloheptane or $CH(R^d)_2$.)

In another embodiment, or a stereoisomer or pharmaceutically acceptable salt thereof, there are provided compounds of formula (I) wherein $R^1$ is a 5- to 10-membered saturated or partially saturated heterocycle containing one heteroatom selected from O and $NR^{1b}$, substituted with 0-2 $R^{1a}$, wherein the heterocycle is selected from, octahydrocylopentapyrrolyl, pyrrolidinyl and piperidinyl;

$R^{1a}$ is selected independently at each occurrence from fluoro, methyl, ethyl, $OR^b$, $CH_2R^a$, and cyclobutyl;

$R^{1b}$ is selected from hydrogen, methyl, ethyl, $CH_2CH(CH_3)R^a$, $(CH_2)_2R^a$, $CH_2CH(R^a)CH_3$, $SO_2R^c$, $C(O)R^{1d}$ and —$C(O)_2R^b$; or pyridazinyl pyrimidinyl, pyrazinyl, pyridinyl, and thiazolyl group, each group substituted by 0-2 $R^a$; and $R^{1d}$ is methyl, $CH(R^d)CH^3$, $CH_2R^d$, cyclobutyl($R^d$)$_{0-2}$, cyclopropyl($R^d$)$_{0-2}$, $CH_2R^d$, $C(CH_3)_2(R^d)$, oxabicycloheptane or $CH(R^d)_2$.

In another embodiment, there are provided compounds of formula (I), or a stereoisomer or pharmaceutically acceptable salt thereof, wherein $R^1$ is a heterocycle containing a heteroatom, $NR^{1b}$, wherein said heterocycle is pyrrolidinyl, further substituted with 0-2 $R^{1a}$.

In another embodiment, there are provided compounds of formula (I), or a stereoisomer or pharmaceutically acceptable salt thereof, wherein $R^1$ is

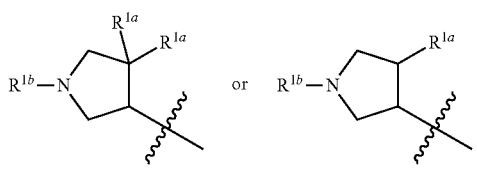

A more preferred embodiment provides compounds of formula (I) in which $R^1$ is

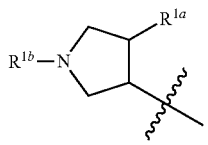

and $R^{1a}$ is methyl, ethyl or fluoromethylene.

In another embodiment, there are provided compounds of formula (I), or a stereoisomer or pharmaceutically acceptable salt thereof, wherein $R^1$ is a piperidinyl having the formula:

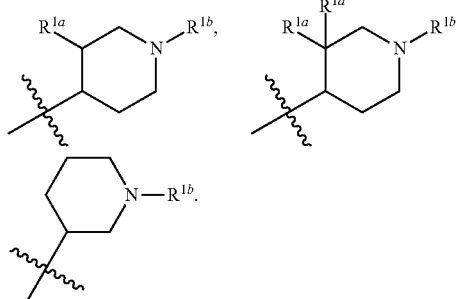

In another embodiment, there are provided compounds of formula (I), or a stereoisomer or pharmaceutically acceptable salt thereof, wherein $R^1$ is octahydrocylopentapyrrolyl having the formula

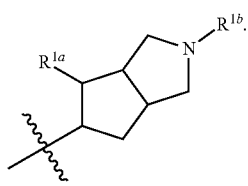

In another embodiment, there are provided compounds of formula (I), or a stereoisomer or pharmaceutically acceptable salt thereof, wherein $R^1$ is selected from:

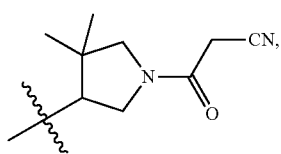

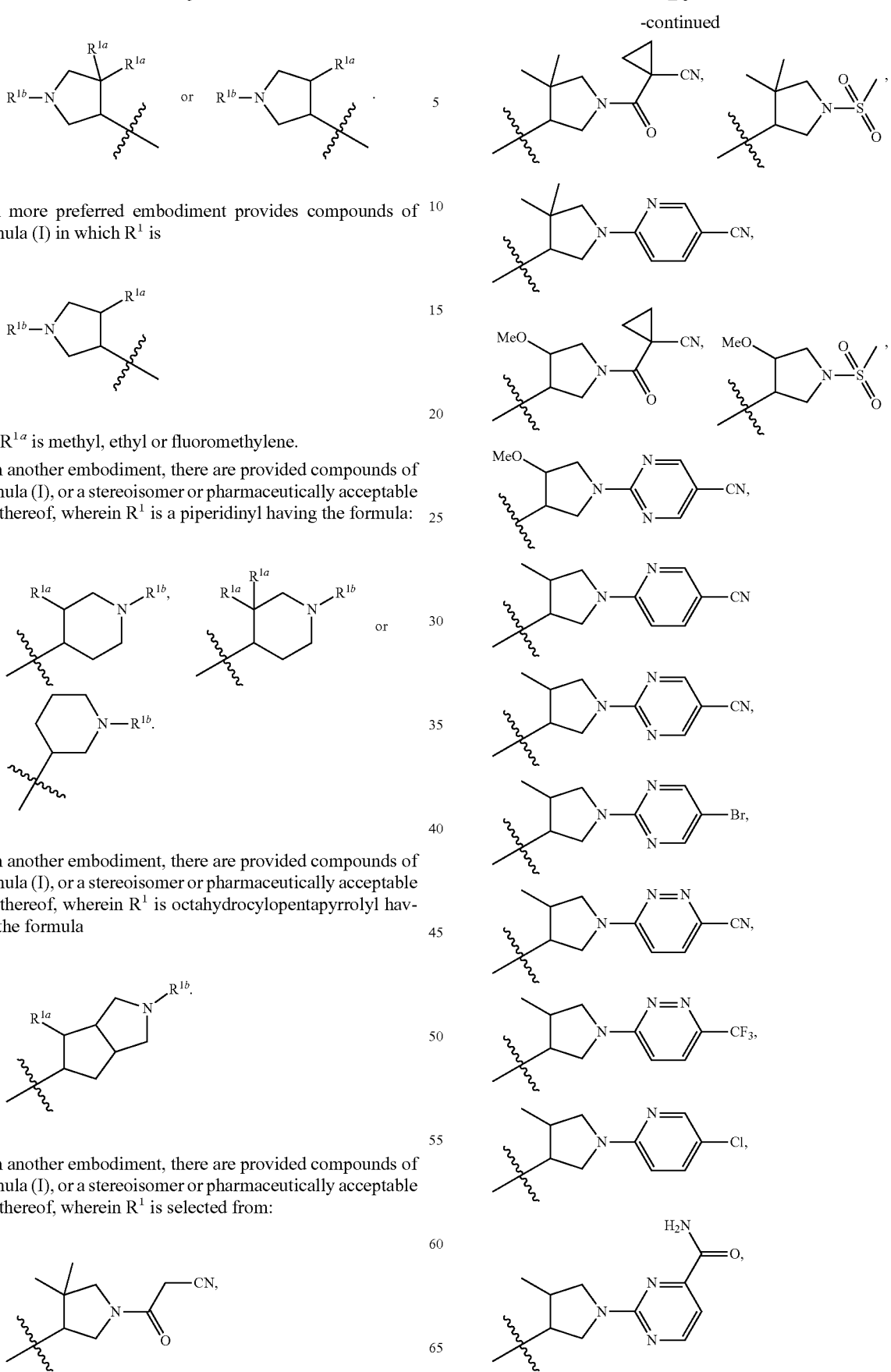

-continued
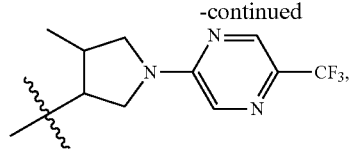
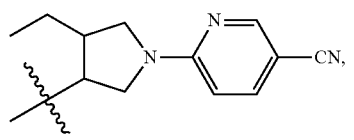
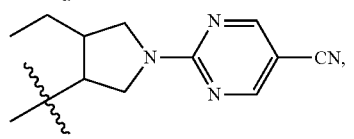
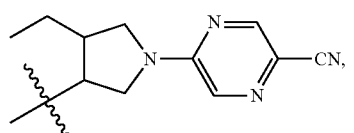
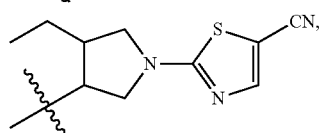
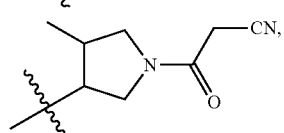
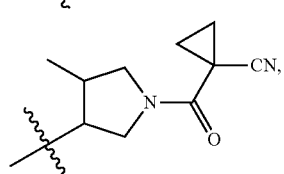
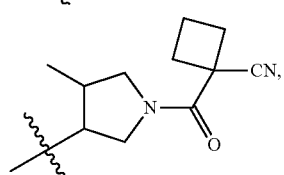
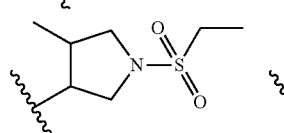
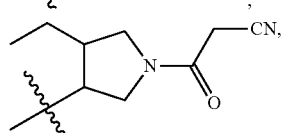
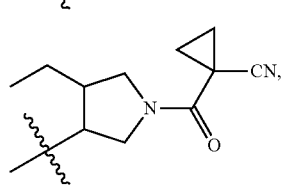
-continued
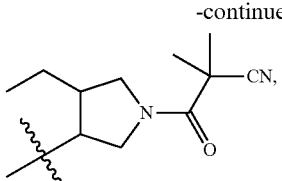
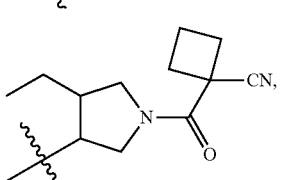
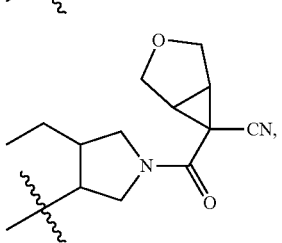
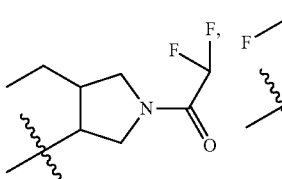
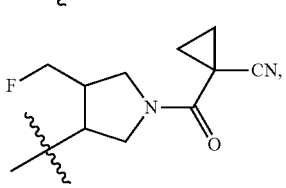
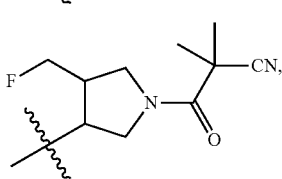
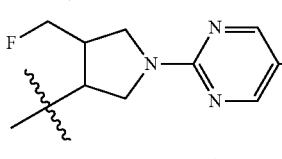
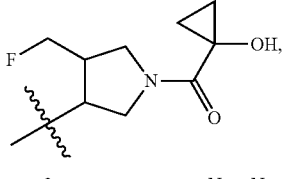
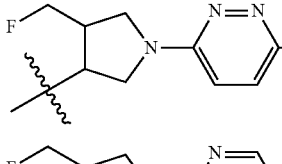
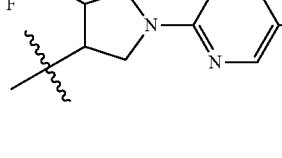

-continued

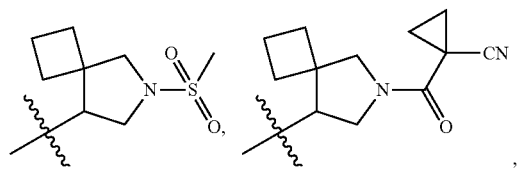

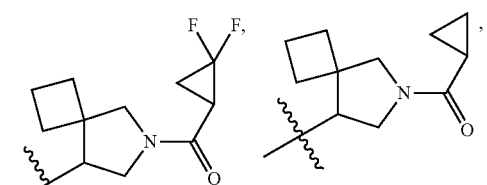

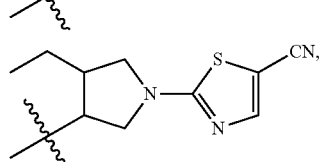

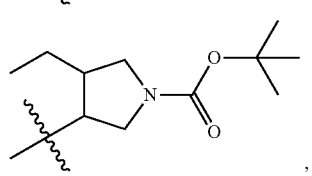

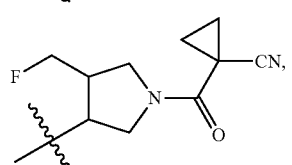

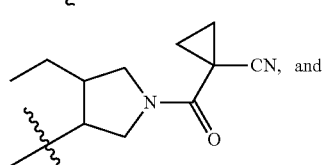

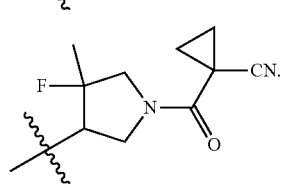

In another embodiment, there are provided compounds of formula (I), or a stereoisomer or pharmaceutically acceptable salt thereof, wherein $R^1$ is a heterocycle containing a heteroatom, $NR^{1b}$, wherein said heterocycle is piperidinyl, further substituted with 0-2 $R^{1a}$.

In another embodiment, there are provided compounds of formula (I), or a stereoisomer or pharmaceutically acceptable salt thereof, wherein $R^1$ is selected from:

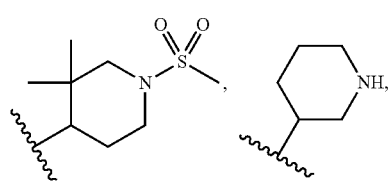

-continued

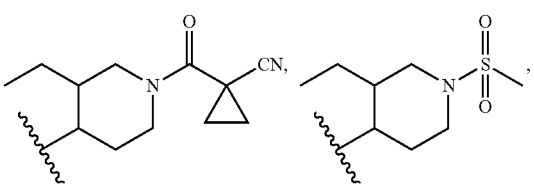

-continued

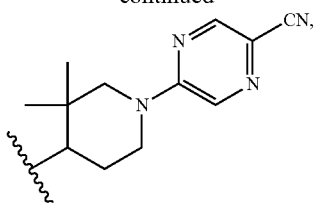

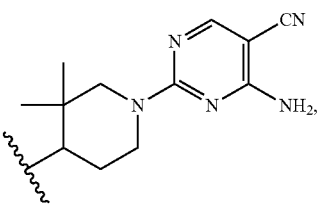

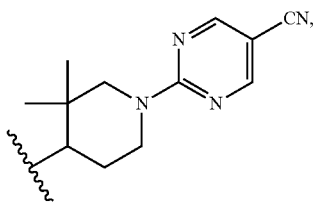

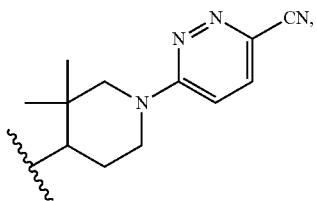

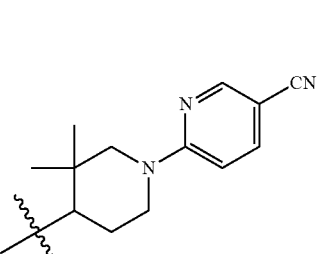

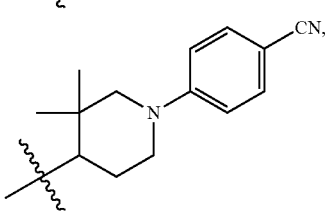

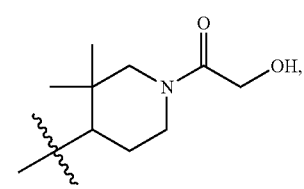

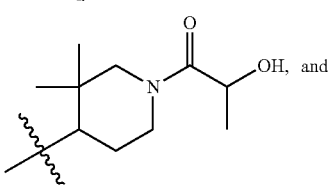

-continued

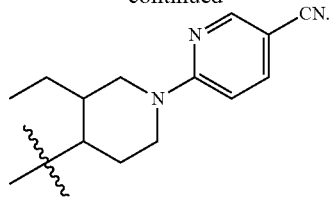

In another embodiment, there are provided compounds of formula (I) wherein $R^1$ is a heterocycle containing a heteroatom, $NR^{1b}$, wherein said heterocycle is octahydrocylopentapyrrolyl, further substituted with 0-2 $R^{1a}$.

In another embodiment, there are provided compounds of formula (I), or a stereoisomer or pharmaceutically acceptable salt thereof, wherein $R^1$ is selected from:

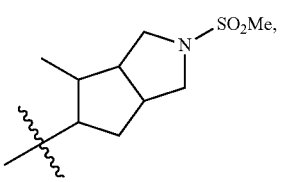

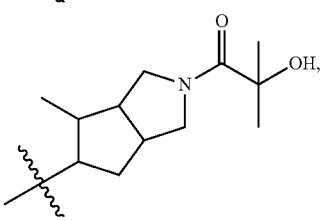

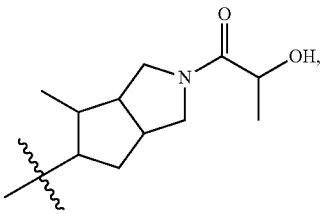

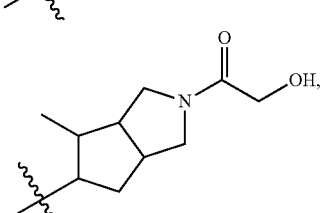

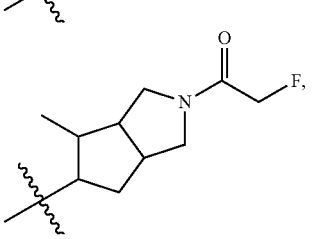

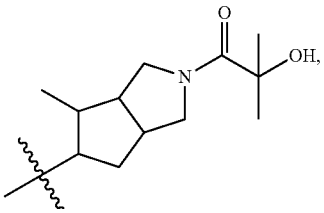

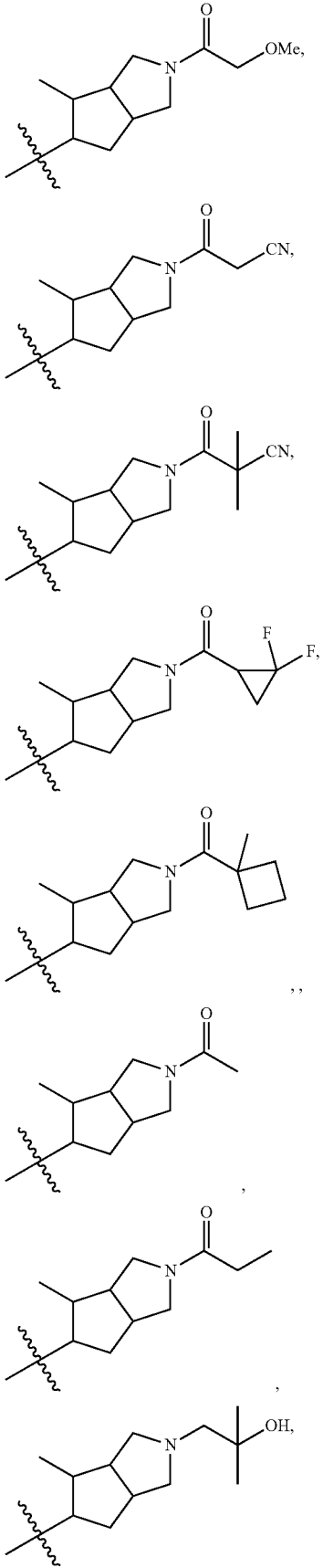

In another embodiment, there are provided compounds of formula (I), or a stereoisomer or pharmaceutically acceptable salt thereof, wherein:

R² is selected from NR^b C(O)R^{2b} and a group selected from phenyl, pyridyl, morpholinyl, pyridinyl, quinolinyl, pyrrolidinonyl, pyrazolyl, pyrimidinyl, imidazolidinonyl, pyradizinyl, oxadiazolyl, tetrazolyl, dihydrobenzooxazinyl, pyridinonyl, oxadiazolyl, triazolyl and oxazolyl, each group substituted with 0-3 R^{2a}; and R^{2a} is independently at each occurrence OR^b, cyano, CF₃, (CH₂)ₙC(O)R^{b'}, C(O)₂R^b, fluoro, methyl, (CH₂)ᵣC(O)N(R^{11})(R^{11}), isopropyl, propyl, ethyl, isobutyl, (CH₂)₂R^a, phenyl, =O, N(R^{11})(R^{11}), CH(R^a)₂, morpholinyl, C(CH₃)₂R^a, S(O)₂R^c, CD₃, CH₂CH(R^a)(R^a), CH₂C(CH₃)₂R^a, CH₂CH(R^a)CH₃, CH(R^a)₂, CH₂NR^b C(O)R^{2b} or (CH₂)₂R^a.

In another embodiment, there are provided compounds of formula (I), or a stereoisomer or pharmaceutically acceptable salt thereof, wherein R² is phenyl substituted by 0-3 R^{2a}.

In an alternate embodiment, there are provided compounds of formula (I), or a stereoisomer or pharmaceutically acceptable salt thereof, wherein R² is selected from pyridyl, morpholinyl, pyridinyl, quinolinyl, pyrrolidinonyl, pyrazolyl, pyrimidinyl, imidazolidinonyl, pyradizinyl, oxadiazolyl, tetrazolyl, dihydrobenzooxazinyl, pyridinonyl, oxadiazolyl, triazolyl and oxazolyl, each group substituted with 0-3 R^{2a}.

In another embodiment, there are provided compounds of formula (I), or a stereoisomer or pharmaceutically acceptable salt thereof, wherein:

R^a is independently at each occurrence methyl, ethyl, CF₃, CN, OH, OR^b, bromo, chloro or fluoro, or N(R^c)(R^c);

R^b is selected independently at each occurrence from hydrogen, methyl, ethyl, n-pentyl, n-propyl, t-butyl, CH₂R^d, C(CH₃)₂R^d, CH(CH₃)R^d, CH(R^d)CH₃, CH(R^d)CH₂CH₃, -C(CH₃)₂R^d, CH₂C(CH₃)₂R^d, (CH₂)₂R^d, —CH₂CH(CH₃) R^d, and CH(R^d)₂: and cyclopropyl, azetidinyl, pyrrolidinyl and morpholinyl, each group substituted by 0-2 R^d;

R^c is independently at each occurrence hydrogen, methyl or ethyl,

R^d is independently at each occurrence hydrogen, OH, CN, CF₃, F, OR^e or methyl;

R^e is methyl; and n is 0-2.

In another embodiment, there are provided compounds of formula (I), or a stereoisomer or pharmaceutically acceptable salt thereof, wherein R¹ is selected from:

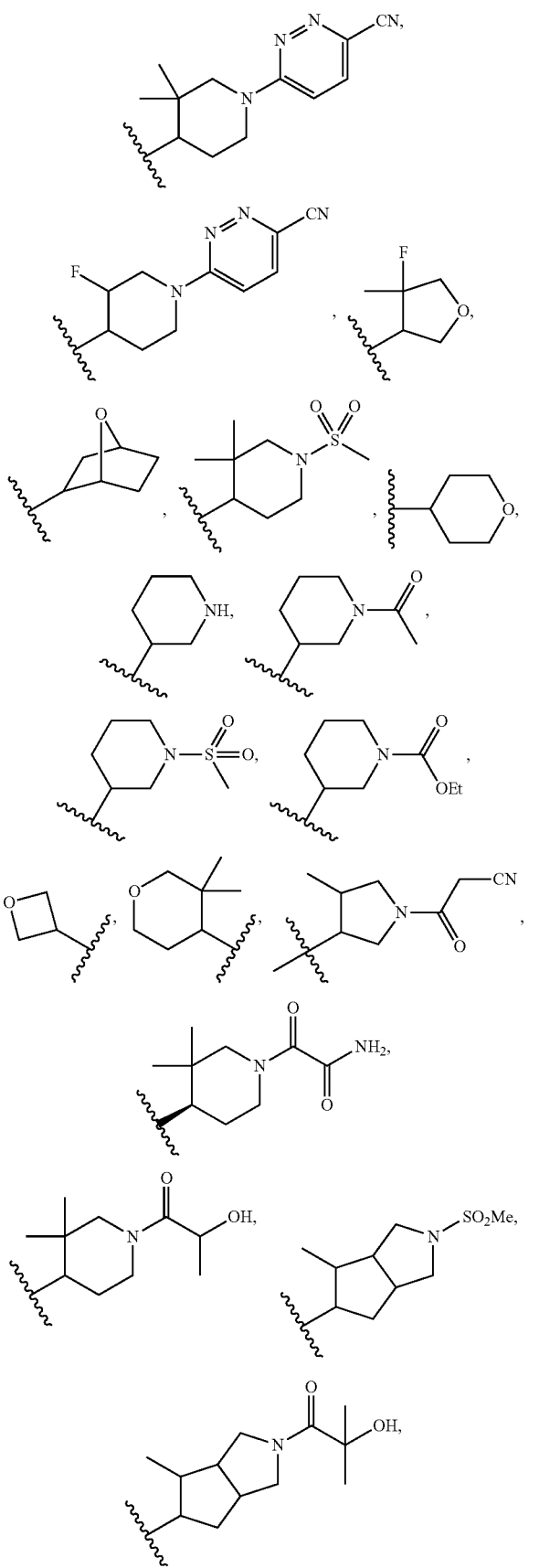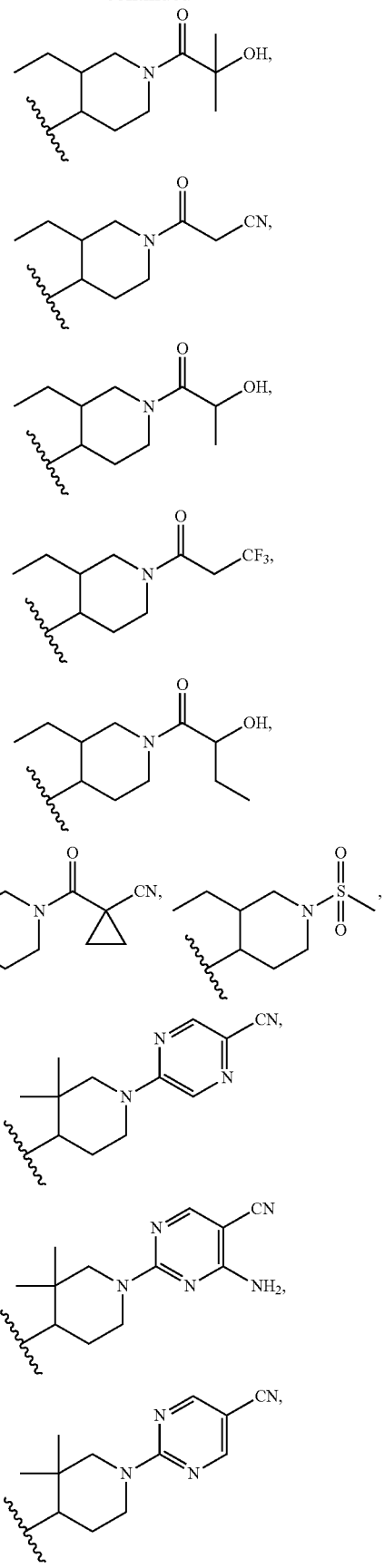

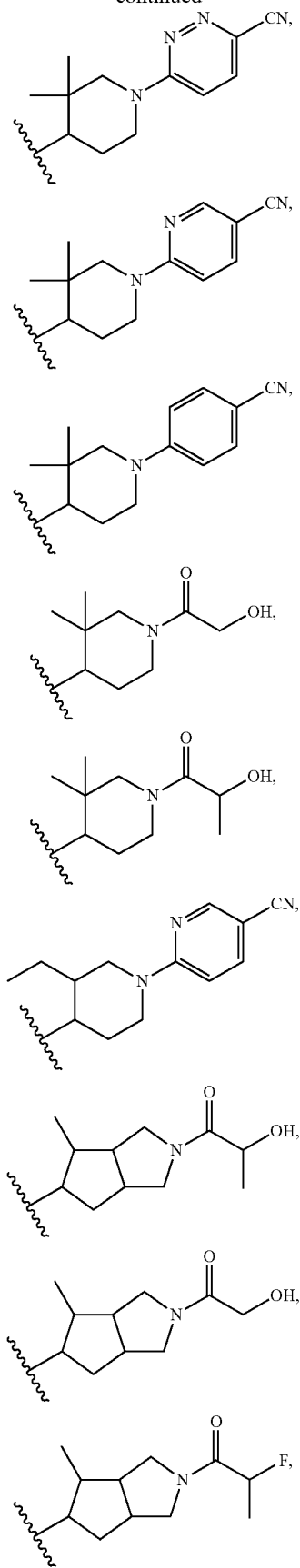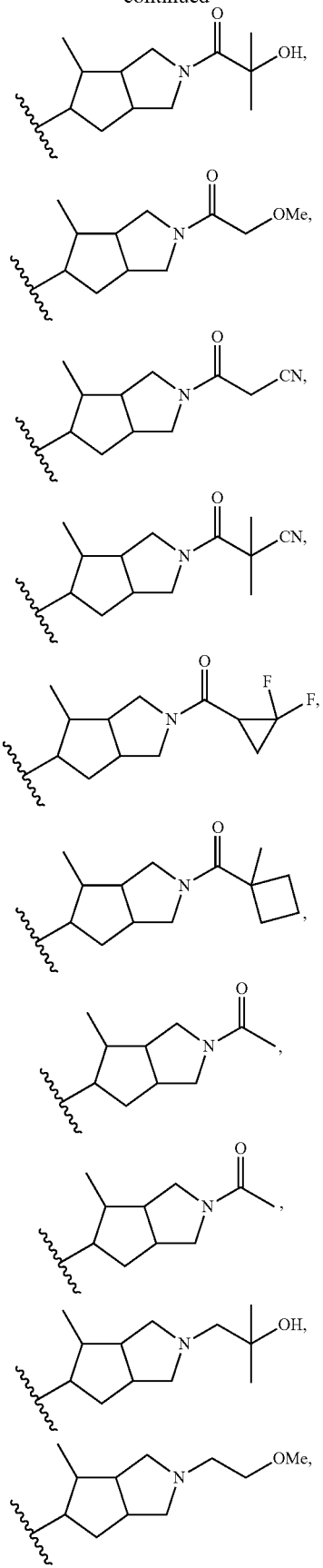

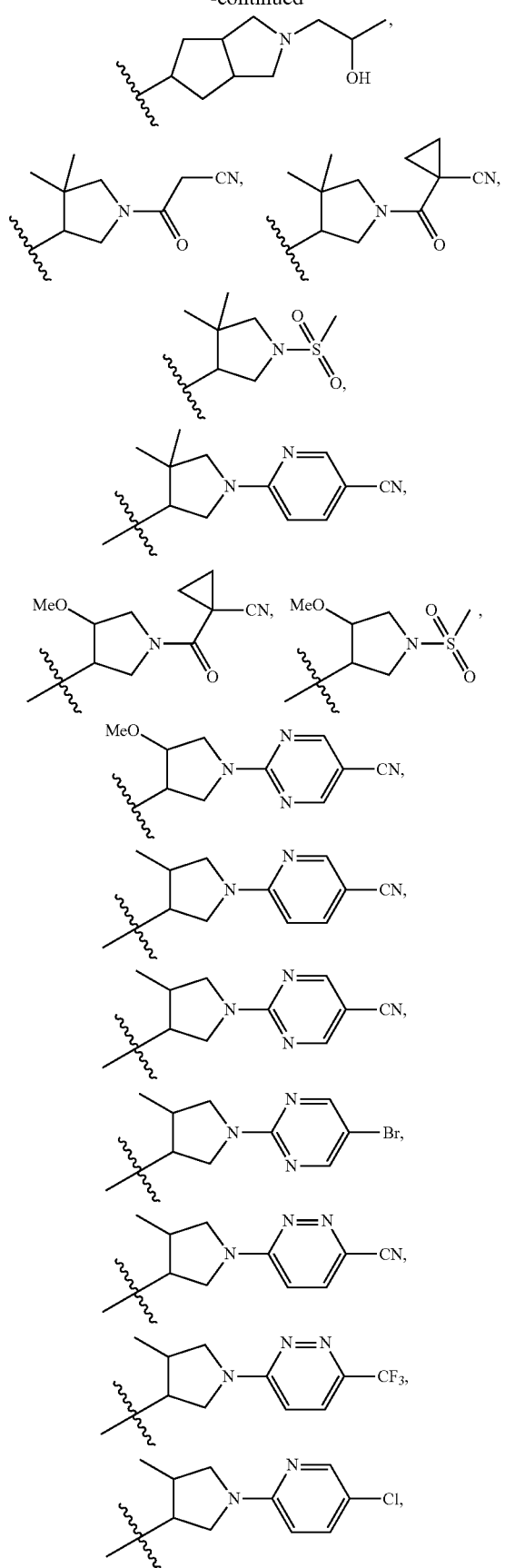
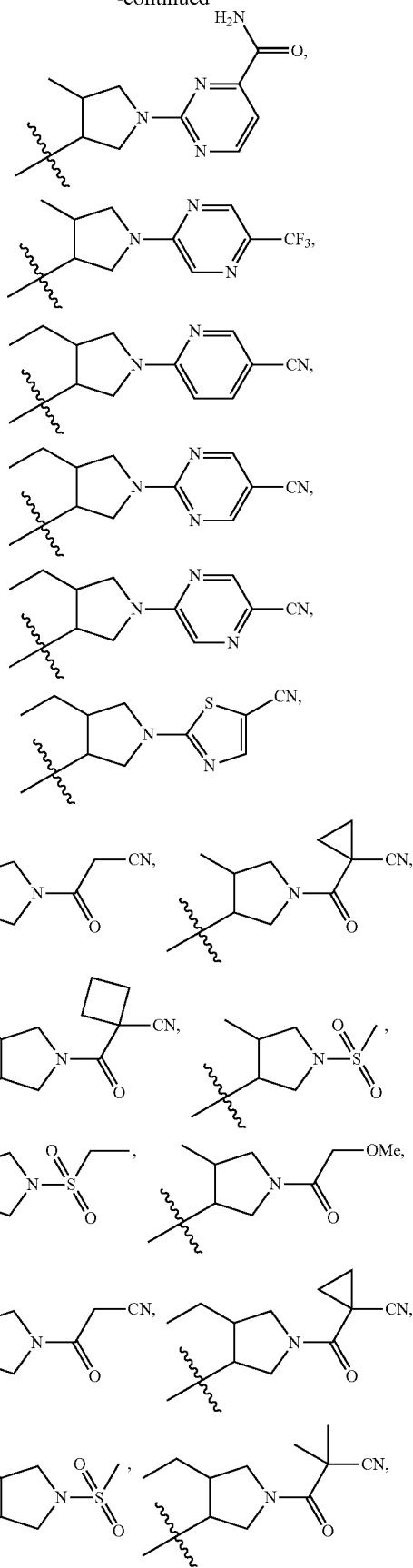

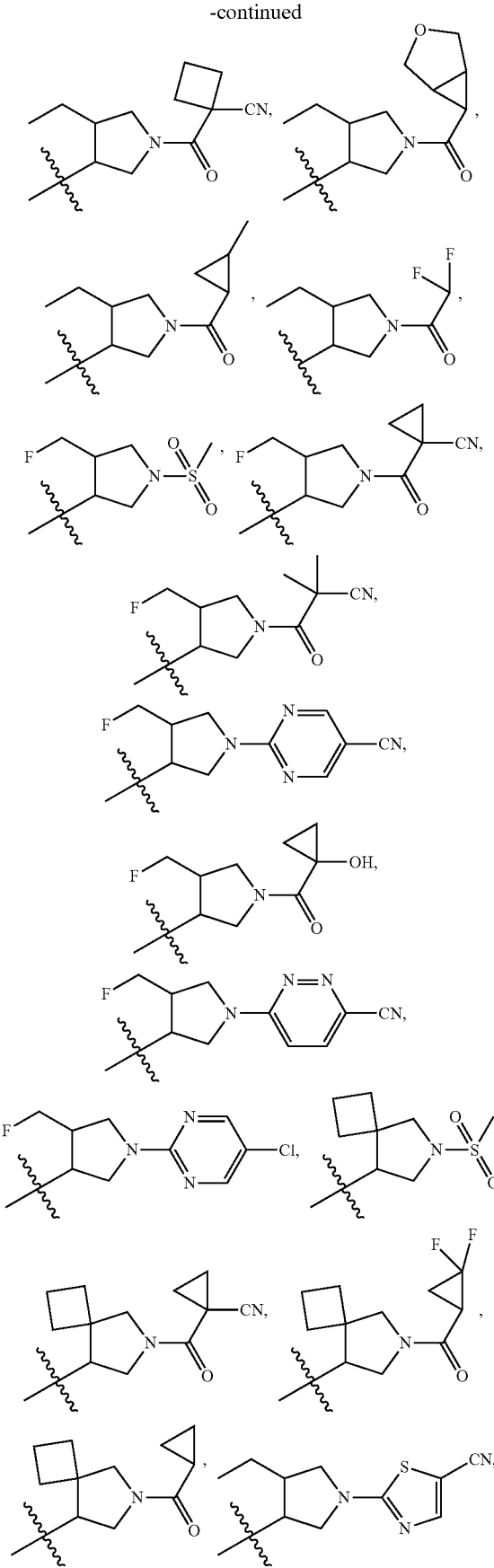
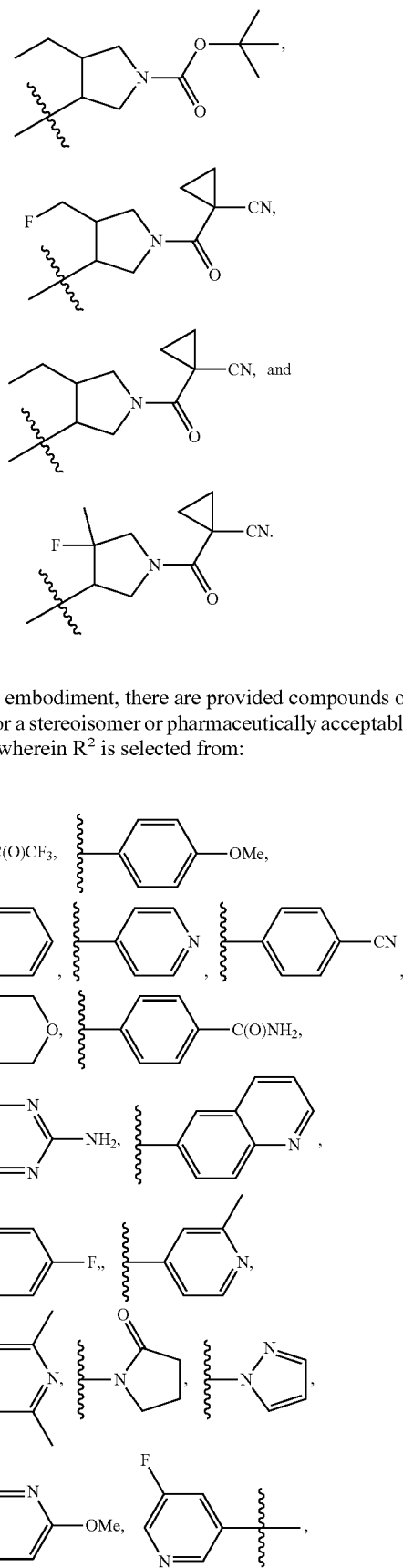
In another embodiment, there are provided compounds of formula (I), or a stereoisomer or pharmaceutically acceptable salt thereof, wherein $R^2$ is selected from:
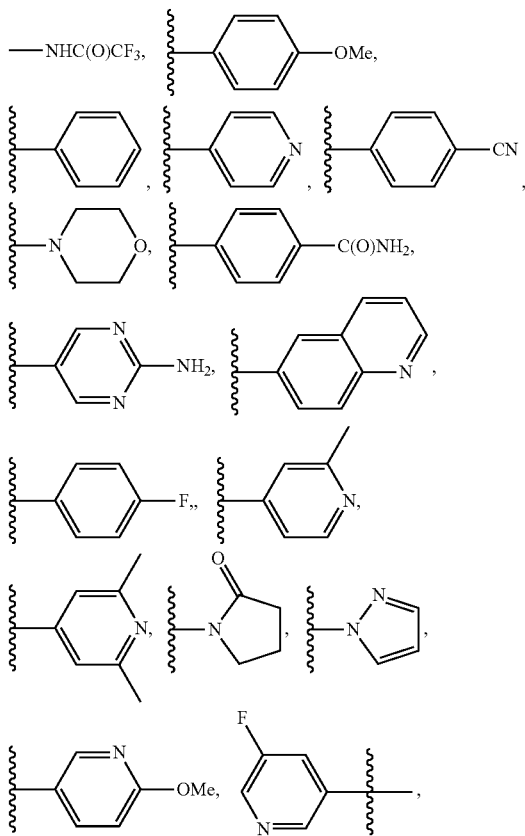

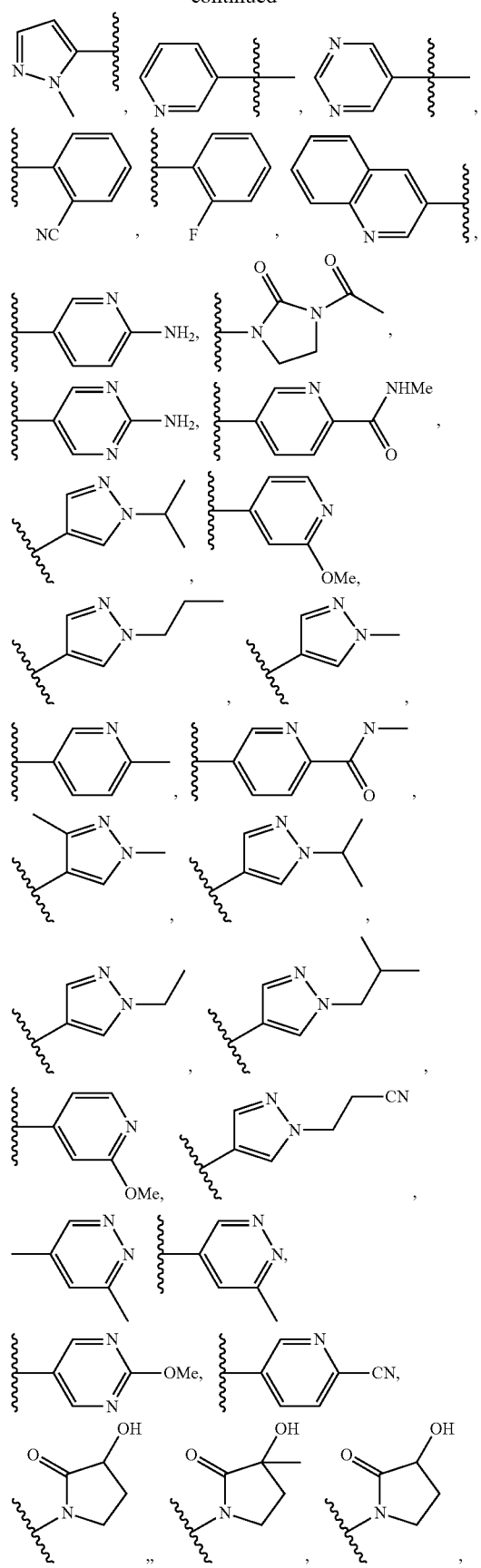
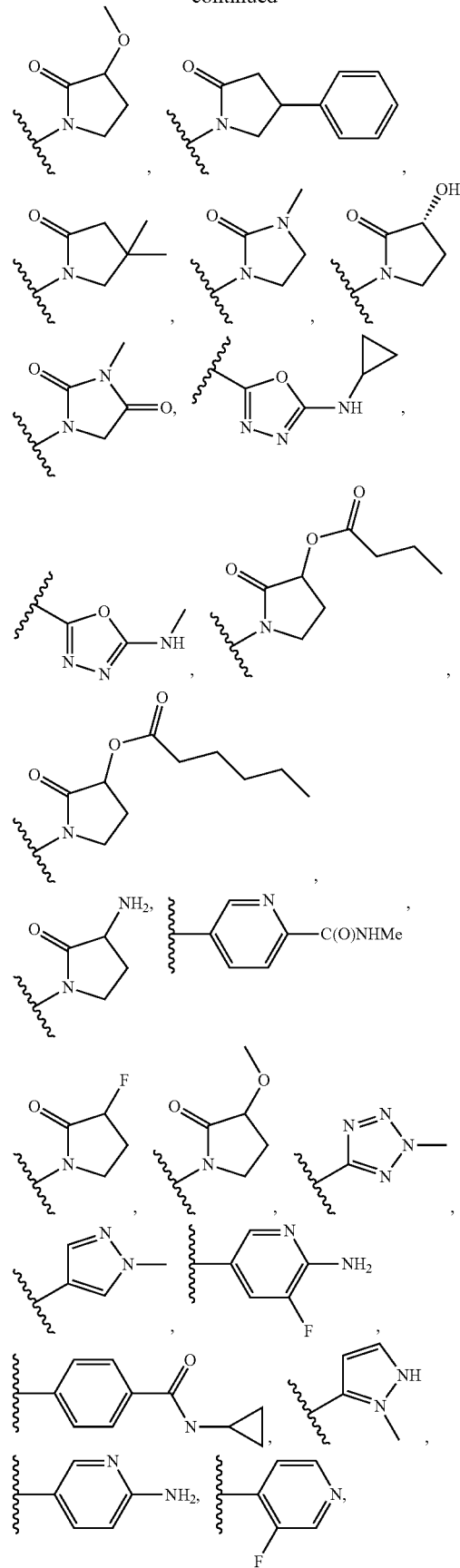

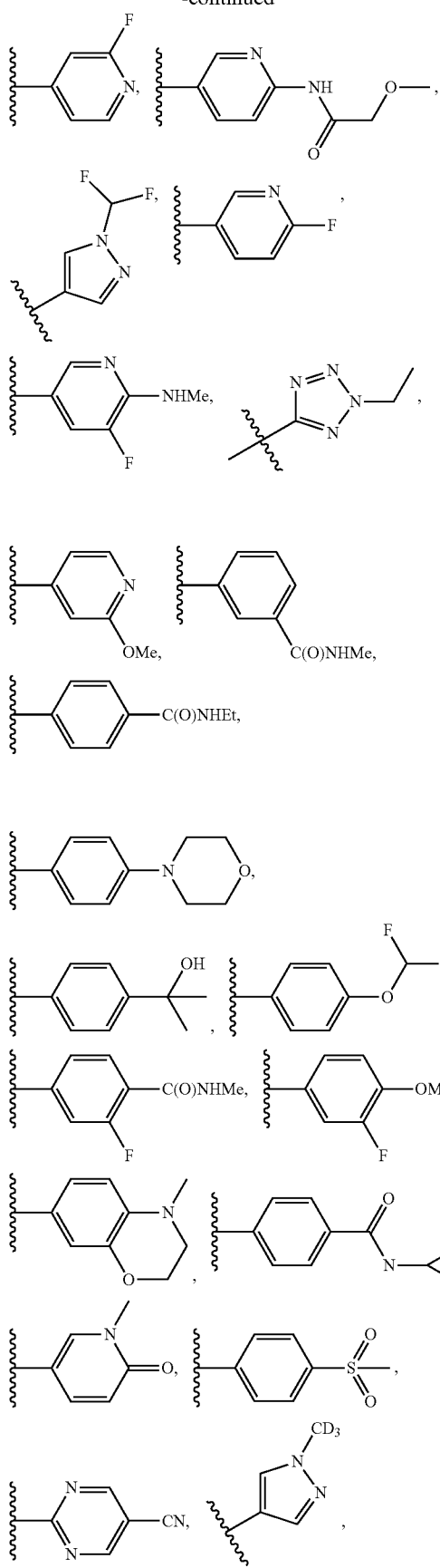
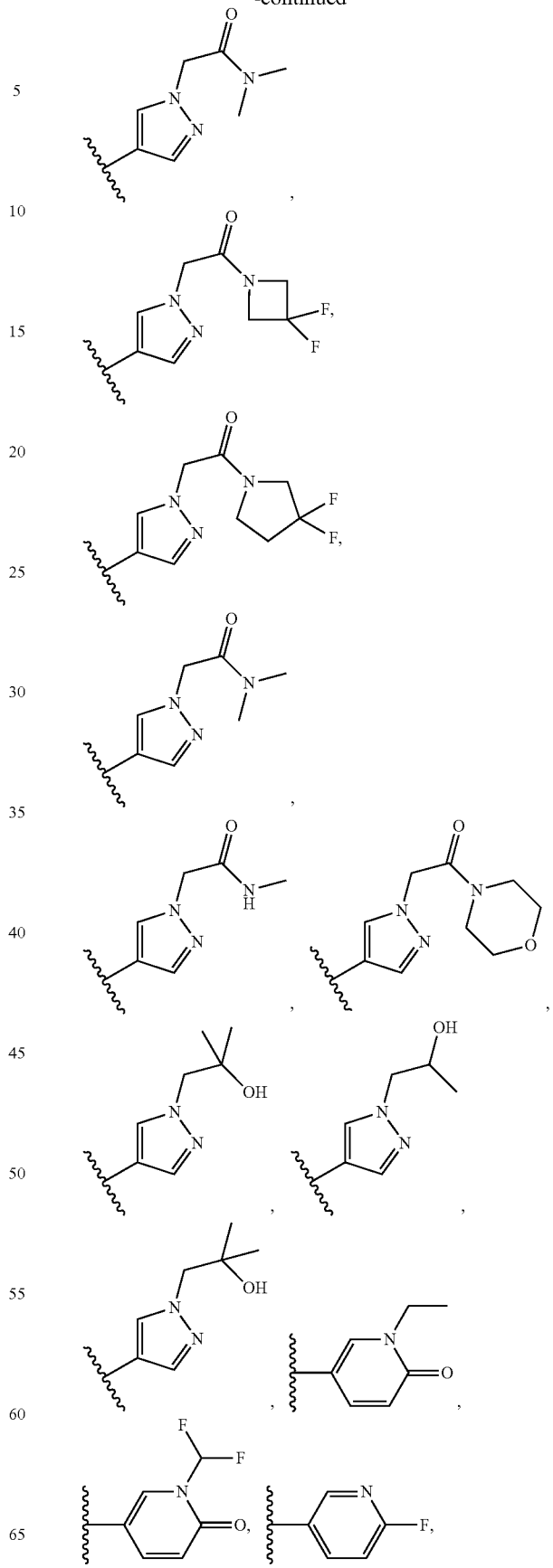

-continued
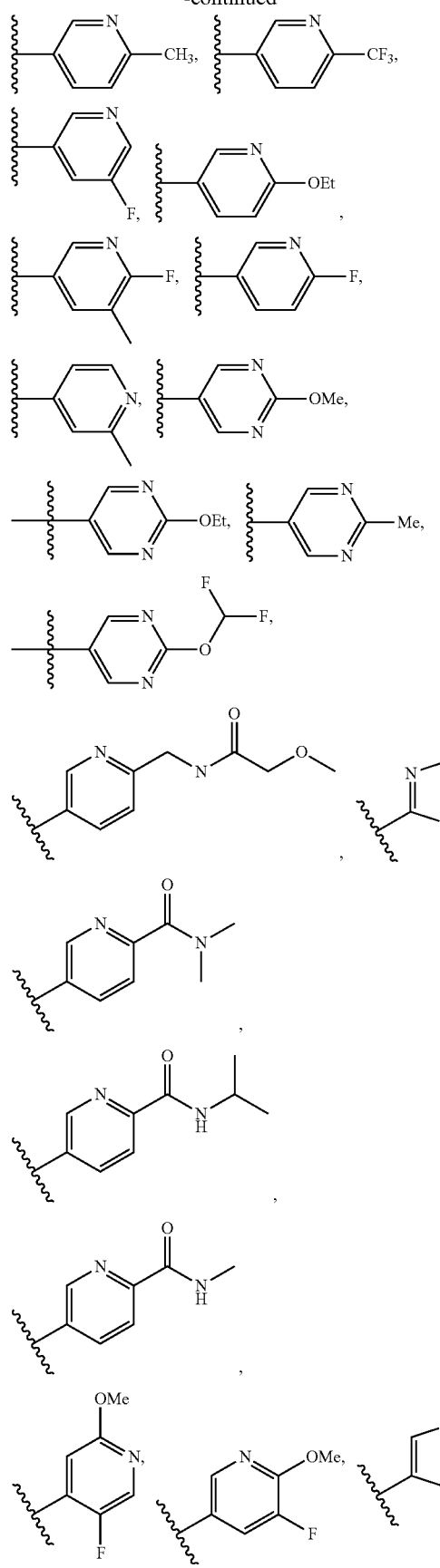
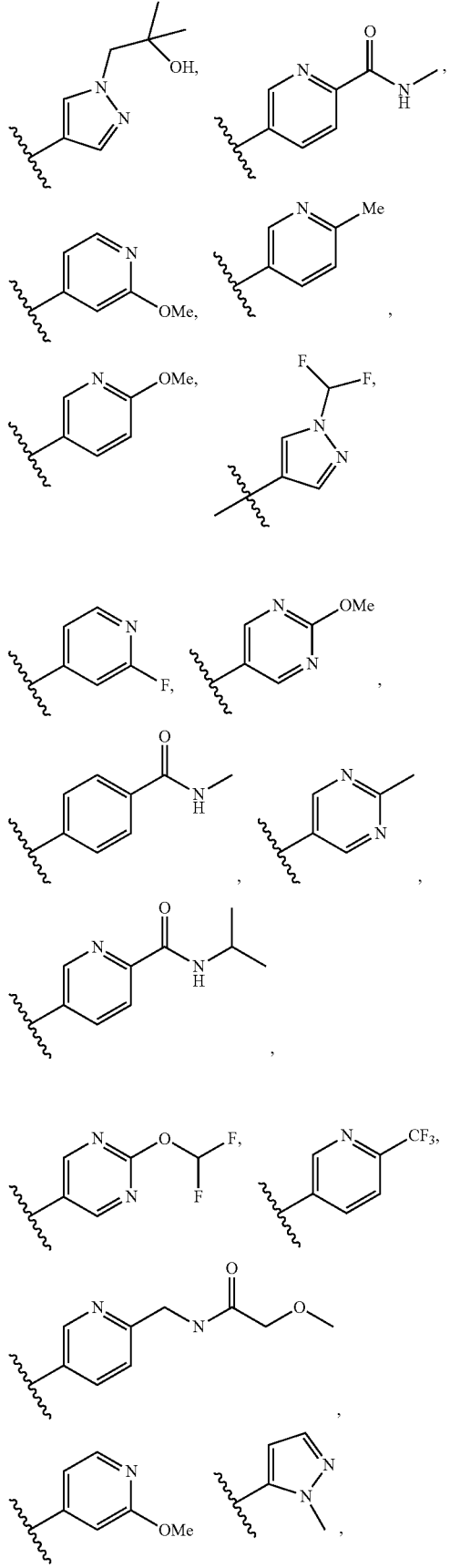

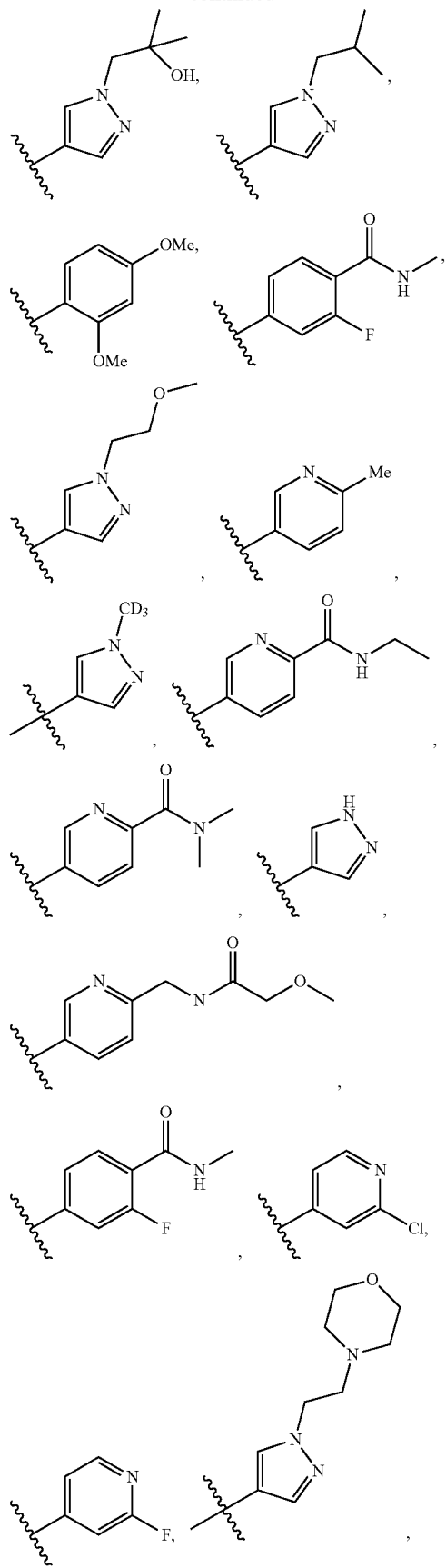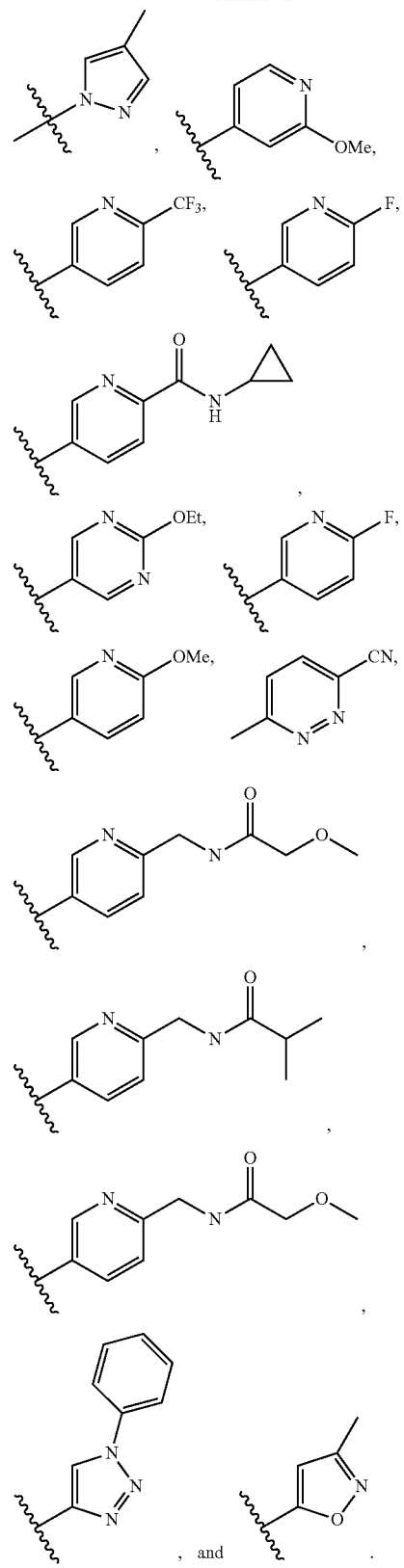
In another embodiment, there are provided compounds of formula (I), or a stereoisomer or pharmaceutically acceptable salt thereof, wherein $R^1$ is selected from:

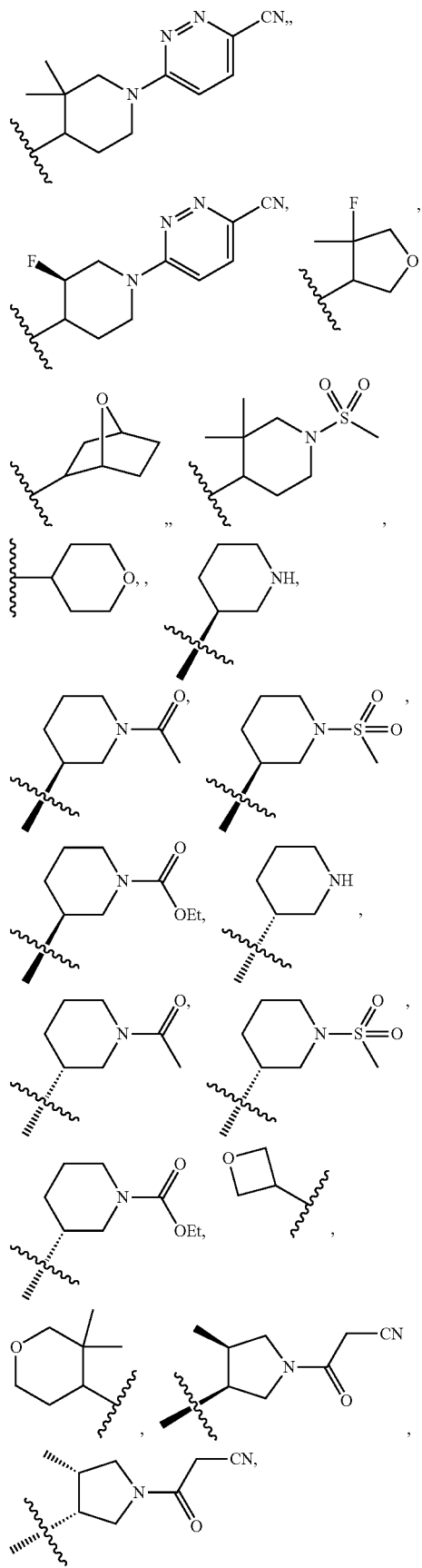
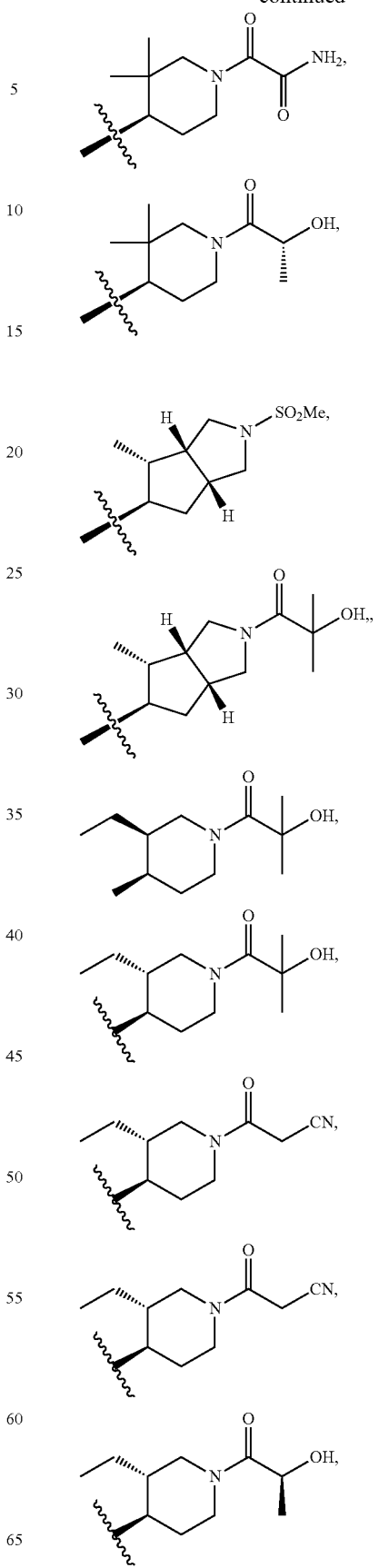

-continued
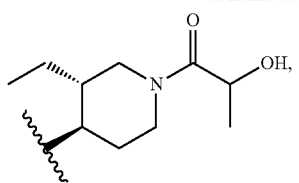
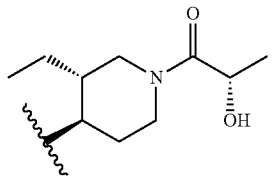
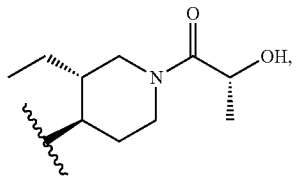
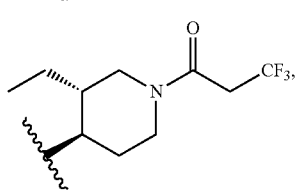
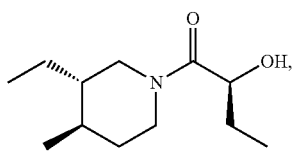
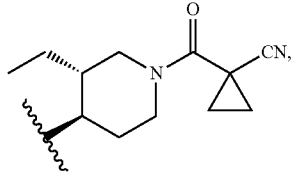
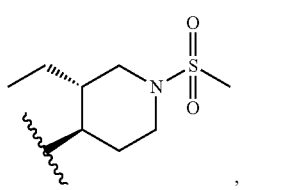
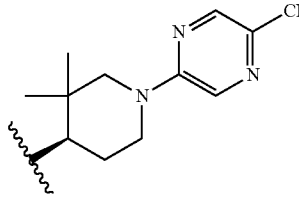
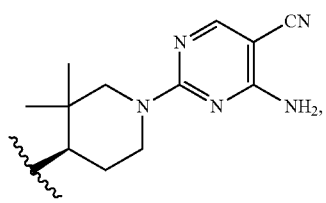
-continued
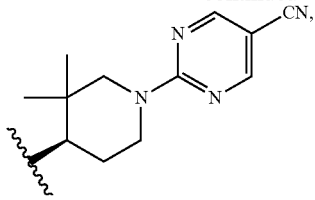
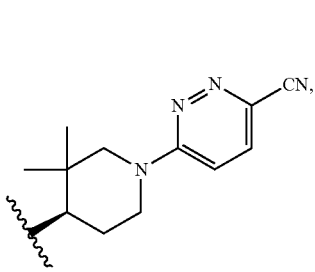
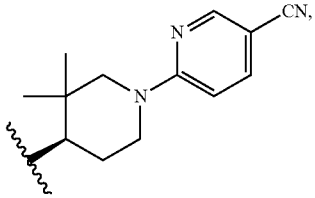
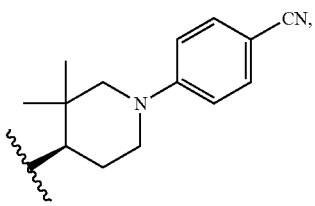
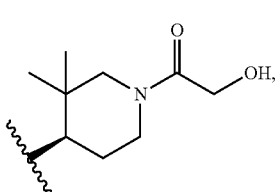
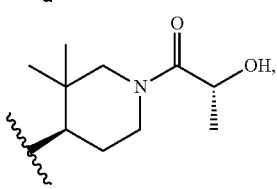
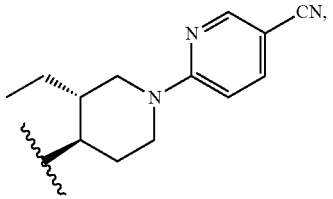
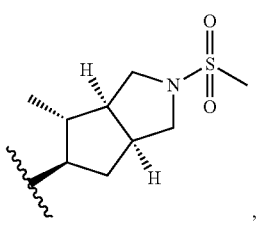

-continued
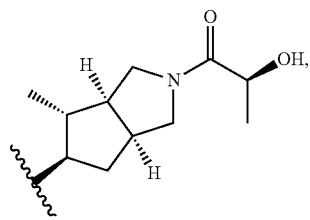
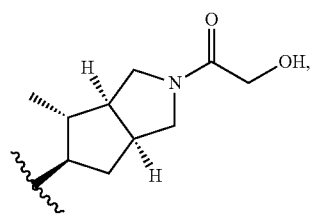
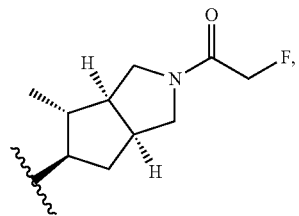
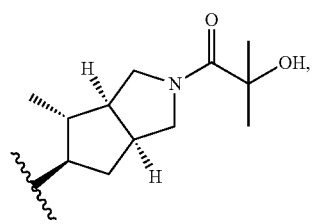
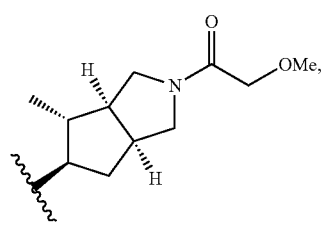
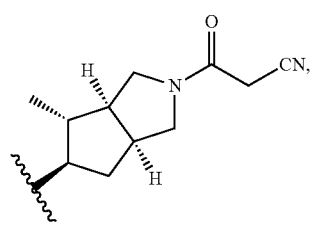
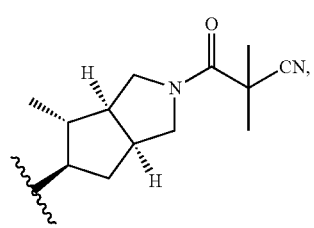
-continued
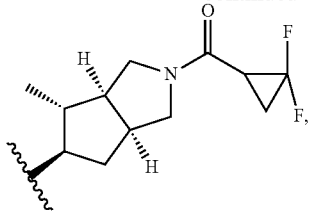
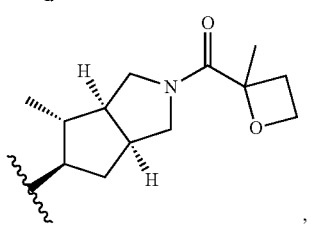
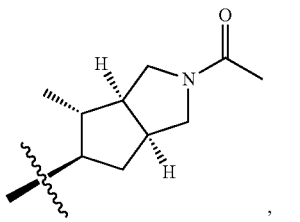
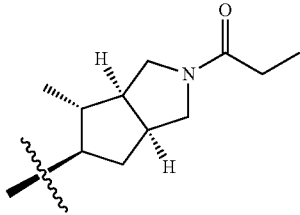
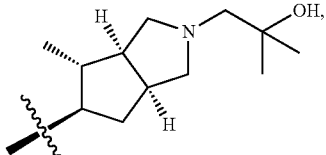
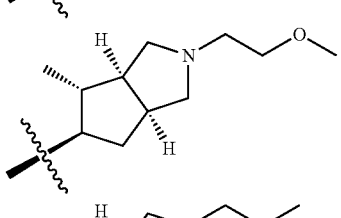
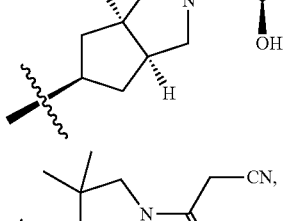
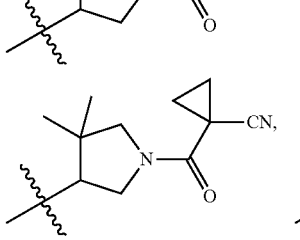 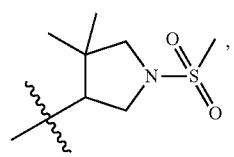

-continued
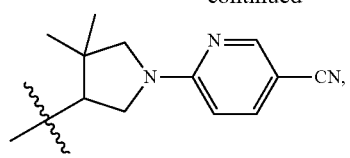
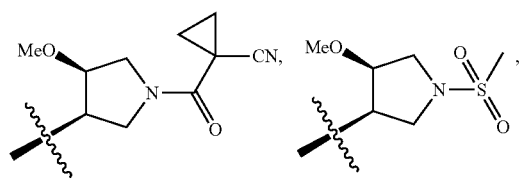
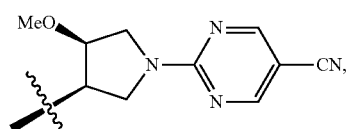
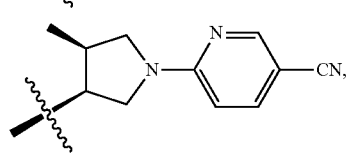
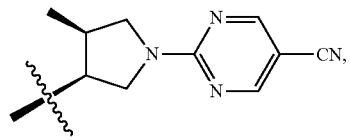
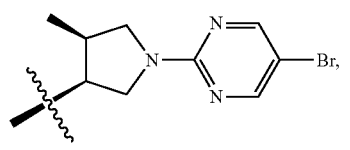
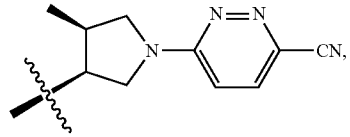
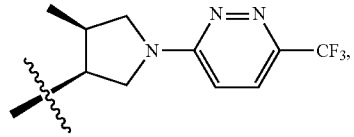
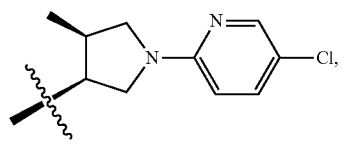
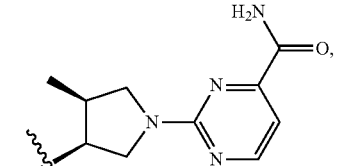
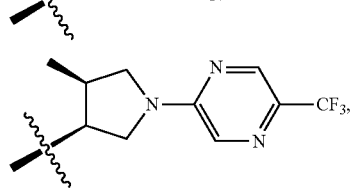
-continued
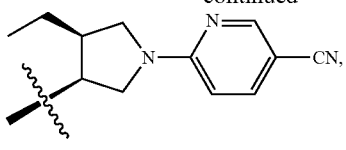
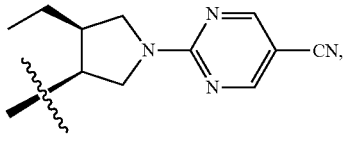
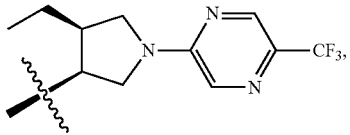
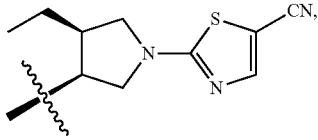
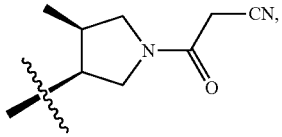
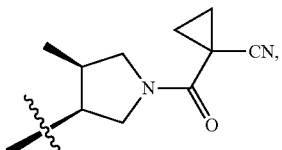
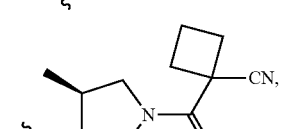
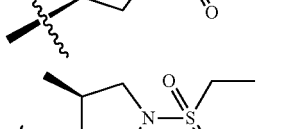
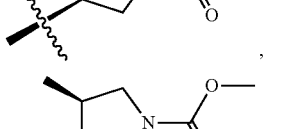
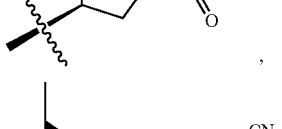
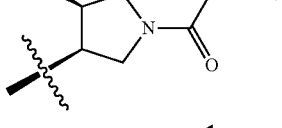
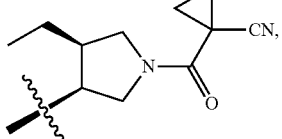

-continued
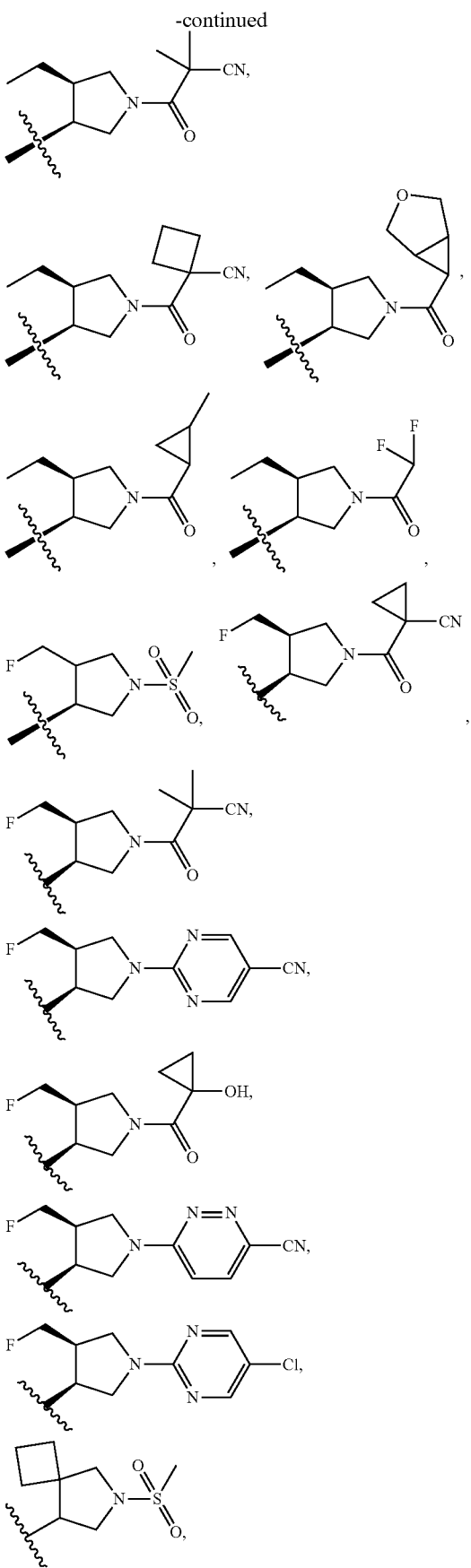
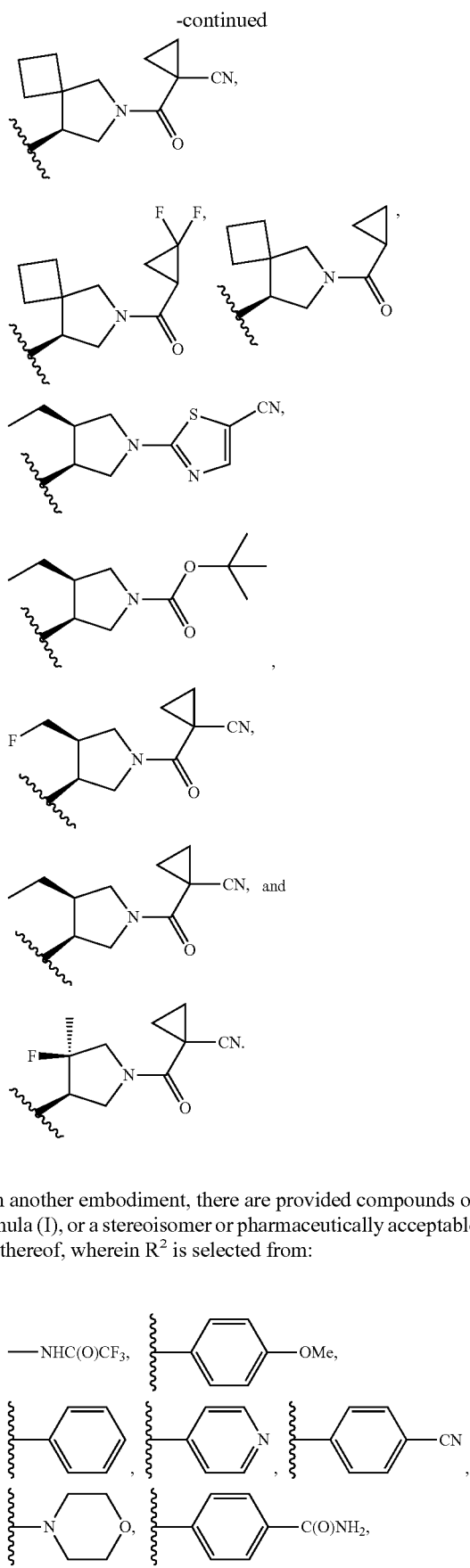
In another embodiment, there are provided compounds of formula (I), or a stereoisomer or pharmaceutically acceptable salt thereof, wherein $R^2$ is selected from:

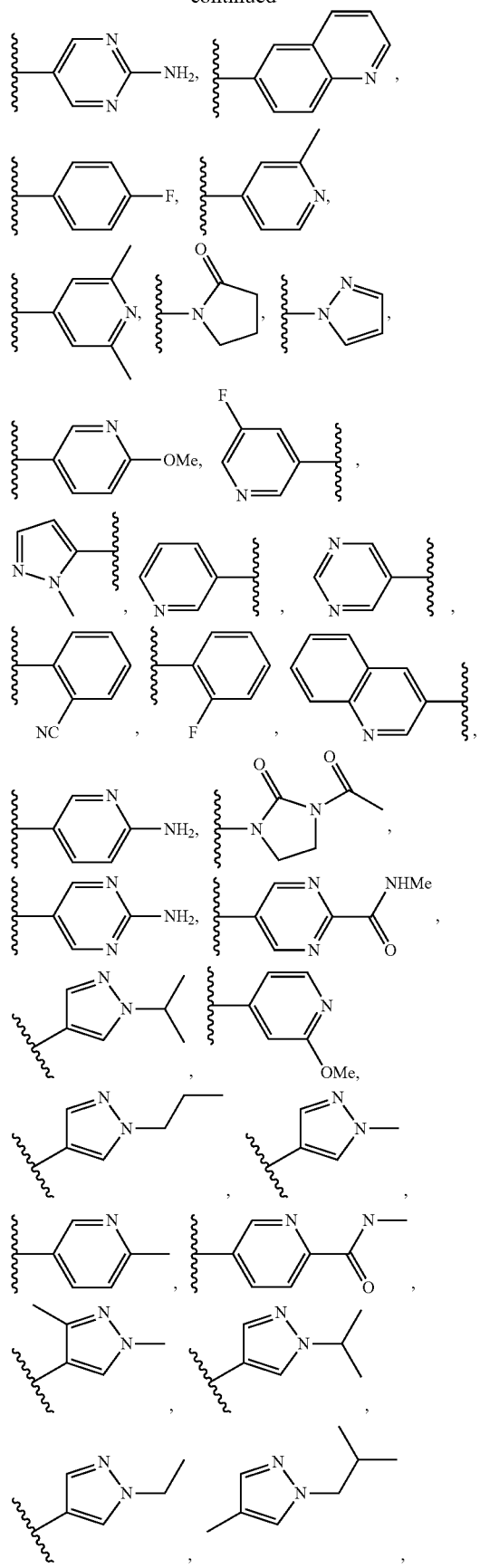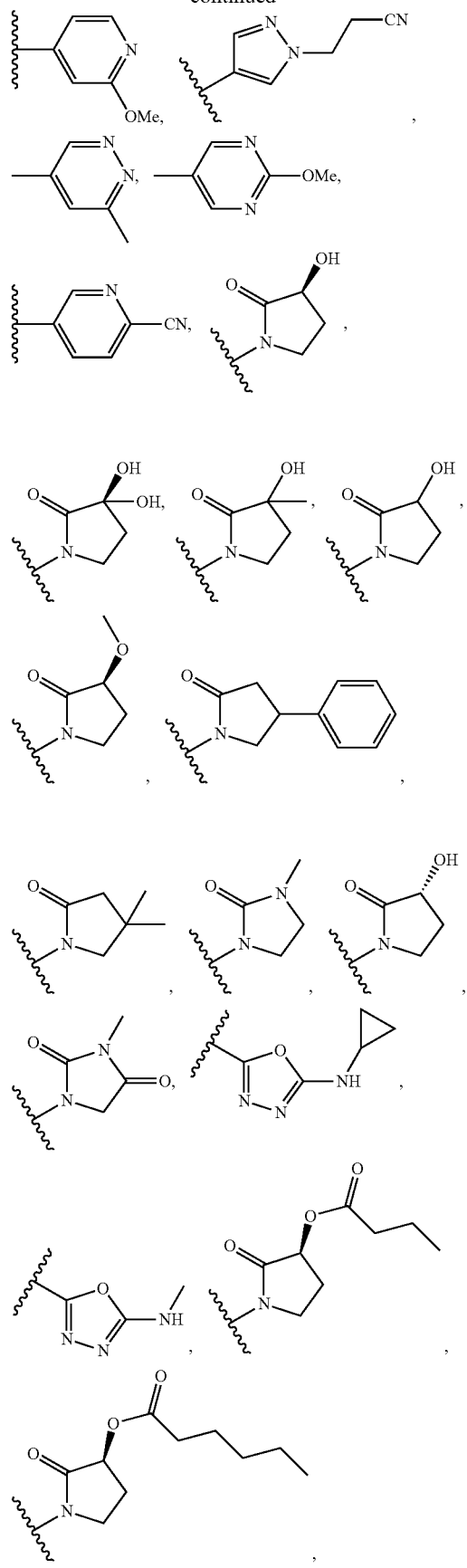

-continued
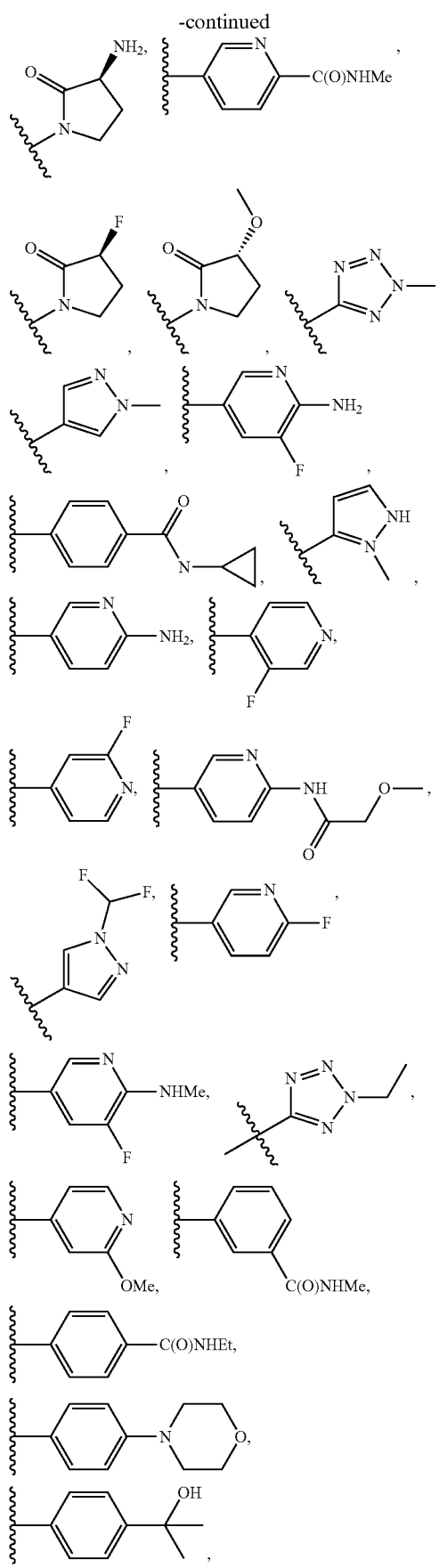
-continued
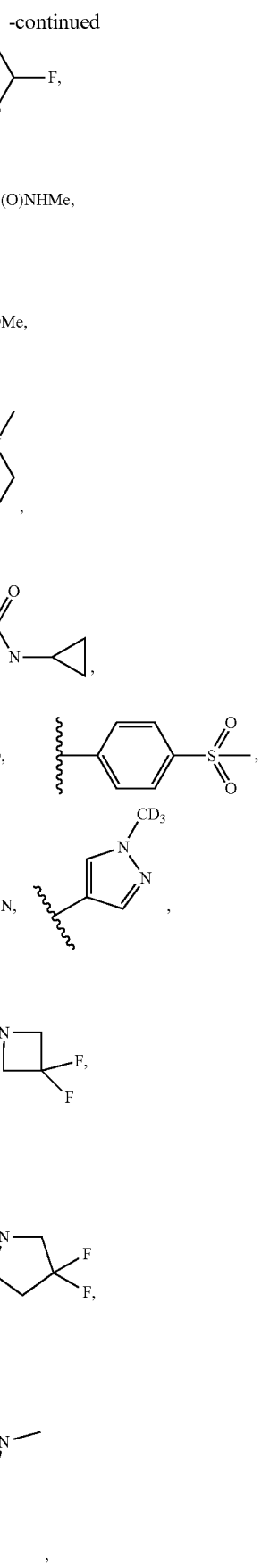

-continued

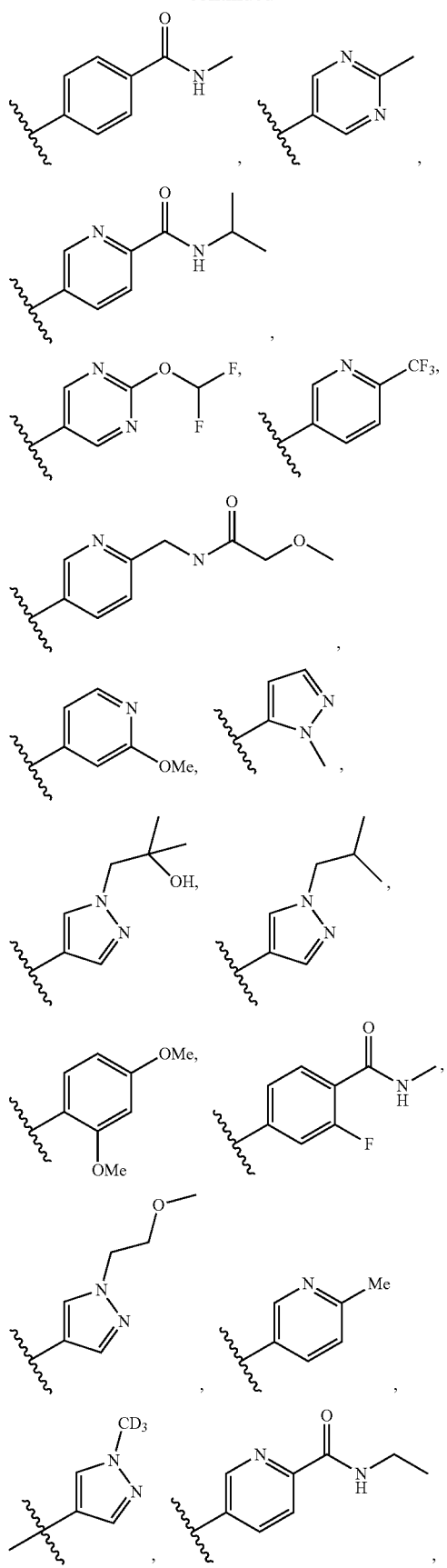
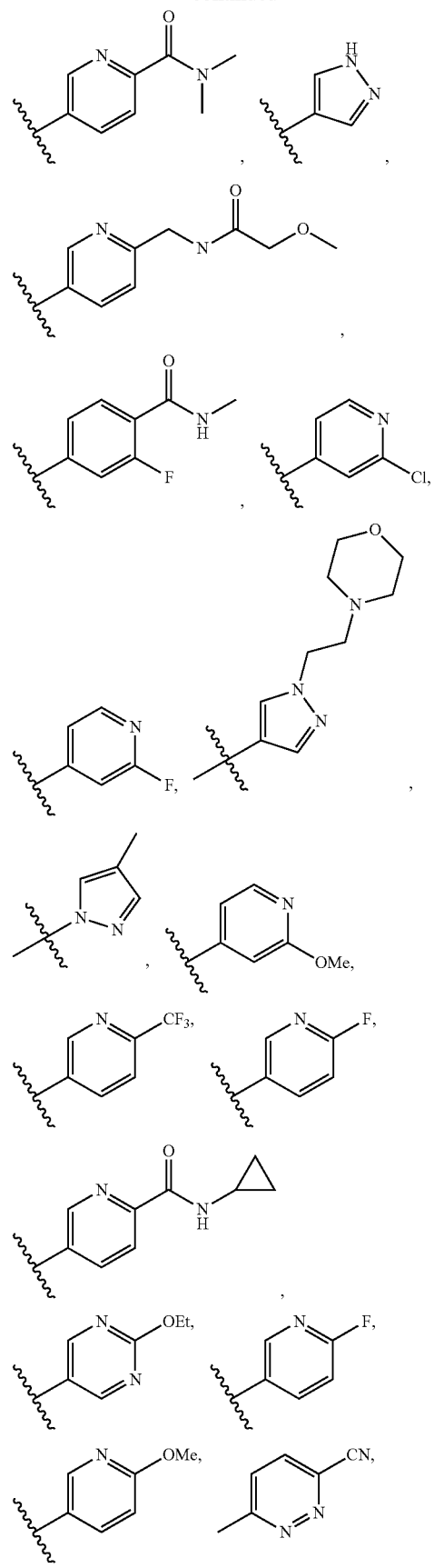

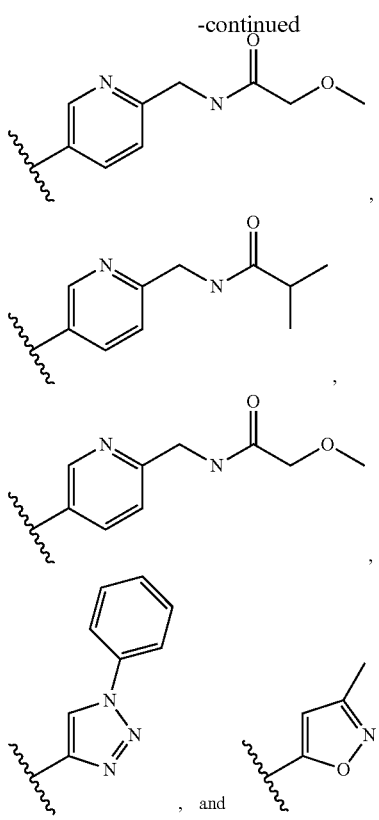

In another embodiment are compounds of Formula (I), wherein the compound of formula (I) is selected from the Examples herein, or a pharmaceutically-acceptable salt thereof.

In another embodiment the present invention provides a pharmaceutical composition comprising a pharmaceutically acceptable carrier and at least one of the compounds of the present invention, or a stereoisomer or pharmaceutically acceptable salt thereof.

In another embodiment, the present invention provides a pharmaceutical composition comprising a compound of formula I, or pharmaceutically acceptable salt thereof, and a pharmaceutically acceptable carrier or diluent.

In another embodiment, the present invention provides a pharmaceutical composition, comprising: a pharmaceutically acceptable carrier and a therapeutically effective amount of at least one of the compounds of the present invention, or a stereoisomer or pharmaceutically acceptable salt thereof.

In another embodiment, the present invention provides a method for treating inflammatory or autoimmune disease: administering to a patient in need of such treatment a therapeutically effective amount of at least one of the compounds of the present invention, or a stereoisomer or a pharmaceutically acceptable salt thereof, in combination with at least one other therapeutic agent, or a stereoisomer or a pharmaceutically acceptable salt thereof.

In another embodiment, the present invention provides a method for treating inflammatory and/or autoimmune diseases comprising: administering to a patient in need of such treatment a therapeutically effective amount of at least one of the compounds of the present invention, or a stereoisomer or a pharmaceutically acceptable salt thereof.

In another embodiment, the present invention provides a method of treating a patient in need of inflammatory and/or autoimmune diseases treatment, comprising: administering a compound of the present invention, or a stereoisomer or a pharmaceutically acceptable salt thereof, in an amount effective to treat the inflammatory and/or autoimmune diseases.

In another embodiment, the present invention provides a method of treating inflammatory or autoimmune diseases, wherein the inflammatory or autoimmune diseases is selected from Crohn's, ulcerative colitis, asthma, Graves' disease, rheumatoid arthritis, systemic lupus erythematosis, psoriasis, dry eye, multiple sclerosis, psoriatic arthritis and ankylosing spondylities, solid organ transplant rejection, islet cell transplant rejection and graft vs. host disease.

In another embodiment, the present invention provides a novel method, comprising: administering a compound of the present invention or a stereoisomer or a pharmaceutically acceptable salt, thereof in an amount effective to treat an inflammatory and/or autoimmune diseases.

In another embodiment, the present invention provides a method for treating inflammatory and/or autoimmune diseases comprising: administering to a patient in need of such treatment a therapeutically effective amount of a compound of formula (I) or a stereoisomer or a pharmaceutically acceptable salt thereof, in combination with at least one other anti-cancer agent or antiproliferative agent and/or another agent, or a stereoisomer or a pharmaceutically acceptable salt thereof.

In another embodiment, the present invention provides a method for treating inflammatory and/or autoimmune diseases comprising: administering to a patient in need of such treatment a therapeutically effective amount of at least one of the compounds of the present invention or a stereoisomer or a pharmaceutically acceptable salt, thereof, in combination with at least one other therapeutic agent, or a stereoisomer or a pharmaceutically acceptable salt thereof.

In another embodiment, the present invention provides a compound of the present invention for use in therapy.

In another embodiment, the present invention provides a compound of the present invention for use in therapy for treating an inflammatory and/or autoimmune disease.

In another embodiment, the present invention also provides the use of a compound of formula I of the present invention for the manufacture of a medicament for the treatment of aninflammatory and/or autoimmune disease.

The present invention may be embodied in other specific forms without departing from the spirit or essential attributes thereof. This invention encompasses all combinations of preferred aspects and/or embodiments of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

Definitions

The following are definitions of terms that may be used in the present specification. The initial definition provided for a group or term herein applies to that group or term throughout the present specification individually or as part of another group, unless otherwise indicated.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

"Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

"Halo" or "halogen" includes fluoro, chloro, bromo, and iodo.

The term "cycloalkyl" refers to cyclized alkyl groups, including mono-, bi- or poly-cyclic ring systems. $C_{3-10}$ cycloalkyl is intended to include $C_3$, $C_4$, $C_5$, $C_6$, and $C_7$, $C_8$, $C_9$, and $C_{10}$ cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3, 4, 5, 6, or 7-membered monocyclic or bicyclic or 7, 8, 9, or 10-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0] bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "substituted aryl" refers to an aryl group substituted by, for example, one to four substituents such as alkyl, substituted alkyl, alkenyl, substituted alkenyl, alkynyl, substituted alkynyl, aryl, substituted aryl, arylalkyl, halo, trifluoromethoxy, trifluoromethyl, hydroxy, alkoxy, alkanoyl, alkanoyloxy, aryloxy, arylalkyloxy, amino, alkylamino, arylamino, arylalkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, halo, alkyl, alkoxy, alkenyl, alkynyl, aryl or arylalkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole.

As used herein, the term "heterocycle", "heterocyclyl", "heterocyclic system" or "heterocyclic group" is intended to mean a stable 5, 6, or 7-membered monocyclic or bicyclic or 7, 8, 9, 10, 11, 12, 13, or 14-membered bicyclic heterocyclic ring which is saturated, partially unsaturated or fully unsaturated, and which consists of carbon atoms and 1, 2, 3 or 4 heteroatoms independently selected from N, O and S; and including any bicyclic group in which any of the above-defined heterocyclic rings is fused to a benzene ring. The nitrogen and sulfur heteroatoms may optionally be oxidized (i.e., N→O and $S(O)_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azocinyl, benzimidazolyl, benzofuranyl, benzothiofuranyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Preferred 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5 to 6 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

In another embodiment, heterocycles include, but are not limited to, pyridyl, pyridinyl, isoxazyl, isoquinolinyl, thienyl, pyrazolyl, furanyl, pyrrolyl, thiazolyl, imidazolyl, pyrazinyl, thiadiazolyl, pyrimidinyl, pyridazinyl, oxazolyl, isothiazolyl, oxadiazolyl, indanonyl, piperazinyl, pyranyl, or pyrrolyl Also included are smaller heterocyclyls, such as, epoxides, oxetanes and aziridines.

The term heterocyclo or heteroaryl includes substituents having a benzo ring or a cycloalkyl ring fused to another ring containing 1 to 4 heteroatoms selected from N, O, or S, including, but not limited to rings which contain —O$(CH_2)_n$—O— attached to adjacent atoms or the same ring atom.

As used herein, the term "aromatic heterocyclic group" or "heteroaryl" is intended to mean a stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, benzodioxane, and the like. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and $S(O)_p$). It is to be noted that total number of S and O atoms in the aromatic heterocycle is not more than 1. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "carbocyclic ring" or "carbocyclyl" refers to stable, saturated, partially saturated or unsaturated, mono or bicyclic hydrocarbon rings that contain 3-12 atoms. Particularly, this includes a monocyclic ring containing 5 or 6 atoms or a bicyclic ring containing 9 or 10 atoms. Suitable values include cyclopropyl, cyclobutyl, cyclopentyl, cyclohexyl, cycloheptyl, dihydroindenyl and tetrahydronaphthyl. The term "optionally substituted" as it refers to "carbocyclic ring" or "carbocyclyl" herein indicates that the carbocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "heteroatoms" shall include oxygen, sulfur and nitrogen.

The compounds of formula I may exist as a free form (with no ionization) or may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include 13C and 14C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Compounds of the formula I may also have prodrug forms. Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 112, pp. 309-396, edited by K. Widder, et al. (Academic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews*, 8, 1-38 (1992).

It should further be understood that solvates (e.g., hydrates) of the compounds of formula I are also with the scope of the present invention. Methods of solvation are generally known in the art.

"Stable compound" and "stable structure" are meant to indicate a compound that is sufficiently robust to survive isolation to a useful degree of purity from a reaction mixture, and formulation into an efficacious therapeutic agent. It is preferred that there presently recited compounds do not contain a N-halo, $S(O)_2H$, or $S(O)H$ group. The present invention is directed to stable compounds. Compounds of the invention are intended to cover compounds which are stable compounds.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination. "Therapeutically effective amount" is also intended to include an amount of the combination of compounds which is effective for the treatment of disease.

The present invention further includes compositions comprising one or more compounds of the present invention and a pharmaceutically acceptable carrier.

A "pharmaceutically acceptable carrier" refers to media generally accepted in the art for the delivery of biologically active agents to animals, in particular, mammals.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th ed., Mack Publishing Company, Easton, Pa., 1985, which is incorporated herein by reference in its entirety.

Utility

The compounds of the invention modulate kinase activity, including the modulation of JAK3. Other types of kinase activity that may be modulated by the compounds of the instant invention include, but are not limited to, other members of the JAK family of enzymes, such as JAK1.

Accordingly, compounds of formula (I) have utility in treating conditions associated with the modulation of kinase activity, and particularly the selective inhibition of JAK3 activity or the inhibition of other JAK family kinases such as JAK1. Such conditions include T-cell mediated diseases in which cytokine levels are modulated as a consequence of intracellular signaling. In another embodiment, compounds of formula (I) have advantageous functional selectivity for JAK3 activity versus other JAK family kinases such as JAK2, preferably from at least 10 fold to over 100 fold more selective.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors of JAK3 and other JAK family kinases such as JAK1, compounds of Formula (I) are useful in treating cytokine-associated conditions including, but not limited to, autoimmune diseases such as Crohn's and ulcerative colitis, asthma, autoimmune diseases such as Graves' disease, rheumatoid arthritis, systemic lupus erythematosis, psoriasis, dry eye, multiple sclerosis, psoriatic arthritis and ankylosing spondylities, plus conditions such as solid organ transplant rejection, islet cell transplant rejection and graft vs. host disease.

In view of their activity as inhibitors of JAK3, compounds of Formula (I) are useful in treating malignancies where JAK3 has undergone mutation or overexpression, or where JAK3 plays an important role in growth or survival of the malignant cells. Such malignancies include acute megakaryoblastic leukemia (AMKL), cutaneous T cell lymphoma (CTCL), anaplastic lymphoma kinase (ALK)-expressing anaplastic large cell lymphoma (ALK(+)ALCL), acute lymphoblastic leukemia (ALL) with JAK3 mutations, and cutaneous T-cell lymphoma (CTCL).

More particularly, the specific conditions or diseases that may be treated with the inventive compounds include, without limitation, asthma, allergies, glomerulonephritis, rheumatoid arthritis, systemic lupus erythematosis, scleroderma, chronic thyroiditis, Graves' disease, autoimmune gastritis, diabetes, autoimmune hemolytic anemia, autoimmune neutropenia, thrombocytopenia, atopic dermatitis, myasthenia gravis, multiple sclerosis, inflammatory bowel disease, ulcerative colitis, Crohn's disease, psoriasis, graft vs. host disease, pancreatic 13-cell disease; rheumatoid spondylitis, allograft rejections, ulcerative colitis, dry eye and pemphigus vulgaris. Preferred methods of treatment are those wherein the condition is selected from allograft rejection, rheumatoid arthritis, psoriasis, ankylosing spondylitis, psoriatic arthritis, multiple sclerosis, lupus and dry eye.

When the terms "JAK3-associated condition" or "JAK3-associated disease or disorder" are used herein, each is intended to encompass all of the conditions identified above as if repeated at length, as well as any other condition that is affected by JAK3 kinase activity.

The present invention thus provides methods for treating such conditions, comprising administering to a subject in need thereof a therapeutically-effective amount of at least one compound of Formula (I) or a salt thereof "Therapeutically effective amount" is intended to include an amount of a compound of the present invention that is effective when administered alone or in combination to inhibit JAK3 and other JAK family kinases and/or treat diseases.

The methods of treating JAK3 kinase-associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit JAK3 and/or treat diseases associated with JAK3.

Exemplary of such other therapeutic agents include abatacept, belatacept, corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; p38 inhibitors such as BMS-582949, steroids such as prednisone or dexamethasone; antiviral agents such as abacavir; antiproliferative agents such as methotrexate, leflunomide, FK506 (tacrolimus, Prograf); cytotoxic drugs such as azathiprine and cyclophosphamide; TNF-α inhibitors such as tenidap, anti-TNF antibodies or soluble TNF receptor, and rapamycin (sirolimus or Rapamune) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating JAK3 kinase-associated conditions, including IL-2, IL-4, IL-6, IL-7, IL-9, IL-15, IL-21, and IFNγ mediated conditions, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th ed., 1985, which is incorporated herein by reference in its entirety.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g.,) GANTREZ®; and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of JAK3 enzyme levels.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to treat the cancer.

By way of general guidance, the daily oral dosage of each active ingredient, when used for the indicated effects, will range between about 0.001 to 1000 mg/kg of body weight, preferably between about 0.001 to 100 mg/kg of body weight per day, and most preferably between about 0.001 to 20 mg/kg/day. Intravenously, the most preferred doses will range from about 0.1 to about 10 mg/kg. Compounds of this invention may be administered in a single daily dose, or the total daily dosage may be administered in divided doses of two, three, or four times daily. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfate, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of JAK3 enzyme levels.

Biological Assays

JAK3 Kinase Assay Protocol (Caliper)

The assay reactions were performed in U-bottom 384-well plates. The final assay volume was 30 µl prepared from 15 µl additions of enzyme and substrates (fluoresceinated peptide and ATP) and test compounds in assay buffer (100 mM HEPES pH 7.4, 10 mM $MgCl_2$, 25 mM beta-glycerol phosphate 0.015% Brij35 and 4 mM DTT). The reaction was initiated by the combination of GST-JAK3 enzyme with substrates and test compounds. The reactions were incubated at room temperature for 3 hours and terminated by adding 60 µl of 35 mM EDTA to each sample. Each reaction mixture was analyzed on the Caliper LabChip 3000 (Caliper, Hopkinton, Mass.) by electrophoretic separation of the fluorescent substrate and phosphorylated product. Inhibition data were calculated by comparison with no enzyme control reactions for 100% inhibition, and vehicle-only treated reactions for 0% inhibition. The final concentration of reagents in the assay was: ATP, 8 µM; fluoresceinated peptide, 1.5 µM; GST-JAK3, 4.5 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations. $IC_{50}$ values were derived by non-linear regression analysis.

JAK3 Kinase Assay Protocol (Filter)

Kinase reactions consisted of 5 ng of JAK3 enzyme, 30 uM CSKtide substrate, 0.2 µCi $^{33}$P γ-ATP, 8 µM ATP in 30 µl kinase buffer (50 mM Hepes, pH 8.0, 10 mM $MgCl_2$, 1 mM EGTA, 2 mM DTT). Reactions were incubated for 30 minutes at room temperature and stopped by the addition of cold trichloroacetic acid (TCA) to a final concentration of 15%. TCA precipitates were collected onto 384 well phosphocellulose filters (Millipore) using a Platemate to transfer the reaction mixture, washed on an EMBLA plate washer and the filters were quantitated using a TopCount 384-well liquid scintillation counter. Dose response curves were generated to determine the concentration required inhibiting 50% of kinase activity ($IC_{50}$). Compounds were dissolved at 10 mM in dimethylsulfoxide (DMSO) and evaluated at six concentrations, each in triplicate. The final concentration of DMSO in the assay equaled 2%. $IC_{50}$ values were derived by non-linear regression analysis.

JAK2 Kinase Assay Protocol

The assay reactions were performed in U-bottom 384-well plates. The final assay volume was 30 µl prepared from 15 µl additions of enzyme and substrates (fluoresceinated peptide and ATP) and test compounds in assay buffer (100 mM HEPES pH 7.4, 10 mM $MgCl_2$, 25 mM beta-glycerol phosphate, 0.015% Brij35 and 4 mM DTT). The reaction was initiated by the combination of GST-JAK2 enzyme with substrates and test compounds. The reactions were incubated at room temperature for 3 hours and terminated by adding 60 µl of 35 mM EDTA to each sample. Each reaction mixture was analyzed on the Caliper LabChip 3000 (Caliper, Hopkinton, Mass.) by electrophoretic separation of the fluorescent substrate and phosphorylated product. Inhibition data were calculated by comparison with no enzyme control reactions for 100% inhibition, and vehicle-only treated reactions for 0% inhibition. The final concentration of reagents in the assay was: ATP, 30 µM; fluoresceinated peptide, 1.5 µM; GST-JAK2, 1.5 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations. $IC_{50}$ values were derived by non-linear regression analysis.

JAK1 Kinase Assay Protocol

The assay reactions were performed in U-bottom 384-well plates. The final assay volume was 30 µl prepared from 15 µl additions of enzyme and substrates (fluoresceinated peptide and ATP) and test compounds in assay buffer (20 mM HEPES pH 7.4, 10 mM $MgCl_2$, 25 mM beta-glycerol phosphate, 0.015% Brij35 and 4 mM DTT). The reaction was initiated by the combination of GST-JAK1 enzyme with substrates and test compounds. The reactions were incubated at room temperature for 3 hours and terminated by adding 60 µl of 35 mM EDTA to each sample. Each reaction mixture was analyzed on the Caliper LabChip 3000 (Caliper, Hopkinton, Mass.) by electrophoretic separation of the fluorescent substrate and phosphorylated product. Inhibition data were calculated by comparison with no enzyme control reactions for 100% inhibition, and vehicle-only treated reactions for 0% inhibition. The final concentration of reagents in the assays was: ATP, 100 µM; fluoresceinated peptide, 1.5 µM; GST-JAK1, 12.5 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations. $IC_{50}$ values were derived by non-linear regression analysis.

TYK2 Kinase Assay Protocol

The assay reactions were performed in U-bottom 384-well plates. The final assay volume was 30 µl prepared from 15 µl additions of enzyme and substrates (fluoresceinated peptide and ATP) and test compounds in assay buffer (20 mM HEPES pH 7.4, 10 mM $MgCl_2$, 25 mM beta-glycerol phosphate, 0.015% Brij35 and 4 mM DTT).

The reaction was initiated by the combination of HIS-TYK2 enzyme with substrates and test compounds. The reactions were incubated at room temperature for 3 hours and terminated by adding 60 µl of 35 mM EDTA to each sample. Each reaction mixture was analyzed on the Caliper LabChip 3000 (Caliper, Hopkinton, Mass.) by electrophoretic separation of the fluorescent substrate and phosphorylated product. Inhibition data were calculated by comparison with no enzyme control reactions for 100% inhibition, and vehicle-only treated reactions for 0% inhibition. The final concentration of reagents in the assay was: ATP, 70 µM; fluoresceinated peptide, 1.5 µM; HIS-TYK2, 2.25 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations. $IC_{50}$ values were derived by non-linear regression analysis.

IL-2 Dependent T Cell Proliferation Assay Protocol

IL-2 Expanded PHA Blasts (Activated T cells) were prepared from peripheral blood mononuclear cells (PBMC). PBMCs were prepared from human whole blood. 15 ml blood was mixed with 15 ml RPMI (Gibco#61870) in a 50 ml centrifuge tube and under laid with 12 ml lymphocyte separation media (LSM) (MC Biomedicals #1492254). Tubes were centrifuged at 1800 rpm for 25 minutes and allowed to stop without braking. Red blood cells pelleted under the separation media and the PBMCs were trapped at the interface between the LSM and the serum/RPMI layers. The serum/RPMI mix was pipetted from above the PBMC layer and discarded. The PBMCs from 2 tubes were collected in a pipette along with some of the LSM layer and combined into a single tube. Each tube was brought to 50 ml and centrifuged at 1400 rpm for 10 minutes. Cell pellets were resuspended in RPMI, combined into 1 tube and centrifuged for 5 minutes at 1200 rpm. Cells were resuspended in cell culture media (RPMI w/10% fetal bovine serum (Summit Biotechnology #

RS-50-05), 100 U/ml penicillin and 100 μg/ml streptomycin (Gibco #14140-122)) with 5 μg/ml PHA (Sigma #L1668) at $2\times10^6$ cells/ml and incubated for 3 days at 37° C. in 5% $CO_2$. Cells were washed 3× and resuspended at $5\times10^5$ cells/ml and 25 units/ml IL-2 (BD Bioscience #356043) was added. After 4 days incubation at 37° C. in 5% $CO_2$ the cells were washed 3× and resuspended at $2\times10^6$ cells/ml and rested 2 hours at 37° C. in 5% $CO_2$ before use.

Compounds were diluted in DMSO (in triplicate) to 800× final high concentration in the assay and 3-fold serial dilutions were performed to give six concentrations. Each concentration was diluted 1:20 in media to give the intermediate concentration. DMSO was diluted 1:20 in media for use in wells without compound.

45 μl media plus 5 μl of the intermediate dilution of compound or DMSO was added to each test well in the assay plate. 100 μl of cells at $3\times10^5$ cells/ml were added to each well. Plates were Incubated 60 minutes at 37° C. in 5% CO2 and 50 μl of IL-2 at 200 units/ml to each well. Negative control wells received 100 μl media. The plates were incubated 3 days at 37° C. in 5% CO2. 0.5 μC $^3$H-Thymidine in 20 μl media was added to each well and the plates incubated 6 hours at 37° C. in 5% CO2. The plates were harvested onto a Unifilter-96 GF/C Filter Plate (Perkin Elmer 6005174) using a Packard Filtermate Harvester. The bottom of each dried filter plate was sealed, 50 μl Microscint 20 (Perkin Elmer #6013621) added to each well and the top of the plate sealed. Proliferation as measured by $^3$H-Thymidine incorporation was determined by counting on a Packard TopCount-NXT.

IL-2 Induced STAT3 Phosphorylation in PHA Blasts Assay

IL-2 Expanded PHA Blasts were prepared (see IL-2 Dependent T Cell Proliferation Assay Protocol for preparation of IL-2 expanded PHA blasts). Compounds were diluted in DMSO (in duplicate) to 333.3× final high concentration in the assay and 3-fold serial dilutions were performed to give six concentrations. Each concentration was diluted 1:20 in media to give the intermediate concentration. DMSO was diluted 1:20 in RPMI media (Gibco#61870) for use in wells without compound.

173 μl/well of a PHA blast cell suspension at $5.78\times10^6$ cells/ml was added to a round bottom tissue culture plate (Falcon #353077) followed by 12 μl of the Intermediate compound dilution or DMSO for wells without compound. The plate was incubated at 37° C. in 5% $CO_2$ for 30 minutes. 15 μl of 266.7 ng/ml IL-2 (R&D #202-IL-050) in media was added to each well or media only to negative control wells. The plates were mixed on an orbital shaker for 1 minute and incubated at 37° C. in 5% $CO_2$ for a total 10 minutes. Plates were centrifuged 4 minutes at 1500 rpm and 150 μl of culture supernatant was removed from each well leaving the pellet intact. Plates were mixed on an orbital shaker for 1 minute and 50 μl of 2× lysis buffer was added (20 mM Tris, pH7.5, 0.2 M NaCl, 2 mM EDTA, 2 mM EGTA, 2 mM NaF, 2 mM β-Glycerophosphate, 40 mM Sodium Pyrophosphate, 4 mM $Na_3VO_4$ (add at time of use), 2% Triton X-100 (Sigma T9284), 20% Glycerol (EM Science GX0185-6), 0.2% SDS (Bio-Rad #161-0416), 1.0% Deoxycholate (Sigma D5670), 2× Protease Inhibitor Cocktail (Sigma P2714, dissolved in 10 ml PBS to give 10× concentration, add at time of use)). The plates were incubated on ice for 1 hour and the lysate in each well was mixed by pipetting up and down 5-6 times. STAT3 phosphorylation levels were determined by ELISA (PathScan Phospho-STAT3 ELISA Antibody Pair, Cell Signaling #7146).

ELISA plates were coated with 100 μl/well of a 1:100 dilution of Capture antibody in PBS and incubated at least overnight at 4° C. On day of use plates were washed 3× with wash buffer (PBS (Gibco #14190)+0.05% Tween 20). Plates were blocked with 200 μl/well of Assay Buffer 1 (AB1) (PBS+1% BSA+0.1% Tween 20(Bio-Rad #161-0416)) for 2 hours at room temperature. Plates were washed 3× and 90 μl/well AB1 buffer added. 10 μl/well of assay sample or standards were added followed by 100 μl/well of a 1:100 dilution of Detection Antibody in AB1 Buffer. Plates were incubated overnight at 4° C. and then washed 6×. 100 μl/well of a 1:1000 dilution of anti-mouse IgG HRP-Linked Antibody in AB 1 Buffer was added to each well and plates were incubated 1 hour at room temperature. Plates were washed 6×. 100 μl of a 1:1 mix of TMB Peroxidase Substrate (KPL #50-76-01) and Peroxidase Substrate Solution (KPL #50-65-00) was added and the plates were incubated in the dark at room temperature for 10-30 min. The reaction was stopped with 100 μl/well of 1N $H_2SO_4$ and the plates were read at 450 nm with correction at 650 nm within 30 min.

pSTAT3 Standards were prepared from IL-6 stimulated TF-1 cells. TF-1 cells were washed 3× and resuspended at $1\times10^6$ cells/ml and rested overnight without GM-CSF at 37° C. in 5% $CO_2$. The cells were washed 1× and resuspended at $5\times10^6$ cells/ml. IL-6 was added to 20 ng/ml and cells incubated at 37° C. in 5% $CO_2$ for 15 minutes, spun 4 minutes at 1500 rpm and the supernatant removed. 150 μl lysis buffer was added for every $5\times10^6$ cells and incubated on ice for 60 minutes. Using a syringe fitted with a 21 gauge needle, lysates were passed 6 times through the needle. The lysates were transferred to microfuge tubes and centrifuged at 14K rpm for 10 minutes and the supernatants were combined and aliquots frozen on dry ice and stored at −80° C. The lysate was assigned a value of 100 units/ml of pSTAT3 and used as a standard in the pSTAT3 ELISA assay. Standards were diluted in a 1:2 dilution series using a 1:1 mix of 2× lysis buffer and Media.

EPO Induced STAT5A Phosphorylation in TF-1 Cells

TF-1 Cells were carried in cell culture media (RPMI w/10% fetal bovine serum (Summit Biotechnology # RS-50-05), 100 U/ml penicillin and 100 μg/ml streptomycin (Gibco #14140-122))+2 ng/ml GM-CSF (R&D #215GM). On the day before use the cells were washed 3×, resuspended at $1\times10^6$ cells/ml in media without GM-CSF and rested overnight at 37° C. in 5% $CO_2$. The cells were washed 1× and resuspended in media at $2.78\times10^6$ cells/ml. Compounds were prepared as in the IL-2 Induced STAT3 phosphorylation in PHA blasts assay.

173 μl/well of a TF-1 cell suspension at $2.78\times10^6$ cells/ml was added to each well of a round bottom tissue culture plate (Falcon #353077) followed by 12 μl of the Intermediate compound dilution or DMSO for wells without compound. The plate was incubated at 37° C. in 5% $CO_2$ for 30 minutes. 15 μl of 13.33 units/ml recombinant human EPO (R&D #287-TC) in media was added to each well or media only to negative control wells. The plates were mixed on an orbital shaker for 1 minute and incubated at 37° C. in 5% $CO_2$ for a total 10 minutes. Plates were centrifuged 4 minutes at 1500 rpm and 150 μl of culture supernatant was removed from each well leaving the pellet intact. Plates were mixed on an orbital shaker for 1 minute and 50 μl of 2× lysis buffer was added (20 mM Tris, pH7.5, 0.2 M NaCl, 2 mM EDTA, 2 mM EGTA, 2 mM NaF, 2 mM β-Glycerophosphate, 40 mM Sodium Pyrophosphate, 4 mM $Na_3VO_4$ (add at time of use), 2% Triton X-100 (Sigma T9284), 20% Glycerol (EM Science GX0185-6), 0.2% SDS (Bio-Rad #161-0416), 1.0% Deoxycholate (Sigma D5670), 2× Protease Inhibitor Cocktail (Sigma P2714, dissolved in 10 ml PBS to give 10× concentration, add at time of use)). The plates were incubated on ice for 1 hour and the lysate in each well was mixed by pipetting up and down 5-6 times. STAT5A phosphorylation levels were determined by ELISA.

ELISA plates (NUNC #439454) were coated with 100 μl/well of a 1:500 dilution of Capture antibody (Invitrogen #13-3600) in carbonate/bicarbonate buffer (Sigma # C3041) and incubated at least overnight at 4° C. On day of use plates were washed 3× with wash buffer (PBS (Gibco #14190)+ 0.05% Tween 20 (Bio-Rad #170-6531)). Plates were blocked with 200 μl/well of Assay Buffer 2 (AB2) (PBS+2% BSA (Sigma # A-9576)+0.1% Tween 20 (Bio-Rad #161-0416)) for 2 hours at room temperature. Plates were washed 3× and 90 μl/well AB2 buffer added. 10 μl/well of assay sample or standards were added followed by 100 μl/well of a 1:4000 dilution of Detection Antibody (Genway #18-785-210434) in AB2 Buffer. Plates were incubated overnight at 4° C. and then washed 6×. 100 μl/well of a 1:3000 dilution of HRP-Goat anti-rabbit IgG (Invitrogen #65-6120 in AB2 Buffer was added to each well and plates were incubated 1 hour at room temperature. Plates were washed 6×. 100 μl of a 1:1 mix of TMB Peroxidase Substrate (KPL #50-76-01) and Peroxidase Substrate Solution (KPL #50-65-00) was added and the plates were incubated in the dark at room temperature for 10-30 minutes. The reaction was stopped with 100 μl/well of 1N $H_2SO_4$ and the plates were read at 450 nm with correction at 650 nm within 30 min. pSTAT5A Standards were prepared from GM-CSF stimulated TF-1 cells. TF-1 cells were washed 3× and resuspended at $1\times10^6$ cells/ml and rested overnight without GM-CSF at 37° C. in 5% $CO_2$. The cells were washed 1× and resuspended at $5\times10^6$ cells/ml. GM-CSF was added to 50 ng/ml and cells incubated at 37° C. in 5% $CO_2$ for 15 minutes, spun 4 minutes at 1500 rpm and the supernatant removed. 150 μl lysis buffer was added for every $5\times10^6$ cells and incubated on ice for 60 minutes. Using a syringe fitted with a 21 gauge needle, lysates were passed 6 times through the needle. The lysates were transferred to microfuge tubes and centrifuged at 14K rpm for 10 minutes and the supernatants were combined and aliquots frozen on dry ice and stored at −80° C. The lysate was assigned a value of 100 units/ml of pSTAT5A and used as a standard in the pSTAT5A ELISA assay. Standards were diluted in a 1:2 dilution series using a 1:1 mix of 2× lysis buffer and Media.

IFNα Induced STAT3 Phosphorylation in PHA Blasts

IFNα induced STAT3 phosphorylation in PHA blasts was performed exactly as the IL-2 Induced STAT3 phosphorylation in PHA blasts assay except the cells were stimulated with 15 μl/well of 13,333 units/ml IFNα2a (R&D #11105-1) in media.

Myosin Light Chain Phosphorylation (pMLC) Assay

Mouse aortic smooth muscle A7r5 cells are cultured in complete DMEM Media (Gibco Cat. #11995) substituted with 10% FBS (Gibco Cat. # SH30071) and 1% Penicillin/Streptomycin (Gibco Cat. #15140). $1.5\times10^3$ cells are plated in 384-well tissue culture plates (Becton Dickinson Cat. #3962) and incubated overnight at 37° C. and 5% $CO_2$. Cells are then incubated with test compounds (serially diluted 3-fold with final concentrations ranging from 20 μM to 340 μM) for 60 minutes at 37° C. and 5% $CO_2$. Cell culture media is removed and cells are fixed with 4% paraformaldehyde (JT Baker Cat. #2106) for 60 min at room temperature. After removal of the fixing reagent, 1× permeabilization buffer (Thermo Cat. #1860291) is added for 10 min incubation at room temperature. Permeabilization buffer is removed and 1× blocking solution (Thermo Cat. #1860291) is added for 60 min incubation at room temperature. Blocking solution is removed and cells are incubated overnight at 4° C. with primary anti-pMLC antibody (Cell Signaling Cat. #3674) diluted in 1× blocking buffer for a final concentration of 70 ng/ml. Primary antibody is removed followed by 3 washes with 1×PBS (Gibco Cat. #14190). Cells are incubated for 60 min at room temperature with secondary AlexaFluor 488 Goat-anti rabbit IgG (H+L) antibody (Invitrogen Molecular Probes Cat. # A11008) at a final concentration of 5 ug/ml in 1× blocking buffer mixed with Hoechst nuclear stain (Invitrogen Molecular Probes Cat. # H3570) at 5 ug/ml final concentration. Cells are then washed 3 times with 1×PBS to remove reagents. The plates containing 30 ul 1×PBS per well are then scanned on the Cellomics ArrayScan imager using the Cell Health Profiling BioApplication. The Mean Ring Spot Average Intensity of the FITC channel is used as the final readout to calculate $IC_{50}$ values. 0% inhibition is determined with 0.2% DMSO and 100% inhibition is determined with 1 mM of the Rho Kinase inhibitor H-1152P (Calbiochem Cat. #555550).

The Examples herein have been tested and have been found to have activity of less than or equal to 1 uM in at least one of the JAK3 assays described above. The compounds listed in Table 1 have been tested in the above assays with the results The Examples herein have been tested and have been found to have activity of less than or equal to 1 uM in at least one of the JAK3 assays described above. The compounds listed in Table 1 have been tested in the above assays with the results indicated.

TABLE 1

| Example# | LLE_JAK3_FB (IC50, uM) | LLE_JAK1 (IC50, uM) |
|---|---|---|
| 28 | 0.0076 | 0.0216 |
| 29 | 0.07 | 0.12 |
| 30 | 0.11 | 0.19 |
| 31 | 0.07 | 0.12 |
| 32 | 0.1484 | 0.8134 |
| 33 | 0.04 | 0.11 |
| 34 | 0.04 | 0.08 |
| 35 | 0.04 | 0.04 |
| 40 | 0.0151 | 0.0403 |
| 46 | 0.0209 | 0.0580 |
| 48 | 0.0571 | 0.0534 |
| 51 | 0.2846 | 0.9033 |
| 52 | 0.0022 | 0.0017 |
| 53 | 0.0014 | 0.0016 |
| 54 | 0.1334 | 0.1101 |
| 55 | 0.0009 | 0.0044 |
| 56 | 0.0033 | 0.0080 |
| 59 | 0.0006 | 0.0002 |
| 60 | 0.0018 | 0.0008 |
| 61 | 0.0004 | 0.0003 |
| 62 | 0.0010 | 0.0036 |
| 63 | 0.0007 | 0.0004 |
| 67 | 0.0004 | 0.0013 |
| 69 | 0.0015 | 0.0012 |
| 70 | 0.0004 | 0.0003 |
| 83 | 0.0015 | 0.0014 |
| 93 | 0.0004 | |
| 97 | 0.0014 | 0.0031 |
| 105 | 0.0002 | 0.0007 |
| 107 | 0.0114 | 0.0210 |
| 122 | 0.0014 | 0.0024 |
| 126 | 0.0015 | 0.0010 |
| 127 | 0.0056 | 0.0076 |
| 131 | 0.0071 | 0.0036 |
| 134 | 0.0070 | 0.0045 |
| 137 | 0.0014 | 0.0020 |
| 151 | 0.0067 | 0.0075 |
| 152 | 0.0078 | 0.0090 |
| 173 | 0.0004 | 0.0008 |
| 175 | 0.0015 | 0.0019 |
| 182 | 0.0003 | 0.0008 |
| 183 | 0.0002 | 0.0008 |
| 184 | 0.0004 | 0.0002 |

TABLE 1-continued

| Example# | LLE_JAK3_FB (IC50, uM) | LLE_JAK1 (IC50, uM) |
|---|---|---|
| 185 | 0.0006 | 0.0003 |
| 188 | 0.0005 | 0.0004 |
| 194 | 0.0014 | 0.0015 |
| 201 | 0.0014 | 0.0005 |
| 213 | 0.0075 | 0.0047 |
| 220 | 0.0015 | 0.0011 |
| 221 | 0.0014 | 0.0010 |
| 239 | 0.0005 | 0.0005 |
| 252 | 0.0086 | 0.0043 |
| 257 | 0.0003 | 0.0012 |
| 275 | 0.0097 | 0.0062 |
| 280 | 0.0089 | 0.0009 |
| 281 | 0.0118 | 0.0018 |
| 292 | 0.0005 | 0.0007 |
| 303 | 0.0015 | 0.0005 |
| 305 | 0.0015 | 0.0011 |
| 308 | 0.0066 | 0.0015 |
| 315 | 0.0089 | 0.0080 |

METHODS OF PREPARATION

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Examples of compounds of the present invention prepared by methods described in the general schemes are given in the preparations and examples and intermediates section set out hereinafter. Example compounds are typically prepared as racemic mixtures. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

Abbreviations

Ac acetyl
ACN acetonitrile
AcOH or HOAc acetic acid
aq. aqueous
anhyd. anhydrous
ATP adenosine triphosphate
Bn benzyl
Bu butyl
Boc tert-butoxycarbonyl
BOP Benzotriazole-1-yl-oxy-tris-(dimethylamino)-phosphonium hexafluorophosphate
CDI carbonyldiimidazole
° C. degrees Centigrade
Cbz carbobenzyloxy
Conc. concentration
d days
DAST (diethylamino)sulfur trifluoride
DBU 1,8-Diazabicyclo[5.4.0]undec-7-ene
DCE 1,2-dichloroethane
DCM dichloromethane
DEA diethylamine
DIEA or DIPEA diisopropylethylamine
DMAP dimethylaminopyridine
DMA N,N-dimethylacetamide
DME 1,2-dimethoxyethane
DMF dimethylformamide
DMSO dimethylsulfoxide
DPPA diphenylphosphorylazide
dppf 1,1'-Bis(diphenylphosphino)ferrocene
DTT dithiothreitol
EDC or EDCI or EDAC 1-(3-Dimethylaminopropyl)-3-ethylcarbodiimide hydrochloride
EDTA ethylenediaminetetraacetic acid
EGTA ethylene glycol tetraacetic acid
% ee percent enantiomeric excess
(+/−) or (±) racemic
eq. or Eq. or equiv. equivalents
EtOAc or EA Ethyl acetate
Et Ethyl
EtOH Ethanol
Ex example
GST glutathione S-transferase
H Hydrogen
HATU N,N,N,N-tetramethyl-O-(7-azabenzotriazol-1-yl) uronium hexafluorophosphate
Hex hexanes
HIS histidine
h or hr Hours
i iso
IPA isopropanol
Hz hertz
MHz megahertz
HPLC High pressure liquid chromatography
RP-HPLC Reverse-phase High pressure liquid chromatography
HOBT 1-Hydroxybenzotriazole hydrate
Lawesson's Reagent [2,4-bis(4-methoxyphenyl)-1,3-dithia-2,4-diphosphetane-2-4-disufide
LC liquid chromatography
LCMS or LC/MS liquid chromatograph mass spectrometry
LDA lithium diisopropylamide
m-CPBA or MCPBA meta-chloroperbenzoic acid
Me methyl
MeOH methanol
min. minutes
$M^+$ $(M+H)^+$
$M^{+1}$ $(M+H)^+$
MS mass spectrometry
MSA methanesulfonic acid
MTBE methyl tert-butyl ether
m/z mass to charge ratio
N Normal
NMP N-methylpyrrolidinone
NMR nuclear magnetic resonance
PBMC peripheral blood mononuclear cells
PhCONCS benzyolyisothiocyanate
Pd/C palladium on carbon
Ph phenyl
Pr propyl
PHA phytohemagglutinin
ppm parts per million
PSI or psi pounds per square inch quant. quantitative
Ret Time or Rt retention time
rt or RT room temperature
sat. or sat'd. saturated
sec seconds
SFC super critical fluid
S-Tol-BINAP (S)-(−)-2,2'-Bis(di-p-tolylphosphino)-1,1'-binapthyl
SM or sm starting material
t tert
TEA triethylamine
TFA trifluoroacetic acid
THF tetrahydrofuran
TLC thin layer chromatography
TMS-I or TMSI iodotrimethylsilane
p-TSA para-toluenesulfonic acid
Xantphos® (9,9-dimethyl-9H-xanthene-4,5-diyl)bis[diphenylphosphine]
t triplet
m multiplet
s singlet
d doublet
br. s. broad singlet
dd doublet of doublets
tt triplet of triplets
ddd doublet of doublet of doublets
q quartet
quin. Quintet
W/V or w/v weight to volume
X-Phos dicyclohexyl(2',4',6'-triisopropylbiphenyl-2-yl)phosphine The compounds of formula I may be prepared by the processes described herein in the following reaction schemes. Examples of suitable reagents and procedures for conducting these reactions appear hereinafter and in the working examples included therein. Protection and deprotection in the schemes herein may be carried out by procedures generally known in the art (See, for example, T. W. Greene & P. G. M. Wuts, *Protecting Groups in Organic Synthesis*, 3$^{rd}$ Edition, Wiley, (1999)).

Compounds of the formula I can be prepared from pyrroles of the formula II as depicted in Scheme A. Pyrroles of formula II may be obtained by processes known in the art. Reacting a pyrrole of formula II wherein $R^2$ is as previously defined with an aminating reagent, such as chloramine, in the presence of a base, such as sodium hydride, in a solvent, such as DMF, affords the aminated pyrrole of formula III. Compounds of formula III can be reacted with a malonate, such as diethyl-2-(ethoxymethylene)malonate, to afford a compound of formula IV. Compounds of formula III can be thermolyzed in a high boiling solvent, such as Dowtherm, to afford cyclized products of the formula V. Reaction of compounds of formula V with a chlorinating agent, such as phosphorus oxychloride, followed by quenching the obtained intermediate with a nucleophilic alcohol, such as ethanol, affords chloride products of the formula VIa as the major product. Alternatively, quenching the obtained intermediate with a nucleophilic amine of the formula $R^3NH_2$, such as ammonia ($R^3$=H), at ambient temperatures affords products of the formula VII as the major product. Alternatively, compounds of the formula VIa can be reacted with hydrolysing agents, such as lithium hydroxide, to afford products of the formula VIb where $R^{3'}$=H, followed by reaction with a chlorinating agent, such as oxalyl chloride, and quenching the obtained intermediate with a nucleophilic amine of the formula $R^3NH_2$ to afford compounds of the formula VII. Compounds of the formula VII can then be coupled to amines of the formula $R^1NH_2$ in the presence of a suitable base in a suitable solvent to afford compounds of the formula I. Examples of suitable bases for the coupling include NaH, Et$_3$N, DIPEA, K$_2$CO$_3$ or Na$_2$CO$_3$ and suitable solvents include THF, CH$_3$CN, DMF, NMP, DMA, CH$_2$Cl$_2$. Most preferable base is DIPEA and more preferable solvents include DMF, NMP, and DMA.

SCHEME A

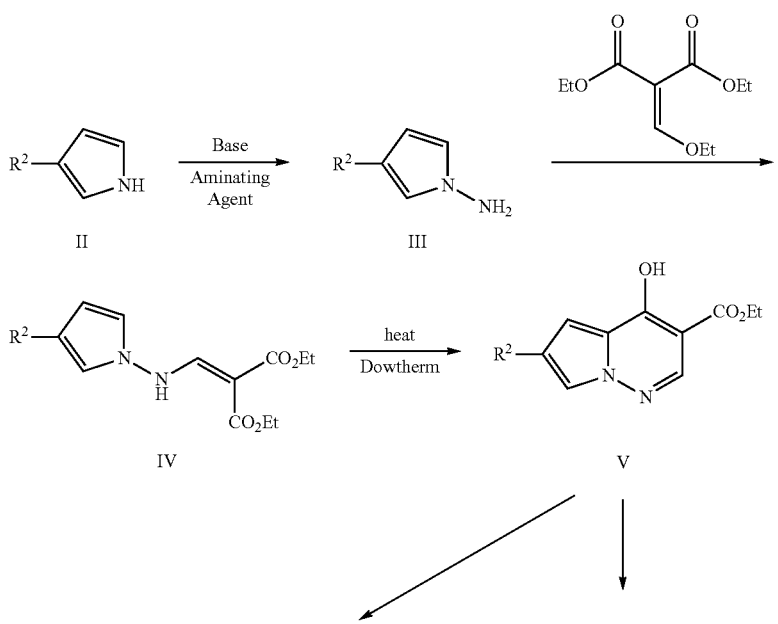

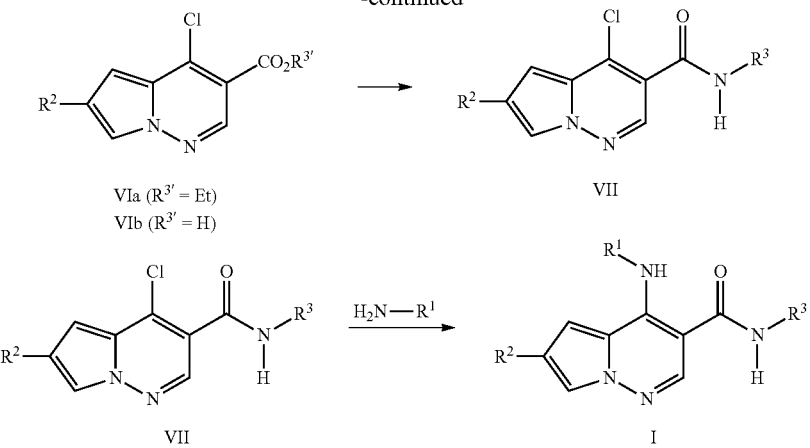

VIa (R³' = Et)
VIb (R³' = H)

VII

I

Scheme B depicts an alternative route to the synthesis of compounds of the formula I starting from pyrroles of the formula VIII. Pyrroles of formula VIII wherein $R^2$ is as previously defined, but most commonly is bromo, ethyl carboxylate, substituted or unsubstituted aryl or heteroaryl, may be obtained by processes known in the art. Reaction of pyrroles of the formula VIII with an aminating reagent, such as chloramine, in the presence of a suitable base, such as NaH, in a solvent, such as DMF, affords compounds of the formula IX. Compounds of the formula IX can be condensed with an acetal of the formula $(R'O)_2CHCH_2CN$ in the presence of an acid catalyst, such as p-TSA, in a solvent, such as toluene, to afford compounds of the formula X followed by base induced cyclization employing a base such as DBU, in a solvent such as toluene to afford compounds of the formula XI. Reaction of compounds of the formula XI with a chlorinating agent, such as $POCl_3$, affords compounds of the formula XII. Hydrolysis of the compounds of the formula XII using an aqueous acid, such as sulfuric acid, affords compounds of the formula XIII which can be coupled with amines of the formula $R^1NH_2$ as previously described in Scheme A to afford compounds of the formula I.

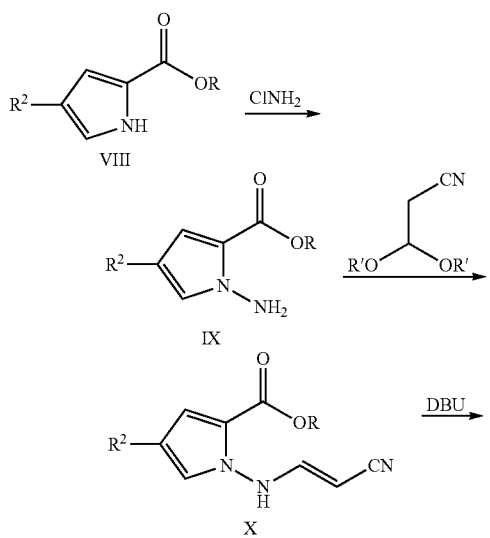

SCHEME B

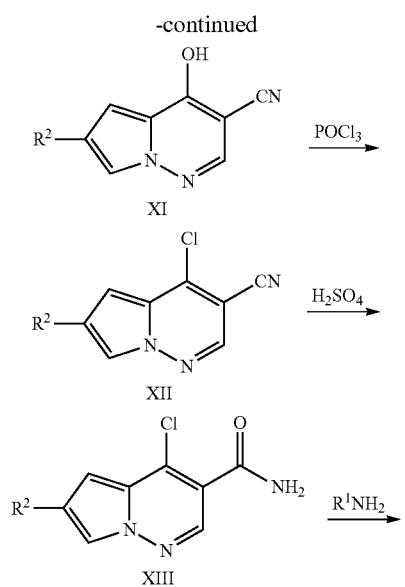

Scheme C depicts an alternative method for cyclization to afford compounds of the formula I. N-aminated pyrroles of the formula IX wherein $R^2$ is as previously defined, but most commonly is bromo, substituted or unsubstituted aryl or heteroaryl, may be obtained by the methods previously described. Reaction of the compounds of the formula IX with ethyl-3-ethoxy acrylate in the presence of an acid catalyst, such as p-TSA, in a suitable solvent, such as ethanol, affords compounds of the formula XIV. Compounds of the formula XIV can be cyclized in the presence of a suitable base, such as DBU, in a suitable solvent, such as EtOH, to afford compounds of the formula VIa. Compounds of the formula VIa can then be converted into compounds of the formula I as previously described in Scheme A.

SCHEME C

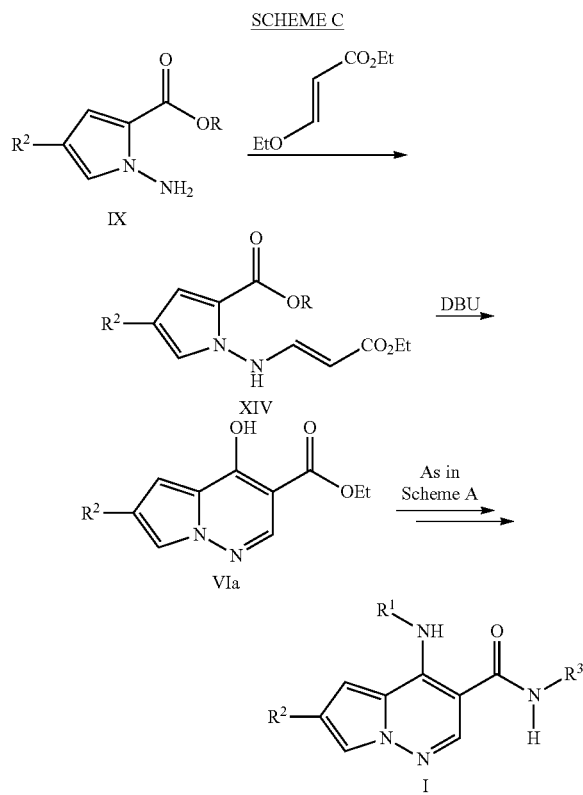

Scheme D depicts the synthetic route to compounds of the formula XVII, which are compounds of the formula I wherein $R^2$ is 1,2,4-oxadiazol-5-yl optionally substituted with $R^{2b}$. Compounds of the formula XV, which belong to compounds of the formula I wherein $R^2$ is —$CO_2R^{2b}$, can be hydrolyzed in the presence of hydroxide, such as sodium hydroxide, in a suitable solvent, such as methanol, to afford compounds of the formula XVI. Compounds of the formula XVI can then be coupled with N-hydroxy amidooximes of the formula $R^{2b}$—C($NH_2$)=NOH in the presence of suitable coupling reagents, such as EDCI and HOBt, in a suitable solvent, such as DMF, then cyclized by heating to afford products of the formula XVII, which are compounds of the formula I wherein $R^2$ is 1,2,4-oxadiazol-5-yl optionally substituted with $R^{2b}$.

SCHEME D

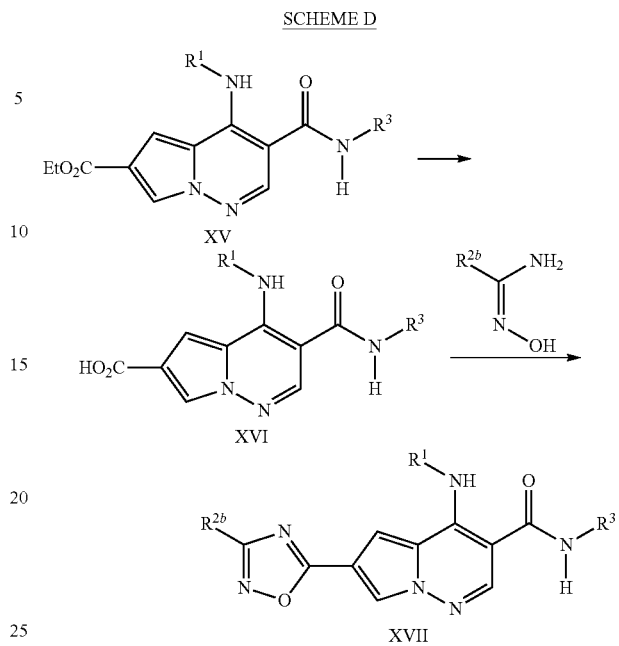

As depicted in Scheme E, compounds of the formula XVIII, which are compounds of the formula I wherein $R^2$ is bromo and prepared as previously described in Scheme B, can be reacted with boronic acids of the formula $R_2B(OH)_2$ or boronate esters of the formula $R_2B(OR)_2$ under Suzuki-Miyaura coupling conditions which are readily known to those skilled in the art, to afford compounds of the formula XIX, which are compounds of the formula I wherein $R^2$ is substituted or unsubstituted aryl or heteroaryl. Alternatively, compounds of the formula XIX can be prepared by reacting compounds of the formula XVIII with diboranes of the general formula $(RO)_2B$—$B(OR)_2$ under palladium catalyzed conditions readily known to those skilled in the art to afford compounds of the formula XX. Compounds of the formula XX can then be coupled to reagents of the type $R^2$—X, where X is most commonly chloro, bromo, or trifluoromethanesulfonate to afford compounds of the formula XIX, which are compounds of the formula I wherein $R^2$ is substituted or unsubstituted aryl or heteroaryl.

SCHEME E

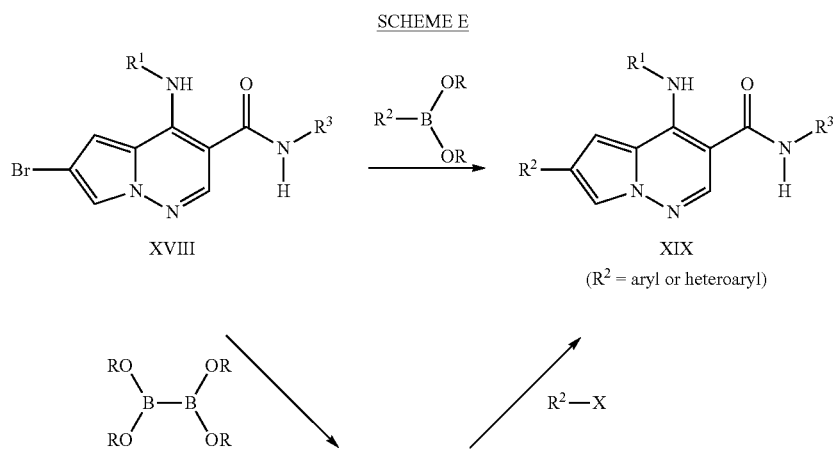

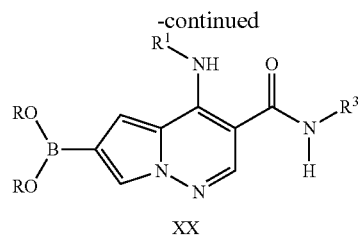

XX

As depicted in Scheme F, compounds of the formula XVIII, which are compounds of the formula I wherein $R^2$ is bromo and prepared as previously described in Scheme B, can be reacted with amides or lactams of the formula $(R^{2b})C(O)NHR^b$ in the presence of a copper catalyst, such as copper iodide, in the presence of a suitable ligand, such as N1,N2-dimethylethane-1,2-diamine, in the presence of a suitable base, such as $K_2CO_3$, in a suitable solvent, such as dioxane, to afford products of the formula XXI, which are compounds of the formula I wherein $R^2$ is —$N(R^b)C(O)R^{2b}$. Under similar reaction conditions, compounds of the formula XVIII can be coupled with carbamates of the formula $(R^{2b}O)C(O)NHR^b$ to afford compounds of the formula XXII, which are compounds of the formula I wherein $R^2$ is —$N(R^b)C(O)OR^{2b}$. Similarly, compounds of the formula XVIII can be coupled with ureas of the formula $(R^{11})_2NC(O)NHR^b$ to afford compounds fo the formula XXIII, which are compounds of the formula I wherein $R^2$ is —$N(R^b)C(O)N(R^{11})_2$

SCHEME F

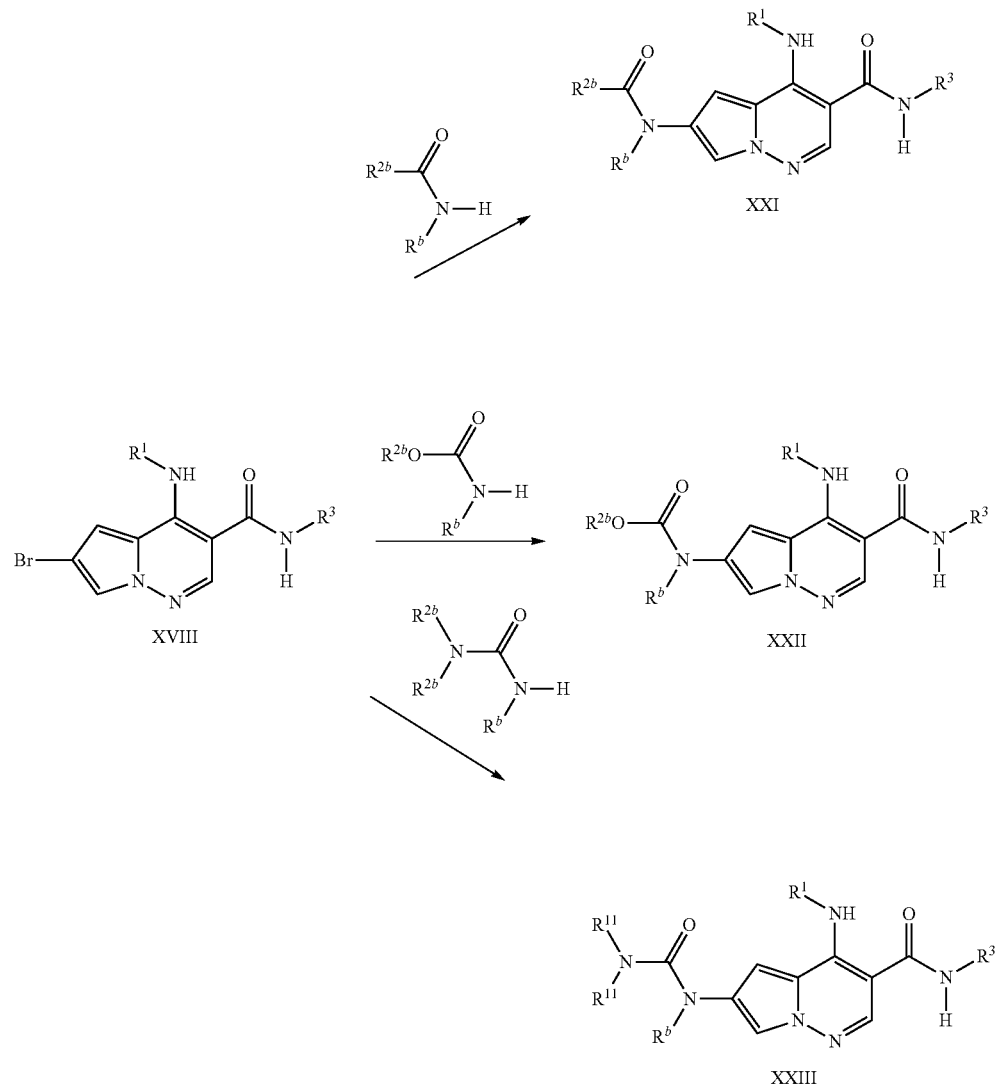

As depicted in Scheme G, compounds of the formula XVIII, which are compounds of the formula I wherein $R^2$ is bromo and prepared as previously described in Scheme B, can be reacted with sulfonamides or sultams of the formula $(R^{2b})S(O)_2NHR^b$ in the presence of a copper catalyst, such as copper iodide, in the presence of a suitable ligand, such as N1,N2-dimethylethane-1,2-diamine, in the presence of a suitable base, such as $K_2CO_3$, in a suitable solvent, such as dioxane, to afford products of the formula XXIV, which are compounds of the formula I wherein $R^2$ is —$N(R^b)S(O)_2R^{2b}$. Under similar reaction conditions, compounds of the formula XVIII can be coupled with sulfonoureas of the formula $(R^{11})_2NS(O)_2NHR^b$ to afford compounds of the formula XXV, which are compounds of the formula I wherein $R^2$ is —$N(R^b)S(O)_2N(R^{11})_2$.

As depicted in Scheme I, compounds of the formula XVI, which are compounds of the formula I wherein $R^2$ is —$CO_2H$ and prepared as previously described in Scheme D, can be converted to compounds of the formula XXVII, which are compounds of the formula I wherein $R^2$ is —$NHCO_2Bn$, using standard Curtius rearrangement conditions readily known to those skilled in the art. Preferred conditions include, but are not limited to, heating in the presence of diphenylphosphorylazide (DPPA), in the presence of benzyl alcohol (BnOH) in the presence of a suitable base, such as triethylamine, in a suitable solvent such as toluene. Compounds of the formula XXVII can be deprotected using conditions readily known to those skilled in the art, to afford compounds of the formula XXVIII, which are compounds of formula I wherein $R_2$ is —$NH_2$. Preferred conditions for deprotection include, but are not limited to, reacting compounds of the formula XXVII with palladium catalysts, such as palladium on carbon, in the presence of hydrogen, in a suitable solvent, such as ethanol.

SCHEME G

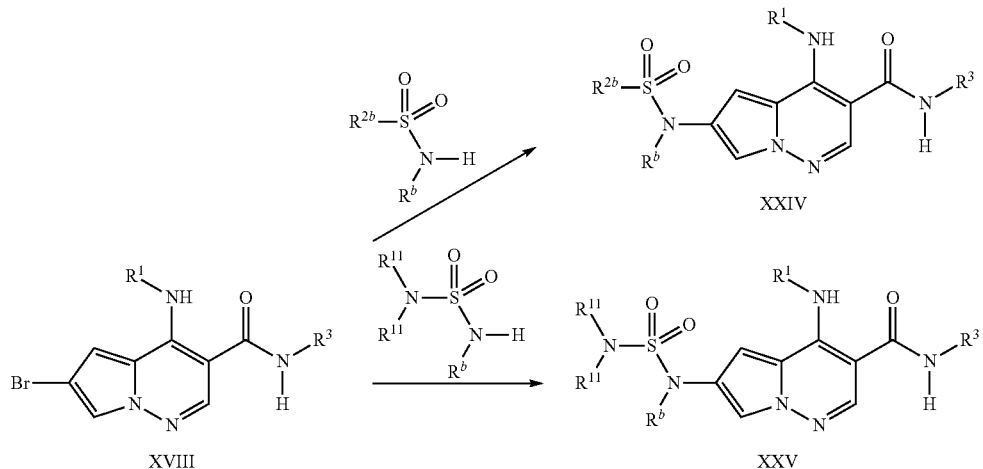

As depicted in Scheme H, compounds of the formula XVIII, which are compounds of the formula I wherein $R^2$ is bromo and prepared as previously described in Scheme B, can be coupled with heterocyclo compounds of the formula (Het)NH wherein (Het)NH represents any substituted or unsubstituted 4-10 membered heterocyclo group. Coupling of said heteroaryl groups can be performed in the presence of a copper catalyst, such as copper iodide, in the presence of a suitable ligand, such as N1,N2-dimethylethane-1,2-diamine, in the presence of a suitable base, such as $K_2CO_3$, in a suitable solvent, such as dioxane, to afford products of the formula XXVI, which are compounds of the formula I wherein $R^2$ is —N(Het) as defined previously.

SCHEME H

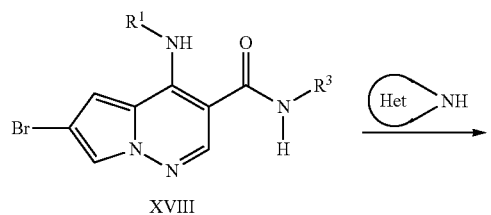

SCHEME I

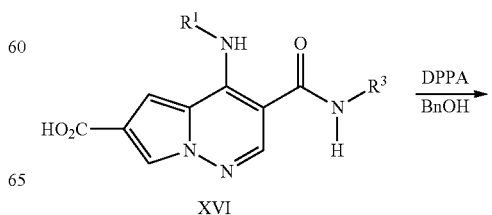

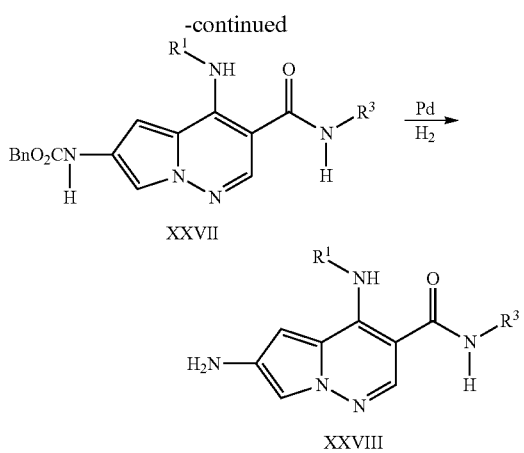

As depicted in Scheme J, alternative routes of preparation for compounds of the formula XXI, XXII, and XXIII as previously described in Scheme F wherein $R^b$ is hydrogen include reacting compounds of the formula XXVIII with acylating agents such as acid chlorides of the formula $(R^{2b})C(O)Cl$, chloroformates of the formula $(R^{2b}O)C(O)Cl$ and carbamoyl chlorides of the formula —$(R^{11})_2NC(O)Cl$ or isocyanates of the formula —$(R^{11})_2NC(O)$, respectively. Couplings can be carried out in the presence of a suitable base, such as triethylamine, in the presence of a suitable solvent, such as dichloromethane.

As depicted in Scheme K, compounds of the formula XVIII, which can be prepared as previously described in Scheme B wherein $R^2$ is bromo, can be reacted with cyanide to afford compounds of the formula XXIX, which are compounds of formula I wherein $R^2$ is cyano. Preferred conditions for coupling include, but are not limited to, reacting in the presence of a suitable cyanide reagent, such as zinc(II) cyanide, in the presence of a palladium catalyst, such as $Pd(COCF_3)_2$, in the presence of a phosphine ligand, such as 1,1'-binaphthyl-2-yldi-tert-butylphosphine, in a suitable solvent such as DMA.

SCHEME K

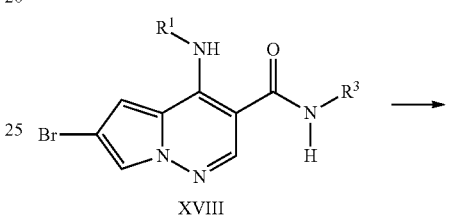

SCHEME J

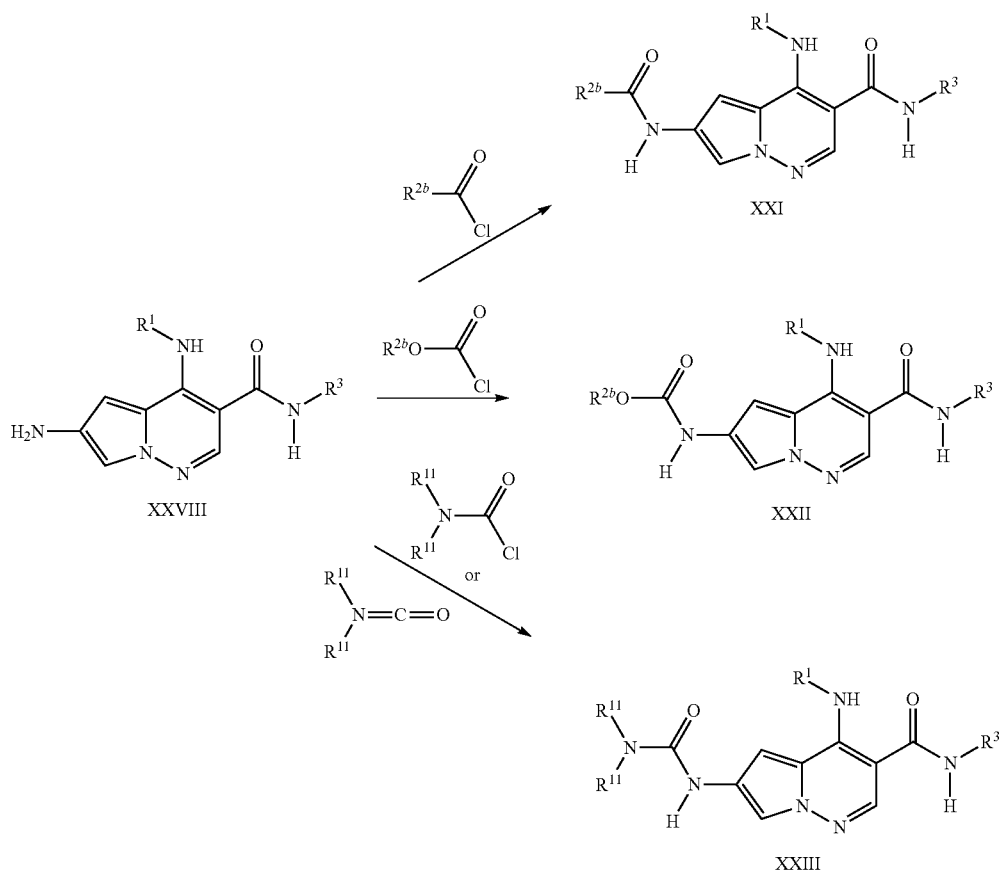

-continued

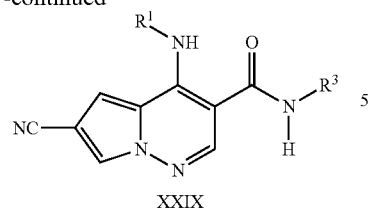

XXIX

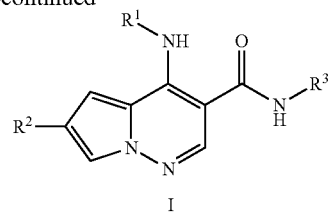

I

As depicted in Scheme L, compounds of the formula I can also be prepared by reacting compounds of the formula XXX, which are prepared as depicted in Scheme B where $R^2$ is bromo, with a thiolate, such as sodium ethylthiolate, to afford a compound of the formula XXXI. Installation of additional $R^2$ groups can then be accomplished by reacting compounds of the formula XXXI with coupling reagents, such as boronic acids or boronate esters, under standard coupling conditions readily known in the art, to afford compounds of the formula XXXII. Compounds of the formula XXXII can then be oxidized using oxidizing agents, such as oxone, to afford compounds of the formula XXXIII which can be coupled with amines of the formula $R^1$—$NH_2$ to afford compounds of the formula I. Preferred conditions for coupling of $R^1$—$NH_2$ include, but are not limited to, reaction of compounds of the formula XXXIII in the presence of an amine, such as DIPEA, in a suitable solvent, such as THF.

As depicted in Scheme M, compounds of the formula XVI, which are compounds of the formula I wherein $R^2$ is —$CO_2H$ and prepared as previously described in Scheme D, can be converted to compounds of the formula XXXIV using standard amide coupling conditions readily known to those skilled in the art. Compounds of the formula XXXIV can be reacted with di(1H-imidazol-1-yl)methanethione followed by alkylation with iodomethane to afford compounds of the formula XXXV. Compounds of the formula XXXV can be coupled with amines of the formula $(R^{2b})_2NH$ by thermolysis at higher temperatures (>100° C.) or compounds of the formula XXXV can be oxidized to afford a sulfoxide and/or sulfone intermediate using an oxidizing agent, such as oxone, followed by coupling with amines of the formula $(R^{2b})_2NH$ under lower temperatures (<100° C.) to afford compounds of the formula XXXVI.

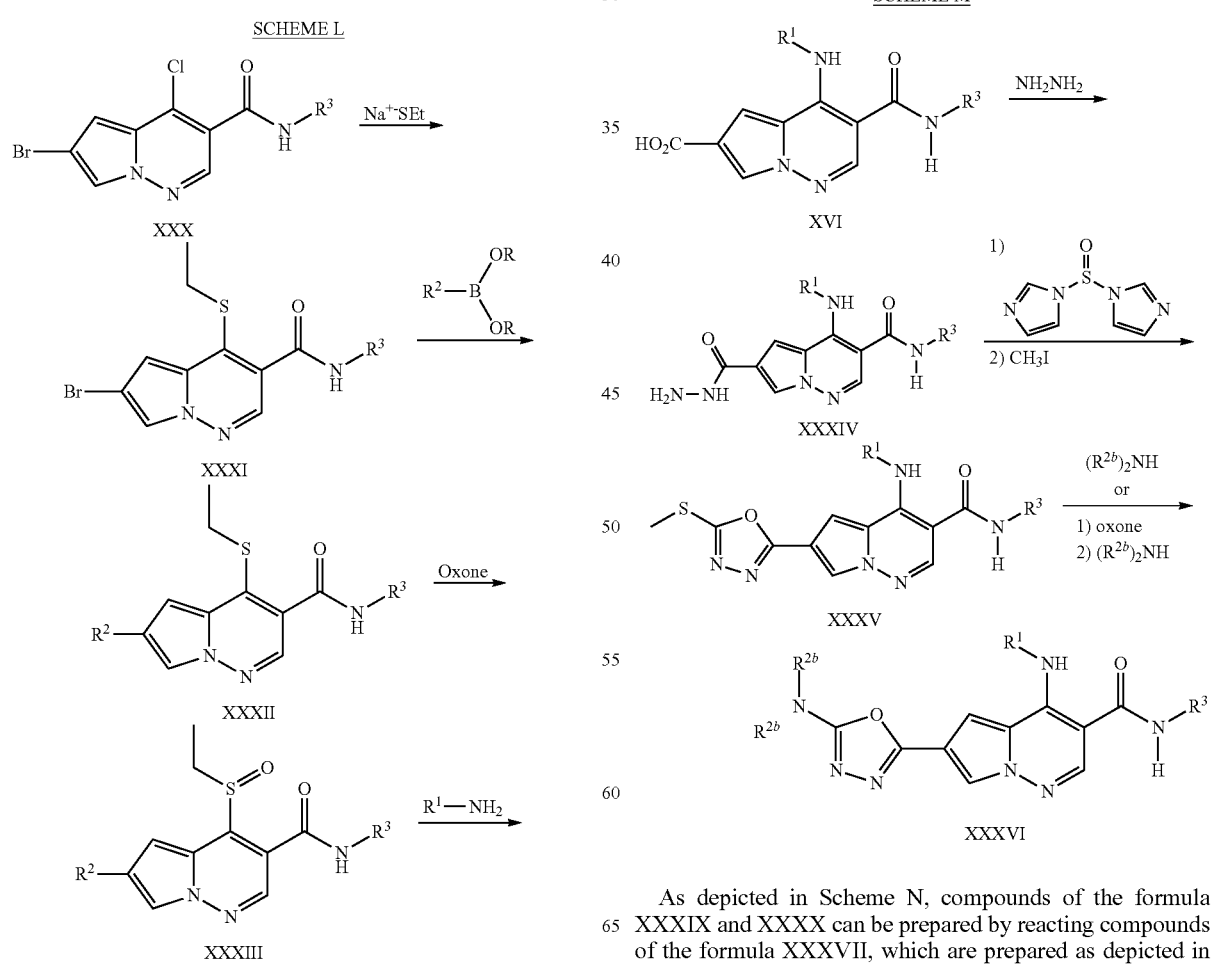

As depicted in Scheme N, compounds of the formula XXXIX and XXXX can be prepared by reacting compounds of the formula XXXVII, which are prepared as depicted in Scheme B where $R^2$ is bromo, with TMS acetylene in the presence of a suitable palladium catalyst, such as PdCl₂ (Ph₃P)₂, and a suitable copper salt, such as copper (I) iodide, and in the presence of a suitable base such as diisopropylethylamine in a suitable solvent, such as DMF, to afford compounds of the type XXXVIII where $R^2$ is alkynyl. Compounds such as XXXVIII can then be reacted with azides represented by $R^{2b}N_3$, in the presence of a suitable catalyst, such as copper sulfate, in a suitable solvent such as aqueous tert-butanol, to afford compounds of the formula XXXIX wherein $R^2$ is 1,2,3-triazolyl optionally substituted with $R^{2b}$. Alternatively, compounds such as XXXVIII can then be reacted with N-hydroxamoyl chlorides represented by $R^{2b}C$ (Cl)=NOH, in the presence of a suitable base, such as triethylamine, in a suitable solvent such as dichloromethane, to afford compounds of the formula XXXX wherein $R^2$ is isooxazol-5-yl optionally substituted with $R^{2b}$.

SCHEME N

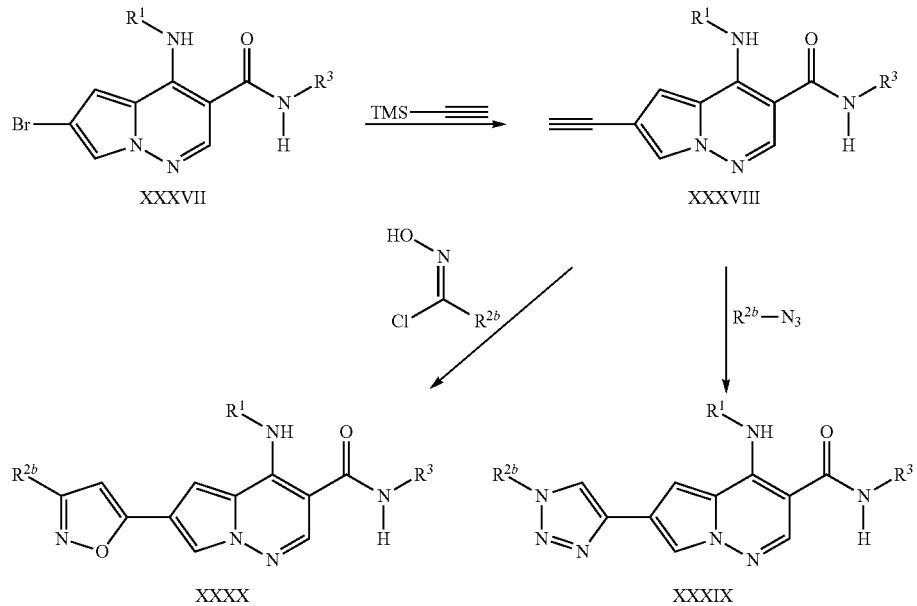

As depicted in Scheme O, compounds of the formula XXXXI and XXXXII can be prepared by reacting compounds of the formula XXIX, which are prepared as depicted in Scheme K where $R^2$ is cyano, with an azide reagent, such as $Me_3SnN_3$, at elevated temperatures, such as 150-200 degrees Celsius, in a suitable solvent, such as NMP, followed by reacting the obtained intermediate with a suitable alkylating reagent $R^{2b}$—X, such as methyl iodide, in the presence of a suitable base, such as potassium carbonate, in a suitable solvent, such as NMP, to afford compounds of the formula XXXXI and XXXXII which are optionally substituted with $R^{2b}$.

SCHEME O

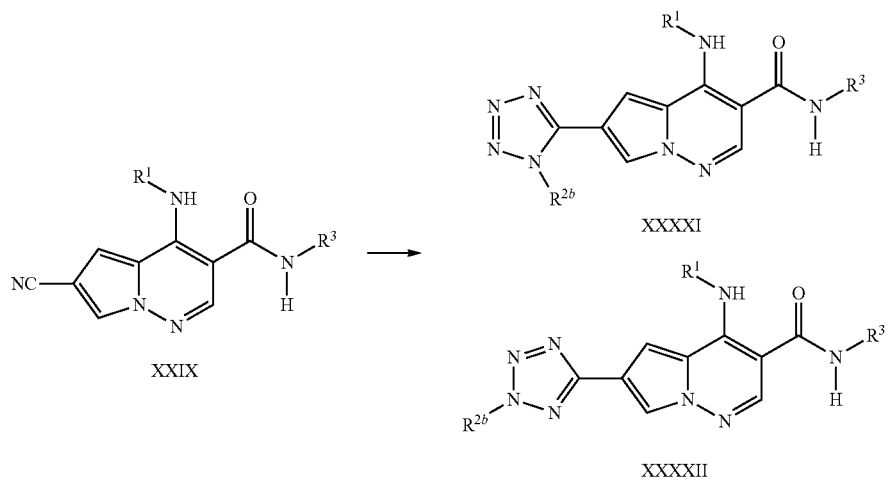

As depicted in Scheme P, pyrrolidine compounds of the formula LI can be prepared from the coupling of pyrrolidine intermediates of the formula XXXXIII with pyrrolopyridazine intermediates of the formula XVIII (prepared as in Scheme E) to afford compounds of the formula IL where PG is a suitable protecting group, such as tert-butoxycarbonyl (Boc) or benzyloxycarbonyl (Cbz). Compounds of the formula IL can be functionalized with a suitable $R^2$ group by methods known in the art and by methods described herein followed by deprotection (removel of PG) using methods known in the art to afford compounds of the formula L. Compounds of the formula L can be functionalized with suitable $R^{1b}$ groups by methods known in the art and by using methods described herein to afford compounds of the formula L1.

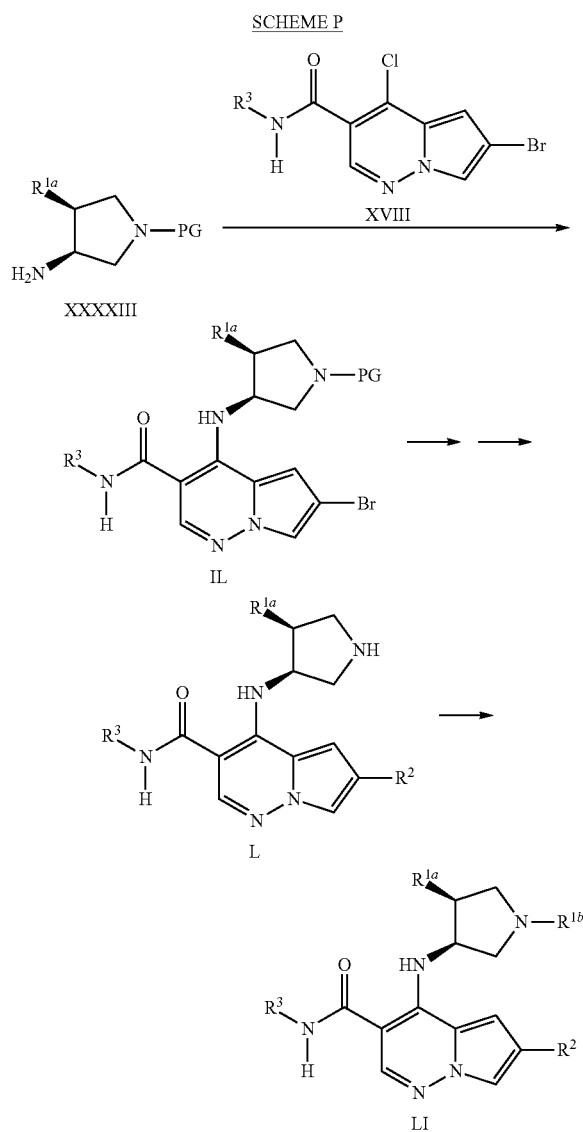

SCHEME P

Suitably substituted pyrrolidine intermediates represented by $R^1NH_2$ can be prepared by methods known by those skilled in the art (for example, see *Targets in Heterocyclic Synthesis* 2009, 13, p 147-171 and *Tetrahedron* 2004, 60(8), 1701-1729 and references therein). More specifically, as depicted in Scheme Q, suitably substituted pyrrolidine intermediates of the formula LVI can be prepared from compounds of the formula LII where PG is a suitable protecting group (PG) such as butoxycarbonyl (Boc) or benzyloxycarbonyl (Cbz). Oxidation using suitable oxidizing reagents, such as mCPBA, affords compounds of the formula LIII followed by epoxide opening with nucleophilic reagents, such as alkyl grignards in the presence of a copper salt, such as copper iodide, affords compounds of the formula LIV wherein Iea is a suitable alkyl group. Alternatively, reacting compounds of the formula LIII with alcohols, such as methanol, in the presence of a suitable acid catalyst, such as sulfuric acid, affords compounds of the formula LIV wherein $R^{1a}$ is a suitable alkoxy group. Compounds of the formula LIV can then be reacted with suitable activating reagents, such as toluenesulfonyl chloride, in the presence of a suitable base, such as pyridine, in the presence of a suitable solvent such as dichloromethane, followed by reaction of the activated alcohol intermediate with a suitable azide reagent, such as sodium azide, to afford compounds of the formula LV. Compounds of the formula LV can be reacted with a suitable reducing reagent, such as triphenylphosphine, in a suitable solvent to afford pyrrolidine compounds of the formula LVI. Enantiopure compounds of the formula LVI having the preferred 3-(S) configuration can be obtained by resolution using chiral chromatography methods which are known by those skilled in the art.

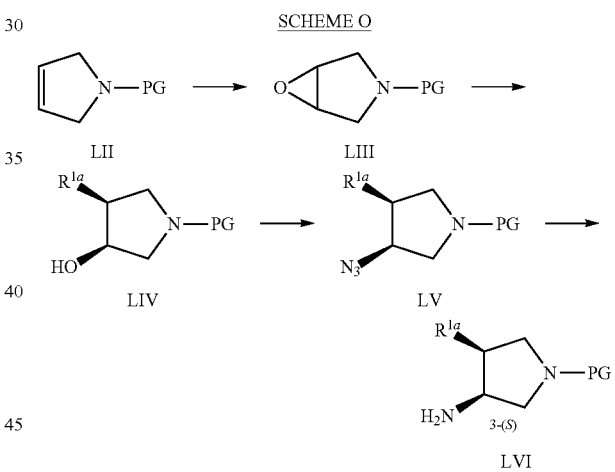

SCHEME O

Suitably substituted piperidine intermediates represented by $R^1NH_2$ can be prepared by methods known by those skilled in the art (for example, see *Targets in Heterocyclic Synthesis* 2009, 13, p 147-171 and *Tetrahedron* 2004, 60(8), 1701-1729 and references therein). More specifically, as depicted in Scheme R, suitably substituted piperidine intermediates of the formula LXI can be prepared from available compounds of the formula LVII where PG is a suitable protecting group (PG) such as butoxycarbonyl (Boc) or benzyloxycarbonyl (Cbz). Reaction with α-methylbenzylamine in a suitable solvent, such as benzene, in the presence of a water scavenger, such as molecular sieves, affords imine compounds of the formula LVIII. Reduction of the imines using a suitable reducing agent, such as sodium borohydride, in a suitable solvent, such as ethanol, affords amines of the formula LIX. Hydrogenolysis using a suitable catalyst, such as palladium hydroxide on carbon, in a suitable solvent, such as acetic acid, in the presence of hydrogen gas affords amines of the formula LX which can be transformed to final compounds of the formula LXI as previously described in Scheme R. Enantiopure compounds of the formula LXI having the preferred (R)-configuration can be obtained by using enantiopure (R)-α-methylbenzylamine in the preparation.

SCHEME R

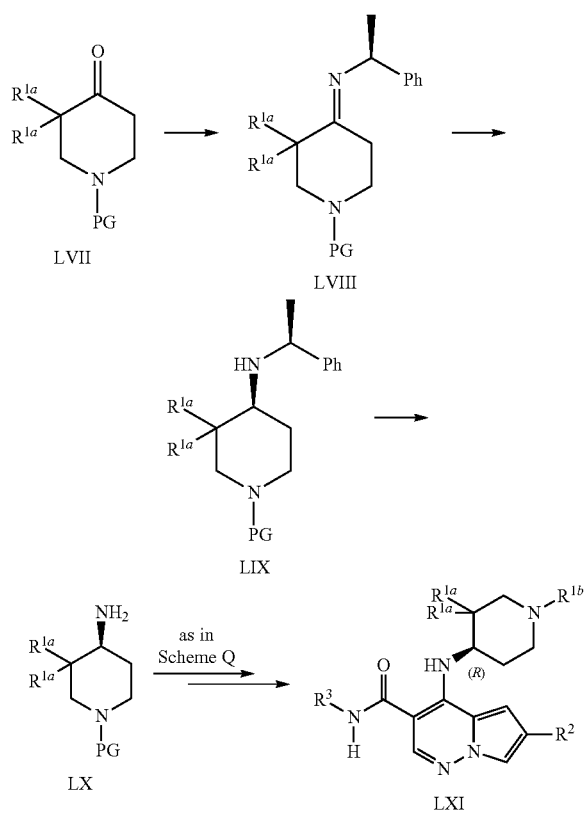

Analytical HPLC Conditions:
Method A:
Linear gradient of 0 to 100% solvent B over 4 min, with 1 min hold at 100% B
UV visualization at 220 nm
Column: YMC S50DS-A S5 4.6×50 mm
Flow rate: 4 mL/min
Solvent A: 0.2% phosphoric acid, 90% water, 10% methanol
Solvent B: 0.2% phosphoric acid, 90% methanol, 10% water
Method B:
Column: YMC ProC18 S5 ODS (50×4 6 mm),
Linear gradient of 0 to 100% solvent B over 4 min, with 1 min hold at 100% B
Solvent A: 10% MeOH-90% $H_2O$-0.2% $H_3PO_4$
Solvent B: 90% MeOH-10% $H_2O$-0.2% $H_3PO_4$,
Flow rate: 4 mL/min
Products detected at 220 nm.
Method C:
Column: XBridge (150×4.6 mm), 3.5 μm SC/840
Flow rate: 1 mL/min
Solvent A: 10 mM $NH_4HCO_3$ in water pH=9.5 adjusted using dil. Ammonia
Solvent B: MeOH
Products detected at 220 nm Method D:
Column: LUNA 5 u C18 21×100
Flow rate=40 mL/min
Solvent A: 10% MeOH/H2O with 0.1% TFA
Solvent B: 90% MeOH/H2O with 0.1% TFA
Start 35% Solvent B to 85% Solvent B over 12 min gradient
Method E:
Column: Sunfire C18, (150×4.6 mm), 3.5 μm, SC/862
Linear gradient of 0 to 100% solvent B over 12 min, then 3 min hold at 100% B
Flow rate: 1 mL/min
Buffer: 0.5% TFA, in water with pH adjusted to 2.5 using dilute ammonia
Solvent A: Buffer:acetonitrile (95:5)
Solvent B: acetonitrile
Products detected at 220 nm
Method F:
Column: Waters Acquity UPLC BEH C18, 2.1×50 mm, 1.7-μm particles Linear
gradient of 0 to 100% solvent B over 3 min, with 0.75 min hold at 100% B.
Flow rate: 1.1 mL/min
Solvent A: 5:95 acetonitrile:water with 0.05% TFA
Solvent B: 95:5 acetonitrile:water with 0.05% TFA
Temperature: 50° C.
Products detected at 220 nm
Method G:
Column: X bridge phenyl (4.6×150 mm)
Linear gradient of 0 to 100% solvent B over 12 min, then 3 min hold at 100% B
Flow rate: 1 mL/min
Solvent A: 5% MeCN-95% H2O-0.05% TFA
Solvent B: 95% MeOH-5% H2O-0.05% TFA
Products detected at 220 nm
Method H:
Column: YMC Combiscreen ODS-A, 4.6×50 mm
Mobile phase: 10-90% aq $CH_3OH$/0.2% $H_3PO_4$,
Gradient=4.0 min. linear with 1.0 min. hold
Flow rate: 4 ml/min
Pdt detected at 220 nm or 254 nm detection wavelength.
Method I:
Column: Supelco Ascentis C18, 4.6×50 mm, 2.7 um
Flow rate: 4 mL/min
Solvent A: 5:95 acetonitrile:water with 0.05% TFA
Solvent B: 95:5 acetonitrile:water with 0.05% TFA
Linear gradient of 0 to 100% solvent B over 4 min, with 1 min hold at 100% B
UV visualization at 220 nm
Method J:
Column: Supelco Ascentis C18, 4.6×50 mm, 2.7 um
Flow rate: 4 mL/min
Solvent A: 5:95 acetonitrile:water with 10 mM NH4OAc
Solvent B: 95:5 acetonitrile:water with 10 mM NH4OAc
Linear gradient of 0 to 100% solvent B over 4 min, with 1 min hold at 100% B
UV visualization at 220 nm
Method K:
Column: Walters Xbridge C18, 4.6×50 mm, 5 um
Flow rate: 4 mL/min
Solvent A: 5:95 acetonitrile:water with 10 mM NH4OAc
Solvent B: 95:5 acetonitrile:water with 10 mM NH4OAc
Linear gradient of 0 to 100% solvent B over 4 min, with 1 min hold at 100% B
UV visualization at 220 nm
Method L:
Column: Chromalith Speedrod C18, (50×4 6 mm)
Linear gradient of 0 to 100% solvent B over 4 min
Flow rate: 4 mL/min Solvent A: 10% MeOH-90% H2O-0.2% $H_3PO_4$
Solvent B: 90% MeOH-10% H2O-0.2% $H_3PO_4$
Products detected at 220 nm
Method M:
Column: Supelco Ascentis Express C18, 5×4.6 mm, 2.7 um
Flow rate: 4 mL/min
Solvent A: 5:95 acetonitrile:water with 0.05% TFA
Solvent B: 95:5 acetonitrile:water with 0.05% TFA
Linear gradient of 0 to 100% solvent B over 4 min, with 1 min hold at 100% B
UV visualization at 220 nm
Method N:
Column: Supelco Ascentis Express C18, 4.6×50 mm, 2.7 um
Flow rate: 4 mL/min
Solvent A: 5:95 acetonitrile:water with 10 mM ammonium acetate
Solvent B: 95:5 acetonitrile:water with 10 mM ammonium acetate
Linear gradient of 0 to 100% solvent B over 4 min, with 1 min hold at 100% B
UV visualization at 220 nm
Method O:
Column: YMC Combiscreen ODS-A, 4.6×50 mm
Mobile phase: 10-90% aq $CH_3OH$/0.1% TFA,
Gradient=4.0 min. linear with 1.0 min. hold
Flow rate: 4 ml/min
Pdt detected at 220 nm or 254 nm detection wavelength.
Preparative HPLC Conditions:
Method A:
Column: Luna 5 u C18 30×100 mm
Flow rate=40 mL/min
Solvent A=10% MeOH-90% H20-0.1% TFA
Solvent B=90% MeOH-10% H20-0.1% TFA,
Start % B=30, Final % B=100, linear gradient time=10 min
Pdts detected at 220 wavelength.
Method B:
Column: Waters XBridge C18, 19×250 mm, 5-μm particles
Mobile Phase A: 5:95 acetonitrile:water with 10 mM ammonium acetate;
Mobile Phase B: 95:5 acetonitrile:water with 10 mM ammonium acetate;
Flow: 20 mL/min.
Products detected by mass spectrometry.
Analytical LCMS Conditions:
Method A:
Column: Phenomenex Luna 5 u C18 30×4 6 mm
Linear gradient of 0-100% solvent B over 2 min, then 0.5 min hold at 100% B
Flow rate: 4 mL/min
Solvent A: 10% MeOH-90% H2O-0.1% TFA
Solvent B: 90% MeOH-10% $H_2O$-0.1% TFA
Products detected at 220 wavelength w/positive or negative ionization mode
Method B:
Column: BEH C18 2.1×50 mm 17 u
Linear gradient of 0-100% solvent B over 2 min, then 0.5 min hold at 100% B
Flow rate: 1 mL/min
Solvent A: 100% water w/0.05% TFA
Solvent B: 100% acetonitrile w/0.05% TFA
Products detected at 220 wavelength w/positive ionization mode
Method C:
Column: XBridge (150×4.6 mm), 3.5 μm SC/840
Flow rate: 1 mL/min
Solvent A: 10 mM $NH_4HCO_3$ in water pH=9.5 adjusted using dil. Ammonia
Solvent B: MeOH
Products detected by positive or negative ionization
Method D:
Column-Ascentis Express C18 (50×2-1 mm 2.7 μm)
Mobile Phase A: 2% acetonitrile-98% Water-10 mM Ammonium formate;
Mobile Phase B-98% acetonitirile-2% water-10 mM Ammonium formate;
Flow: 1 mL/min.
Products detected at 220 wavelength w/positive ionization mode.
Method E:
Column: Purosphoer@ star rp-18 (4.6×30) mm, 3 μm
Linear gradient of 0-100% solvent B over 2 min, then 0.5 min hold at 100% B
Flow rate: 2.5 mL/min
Solvent A: 20 mM of ammonium acetate in 90% water-10% acetonitrile
Solvent B: 20 mM of ammonium acetate in 10% water-90% acetonitrile
Products detected at 220 wavelength w/positive or negative ionization mode
Method F:
Column: Purosphoer@ star rp-18 (4.6×30) mm, 3 μm
Linear gradient of 0-100% solvent B over 2 min, then 0.5 min hold at 100% B
Flow rate: 2.5 mL/min
Solvent A: 20 mM of ammonium acetate in 90% water-10% acetonitrile
Solvent B: 20 mM of ammonium acetate in 10% water-90% acetonitrile
Products detected at 220 wavelength w/positive or negative ionization mode
Products detected at 220 wavelength w/positive or negative ionization mode.
Method G:
Column: Zorbox SB C18 (4.6×50 mm), 5 μm
Linear gradient of 0-100% solvent B over 4 min, then 1 min hold at 100% B
Flow rate: 5 mL/min
Solvent A: 10% methanol-90% water-0.1% TFA
Solvent B: 90% Methanol-10% water-0.1% TFA
Products detected at 220 wavelength w/positive ionization mode
Method H:
Column: Waters Acquity BEH C18 2.1×50 mm 1 um
Linear gradient of 0-100% solvent B over 3 min, then 0.75 min hold at 100% B
Flow rate: 1.11 mL/min
Solvent A: 5:95 acetonitrile:water with 10 mM ammonium acetate
Solvent B: 95:5 acetonitrile:water with 10 mM ammonium acetate
Temperature=50° C.
Products detected at 220 wavelength w/positive ionization mode
Method I:
Column: Waters Acquity BEH C18 2.1×50 mm 1 um
Linear gradient of 0-100% solvent B over 3 min, then 0.75 min hold at 100% B
Flow rate: 1.11 mL/min
Solvent A: 5:95 acetonitrile:water with 0.05% TFA
Solvent B: 95:5 acetonitrile:water with 0.05% TFA
Temperature=50° C.

Products detected at 220 wavelength w/positive ionization mode
Method J:
Column: Phenominex, 2.5 micron, 2.0×30 mm
Mobile phase: 10-90% aq $CH_3OH$/0.1% TFA,
Gradient=4.0 min. linear with 1.0 min. hold
Flow rate: 1 ml/min
Pdt detected at 220 nm or 254 nm detection wavelength.
Method K:
Column: Luna C18 4.6×30 mm, 3 micron
Linear gradient of 0-95% solvent B over 2 min
Flow rate: 4 mL/min
Solvent A: 10:90 H2O:MeOH TFA
Solvent B: 10:90 H2O:MeOH TFA; 0%-95% B in 2 min; 4 mL/min flow.
Product detected by positive ionization mode.

Intermediates

Intermediate 1 ethyl 3-carbamoyl-4-chloropyrrolo[1,2-b]pyridazine-6-carboxylate

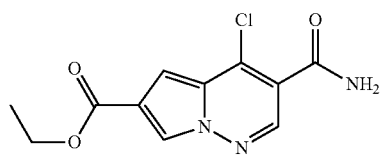 [SMILES: CCOC(=O)c1cc2c(Cl)c(C(N)=O)cnn2c1]

Step 1: Ethyl 2-formamidoacetate

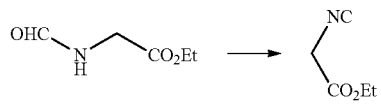

To a 5 L three neck round bottom flask equipped with a mechanic stirrer, a pressure-equalizing funnel and a condenser bearing a calcium chloride drying tube was added glycine ethyl ester hydrochloride (500 g, 3.583 mol) and methyl formate (1.8 L). The suspension was brought to reflux and triethylamine (556 mL) was added to the reaction. The reaction was stirred and refluxed overnight. The reaction was cooled to room temperature and filtered through a Buchner funnel to remove triethylamine hydrochloride salt. The filtrate was concentrated and dried over high vacuum to yield 320 g (93%) of the title compound.

Step 2: Ethyl 2-isocyanoacetate

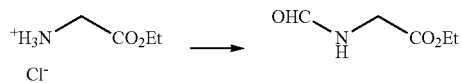

To a round bottom flask was added ethyl 2-formamidoacetate (600 g, 4.5 mol), dry $CH_2Cl_2$ (6 L) and triethylamine (1.512 kg). The reaction mixture was cooled to −10° C. and then $POCl_3$ (700 g) was added dropwise at −10° C. After the addition, the reaction was stirred at 0° C. for additional 1 hour. The reaction was cooled to −20° C. and slowly was saturated sodium carbonate solution (3.6 L) added to the reaction. After the addition, the reaction was brought to room temperature and was stirred at room temperature for 0.5 hr. Then the organic layer was separated and the aqueous layer was extracted with $CH_2Cl_2$ (2×3 L). The combined organic layer was washed with brine and dried over anhydrous $K_2CO_3$ solid. The solution was filtered and concentrated at 45° C. to yield 560 g (96%) title compound. $H^1$ NMR (400 MHz, $CDCl_3$) δ ppm: 8.2 (1H, s), 6.9 (1H, br s), 4.14 (2H, q, J=4 Hz), 3.91 (2H, d, J=6.4 Hz), 1.19 (3H, t, J=4 Hz).

Step 3: Diethyl 1H-pyrrole-2,4-dicarboxylate

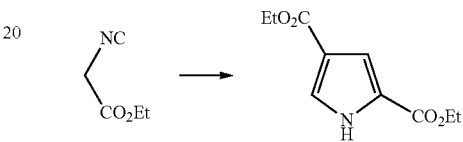

To a round bottom flask under argon was added ethyl 2-isocyanoacetate (100 g, 0.884 mol), dry THF (1.0 L) followed by DBU (132 g, 0.867 mol). The reaction was cooled to 0° C. and formaldehyde (16 g) was added portionwise into the reaction mixture. The reaction was then stirred at room temperature overnight. Then THF was removed under high vacuum and the residue as dissolved with water and extracted with EtOAc (2×1 L). The combined organic layer was washed with water and brine and concentrated. The residue was purified by flash silica gel column chromatography to yield 40 g (26%) of a white solid as the title compound. $H^1$ NMR (400 MHz, $CDCl_3$) δ ppm: 9.85 (1H, br s), 7.54 (1H, m), 7.30 (1H, m), 4.36-4.6 (4H, merging quartets), 1.37-1.26 (6H, merging triplets). LCMS (condition A): m/z=210.2 −ve.

Step 4: Diethyl 1-amino-1H-pyrrole-2,4-dicarboxylate

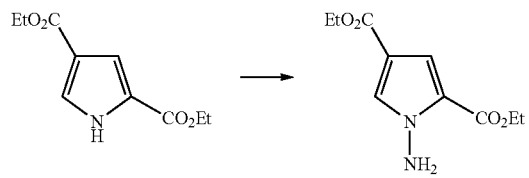 [SMILES: CCOC(=O)c1c[nH]c(C(=O)OCC)c1 ; CCOC(=O)c1cc(C(=O)OCC)n(N)c1]

To a flask was added MTBE (2 L) and ammonium chloride (60 g, 1.13 mol). The reaction was cooled to −20° C. Then concentrated aq ammonium hydroxide (160 mL) was added to the reaction followed by slow addition of commercial-grade sodium hypochlorite solution (149 g, 1.5 L). After addition, the reaction was stirred at −20° C. for additional 30 minutes. The MTBE layer was separated and washed with brine and dried over $Na_2SO_4$. In a separate flask under nitrogen was added diethyl 1H-pyrrole-2,4-dicarboxylate (40 g, 190 mmol) and dry DMF (400 mL). The reaction was cooled to 0° C. whereupon sodium hydroxide (190 mmol) was added portionwise to the reaction. The reaction was stirred at 0° C. for additional 1 hour before it was cooled to −20° C. At this time, the previously prepared MTBE solution of chloramine was added slowly to the reaction and the reaction was stirred at −20° C. for 1 hour. The reaction was quenched with saturated sodium thiosulfate solution. The organic layer of the reaction was separated and washed with water and brine, dried over sodium sulfate, filtered and concentrated to yield 40 g (95%) of the title compound. $H^1$ NMR (400 MHz, $CDCl_3$) δ ppm: 7.48 (1H, d, J=1.6 Hz), 7.24 (1H, d, J=1.6 Hz), 5.65 (2H, s), 4.32-4.23 (4H, merging quartets), 1.367-1.32 (6H, merging triplets). LCMS (condition A) m/z=227.2 +ve.

Step 5: Ethyl 3-cyano-4-hydroxypyrrolo[1,2-b]pyridazine-6-carboxylate

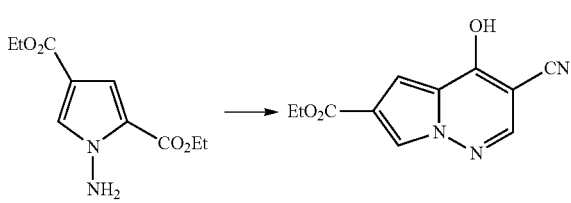 [SMILES: CCOC(=O)c1cc(C(=O)OCC)n(N)c1 ; CCOC(=O)c1cc2c(O)c(C#N)cnn2c1]

To a round bottom flask was added diethyl 1-amino-1H-pyrrole-2,4-dicarboxylate (40 g, 177 mmol), diethoxypropionitrile (53 mL) and p-TSA (10 g, 0.052 mmol). The reaction was heated at 125° C. for 3 hours and the EtOH was removed. The reaction was cooled to room temperature before DBU (30 g, 340 mmol) was added. The reaction was then heated at 80° C. for 2 hours. The reaction was cooled to room temperature and diluted with $CH_2Cl_2$. The mixture was washed with 5% citric acid solution (2×), water and brine solution. The organic layer was concentrated and the residue was purified by flash silica gel column chromatography (10% MeOH in $CHCl_3$) to yield 20 g (50%) of the title compound as a brown oil. LCMS (condition A): m/z=230.2 −ve. $H^1$ NMR (400 MHz, $CDCl_3$) δ ppm: 9.53 (1H, br s), 8.32 (1H, s), 7.75 (1H, s), 6.75 (1H, s), 4.25 (2H, q), 1.28 (3H, t).

Step 6: Ethyl 4-chloro-3-cyanopyrrolo[1,2-b]pyridazine-6-carboxylate

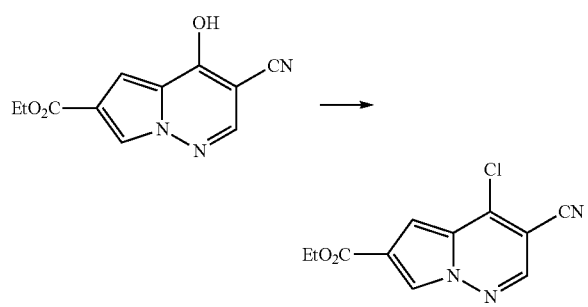

To a round bottom flask was added $POCl_3$ (200 mL) and ethyl 3-cyano-4-hydroxypyrrolo[1,2-b]pyridazine-6-carboxylate (20 g, 80 mmol). The reaction was heated under nitrogen at 75° C. for 2 hours. The reaction was cooled to room temperature and $POCl_3$ was removed under vacuum. The residue was poured onto ice-water. The aqueous solution was extracted with $CH_2Cl_2$. The organic layer was washed with saturated sodium carbonate solution, dried and concentrated. The resulting residue was purified by flash silica gel column chromatography to yield 10 g (48%) of the title compound as a yellow solid. $H^1$ NMR (400 MHz, $CDCl_3$) δ ppm: 8.33 (1H, d, J=1.3 Hz), 8.11 (1H, s), 7.41 (1H, d, J=1.6 Hz), 4.41 (2H, q, J=6.8 Hz), 1.41 (3H, t, J=6.8 Hz).

Step 7: Ethyl 3-carbamoyl-4-chloropyrrolo[1,2-b]pyridazine-6-carboxylate (Intermediate 1)

To a round bottom flask was added concentrated $H_2SO_4$ (100 mL) followed by ethyl 4-chloro-3-cyanopyrrolo[1,2-b]pyridazine-6-carboxylate (10 g, 40 mmol). The reaction was stirred at room temperature under nitrogen overnight. The reaction mixture was poured onto ice cold saturated sodium carbonate solution. The aqueous solution was extracted with EtOAc (4×) and the combined organic layer was concentrated to yield 7 g (70%) of the title compound as a yellow solid. HPLC (condition S): retention time=8.04 min. LCMS (condition A): m/z=268.0 +ve. $H^1$ NMR (400 MHz, $CDCl_3$) δ ppm: 8.49 (1H, d, J=1.6 Hz), 8.40 (1H, s), 8.08 & 7.98 (1H, two br s), 7.12 (1H, d, J=1.6 Hz), 4.34 (2H, q, J=7.2 Hz), 1.34 (3H, t, J=7.2 Hz).

Intermediate 2

6-bromo-4-chloropyrrolo[1,2-b]pyridazine-3-carboxamide

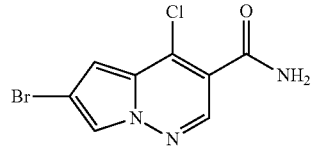 [SMILES: NC(=O)c1cnn2cc(Br)cc2c1Cl]

Step 1:
1-(4-Bromo-1H-pyrrol-2-yl)-2,2,2-trichloroethanone

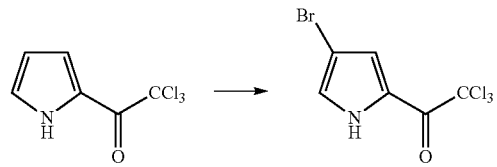

To a 100 mL 3-neck round bottom equipped with a dropping funnel was added trichloroacetyl pyrrole (50 g, 236.4 mmol) and $CCl_4$ (1.0 L). After trichloroacetyl pyrrole was dissolved, the reaction was cooled to 0° C. and iodine (0.176 g) was added to the reaction. At this time, a solution of bromine (12 mL) in $CCl_4$ (100 mL) was added dropwise very slowly to the reaction through a dropping funnel over 20 minutes and the resulting mixture was stirred at 0° C. for additional 20 minutes. The resulting mixture was transferred into a separatory funnel and washed with 10% $Na_2S_2O_3$ solution, saturated $NaHCO_3$ solution and brine (2×). The organic layer was dried and concentrated to give 50 g (60%) of the title compound as a white solid. LCMS (condition A):

m/z=287.8, 289.8, 290.8 −ve. H¹ NMR (400 MHz, CDCl₃) δ ppm: 12.8 (1H, br.s), 7.56 (1H, m), 7.33 (1H, m).

Step 2: Methyl 4-bromo-1H-pyrrole-2-carboxylate

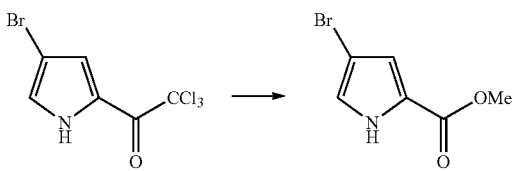

To a dry round bottom flask containing dry MeOH (60 mL) was added sodium (5 g, 257.7 mmol) portionwise. After all the sodium was dissolved, the solution was slowly added to a flask which contained 1-(4-bromo-1H-pyrrol-2-yl)-2,2,2-trichloroethanone (50.0 g, 171.8 mmol) in MeOH (860 mL) through a dropping funnel giving a yellow reaction mixture. After the addition was complete, the reaction was stirred for an additional 10 minutes, then concentrated and cooled in an ice bath. The resulting solid that precipitated was collected by vacuum filtration and washed with water until neutral pH. The solid was dried to yield 25 g (71%) of the title compound as a white solid. LCMS (condition A): m/z=204.0 −ve. H¹ NMR (400 MHz, DMSO-d₆) δ ppm: 7.16 (1H, d, 1.2H), 6.89 (1H, d, 1.2H).

Step 3: Methyl 1-amino-4-bromo-1H-pyrrole-2-carboxylate

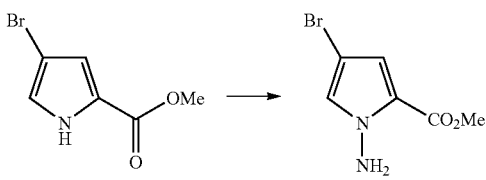 [SMILES: COC(=O)c1cc(Br)c[nH]1 ; COC(=O)c1cc(Br)cn1N]

To a 5 L 3-neck round bottom flask was added conc. NH₄OH (2.0 L) and the solution was cooled to −20° C. Ammonia gas was purged into the solution until the volume doubled. In a separate 10 L 3-neck round bottom flask was added solid NH₄Cl (87 g) and MTBE (5.0 L) and the mixture was cooled to −5° C. At this time, 555 mL of the previously prepared concentrated NH₄OH solution was added to this mixture followed by a slow addition of commercial grade sodium hypochlorite solution (2.0 L) over 60 minutes. After the addition was complete, the reaction was stirred at −5° C. for additional 30 minutes. The MTBE layer was separated and washed with brine (720 mL) and was dried over Na₂SO₄ and decanted. To a separate 20 L round bottom flask was added methyl 4-bromo-1H-pyrrole-2-carboxylate (100 g, 0.49 mol) and DMF (2.0 L) under nitrogen. Then sodium hydride (60% dispersion in mineral oil, 24 g, 0.58 mol) was added to the reaction portionwise at room temperature. After the addition was complete, the reaction mixture was stirred at room temperature for 45 minutes, cooled to −20° C., and then the previously prepared chloramine solution was added in one portion to the reaction mixture. The resulting mixture was allowed to warm to ambient temperature and stirred for 30 minutes. The reaction mixture was washed with 10% aq. Na₂S₂O₃ solution (720 mL) and the organic layer was separated and washed again with water (720 mL) and brine (720 mL) before drying over Na₂SO₄, filtering and concentrating under vacuum to afford ~52 g of a semi-solid as the crude product. To this material was added toluene (1.2 L) to give a homogeneous mixture. Methane sulfonic acid (60 g, 0.62 mol) was added dropwise and stirred for 30 minutes. The resulting precipitated solid was collected by vacuum filtration and was rinsed with additional toluene and dried to yield 139 g (90%) of the methane sulfonic acid salt of the title compound. HPLC (condition S): retention time=8.922 min. LCMS (condition A): m/z 218.0 −ve. H¹ NMR (400 MHz, DMSO-d₆) δ ppm: 7.21 (1H, d, 2.0 Hz), 6.77 (1H, d, 2.0 Hz), 3.75 (3H, s), 2.50 (3H, s).

Step 4: 6-Bromo-4-hydroxypyrrolo[1,2-b]pyridazine-3-carbonitrile

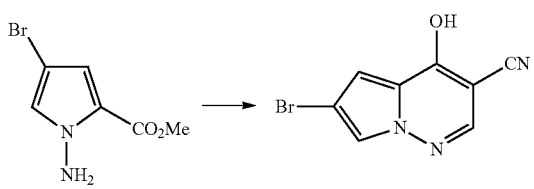 [SMILES: COC(=O)c1cc(Br)cn1N ; N#Cc1cnn2cc(Br)cc2c1O]

To a round bottom flask was added the methane sulfonic acid salt of methyl 1-amino-4-bromo-1H-pyrrole-2-carboxylate (140 g, 0.444 mol), isopropanol (700 mL) and 3,3-diethoxypropionitrile (128 g, 0.888 mol). The reaction mixture was slowly brought to 85° C. over 1 hour and then stirred at 85° C. for 2 hours. At this time, the ethanol that was generated and the isopropanol was removed under vacuum. The resulting residue was dissolved in CH₂Cl₂ and washed with water and brine solution. The organic layer was separated, dried over Na₂SO₄, filtered and concentrated. The resulting residue was transferred into a 2 L round bottom flask and dichloroethane (900 mL) and DBU (210 gm, 1.36 mol) were successively added to the reaction mixture. The resulting mixture was then stirred at 85° C. for 5 hours then cooled to rt and diluted with CH₂Cl₂ followed by washing with water then brine solution. The organic layer was separated, dried over Na₂SO4, filtered and concentrated. The resulting residue was purified by flash silica gel column chromatography to yield 58 g of title compound as the crude product containing residual DBU. This material was used as is in the next transformation. LCMS (condition A) m/z=236.0 −ve. H¹ NMR (400 MHz, DMSO-d₆) δ ppm: 9.76 (1H, br.s), 7.62 (1H, s), 7.39 (1H, d, 2.0 Hz), 6.43 (1H, d, 2.0 Hz). The product is contaminated with DBU and was used directly as such without further purification in the next step.

Step 5: 6-Bromo-4-chloropyrrolo[1,2-b]pyridazine-3-carbonitrile

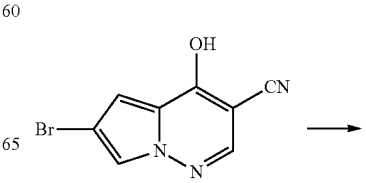

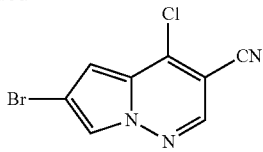

To a 25 mL round bottom flask was added 6-bromo-4-hydroxypyrrolo[1,2-b]pyridazine-3-carbonitrile (16.5 g, 69.47 mmol) and POCl₃ (85 mL, 0.88 mol) and the reaction mixture was stirred and heated at 75° C. for 3 hours. The POCl₃ was removed under vacuum and the resulting residue was dissolved in CH₂Cl₂. The solution was cooled to 0° C. and saturated aq. NaHCO₃ solution was added and the biphasic mixture was stirred vigorously while allowing to warm to rt. The organic layer was separated and concentrated and the obtained residue was purified by flash silica gel column chromatography to yield 8.5 g (29%) of the title compound as a yellow solid. HPLC (condition P): retention time=16.74 min. H¹ NMR (400 MHz, CDCl₃) δ ppm: 8.09 (1H, s), 7.94 (1H, d, 2.0 Hz), 7.06 (1H, d, 2.0 Hz).

Step 6: 6-Bromo-4-chloropyrrolo[1,2-b]pyridazine-3-carboxamide (Intermediate 2)

To a 50 mL round bottom flask was added 6-bromo-4-chloropyrrolo[1,2-b]pyridazine-3-carbonitrile (12 g, 0.046 mol) and concentrated H₂SO₄ (60 mL). The reaction mixture was heated at 55° C. for 2 hours then cooled to room temperature and slowly diluted with ice water to precipitate the product which was collected by vacuum filtration, rinsed with water and dried to yield 11.2 g (89%) of the title compound as a yellow solid. HPLC (condition P): retention time=7.780 min. LCMS (condition C): m/z 274.0, 276.0 –ve. H¹ NMR (400 MHz, DMSO-d₆) δ ppm: 8.32 (2H, s), 8.05 (1H, s), 7.90 (1H, s), 7.01 (1H, s).

Intermediate 3

(+/+(cis)-tert-butyl-4-amino-3-fluoropiperidine-1-carboxylate

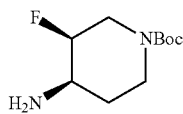 [SMILES: CC(C)(C)OC(=O)N1CC[C@@H](N)[C@@H](F)C1]

Step 1: tert-butyl 4-(trimethylsilyloxy)-5,6-dihydropyridine-1(2H)-carboxylate

To a stirred solution of tert-butyl 4-oxopiperidine-1-carboxylate (1.0 g, 5 mmol) in dry DMF (5 mL) under argon was added triethylamine (1.67 mL, 12 mmol) followed by TMSCl (0.95 mL, 7.5 mmol), and the reaction mixture was stirred at 80° C. for 16 h under argon. The reaction mixture was diluted with hexane (10 mL) and washed with cold saturated sodium bicarbonate (3×10 mL). The organic layer was dried over anhyd. Na₂SO₄ and concentrated under vacuum. The crude product obtained was purified by flash chromatography to give the title compound as a colorless oil (1.2 g, 88%). LCMS (Condition D): m/z 272 +ve with retention time=2.18 min. ¹H-NMR (400 MHz, CDCl₃): δ ppm: 4.80 (s, 1H), 3.88 (bs, 1H), 3.52-3.55 (t, J=6 Hz, 2H), 2.11 (bs, 2H), 1.47 (s, 9H), 0.20 (s, 9H).

Step 2: (+/–)-tert-butyl 3-fluoro-4-oxopiperidine-1-carboxylate

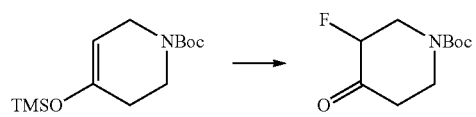

To a stirred solution of tert-butyl 4-(trimethylsilyloxy)-5,6-dihydropyridine-1(2H)-carboxylate (0.5 g, 1.84 mmol) in dry acetonitrile (5.0 mL) was added SelectFluor (0.654 g, 1.84 mmol), and the reaction mixture was stirred for 75 minutes. At this time, the reaction mixture was diluted with ethyl acetate (50 mL) and washed with brine (50 mL), dried over anhyd. Na₂SO₄ and concentrated under vacuum to give the title compound (0.25 g, 62%) which was used as obtained for the next transformation. LCMS (Condition D): m/z 218.2 +ve with retention time=1.51 min. ¹H-NMR (400 MHz, CDCl₃) δ ppm: 4.30-4.42 (m, 1H), 3.72-3.84 (m, 1H), 3.42-3.58 (m, 3H), 1.93-1.97 (m, 1H), 1.70-1.74 (m, 1H), 1.46 (s, 9H). ¹⁹F-NMR (400 MHz in CDCl₃): δ ppm: –203.24 (1F).

Step 3: (+/+)-(cis)-tert-butyl-4-(benzylamino)-3-fluoropiperidine-1-carboxylate and (+/–)-(trans)-tert-butyl-4-(benzylamino)-3-fluoropiperidine-1-carboxylate

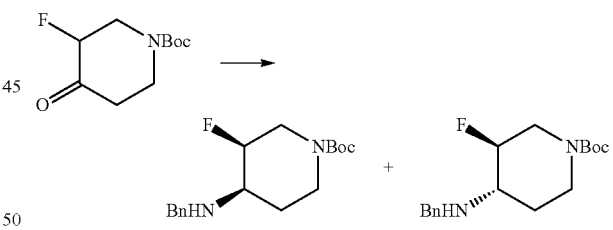

A mixture of (+/–)-tert-butyl 3-fluoro-4-oxopiperidine-1-carboxylate (0.33 g, 1.52 mmol), benzylamine (0.16 mL, 1.52 mmol) and sodium triacetoxyborohydride (0.382 g, 1.8 mmol) in dry 1,2-dichloroethane (6 mL) was stirred at room temperature for 2 h. The reaction mixture was quenched with saturated aq. K₂CO₃ solution (25 mL) and extracted with ethyl acetate (2×40 mL). The combined organic extracts were dried over anhyd. Na₂SO₄ and concentrated under vacuum. The crude product obtained was purified by flash chromatography to give the cis isomer of the title compound (200 mg, 42.6%) as the major product and the trans isomer of the title compound (20 mg, 4.26%) as the minor product. Cis isomer: HPLC (condition D): retention time=10.20 min. LCMS (condition E): m/z 308.4 +ve with retention time=1.84 min. ¹H-NMR (400 MHz, CDCl₃) δ ppm: 7.32-7.37 (m, 4H), 7.24-7.29 (m, 2H), 4.69-4.82 (m, 1H), 4.32 (s, 1H), 4.11-4.16

(m, 1H), 3.88 (s 2H), 2.91-3.04 (dd, J=35.6 Hz, J=14 Hz, 1H), 2.66-2.80 (m, 2H), 1.78 (bs, 1H), 1.63-1.72 (m, 1H), 1.47 (s, 9H). $^{19}$F-NMR (400 MHz in CDCl$_3$): δ ppm: −204.51 (1F). Trans isomer: HPLC (condition D): retention time=11.05 min. LCMS (condition E): m/z 308.4 +ve with retention time=1.99 min. $^1$H-NMR (400 MHz, CDCl$_3$) δ ppm: 7.31-7.37 (m, 4H), 7.25-7.28 (m, 1H), 4.25-4.30 (m, 2H), 3.89-3.93 (d, J=13.6 Hz, 2H), 2.93 (bs, 1H), 2.80-2.89 (m, 2H), 1.96-2.01 (m, 1H), 1.48 (s, 9H), 1.37-1.40 (d, J=13 Hz, 1H). $^{19}$F-NMR (400 MHz in CDCl$_3$): δ ppm: −189.58 (1F).

Step 4: (+/−)-(cis)-tert-butyl-4-amino-3-fluoropiperidine-1-carboxylate (Intermediate 3)

A mixture of (+/−)-(cis)-tert-butyl-4-(benzylamino)-3-fluoropiperidine-1-carboxylate (100 mg, 0.32 mmol) and 10% Pd/C (10 mg) in methanol (20 mL) was stirred under a balloon of hydrogen for 2 h at room temperature. The reaction mixture was purged with argon, filtered over Celite, rinsed with methanol (10 mL) and the resulting filtrate was concentrated under vacuum to give the title compound as a colorless oil (60 mg, 85%). $^1$H-NMR (400 MHz, CDCl$_3$) δ ppm: 4.49-4.61 (d, J=48.4 Hz, 1H), 4.30 (s, 1H), 4.07 (s, 1H), 2.84-3.08 (m, 3H), 1.67-1.69 (m, 2H), 1.47 (s, 9H), 1.32 (s, 2H). $^{19}$F-NMR (400 MHz in CDCl$_3$): δ ppm: −205.75-206.03 (1F).

Intermediate 4

4-fluoro-4-methyltetrahydrofuran-3-amine

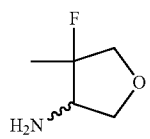

Step 1: (+/−)-trans-4-aminotetrahydrofuran-3-ol

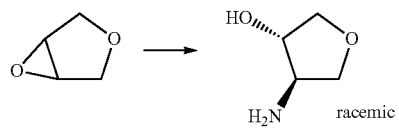 [SMILES: C1OCC2OC12 ; N[C@@H]1COC[C@H]1O]

3,6-dioxabicyclo[3.1.0]hexane (5.20 g, 60.4 mmol) was added to a 7 M methanol solution of ammonia (40 mL, 280 mmol) in a steel bomb. The container was sealed, heated in a 80° C. oil bath for 18 h, cooled with an ice-water bath and opened. The mixture was concentrated to give trans-4-aminotetrahydrofuran-3-ol as light brown liquid. $^1$H NMR is consistent with the desired product, but contaminated with impurities. The crude material was taken to the next reaction without purification.

Step 2: (+/−)-benzyl trans-4-hydroxytetrahydrofuran-3-ylcarbamate

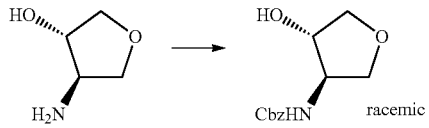 [SMILES: N[C@@H]1COC[C@H]1O ; O=C(N[C@@H]1COC[C@H]1O)OCc1ccccc1]

A mixture of the crude trans-4-aminotetrahydrofuran-3-ol (from Step 1), sodium carbonate (7.68 g, 72.5 mmol), tetrahydrofuran (100 mL) and water (100 mL) was cooled to 0° C. and stirred vigorously. Benzyl chloroformate (9.48 mL, 66.4 mmol) was added dropwise. The resulting mixture was stirred at room temperature for 2 h. The organic solvent was removed in vacuo. The aqueous residue was diluted with water (50 mL) and extracted with ethyl acetate (3×70 mL). The combined extracts were dried (MgSO4) and concentrated. Silica gel chromatography, eluting with 30-100% ethyl acetate in hexanes, gave benzyl trans-4-hydroxytetrahydrofuran-3-ylcarbamate as a white solid (8.43 g, 59% yield for 2 steps). 1H NMR (400 MHz, chloroform-d) δ ppm 7.28-7.51 (5 H, m), 5.11 (2 H, br. s.), 4.92 (1 H, br. s.), 4.32 (1 H, br. s.), 3.93-4.17 (3 H, m), 3.50-3.80 (2 H, m), 2.69 (1 H, br. s.); MS (ES+) m/z: 238.1 (M+H); LC retention time: 2.595 min (analytical HPLC Method H).

Step 3: (+/−)-benzyl 4-oxotetrahydrofuran-3-ylcarbamate

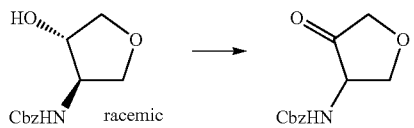 [SMILES: O=C(N[C@@H]1COC[C@H]1O)OCc1ccccc1 ; O=C(NC1COCC1=O)OCc1ccccc1]

Dimethyl sulfoxide (3.54 mL, 49.8 mmol) was added dropwise over 10 min to a vigorously stirred mixture of a 2 M dichloromethane solution of oxalyl chloride (12.46 mL, 24.91 mmol) and dichloromethane (40 mL) at −78° C. After another 15 min at −78° C., a solution of benzyl trans-4-hydroxytetrahydrofuran-3-ylcarbamate (3.94 g, 16.61 mmol, from Step 2) in dichloromethane (20 mL) was added dropwise over 15 min. After 30 min at −78° C., the mixture was diluted with dichloromethane (20 mL). Triethylamine (9.26 mL, 66.4 mmol) was added. The mixture became a thick slurry (a large stir bar was necessary for efficient stirring). The mixture was stirred at −78° C. for 30 min, at ambient temperature for 40 min, quenched with water (150 mL) and extracted with dichloromethane (3×100 mL). The combined extracts were dried (MgSO4) and concentrated. Silica gel chromatography, eluting with 20-50% ethyl acetate in hexanes, gave benzyl 4-oxotetrahydrofuran-3-ylcarbamate as tan solid (3.579 g, 92% yield). 1H NMR (400 MHz, chloroform-d) δ ppm 7.28-7.47 (5 H, m), 5.21 (1H, br. s.), 5.01-5.16 (2 H, m), 4.69 (1 H, t, J=8.58 Hz), 4.15-4.31 (2 H, m), 3.92 (1 H, d, J=17.61 Hz), 3.79 (1 H, t, J=9.57 Hz).

Step 4: (+/−)-benzyl 4-hydroxy-4-methyltetrahydrofuran-3-ylcarbamate

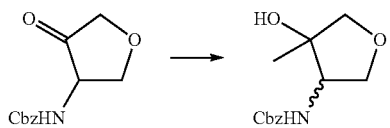 [SMILES: O=C(NC1COCC1=O)OCc1ccccc1 ; CC1(O)COCC1NC(=O)OCc1ccccc1]

A 3 M ether solution of methylmagnesium bromide (4.07 mL, 12.20 mmol) was added dropwise to a solution of benzyl 4-oxotetrahydrofuran-3-ylcarbamate (1.305 g, 5.55 mmol, from Step 3) in tetrahydrofuran (50 mL) at 0° C. Gas evolution was observed during the addition, indicating formation of methane. After 1 h at 0° C., the mixture was quenched with saturated ammonium chloride (75 mL) and extracted with ethyl acetate three times. The combined extracts were dried (MgSO4) and concentrated. Silica gel chromatography, eluting with 20-70% ethyl acetate in hexanes, gave impure material. 1H NMR showed presence of the desired product. The impure material was combined with the material from another run (from 2.18 g of ketone starting material) and taken to the next reaction without purification.

Step 5: benzyl 4-fluoro-4-methyltetrahydrofuran-3-ylcarbamate

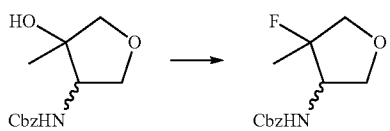 [SMILES: CC1(O)COCC1NC(=O)OCc1ccccc1 ; CC1(F)COCC1NC(=O)OCc1ccccc1]

(Diethylamino)sulphur trifluoride (2.103 mL, 15.92 mmol) was added dropwise to a solution of impure benzyl 4-hydroxy-4-methyltetrahydrofuran-3-ylcarbamate (2.00 g, from Step 4) in dichloromethane (50 mL) at −78° C. After 45 min at −78° C., the mixture was quenched with saturated sodium bicarbonate (100 mL) and allowed to warm to room temperature. After separation of the two phases, the aqueous phase was extracted with dichloromethane (3×50 mL). The combined extracts were dried (MgSO4) and concentrated. The mixture was purified by silica gel chromatography, eluting with 10-50% ethyl acetate in hexanes. None of the fractions were found to be free of impurities. All fractions containing the desired product were combined to give impure benzyl 4-fluoro-4-methyltetrahydrofuran-3-ylcarbamate (597 mg). The mixture was taken to the next step without purification.

Step 6: (+/−)-4-fluoro-4-methyltetrahydrofuran-3-amine (Intermediate 4)

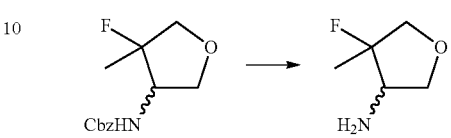

A mixture of crude benzyl 4-fluoro-4-methyltetrahydrofuran-3-ylcarbamate (0.597 g, from Step 5), 10% palladium on carbon (0.200 g), 1 N hydrochloric acid (5 mL, 5.00 mmol) and methanol (20 mL) was purged with hydrogen and reacted with 40 psi hydrogen using a Parr Shaker for 2.5 h. The mixture was filtered through a celite pad and the pad rinsed with methanol. The filtrate was concentrated to give crude 4-fluoro-4-methyltetrahydrofuran-3-amine hydrochloride as a tan solid (363 mg). 1H and F NMR showed patterns consistent with the desired product, as a ca. 2:1 mixture of two diastereomers. This material was taken to the next reaction without further purification.

Intermediate 5 (Racemic)

(+/−)-(cis)-benzyl 3-amino-4-methylpyrrolidine-1-carboxylate

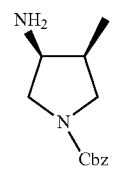 [SMILES: C[C@H]1CN(C(=O)OCc2ccccc2)C[C@H]1N]

Step 1: benzyl 6-oxa-3-azabicyclo[3.1.0]hexane-3-carboxylate

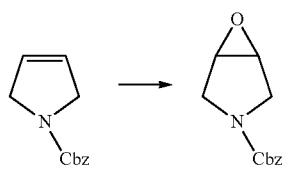 [SMILES: O=C(OCc1ccccc1)N1CC=CC1 ; O=C(OCc1ccccc1)N1CC2OC2C1]

To solution of benzyl 2,5-dihydro-1H-pyrrole-1-carboxylate (10.0 g, 49.2 mmol) in dichloromethane (197 mL) at 0° C. was added m-CPBA (16.98 g, 98 mmol) in several portions and the resulting mixture was allowed to warm to rt and stir overnight. The resulting white heterogeneous mixture obtained was diluted with dichloromethane (150 mL) and aq. sat. sodium bicarbonate (150 mL). The mixture was stirred and the resulting layers were separated and the organic portion was washed successively with aq. sat. sodium bicarbonate (150 mL), water, brine, before drying over anhyd. sodium sulfate, filtering and concentrating in vacuo to a colorless oil (~14 g). This crude material was subjected to purification by preparative chromatography using Hex/EtOAc mixtures as the eluant and an 80 g silica gel cartridge. Fractions containing the major product were combined and concentrated to afford the title compound (9.60 g, 43.8 mmol, 89%) as a colorless oil. LCMS: 220.2 (M+H)+; $^1$H NMR (400 MHz, METHANOL-$d_4$): δ 7.41-7.31 (m, 4H), 5.14 (d, J=1.1 Hz, 2H), 3.84-3.74 (m, 4H), 3.42 (t, J=13.8 Hz, 2H).

Step 2: (+/−)-(trans)-benzyl 3-hydroxy-4-methylpyrrolidine-1-carboxylate

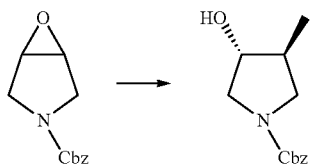 [SMILES: O=C(OCc1ccccc1)N1CC2OC2C1 ; C[C@H]1CN(C(=O)OCc2ccccc2)C[C@@H]1O]

To solution of benzyl 6-oxa-3-azabicyclo[3.1.0]hexane-3-carboxylate (9.6 g, 43.8 mmol) in THF (150 mL) was added copper cyanide (3.92 g, 43.8 mmol) and the resulting suspension was cooled to −20° C. with dry ice-ice-water-acetone bath. Methylmagnesium bromide (3 M in diethylether) (29.2 mL, 88 mmol) was added via syringe dropwise and the resulting mixture was stirred at this temperature for 1 h. At this time, TLC analysis of the resulting slurry (after quenching an aliquot with MeOH) indicated total comsumption of substrate to give a single, more polar component. At this time, the reaction was carefully quenched at −20° C. by a slow dropwise addition of 50 mL of sat. aq. ammonium chloride. The cooling bath was removed and the mixture was allowed to stir vigorously for 1 h while warming to rt. Solid was removed by vacuum filtration through Celite and the filter cake was rinsed with dichloromethane (80 mL×3). The resulting two layers of the filtrate were separated and the aqueous portion was extracted with dichloromethane (80 mL). The combined organic portions were washed with brine and dried over magnesium sulfate, filtered and concentrated to afford the title compound as a clear oil (9.2 g, 39.1 mmol, 89% yield). HPLC (method B) retention time=2.64 min. and LCMS (m+1)=236.2.

Step 3: (+/−)-(trans)-benzyl 3-methyl-4-(tosyloxy)pyrrolidine-1-carboxylate

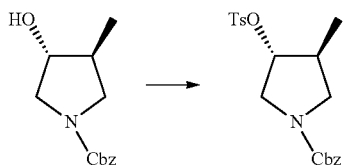 [SMILES: C[C@H]1CN(C(=O)OCc2ccccc2)C[C@@H]1O ; Cc1ccc(S(=O)(=O)O[C@H]2CN(C(=O)OCc3ccccc3)C[C@@H]2C)cc1]

(+/−)-(trans)-benzyl 3-hydroxy-4-methylpyrrolidine-1-carboxylate (9.2 g, 39.1 mmol) in pyridine (50 mL) at 5° C. was added tosyl chloride (9.69 g, 50.8 mmol) in one portion and the resulting mixture was allowed to warm to rt and stir overnight. The reaction mixture was concentrated and the residue was taken up in dichloromethane (400 mL) and washed with water (50 mL×2), 0.5 N HCl (50 mL×2), water, sat aq. sodium bicarbonate (50 mL×2), brine, then dried over magnesium sulfate, filtered and concentrated to give a dark oil as the crude title compound which was used directly without any further purification. HPLC (method B) retention time=3.60 min. LCMS (m+1)=390.

Step 4: (+/−)-(cis)-benzyl 3-azido-4-methylpyrrolidine-1-carboxylate

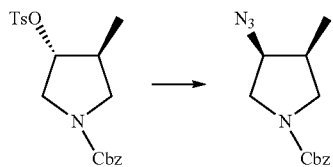 [SMILES: Cc1ccc(S(=O)(=O)O[C@H]2CN(C(=O)OCc3ccccc3)C[C@@H]2C)cc1 ; C[C@H]1CN(C(=O)OCc2ccccc2)C[C@H]1N=[N+]=[N-]]

(+/−)-(trans)-benzyl 3-methyl-4-(tosyloxy)pyrrolidine-1-carboxylate (5.00 g, 12.84 mmol) and sodium azide (2.087 g, 32.1 mmol) in DMF (10 mL) was heated under argon at 85° C. for 18 h. The resulting mixture was cooled and diluted with EtOAc and sat. sodium bicarbonate, washed with water, brine, dried over magnesium sulfate, filtered and concentrated to give a tan oil which was purified via preparative chromatography using Hexanes/EtOAc mixtures as the eluant and 40 g silica cartridge. Fractions containing the major product were combined and concentrated to afford the title compound as a near colorless oil (2.01 g, 7.72 mmol, 60%). HPLC (method B) retention time=3.30 min. LCMS (m+Na)=283.2. $^1$H NMR (400 MHz, CHLOROFORM-d) δ 7.41-7.30 (m, 5H), 5.15 (d, J=6.2 Hz, 2H), 4.00 (t, J=4.3 Hz, 1H), 3.76-3.55 (m, 3H), 3.16-3.02 (m, 1H), 2.47-2.30 (m, 1H), 1.13 (t, J=7.0 Hz, 3H).

Step 5: (+/−)-(cis)-benzyl 3-amino-4-methylpyrrolidine-1-carboxylate (Intermediate 5)

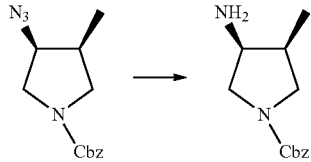 [SMILES: C[C@H]1CN(C(=O)OCc2ccccc2)C[C@H]1N=[N+]=[N-] ; C[C@H]1CN(C(=O)OCc2ccccc2)C[C@H]1N]

To solution of (+/−)-(cis)-benzyl 3-azido-4-methylpyrrolidine-1-carboxylat (2.00 g, 7.68 mmol) in acetonitrile (30 mL) and water (3 mL) was added triphenylphosphine (2.42 g, 9.22 mmol) in one portion as solid and the resulting mixture was stirred at rt for 30 min then heated to 60° C. overnight. The resulting mixture was concentrated and taken up in diethyl ether (300 mL), extracted with aq 2N HCl (30 mL×4). The combined aqueous washes were washed with diethyl ether, then the aqueous portion was cooled with ice-bath and was made basic by slowly adding 2N aq NaOH to pH>10. The aqueous mixture was extracted with ether (80 mL×4) and the combined ether extracts were washed with brine, dried over magnesium sulfate, filtered and concentrated to dryness to afford the title compound as a tan oil (1.67 g, 7.13 mmol, 93%). HPLC (method B) retention time=1.51 min. LCMS (m+1)=235.2. $^1$H NMR (400 MHz, METHANOL-$d_4$) δ 7.42-7.32 (m, 4H), 5.14 (s, 2H), 3.65-3'50 (m, 2H), 3.43 (td, J=5.2, 3.4 Hz, 1H), 3.32-3.28 (m, 1H), 3.25-3.14 (m, 1H), 2.33 (dsxt, J=13.7, 7.0 Hz, 1H), 1.07 (dd, J=6.8, 3.3 Hz, 3H).

Intermediate 5 (Enantiopure)

(3S,4S)-benzyl 3-amino-4-methylpyrrolidine-1-carboxylate

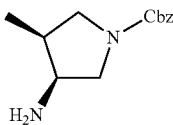

Step 1: benzyl 6-oxa-3-azabicyclo[3.1.0]hexane-3-carboxylate

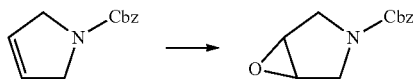 [SMILES: O=C(OCc1ccccc1)N1CC=CC1 ; O=C(OCc1ccccc1)N1CC2OC2C1]

To a 1 L RB flask equipped with magnetic stirring bar was added benzyl 2,5-dihydro-1H-pyrrole-1-carboxylate (25 g, 123 mmol) and $CH_2Cl_2$ (246 ml). The resulting solution was cooled in an ice bath to 0° C., whereupon mCPBA (42.5 g, 246 mmol) was added in three portions over ~15 min. The resulting slurry was naturally warmed up to rt over 2 days. LCMS indicates a complete reaction. The reaction was worked up as follows: the heterogeneous mixture was cooled to −15° C. for 1 hour, filtered to remove the solid which was rinsed with cold DCM. The resulting filtrate was washed with 1N aq. NaOH (4×100 mL), water (100 mL) and brine, then dried with anhydrous sodium sulfate. DCM phase was concentrated to benzyl 6-oxa-3-azabicyclo[3.1.0]hexane-3-carboxylate (24.5 g, 91% yield) as light yellow oil. $^1$H NMR (400 MHz, CHLOROFORM-d) δ ppm 7.31-7.44 (5 H, m), 5.08-5.21 (2 H, m), 3.90 (2 H, dd, J=19.70, 12.65 Hz), 3.65-3.77 (2 H, m), 3.42 (2 H, ddd, J=12.76, 6.16, 1.10 Hz); LCMS (Chromolith RP-18e 2.0×50 mm, 0.8 mL/min, Solvent A: 10% MeOH/water with 0.1% TFA, Solvent B: 90% MeOH/water with 0.1% TFA, gradient with 0-100% B over 4 minutes) retention time: 2.41 min; MS (ES+) m/z: 242.0 (M+Na$^+$);

Step 2: (3R,4S)-benzyl 3-hydroxy-4-methylpyrrolidine-1-carboxylate

3M methylmagnesium bromide in ether (99 ml, 296 mmol) was added dropwise over 1 hour to a suspension of benzyl 6-oxa-3-azabicyclo[3.1.0]hexane-3-carboxylate (26 g, 119 mmol) and copper bromide-dimethyl sulfide complex (24.38 g, 119 mmol) in anhydrous THF (250 ml) at −40° C. under a nitrogen atmosphere. The reaction was allowed to stir at this temperature for an additional 1 hour before cautiously quenching of the reaction using 125 mL sat. ammonium chloride. The reaction was then allowed to warm to rt and diluted with water (125 mL), then extracted with ethyl acetate (3×150 mL). Ethyl acetate phases were combined, washed with brine, then dried with $Na_2SO_4$. After concentration, the crude material was purified by flash chromatography. (+/−)-benzyl 3-hydroxy-4-methylpyrrolidine-1-carboxylate (24.5 g, 104 mmol, 88% yield) was obtained as light yellow oil. $^1$H NMR (400 MHz, CHLOROFORM-d) δ ppm 7.28-7.46 (5 H, m), 5.14 (2 H, s), 3.93-4.05 (1 H, m), 3.63-3.78 (2 H, m), 3.25-3.43 (1 H, m), 3.12 (1 H, ddd, J=13.26, 10. This material was resolved using the following chiral SFC conditions: column. Chiralpak AD-H 5×25 cm, 5 μm, Column Temp. 40° C., Flow rate: 290 mL/min, Mobile Phase: CO2/MeOH=82/18, Injection Volume: 2.5 mL (Conc. 118 mg/mL), detector wavelength: 212 nm. The isolated isomers were named "Pk1" and "Pk2" in the elution order. Fractions containing Pk2 were concentrated to afford 10 g of (3R,4S)-benzyl 3-hydroxy-4-methylpyrrolidine-1-carboxylate as a yellow oil. 84, 5.17 Hz), 2.06-2.26 (1 H, m), 1.90 (1 H, d, J=8.36 Hz), 1.03 (3 H, dd, J=6.71, 5.39 Hz); LCMS (Chromolith RP-18e 2.0×50 mm, 0.8 mL/min, Solvent A: 10% MeOH/water with 0.1% TFA, Solvent B: 90% MeOH/water with 0.1% TFA, gradient with 0-100% B over 4 minutes) retention time: 2.56 min; MS (ES+) m/z: 236.0 (M+H$^+$); HPLC retention time: 3.028 min (analytical HPLC Method H). Chiral purity: 99.9% ee (chiral HPLC conditions: column. Chiralpak AD-H (25×0.46 cm, 5 μm), 30% MeOH in CO2, 3 mL/min, 40° C., 200-400 nm, 100 bars).

Step 3: (3S,4R)-benzyl 3-methyl-4-(tosyloxy)pyrrolidine-1-carboxylate

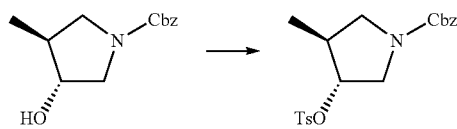 [SMILES: C[C@H]1CN(C(=O)OCc2ccccc2)C[C@@H]1O ; Cc1ccc(S(=O)(=O)O[C@H]2CN(C(=O)OCc3ccccc3)C[C@@H]2C)cc1]

(3R,4S)-benzyl 3-hydroxy-4-methylpyrrolidine-1-carboxylate (19.6 g, 83 mmol) was dissolved in pyridine (83 ml). To the above solution, Ts-Cl (22.2 g, 117 mmol) was added in portions at rt. After overnight stirring, the reaction mixture was concentrated in vacuo to remove pyridine. The residue was quenched with ice water (200 mL), extracted with ethyl acetate (3×150 mL). The combined ethyl acetate phase was washed with water, 1N HCl, water and sat. NaHCO$_3$, then dried with Na$_2$SO$_4$. After concentration, (3S,4R)-benzyl 3-methyl-4-(tosyloxy)pyrrolidine-1-carboxylate (30 g, 92% yield) was obtained as light yellow oil. $^1$H NMR (400 MHz, CHLOROFORM-d) δ ppm 7.76-7.83 (2 H, m), 7.30-7.40 (7 H, m), 5.11 (2 H, s), 4.57-4.64 (1 H, m), 3.56-3.73 (2 H, m), 3.38-3.54 (1 H, m), 3.08-3.19 (1 H, m), 2.33-2.55 (4 H, m), 0.97 (3 H, dd, J=14.86, 7.15 Hz); LCMS (Chromolith RP-18e 2.0×50 mm, 0.8 mL/min, Solvent A: 10% MeOH/water with 0.1% TFA, Solvent B: 90% MeOH/water with 0.1% TFA, gradient with 0-100% B over 4 minutes) retention time: 3.60 min; MS (ES+) m/z: 390 (M+H⁺);

Step 4: (3S,4S)-benzyl 3-azido-4-methylpyrrolidine-1-carboxylate

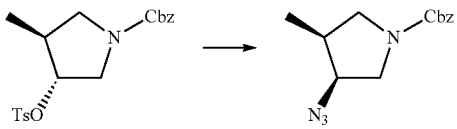 [SMILES: Cc1ccc(S(=O)(=O)O[C@H]2CN(C(=O)OCc3ccccc3)C[C@@H]2C)cc1 ; C[C@H]1CN(C(=O)OCc2ccccc2)C[C@H]1N=[N+]=[N-]]

(3S,4R)-benzyl 3-methyl-4-(tosyloxy)pyrrolidine-1-carboxylate (20 g, 51.4 mmol) was dissolved in DMF (42.8 ml). Sodium azide (5.68 g, 87 mmol) was added at rt and heated up to 85° C. overnight. LCMS shows a complete conversion. The reaction mixture was cooled to rt, quenched with ice water, extracted with ethyl acetate. Organic phases were combined, washed with water, brine, then dried with $Na_2SO_4$. After concentration, (3S,4S)-benzyl 3-azido-4-methylpyrrolidine-1-carboxylate (13 g, 97% yield) was obtained as a yellowish oil and used directly for the next reduction. ¹H NMR (400 MHz, CHLOROFORM-d) δ ppm 7.29-7.44 (5 H, m), 5.08-5.22 (2 H, m), 3.94-4.04 (1 H, m), 3.52-3.76 (3 H, m), 3.00-3.15 (1 H, m), 2.29-2.48 (1 H, m), 1.13 (3 H, t, J=7.04 Hz); LCMS (Chromolith RP-18e 2.0×50 mm, 0.8 mL/min, Solvent A: 10% MeOH/water with 0.1% TFA, Solvent B: 90% MeOH/water with 0.1% TFA, gradient with 0-100% B over 4 minutes) retention time: 3.41 min; MS (ES+) m/z: 261.0 (M+H⁺);

Step 5: (3S,4S)-benzyl 3-amino-4-methylpyrrolidine-1-carboxylate (Intermediate 5)

Triphenylphosphine (11.96 g, 45.6 mmol) was added to a stirred acetonitrile (164 ml) and water (16.44 ml) solution of benzyl 3-azido-4-methylpyrrolidine-1-carboxylate (11.3 g, 43.4 mmol). The reaction mixture was heated up to 60° C. overnight. The reaction mixture was concentrated. The resulting residue was diluted with 50 mL ice water, treated with 1N HCl (47.8 ml, 47.8 mmol). The aqueous acidic solution (pH 1) was extracted with EtOAc (4×100 mL) to remove $Ph_3P$ and $Ph_3PO$ by-products/impurities. The acidic aqueous portion containing the product was cooled in an ice bath. neutralized with 1N NaOH (52.1 ml, 52.1 mmol). The resulting cloudy mixture was then extracted with DCM (3×150 mL). The combined DCM phases were washed with brine, dried over anhydrous sodium sulfate. After concentration, (3S,4S)-benzyl 3-amino-4-methylpyrrolidine-1-carboxylate (9.8 g, 96% yield) was obtained as a light yellow oil. ¹H NMR (400 MHz, CHLOROFORM-d) δ ppm 7.31-7.47 (5 H, m), 5.09-5.23 (2 H, m), 3.42-3.69 (3 H, m), 3.12-3.38 (2 H, m), 2.17-2.36 (1 H, m), 1.31 (2 H, br), 1.06 (3 H, dd, J=6.82, 3.30 Hz); LCMS (Chromolith RP-18e 2.0×50 mm, 0.8 mL/min, Solvent A: 10% MeOH/water with 0.1% TFA, Solvent B: 90% MeOH/water with 0.1% TFA, gradient with 0-100% B over 4 minutes) retention time: 1.97 min; MS (ES+) m/z: 235.1 (M+H⁺);

Intermediate 6

(R)-tert-butyl 4-amino-3,3-dimethylpiperidine-1-carboxylate

Step 1: (R,E)-tert-butyl 3,3-dimethyl-4-(1-phenylethylimino)piperidine-1-carboxylate

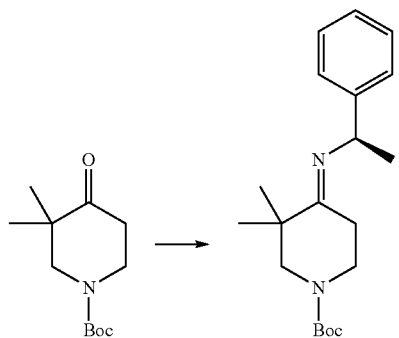 [SMILES: CC(C)(C)OC(=O)N1CCC(=O)C(C)(C)C1 ; C[C@@H](/N=C1\CCN(C(=O)OC(C)(C)C)CC1(C)C)c1ccccc1]

A solution of (R)-1-phenylethanamine (2.56 g, 21.12 mmol) and triethylamine (14.7 mL, 106 mmol) in dichloromethane (40 mL) was cooled in an ice bath and titanium tetrachloride (8.80 mL, 8.80 mmol) was added dropwise giving a light brown mixture. The cold bath was removed and tert-butyl 3,3-dimethyl-4-oxopiperidine-1-carboxylate (4.00 g, 17.60 mmol) was added as solid in one portion and the resulting mixture was allowed to stir at rt overnight. To the resulting mixture was added 75 mL of diethyl ether and the mixture was stirred at rt for 15 min then filtered through a pad of Celite to remove the solids and the filter cake was rinsed with additional ether (30 mL×2). The resulting clear yellow filtrate was concentrated on a rotovap to afford a yellow liquid as the title compound (5.80 g, 17.6 mmol, quantitative). This material was used directly without any further purification.

Step 2: (R)-tert-butyl 3,3-dimethyl-4-((R)-1-phenylethylamino)piperidine-1-carboxylate

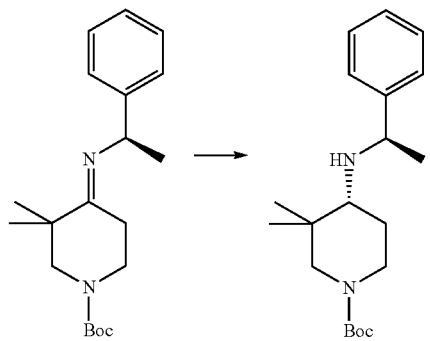 [SMILES: C[C@@H](/N=C1\CCN(C(=O)OC(C)(C)C)CC1(C)C)c1ccccc1 ; C[C@@H](N[C@@H]1CCN(C(=O)OC(C)(C)C)CC1(C)C)c1ccccc1]

Dissolved (R,E)-tert-butyl 3,3-dimethyl-4-(1-phenylethylimino)piperidine-1-carboxylate (5.80 g, 17.55 mmol) in ethanol (50 mL) and cooled to −78° C. then added sodium borohydride (0.332 g, 8.78 mmol) and let resulting mixture stir at −78° C. for 2 h. Then the mixture was cooled 2 N aq HCl (10 mL) was added dropwise slowly and the resulting mixture was allowed to stir vigorously for 30 min. The mixture was cooled and made basic by addition of 10% aq sodium carbonate and then concentrated to remove most of the ethanol. The resulting aqueous portion was extracted with EtOAc (3×100 mL) and the combined extracts were washed with brine, dried over anhyd. sodium sulfate, decanted and concentrated under vacuum to afford a yellow liquid as the crude product. This material was purified via preparative ISCO chromatography (Hex/EtOAc; 120 g silica gel column) and the fractions containing the major product were concentrated to afford the title compound as a near colorless oil (3.0 g, 9.0 mmol, 51%). HPLC (Method B) retention time=2.25 min. LCMS (m+1)= 333.2. $^1$H NMR (500 MHz, MeOD): δ ppm 7.31-7.42 (4 H, m), 7.22-7.29 (1 H, m), 3.88-3.98 (1 H, m), 3.83 (1 H, q, J=6.66 Hz), 3.63-3.72 (1 H, m), 2.49-2.85 (2 H, m), 2.34 (1 H, dd, J=10.82, 4.16 Hz), 1.47 (9H, s), 1.36 (3 H, d, J=6.66 Hz), 1.22-1.33 (2 H, m), 1.05 (3 H, s), 0.90 (3 H, s). Fractions containing a minor product believed to be the minor diastereomer were also concentrated to afford a clear oil. HPLC (Method B) retention time=2.50 min. LCMS (m+1)=333.2.

Step 3: (R)-tert-butyl 4-amino-3,3-dimethylpiperidine-1-carboxylate (Intermediate 6)

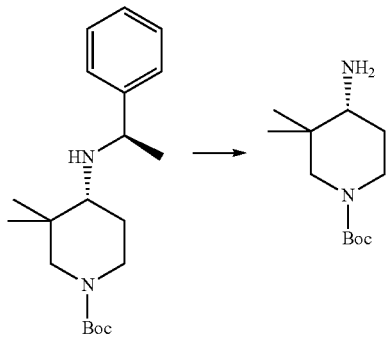 [SMILES: C[C@@H](N[C@@H]1CCN(C(=O)OC(C)(C)C)CC1(C)C)c1ccccc1 ; CC(C)(C)OC(=O)N1CC[C@@H](N)C(C)(C)C1]

A pressure bottle was charged with palladium on carbon (0.192 g, 0.180 mmol) and (R)-tert-butyl 3,3-dimethyl-4-((R)-1-phenylethylamino)piperidine-1-carboxylate (3.00 g, 9.02 mmol) in ethanol (60 mL) and the resulting mixture was shaken under 50 psi of hydrogen on a Parr apparatus. After 5 h, the catalyst was removed by filtration, rinsed with methanol, and the filtrate was concentrated in vacuo to afford the title compound as a clear oil (2.0 g, 8.76 mmol, 97%). Material was not further purified and was used directly in next transformation. $^1$H NMR (500 MHz, METHANOL-d$_4$) δ 4.07 (d, J=13.0 Hz, 1H), 3.78-3.62 (m, 1H), 3.01-2.62 (m, 2H), 2.56 (dd, J=11.1, 4.2 Hz, 1H), 1.74-1.63 (m, 1H), 1.51 (s, 9H), 1.49-1.43 (m, 1H), 1.00 (s, 3H), 0.88 (s, 3H).

Intermediate 7 tert-butyl 5-amino-4-methylhexahydrocyclopenta[c]pyrrole-2(1H)-carboxylate

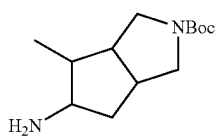 [SMILES: CC1C(N)CC2CN(C(=O)OC(C)(C)C)CC21]

Step 1: tert-butyl allyl(prop-2-yn-1-yl)carbamate

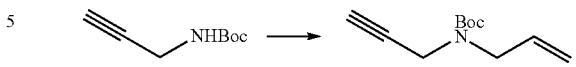

Sodium hydride (6.53 g, 163 mmol, 60% in mineral oil) was added in small portions over 1 min to a solution of tert-butyl prop-2-ynylcarbamate (19.5 g, 126 mmol) in N,N-dimethylformamide (300 mL) at room temperature. Formation of hydrogen bubbles was observed along with gentle warming of the resulting suspension. After 30 min at room temperature, the mixture was cooled to 0° C. Allyl bromide (13.05 mL, 151 mmol) was added dropwise. The mixture was stirred at 0° C. for 20 min and at ambient temperature for 2.5 h. The mixture was carefully quenched with water (400 mL), and extracted with ether (3×300 mL). The combined extracts were dried (MgSO$_4$) and concentrated. Silica gel chromatography, eluting with 0-10% ethyl acetate in hexanes, gave tert-butyl allyl(prop-2-yn-1-yl)carbamate as light tan liquid (23.3 g, 95% yield). 1H NMR (400 MHz, chloroform-d) δ ppm 5.67-5.89 (1 H, m), 5.08-5.28 (2 H, m), 3.71-4.21 (4 H, m), 2.18 (1 H, t, J=2.42 Hz), 1.47 (9 H, s).

Step 2: tert-butyl allyl(but-2-yn-1-yl)carbamate

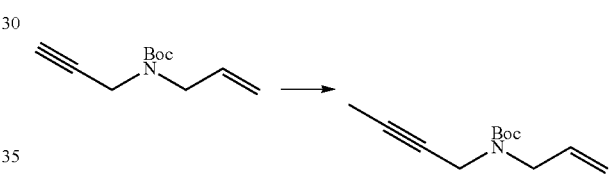

A 2.5 M hexane solution of n-butyllithium (40.8 mL, 102 mmol) was added dropwise over 30 min to a solution of tert-butyl allyl(prop-2-ynyl)carbamate (17.3 g, 89 mmol) in tetrahydrofuran (100 mL) at −10° C. After 5 min at −10° C., hexamethyl phosphoramide (17.73 mL, 102 mmol) and iodomethane (7.20 mL, 115 mmol) were added sequentially. The resultant mixture was stirred at −10° C. for 1 h, at ambient temperature for 1 h and quenched with saturated ammonium chloride (50 mL). After evaporation of the tetrahydrofuran solvent in vacuo, the residue was diluted with ethyl acetate (400 mL), washed with water, brine, dried (MgSO4) and concentrated. Silica gel chromatography, eluting with 0-100% dichloromethane in hexanes, gave tert-butyl allyl (but-2-yn-1-yl)carbamate (14.1 g, 76% yield). 1H NMR (400 MHz, chloroform-d) δ ppm 5.62-5.92 (1 H, m), 4.93-5.40 (2 H, m), 3.63-4.11 (4 H, m), 1.81 (3 H, s), 1.48 (9 H, s).

Step 3: tert-butyl 6-methyl-5-oxo-3,3a,4,5-tetrahydrocyclopenta[c]pyrrole-2(1H)-carboxylate

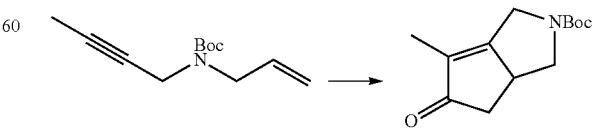

Dicobalt octacarbonyl (28.1 g, 82 mmol) was added to a solution of tert-butyl allyl(but-2-yn-1-yl)carbamate (16.4 g, 78 mmol) in dichloromethane (700 mL) at room temperature. The resulting mixture was and stirred under nitrogen for 1.5 h at room temperature, then cooled to 0° C. N-methylmorpholine-N-oxide (55.1 g, 470 mmol) was added in small portions over 1 h. The resultant mixture was stirred at 0° C. for 1 h, at ambient temperature for 2 h and filtered through a silica gel pad. The filter cake was washed with 1:1 mixture of ethyl acetate and hexanes until free of product. The filtrate was concentrated. Silica gel chromatography, eluting with 20-45% ethyl acetate in hexanes, gave tert-butyl 6-methyl-5-oxo-3,3a,4,5-tetrahydrocyclopenta[c]pyrrole-2(1H)-carboxylate (11.7 g, 63% yield). 1H NMR (400 MHz, chloroform-d) δ ppm 4.18 (2 H, d, J=16.29 Hz), 3.92-4.14 (1 H, m), 2.97-3.25 (1 H, m), 2.73-2.87 (1 H, m), 2.52-2.73 (1 H, m), 2.08-2.26 (1 H, m), 1.77 (3 H, s), 1.49 (9 H, s).

Step 4: tert-butyl 4-methyl-5-oxohexahydrocyclopenta[c]pyrrole-2(1H)-carboxylate

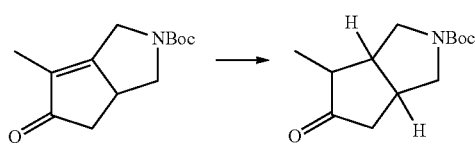 [SMILES: CC1=C2CN(C(=O)OC(C)(C)C)CC2CC1=O ; CC1C(=O)CC2CN(C(=O)OC(C)(C)C)CC21]

A mixture of tert-butyl 6-methyl-5-oxo-3,3a,4,5-tetrahydrocyclopenta[c]pyrrole-2(1H)-carboxylate (11.6 g, 48.9 mmol), 20% palladium hydroxide on carbon (3.43 g) in methanol (30 mL) and dichloromethane (30.0 mL) was stirred under 20 psi hydrogen for 3 h. The mixture was then filtered to remove the solid catalyst. The filtrate was concentrated. Silica gel chromatography, eluting with 5-60% ethyl acetate in hexanes, gave tert-butyl 4-methyl-5-oxohexahydrocyclopenta[c]pyrrole-2(1H)-carboxylate as a 3 to 1 mixture of endo- and exo-isomers (10.7 g, 91% yield).

Step 5: tert-butyl 5-(benzylamino)-4-methylhexahydrocyclopenta[c]pyrrole-2(1H)-carboxylate

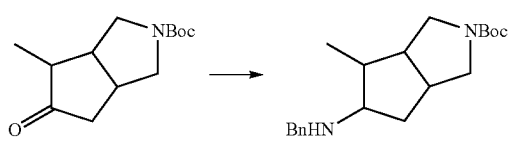

A solution of tert-butyl 4-methyl-5-oxohexahydrocyclopenta[c]pyrrole-2(1H)-carboxylate (10.7 g, 44.7 mmol) and benzyl amine (7.67 g, 71.5 mmol) in 1,2-dichloroethane (250 mL) was stirred at room temperature for 2 h. Anhydrous magnesium sulfate (20 g, 166 mmol) was added. The resultant suspension was stirred at room temperature for additional 2 h. Sodium triacetoxyborohydride (18.95 g, 89 mmol) was added. After 60 h at room temperature, the mixture was quenched with saturated sodium bicarbonate (100 mL) and extracted with ethyl acetate (3×150 mL). The combined organic extracts were washed with water, brine, dried (MgSO4) and concentrated. Silica gel chromatography, eluting with 0-8% methanol in dichloromethane, gave tert-butyl 5-(benzylamino)-4-methylhexahydrocyclopenta[c]pyrrole-2 (1H)-carboxylate as a mixture of stereoisomers (13.2 g), which was taken to the next reaction without separation.

Step 6: tert-butyl 5-amino-4-methylhexahydrocyclopenta[c]pyrrole-2(1H)-carboxylate (Intermediate 7)

A mixture of tert-butyl 5-(benzylamino)-4-methylhexahydrocyclopenta-[c]pyrrole-2(1H)-carboxylate (13.2 g, 39.9 mmol) and 20% palladium hydroxide on carbon (4.21 g, 5.99 mmol) was stirred under 30 psi hydrogen for 5 h. The mixture was filtered through a celite pad to remove the solid catalyst. The filter cake was rinsed with methanol. The filtrate was concentrated to give crude tert-butyl 5-amino-4-methylhexahydrocyclopenta[c]pyrrole-2(1H)-carboxylate (10.3 g) as an approximately 3:1:1 mixture of three isomers. The material was taken to the next step without further purification. MS (ES+) m/z: 241.2 (M+H).

Intermediate 8

(3R,4R)-tert-butyl 4-amino-3-ethylpiperidine-1-carboxylate

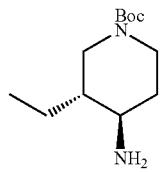

Step 1:
Benzylpiperidin-4-ylidene)-1-phenylethanamine

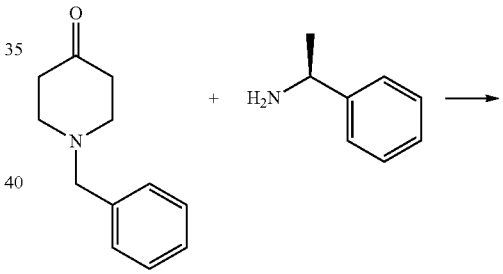

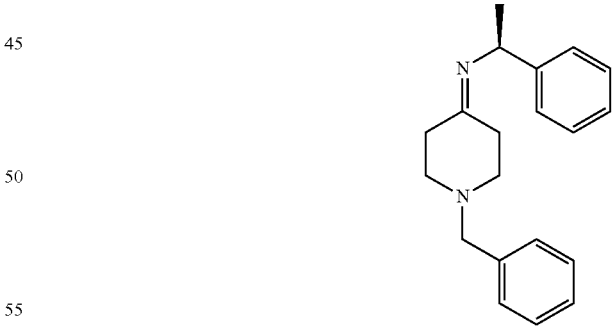

To a solution of (S)-1-phenylethanamine (1.921 g, 15.85 mmol) in benzene (8.81 ml) were added molecular sieves in water and 1-benzylpiperidin-4-one (2.50 g, 13.21 mmol). The reaction was stirred at room temperature for 5 hrs. The product mixture was filtered and concentrated under reduced pressure to give a yellow oil, which was standing under vacuum at 45° C. for 14 hrs to remove the residual reactant, yielding (S)—N-(1-benzylpiperidin-4-ylidene)-1-phenylethanamine (3.24 g, 11.08 mmol, 84.0% yield) as a yellow oil. 1H NMR (400 MHz, methanol-d4) δ 7.33-7.25 (m, 10H), 4.81-4.76 (m, 1H), 3.54 (s, 2H), 2.72-2.33 (m, 8H), 1.47 (d, J=6.6 Hz, 3H). LCMS (method K) m/z 291.3 ([M+H]⁺).

Step 2: (3R,4R)-1-benzyl-3-ethyl-N—((S)-1-phenylethyl)piperidin-4-amine

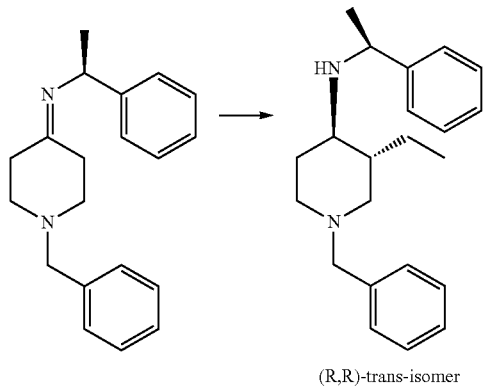 [SMILES: C[C@H](N=C1CCN(Cc2ccccc2)CC1)c1ccccc1 ; CC[C@@H]1CN(Cc2ccccc2)CC[C@H]1N[C@@H](C)c1ccccc1]

(R,R)-trans-isomer

To a solution of LDA (7.20 ml, 14.40 mmol) in THF (22.16 ml) cooled to −10° C. was added a THF (5 ml) solution of (S)—N-(1-benzylpiperidin-4-ylidene)-1-phenylethanamine (3.24 g, 11.08 mmol). The reaction was stirred for 30 minutes. Ethyl iodide (1.164 ml, 14.40 mmol) was added, and stirring was continued for 1 hr. The reaction solution was cooled to −78° C. Ethanol (22.16 ml) and sodium borohydride (0.545 g, 14.40 mmol) were added. Stirring was continued for 15 minutes. The reaction flask was transferred to a −10° C. bath and stirring was continued for 1 hr. The reaction was allowed to warm to room temperature, concentrated to half volume and quenched by dropwise addition of 6.0 N HCl until gas evolution ceased. The solution was diluted with water (10 ml), adjusted to pH12 with 6.0 N NaOH, and extracted with ethyl acetate (3×, 100 ml). The combined ethyl acetate extracts were dried with sodium sulfate, filtered, and concentrated to give a yellow oil. The crude product mixture was purified via medium pressure chromatography (silica gel column, EtOAc/hexanes eluent, 40-100% gradient elution). The 40% EtOAc/hexanes fraction yielded two cis-isomers, the fast eluting isomer (499.3 mg, 14.0% yield) and the slow eluting isomer (319.1 mg, 8.9% yield). The 100% EtOAc fraction yielded a single trans-isomer, (3R,4R)-1-benzyl-3-ethyl-N-((S)-1-phenylethyl)piperidin-4-amine (679.2 mg, 2.106 mmol, 19.0% yield) as a colorless oil. LCMS (method K) m/z 323.4 ([M+H]⁺).

Step 3: (3R,4R)-3-ethyl-N—((S)-1-phenylethyl)piperidin-4-amine

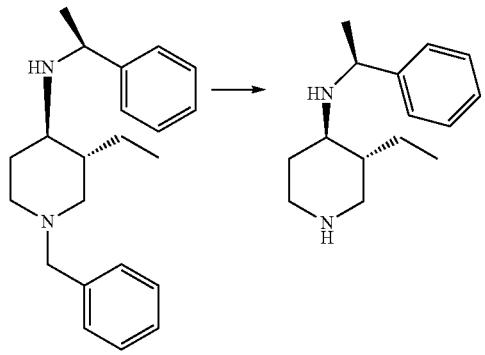 [SMILES: CC[C@@H]1CN(Cc2ccccc2)CC[C@H]1N[C@@H](C)c1ccccc1 ; CC[C@@H]1CNCC[C@H]1N[C@@H](C)c1ccccc1]

To a solution of (3R,4R)-1-benzyl-3-ethyl-N—((S)-1-phenylethyl)piperidin-4-amine (679.2 mg, 2.106 mmol) in 1,2-dichloroethane (3.50 ml) at 0° C. was added 1-chloroethyl chloroformate (0.276 ml, 2.53 mmol) dropwise. After stirring for 20 minutes, the ice-bath was removed and the reaction was heated to reflux for 1 hr. The reaction was cooled to room temperature and concentrated under reduced pressure. Methanol (10.5 ml) was added, and the reaction was heated to reflux for 2 hrs. After removal of the solvent, the residue was partitioned between ethyl acetate and water. The organic layer was washed with brine, dried with sodium sulfate, filtered, and concentrated under reduced pressure, yielding (3R,4R)-3-ethyl-N—((S)-1-phenylethyl)piperidin-4-amine (443 mg, 1.906 mmol, 91.0% yield) as a yellow oil. LCMS (Method K) m/z 233.3 ([M+H]⁺).

Step 4: (3R,4R)-tert-butyl 3-ethyl-4-(((S)-1-phenylethyl)amino)piperidine-1-carboxylate

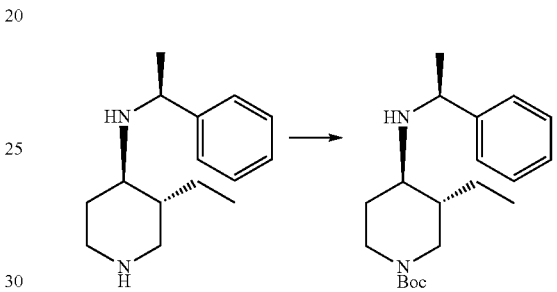

To a solution of (3R,4R)-3-ethyl-N—((S)-1-phenylethyl) piperidin-4-amine (443 mg, 1.906 mmol) in dichloromethane (6.4 ml) were added diisopropylethylamine (832 µl, 4.77 mmol) and di-tert-butyl dicarbonate (664 µl, 2.86 mmol). The reaction was stirred at room temperature for 2 hrs. After removal of the solvent, the residue was partitioned between ethyl acetate and water. The organic layer was washed with brine, dried with sodium sulfate, filtered and concentrated under reduced pressure. The crude product was purified via medium pressure chromatography (silica gel column, EtOAc/hexanes eluent, 0-100% gradient elution) to yield (3R,4R)-tert-butyl 3-ethyl-4-(((S)-1-phenylethyl)amino)piperidine-1-carboxylate (430.5 mg, 1.295 mmol, 67.9% yield) as a white solid. LCMS (method K) m/z 333.3 ([M+H]⁺).

Step 5: (3R,4R)-tert-butyl 4-amino-3-ethylpiperidine-1-carboxylate (Intermediate 8)

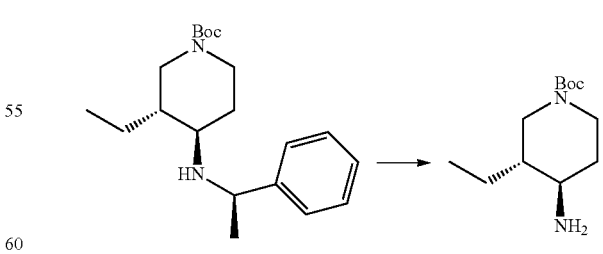

A flask was flushed with nitrogen and charged with 20% palladium hydroxide on carbon (91 mg, 0.647 mmol). A solution of (3R,4R)-tert-butyl 3-ethyl-4-(((R)-1-phenylethyl) amino)piperidine-1-carboxylate (430.5 mg, 1.295 mmol) in acetic acid (8.6 ml) was added. The flask was flushed with nitrogen, sealed, evacuated briefly, and charged with hydrogen. The mixture was stirred at room temperature for 14 hrs. The flask was evacuated, backfilled with nitrogen, and opened. The reaction mixture is filtered through celite. The filtrate was concentrated by azeotropical distillation with toluene (3×25 ml) under reduced pressure to remove the residual acetic acid, yielding (3R,4R)-tert-butyl 4-amino-3-ethylpiperidine-1-carboxylate, HOAc salt (351 mg, 1.217 mmol, 94.0% yield) as a white solid. $^1$H NMR (400 MHz, methanol-$d_4$) δ 4.16 (d, J=11.2 Hz, 1H), 4.07 (d, J=13.9 Hz, 1H), 3.03-2.85 (m, 2H), 2.56 (br. s., 1H), 2.02-1.94 (m, 1H), 1.92 (s, 3H), 1.77-1.66 (m, 1H), 1.53-1.36 (m, 10H), 1.32-1.16 (m, 1H), 1.00 (t, J=7.5 Hz, 3H).

Intermediate 9

(3S,4S)-benzyl 3-amino-4-ethylpyrrolidine-1-carboxylate

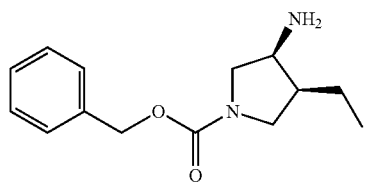 [SMILES: CC[C@H]1CN(C(=O)OCc2ccccc2)C[C@H]1N]

Step 1: (3S,4R)-benzyl 3-ethyl-4-hydroxypyrrolidine-1-carboxylate

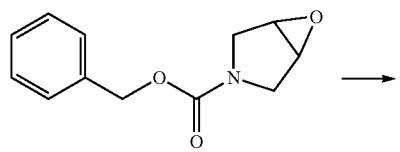

A mixture of benzyl 6-oxa-3-azabicyclo[3.1.0]hexane-3-carboxylate (4 g, 18.25 mmol) and Bromo(dimethylsulfide)copper(I) (3.75 g, 18.25 mmol) in Tetrahydrofuran (40 ml) was cooled to −30° C. A 3M solution of ethylmagnesium bromide (15.20 ml, 45.6 mmol) in Et$_2$O was added dropwise to the reaction mixture over 35 minutes, maintaining an internal temperature of at or below −30° C. After the addition was complete, the resulting reaction mixture was allowed to warm to −15° C. over 45 minutes. At this time, the reaction was checked by HPLC. The reaction mixture was allowed to gradually warm up to rt and HPLC indicated that the reaction was complete. The reaction mixture was diluted with EtOAc (50 mL). The reaction mixture was then cooled in an ice bath and was quenched by slow addition of sat'd aq ammonium chloride (~10 mL). The organic layer was separated and was washed with H$_2$O (20 ml). The organic layer was concentrated and the crude was purified by silica gel chromatography to give (3S,4R)-benzyl 3-ethyl-4-hydroxypyrrolidine-1-carboxylate (17.25 g, 69.2 mmol, 69.0% yield). LCMS: (M+23)=242, t=1.87 min.

Step 2: (3S,4R)-benzyl 3-ethyl-4-(tosyloxy)pyrrolidine-1-carboxylate

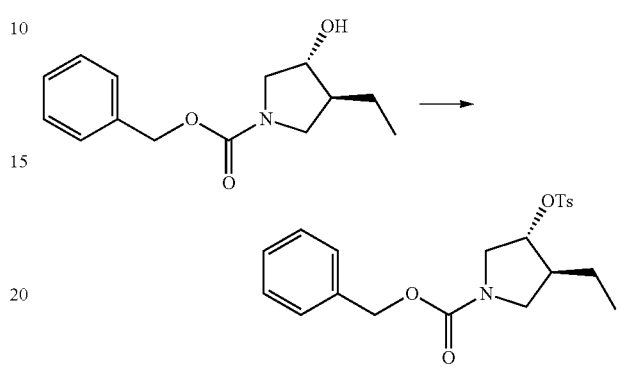

(3S,4R)-benzyl 3-ethyl-4-hydroxypyrrolidine-1-carboxylate (18.9 g, 76 mmol), 4-methylbenzene-1-sulfonyl chloride (21.68 g, 114 mmol) were dissolved in DCM (100 mL) and cooled in an ice bath. Added N,N-dimethylpyridin-4-amine (1.852 g, 15.16 mmol) and triethylamine (11.51 g, 114 mmol) and let the reaction mixture warm to RT overnight. The suspension was passed over a silica column and eluted with Heptanes/EA (9:1 to 4:1 mixtures) to give (3S,4R)-benzyl 3-ethyl-4-(tosyloxy)pyrrolidine-1-carboxylate (28.7 g, 71.1 mmol, 94% yield). LCMS:M+1=404, t=3.07 min.

Step 3: (3R,4S)-benzyl 3-azido-4-ethylpyrrolidine-1-carboxylate

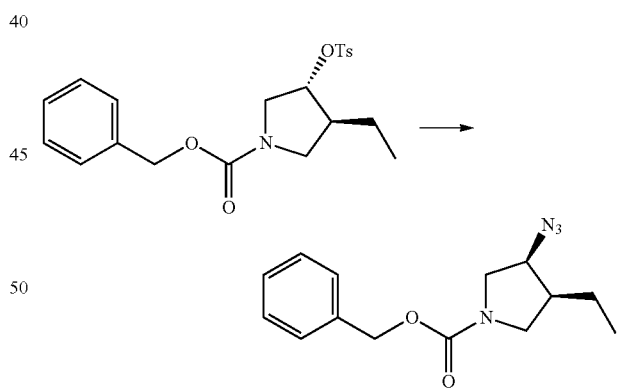

(3S,4R)-benzyl 3-ethyl-4-(tosyloxy)pyrrolidine-1-carboxylate (21.25 g, 52.7 mmol) in DMF (50 mL) was added to a solution of sodium azide (8.56 g, 132 mmol) in DMF (50 mL) and water (30 mL) and heated to a bath temp. of 100 degreees Celsius overnight. The reaction mixture was diluted with ethyl acetate/water and stirred. The organic layer was washed with water, dried (Na$_2$SO$_4$) and concentrated to give (3S,4S)-benzyl 3-azido-4-ethylpyrrolidine-1-carboxylate (14.5 g, 52.9 mmol, 100% yield). 1H NMR (400 MHz, chloroform-d) δ ppm 7.34-7.41 (5 H, m), 5.13-5.21 (2 H, m), 4.08-4.11 (1 H, m),
LCMS:M+23=299, t=2.15 min.

Step 4: (3S,4S)-benzyl 3-amino-4-ethylpyrrolidine-1-carboxylate (Intermediate 9)

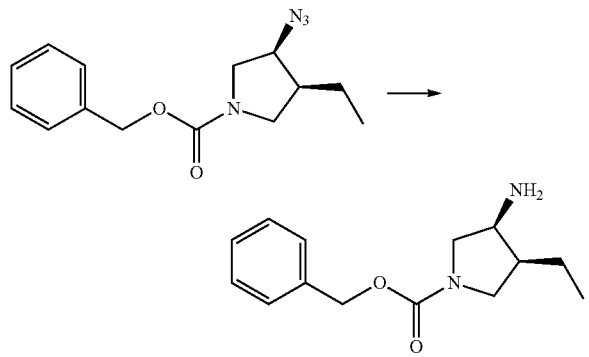

(3S,4S)-benzyl 3-azido-4-ethylpyrrolidine-1-carboxylate (14.0 g, 51.0 mmol) was dissolved in acetonitrile (200 mL). Added water (20 mL) and stirred at RT to a clear solution. This soln. was warmed to 60° C. for 6.5 hrs. Acetonitrile was removed in vacuo and residual aqueous portion was diluted with 1N HCl (100 mL) which was washed with ethyl acetate (5×50 mL) until all Ph₃P and Ph₃P oxide was removed from the aqueous portion. The aqueous portion which contains HCl salt of the amine was cooled to ~5 deg. This acidic soln was made basic (pH 12) with 1N NaOH. Extracted this basic milky suspension with DCM (5×, 50 mL), dried (Na2SO4) and concentrated. On vacuum overnight gave (3S,4S)-benzyl 3-amino-4-ethylpyrrolidine-1-carboxylate (11.01 g, 44.3 mmol, 87% yield). LCMS:M+1=249, t=1.39 min. This material was resolved using the following chiral SFC conditions [column: Chiralpak AD-H 5×25 cm, 5 μm, Column Temp. 48° C., Flow rate: 290 mL/min, Mobile Phase: CO2/MeOH=77/23 with 0.3% triethylamine, Injection Volume: 3 mL (Conc. 68.8 mg/mL), detector wavelength: 215 nm, 100 bars]. The isolated isomers were named "Pk1" and "Pk2" in the elution order. Fractions containing Pk1 were concentrated to afford 5.1 g of the desired (3S,4S)-benzyl 3-amino-4-ethylpyrrolidine-1-carboxylate (Intermediate 9). Chiral purity: >99% ee (chiral HPLC conditions: column: Chiralpak AD-H (25×0.46 cm, 5 μm), 30% MeOH in CO2 with 0.3% triethylamine, 3 mL/min, 40° C., 200-400 nm, 100 bars). ¹H NMR (400 MHz, chloroform-d) δ ppm 7.33-7.42 (5 H, m), 5.12-5.17 (2 H, m), 3.51-3.67 (3H, m), 3.32-3.40 (1 H, m), 3.14-3.21 (1 H, m), 2.0-2.15 (1 H, m), 1.44-1.55 (2 H, m), 0.97-1.02 (5 H, m). LCMS: (M+1)=249, t=1.39 min.

Intermediate 10

(3S,4S)-benzyl 3-amino-4-(fluoromethyl)pyrrolidine-1-carboxylate

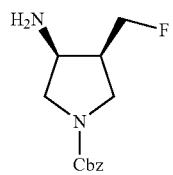

Step 1: 1-benzyl 3-methyl 4-oxopyrrolidine-1,3-dicarboxylate

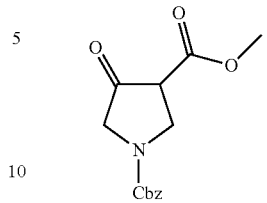

A solution of Carbobenzyloxyglycine methyl ester (10 g, 44.8 mmol) and Methyl acrylate (4.03 mL, 44.8 mmol) in Toluene (100 mL) at 0° C. was added 60% NaH in mineral oil (1.971 g, 49.3 mmol) which was stirred for 10 minutes, and then it was warmed up to RT and stirred for 20 minutes. The reaction mixture was heated to 50° C. for 3 hrs. The reaction mixture was quenched with 10% citric acid solution until pH about 3, and then it was extracted with 100 mL×3 of EtOAc. The combined organic phases were washed with 100 mL of brine and dried over Na2SO4. Filtration and concentration to yield the product (12 g, 96% yield). MS (ES+) m/z: 278.2 (M+H); HPLC retention time: 2.44 min (analytical HPLC Method H).

Step 2: 1-benzyl 3-methyl 4-(methoxyimino)pyrrolidine-1,3-dicarboxylate

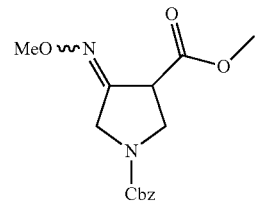

A solution of 1-benzyl 3-methyl 4-oxopyrrolidine-1,3-dicarboxylate (12 g, 43.2 mmol) in pyridine (50 mL) at 0° C. was added O-METHYLHYDROXYLAMINE HYDROCHLORIDE (5.51 g, 66.0 mmol) which was stirred for 10 minutes, and then it was warmed up to RT and stirred for 16 hrs. The reaction mixture was concentrated to yield a crude product which was partitioned in 300 mL of 1N HCl and 300 mL of EtOAc. The organic layer was washed with 100 mL of brine. The combined aqueous phases were extracted with 200 mL of EtOAc. The combined organic phases were dried over Na2SO4. Filtration and concentration to yield the product (12.6 g, 95% yield).

Step 3: (+/−)-cis-benzyl 3-((tert-butoxycarbonyl)amino)-4-(hydroxymethyl)pyrrolidine-1-carboxylate

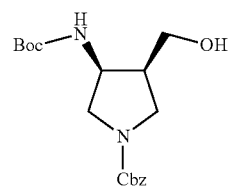

A solution of 1-benzyl 3-methyl 4-(methoxyimino)pyrrolidine-1,3-dicarboxylate (12.6 g, 41.1 mmol) in THF (100 mL) at −78° C. was added borane THF complex (1M in THF, 148 mL, 148 mmol) dropwise and stirred for 1.5 hrs, and then it was warmed to 0° C. and stirred for 2 hrs and further warmed up to RT and stirred for 16 hrs. The reaction was quenched with water at 0° C. until effervescence ceased, and to it was added K₂CO₃ (5.68 g, 41.1 mmol). The reaction mixture was warmed up to RT and stirred for 1 hr. (Boc)₂O (11.46 mL, 49.4 mmol) was added. The reaction mixture was stirred at RT for 16 hrs. The reaction mixture was added 200 mL of water and 500 mL of EtOAc and stirred for 10 minutes. The organic phase was separated and washed with 200 mL of brine, dried over Na2SO4, and then it was filtered, concentrated and purified by silica gel chromatography, eluting with 0-70% ethyl acetate in hexanes, to give the racemic title compound (5.46 g, 38% yield). ¹H NMR (400 MHz, CHLOROFORM-d) δ 7.41-7.30 (m, 5H), 5.15 (d, J=1.3 Hz, 2H), 4.86-4.72 (m, 1H), 4.30 (br. s., 1H), 3.94-3.85 (m, 1H), 3.66 (dd, J=11.9, 5.1 Hz, 2H), 3.59-3.44 (m, 3H), 2.96 (q, J=11.4 Hz, 1H), 2.57 (br. s., 1H), 1.50-1.44 (m, 9H). MS (ES+) m/z: 351.1 (M+H); HPLC retention time: 2.79 min (analytical HPLC Method H).

Step 4: (+/−)-cis-benzyl 3-(tert-butoxycarbonylamino)-4-(fluoromethyl)pyrrolidine-1-carboxylate

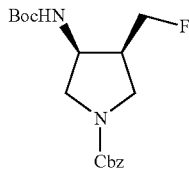

To a solution of (+/−)benzyl 3-((tert-butoxycarbonyl)amino)-4-(hydroxymethyl)pyrrolidine-1-carboxylate (4.70 g, 13.41 mmol) and Et₃N (2.52 mL, 18.11 mmol) in dichloromethane (100 mL) was added methanesulfonyl chloride (1.254 mL, 16.10 mmol) dropwise at 0° C. and the resulting mixture was stirred at RT for 1 hr. The reaction mixture was diluted with 50 mL of CH2Cl2 and then washed with 50 mL of 10% Citric acid solution, 50 mL of brine and dried over Na2SO4. Filtration and concentration yielded the crude mesylate intermediate which was used directly in next transformation without any further purification. MS (ES+) m/z: 429.1 (M+H); HPLC retention time: 2.836 min (analytical HPLC Method H). To a solution of (+/−)-benzyl 3-((tert-butoxycarbonyl)amino)-4-(((methylsulfonyl)oxy)methyl)pyrrolidine-1-carboxylate (5.75 g, 13.41 mmol) in THF (50 mL) was added TBAF (1M in THF, 30.8 mL, 30.8 mmol) at 0° C. followed by warming to rt and stirring for 16 hrs. The reaction mixture was then heated to 55° C. for 5 hrs before cooling and concentrating to yield the crude fluoro intermediate. To this material was added 150 mL of water and the resulting mixture was extracted with 200 mL×2 of EtOAc. The combined organic phases were washed with 200 mL of brine and dried over Na2SO4, filtered, concentrated and purified by silica gel chromatography, eluting with 0-50% ethyl acetate in hexanes, to give the title compound (2.307 g, 49% yield). ¹H NMR (400 MHz, CHLOROFORM-d) d 7.42-7.31 (m, 5H), 5.16 (d, J=2.6 Hz, 2H), 4.85-4.67 (m, 1H), 4.66-4.55 (m, 1H), 4.54-4.32 (m, 1H), 3.79-3.64 (m, 2H), 3.49-3.28 (m, 2H), 2.79-2.56 (m, 1H), 1.47 (s, 9H). MS (ES+) m/z: 353.1 (M+H); HPLC retention time: 3.008 min (analytical HPLC Method H).

Step 5: (3S,4S)-benzyl 3-(tert-butoxycarbonylamino)-4-(fluoromethyl)pyrrolidine-1-carboxylate and (3R,4R)-benzyl 3-(tert-butoxycarbonylamino)-4-(fluoromethyl)pyrrolidine-1-carboxylate

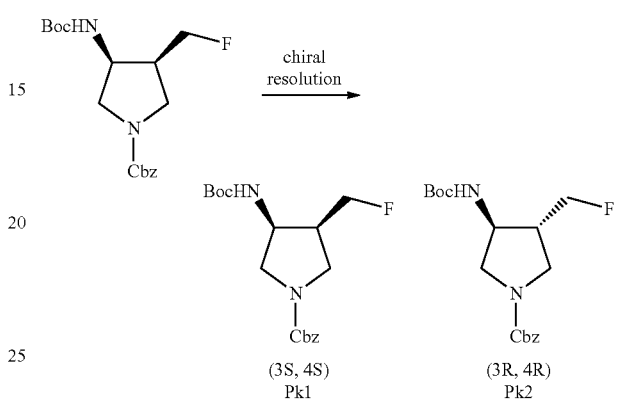

(+/−)Benzyl 3-((tert-butoxycarbonyl)amino)-4-(fluoromethyl)pyrrolidine-1-carboxylate (2.307 g, 6.55 mmol) was separated under the following chiral SFC conditions: column: Chiralpak AD-H 25×3 cm, 5 μm, Column Temp. 45° C., Flow rate: 150 mL/min, Mobile Phase: CO2/MeOH=65/35, Injection Volume: 1.5 mL (Conc. 50 mg/mL), detector wavelength: 220 nm. The isolated isomers were named "Pk1" and "Pk2" in the elution order. The Pk1 was collected as the desired (3S, 4S)-enantiomeric product (1.012 g, 44% yield). ¹H NMR (500 MHz, CHLOROFORM-d) δ 7.43-7.31 (m, 5H), 5.16 (d, J=4.2 Hz, 2H), 4.87-4.66 (m, 1H), 4.65-4.34 (m, 2H), 3.80-3.66 (m, 2H), 3.48-3.27 (m, 2H), 2.77-2.60 (m, 1H), 1.47 (s, 9H). MS (ES+) m/z: 353.1 (M+H); HPLC retention time: 3.028 min (analytical HPLC Method H). Chiral purity: 99.9% ee (chiral HPLC conditions: column: Chiralpak AD-H (25× 0.46 cm, 5 μm), 35% MeOH in CO2, 3 mL/min, 45° C., 220 nm, 100 bar).

Step 6: (3S,4S)-benzyl 3-amino-4-(fluoromethyl)pyrrolidine-1-carboxylate (Intermediate 10)

A solution of (3S,4S)-benzyl 3-((tert-butoxycarbonyl)amino)-4-(fluoromethyl)pyrrolidine-1-carboxylate (Pk1) (1.012 g, 2.87 mmol) in CH₂Cl₂ (10 mL) at 0° C. was added TFA (2.212 mL, 28.7 mmol) and the resulting mixture was allowed to warm to rt and stir for 1 hr. The reaction mixture was concentrated and redissolved in 70 mL of CH2Cl2 and was washed with 20 mL of 2M Na2CO3 solution and 20 mL of brine then dried over Na2SO4. Filtration and concentration afforded the title compound (0.718 g, 99% yield). ¹H NMR (500 MHz, CHLOROFORM-d) δ 7.41-7.31 (m, 5H), 5.24-5.08 (m, 2H), 4.77-4.43 (m, 2H), 3.75-3.57 (m, 3H), 3.37 (s, 2H), 2.66-2.49 (m, 1H). MS (ES+) m/z: 253.2 (M+H); HPLC retention time: 1.023 min (analytical HPLC Method H). Chiral purity: 99.9% ee (chiral HPLC conditions: column:

Chiralpak AD-H (25×0.46 cm, 5 μm), 35% MeOH in CO2, 3 mL/min, 45° C., 220 nm, 100 bar).

Intermediate 11 (Racemic)

(+/−)-Benzyl 4-amino-3,3-dimethylpyrrolidine-1-carboxylate

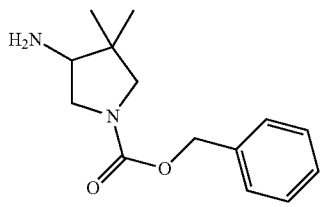 [SMILES: CC1(C)CN(C(=O)OCc2ccccc2)CC1N]

Step 1: (+/−)-1-benzyl-3-hydroxy-4,4-dimethylpyrrolidin-2-one

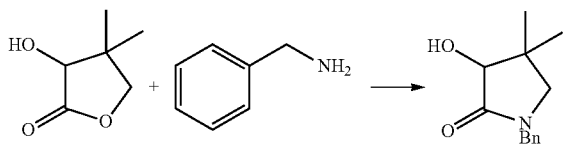

A mixture of 3-hydroxy-4,4-dimethyldihydrofuran-2(3H)-one (4.5 g, 34.6 mmol), phenylmethanamine (5.66 mL, 51.9 mmol) and p-toluenesulfonic acid (0.595 g, 3.46 mmol) was sealed in a reaction vial and heated in microwave at 210° C. for 3 h. The mixture was diluted with ethyl acetate (300 mL). The organic layer was washed with 1N HCl (30 mL) three times, brine (20 mL), dried and concentrated. The residue was purified via silica gel chromatography, eluting with 20-50% ethyl acetate in hexanes, to give the title compound as a yellow oil (3.4 g, 45% yield). $^1$H NMR (400 MHz, CHLOROFORM-d) δ 7.37-7.29 (m, 3H), 7.26-7.22 (m, 2H), 4.55-4.36 (m, 2H), 4.02 (s, 1H), 3.37 (br. s., 1H), 3.00-2.83 (m, 2H), 1.18 (s, 3H), 0.96 (s, 3H); MS (ES+) m/z: 219.1, 220.1 (M+H); LC retention time: 2.83 min (analytical HPLC Method I).

Step 2: (+/−)-1-benzyl-4,4-dimethylpyrrolidin-3-ol

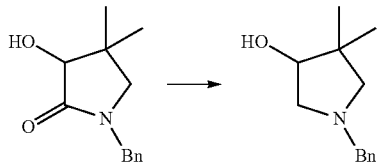 [SMILES: CC1(C)CN(Cc2ccccc2)C(=O)C1O ; CC1(C)CN(Cc2ccccc2)CC1O]

A solution of 1-benzyl-3-hydroxy-4,4-dimethylpyrrolidin-2-one (2.8 g, 12.8 mmol) in tetrahydrofuran (15 mL) at −30° C., was added lithium aluminum hydride (1.1 g, 38.0 mmol) portion-wise with care. The mixture was stirred and gradually warmed to rt over 1 h, then heated at reflux for 8 h. The mixture was cooled to −30° C., and added several drops of water slowly with stirring. Then to the mixture was added ether (150 mL) and warmed to rt with stirring. The mixture was filtered through a celite pad, rinsed with ether, and concentrated to give 3.5 g of a yellow oil. The crude was purified by silica gel chromatography, eluting with 0-20% methanol in dichloromethane to give 1-benzyl-4,4-dimethylpyrrolidin-3-ol (2.48 g, 95% yield). $^1$H NMR (400 MHz, CHLOROFORM-d) δ 7.33 (d, J=4.4 Hz, 5H), 3.52 (s, 1H), 2.95 (dd, J=10.1, 5.5 Hz, 1H), 2.60 (dd, J=10.1, 3.3 Hz, 1H), 2.55 (d, J=9.0 Hz, 1H), 2.30 (d, J=9.0 Hz, 1H), 1.60 (br. s., 3H), 1.08 (d, J=2.0 Hz, 6H). MS (ES+) m/z: 206.12 (M+H); LC retention time: 0.76 min (analytical HPLC Method I).

Step 3: (+/−)-4,4-dimethylpyrrolidin-3-ol

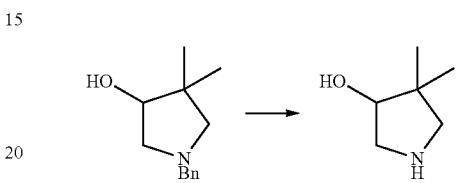

To a solution of 1-benzyl-4,4-dimethylpyrrolidin-3-ol (4.6 g, 22.1 mmol) in ethanol (25 mL), was added palladium hydroxide 20% wt on carbon (0.944 g, 1.34 mmol). The reaction vessel was filled with nitrogen, pumped under vacuum and backfilled with hydrogen three times. The reaction was shaken on a Parr apparatus with hydrogen (40 psi) for 18 h. To the reaction was added celite, ethanol and a couple drops of water, then filtered to remove the catalyst. The filter cake was rinsed with ethanol, and the filtrate was concentrated to give an oil (3.2 g) as the title compound which was used directly in the next transformation.

Step 4: (+/−)-benzyl 4-hydroxy-3,3-dimethylpyrrolidine-1-carboxylate

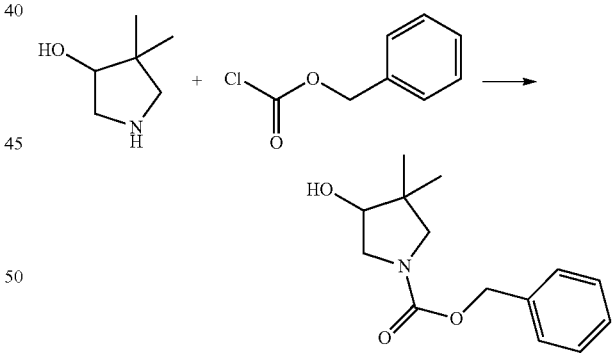

A solution of 4,4-dimethylpyrrolidin-3-ol (2.58 g, 22.4 mmol) in dichloromethane (90 mL), was added 1N sodium hydroxide (90 mL, 90 mmol), then benzyl carbonochloridate (4.16 mL, 24.6 mmol) at rt. The mixture was vigorously stirred for 18 h. The reaction was diluted with dichloromethane and water. The organic phase was separated, dried and concentrated. The crude was purified by silica gel chromatography, eluting with 20-50% ethyl acetate in hexanes to afford benzyl 4-hydroxy-3,3-dimethylpyrrolidine-1-carboxylate (4.07 g, 73% yield). $^1$H NMR (400 MHz, CHLOROFORM-d) δ 7.52-7.28 (m, 5H), 5.14 (s, 2H), 3.97-3.80 (m, 1H), 3.74 (td, J=11.3, 5.2 Hz, 1H), 3.49 (d, J=5.5 Hz, 1H), 3.43-3.18 (m, 2H), 1.74 (br. s., 1H), 1.09 (d, J=3.3 Hz, 3H), 1.03 (d, J=4.6 Hz, 3H). MS (ES+) m/z: 250.1 (M+H); LC retention time: 2.84 min (analytical HPLC Method I).

Step 5: Benzyl 3,3-dimethyl-4-oxopyrrolidine-1-carboxylate

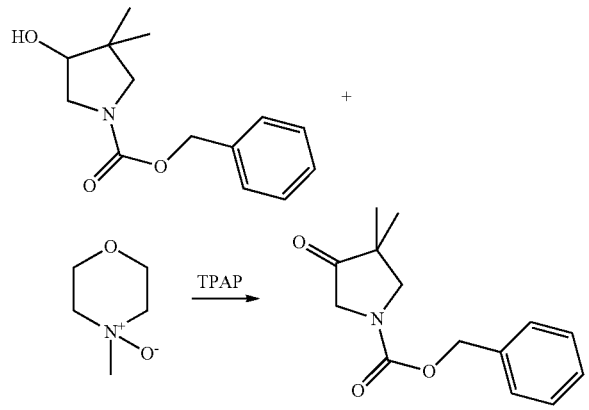

A suspension of benzyl 4-hydroxy-3,3-dimethylpyrrolidine-1-carboxylate (4.07 g, 16.3 mmol) in acetonitrile (50 mL), was added 4-methylmorpholine-4-oxide (3.82 g, 32.7 mmol) and tetrapropylammonium perruthenate (0.42 mL, 1.63 mmol). The mixture was stirred at rt for 18 h. The reaction was concentrated and purified using silica gel chromatography, eluting with 0-30% ethyl acetate in hexanes. Benzyl 3,3-dimethyl-4-oxopyrrolidine-1-carboxylate (2.92 g, 68% yield) was obtained as a colorless oil. $^1$H NMR (400 MHz, CHLOROFORM-d) δ 7.49-7.31 (m, 5H), 5.19 (s, 2H), 3.93 (br. s., 2H), 3.61 (s, 2H), 1.17 (s, 6H); MS (ES+) m/z: 248.1 (M+H); LC retention time: 3.24 min (analytical HPLC Method I).

Step 6: (Z)-benzyl 4-(methoxyimino)-3,3-dimethylpyrrolidine-1-carboxylate

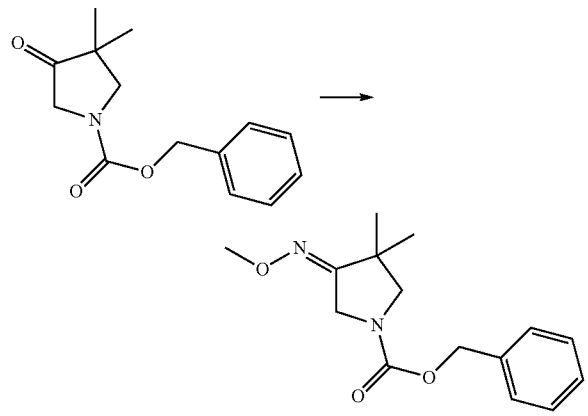

To a solution of benzyl 3,3-dimethyl-4-oxopyrrolidine-1-carboxylate (2.91 g, 11.8 mmol) in MeOH (10 mL) was added sodium acetate (1.93 g, 23.5 mmol) and o-methylhydroxylamine hydrochloride (1.97 g, 23.5 mmol). The mixture was stirred at rt for 18 h. The reaction was concentrated and then diluted with dichloromethane (200 mL). The organic layer was washed with water (20 mL) and aq. sodium bicarbonate, dried over magnesium sulfate, filtered and concentrated. (Z)-benzyl 4-(methoxyimino)-3,3-dimethylpyrrolidine-1-carboxylate (3.17 g, 97% yield) was obtained as a colorless oil. m/z: 277.17 (M+H); LC retention time: 2.83 min (analytical HPLC Method I).

Step 7: (+/−)-Benzyl 4-amino-3,3-dimethylpyrrolidine-1-carboxylate (Intermediate 11)

To a solution of (Z)-benzyl 4-(methoxyimino)-3,3-dimethylpyrrolidine-1-carboxylate (3.17 g, 11.5 mmol) in tetrahydrofuran (10 mL), was added borane in THF (24.1 mL, 24.1 mmol) at rt. The reaction was heated at reflux overnight. The reaction was cooled, quenched with 6N aq. sodium hydroxide, then diluted by water, and extracted with ether. The organic layer was dried over MgSO$_4$, concentrated, and purified by silica gel chromatography, eluting with 0-20% methanol in dichloromethane to give benzyl 4-amino-3,3-dimethylpyrrolidine-1-carboxylate (1.92 g, 67.4 yield). $^1$H NMR (400 MHz, CHLOROFORM-d) δ 7.45-7.31 (m, 5H), 5.32 (s, 2H), 5.15 (s, 2H), 4.07-3.91 (m, 1H), 3.56 (dd, J=12.1, 6.4 Hz, 1H), 3.51-3.32 (m, 1H), 3.22-3.06 (m, 1H), 2.83-2.75 (m, 1H), 1.17 (s, 3H), 1.10 (s, 3H). MS (ES+) m/z: 248.2, 249.1 (M+H); LC retention time: 2.24 min (analytical HPLC Method I).

Intermediate 11 (Enantiopure)

(S)-Benzyl 4-amino-3,3-dimethylpyrrolidine-1-carboxylate

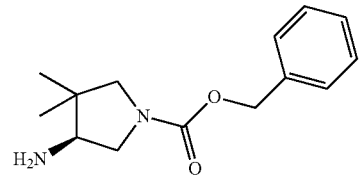 [SMILES: CC1(C)CN(C(=O)OCc2ccccc2)C[C@H]1N]

(+/−)-Benzyl 4-amino-3,3-dimethylpyrrolidine-1-carboxylate (Intermediate 11, 0.48 g was resolved via chiral SFC chromatography under the following conditions: column OD-H (0.46×25 cm), 20% MeOH with 0.1% DEA in CO2, 3 mL/min, 40° C., 140 bars. The second fraction was concentrated to afford the title compound (S)-benzyl 4-amino-3,3-dimethylpyrrolidine-1-carboxylate (0.2 g, 42% yield).

Intermediate 12 (Racemic)

(+/−)-Cis-benzyl 3-amino-4-methoxypyrrolidine-1-carboxylate

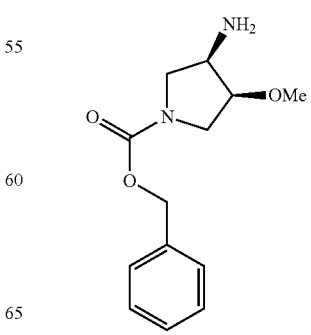

Step 1: Benzyl 6-oxa-3-azabicyclo[3.1.0]hexane-3-carboxylate

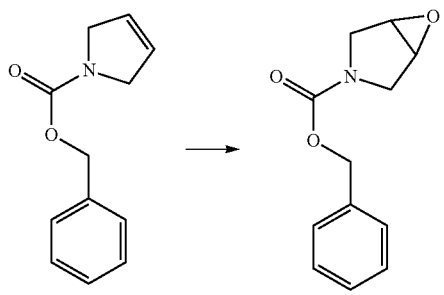 [SMILES: O=C(OCc1ccccc1)N1CC=CC1 ; O=C(OCc1ccccc1)N1CC2OC2C1]

Benzyl 2,5-dihydro-1H-pyrrole-1-carboxylate (24.00 g, 118 mmol) was dissolved in DCM (200 mL). Nitrogen was bubbled through it for ten minutes. Cooled to ~0 degrees Celsius and added 3-chlorobenzoperoxoic acid (33.1 g, 148 mmol) in small portions with stirring. Let the suspension to stir overnight without removing the cold bath. The suspension was removed by filtration and the organic layer was washed with sat'd NaHCO3. The DCM soln. was dried (Na2SO4) and concentrated to give benzyl 6-oxa-3-azabicyclo[3.1.0]hexane-3-carboxylate (22.5 g, 103 mmol, 87% yield). LCMS: M+23=242. Rt=1.57 min.

Step 2: (+/−)-Trans-benzyl 3-hydroxy-4-methoxypyrrolidine-1-carboxylate

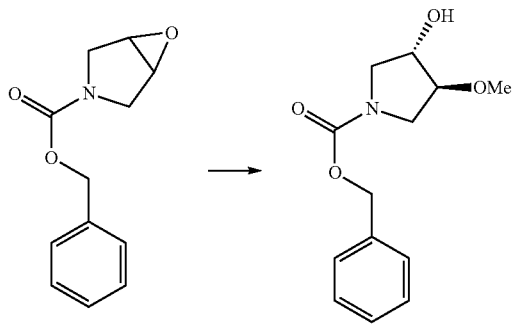 [SMILES: O=C(OCc1ccccc1)N1CC2OC2C1 ; CO[C@H]1CN(C(=O)OCc2ccccc2)C[C@@H]1O]

Benzyl 6-oxa-3-azabicyclo[3.1.0]hexane-3-carboxylate (21.0 g, 96 mmol) was dissolved in MeOH (200 mL). Added sulfuric acid (3.64 g, 37.1 mmol) dropwise. After ~3 hrs the reaction was concentrated and the residue was diluted with ethyl acetate and neutralized with 1N aq. NaOH. The organic extract was dried (Na2SO4) and concentrated. The reaction product was purified by silica gel column chromatography eluting with Hexane/Acetone mixtures to give (+/−)-Trans-benzyl 3-hydroxy-4-methoxypyrrolidine-1-carboxylate (16.8 g, 66.9 mmol, 69.8% yield) LCMS:M+1=252, Rt=1.42 min.

Step 3: (+/−)-Trans-benzyl 3-methoxy-4-(tosyloxy)pyrrolidine-1-carboxylate

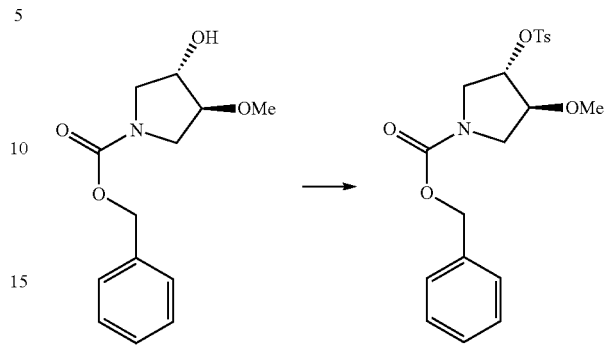

(+/−)-Trans-Benzyl 3-hydroxy-4-methoxypyrrolidine-1-carboxylate (7.7 g, 30.6 mmol) and N,N-dimethylpyridin-4-amine (0.374 g, 3.06 mmol) were dissolved in DCM (75 mL). Cooled to 0 deg. Celsius and added 4-methylbenzene-1-sulfonyl chloride (8.76 g, 46 mmol) and triethylamine (6.41 ml, 46.0 mmol). The reaction was stirred to warm to RT overnight. The solvent was removed and the residue was passed thru a pad of silica to give the product, (+/−)-Trans-benzyl 3-methoxy-4-(tosyloxy)pyrrolidine-1-carboxylate (10.3 g, 25.4 mmol, 83% yield).

Step 4: (+/−)-Cis-benzyl 3-azido-4-methoxypyrrolidine-1-carboxylate

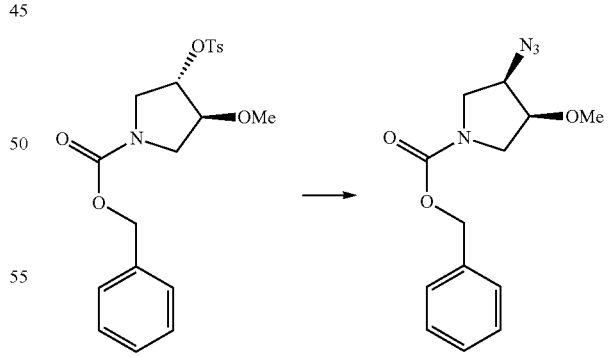

(+/−)-Trans-benzyl 3-methoxy-4-(tosyloxy)pyrrolidine-1-carboxylate (10.3 g, 25.4 mmol) was added to the soln. of sodium azide (5.78 g, 89 mmol) in water (10 mL) and DMF (60 mL) and heated to 100 deg. Celsius overnight. Diluted with EA/water and stirred. The organic layer dried (Na2SO4) and concentrated to give (+/−)-Cis-benzyl 3-azido-4-methoxypyrrolidine-1-carboxylate (6.3 g, 22.80 mmol, 90% yield). 1H NMR (400 MHz, chloroform-d) δ ppm 7.34-7.43

Step 5: (+/−)-Cis-benzyl 3-amino-4-methoxypyrrolidine-1-carboxylate

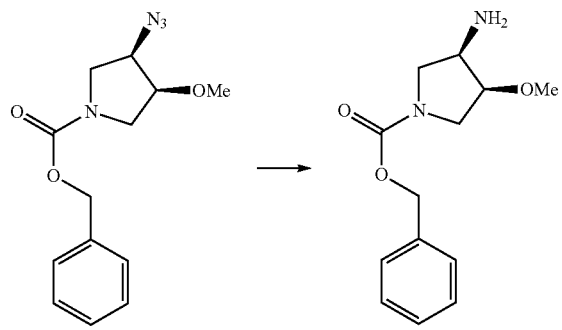 [SMILES: CO[C@H]1CN(C(=O)OCc2ccccc2)C[C@H]1N=[N+]=[N-] ; CO[C@H]1CN(C(=O)OCc2ccccc2)C[C@H]1N]

(+/−)-Cis-benzyl 3-azido-4-methoxypyrrolidine-1-carboxylate (5.43 g, 19.65 mmol) was dissolved in THF (50 mL) and added triphenylphosphine (5.41 g, 20.64 mmol) and stirred at RT overnight. Added water (6 mL) and warmed to 60 deg. C. for ~6 hrs. THF was removed in vacuo and the aqueous portion was diluted with 1N HCl (50 mL) and extracted 5× with EA (20 mL) to remove all of triphenylphosphine and triphenylphosphine oxide. The aq. portion was cooled to ~5 deg. C. and adjusted to pH of 10 by dropwise addition of 1N NaOH. Extracted with DCM (5×) and the organic extractions were combined, dried (Na2SO4) and concentrated. This material was combined with another similar reaction performed on 22.8 mmol scale to afford a total of 8.0 g (75%) of the title compound. 1H NMR (400 MHz, CDCl3) δ ppm 7.36 (5 H, m), 5.34 (2 H, m), 3.45-3.73 (5 H, m), 3.42 (3 H, s), 3.13-3.22 (1 H, d, m), 1.28-1.31 (2 H, br s). LCMS: M+1=251, Rt=1.54 min.

Intermediate 12 (Enantiopure)

(3R,4S)-benzyl 3-amino-4-methoxypyrrolidine-1-carboxylate

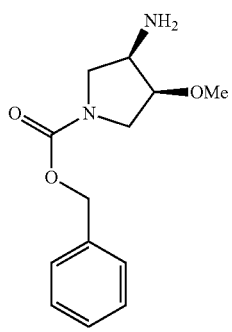 [SMILES: CO[C@H]1CN(C(=O)OCc2ccccc2)C[C@H]1N]

(+/−)-Cis-benzyl 3-azido-4-methoxypyrrolidine-1-carboxylate (8.0 g) was resolved using the following chiral SFC conditions: column: Chiralpak AD-H 25×3 cm, 5 μm, Column Temp. 48° C., Flow rate: 140 mL/min, Mobile Phase: 65/35=CO2/1:1 MeOH:ACN (v/v) with 0.1% triethylamine, Injection Volume: 3 mL (Conc. 59.3 mg/mL), detector wavelength: 215 nm. The isolated isomers were named "Pk1" and "Pk2" in the elution order. The Pk1 was collected and concentrated to afford 3.82 g of the desired (3R,4S)-enantiomeric product. 1H NMR (400 MHz, CDCl3) δ ppm 7.36 (5H, m), 5.34 (2 H, m), 3.45-3.73 (5 H, m), 3.42 (3 H, s), 3.13-3.22 (1 H, d, m), 1.28-1.31 (2 H, br s). LCMS: M+1=251, t=1.54 min. Chiral purity: 99.9% ee (chiral HPLC conditions: column: Chiralpak AD-H (25×0.46 cm, 5 μm), 60/40=CO2/1:1 MeOH:ACN (v/v) with 0.1% triethylamine, 3 mL/min, 48° C., 215 nm, 100 bar).

Intermediate 13 (Racemic)

tert-butyl (6-benzyl-6-azaspiro[3.4]octan-8-yl)carbamate

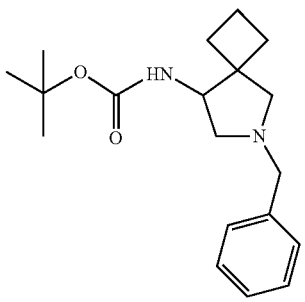 [SMILES: CC(C)(C)OC(=O)NC1CN(Cc2ccccc2)CC12CCC2]

Step 1: 1-(Ethoxycarbonyl)cyclobutanecarboxylic acid

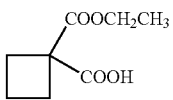

Potassium hydroxide (aq 10% b/w) (152.3 mL, 272 mmol) was added dropwise over 50 minutes to a 0° C. solution of diethyl cyclobutane-1,1-dicarboxylate (49.52 g, 247 mmol) in 95% ethanol (220 mL). Stirring was continued overnight while allowing the ice bath to warm to r. t. LC/MS after 1 hr indicated a 79.4% complete reaction, ca. 86% after overnight. Additional 10% aq KOH was added (0.11 eq, 15.26 mL, total now 1.21 eq) in small portions over 2 minutes, and stirring was continued for 1 hr. LC/MS after 37 min indicated 96% complete reaction. More 10% aq KOH solution was added in small portions over 2 minutes (0.11 eq, 15.26 mL, total now 1.32 eq), and stirring was continued for 37 minutes. LC/MS after 27 min indicated a complete reaction, with minimal formation of the dicarboxylic acid side product (5.5%). The reaction flask was immersed in an ice bath and acidified by the slow addition of 20% HCl, (ca. 220 mL). Most of the ethanol was removed under high vacuum with minimal heat (Bath less than 50° C.). Brine was added (100 mL), followed by 3 extractions with EtOAc (250 mL each). The combined EtOAc layers were washed with 100 mL of brine, dried over Na2SO4, and concentrated under vacuum to yield the title compound as an oil which after standing under vacuum became a white solid. LC/MS: m/e 173.14 (M+H), 195.12 (M+H+ Na), 155.11 (M+H-18, water). This material was used in the next step without additional purification.

Step 2: Ethyl 1-(benzylcarbamoyl)cyclobutanecarboxylate

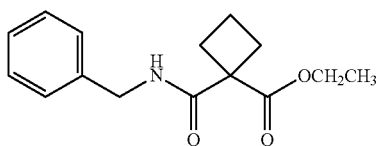 [SMILES: CCOC(=O)C1(C(=O)NCc2ccccc2)CCC1]

Ethyl chloroformate (27.6 mL, 290 mmol) was added dropwise over 30 minutes to a stirred solution of 1-(ethoxycarbonyl)cyclobutanecarboxylic acid (44.56 g, 259 mmol) and triethylamine (47.1 ml, 338 mmol) in chloroform (519 mL) @ 0° C. under $N_2$. After 10 minutes, the ice bath was removed, and the solution was stirred for 1 hr 15 min. LC/MS after 1 hr indicated no starting material remaining. The reaction mixture was then re-cooled in an ice bath, and a solution of benzylamine (29.1 mL, 266.8 mmol) in 45 mL of chloroform was added dropwise over 0.5 h; there was visible ($CO_2$) gas evolution during the benzylamine addition process. The ice bath was removed and stirring was continued for 1 hr 40 min. LC/MS after 1 hr 10 min indicated a complete reaction. The reaction was washed three times with 300 mL total of 2N HCl, brine, dried over $Na_2SO_4$, and concentrated under vacuum to yield 66.71 g of yellow oil. LC/MS: m/e 262.12 (M+H), 216.10 (M+H-46, ethanol). The crude product was purified by column chromatography to yield 57.48 g of the title compound as very pale yellow oil. LC/MS: m/e 262.1 (M+H).

Step 3: 1-Acetyl-N-benzylcyclobutanecarboxamide

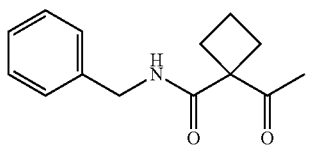 [SMILES: CC(=O)C1(C(=O)NCc2ccccc2)CCC1]

((Trimethylsilyl)methyl)lithium (1.0 M in pentane) (908 mL, 908 mmol) was added dropwise over 1 hr 20 min to a 0° C. solution of ethyl 1-(benzylcarbamoyl)cyclobutanecarboxylate (52.7 g, 202 mmol) in THF (703 mL) under $N_2$. Stirring @ 0° C. was continued for 2 hrs during which time the solution became red. LC/MS after 1 hr looked the same as after 30 minutes, a complete reaction (m/e 232.1, M+H for desired product). While still @ 0° C., the reaction was quenched by the addition of anhydrous methanol (246 mL, over 45 minutes). There was solid formation which after ca. 30 minutes cleared up to form a turbid yellow solution. Note: methanol addition was dropwise; when further addition no longer caused extensive precipitation, the addition was accelerated to a slow stream. After 5 minutes, the ice bath was removed and stirring was continued for 30 minutes. Brine was added (800 mL), the layers were separated, the brine layer was extracted twice with EtOAc (300 mL each), the combined organic layers were washed with brine (200 mL), dried over $Na_2SO_4$, and concentrated under vacuum to yield 50.19 g of a yellow solid. The crude product was stirred and soni-cated for 30 minutes in 400 mL of hexane. The product was collected by filtration and rinsed with hexane to yield ca. 40 g of a yellow solid with some sticky lumps. The solid was sonicated again for several minutes in 400 mL of hexane, collected by filtration, rinsed with hexane, and dried under vacuum to yield 35.82 g of an off-white solid. The combined hexane filtrate was concentrated under vacuum to yield 8.67 g of a yellow oil, which by LC/MS contained desired product. Flash chromatography of the filtrate on silica gel (Teledyne-Isco RediSep Rf 80 g column), eluting with 250 mL of hexane, 400 mL of 80:20, and 400 mL of 40:60 hexane:EtOAc yielded 5.15 g of an off-white solid. The chromatographed solid was similar in purity to the triturated solid, and the two solids were combined to afford 40.97 g of the title compound as an off-white solid. LC/MS: m/e 232.1 (M+H). $^1$H NMR (400 MHz, CHLOROFORM-d) δ 7.48-7.17 (m, 5H), 5.78 (br. s., 1H), 4.44 (d, J=5.9 Hz, 2H), 2.62-2.46 (m, 4H), 2.16 (s, 3H), 2.01-1.88 (m, 1H), 1.88-1.75 (m, 1H).

Step 4: N-Benzyl-1-(2-bromoacetyl)cyclobutanecarboxamide

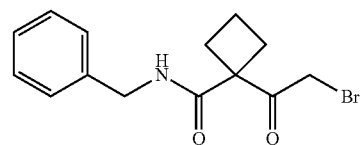 [SMILES: O=C(CBr)C1(C(=O)NCc2ccccc2)CCC1]

Bromine (0.593 mL, 11.51 mmol) was added dropwise to a 0° C. stirred solution of 1-acetyl-N-benzylcyclobutanecarboxamide (2.22 g, 9.60 mmol) in ethanol (35.5 mL). After 15 minutes, the ice bath was removed. The flask was sealed, and stirring was continued for 6.5 hrs. HPLC and LC/MS after 5 hrs indicated a complete or nearly complete reaction. The reaction was quenched by the addition of 25 mL of sat. aq NaHSO3 soluition. EtOAc was added (50 mL), the layers were separated, the aq layer was extracted with EtOAc (20 mL), the combined EtOAc layers were washed with water, brine, dried over $Na_2SO_4$, and concentrated under vacuum to give the crude product (2.80 g) as an oily yellow solid. The crude product was sonicated briefly in hexane. The ppt was collected by filtration, rinsed with hexane, and dried under vacuum to yield 2.33 g of the title compound as a pale yellow solid. LC/MS: m/e 312.08 (one of 2 Br-pattern peaks, M+H).

Step 5: 6-Benzyl-6-azaspiro[3.4]octane-5,8-dione

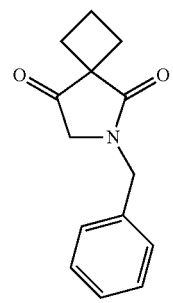 [SMILES: O=C1CN(Cc2ccccc2)C(=O)C12CCC2]

Sodium hydride (60% mineral oil dispersion) (0.366 g, 9.14 mmol) was added to a somewhat turbid solution of N-benzyl-1-(2-bromoacetyl)cyclopentanecarboxamide (2.28 g, 7.03 mmol) in THF (68.3 mL) at 0° C. under a nitrogen atmosphere during which time gas evolution was noted. Stirring @ 0° C. was continued for 55 minutes. HPLC and LC/MS after 30 minutes indicated that the reaction was essentially complete (m/e 244.19, M+H for desired product; no sm detected). The reaction, was maintained at 0° C., diluted with EtOAc (100 mL) and 40 mL of sat. aq NH$_4$Cl solution, and finally 40 mL of water. The layers were separated, the organic layer was washed with 40 mL of water, and 40 mL of brine, the organic layer was dried over Na$_2$SO$_4$, and concentrated under vacuum to yield 1.86 g of a tan viscous oil. Flash chromatography on silica gel (Teledyne-Isco RediSep Rf 40 g column), eluting with 100 mL of 95:5, 400 mL of 90:10, and 300 mL of 80:20 hexane:EtOAc yielded 1.44 g of the title compound as a viscous pale yellow oil. LC/MS: m/e 244.16 (M+H), 276.2 (M+H+methanol, hemiacetal formation). +/−MS: m/e 244.2 (M+H), 242.4 (M−H). $^1$H NMR (400 MHz, CHLOROFORM-d) δ 7.41-7.23 (m, 5H), 4.64 (s, 2H), 3.69 (s, 2H), 2.10-1.97 (m, 2H), 1.97-1.81 (m, 6H).

Step 6: (Z,E)-2-benzyl-8-hydroxyimino)-6-azaspiro [3.4]octane-5-one

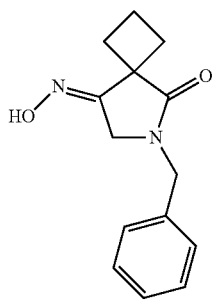

A solution of 6-benzyl-6-azaspiro[3.4]octane-5,8-dione (1.36 g, 5.6 mmol), hydroxylamine hydrochloride (1.17 g, 16.80 mmol), and trimethylamine (2.34 mL, 16.8 mmol) in ethanol (50.9 mL) was stirred at r. t. for 16 hrs. MS analysis of an aliquot after 16 hrs indicated that the reaction had essentially proceeded to completion (m/e 259.2, M+H for desired product); no sm was detected. Ethanol was removed under vacuum. ethyl acetate, THF, and 0.5N HCl were added. The layers were separated, the organic layer was washed twice with 0.5N HCl, and once with brine, and the organic layer was dried over Na$_2$SO$_4$, and concentrated under vacuum to yield a white solid. Note: a white interface ppt was collected by filtration, rinsed with EtOAc then water, dried under vacuum, and combined with the product obtained from organic layer concentration. The combined product was suspended in water, sonicated briefly, collected by filtration, rinsed with water, and dried under vacuum to yield 1.31 g of the title compound as a white solid. LC/MS: m/e 259.27 (M+H). $^1$H NMR (400 MHz, Methanol-d$_4$) δ 7.48-7.12 (m, 5H), 4.56 (s, 2H), 4.01 (s, 2H), 2.15-1.97 (m, 2H), 1.88 (br. s., 6H).

Step 7:
8-Amino-6-benzyl-6-azaspiro[3.4]octan-5-one

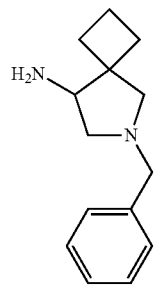 [SMILES: NC1CN(Cc2ccccc2)CC12CCC2]

Lithium aluminum hydride (0.536 g, 14.13 mmol) was suspended in 32.0 mL of dry THF under N$_2$ @ 0° C. A solution of 6-benzyl-8-(hydroxyimino)-6-azaspiro[3.4]octan-5-one (1.33 g, 5.43 mmol) in THF (64.7 mL) was added dropwise over 20 minutes, causing gas evolution. The ice bath was removed and stirring was continued for 5 minutes. The suspension was then gradually heated to reflux temperature. The substrate dissolved as reflux began, and later there was some precipitation. Reflux was continued for 55 minutes. LC/MS and +/−MS analysis after 50 min indicated a complete or near complete reaction. After cooling to r. t., the reaction flask was immersed in a 0° C. ice bath, and sat. aq Na$_2$SO$_4$ solution was added dropwise, allowing gas evolution to subside between additions. The precipitate was collected by filtration over Na$_2$SO$_4$, and after THF rinsing of the filter cake, the filtrate was concentrated under vacuum to yield 1.17 g of yellow oil. This material was purified by flash chromatography on silica gel (Teledyne-Isco RediSep Rf 24 g column), eluting with 100 mL of CH$_2$Cl$_2$, 300 mL of 95:5 CH$_2$Cl$_2$:CH$_3$OH, and 300 mL of 90:9:1 CH$_2$Cl$_2$:CH$_3$OH: NH$_4$OH to yield 0.827 g of the title compound as a pale yellow oil. LC/MS: m/e 217.36 (M+H): $^1$H NMR (400 MHz, CHLOROFORM-d) δ 7.71-6.82 (m, 5H), 3.77-3.50 (m, 2H), 3.26-2.89 (m, 2H), 2.82-2.57 (m, 2H), 2.34-2.06 (m, 2H), 1.97-1.67 (m, 4H), 1.54 (br. s., 2H).

Step 8: tert-Butyl 6-benzyl-6-azaspiro[3.4]octan-8-ylcarbamate, (S)-tert-butyl 6-benzyl-6-azaspiro[3.4] octan-8-ylcarbamate and (R)-tert-Butyl 6-benzyl-6-azaspiro[3.4]octan-8-ylcarbamate

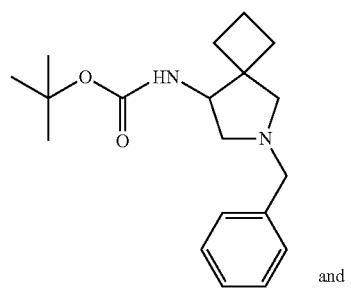
and

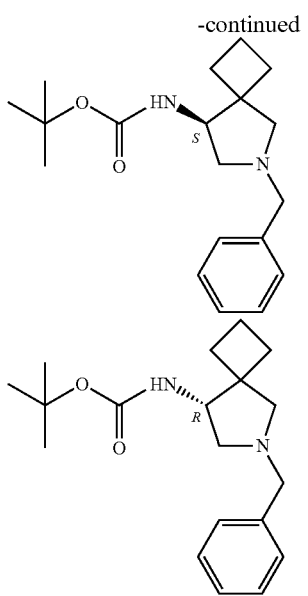

and

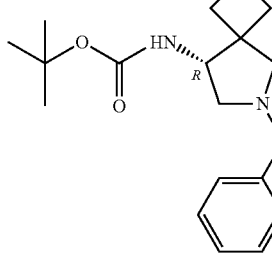

Triethylamine (0.782 ml, 5.61 mmol) was added to a stirred solution of 8-Amino-6-benzyl-6-azaspiro[3.4.]octan-5-one (0.4309 g, 1.871 mmol) in dichloromethane (9.31 mL) @ 0° C. under N2. Ditertbutyldicarbonate (0.612 g, 2.81 mmol) was slowly added, and after 15 minutes, the ice bath was removed and stirring was continued for 2 hrs. +/−MS after 1 hr 45 min indicated a nearly complete reaction. Additional ditertbutyldicarbonate was added (81.6 mg, 0.20 eq), and stirring was continued for 3 hrs. +/−MS analysis after 45 m indicated the presence of the product (m/e 331.3, M+H); with essentially no starting material remaining. Solvent was removed under vacuum. The residue was purified by flash chromatography on silica gel (Teledyne-Isco RediSep Rf 12 g column), eluting with 100 mL of hexane and 200 mL of 80:20 hexane:EtOAc yielded 0.579 g of the title compound as a viscous colorless oil which slowly turns into a white solid under vacuum. LC/MS: m/e 331.30 (M+H), 275.59 (M+H-isobutylene). $^1$H NMR (400 MHz, CHLOROFORM-d) δ 7.38-7.31 (m, 5H), 4.83 (d, J=9.2 Hz, 1H), 4.01-3.90 (m, 1H), 3.71-3.57 (m, 2H), 2.90 (dd, J=9.7, 6.2 Hz, 1H), 2.60 (d, J=9.0 Hz, 1H), 2.51 (dd, J=9.7, 3.5 Hz, 1H), 2.35 (d, J=9.2 Hz, 1H), 1.76-1.55 (m, 8H), 1.47 (s, 9H).

Intermediate 13 (Enantiopure)

(S)-tert-butyl (6-benzyl-6-azaspiro[3.4]octan-8-yl)carbamate

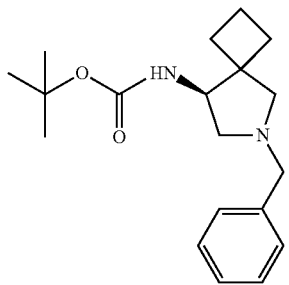 [SMILES: CC(C)(C)OC(=O)N[C@@H]1CN(Cc2ccccc2)CC12CCC2]

Racemic tert-butyl (6-benzyl-6-azaspiro[3.4]octan-8-yl)carbamate (1.26 g) was separated into individual enantiomers using the following preparative SFC conditions:
Preparative Column: Chiralcel OJ-H (5×25 cm, 5 nm)
BPR pressure: 100 bars
Temperature: 45° C.
Flow rate: 200 mL/min
Mobile Phase: CO$_2$/MeOH w 0.1% DEA (95/5)
Detector Wavelength: 220 nm
Separation Program:: Stack injection
Injection: 1 mL with cycle time 95 sec
Sample preparation: 1.26 g/36 mL MeOH, ~35 mg/mL
Fraction '1' was evaporated and dried under vacuum to yield 0.488 g of tan oil assigned as (S)-tert-butyl 6-benzyl-6-azaspiro[3.4]octan-8-ylcarbamate and Fraction '2' was evaporated and dried under vacuum to yield 0.496 g of tan oil assigned as (R)-tert-Butyl 6-benzyl-6-azaspiro[3.4]octan-8-ylcarbamate. Both enantiomers determined to be >99% ee by the following analytical chiral SFC conditions: Column: ChiralCel OJ-H (0.46×25 cm, 5 um), column temp.=45 degrees celsius, flow rate=3 mL/min, mobile phase CO2/MeOH (95/5), detector 200-400 nm, 100 bars.

EXAMPLES

Example 1

(+/−)-4-((1-(6-cyano-3-pyridazinyl)-3,3-dimethyl-4-piperidinyl)amino)-6-(4-methoxyphenyl)pyrrolo[1,2-b]pyridazine-3-carboxamide

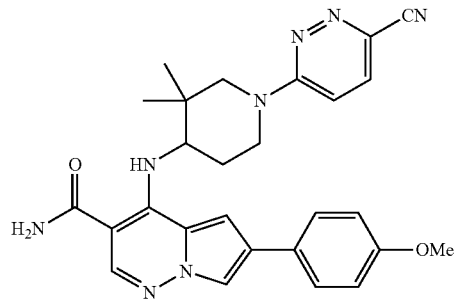 [SMILES: COc1ccc(-c2cc3c(NC4CCN(c5ccc(C#N)nn5)CC4(C)C)c(C(N)=O)cnn3c2)cc1]

Step 1: (+/−)-tert-butyl 4-amino-3,3-dimethylpiperidine-1-carboxylate

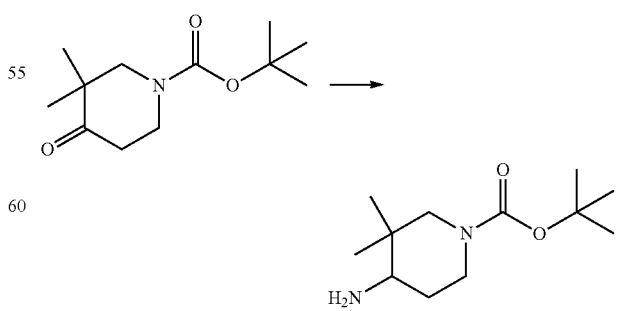

A slurry of tert-butyl 3,3-dimethyl-4-oxopiperidine-1-carboxylate (12.90 g, 56.8 mmol) and ammonium acetate (26.2 g, 341 mmol) in anhydrous methanol (40 mL) was stirred at room temperature under nitrogen for 3 h. After cooling to 0° C., sodium cyanoborohydride (1.783 g, 28.4 mmol) was added. The mixture was stirred at 0° C. for 5 min and at ambient temperature for 22 h. After removal of solvent in vacuo, the residue was treated with water (120 mL), stirred for 20 min, and extracted with dichloromethane (3×60 mL). The combined extracts were dried (MgSO4), concentrated and pumped under vacuum over weekend to give crude tert-butyl 4-amino-3,3-dimethylpiperidine-1-carboxylate (12.54 g). The purity of the product was not determined because of the lack of strong UV chromaphore in LCMS or HPLC, and presence of Boc rotamers in 1H NMR. The material was taken to the next reaction without further purification.

Step 2: tert-butyl 4-(6-bromo-3-carbamoylpyrrolo[1,2-b]pyridazin-4-ylamino)-3,3-dimethylpiperidine-1-carboxylate

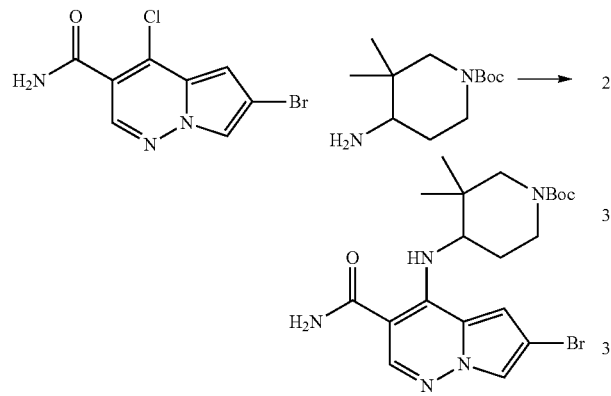

A solution of 6-bromo-4-chloropyrrolo[1,2-b]pyridazine-3-carboxamide (310 mg, 1.129 mmol, Intermediate 2), tert-butyl 4-amino-3,3-dimethylpiperidine-1-carboxylate (387 mg), N,N-diisopropylethylamine (0.592 mL, 3.39 mmol) and N,N-dimethylformamide (2 mL) was pumped under vacuum and backfiled with nitrogen twice. The reaction vial was sealed and heated to 90° C. for 2 h. The mixture was diluted with water (20 mL) and extracted with ethyl acetate twice. The organic layer was washed with brine and concentrated. Silica gel chromatography, eluting with 0-60% ethyl acetate in hexanes, gave the title compound as a brown solid (0.3510 g, 67% yield). MS (ES+) m/z: 466.1, 468.1 (M+H); LC retention time: 4.488 min (analytical HPLC Method H).

Step 3: (+/−)-6-bromo-4-(3,3-dimethylpiperidin-4-ylamino)pyrrolo[1,2-b]pyridazine-3-carboxamide

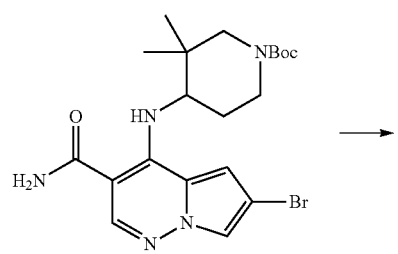

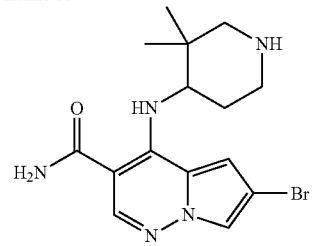

Trifluoroacetic acid (1.5 mL, 19.47 mmol) was added to a stirred suspension of tert-butyl 4-(6-bromo-3-carbamoylpyrrolo[1,2-b]pyridazin-4-ylamino)-3,3-dimethylpiperidine-1-carboxylate (351 mg, 0.753 mmol, from Step 2) in methanol (1 mL) at room temperature. The mixture was stirred at room temperature for 4.5 h, concentrated and pumped under vacuum to give the TFA salt of the title compound (303 mg, 84% yield). 1H NMR (500 MHz, DMSO-d6) δ ppm 10.98 (1 H, d, J=9.43 Hz), 9.22 (1 H, br. s.), 8.39 (1 H, br. s.), 8.27 (1 H, s), 7.90 (1 H, d, J=1.66 Hz), 7.22 (1 H, d, J=1.39 Hz), 4.19-4.26 (1 H, m), 3.20 (2 H, br. s.), 3.04-3.11 (2 H, m), 2.02 (1 H, dd, J=14.43, 3.05 Hz), 1.69-1.80 (1 H, m), 1.17 (3 H, s), 0.97 (3 H, s); MS (ES+) m/z: 366.1, 368.1 (M+H); LC retention time: 2.691 min (analytical HPLC Method H).

Step 4: (+/−)-6-bromo-4-(1-(6-cyanopyridazin-3-yl)-3,3-dimethylpiperidin-4-ylamino)pyrrolo[1,2-b]pyridazine-3-carboxamide

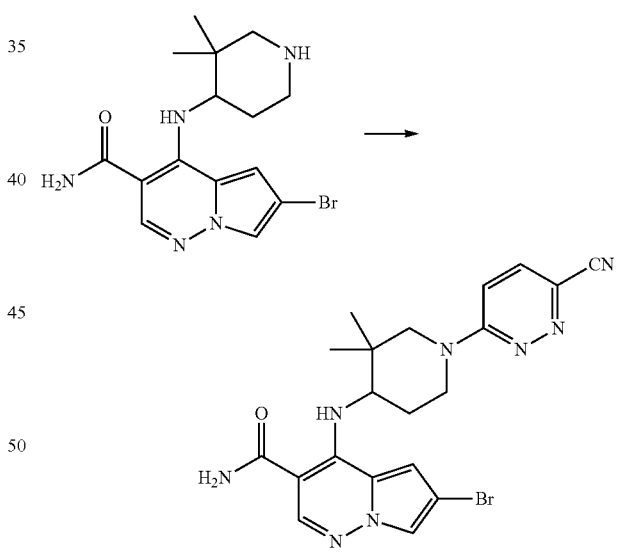

A stirred suspension of 6-bromo-4-(3,3-dimethylpiperidin-4-ylamino)pyrrolo[1,2-b]pyridazine-3-carboxamide TFA salt (139.5 mg, 0.290 mmol, from Step 2), 6-chloropyridazine-3-carbonitrile (81 mg, 0.581 mmol) and N,N-diisopropylethylamine (0.152 mL, 0.871 mmol) in N,N-dimethylformamide (1 mL) was heated in a sealed tube at 90° C. for 2.5 h. The mixture was diluted with water (20 mL) and extracted with ethyl acetate. The organic extract was concentrated and purified by silica gel chromatography, eluting with 0-100% ethyl acetate in hexanes, to give the title compound as a brown glassy solid (0.0711 g, 52% yield). 1H NMR (400 MHz, chloroform-d) δ ppm 10.70 (1 H, d, J=9.02 Hz), 7.89 (1 H, s), 7.64 (1 H, d, J=1.76 Hz), 7.45 (1 H, d, J=9.68 Hz), 6.90 (1 H, d, J=9.46 Hz), 6.82 (1 H, d, J=1.54 Hz), 5.51 (2 H, br. s.), 4.39 (1 H, d, J=13.64 Hz), 4.18 (1 H, d, J=13.42 Hz), 4.09 (1 H, td, J=9.35, 3.96 Hz), 3.54 (1 H, ddd, J=13.75, 10.34, 3.41 Hz), 3.28 (1 H, d, J=13.86 Hz), 2.18-2.28 (1 H, m), 1.93 (1H, dddd, J=14.09, 10.01, 9.90, 4.29 Hz), 1.14 (3 H, s), 1.13 (3 H, s); MS (ES+) m/z: 469.2, 471.2 (M+H); LC retention time: 3.871 min (analytical HPLC Method H).

Step 5: (+/−)-4-((1-(6-cyano-3-pyridazinyl)-3,3-dimethyl-4-piperidinyl)amino)-6-(4-methoxyphenyl)pyrrolo[1,2-b]pyridazine-3-carboxamide (Example 1)

A mixture of 6-bromo-4-(1-(6-cyanopyridazin-3-yl)-3,3-dimethylpiperidin-4-ylamino)pyrrolo[1,2-b]pyridazine-3-carboxamide (20 mg, 0.043 mmol, from Step 4), 4-methoxyphenylboronic acid (13.0 mg, 0.085 mmol), potassium phosphate (27.1 mg, 0.128 mmol), palladium(II) chloride (1.0 mg, 4.26 μmol), 1,1'-bis(di-tert-butylphosphino)ferrocene (2.0 mg, 4.26 μmol) and N,N-dimethylformamide (0.5 mL) was pumped under vacuum and backfilled with nitrogen twice. The reaction vial was sealed and heated to 90-95° C. for 1.5 h. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min. Fractions containing the desired product were combined and dried via centrifugal evaporation to give the title compound (9.2 mg, 44% yield). 1H NMR (400 MHz, DMSO-d6) δ ppm 10.96 (1 H, d, J=9.02 Hz), 8.21 (1 H, s), 8.08 (1 H, s), 7.94 (1 H, s), 7.79 (1 H, d, J=9.68 Hz), 7.74 (2 H, d, J=8.80 Hz), 7.42 (1 H, d, J=9.68 Hz), 7.25 (1 H, s), 6.97 (2 H, d, J=8.80 Hz), 4.50 (1 H, d, J=13.20 Hz), 4.37 (1 H, td, J=9.30, 4.07 Hz), 4.24 (1 H, d, J=12.98 Hz), 3.78 (3 H, s), 3.49-3.59 (1 H, m), 3.11-3.14 (1 H, m), 2.10-2.18 (1 H, m), 1.75 (1 H, br. s.), 1.05 (3 H, s), 1.00 (3 H, s); MS (ES+) m/z: 497.4 (M+H); LC retention time: 2.420 min (analytical HPLC Method I).

Examples 2-7

According to the procedure described for Example 1, Examples 2-7 were prepared by Suzuki coupling with (+/−)-6-bromo-4-(1-(6-cyanopyridazin-3-yl)-3,3-dimethylpiperidin-4-ylamino)pyrrolo[1,2-b]pyridazine-3-carboxamide (from Step 4 of Example 1) with appropriate boronic acids or boronic acid esters, which were commercially available. All Examples were analyzed using HPLC Method I.

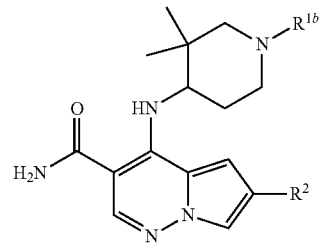

| Ex # | Name | —R$^{1b}$ | —R$^2$ | HPLC Rt (minutes) | LCMS [m/z (M + H)] |
|---|---|---|---|---|---|
| 2 | 4-(1-(6-cyanopyridazin-3-yl)-3,3-dimethylpiperidin-4-ylamino)-6-phenylpyrrolo[1,2-b]pyridazine-3-carboxamide | pyridazine-CN | phenyl | 2.668 | 467.10 |
| 3 | 4-(1-(6-cyanopyridazin-3-yl)-3,3-dimethylpiperidin-4-ylamino)-6-(pyridin-4-yl)pyrrolo[1,2-b]pyridazine-3-carboxamide | pyridazine-CN | pyridin-4-yl | 1.427 | 468.2 |
| 4 | 6-(4-cyanophenyl)-4-(1-(6-cyanopyridazin-3-yl)-3,3-dimethylpiperidin-4-ylamino)pyrrolo[1,2-b]pyridazine-3-carboxamide | pyridazine-CN | 4-cyanophenyl | 2.535 | 492.09 |
| 5 | 4-(1-(6-cyanopyridazin-3-yl)-3,3-dimethylpiperidin-4-ylamino)-6-(2-morpholinopyrimidin-5-yl)pyrrolo[1,2-b]pyridazine-3-carboxamide | pyridazine-CN | 2-morpholinopyrimidin-5-yl | 2.185 | 554.21 |

-continued

| Ex # | Name | —R$^{1b}$ | —R$^2$ | HPLC Rt (minutes) | LCMS [m/z (M + H)] |
|---|---|---|---|---|---|
| 6 | 6-(4-carbamoylphenyl)-4-(1-(6-cyanopyridazin-3-yl)-3,3-dimethylpiperidin-4-ylamino)pyrrolo[1,2-b]pyridazine-3-carboxamide | 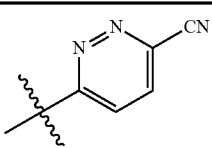 | 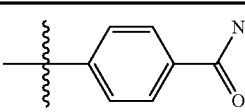 | 1.902 | 510.14 |
| 7 | 6-(2-aminopyrimidin-5-yl)-4-(1-(6-cyanopyridazin-3-yl)-3,3-dimethylpiperidin-4-ylamino)pyrrolo[1,2-b]pyridazine-3-carboxamide | 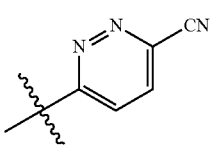 | 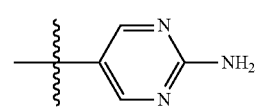 | 1.690 | 484.13 |

Examples 8-14

Examples 8-14 were prepared following conditions described for Example 1, where (+/−)-tert-butyl 4-amino-3,3-dimethylpiperidine-1-carboxylate was replaced with (+/−)-(cis)-tert-butyl-4-amino-3-fluoropiperidine-1-carboxylate (Intermediate 3). Examples 9, 11, 13 and 14 were analyzed using HPLC Method I. Examples 8, 10 and 12 were analyzed using HPLC Method J.

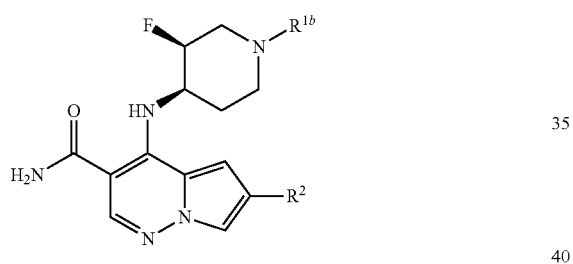

| Ex # | Name | —R$^{1b}$ | —R$^2$ | HPLC Rt (minutes) | LCMS [m/z (M + H)] |
|---|---|---|---|---|---|
| 8 | 4-((3S,4R)-1-(6-cyanopyridazin-3-yl)-3-fluoropiperidin-4-ylamino)-6-phenylpyrrolo[1,2-b]pyridazine-3-carboxamide | 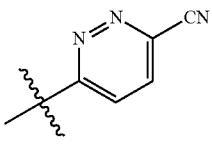 | 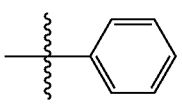 | 2.525 | 457.3 |
| 9 | 4-((3S,4R)-1-(6-cyanopyridazin-3-yl)-3-fluoropiperidin-4-ylamino)-6-(1-methyl-1H-pyrazol-5-yl)pyrrolo[1,2-b]pyridazine-3-carboxamide | 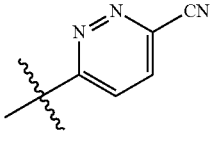 [SMILES: *c1ccc(C#N)nn1] | 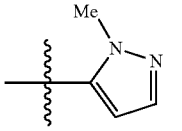 | 1.938 | 461.04 |
| 10 | 4-((3S,4R)-1-(6-cyanopyridazin-3-yl)-3-fluoropiperidin-4-ylamino)-6-(4-methoxyphenyl)pyrrolo-[1,2-b]pyridazine-3-carboxamide | 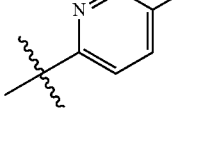 | 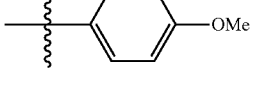 | 2.208 | 487.3 |

-continued

| Ex # | Name | —R$^{1b}$ | —R$^2$ | HPLC Rt (minutes) | LCMS [m/z (M + H)] |
|---|---|---|---|---|---|
| 11 | 4-((3S,4R)-1-(6-cyanopyridazin-3-yl)-3-fluoropiperidin-4-ylamino)-6-(quinolin-6-yl)pyrrolo[1,2-b]pyridazine-3-carboxamide | | | 1.670 | 508.10 |
| 12 | 4-((3S,4R)-1-(6-cyanopyridazin-3-yl)-3-fluoropiperidin-4-ylamino)-6-(4-fluorophenyl)pyrrolo[1,2-b]pyridazine-3-carboxamide | | | 2.298 | 475.3 |
| 13 | 4-((3S,4R)-1-(6-cyanopyridazin-3-yl)-3-fluoropiperidin-4-ylamino)-6-(pyridin-4-yl)pyrrolo[1,2-b]pyridazine-3-carboxamide | | | 1.545 | 458.09 |
| 14 | 4-((3S,4R)-1-(5-cyanopyridin-2-yl)-3-fluoropiperidin-4-ylamino)-6-phenylpyrrolo[1,2-b]pyridazine-3-carboxamide | | | 2.636 | 456.09 |

Examples 15-37

All examples of chiral compounds in the following table were prepared as racemates. According to the procedures described in Step 2 and Step 5 of Example 1, Examples 15-37 were prepared from 6-bromo-4-chloropyrrolo[1,2-b]pyridazine-3-carboxamide (Intermediate 2) and coupling with the appropriate amines using the method in Step 2 of Example 1 followed by Suzuki coupling with the appropriate commercially available boronic acids or boronic esters using the method in Step 5 of Example 1. The hydrochloride salt of 4-fluoro-4-methyltetrahydrofuran-3-amine (Intermediate 4) was used for the synthesis of Examples 15-22 and 7-oxabicyclo[2.2.1]hept-5-en-2-amine (prepared according to *Heterocycles* 1976, 4(1), 19-22) was used for the synthesis of Examples 23-26. Commerically available 4-amino-tetrahydropyran and 2-amino-oxetane were used for Examples 27-35 and 36, respectively. In the case of Example 37, the hydrochloride salt of 3,3-dimethyltetrahydro-2H-pyran-4-amine hydrochloride [prepared by following the literature method US2005/0101628(A1)] was used. Examples 15 and 16 were analyzed using HPLC conditions F. Examples 17-24 and 31-35 were analyzed using HPLC Method I. Examples 25 and 26 were analyzed using HPLC Method J. Examples 27, 29, 30 and 36 were analyzed using HPLC Method E. Example 28 was analyzed using HPLC Method B. Example 37 was analyzed using HPLC Method L.

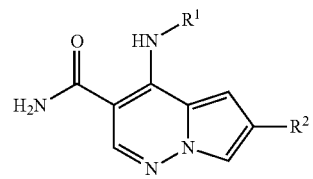

| Ex # | Name | —R$^1$ | —R$^2$ | HPLC Rt (minutes) | LCMS [m/z (M + H)] |
|---|---|---|---|---|---|
| 15 | 4-(4-fluoro-4-methyltetrahydrofuran-3-ylamino)-6-phenylpyrrolo[1,2-b]pyridazine-3-carboxamide | Diastereomer 1 | | 1.61 | 355.2 |

-continued

| Ex # | Name | —R¹ | —R² | HPLC Rt (minutes) | LCMS [m/z (M + H)] |
|---|---|---|---|---|---|
| 16 | 4-(4-fluoro-4-methyltetrahydrofuran-3-ylamino)-6-phenylpyrrolo[1,2-b]pyridazine-3-carboxamide | 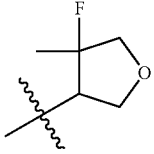 Diastereomer 2 | 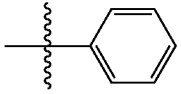 [SMILES: *c1ccccc1] | 1.72 | 355.2 |
| 17 | 4-(4-fluoro-4-methyltetrahydrofuran-3-ylamino)-6-(pyridin-4-yl)pyrrolo[1,2-b]pyridazine-3-carboxamide | 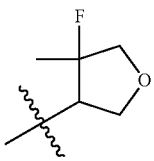 Diastereomer 1 | 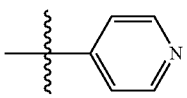 | 0.993 | 356.07 |
| 18 | 4-(4-fluoro-4-methyltetrahydrofuran-3-ylamino)-6-(pyridin-4-yl)pyrrolo[1,2-b]pyridazine-3-carboxamide | 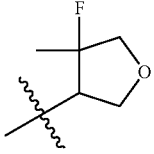 Diastereomer 2 | 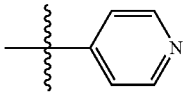 [SMILES: *c1ccncc1] | 1.015 | 356.03 |
| 19 | 4-(4-fluoro-4-methyltetrahydrofuran-3-ylamino)-6-(2-methylpyridin-4-yl)pyrrolo[1,2-b]pyridazine-3-carboxamide | 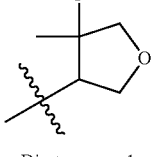 Diastereomer 1 | 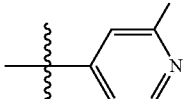 | 1.318 | 370.06 |
| 20 | 4-(4-fluoro-4-methyltetrahydrofuran-3-ylamino)-6-(2-methylpyridin-4-yl)pyrrolo[1,2-b]pyridazine-3-carboxamide | 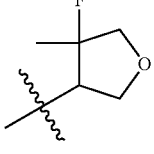 Diastereomer 2 | 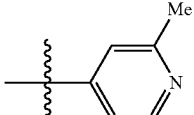 | 1.305 | 370.05 |
| 21 | 6-(2,6-dimethylpyridin-4-yl)-4-(4-fluoro-4-methyltetrahydrofuran-3-ylamino)pyrrolo[1,2-b]pyridazine-3-carboxamide | 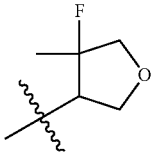 Diastereomer 1 | 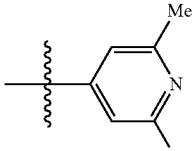 | 1.382 | 384.06 |
| 22 | 6-(2,6-dimethylpyridin-4-yl)-4-(4-fluoro-4-methyltetrahydrofuran-3-ylamino)pyrrolo[1,2-b]pyridazine-3-carboxamide | 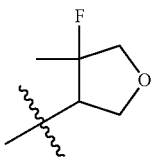 Diastereomer 2 | 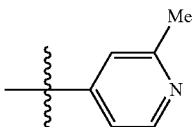 | 1.378 | 384.06 |

-continued

| Ex # | Name | —R¹ | —R² | HPLC Rt (minutes) | LCMS [m/z (M + H)] |
|---|---|---|---|---|---|
| 23 | 4-(7-oxabicyclo[2.2.1]heptan-2-ylamino)-6-phenylpyrrolo[1,2-b]pyridazine-3-carboxamide | 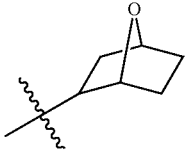 Diastereomer 1 | 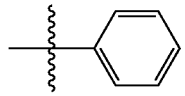 | 2.130 | 349.2 |
| 24 | 4-(7-oxabicyclo[2.2.1]heptan-2-ylamino)-6-phenylpyrrolo[1,2-b]pyridazine-3-carboxamide | 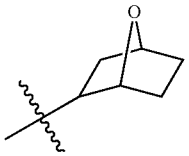 Diastereomer 2 | 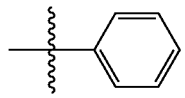 | 2.212 | 349.04 |
| 25 | 4-(7-oxabicyclo[2.2.1]heptan-2-ylamino)-6-(pyridin-4-yl)pyrrolo[1,2-b]pyridazine-3-carboxamide | 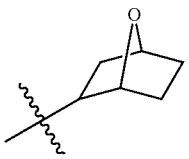 Diastereomer 1 | 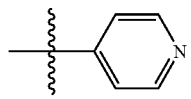 [SMILES: *c1ccncc1] | 1.518 | 350.3 |
| 26 | 4-(7-oxabicyclo[2.2.1]heptan-2-ylamino)-6-(pyridin-4-yl)pyrrolo[1,2-b]pyridazine-3-carboxamide | 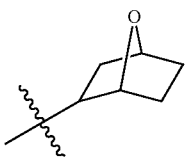 Diastereomer 2 | 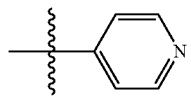 [SMILES: *c1ccncc1] | 1.487 | 350.3 |
| 27 | 6-(4-phenyl)-4-(tetrahydro-2H-pyran-4-ylamino)pyrrolo[1,2-b]pyridazine-3-carboxamide | 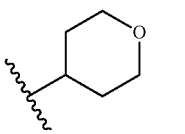 | 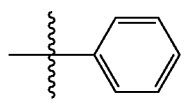 | 7.74 | 337.11 |
| 28 | 6-(4-fluorophenyl)-4-(tetrahydro-2H-pyran-4-ylamino)pyrrolo[1,2-b]pyridazine-3-carboxamide | 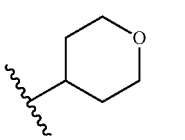 | 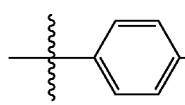 | 3.38 | 355.10 |
| 29 | 6-(5-fluoro-3-pyridinyl)-4-(tetrahydro-2H-pyran-4-ylamino)pyrrolo[1,2-b]pyridazine-3-carboxamide | 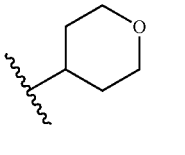 | 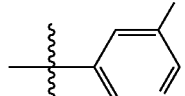 | 5.67 | 356.07 |
| 30 | 6-(1-methyl-1H-pyrazol-5-yl)-4-(tetrahydro-2H-pyran-4-ylamino)pyrrolo[1,2-b]pyridazine-3-carboxamide | 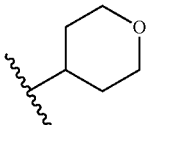 | 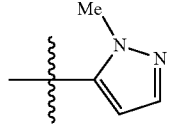 [SMILES: *c1ccnn1C] | 5.29 | 341.12 |
| 31 | 6-(3-pyridinyl)-4-(tetrahydro-2H-pyran-4-ylamino)pyrrolo[1,2-b]pyridazine-3-carboxamide | 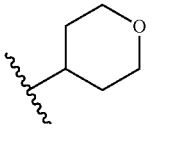 | 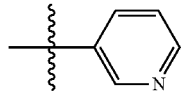 | 0.98 | 338.03 |

| Ex # | Name | —R¹ | —R² | HPLC Rt (minutes) | LCMS [m/z] (M + H) |
|---|---|---|---|---|---|
| 32 | 6-(5-pyrimidinyl)-4-(tetrahydro-2H-pyran-4-ylamino)pyrrolo[1,2-b]pyridazine-3-carboxamide | tetrahydropyran-4-yl | 5-pyrimidinyl | 1.26 | 339.03 |
| 33 | 6-(2-cyanophenyl)-4-(tetrahydro-2H-pyran-4-ylamino)pyrrolo[1,2-b]pyridazine-3-carboxamide | tetrahydropyran-4-yl | 2-cyanophenyl | 1.92 | 362.03 |
| 34 | 6-(2-fluorophenyl)-4-(tetrahydro-2H-pyran-4-ylamino)pyrrolo[1,2-b]pyridazine-3-carboxamide | tetrahydropyran-4-yl | 2-fluorophenyl | 2.11 | 355.01 |
| 35 | 6-(3-quinolinyl)-4-(tetrahydro-2H-pyran-4-ylamino)pyrrolo[1,2-b]pyridazine-3-carboxamide | tetrahydropyran-4-yl | 3-quinolinyl | 1.33 | 388.06 |
| 36 | 4-(oxetan-3-ylamino)-6-phenylpyrrolo[1,2-b]pyridazine-3-carboxamide | oxetan-3-yl | phenyl | 7.44 | 309.13 |
| 37 | (+/−)-4-((3,3-dimethyltetrahydro-2H-pyran-4-yl)amino)-6-phenylpyrrolo[1,2-b]pyridazine-3-carboxamide | 3,3-dimethyltetrahydropyran-4-yl | phenyl | 3.84 | 365.22 |

Example 38

(+/−)-4-((1-(6-cyano-3-pyridazinyl)-3,3-dimethyl-4-piperidinyl)amino)-6-(((trifluoroacetyl)amino)pyrrolo[1,2-b]pyridazine-3-carboxamide

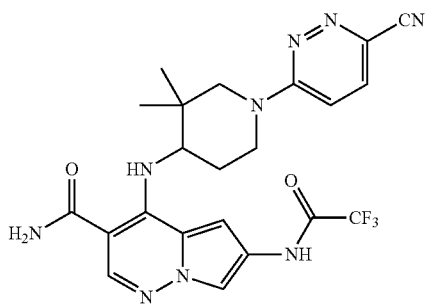 [SMILES: CC1(C)CN(c2ccc(C#N)nn2)CCC1Nc1c(C(N)=O)cnn2cc(NC(=O)C(F)(F)F)cc12]

A mixture of 6-bromo-4-(1-(6-cyanopyridazin-3-yl)-3,3-dimethylpiperidin-4-ylamino)pyrrolo[1,2-b]pyridazine-3-carboxamide from Step 4 of Example 1 (20 mg, 0.043 mmol), 2,2,2-trifluoroacetamide (9.6 mg, 0.085 mmol), copper(I) iodide (1.6 mg, 8.52 μmol), potassium carbonate (11.8 mg, 0.085 mmol) and N1,N2-dimethylethane-1,2-diamine (10 μl, 0.094 mmol) in dioxane (0.5 mL) was pumped and backfilled with nitrogen twice. The reaction vial was sealed and stirred at 90-95° C. for 16 h. LCMS analysis showed the reaction was ~40% complete. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 0.05% TFA; Mobile Phase B: 95:5 acetonitrile:water with 0.05% TFA; Gradient: 20-55% B over 25 minutes, then a 15-minute hold at 55% B; Flow: 20 mL/min. Fractions containing the desired product were combined and dried via centrifugal evaporation to give the title compound, assumed as TFA salt (4 mg, 15% yield). 1H NMR (500 MHz, 1:1 mixture of chloroform-d/methanol-d4) δ ppm 8.11 (1 H, s), 7.96 (1 H, d, J=1.66 Hz), 7.55-7.58 (1 H, m), 7.15-7.21 (2 H, m), 4.22 (1 H, d, J=13.04

Hz), 4.17 (1 H, dd, J=10.40, 3.75 Hz), 3.42-3.51 (1 H, m), 3.20 (1 H, d, J=13.87 Hz), 2.24 (1 H, dd, J=13.87, 3.61 Hz), 1.85-1.94 (1 H, m), 1.11 (3 H, s), 1.10 (3 H, s); MS (ES+) m/z: 502.13 (M+H); LC retention time: 2.225 min (analytical HPLC Method C).

Examples 39-41

Following conditions described for Example 38, Examples 39 and 40 were prepared by coupling Intermediate 2 with Intermediate 4 using the method in Step 2 of Example 1 followed by coupling with 2-pyrrolidinone using the method described for the preparation of Example 38. In a similar manner, Example 41 was prepared by coupling 6-bromo-4-(1-(6-cyanopyridazin-3-yl)-3,3-dimethylpiperidin-4-ylamino)pyrrolo[1,2-b]pyridazine-3-carboxamide from Step 4 of Example 1 with pyrazole using the method described for the preparation of Example 38. Example 41 was analyzed using HPLC Method C. Examples 39 and 40 were analyzed using HPLC Method L.

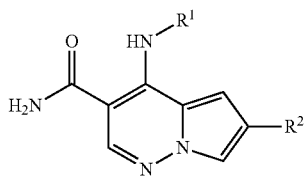

Example 42

(+/−)-4-((3,3-dimethyl-1-(methylsulfonyl)-4-piperidinyl)amino)-6-phenylpyrrolo-[1,2-b]pyridazine-3-carboxamide

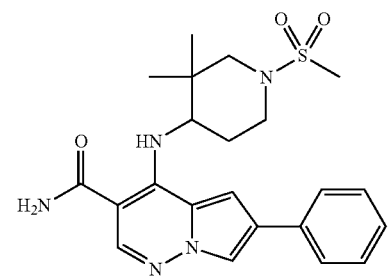 [SMILES: CC1(C)CN(S(C)(=O)=O)CCC1Nc1c(C(N)=O)cnn2cc(-c3ccccc3)cc12]

| Ex # | Name | —R¹ | —R² | HPLC Rt (minutes) | LCMS [m/z (M + H) |
|---|---|---|---|---|---|
| 39 | 4-(4-fluoro-4-methyltetrahydrofuran-3-ylamino)-6-(2-oxopyrrolidin-1-yl)pyrrolo[1,2-b]pyridazine-3-carboxamide | (4-fluoro-4-methyltetrahydrofuran-3-yl) Diastereomer 1 | 2-oxopyrrolidin-1-yl | 1.01 | 362.2 |
| 40 | 4-(4-fluoro-4-methyltetrahydrofuran-3-ylamino)-6-(2-oxopyrrolidin-1-yl)pyrrolo[1,2-b]pyridazine-3-carboxamide | (4-fluoro-4-methyltetrahydrofuran-3-yl) Diastereomer 2 | 2-oxopyrrolidin-1-yl | 1.07 | 362.2 |
| 41 | 4-(1-(6-cyanopyridazin-3-yl)-3,3-dimethylpiperidin-4-ylamino)-6-(1H-pyrazol-1-yl)pyrrolo[1,2-b]pyridazine-3-carboxamide | 1-(6-cyanopyridazin-3-yl)-3,3-dimethylpiperidin-4-yl | 1H-pyrazol-1-yl | 2.137 | 457.14 |

Step 1: 6-bromo-4-(3,3-dimethyl-1-(methylsulfonyl) piperidin-4-ylamino)pyrrolo[1,2-b]pyridazine-3-carboxamide

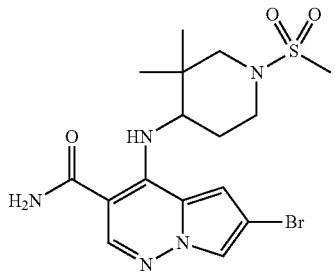 [SMILES: CC1(C)CN(S(C)(=O)=O)CCC1Nc1c(C(N)=O)cnn2cc(Br)cc12]

To a cloudy solution of (+/−)-6-bromo-4-(3,3-dimethylpiperidin-4-ylamino)pyrrolo[1,2-b]pyridazine-3-carboxamide from Step 3 of Example 1 (300 mg, 0.625 mmol) and DIPEA (0.436 mL, 2.499 mmol) in dichloromethane (10 mL) at 0° C. was added methanesulfonyl chloride (0.058 mL, 0.750 mmol) and the resulting mixture was stirred at rt for 3 h. Reaction was diluted with dichloromethane (150 mL), washed with water and brine, dried over MgSO4, filtered and concentrated to afford the title compound as a tan solid (94% yield). HPLC (condition B): retention time=3.11 min. LCMS (condition H): m/z 444, 446 +ve.

Step 2: (+/−)-4-((3,3-dimethyl-1-(methylsulfonyl)-4-piperidinyl)amino)-6-phenylpyrrolo-[1,2-b]pyridazine-3-carboxamide (Example 42)

Prepared according to the procedure described in Step 5 of Example 1 to afford the title compound as a tan solid (13% yield). HPLC (condition B): retention time=3.45 min. LCMS (condition B): m/z 442.3. 1H NMR (400 MHz, MeOD) δ ppm 1H NMR (400 MHz, MeOD) δ ppm 8.14 (1 H, s), 7.89-8.01 (1 H, m), 7.70 (2 H, d, J=7.26 Hz), 7.31-7.45 (2 H, m), 7.15-7.30 (2 H, m), 4.19 (1 H, dd, J=10.34, 3.96 Hz), 3.58-3.77 (1 H, m), 3.30-3.36 (1 H, m), 3.09-3.23 (1 H, m), 2.92 (1 H, d, J=12.10 Hz), 2.87 (3 H, s), 2.12-2.31 (1 H, m), 1.78-2.03 (1 H, m), 1.20 (3 H, s), 1.08 (3 H, s).

Example 43

(+/−)-4-(3,3-dimethyl-1-(methylsulfonyl)piperidin-4-ylamino)-6-(6-methoxypyridin-3-yl)pyrrolo[1,2-b]pyridazine-3-carboxamide

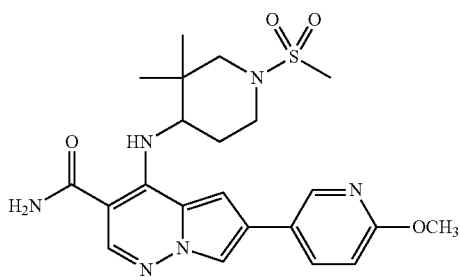 [SMILES: COc1ccc(-c2cc3c(NC4CCN(S(C)(=O)=O)CC4(C)C)c(C(N)=O)cnn3c2)cn1]

Prepared as described in Step 2 of Example 42 by using 6-methoxypyridin-3-ylboronic acid in place of phenyl boronic acid to afford the title compound as a tan solid (11% yield). HPLC (condition B): retention time=3.19 min. LCMS (condition B): m/z 473.2. 1H NMR (400 MHz, MeOD) δ ppm 8.51 (1 H, d, J=2.20 Hz), 8.09-8.23 (2 H, m), 7.96 (1 H, d, J=1.76 Hz), 7.20 (1 H, d, J=1.76 Hz), 6.95 (1 H, d, J=8.80 Hz), 4.18 (1 H, dd, J=10.23, 3.85 Hz), 3.97-4.03 (3 H, m), 3.63 (1 H, d, J=10.12 Hz), 3.33 (1 H, d, J=1.76 Hz), 3.10-3.23 (1 H, m), 2.91 (1 H, d, J=11.88 Hz), 2.86 (3 H, s), 2.20 (1 H, d, J=9.68 Hz), 1.80-1.98 (1 H, m), 1.18 (3 H, s), 1.08 (3 H, s).

Example 44

6-phenyl-4-((3S)-3-piperidinylamino)pyrrolo[1,2-b]pyridazine-3-carboxamide

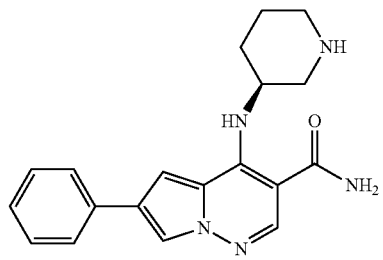 [SMILES: NC(=O)c1cnn2cc(-c3ccccc3)cc2c1N[C@H]1CCCNC1]

Step 1: (S)-tert-butyl 3-(6-bromo-3-carbamoylpyrrolo[1,2-b]pyridazin-4-ylamino)piperidine-1-carboxylate

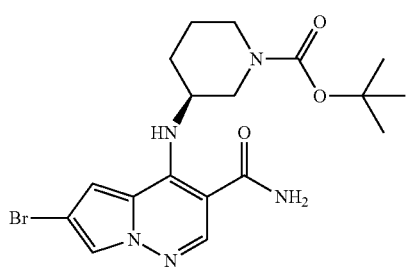 [SMILES: CC(C)(C)OC(=O)N1CCC[C@H](Nc2c(C(N)=O)cnn3cc(Br)cc23)C1]

A solution of 6-bromo-4-chloropyrrolo[1,2-b]pyridazine-3-carboxamide (Intermediate 2, 171 mg, 0.62 mmol) and (S)-tert-butyl 3-aminopiperidine-1-carboxylate (125 mg, 0.62 mmol) in DMF (4 mL) was added DIPEA (0.326 mL, 1.87 mmol). The mixture was heated at 80° C. for 18 h then cooled to rt. Water (16 mL) was added and the resulting suspension was stirred for 1 h. The solids were filtered, rinsed with water (2×), and then dried to afford the crude product which was purified via silica gel chromatography (10% to 50% ethyl acetate in hexanes) to afford the title compound (175 mg, 64% yield) as a pale yellow solid. 1H NMR (DMSO-d6, 400 MHz) δ 10.89 (br s, 1H), 8.26 (s, 1H), 7.90 (d, J=1.5

Hz, 1H), 7.00 (br m, 2H), 4.18 (s, 1H), 3.68 (m, 1H), 3.35 (m, 3H), 1.99 (m, 1H), 1.70 M, 1H), 1.57 (m, 1H), 1.23 br s, 9H).

Step 2: (S)-tert-butyl 3-(3-carbamoyl-6-phenylpyrrolo[1,2-b]pyridazin-4-ylamino)piperidine-1-carboxylate

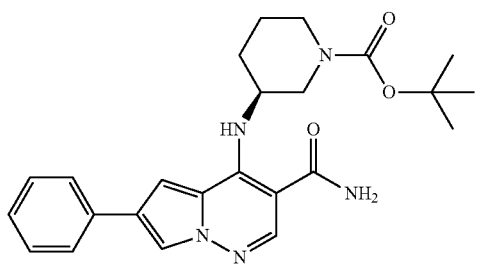 [SMILES: CC(C)(C)OC(=O)N1CCC[C@H](Nc2c(C(N)=O)cnn3cc(-c4ccccc4)cc23)C1]

A solution of (S)-tert-butyl 3-(6-bromo-3-carbamoylpyrrolo[1,2-b]pyridazin-4-ylamino)piperidine-1-carboxylate (75 mg, 0.17 mmol), phenylboronic acid (31.3 mg, 0.26 mmol), and PdCl$_2$(dppf) 6.3 mg, (0.009 mmol) in DMF (1.5 mL) was added aq. K$_3$PO$_4$ (2M, 0.26 mL) then heated at 130° C. for 25 min. The mixture was poured into ethyl acetate (with 20% heptane) and washed with water then sat. aq. NaHCO$_3$. The organic layer was dried over Na$_2$SO$_4$, filtered and concentrated. The crude product was purified via column chromatography (50-75% ethyl acetate in heptane) to afford the title compound (63 mg, 85% yield). LCMS 436.16 (M+H)$^+$; HPLC (conditions L): retention time=4.02 min.

Step 3: 6-phenyl-4-((3S)-3-piperidinylamino)pyrrolo[1,2-b]pyridazine-3-carboxamide (Example 44)

A flask containing (S)-tert-butyl 3-(3-carbamoyl-6-phenylpyrrolo[1,2-b]pyridazin-4-ylamino)piperidine-1-carboxylate (62 mg, 0.142 mmol) was added HCl in dioxane (2 mL, 8 mmol). TLC indicated complete consumption of starting material at 3 h at which time the volatiles were removed via nitrogen sweep and the crude salt was dried under high vacuum to afford the hydrochloride salt of the title compound (58.4 mg, 87% yield) as a yellow solid. A portion of the solids were purified via preparative HPLC (Phenomenex Luna 21.2×100 mm, 1/9 MeOH/H2O to 9/1 MeOH/H2O, 0.1% TFA; 20 mL/min, 10 minute gradient). LCMS: 336.1 (M+H)$^+$; HPLC (conditions E): retention time=5.82 min; $^1$H NMR (MeOD, 400 MHz) δ 8.21 (s, 1H), 8.05 (d, J=1.8 Hz, 1H), 7.78 (dd, J=1.4, 8.4 Hz, 2H), 7.75 (t, J=7.9 Hz, 2H), 7.26 (m, 2H), 4.68 (m, 1H), 3.73 (dd, J=3.5, 9.0 Hz, 1H), 3.35 (m, 1H), 3.17 (m, 2H), 2.34 (m, 1H), 2.17 (m, 1H), 1.99 (m, 1H), 1.85 (m, 1H).

Example 45

4-(((3S)-1-acetyl-3-piperidinyl)amino)-6-phenylpyrrolo[1,2-b]pyridazine-3-carboxamide

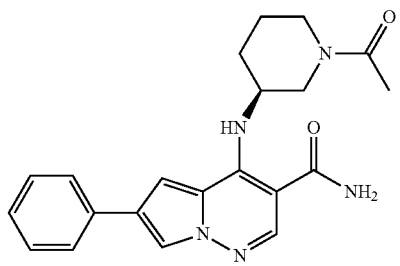 [SMILES: CC(=O)N1CCC[C@H](Nc2c(C(N)=O)cnn3cc(-c4ccccc4)cc23)C1]

A suspension of (S)-6-phenyl-4-(piperidin-3-ylamino)pyrrolo[1,2-b]pyridazine-3-carboxamide hydrochloride salt (Example 44, 12.2 mg, 0.033 mmol) in CH$_2$Cl$_2$ (0.3 mL) was added acetic anhydride (3.72 µL, 0.04 mmol) followed by DIPEA (0.017 mL, 0.1 mmol). The reaction was stirred for 1 h at which time the starting material had been consumed as judged by HPLC. The solvents were removed and the product purified via reverse phase preparative HPLC. LCMS: 378 (M+H)$^+$; HPLC (conditions E): retention time=7.41 min; $^1$H NMR (MeOD, 400 MHz) δ 8.17 (d, J=13 Hz, 1H), 7.97 (dd, J=1.7, 12.3 Hz, 1H), 7.75 (m, 3H), 7.40 (m, 3H), 7.27 (m, 1H), 4.38 (m, 1H), 3.83-3.94 (m, 2H), 3.42 (m, 2H), 2.21 (s, 3H), 1.98 (m, 1H), 1.87 (m, 1H), 1.75 (m, 1H).

Examples 46-51

Examples 46 and 47 in the table below were prepared from (S)-6-phenyl-4-(piperidin-3-ylamino)pyrrolo[1,2-b]pyridazine-3-carboxamide hydrochloride salt (Example 44) using the procedure described for the preparation of Example 45 and by substituting acetic anhydride with methanesulfonyl chloride or ethyl chloroformate, respectively. Additionally, Examples 48 through 51 were prepared in an identical fashion starting from 6-bromo-4-chloropyrrolo[1,2-b]pyridazine-3-carboxamide (Intermediate 2) and (R)-tert-butyl 3-aminopiperidine-1-carboxylate.

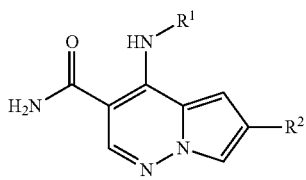

| Ex# | Name | R¹ | R² | HPLC Rt, min (Method) | LCMS m/z (Method) |
|---|---|---|---|---|---|
| 46 | 4-(((3S)-1-(methylsulfonyl)-3-piperidinyl)amino)-6-phenylpyrrolo[1,2-b]pyridazine-3-carboxamide | piperidinyl-N-SO2Me | phenyl | 8.15 (E) | 414.05 |
| 47 | ethyl (3S)-3-((3-carbamoyl-6-phenylpyrrolo[1,2-b]pyridazin-4-yl)amino)-1-piperidinecarboxylate | piperidinyl-N-C(O)OEt | phenyl | 8.75 (E) | 408.12 |
| 48 | (R)-6-phenyl-4-(piperidin-3-ylamino)pyrrolo[1,2-b]pyridazine-3-carboxamide, HCl | piperidinyl-NH | phenyl | 1.36 (I) | 336.16 |
| 49 | 4-(((3R)-1-acetyl-3-piperidinyl)amino)-6-phenylpyrrolo[1,2-b]pyridazine-3-carboxamide | piperidinyl-N-C(O)Me | phenyl | 1.94 (I) | 378.1 |
| 50 | 4-(((3R)-1-(methylsulfonyl)-3-piperidinyl)amino)-6-phenylpyrrolo[1,2-b]pyridazine-3-carboxamide | piperidinyl-N-SO2Me | phenyl | 2.04 (I) | 414.07 |
| 51 | ethyl (3R)-3-((3-carbamoyl-6-phenylpyrrolo[1,2-b]pyridazin-4-yl)amino)-1-piperidinecarboxylate | piperidinyl-N-C(O)OEt | phenyl | 2.38 (I) | 408.2 |

Example 52

(+/−)-(cis)-4-1-(2-cyanoacetyl)-4-methylpyrrolidin-3-ylamino)-6-(6-methoxypyridin-3-yl)pyrrolo[1,2-b]pyridazine-3-carboxamide

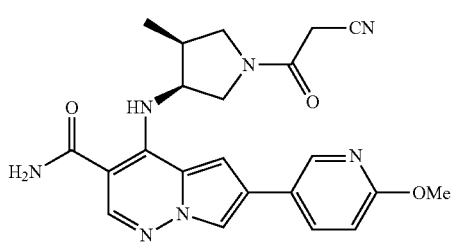 [SMILES: COc1ccc(-c2cc3c(N[C@@H]4CN(C(=O)CC#N)C[C@@H]4C)c(C(N)=O)cnn3c2)cn1]

Step 1: (+/−)-(cis)-benzyl 3-(6-bromo-3-carbamoylpyrrolo[1,2-b]pyridazin-4-ylamino)-4-methylpyrrolidine-1-carboxylate

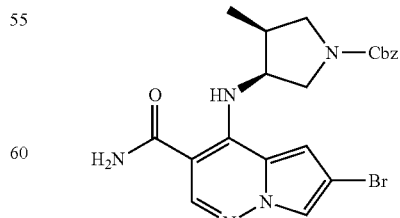

Intermediate 2 (1000 mg, 3.64 mmol), (+/−)-(cis)-benzyl 3-amino-4-methylpyrrolidine-1-carboxylate (Intermediate 5, 1024 mg, 4.37 mmol) and DIPEA (1.27 mL, 7.29 mmol) in DMA (4.0 mL) was heated at 90° C. for 5 h then was allowed to cool to rt and stir overnight. The reaction mixture was added to crushed ice, stirred for 30 min, and the resulting solid that had precipitated was collected by vacuum filtration and was rinsed with water and dried to afford the title compound as a cream colored solid. HPLC (method B) retention time=3.67 min. LCMS (m+1)=472/474 (1:1).

Step 2: (+/−)-(cis)-benzyl 3-(3-carbamoyl-6-(6-methoxypyridin-3-yl)pyrrolo[1,2-b]pyridazin-4-ylamino)-4-methylpyrrolidine-1-carboxylate

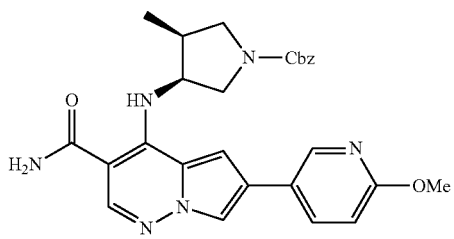 [SMILES: COc1ccc(-c2cc3c(N[C@@H]4CN(C(=O)OCc5ccccc5)C[C@@H]4C)c(C(N)=O)cnn3c2)cn1]

A mixture of (+/−)-(cis)-benzyl 3-(6-bromo-3-carbamoylpyrrolo[1,2-b]pyridazin-4-ylamino)-4-methylpyrrolidine-1-carboxylate (0.40 g, 0.847 mmol), (6-methoxypyridin-3-yl)boronic acid (0.168 g, 1.10 mmol), palladium acetate (9.51 mg, 0.042 mmol) and 2-(Dicyclohexylphosphino)-2',4',6'-triisopropylbiphenyl (0.040 g, 0.085 mmol) in dioxane (3.0 mL) was degassed by purging with argon for 3 min. Aqueous potassium phosphate (2.0 M) (1.27 mL, 2.54 mmol) was added and purging with argon was continued for 2 min. The reaction vial was sealed and heated at 95° C. for 3 h then the resulting mixture was cooled and concentrated to remove dioxane and the residue was taken up in EtOAc (300 mL). The resulting solution was washed with water, brine and dried over MgSO4, filtered and concentrated to afford a yellow solid as the crude product mixture. This material was purified by preparative chromatography using CH2Cl2/MeOH mixtures as the eluant and a 40 g silica cartridge. Fractions containing the major product were combined and concentrated to afford a bright yellow solid as the title compound. HPLC (method B) retntion time=3.65 min. LCMS (m+1)=501.3.

Step 3: (+/−)-(cis)-6-(6-methoxypyridin-3-yl)-4-((3S,4S)-4-methylpyrrolidin-3-ylamino)pyrrolo[1,2-b]pyridazine-3-carboxamide

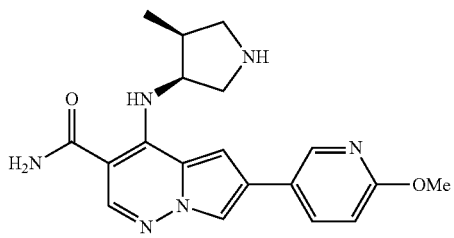 [SMILES: COc1ccc(-c2cc3c(N[C@@H]4CNC[C@@H]4C)c(C(N)=O)cnn3c2)cn1]

To slurry of (+/−)-(cis)-benzyl 3-(3-carbamoyl-6-(6-methoxypyridin-3-yl)pyrrolo[1,2-b]pyridazin-4-ylamino)-4-methylpyrrolidine-1-carboxylate (330 mg, 0.659 mmol) in ethanol (20 mL) under argon was added palladium hydroxide (60 mg) and the flask was purged with hydrogen gas and allowed to stir under a balloon of hydrogen for 3 h. The reaction mixture was filtered through a pad of celite and rinsed with additional ethanol, and the resulting filtrate was concentrated to afford the title compound as a yellow solid (230 mg, 0.628 mmol, 95%). HPLC (method B) retention time=2.27 min. LCMS (m+1)=367.3. $^1$H NMR (400 MHz, METHANOL-$d_4$) δ 8.79 (d, J=2.0 Hz, 1H), 8.70 (dd, J=9.0, 2.4 Hz, 1H), 8.28 (s, 1H), 8.21 (d, J=1.8 Hz, 1H), 7.46-7.41 (m, 2H), 5.23 (br. s., 1H), 4.20 (s, 3H), 3.96 (dd, J=12.5, 5.3 Hz, 1H), 3.75 (dd, J=11.8, 7.8 Hz, 1H), 3.55 (d, J=12.5 Hz, 1H), 3.20 (t, J=11.6 Hz, 1H), 2.97-2.83 (m, 1H), 1.31 (d, J=7.0 Hz, 3H).

Step 4: (+/−)-(cis)-4-1-(2-cyanoacetyl)-4-methylpyrrolidin-3-ylamino)-6-(6-methoxypyridin-3-yl)pyrrolo[1,2-b]pyridazine-3-carboxamide (Example 52)

To solution of (+/−)-(cis)-6-(6-methoxypyridin-3-yl)-4-((3S,4S)-4-methylpyrrolidin-3-ylamino)pyrrolo[1,2-b]pyridazine-3-carboxamide (120 mg, 0.327 mmol), 2-cyanoacetic acid (33.4 mg, 0.393 mmol) and BOP (217 mg, 0.491 mmol) in DMF (1.5 mL) was added DIPEA (0.114 mL, 0.655 mmol) and the resulting mixture was stirred at rt for 3 h. The reaction was diluted with MeOH and purified by reverse-phase preparative HPLC. The fraction containing the major product was treated with 2 mL of satd. aq. NaHCO3 and was extracted with EtOAc (10 mL×4). The combined organic extracts were dried over MgSO4, filtered and concentrated to afford the title compound as a beige solid. HPLC (method B) retention time=2.68 min. LCMS (m+1)=434.3 $^1$H NMR (500 MHz, METHANOL-$d_4$) δ 8.54 (dd, J=5.7, 2.4 Hz, 2H), 8.24-8.20 (m, 2H), 8.08 (ddd, J=8.7, 6.7, 2.4 Hz, 2H), 8.04-8.02 (m, 1H), 7.28-7.25 (m, 2H), 6.90 (d, J=8.6 Hz, 2H), 5.14-4.99 (m, 2H), 4.07 (dd, J=10.7, 5.1 Hz, 1H), 4.01-3.98 (m, 5H), 3.97-3.76 (m, 4H), 3.44 (t, J=10.3 Hz, 1H), 2.94-2.71 (m, 2H), 1.27 (dd, J=6.9, 4.7 Hz, 5H)

Examples 53 and 54

(3S,4S)-4-1-(2-cyanoacetyl)-4-methylpyrrolidin-3-ylamino)-6-(6-methoxypyridin-3-yl)pyrrolo[1,2-b]pyridazine-3-carboxamide (Example 53) and (3R,4R)-4-1-(2-cyanoacetyl)-4-methylpyrrolidin-3-ylamino)-6-(6-methoxypyridin-3-yl)pyrrolo[1,2-b]pyridazine-3-carboxamide (Example 54)

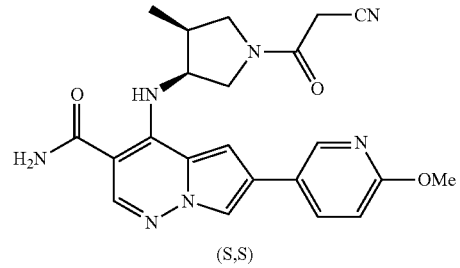

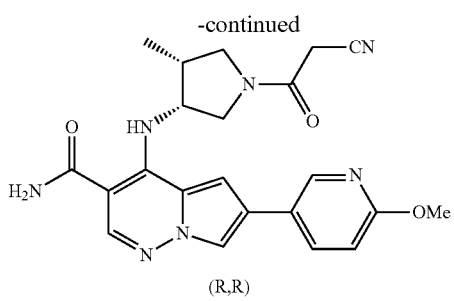

(R,R)

(+/−)-(cis)-4-1-(2-cyanoacetyl)-4-methylpyrrolidin-3-ylamino)-6-(6-methoxypyridin-3-yl)pyrrolo[1,2-b]pyridazine-3-carboxamide (Example 52, 0.09 g) were resolved under the following chiral SFC conditions: column: Lux Cell-4 25×3 cm, 5 μm; Column Temp. 28° C.; Flow rate: 150 mL/min.; mobile phase: CO2/(MeOH+0.5% DEA)=60:40; Injection Volume: 2.0 mL(Conc. 4.5 mg/mL); Detector Wavelength: 278 nm. The enantiomeric purity of first eluted enantiomer having a retention time of 6.24 min. was determined to be 99.8% enantiomerically pure, and the second eluted enantiomer having a retention time of 7.23 min. was determined to have enantiomeric purity of 95.1%.

Example 55

(R)-4-(1-(2-amino-2-oxoacetyl)-3,3-dimethylpiperidin-4-ylamino)-6-(6-methoxypyridin-3-yl)pyrrolo[1,2-b]pyridazine-3-carboxamide

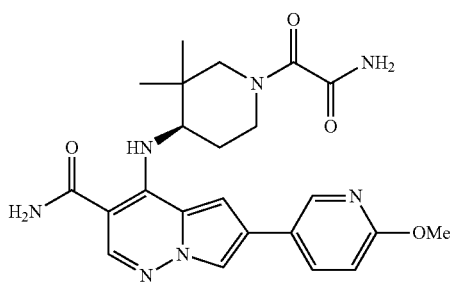 [SMILES: COc1ccc(-c2cc3c(N[C@@H]4CCN(C(=O)C(N)=O)CC4(C)C)c(C(N)=O)cnn3c2)cn1]

Step 1: (R)-tert-butyl 4-(6-bromo-3-carbamoylpyrrolo[1,2-b]pyridazin-4-ylamino)-3,3-dimethylpiperidine-1-carboxylate

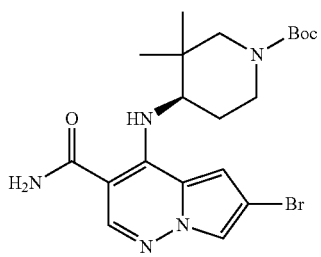 [SMILES: CC(C)(C)OC(=O)N1CC[C@@H](Nc2c(C(N)=O)cnn3cc(Br)cc23)C(C)(C)C1]

6-bromo-4-chloropyrrolo[1,2-b]pyridazine-3-carboxamide (Intermediate 2, 600 mg, 2.186 mmol), (R)-tert-butyl 4-amino-3,3-dimethylpiperidine-1-carboxylate (549 mg, 2.404 mmol) and DIPEA (0.764 mL, 4.37 mmol) in DMA (3.0 mL) was heated at 90° C. for 3 h. The mixture was cooled and added to crushed ice, stirred for 30 min, then extracted with EtOAc (100 mL×3). The combined organic extracts were washed with brine, filtered and concentrated to afford brown oil, which was added to water and stirred for 2 h to afford a solid which was collected by vacuum filtration and dried to afford the title compound as a tan solid (546 mg, 1.17 mmol, 54%). HPLC (Method B) retention time=3.91 min. LCMS (m+1)=466/468(1:1).

Step 2: (R)-tert-butyl 4-(3-carbamoyl-6-(6-methoxypyridin-3-yl)pyrrolo[1,2-b]pyridazin-4-ylamino)-3,3-dimethylpiperidine-1-carboxylate

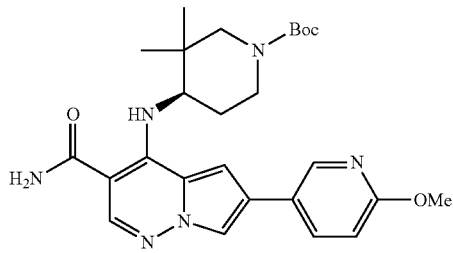 [SMILES: COc1ccc(-c2cc3c(N[C@@H]4CCN(C(=O)OC(C)(C)C)CC4(C)C)c(C(N)=O)cnn3c2)cn1]

A stirred DMF (8.0 mL) solution of (R)-tert-butyl 4-(6-bromo-3-carbamoylpyrrolo[1,2-b]pyridazin-4-ylamino)-3,3-dimethylpiperidine-1-carboxylate (1.20 g, 2.57 mmol), 6-methoxypyridin-3-ylboronic acid (0.787 g, 5.15 mmol), potassium phosphate (1.639 g, 7.72 mmol), palladium acetate (0.058 g, 0.257 mmol) and 1,1'-Bis(di-tert-butylphosphino) ferrocene (0.124 g, 0.257 mmol) was degassed by purging with argon for 5 min. The sealed tube was then heated at 90° C. for 1 h then cooled and partitioned between ethyl acetate and water. The layers were separated and the organic portion was washed with water, 10% LiCl (×2), brine and dried over anhyd. magnesium sulfate, filtered and concentrated under vacuum to afford the title compound as a tan solid (1.30 g, quantitative). HPLC (Method B) retention time=3.90 min. LCMS (m+1)=495.3. Material contained ~10% of unreacted bromide starting material but was used without any further purification in next transformation.

Step 3: (R)-4-(3,3-dimethylpiperidin-4-ylamino)-6-(6-methoxypyridin-3-yl)pyrrolo[1,2-b]pyridazine-3-carboxamide

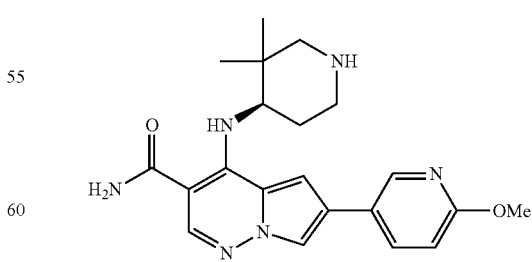

To solution of (R)-tert-butyl 4-(3-carbamoyl-6-(6-methoxypyridin-3-yl)pyrrolo[1,2-b]pyridazin-4-ylamino)-3,3-dimethylpiperidine-1-carboxylate (1.30 g, 2.63 mmol) in dichloromethane (4 mL) was added TFA (5.99 g, 52.6 mmol)

and the resulting solution was stirred for 30 min at rt. The mixture was concentrated and the residue was dissolved in dichloromethane (20 mL) and reconcentrated. The process was repeated 2 additional times with dichloromethane then three additional times using diethyl ether to afford the TFA salt of the title compound as a cream-colored solid (1.30 g, 97% yield). HPLC (Method B) retention time=2.41 min. LCMS (m+1)=395.2.

Step 4: (R)-4-(1-(2-amino-2-oxoacetyl)-3,3-dimethylpiperidin-4-ylamino)-6-(6-methoxypyridin-3-yl)pyrrolo[1,2-b]pyridazine-3-carboxamide (Example 55)

To solution of (R)-4-(3,3-dimethylpiperidin-4-ylamino)-6-(6-methoxypyridin-3-yl)pyrrolo[1,2-b]pyridazine-3-carboxamide TFA salt (20 mg, 0.039 mmol), 2-amino-2-oxoacetic acid (4.20 mg, 0.047 mmol) and HATU (22.43 mg, 0.059 mmol) in DMF (0.3 mL) was added triethylamine (0.022 mL, 0.157 mmol) and the resulting mixture was stirred at rt overnight. The mixture was quenched with 0.3 mL of MeOH, diluted with MeOH, filtered and was purified via preparative reverse phase HPLC. The fraction containing the major product was concentrated under vacuum to afford the title compound as a tan solid (10 mg, 0.015 mmol, 38%). HPLC (Method B) retention time=2.88 min. LCMS (m+1)=466.3. $^1$H NMR (400 MHz, METHANOL-$d_4$) δ 8.59 (t, J=2.2 Hz, 1H), 8.24 (dt, J=8.7, 2.8 Hz, 1H), 8.21 (s, 1H), 8.03 (t, J=2.0 Hz, 1H), 7.31 (dd, J=5.7, 1.8 Hz, 1H), 7.05 (dd, J=8.5, 2.3 Hz, 1H), 4.46-4.30 (m, 2H), 4.07-4.00 (m, 4H), 3.78 (dd, J=13.8, 1.7 Hz, 1H), 3.68-3.51 (m, 1H), 3.21-3.08 (m, 1H), 2.23 (dt, J=13.6, 4.0 Hz, 1H), 2.04-1.75 (m, 1H), 1.22-1.06 (m, 6H).

Example 56

4-((R)-1-(R)-2-hydroxypropanoyl)-3,3-dimethylpiperidin-4-ylamino)-6-(6-methoxypyridin-3-yl)pyrrolo[1,2-b]pyridazine-3-carboxamide To a solution of (R)-4-(3,3-dimethylpiperidin-4-ylamino)-6-(6-methoxypyridin-3-yl)pyrrolo[1,2-b]pyridazine-3-carboxamide TFA salt from Step 3 of Example 55 (25 mg, 0.049 mmol), (R)-2-hydroxypropanoic acid (6.64 mg, 0.074 mmol) and BOP (32.6 mg, 0.074 mmol) in DMF (0.3 mL) was added triethylamine (0.027 mL, 0.197 mmol) and the resulting mixture was stirred at rt for 4 h. The mixture was diluted with MeOH and was purified by reverse-phase preparative HPLC to afford the title compound. HPLC (method F) retention time=1.32 min LCMS MH+=467.2.$^1$H NMR (500 MHz, METHANOL-$d_4$) δ 8.55 (d, J=2.0 Hz, 1H), 8.27 (s, 1H), 8.12-8.03 (m, 1H), 7.99 (d, J=1.5 Hz, 1H), 7.23-7.17 (m, 1H), 6.99 (d, J=8.4 Hz, 1H), 4.78-4.69 (m, 1H), 4.40-4.32 (m, 1H), 4.26-4.15 (m, 1H), 4.13-4.04 (m, 4H), 3.90-3.79 (m, 1H), 3.66-3.53 (m, 1H), 3.17-3.10 (m, 1H), 2.39-2.28 (m, 1H), 2.10-1.91 (m, 1H), 1.53-1.47 (m, 3H), 1.31-1.19 (m, 6H).

Examples 57 and 58

According to the methods described for the preparation of Example 55, Examples 57 and 58 were prepared using the appropriate commercially available carboxylic acids for the amide coupling and commercially available boronic acids or esters for the Suzuki coupling to afford the final compounds. Retention times for Examples 57 and 58 were measured using analytical LCMS Method I.

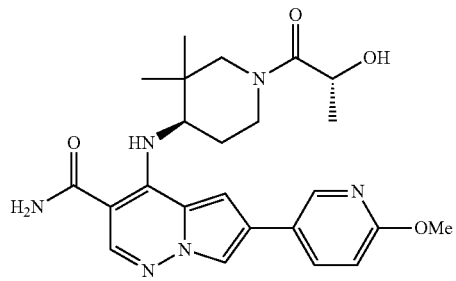 [SMILES: COc1ccc(-c2cc3c(N[C@@H]4CCN(C(=O)[C@@H](C)O)CC4(C)C)c(C(N)=O)cnn3c2)cn1]

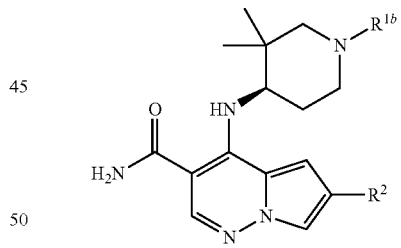

| Ex # | Name | —R$^{1b}$ | —R$^2$ | HPLC or LCMS Rt (minutes) | LCMS [m/z (M + H)] |
|---|---|---|---|---|---|
| 57 | (R)-4-(1-(2-hydroxyacetyl)-3,3-dimethylpiperidin-4-ylamino)-6-(6-(methylcarbamoyl)pyridin-3-yl)pyrrolo[1,2-b]pyridazine-3-carboxamide | ⤳↯OH (O) | ⤳-pyridyl-C(O)NH— | 1.07 | 480.4 |

| Ex # | Name | —R$^{1b}$ | —R$^2$ | HPLC or LCMS Rt (minutes) | LCMS [m/z (M + H)] |
|---|---|---|---|---|---|
| 58 | 4-((R)-1-((R)-2-hydroxypropanoyl)-3,3-dimethylpiperidin-4-ylamino)-6-(1-methyl-1H-pyrazol-4-yl)pyrrolo[1,2-b]pyridazine-3-carboxamide | | | 1.10 | 440.3 |

Example 59

6-(2-amino-5-pyrimidinyl)-4-(((3aS,4R,5R,6aS)-4-methyl-2-(methylsulfonyl)octahydrocyclopenta[c]pyrrol-5-yl)amino)pyrrolo[1,2-b]pyridazine-3-carboxamide

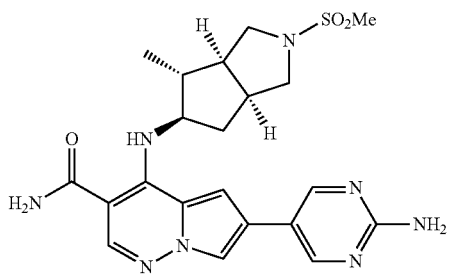 [SMILES: C[C@@H]1[C@H]2CN(S(C)(=O)=O)C[C@H]2C[C@H]1Nc1c(C(N)=O)cnn2cc(-c3cnc(N)nc3)cc12]

Step 1: (3aS,4R,5R,6aS)-tert-butyl 5-((6-bromo-3-carbamoylpyrrolo[1,2-b]pyridazin-4-yl)amino)-4-methylhexahydrocyclopenta[c]pyrrole-2(1H)-carboxylate

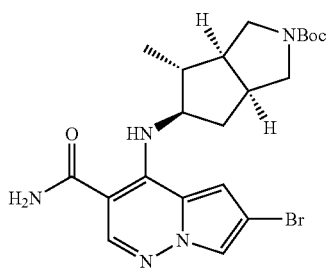

A mixture of 6-bromo-4-chloropyrrolo[1,2-b]pyridazine-3-carboxamide (Intermediate 2, 5.05 g, 18.40 mmol), crude tert-butyl 5-amino-4-methylhexahydrocyclopenta[c]pyrrole-2(1H)-carboxylate (Intermediate 7, 7.07 g) and N,N-diisopropylethylamine (12.85 mL, 73.6 mmol) in N-methylpyrrolidinone (80 mL) was heated to 95° C. for 5 h. The mixture was diluted with ethyl acetate (600 mL), washed with water, brine, dried (MgSO$_4$) and concentrated. Silica gel chromatography, eluting with 0-60% ethyl acetate in hexanes, gave the desired product as a racemic mixture (3.1 g). This mixture was resolved using preparative SFC using the following conditions: Column: ChiralPak AD-H 25×3 cm, 5 μm; Column Temp: 40° C.; Flow rate: 130 mL/min; Mobile Phase: CO2/methanol=50/50; Injection Volume: 5 mL (22.2 mg/mL, 3 g solid in 75 mL methanol and 60 mL chloroform); Detector Wavelength: 263 nm. The first eluted enantiomer was the desired (3aS,4R,5R,6aS)-tert-butyl 5-((6-bromo-3-carbamoylpyrrolo[1,2-b]pyridazin-4-yl)amino)-4-methylhexahydrocyclopenta[c]pyrrole-2(1H)-carboxylate (1.35 g). 1H NMR (400 MHz, chloroform-d) δ ppm 10.40 (1 H, d, J=8.36 Hz), 7.88 (1 H, s), 7.58 (1 H, d, J=1.76 Hz), 6.83 (1 H, d, J=1.76 Hz), 5.64 (2 H, br. s.), 3.86-4.08 (1 H, m), 3.49-3.67 (1 H, m), 3.38-3.50 (2 H, m), 3.14-3.34 (1 H, m), 2.74-2.82 (1 H, m), 2.55-2.68 (1 H, m), 2.18-2.40 (1 H, m), 1.59-1.90 (2 H, m), 1.51 (9 H, s), 1.08-1.19 (3 H, m); MS (ES+) m/z: 478.2, 480.2 (M+H).

Step 2: 6-bromo-4-(((3aS,4R,5R,6aS)-4-methyloctahydrocyclopenta[c]pyrrol-5-yl)amino)pyrrolo[1,2-b]pyridazine-3-carboxamide

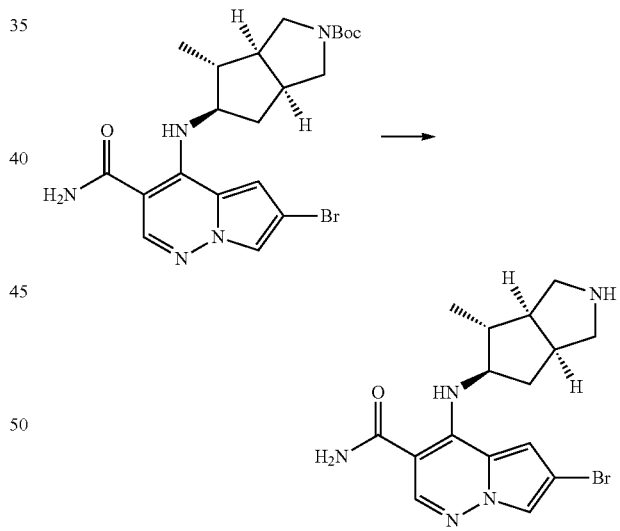

Trifluoroacetic acid (1 mL, 12.98 mmol) was added to a solution of (3 aS,4R,5R,6aS)-tert-butyl 5-(6-bromo-3-carbamoylpyrrolo[1,2-b]pyridazin-4-ylamino)-4-methyl-hexahydrocyclopenta[c]pyrrole-2(1H)-carboxylate (250 mg, 0.523 mmol) in dichloromethane (2 mL). After stirring for 1 h at room temperature, the mixture was concentrated and dried under high vacuum to give 6-bromo-4-(((3aS,4R,5R,6aS)-4-methyloctahydrocyclopenta[c]pyrrol-5-yl)amino)pyrrolo[1,2-b]pyridazine-3-carboxamide TFA salt (255 mg). 1H NMR (400 MHz, methanol-d4) δ ppm 8.15 (1 H, s), 7.66 (1 H, d, J=1.54 Hz), 7.06 (1 H, d, J=1.54 Hz), 4.03-4.34 (1 H, m), 3.31-3.59 (3 H, m), 3.01-3.25 (2 H, m), 2.53-2.83 (2 H, m), 1.60-1.84 (1 H, m), 1.36-1.60 (1 H, m), 1.17 (3 H, d); MS (ES+) m/z: 378.1, 380.1 (M+H).

Step 3: 6-bromo-4-(((3aS,4R,5R,6aS)-4-methyl-2-(methylsulfonyl)octahydrocyclopenta[c]pyrrol-5-yl)amino)pyrrolo[1,2-b]pyridazine-3-carboxamide

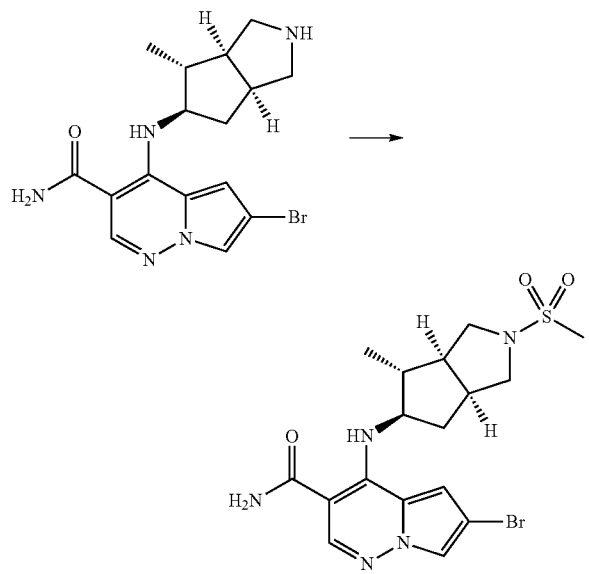

A 1 mL tetrahydrofuran solution of methanesulfonyl chloride (41.9 mg, 0.366 mmol) was added to a solution of 6-bromo-4-((3aS,4R,5R,6aS)-4-methyloctahydrocyclopenta[c]pyrrol-5-ylamino)pyrrolo[1,2-b]pyridazine-3-carboxamide TFA salt (150 mg, 0.305 mmol) and N,N-diisopropylethylamine (0.266 mL, 1.523 mmol) in N,N-dimethylformamide (2 mL) at 0° C. After stirring for 1 h at 0° C., the mixture was quenched with saturated sodium bicarbonate (5 mL), diluted with ethyl acetate (80 ml), washed with water, brine, dried (MgSO$_4$) and concentrated. The residue was purified by silica gel chromatography to provide 6-bromo-4-((3aS,4R,5R,6aS)-4-methyl-2-(methylsulfonyl)octahydrocyclopenta[c]pyrrol-5-yl)amino)pyrrolo[1,2-b]pyridazine-3-carboxamide (105 mg, 76% yield). 1H NMR (400 MHz, DMSO-d6) δ ppm 10.44-11.18 (1 H, m), 8.25 (1 H, s), 7.88 (1 H, d, J=1.76 Hz), 7.13 (1 H, d, J=1.76 Hz), 3.87-4.11 (1 H, m), 3.15-3.24 (3 H, m), 3.02-3.08 (1 H, m), 2.92 (3 H, s), 2.77-2.85 (1 H, m), 2.53-2.64 (1 H, m), 2.27-2.39 (1 H, m), 1.51-1.72 (1 H, m), 1.23-1.33 (1 H, m), 1.06 (3 H, d, J=6.38 Hz); MS (ES+) m/z: 439.2, 441.2 (M+H).

Step 4: 6-(2-amino-5-pyrimidinyl)-4-(((3aS,4R,5R,6aS)-4-methyl-2-(methylsulfonyl)octahydrocyclopenta[c]pyrrol-5-yl)amino)pyrrolo[1,2-b]pyridazine-3-carboxamide (Example 59)

A mixture of 6-bromo-4-methyl-2-(methylsulfonyl)octahydrocyclopenta[c]pyrrol-5-ylamino)pyrrolo[1,2-b]pyridazine-3-carboxamide (15 mg, 0.033 mmol), 5-(4,4,5,5-tetramethyl-1,3,2-dioxaborolan-2-yl)pyrimidin-2-amine (14.5 mg, 0.066 mmol), 2.0 M aqueous potassium phosphate (0.066 mL, 0.131 mmol) and PdCl$_2$(dppf) (2.4 mg, 0.003 mmol) in DMF (0.8 mL) was sealed under nitrogen and heated to 90° C. for 1 h. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 0.05% TFA; Mobile Phase B: 95:5 acetonitrile:water with 0.05% TFA; Gradient: 0-100% B over 25 minutes, then a 5-minute hold at 100% B; Flow: 20 mL/min. Fractions containing the desired product were combined and dried via centrifugal evaporation to give the title compound (13.2 mg, 85% yield). 1H NMR (500 MHz, DMSO-d6) δ 10.81 (d, J=7.9 Hz, 1H), 8.81 (s, 1H), 8.31-8.12 (m, 1H), 7.96 (s, 1H), 7.33 (d, J=1.5 Hz, 1H), 4.36-4.10 (m, 1H), 3.33-3.12 (m, 3H), 3.06-2.99 (m, 1H), 2.95 (s, 3H), 2.91-2.81 (m, 1H), 2.66-2.57 (m, 1H), 2.46-2.29 (m, 1H), 1.68-1.45 (m, 1H), 1.39-1.19 (m, 1H), 1.10 (d, J=6.4 Hz, 3H); MS (ES+) m/z: 471.1 (M+H); LC retention time: 1.330 min (analytical HPLC Method M).

Example 60

6-(3-acetyl-2-oxo-1-imidazolidinyl)-4-(((3aS,4R,5R,6aS)-4-methyl-2-(methylsulfonyl)octahydrocyclopenta[c]pyrrol-5-yl)amino)pyrrolo[1,2-b]pyridazine-3-carboxamide

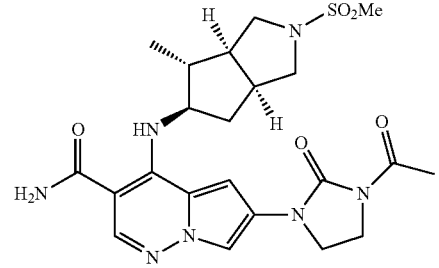 [SMILES: CC(=O)N1CCN(c2cc3c(N[C@@H]4C[C@@H]5CN(S(C)(=O)=O)C[C@@H]5[C@H]4C)c(C(N)=O)cnn3c2)C1=O]

A mixture of 6-bromo-4-((3aS,4R,5R,6aS)-4-methyl-2-(methylsulfonyl)octahydrocyclopenta[c]pyrrol-5-ylamino)pyrrolo[1,2-b]pyridazine-3-carboxamide from Step 3 of Example 59 (12 mg, 0.026 mmol), 1-acetylimidazolidin-2-one (6.7 mg, 0.053 mmol), copper(I) iodide (1 mg, 5 mmol), potassium carbonate (7 mg, 0.053 mmol) and N,N-dimethylethane-1,2-diamine (1 μL, 10 mmol) in dioxane (0.8 mL) was sealed under nitrogen in a vial and heated to 100° C. for 3 h. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-100% B over 25 minutes, then a 5-minute hold at 100% B; Flow: 20 mL/min. Fractions containing the desired product were combined and dried via centrifugal evaporation to give the title compound (3.3 mg, 25% yield). 1H NMR (500 MHz, DMSO-d6) δ 8.24 (s, 1H), 7.92 (d, J=2.0 Hz, 1H), 7.01 (d, J=1.5 Hz, 1H), 4.13-3.98 (m, 1H), 3.97-3.73 (m, 4H), 3.27-3.13 (m, 3H), 3.08 (dd, J=9.7, 3.2 Hz, 1H), 2.95 (s, 3H), 2.82-2.76 (m, 1H), 2.62-2.54 (m, 1H), 2.45 (s, 3H), 2.36-2.26 (m, 1H), 1.63 (td, J=9.7, 6.9 Hz, 1H), 1.41-1.26 (m, 1H), 1.09

(d, J=6.4 Hz, 3H); MS (ES+) m/z: 504.1 (M+H); LC retention time: 1.570 min (analytical HPLC Method M).

Example 61

6-(4-carbamoylphenyl)-4-(((3aS,4R,5R,6aS)-2-gly-coloyl-4-methyloctahydrocyclopenta[c]pyrrol-5-yl)amino)pyrrolo[1,2-b]pyridazine-3-carboxamide

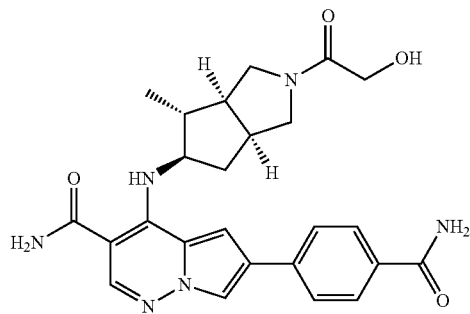 [SMILES: C[C@@H]1[C@H]2CN(C(=O)CO)C[C@H]2C[C@H]1Nc1c(C(N)=O)cnn2cc(-c3ccc(C(N)=O)cc3)cc12]

Step 1: 6-bromo-4-(((3aS,4R,5R,6aS)-2-(2-hydroxy-acetyl)-4-methyloctahydrocyclopenta[c]pyrrol-5-yl)amino)pyrrolo[1,2-b]pyridazine-3-carboxamide

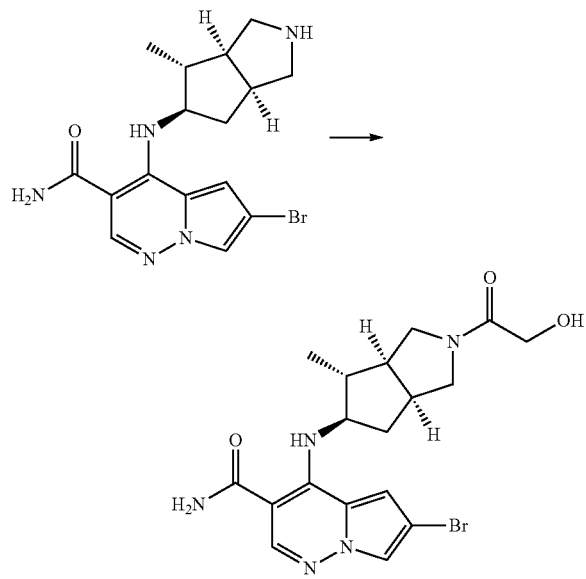

N,N-diisopropylethylamine (0.532 mL, 3.05 mmol) was added to a solution of 6-bromo-4-(((3 aS,4R,5R,6aS)-4-methyloctahydrocyclopenta[c]pyrrol-5-yl)amino)pyrrolo[1,2-b]pyridazine-3-carboxamide TFA salt from Step 2 of Example 59 (250 mg, 0.508 mmol), 2-hydroxyacetic acid (77 mg, 1.016 mmol) and (benzotriazol-1-yloxy)tris(dimethylamine)phosphonium hexafluorophosphate (449 mg, 1.016 mmol) in N,N-dimethylformamide (5 mL). After 1 h at room temperature, the mixture was diluted with saturated sodium bicarbonate (5 mL) and ethyl acetate (100 mL), washed with water, brine, dried (MgSO₄) and concentrated to give the expected product (210 mg). This material was used in the next reaction without purification. 1H NMR (400 MHz, methanol-d4) δ ppm 8.13 (1 H, s), 7.63 (1 H, s), 7.03 (1 H, d, J=1.32 Hz), 4.83-4.96 (2 H, m), 4.06-4.36 (2 H, m), 3.43-3.75 (3 H, m), 3.04-3.10 (1 H, m), 2.80-2.85 (1 H, m), 2.41-2.58 (1 H, m), 1.60-1.94 (1 H, m), 1.39-1.56 (1 H, m), 1.08-1.20 (3 H, m); MS (ES+) m/z: 436.1, 438.2 (M+H).

Step 2: 6-(4-carbamoylphenyl)-4-(((3 aS,4R,5R,6aS)-2-glycoloyl-4-methyloctahydrocyclopenta[c]pyrrol-5-yl)amino)pyrrolo[1,2-b]pyridazine-3-carboxamide (Example 61)

Following conditions described in Step 4 of Example 59, 6-bromo-4-(((3aS,4R,5R,6aS)-2-(2-hydroxyacetyl)-4-methyloctahydrocyclopenta[c]pyrrol-5-yl)amino)pyrrolo[1,2-b]pyridazine-3-carboxamide (22 mg, 0.050 mmol) was coupled with 4-(4,4,5,5-tetramethyl-1,3,2-dioxaborolan-2-yl)benzamide. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-100% B over 25 minutes, then a 5-minute hold at 100% B; Flow: 20 mL/min. Fractions containing the desired product were combined and dried via centrifugal evaporation to give the title compound (6.9 mg, 29% yield). 1H NMR (500 MHz, 1:1 mixture of methanol-d4/chloroform-d) d 8.13 (s, 1H), 7.99-7.87 (m, 3H), 7.76 (d, J=8.4 Hz, 2H), 7.20 (s, 1H), 4.43-4.06 (m, 4H), 3.81-3.45 (m, 3H), 3.01-2.87 (m, 1H), 2.86-2.75 (m, 1H), 2.67 (s, 3H), 2.57-2.39 (m, 1H), 1.89-1.80 (m, 6.9 Hz, 1H), 1.63-1.47 (m, 1H), 1.23 (d, J=6.4 Hz, 3H); MS (ES+) m/z: 477.1 (M+H); LC retention time: 1.213 min (analytical HPLC Method N).

Example 62

6-(2-amino-5-pyrimidinyl)-4-(((3aS,4R,5R,6aS)-2-(2-hydroxy-2-methylpropanoyl)-4-methyloctahydrocyclopenta[c]pyrrol-5-yl)amino)pyrrolo[1,2-b]pyridazine-3-carboxamide

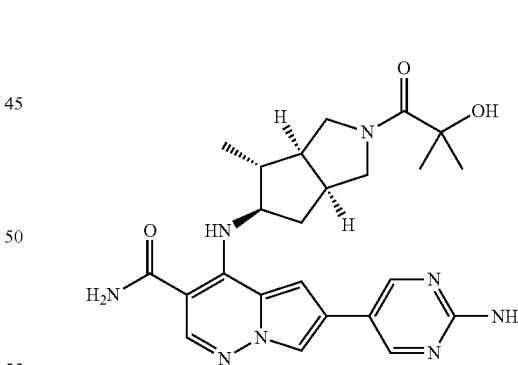

A mixture of 6-bromo-4-(((3aS,4R,5R,6aS)-4-methyloctahydrocyclopenta-[c]pyrrol-5-yl)amino)pyrrolo[1,2-b]pyridazine-3-carboxamide TFA salt from Step 2 of Example 59 (22 mg, 0.045 mmol), 2-hydroxy-2-methylpropanoic acid (5.1 mg, 0.049 mmol), (benzotriazol-1-yloxy)tris(dimethylamine)phosphonium hexafluorophosphate (21.7 mg, 0.049 mmol) and N,N-diisopropylethylamine (0.023 mL, 0.134 mmol) in N,N-dimethylformamide (1 mL) was stirred at room temperature for 2 h. 5-(4,4,5,5-Tetramethyl-1,3,2-dioxaborolan-2-yl)pyrimidin-2-amine (19.8 mg, 0.089 mmol), 2.0 M aqueous K3PO4 (0.089 mL, 0.179 mmol) and PdCl₂

(dppf) (3.27 mg, 4.47 mmol) was added. The reaction vial was sealed under nitrogen and heated to 90° C. for 1 h. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 0.05% TFA; Mobile Phase B: 95:5 acetonitrile:water with 0.05% TFA; Gradient: 0-100% B over 25 minutes, then a 5-minute hold at 100% B; Flow: 20 mL/min. Fractions containing the desired product were combined and dried via centrifugal evaporation to give the title compound (14 mg, 66% yield). 1H NMR (500 MHz, 1:1 mixture of methanol-d4/chloroform-d) d 8.64 (s, 1H), 8.13 (s, 1H), 7.98 (s, 1H), 7.86 (d, J=2.0 Hz, 1H), 7.08 (d, J=2.0 Hz, 1H), 4.35-4.13 (m, 1H), 4.10-3.89 (m, 1H), 3.79-3.49 (m, 3H), 2.95-2.88 (m, 1H), 2.85-2.75 (m, 1H), 2.45-2.20 (m, 1H), 1.78-1.69 (m, 1H), 1.62-1.52 (m, 1H), 1.52-1.36 (m, 6H), 1.21 (d, J=6.9 Hz, 3H); MS (ES+) m/z: 479.2 (M+H); LC retention time: 1.135 min (analytical HPLC Method I).

Example 63

4-(((3aS,4R,5R,6aS)-2-(2-hydroxy-2-methylpropanoyl)-4-methyloctahydrocyclopenta[c]pyrrol-5-yl)amino)-6-(6-(methylcarbamoyl)-3-pyridinyl)pyrrolo[1,2-b]pyridazine-3-carboxamide

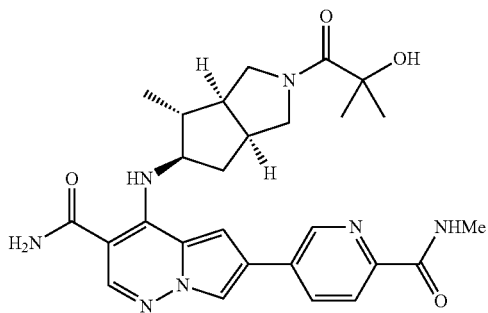 [SMILES: CNC(=O)c1ccc(-c2cc3c(N[C@@H]4C[C@@H]5CN(C(=O)C(C)(C)O)C[C@@H]5[C@H]4C)c(C(N)=O)cnn3c2)cn1]

Step 1: 6-bromo-4-(((3 aS,4R,5R,6aS)-2-(2-hydroxy-2-methylpropanoyl)-4-methyloctahydrocyclopenta[c]pyrrol-5-yl)amino)pyrrolo[1,2-b]pyridazine-3-carboxamide

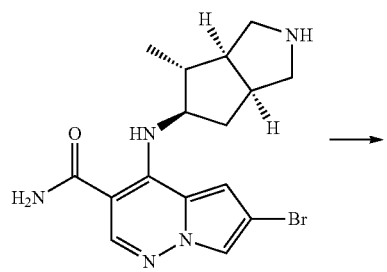

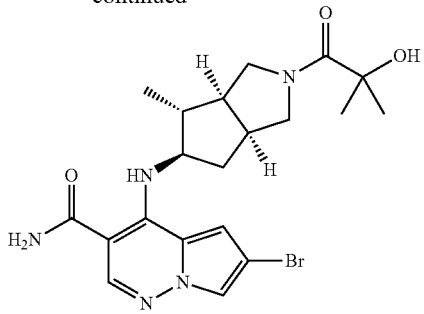

A mixture of 6-bromo-4-(((3aS,4R,5R,6aS)-4-methyloctahydrocyclopenta[c]pyrrol-5-yl)amino)pyrrolo[1,2-b]pyridazine-3-carboxamide TFA salt from Step 2 of Example 59 (151 mg, 0.307 mmol), 2-hydroxy-2-methylpropanoic acid (38.3 mg, 0.368 mmol), triethylamine (0.128 mL, 0.920 mmol) and (benzotriazol-1-yloxy)tris(dimethylamine)phosphonium hexafluorophosphate (163 mg, 0.368 mmol) in dimethylformamide (2 mL) was stirred at room temperature for 2 h. The mixture was diluted with ethyl acetate (80 mL), washed with saturated sodium bicarbonate, water, brine, dried (MgSO$_4$) and concentrated to give the expected product (120 mg). 1H NMR (400 MHz, methanol-d4) d 8.13 (s, 1H), 7.63 (d, J=1.8 Hz, 1H), 7.03 (d, J=1.8 Hz, 1H), 4.35-4.03 (m, 2H), 3.99-3.51 (m, 3H), 2.88-2.79 (m, 1H), 2.72-2.66 (m, 2H), 1.82-1.61 (m, 2H), 1.47-1.39 (m, 6H), 1.16 (d, J=6.6 Hz, 3H); MS (ES+) m/z: 436.1, 438.2 (M+H); LCMS (M+1): 464.1, 466.2.

Step 2: 4-(((3aS,4R,5R,6aS)-2-(2-hydroxy-2-methylpropanoyl)-4-methyloctahydrocyclopenta[c]pyrrol-5-yl)amino)-6-(6-(methylcarbamoyl)-3-pyridinyl)pyrrolo[1,2-b]pyridazine-3-carboxamide (Example 63)

A mixture of 6-bromo-4-(((3aS,4R,5R,6aS)-2-(2-hydroxy-2-methylpropanoyl)-4-methyloctahydrocyclopenta[c]pyrrol-5-yl)amino)pyrrolo[1,2-b]pyridazine-3-carboxamide (32 mg, 0.055 mmol), N-methyl-5-(4,4,5,5-tetramethyl-1,3,2-dioxaborolan-2-yl)picolinamide (29.0 mg, 0.111 mmol) and 2.0 M aqueous K$_3$PO$_4$ (0.111 mL, 0.221 mmol) in dimethylformamide (1 mL) was heated to 90° C. under nitrogen for 1 h. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-100% B over 25 minutes, then a 5-minute hold at 100% B; Flow: 20 mL/min. Fractions containing the desired product were combined and dried via centrifugal evaporation to give the title compound (14.9 mg, 52% yield). 1H NMR (500 MHz, 1:1 mixture of methanol-d4/chloroform-d) d 8.93 (d, J=2.0 Hz, 1H), 8.28-8.08 (m, 3H), 8.04 (d, J=1.5 Hz, 1H), 7.28 (d, J=1.5 Hz, 1H), 4.45-4.19 (m, 2H), 4.03-3.91 (m, 1H), 3.77-3.56 (m, 2H), 3.10-2.99 (m, 3H), 2.96-2.79 (m, 2H), 2.53-2.32 (m, 1H), 1.87-1.75 (m, 1H), 1.66-1.54 (m, 1H), 1.51-1.35 (m, 6H), 1.22 (d, J=6.4 Hz, 3H); MS (ES+) m/z: 520.2 (M+H); LC retention time: 1.135 min (analytical HPLC Method I).

Examples 64-66

According to the procedure described for Example 60, Examples 64-66 were prepared from 6-bromo-4-(((3aS,4R, 5R,6aS)-4-methyl-2-(methylsulfonyl)octahydro-cyclopenta[c]pyrrol-5-yl)amino)pyrrolo[1,2-b]pyridazine-3-carboxamide (from Step 3 of Example 59) and commercially available cyclic ureas or lactams. Retention times for Examples 64 and 65 were measured using analytical LCMS Method H. Retention time for Example 66 was measured using analytical HPLC method G.

Step 1: 6-cyano-4-((3aS,4R,5R,6aS)-4-methyl-2-(methylsulfonyl)octahydrocyclopenta[c]pyrrol-5-yl)amino)pyrrolo[1,2-b]pyridazine-3-carboxamide

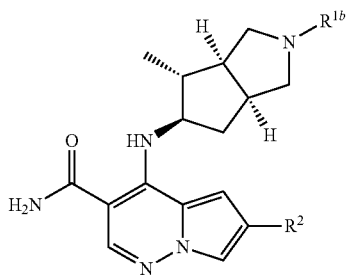

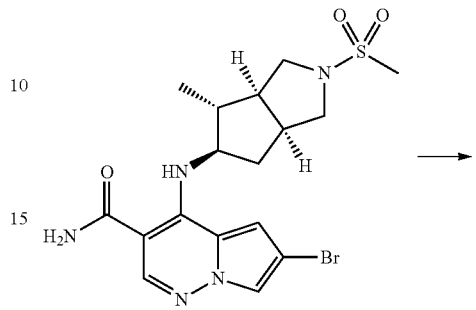

| Ex # | Name | —R$^{1b}$ | —R$^2$ | HPLC or LCMS Rt (minutes) | LCMS [m/z] (M + H) |
|---|---|---|---|---|---|
| 64 | 4-((3aS,4R,5R,6aS)-4-methyl-2-(methylsulfonyl)octahydrocyclopenta[c]-pyrrol-5-ylamino)-6-(3-methyl-2-oxoimidazolidin-1-yl)pyrrolo[1,2-b]pyridazine-3-carboxamide | S(=O)(=O)Me | 3-methyl-2-oxoimidazolidin-1-yl | 1.11 | 476.2 |
| 65 | 6-((R)-3-fluoro-2-oxopyrrolidin-1-yl)-4-((3aS,4R,5R,6aS)-4-methyl-2-(methylsulfonyl)octahydrocyclopenta[c]-pyrrol-5-ylamino)pyrrolo[1,2-b]pyridazine-3-carboxamide | S(=O)(=O)Me | (R)-3-fluoro-2-oxopyrrolidin-1-yl | 1.13 | 479.2 |
| 66 | 6-((S)-3-methoxy-2-oxopyrrolidin-1-yl)-4-((3aS,4R,5R,6aS)-4-methyl-2-(methylsulfonyl)octahydrocyclopenta[c]-pyrrol-5-ylamino)pyrrolo[1,2-b]pyridazine-3-carboxamide | S(=O)(=O)Me | (S)-3-methoxy-2-oxopyrrolidin-1-yl | 6.485 | 491.2 |

Example 67

4-(((3aS,4R,5R,6aS)-4-methyl-2-(methylsulfonyl)octahydrocyclopenta[c]pyrrol-5-yl)amino)-6-(2-methyl-2H-tetrazol-5-yl)pyrrolo[1,2-b]pyridazine-3-carboxamide

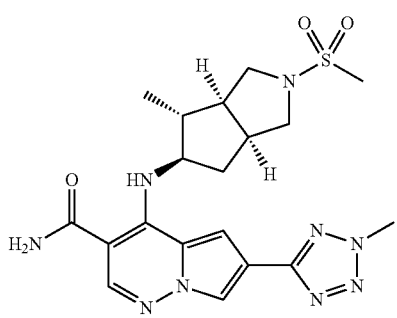 [SMILES: C[C@@H]1[C@H]2CN(S(C)(=O)=O)C[C@H]2C[C@H]1Nc1c(C(N)=O)cnn2cc(-c3nnn(C)n3)cc12]

-continued

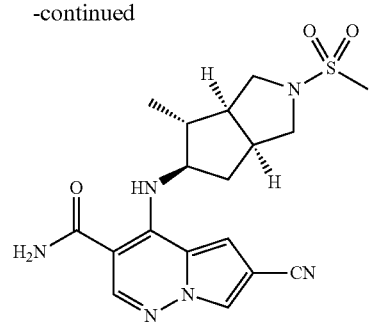

A mixture of 6-bromo-4-(((3aS,4R,5R,6aS)-4-methyl-2-(methylsulfonyl)octahydrocyclopenta[c]pyrrol-5-yl)amino)pyrrolo[1,2-b]pyridazine-3-carboxamide from Step 3 of Example 59 (70 mg, 0.153 mmol) and copper(I) cyanide (27.5 mg, 0.307 mmol) in 1-methyl-2-pyrrolidinone (1 mL) was heated to 220° C. under microwave for 2 h. The resulting mixture was diluted with ethyl acetate (80 mL), washed with saturated NH4Cl, water, brine, dried (MgSO4) and concentrated. The residue was purified by silica gel chromatography, eluting with 60-100% ethyl acetate in hexanes, to give 6-cyano-4-(((3aS,4R,5R,6aS)-4-methyl-2-(methylsulfonyl)octahydrocyclopenta[c]pyrrol-5-yl)amino)pyrrolo[1,2-b]pyridazine-3-carboxamide (35 mg, 56% yield). 1H NMR (400 MHz, DMSO-d6) δ ppm 8.43 (d, J=1.8 Hz, 1H), 8.37 (s, 1H), 7.61 (d, J=1.5 Hz, 1H), 4.24-4.01 (m, 1H), 3.26-3.11 (m, 2H), 3.05 (m, 1H), 2.93 (s, 3H), 2.93-2.83 (m, 1H), 2.61-2.54 (m, 1H), 2.36-2.17 (m, 1H), 1.93-1.82 (m, 1H), 1.70-1.55 (m, 1H), 1.36-1.25 (m, 1H), 1.10-1.02 (m, 3H).

Step 2: 4-(((3aS,4R,5R,6aS)-4-methyl-2-(methylsulfonyl)octahydrocyclopenta[c]pyrrol-5-yl)amino)-6-(2H-tetrazol-5-yl)pyrrolo[1,2-b]pyridazine-3-carboxamide

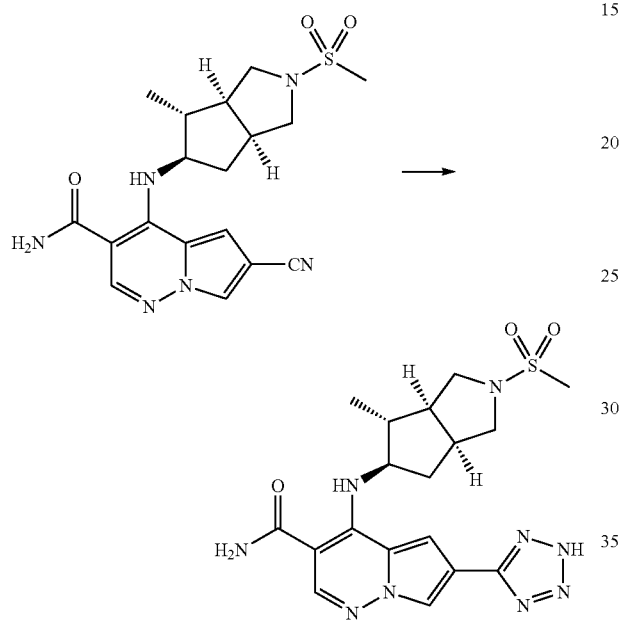

A solution of 6-cyano-4-(((3aS,4R,5R,6aS)-4-methyl-2-(methylsulfonyl)octahydrocyclopenta[c]pyrrol-5-yl)amino)pyrrolo[1,2-b]pyridazine-3-carboxamide (34 mg, 0.084 mmol) and azidotributyltin (0.028 mL, 0.101 mmol) in 1-methyl-2-pyrrolidinone (1 mL) was heated to 180° C. under microwave for 1 h. LCMS analysis showed that the expected product was observed as the major peak. The reaction mixture was taken to the next step without purification. MS (ES+) m/z: 446.1 (M+H).

Step 3: 4-(((3aS,4R,5R,6aS)-4-methyl-2-(methylsulfonyl)octahydrocyclopenta[c]pyrrol-5-yl)amino)-6-(2-methyl-2H-tetrazol-5-yl)pyrrolo[1,2-b]pyridazine-3-carboxamide (Example 67)

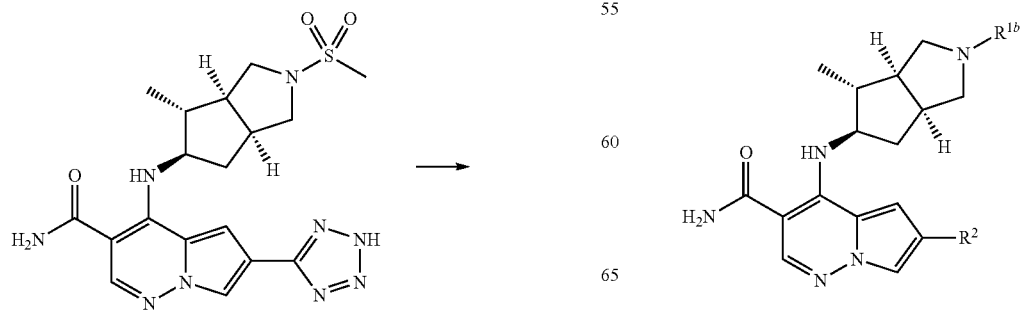

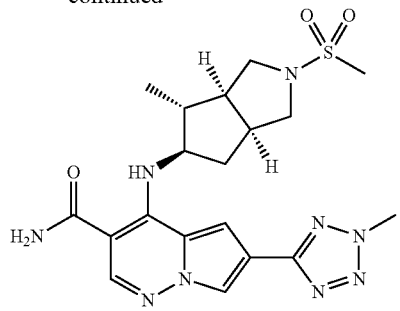

A mixture of the crude 4-(((3aS,4R,5R,6aS)-4-methyl-2-(methylsulfonyl)octahydrocyclopenta[c]pyrrol-5-yl)amino)-6-(1H-tetrazol-5-yl)pyrrolo[1,2-b]pyridazine-3-carboxamide from Step 2, iodomethane (6.8 μl, 0.109 mmol) and potassium carbonate (23.2 mg, 0.168 mmol) in 1-methyl-2-pyrrolidinone (1 mL) was stirred at room temperature for 2 h. Attempted purification by RP-HPLC gave impure product. The mixture was further purified by silica gel chromatography, eluting with 0 to 10% methanol in dichloromethane to give the title compound (4 mg). 1H NMR (400 MHz, DMSO-d6) δ ppm 10.92 (d, J=7.3 Hz, 1H), 8.30 (s, 1H), 8.20 (d, J=1.5 Hz, 1H), 7.40 (d, J=1.5 Hz, 1H), 5.91-5.90 (m, 1H), 4.40 (s, 3H), 4.28-4.05 (m, 1H), 3.35-3.13 (m, 4H), 2.93 (s, 3H), 2.90-2.75 (m, 1H), 2.62-2.55 (m, 1H), 2.46-2.30 (m, 1H), 1.66-1.54 (m, 1H), 1.39-1.29 (m, 1H), 1.08 (d, J=6.6 Hz, 3H); MS (ES+) m/z: 460.3 (M+H); LC retention time: 6.988 min (analytical HPLC Method E).

Examples 68-100

According to the procedure described in Steps 1 and 2 of Example 61 or Steps 1 and 2 of Example 63, Examples 68-100 were prepared from 6-bromo-4-(((3aS,4R,5R,6aS)-4-methyloctahydrocyclopenta[c]pyrrol-5-ylamino)pyrrolo[1,2-b]pyridazine-3-carboxamide from Step 2 of Example 59. Retention times for Examples 70, 72, 73 and 76 were determined using analytical HPLC Methods M, I, N and analytical LCMS method H, respectively. All other retention times were determined using analytical LCMS method I.

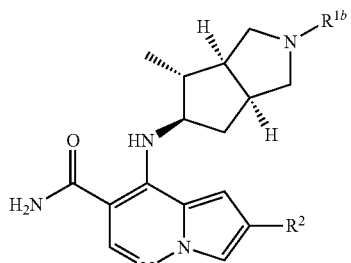

| Ex # | Name | —R^{1b} | —R^2 | HPLC or LCMS Rt (minutes) | LCMS [m/z (M + H)] |
|---|---|---|---|---|---|
| 68 | 4-((3aS,4R,5R,6aS)-2-(2-fluoroacetyl)-4-methyloctahydrocyclopenta[c]pyrrol-5-ylamino)-6-(1-methyl-1H-pyrazol-4-yl)pyrrolo[1,2-b]pyridazine-3-carboxamide | C(=O)CH$_2$F (with Me) | 1-methyl-1H-pyrazol-4-yl | 1.06 | 440.0 |
| 69 | 6-(6-amino-5-fluoropyridin-3-yl)-4-((3aS,4R,5R,6aS)-2-(2-fluoroacetyl)-4-methyloctahydrocyclopenta[c]pyrrol-5-ylamino)pyrrolo[1,2-b]pyridazine-3-carboxamide | C(=O)CH$_2$F (with Me) | 6-amino-5-fluoropyridin-3-yl | 0.86 | 470.0 |
| 70 | 6-(4-(cyclopropylcarbamoyl)phenyl)-4-((3aS,4R,5R,6aS)-2-(2-hydroxyacetyl)-4-methyloctahydrocyclopenta[c]pyrrol-5-ylamino)pyrrolo[1,2-b]pyridazine-3-carboxamide | C(=O)CH$_2$OH (with Me) | 4-(cyclopropylcarbamoyl)phenyl | 1.492 | 517.2 |
| 71 | 4-((3aS,4R,5R,6aS)-2-(2-hydroxyacetyl)-4-methyloctahydrocyclopenta[c]pyrrol-5-ylamino)-6-(6-(methylcarbamoyl)pyridin-3-yl)pyrrolo[1,2-b]pyridazine-3-carboxamide | C(=O)CH$_2$OH (with Me) | 6-(methylcarbamoyl)pyridin-3-yl | 1.05 | 492.0 |
| 72 | 4-((3aS,4R,5R,6aS)-2-((S)-2-hydroxypropanoyl)-4-methyloctahydrocyclopenta[c]pyrrol-5-ylamino)-6-(6-methoxypyridin-3-yl)pyrrolo[1,2-b]pyridazine-3-carboxamide | C(=O)CH(OH)Me (S) | 6-methoxypyridin-3-yl | 1.673 | 479.2 |
| 73 | 6-(4-(cyclopropylcarbamoyl)phenyl)-4-((3aS,4R,5R,6aS)-2-((R)-2-hydroxypropanoyl)-4-methyloctahydrocyclopenta[c]pyrrol-5-ylamino)pyrrolo[1,2-b]pyridazine-3-carboxamide | C(=O)CH(OH)Me (R) | 4-(cyclopropylcarbamoyl)phenyl | 1.523 | 531.2 |
| 74 | 4-((3aS,4R,5R,6aS)-2-(2-hydroxy-2-methylpropanoyl)-4-methyloctahydrocyclopenta[c]pyrrol-5-ylamino)-6-(pyridin-4-yl)pyrrolo[1,2-b]pyridazine-3-carboxamide | C(=O)C(OH)(Me)$_2$ (with Me) | pyridin-4-yl | 0.81 | 463.2 |
| 75 | 6-(3-fluoropyridin-4-yl)-4-((3aS,4R,5R,6aS)-2-(2-hydroxy-2-methylpropanoyl)-4-methyloctahydrocyclopenta[c]pyrrol-5-ylamino)pyrrolo[1,2-b]pyridazine-3-carboxamide | C(=O)C(OH)(Me)$_2$ (with Me) | 3-fluoropyridin-4-yl | 1.01 | 481.2 |
| 76 | 6-(2-fluoropyridin-4-yl)-4-((3aS,4R,5R,6aS)-2-(2-hydroxy-2-methylpropanoyl)-4-methyloctahydrocyclopenta[c]pyrrol-5-ylamino)pyrrolo[1,2-b]pyridazine-3-carboxamide | C(=O)C(OH)(Me)$_2$ (with Me) | 2-fluoropyridin-4-yl | 1.40 | 481.3 |
| 77 | 6-(6-aminopyridin-3-yl)-4-((3aS,4R,5R,6aS)-2-(2-hydroxy-2-methylpropanoyl)-4-methyloctahydrocyclopenta[c]pyrrol-5-ylamino)pyrrolo[1,2-b]pyridazine-3-carboxamide | C(=O)C(OH)(Me)$_2$ (with Me) | 6-aminopyridin-3-yl | 0.84 | 478.2 |

| Ex # | Name | —R$^{1b}$ | —R$^2$ | HPLC or LCMS Rt (minutes) | LCMS [m/z] (M + H) |
|---|---|---|---|---|---|
| 78 | 6-(6-cyanopyridin-3-yl)-4-((3aS,4R,5R,6aS)-2-(2-hydroxy-2-methylpropanoyl)-4-methyloctahydrocyclopenta[c]pyrrol-5-ylamino)pyrrolo[1,2-b]pyridazine-3-carboxamide | C(=O)C(OH)(Me)(Me) | pyridin-3-yl with 6-CN | 1.34 | 488.2 |
| 79 | 6-(6-acetamidopyridin-3-yl)-4-((3aS,4R,5R,6aS)-2-(2-hydroxy-2-methylpropanoyl)-4-methyloctahydrocyclopenta[c]pyrrol-5-ylamino)pyrrolo[1,2-b]pyridazine-3-carboxamide | C(=O)C(OH)(Me)(Me) | pyridin-3-yl with 6-NHC(=O)Me | 0.97 | 520.3 |
| 80 | 6-(6-amino-5-fluoropyridin-3-yl)-4-((3aS,4R,5R,6aS)-2-(2-hydroxy-2-methylpropanoyl)-4-methyloctahydrocyclopenta[c]pyrrol-5-ylamino)pyrrolo[1,2-b]pyridazine-3-carboxamide | C(=O)C(OH)(Me)(Me) | pyridin-3-yl with 6-NH$_2$, 5-F | 0.94 | 496.2 |
| 81 | 4-((3aS,4R,5R,6aS)-2-(2-hydroxy-2-methylpropanoyl)-4-methyloctahydrocyclopenta[c]pyrrol-5-ylamino)-6-(6-(2-methoxyacetamido)pyridin-3-yl)pyrrolo[1,2-b]pyridazine-3-carboxamide | C(=O)C(OH)(Me)(Me) | pyridin-3-yl with 6-NHC(=O)CH$_2$OMe | 1.39 | 550.0 |
| 82 | 4-((3aS,4R,5R,6aS)-2-(2-hydroxy-2-methylpropanoyl)-4-methyloctahydrocyclopenta[c]pyrrol-5-ylamino)-6-(2-methoxypyrimidin-5-yl)pyrrolo[1,2-b]pyridazine-3-carboxamide | C(=O)C(OH)(Me)(Me) | 2-methoxypyrimidin-5-yl | 1.23 | 494.2 |
| 83 | 4-((3aS,4R,5R,6aS)-2-(2-hydroxy-2-methylpropanoyl)-4-methyloctahydrocyclopenta[c]pyrrol-5-ylamino)-6-(1-methyl-1H-pyrazol-4-yl)pyrrolo[1,2-b]pyridazine-3-carboxamide | C(=O)C(OH)(Me)(Me) | 1-methyl-1H-pyrazol-4-yl | 1.10 | 466.3 |
| 84 | 4-((3aS,4R,5R,6aS)-2-(2-hydroxy-2-methylpropanoyl)-4-methyloctahydrocyclopenta[c]pyrrol-5-ylamino)-6-(1-methyl-1H-pyrazol-5-yl)pyrrolo[1,2-b]pyridazine-3-carboxamide | C(=O)C(OH)(Me)(Me) | 1-methyl-1H-pyrazol-5-yl | 1.14 | 466.2 |
| 85 | 6-(1,3-dimethyl-1H-pyrazol-4-yl)-4-((3aS,4R,5R,6aS)-2-(2-methoxyacetyl)-4-methyloctahydrocyclopenta[c]pyrrol-5-ylamino)pyrrolo[1,2-b]pyridazine-3-carboxamide | C(=O)CH$_2$OMe | 1,3-dimethyl-1H-pyrazol-4-yl | 1.25 | 466.4 |
| 86 | 4-((3aS,4R,5R,6aS)-2-(2-cyanoacetyl)-4-methyloctahydrocyclopenta[c]pyrrol-5-ylamino)-6-(2-methoxypyrimidin-5-yl)pyrrolo[1,2-b]pyridazine-3-carboxamide | C(=O)CH$_2$CN | 2-methoxypyrimidin-5-yl | 1.18 | 475.0 |
| 87 | 4-((3aS,4R,5R,6aS)-2-(2-cyano-2-methylpropanoyl)-4-methyloctahydrocyclopenta[c]pyrrol-5-ylamino)-6-(2-methylpyrimidin-5-yl)pyrrolo[1,2-b]pyridazine-3-carboxamide | C(=O)C(CN)(Me)(Me) | 2-methoxypyrimidin-5-yl | 1.77 | 487.0 |

-continued

| Ex # | Name | —R$^{1b}$ | —R$^2$ | HPLC or LCMS Rt (minutes) | LCMS [m/z (M + H)] |
|---|---|---|---|---|---|
| 88 | 4-((3aS,4R,5R,6aS)-2-(2-cyano-2-methylpropanoyl)-4-methyloctahydrocyclopenta[c]pyrrol-5-ylamino)-6-(2-methoxypyrimidin-5-yl)pyrrolo[1,2-b]pyridazine-3-carboxamide | (C(=O)C(Me)(Me)CN) | (2-methoxypyrimidin-5-yl) | 1.34 | 503.1 |
| 89 | 4-((3aS,4R,5R,6aS)-2-(2,2-difluorocyclopropanecarbonyl)-4-methyloctahydrocyclopenta[c]pyrrol-5-ylamino)-6-(1-methyl-1H-pyrazol-4-yl)pyrrolo[1,2-b]pyridazine-3-carboxamide | (2,2-difluorocyclopropanecarbonyl) | (1-methyl-1H-pyrazol-4-yl) | 1.25 | 483.2 |
| 93 | 4-((3aS,4R,5R,6aS)-2-acetyl-4-methyloctahydrocyclopenta[c]pyrrol-5-ylamino)-6-(1-methyl-1H-pyrazol-4-yl)pyrrolo[1,2-b]pyridazine-3-carboxamide | (C(=O)Me) | (1-methyl-1H-pyrazol-4-yl) | 1.11 | 422.4 |
| 94 | 4-((3aS,4R,5R,6aS)-2-acetyl-4-methyloctahydrocyclopenta[c]pyrrol-5-ylamino)-6-(1-ethyl-1H-pyrazol-4-yl)pyrrolo[1,2-b]pyridazine-3-carboxamide | (C(=O)Me) | (1-ethyl-1H-pyrazol-4-yl) | 1.16 | 436.0 |
| 95 | 4-((3aS,4R,5R,6aS)-2-acetyl-4-methyloctahydrocyclopenta[c]pyrrol-5-ylamino)-6-(1-(difluoromethyl)-1H-pyrazol-4-yl)pyrrolo[1,2-b]pyridazine-3-carboxamide | (C(=O)Me) | (1-(difluoromethyl)-1H-pyrazol-4-yl) | 1.28 | 458.0 |
| 96 | 4-((3aS,4R,5R,6aS)-2-acetyl-4-methyloctahydrocyclopenta[c]pyrrol-5-ylamino)-6-(6-amino-5-fluoropyridin-3-yl)pyrrolo[1,2-b]pyridazine-3-carboxamide | (C(=O)Me) | (6-amino-5-fluoropyridin-3-yl) | 0.91 | 452.3 |
| 97 | 6-(6-fluoropyridin-3-yl)-4-((3aS,4R,5R,6aS)-4-methyl-2-propionyloctahydrocyclopenta[c]pyrrol-5-ylamino)pyrrolo[1,2-b]pyridazine-3-carboxamide | (C(=O)Et) | (6-fluoropyridin-3-yl) | 1.66 | 451.0 |
| 98 | 6-(2-fluoropyridin-4-yl)-4-((3aS,4R,5R,6aS)-4-methyl-2-propionyloctahydrocyclopenta[c]-pyrrol-5-ylamino)pyrrolo[1,2-b]pyridazine-3-carboxamide | (C(=O)Et) | (2-fluoropyridin-4-yl) | 1.67 | 451.0 |
| 99 | 6-(5-fluoro-6-(methylamino)pyridin-3-yl)-4-((3aS,4R,5R,6aS)-4-methyl-2-propionyloctahydrocyclopenta[c]-pyrrol-5-ylamino)pyrrolo[1,2-b]pyridazine-3-carboxamide | (C(=O)Et) | (5-fluoro-6-(methylamino)pyridin-3-yl) | 1.01 | 480.0 |
| 100 | 6-(1-methyl-1H-pyrazol-4-yl)-4-((3aS,4R,5R,6aS)-4-methyl-2-propionyloctahydrocyclopenta[c]-pyrrol-5-ylamino)pyrrolo[1,2-b]pyridazine-3-carboxamide | (C(=O)Et) | (1-methyl-1H-pyrazol-4-yl) | 1.35 | 436.0 |

Example 101

6-(2-ethyl-2H-tetrazol-5-yl)-4-(((3aS,4R,5R,6aS)-2-(2-hydroxy-2-methylpropanoyl)-4-methyloctahydrocyclopenta[c]pyrrol-5-yl)amino)pyrrolo[1,2-b]pyridazine-3-carboxamide

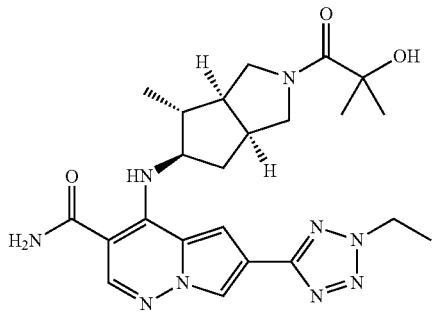 [SMILES: CCn1nnc(-c2cc3c(N[C@@H]4C[C@@H]5CN(C(=O)C(C)(C)O)C[C@@H]5[C@H]4C)c(C(N)=O)cnn3c2)n1]

Example 101 was synthesized from 6-bromo-4-(((3aS,4R,5R,6aS)-2-(2-hydroxy-2-methylpropanoyl)-4-methyloctahydrocyclopenta[c]pyrrol-5-yl)amino)pyrrolo[1,2-b]pyridazine-3-carboxamide (from Step 1 of Example 63) followed by incoporation of the ethyl tetrazole functional group using the procedures described for the preparation of Example 67 and by replacing methyl iodide with ethyl iodide. The crude product was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 25 minutes, then a 5-minute hold at 100% B; Flow: 20 mL/min. Fractions containing the desired product were combined and dried via centrifugal evaporation to give 6-(2-ethyl-2H-tetrazol-5-yl)-4-(((3aS,4R,5R,6aS)-2-(2-hydroxy-2-methylpropanoyl)-4-methyloctahydrocyclopenta[c]pyrrol-5-yl)amino)pyrrolo[1,2-b]pyridazine-3-carboxamide (8.4 mg). 1H NMR (500 MHz, 1:1 mixture of chloroform-d/methanol-d4) δ ppm 8.37-8.10 (m, 2H), 7.48 (d, J=1.5 Hz, 1H), 4.75 (q, J=7.4 Hz, 2H), 4.32-4.14 (m, 1H), 4.08-3.88 (m, 1H), 3.77-3.52 (m, 3H), 2.97-2.75 (m, 2H), 2.57-2.27 (m, 1H), 1.89-1.75 (m, 1H), 1.72 (t, J=7.4 Hz, 3H), 1.66-1.38 (m, 7H), 1.21 (d, J=6.4 Hz, 3H); MS (ES+) m/z: 482.2 (M+H); LC retention time: 1.26 min (analytical LCMS Method I).

Example 102

4-(((3aS,4R,5R,6aS)-2-((R)-2-hydroxypropyl)-4-methyloctahydrocyclopenta[c]pyrrol-5-yl)amino)-6-(1-methyl-1H-pyrazol-4-yl)pyrrolo[1,2-b]pyridazine-3-carboxamide

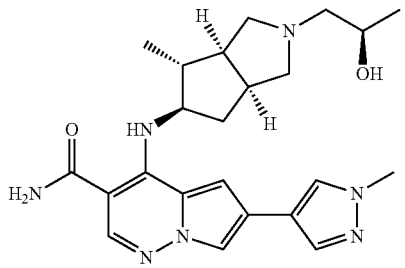 [SMILES: C[C@@H]1[C@H]2CN(C[C@@H](C)O)C[C@H]2C[C@H]1Nc1c(C(N)=O)cnn2cc(-c3cnn(C)c3)cc12]

Hunig's base (0.032 mL, 0.182 mmol) was added to a mixture of 6-(1-methyl-1H-pyrazol-4-yl)-4-(((3aS,4R,5R,6aS)-4-methyloctahydrocyclopenta[c]pyrrol-5-yl)amino)pyrrolo[1,2-b]pyridazine-3-carboxamide TFA salt (15.0 mg, 0.030 mmol, prepared from (3aS,4R,5R,6aS)-tert-butyl 5-((6-bromo-3-carbamoylpyrrolo[1,2-b]pyridazin-4-yl)amino)-4-methylhexahydrocyclopenta[c]pyrrole-2(1H)-carboxylate from Step 1 of Example 59 and using the procedures described in Steps 1-3 of Example 55), (R)-2-methyloxirane (177 mg, 3.04 mmol) and N,N-dimethylformamide (1 mL).

The reaction vial was sealed and placed in a 80° C. heating block for 18 h. The crude material was purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 15 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 25 minutes, then a 15-minute hold at 45% B; Flow: 20 mL/min. Fractions containing the desired product were combined and dried via centrifugal evaporation to give the title compound (1.8 mg, 13% yield). 1H NMR (500 MHz, 1:1 mixture of chloroform-d/methanol-d4) δ ppm 8.07 (s, 1H), 7.76 (s, 1H), 7.73-7.67 (m, 2H), 6.94 (d, J=1.5 Hz, 1H), 4.06 (td, J=9.7, 6.4 Hz, 1H), 3.95 (s, 3H), 3.90 (ddd, J=9.2, 6.2, 3.5 Hz, 1H), 2.83-2.72 (m, 3H), 2.69-2.55 (m, 3H), 2.50-2.37 (m, 2H), 2.33-2.22 (m, 1H), 1.93-1.81 (m, 1H), 1.59-1.47 (m, 1H), 1.17 (dd, J=9.9, 6.4 Hz, 6H); MS (ES+) m/z: 438.1 (M+H); LC retention time: 0.84 min (analytical LCMS Method I).

Examples 103 and 104

Following conditions analogous to the synthesis of Example 102, Examples 103 and 104 were prepared from (3aS,4R,5R,6aS)-tert-butyl 5-((6-bromo-3-carbamoylpyrrolo[1,2-b]pyridazin-4-yl)amino)-4-methylhexahydrocyclopenta[c]pyrrole-2(1H)-carboxylate (from Step 1 of Example 59). Retention times for both examples were measured using analytical LCMS Method I.

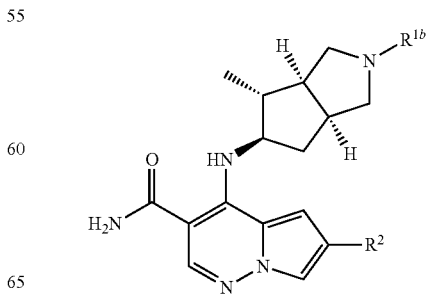

| Ex # | Name | —R¹ᵇ | —R² | HPLC or LCMS Rt (minutes) | LCMS [m/z (M + H)] |
|---|---|---|---|---|---|
| 103 | 4-((3aS,4R,5R,6aS)-2-((R)-2-hydroxypropyl)-4-methyloctahydrocyclopenta[c]pyrrol-5-ylamino)-6-(6-(methylcarbamoyl)pyridin-3-yl)pyrrolo[1,2-b]pyridazine-3-carboxamide | (isopropyl with OH) | (pyridine-CONHMe) | 0.96 | 492.2 |
| 104 | 4-((3aS,4R,5R,6aS)-2-(2-methoxyethyl)-4-methyloctahydrocyclopenta[c]pyrrol-5-ylamino)-6-(1-methyl-1H-pyrazol-4-yl)pyrrolo[1,2-b]pyridazine-3-carboxamide | (CH₂CH₂OMe) | (1-methylpyrazol-4-yl) | 0.89 | 438.1 |

Examples 105-116

Examples 105-116 were prepared from (R)-tert-butyl 4-(6-bromo-3-carbamoylpyrrolo[1,2-b]pyridazin-4-ylamino)-3,3-dimethylpiperidine-1-carboxylate (from Step 1 of Example 55) using the procedures similar to that described in Step 4 of Example 1 and Example 38. The 3-hydroxy-3-methylpyrrolidin-2-one reagent, which was used for preparation of Examples 110 and 112, was synthesized according to a published procedure (Ochiai et al. Tetrahedron 1967, 23, 2641). Example 116 was prepared by treating Example 115 with sodium hydride and iodomethane in N,N-dimethylformamide at room temperature. Retention times for Examples 105-116 were measured using analytical LCMS Method I.

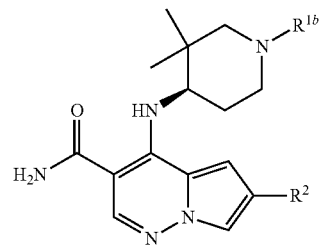

| Ex # | Name | —R¹ᵇ | —R² | HPLC or LCMS Rt (minutes) | LCMS [m/z (M + H)] |
|---|---|---|---|---|---|
| 105 | 4-((R)-1-(5-cyanopyridin-2-yl)-3,3-dimethylpiperidin-4-ylamino)-6-((R)-3-hydroxy-2-oxopyrrolidin-1-yl)pyrrolo[1,2-b]pyridazine-3-carboxamide | (5-cyanopyridin-2-yl) | ((R)-3-hydroxy-2-oxopyrrolidin-1-yl) | 1.24 | 489.3 |
| 106 | 4-((R)-1-(5-cyanopyridin-2-yl)-3,3-dimethylpiperidin-4-ylamino)-6-(3-methyl-2-oxopyrrolidin-1-yl)pyrrolo[1,2-b]pyridazine-3-carboxamide | (5-cyanopyridin-2-yl) | (3-methyl-2-oxopyrrolidin-1-yl) | 1.61 | 487.2 |
| 107 | 4-((R)-1-(5-cyanopyridin-2-yl)-3,3-dimethylpiperidin-4-ylamino)-6-(2-oxo-4-phenylpyrrolidin-1-yl)pyrrolo[1,2-b]pyridazine-3-carboxamide | (5-cyanopyridin-2-yl) | (2-oxo-4-phenylpyrrolidin-1-yl) | 1.87 | 549.3 |
| 108 | (R)-4-(1-(5-cyanopyridin-2-yl)-3,3-dimethylpiperidin-4-ylamino)-6-(4,4-dimethyl-2-oxopyrrolidin-1-yl)pyrrolo[1,2-b]pyridazine-3-carboxamide | (5-cyanopyridin-2-yl) | (4,4-dimethyl-2-oxopyrrolidin-1-yl) | 1.71 | 501.3 |

-continued

| Ex # | Name | —R¹ᵇ | —R² | HPLC or LCMS Rt (minutes) | LCMS [m/z (M + H)] |
|---|---|---|---|---|---|
| 109 | 4-((R)-1-(5-cyanopyrazin-2-yl)-3,3-dimethylpiperidin-4-ylamino)-6-((S)-3-hydroxy-2-oxopyrrolidin-1-yl)pyrrolo[1,2-b]pyridazine-3-carboxamide | | | 1.17 | 490.2 |
| 110 | 4-((R)-1-(5-cyanopyrazin-2-yl)-3,3-dimethylpiperidin-4-ylamino)-6-(3-hydroxy-3-methyl-2-oxopyrrolidin-1-yl)pyrrolo[1,2-b]pyridazine-3-carboxamide | | | 1.25 | 504.3 |
| 111 | 4-((R)-1-(4-amino-5-cyanopyrimidin-2-yl)-3,3-dimethylpiperidin-4-ylamino)-6-((S)-3-hydroxy-2-oxopyrrolidin-1-yl)pyrrolo[1,2-b]pyridazine-3-carboxamide | | | 1.08 | 505.3 |
| 112 | 4-((R)-1-(6-cyanopyridazin-3-yl)-3,3-dimethylpiperidin-4-ylamino)-6-(3-hydroxy-3-methyl-2-oxopyrrolidin-1-yl)pyrrolo[1,2-b]pyridazine-3-carboxamide | | | 1.14 | 504.3 |
| 113 | 4-((R)-1-(5-fluoropyrimidin-2-yl)-3,3-dimethylpiperidin-4-ylamino)-6-((R)-3-hydroxy-2-oxopyrrolidin-1-yl)pyrrolo[1,2-b]pyridazine-3-carboxamide | | | 1.56 | 483.0 |
| 114 | 4-((R)-1-(5-cyanopyrimidin-2-yl)-3,3-dimethylpiperidin-4-ylamino)-6-((R)-3-hydroxy-2-oxopyrrolidin-1-yl)pyrrolo[1,2-b]pyridazine-3-carboxamide | | | 1.26 | 490.2 |
| 115 | 4-((R)-1-(5-cyanopyrimidin-2-yl)-3,3-dimethylpiperidin-4-ylamino)-6-((S)-3-hydroxy-2-oxopyrrolidin-1-yl)pyrrolo[1,2-b]pyridazine-3-carboxamide | | | 1.22 | 490.2 |
| 116 | 4-((R)-1-(5-cyanopyrimidin-2-yl)-3,3-dimethylpiperidin-4-ylamino)-6-((S)-3-methoxy-2-oxopyrrolidin-1-yl)pyrrolo[1,2-b]pyridazine-3-carboxamide | | | 1.67 | 504.0 |

Examples 117-119

According to the procedures described in Steps 4 of Example 1 and Example 142, Examples 117-119 were prepared from (R)-tert-butyl 4-(6-bromo-3-carbamoylpyrrolo[1,2-b]pyridazin-4-ylamino)-3,3-dimethylpiperidine-1-carboxylate (from Step 1 of Example 55). Retention times for Examples 117-119 were measured using analytical LCMS Method I.

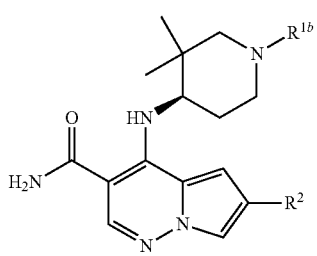

| Ex # | Name | —R$^{1b}$ | —R$^2$ | HPLC or LCMS Rt (minutes) | LCMS [m/z] (M + H) |
|---|---|---|---|---|---|
| 117 | 4-((R)-1-(4-cyanophenyl)-3,3-dimethylpiperidin-4-ylamino)-6-((R)-3-hydroxy-2-oxopyrrolidin-1-yl)pyrrolo[1,2-b]pyridazine-3-carboxamide | 4-cyanophenyl | (R)-3-hydroxy-2-oxopyrrolidin-1-yl | 1.51 | 488.3 |
| 118 | (R)-4-(1-(4-cyanophenyl)-3,3-dimethylpiperidin-4-ylamino)-6-(3-methyl-2-oxoimidazolidin-1-yl)pyrrolo[1,2-b]pyridazine-3-carboxamide | 4-cyanophenyl | 3-methyl-2-oxoimidazolidin-1-yl | 1.71 | 487.4 |
| 119 | (R)-4-(1-(4-cyanophenyl)-3,3-dimethylpiperidin-4-ylamino)-6-(3-methyl-2,4-dioxoimidazolidin-1-yl)pyrrolo[1,2-b]pyridazine-3-carboxamide | 4-cyanophenyl | 3-methyl-2,4-dioxoimidazolidin-1-yl | 1.55 | 501.0 |

Example 120

(R)-4-((1-(6-cyanopyridazin-3-yl)-3,3-dimethylpiperidin-4-yl)amino)-6-(5-(cyclopropylamino)-1,3,4-oxadiazol-2-yl)pyrrolo[1,2-b]pyridazine-3-carboxamide

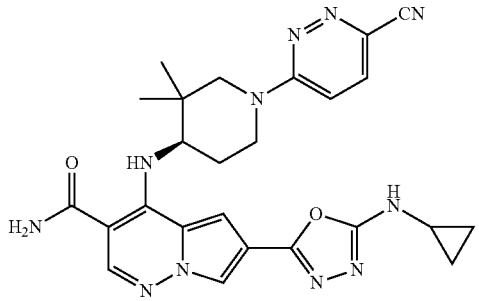 [SMILES: CC1(C)CN(c2ccc(C#N)nn2)CC[C@H]1Nc1c(C(N)=O)cnn2cc(-c3nnc(NC4CC4)o3)cc12]

Step 1: (R)-ethyl 4-((1-(tert-butoxycarbonyl)-3,3-dimethylpiperidin-4-yl)amino)-3-carbamoylpyrrolo[1,2-b]pyridazine-6-carboxylate

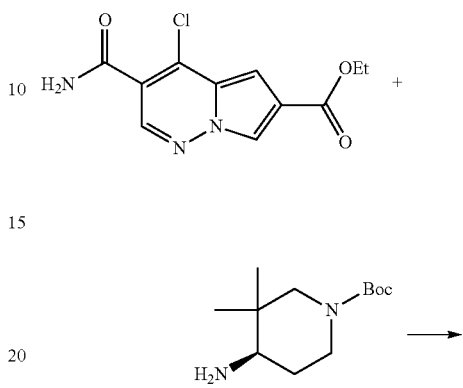

-continued

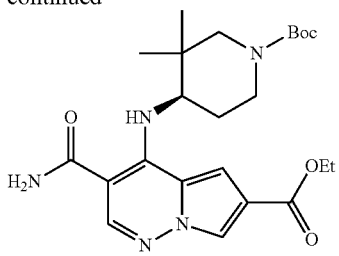

Following the conditions described in Step 2 of Example 1, ethyl 3-carbamoyl-4-chloropyrrolo[1,2-b]pyridazine-6-carboxylate (Intermediate 1, 0.7 g, 2.62 mmol,) was reacted with (R)-tert-butyl 4-amino-3,3-dimethylpiperidine-1-carboxylate (Intermediate 6, 0.657 g, 2.88 mmol) to give (R)-ethyl 4-((1-(tert-butoxycarbonyl)-3,3-dimethylpiperidin-4-yl) amino)-3-carbamoylpyrrolo[1,2-b]pyridazine-6-carboxylate (1.187 g, 99% yield). 1H NMR (400 MHz, chloroform-d) δ ppm 8.05 (d, J=1.8 Hz, 1H), 7.92 (s, 1H), 7.22 (d, J=1.5 Hz, 1H), 5.44 (br. s., 2H), 4.38 (q, J=7.1 Hz, 2H), 4.14-3.93 (m, J=9.6, 9.6, 3.7 Hz, 2H), 3.73 (br. s., 1H), 3.14 (br. s., 1H), 2.89 (br. s., 1H), 2.09-2.00 (m, 1H), 1.84-1.72 (m, 1H), 1.49 (s, 9H), 1.40 (t, J=7.2 Hz, 3H), 1.11 (s, 3H), 1.03 (s, 3H); MS (ES+) m/z: 460.3 (M+H); LC retention time: 4.250 min (analytical HPLC Method H).

Step 2: (R)-4-((1-(tert-butoxycarbonyl)-3,3-dimethylpiperidin-4-yl)amino)-3-carbamoylpyrrolo[1,2-b]pyridazine-6-carboxylic acid

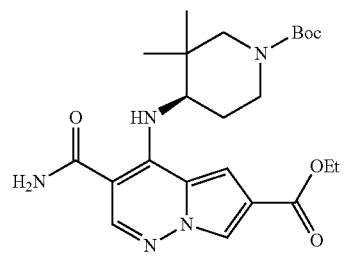

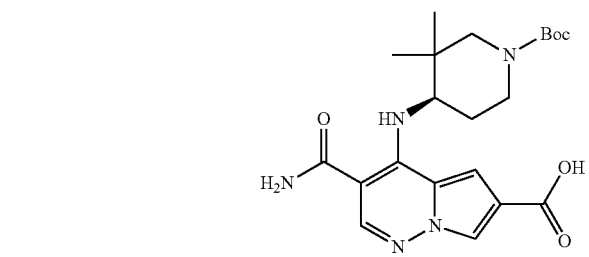

A 2 M aqueous solution of sodium hydroxide (6 mL, 12.00 mmol) was added to a solution of (R)-ethyl 4-((1-(tert-butoxycarbonyl)-3,3-dimethylpiperidin-4-yl)amino)-3-carbamoylpyrrolo[1,2-b]pyridazine-6-carboxylate (1.187 g, 2.58 mmol) in methanol (11 mL) and tetrahydrofuran (11 mL) at room temperature. The resulting mixture was heated at reflux for 40 min and cooled to room temperature. The organic solvents were evaporated in vacuo. The residue was neutralized to pH 5 with 1 N HCl. The resulting precipitate was collected by filtration to give (R)-4-((1-(tert-butoxycarbonyl)-3,3-dimethylpiperidin-4-yl)amino)-3-carbamoylpyrrolo[1,2-b]pyridazine-6-carboxylic acid as brown solid (1.13 g, 97% yield). 1H NMR (400 MHz, DMSO-d6) δ ppm 12.57 (br. s., 1H), 11.16 (d, J=8.8 Hz, 1H), 8.31 (s, 1H), 8.05 (d, J=1.3 Hz, 1H), 7.23 (s, 1H), 4.12-4.00 (m, 1H), 3.87 (br. s., 1H), 3.56 (d, J=12.8 Hz, 1H), 3.01 (br. s., 2H), 1.91 (dd, J=13.5, 3.2 Hz, 1H), 1.56 (d, J=8.1 Hz, 1H), 1.41 (s, 9H), 0.98 (s, 3H), 0.92 (s, 3H); MS (ES+) m/z: 432.2 (M+H); LC retention time: 3.795 min (analytical HPLC Method H).

Step 3: (R)-tert-butyl 4-((3-carbamoyl-6-(hydrazinecarbonyl)pyrrolo[1,2-b]pyridazin-4-yl)amino)-3,3-dimethylpiperidine-1-carboxylate

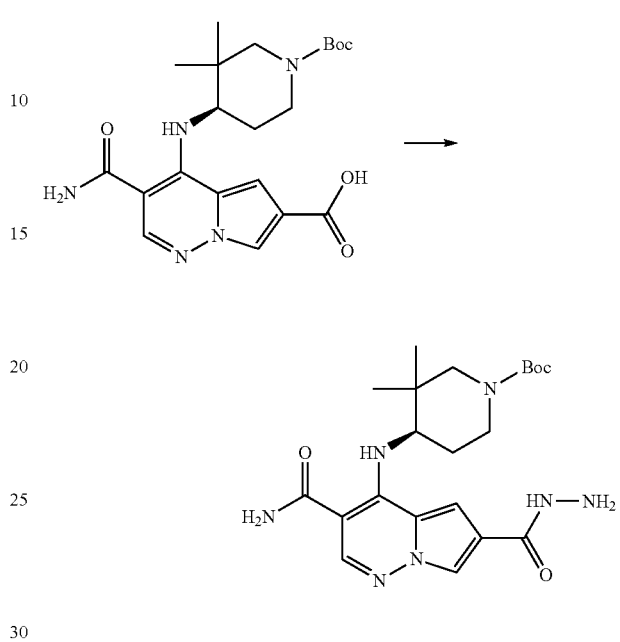

Hunig's base (0.752 mL, 4.30 mmol) was added to a mixture of (R)-4-((1-(tert-butoxycarbonyl)-3,3-dimethylpiperidin-4-yl)amino)-3-carbamoylpyrrolo[1,2-b]pyridazine-6-carboxylic acid (619 mg, 1.435 mmol) and BOP (952 mg, 2.152 mmol) in N,N-dimethylformamide (4 mL). After 1 h at room temperature, hydrazine (0.225 mL, 7.17 mmol) was added. After additional 17 h at room temperature, the mixture was diluted with water to give a suspension. The precipitate was collected by filtration to give (R)-tert-butyl 4-((3-carbamoyl-6-(hydrazinecarbonyl)pyrrolo[1,2-b]pyridazin-4-yl) amino)-3,3-dimethylpiperidine-1-carboxylate (0.4863 g, 76% yield). 1H NMR (400 MHz, DMSO-d6) δ ppm 11.08 (d, J=9.2 Hz, 1H), 9.64 (s, 1H), 8.27 (s, 1H), 8.03 (d, J=1.5 Hz, 1H), 7.31 (d, J=1.5 Hz, 1H), 4.13-4.00 (m, 1H), 3.87 (br. s., 1H), 3.60 (d, J=13.2 Hz, 1H), 3.17 (d, J=7.9 Hz, 1H), 2.92 (br. s., 1H), 1.90 (dd, J=13.4, 3.5 Hz, 1H), 1.62-1.48 (m, 1H), 1.46-1.35 (m, 9H), 0.98 (s, 3H), 0.92 (s, 3H); LC retention time: 3.295 min (analytical HPLC Method H).

Step 4: (R)-tert-butyl 4-((3-carbamoyl-6-(5-(methylthio)-1,3,4-oxadiazol-2-yl)pyrrolo[1,2-b]pyridazin-4-yl)amino)-3,3-dimethylpiperidine-1-carboxylate

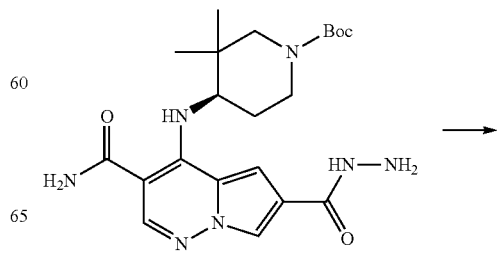

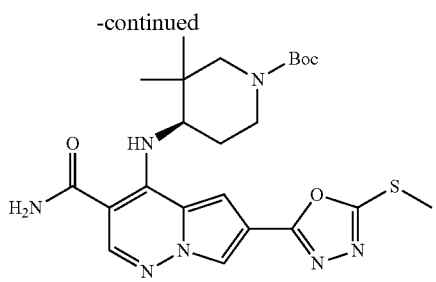

A solution of (R)-tert-butyl 4-((3-carbamoyl-6-(hydrazinecarbonyl)pyrrolo[1,2-b]pyridazin-4-yl)amino)-3,3-dimethylpiperidine-1-carboxylate (380 mg, 0.853 mmol) and di(1H-imidazol-1-yl)methanethione (175 mg, 0.981 mmol) in tetrahydrofuran (10 mL) was stirred at room temperature for 10 min then heated to reflux for 100 min. After cooling to room temperature, triethylamine (0.357 mL, 2.56 mmol) and iodomethane (0.107 mL, 1.706 mmol) were added. The resulting mixture was stirred at room temperature for 5 h. The tetrahydrofuran solvent was evaporated in vacuo. The residue was triturated with water. The solid product was collected by filtration to give (R)-tert-butyl 4-((3-carbamoyl-6-(5-(methylthio)-1,3,4-oxadiazol-2-yl)pyrrolo[1,2-b]pyridazin-4-yl)amino)-3,3-dimethylpiperidine-1-carboxylate as white solid (0.404 g, 94% yield). 1H NMR (400 MHz, chloroform-d) δ ppm 10.78 (d, J=8.4 Hz, 1H), 8.10 (d, J=1.8 Hz, 1H), 7.94 (s, 1H), 5.50 (br. s., 2H), 4.01 (dd, J=9.4, 5.8 Hz, 2H), 3.72 (br. s., 1H), 3.18 (br. s., 1H), 2.91 (br. s., 1H), 2.80 (s, 3H), 2.06 (d, J=14.3 Hz, 1H), 1.89-1.75 (m, 1H), 1.49 (s, 9H), 1.12 (s, 3H), 1.05 (s, 3H); MS (ES+) m/z: 502.3 (M+H); LC retention time: 4.241 min (analytical HPLC Method H).

Step 5: (4R)-tert-butyl 4-((3-carbamoyl-6-(5-(methylsulfinyl)-1,3,4-oxadiazol-2-yl)pyrrolo[1,2-b]pyridazin-4-yl)amino)-3,3-dimethylpiperidine-1-carboxylate

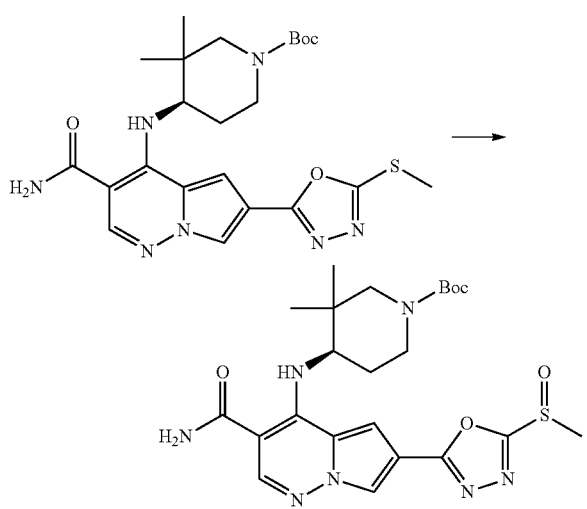

A solution of (R)-tert-butyl 4-((3-carbamoyl-6-(5-(methylthio)-1,3,4-oxadiazol-2-yl)pyrrolo[1,2-b]pyridazin-4-yl)amino)-3,3-dimethylpiperidine-1-carboxylate (306 mg, 0.610 mmol) and mCPBA (265 mg, 1.182 mmol) in chloroform (6 mL) was stirred at room temperature for 2 h. Additional mCPBA (78 mg) was added. After one more hour at room temperature, the staring material was consumed. The crude solution was taken to the next reaction without purification. MS (ES+) m/z: 518.3 (M+H).

Step 6: (R)-6-(5-(cyclopropylamino)-1,3,4-oxadiazol-2-yl)-4-((3,3-dimethylpiperidin-4-yl)amino)pyrrolo[1,2-b]pyridazine-3-carboxamide

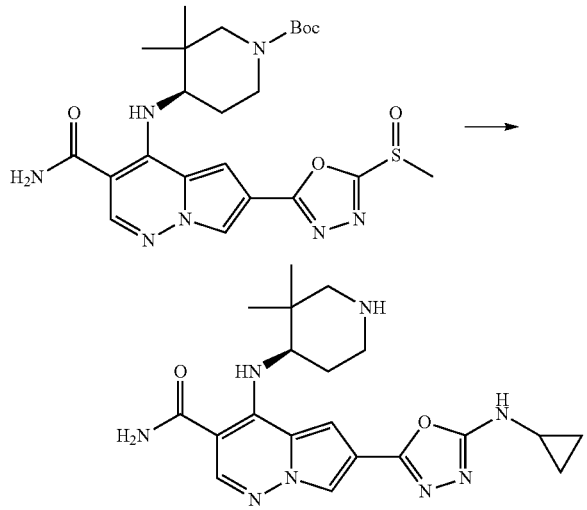

Cyclopropanamine (0.067 mL, 0.966 mmol) was added to a crude solution of (4R)-tert-butyl 4-((3-carbamoyl-6-(5-(methylsulfinyl)-1,3,4-oxadiazol-2-yl)pyrrolo[1,2-b]pyridazin-4-yl)amino)-3,3-dimethylpiperidine-1-carboxylate (⅙ of the total volume from Step 5, 0.097 mmol maximum). After 22 h at room temperature, the reaction was complete. The mixture was concentrated in vacuo. The crude material was dissolved in dichloromethane (0.5 mL) and treated with trifluoroacetic acid (0.100 mL). After stirring overnight at room temperature, the Boc-deprotection was approximately 50% complete. Additional trifluoroacetic acid (0.185 mL) was added. After 30 min at room temperature, the deprotection was complete. The mixture was concentrated and triturated with ether. The ether layer was decanted. The solid residue was used in the next reaction without purification.

Step 7: (R)-6-(5-(cyclopropylamino)-1,3,4-oxadiazol-2-yl)-4-((3,3-dimethylpiperidin-4-yl)amino)pyrrolo[1,2-b]pyridazine-3-carboxamide (Example 120)

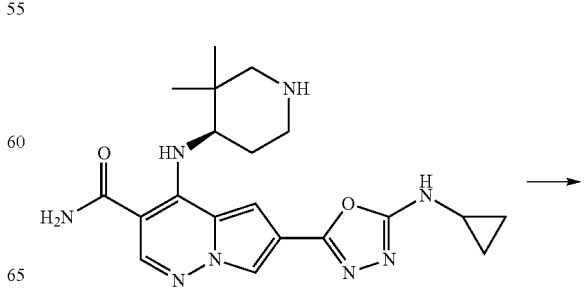

-continued

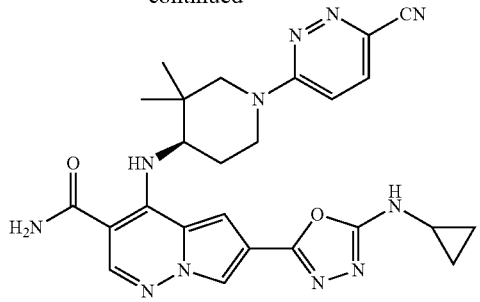

A mixture of the crude (R)-6-(5-(cyclopropylamino)-1,3,4-oxadiazol-2-yl)-4-((3,3-dimethylpiperidin-4-yl)amino)pyrrolo[1,2-b]pyridazine-3-carboxamide from Step 6, 6-chloropyridazine-3-carbonitrile (20.23 mg, 0.145 mmol) and Hunig's base (0.084 mL, 0.483 mmol) in N,N-dimethylformamide (0.5 mL) was stirred at 100° C. in a sealed tube for 30 min. The crude material was purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 25-100% B over 15 minutes, then a 5-minute hold at 100% B; Flow: 20 mL/min. Fractions containing the desired product were combined and dried via centrifugal evaporation to give the title compound (9.8 mg, 19% yield over three steps). 1H NMR (500 MHz, 1:1 mixture of chloroform-d/methanol-d4) δ ppm 8.17 (s, 1H), 7.97 (d, J=1.5 Hz, 1H), 7.59-7.54 (m, 1H), 7.39 (d, J=1.5 Hz, 1H), 7.18 (d, J=9.9 Hz, 1H), 4.45 (d, J=12.4 Hz, 1H), 4.29-4.20 (m, 2H), 3.63-3.53 (m, 1H), 3.27 (d, J=13.9 Hz, 1H), 2.70 (tt, J=6.9, 3.5 Hz, 1H), 2.28-2.18 (m, 1H), 1.96-1.83 (m, 1H), 1.11 (s, 3H), 1.10 (s, 3H), 0.84-0.76 (m, 2H), 0.68-0.59 (m, 2H); MS (ES+) m/z: 514.3 (M+H); LC retention time: 1.23 min (analytical LCMS Method I).

Example 121

(R)-4-((1-(5-cyanopyrimidin-2-yl)-3,3-dimethylpiperidin-4-yl)amino)-6-(5-(methylamino)-1,3,4-oxadiazol-2-yl)pyrrolo[1,2-b]pyridazine-3-carboxamide

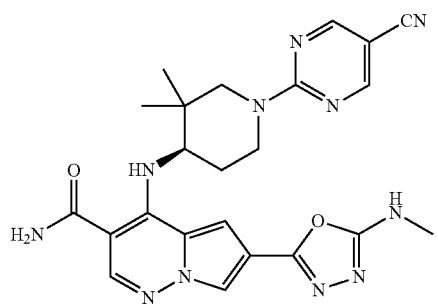 [SMILES: CNc1nnc(-c2cc3c(N[C@@H]4CCN(c5ncc(C#N)cn5)CC4(C)C)c(C(N)=O)cnn3c2)o1]

Following conditions used in the synthesis of Example 120, Example 121 was prepared. The final product was purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 25-100% B over 15 minutes, then a 5-minute hold at 100% B; Flow: 20 mL/min. Fractions containing the desired product were combined and dried via centrifugal evaporation to give the title compound (3.3 mg). 1H NMR (500 MHz, 1:1 mixture of chloroform-d/methanol-d4) δ ppm 8.52 (s, 2H), 8.18 (s, 1H), 7.97 (d, J=1.5 Hz, 1H), 7.37 (d, J=1.5 Hz, 1H), 4.46 (d, J=13.4 Hz, 1H), 4.22 (dd, J=10.2, 3.7 Hz, 1H), 3.61-3.52 (m, 1H), 3.26 (d, J=13.4 Hz, 1H), 2.98 (s, 3H), 2.18 (dd, J=14.1, 3.7 Hz, 1H), 1.89-1.78 (m, 1H), 1.09 (s, 3H), 1.07 (s, 3H); MS (ES+) m/z: 488.2 (M+H); LC retention time: 1.29 min (analytical LCMS Method I).

Example 122

(S)-1-(3-carbamoyl-4-(((R)-1-(5-cyanopyrimidin-2-yl)-3,3-dimethylpiperidin-4-yl)amino)pyrrolo[1,2-b]pyridazin-6-yl)-2-oxopyrrolidin-3-yl butyrate

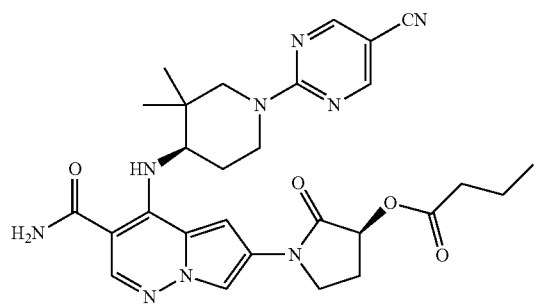 [SMILES: CCCC(=O)O[C@H]1CCN(c2cc3c(N[C@@H]4CCN(c5ncc(C#N)cn5)CC4(C)C)c(C(N)=O)cnn3c2)C1=O]

Butyryl chloride (4 μl, 0.034 mmol) was added to a stirred suspension of 4-(((R)-1-(5-cyanopyrimidin-2-yl)-3,3-dimethylpiperidin-4-yl)amino)-6-((S)-3-hydroxy-2-oxopyrrolidin-1-yl)pyrrolo[1,2-b]pyridazine-3-carboxamide (15 mg, 0.031 mmol, from Example 115) and triethylamine (0.013 mL, 0.092 mmol) in tetrahydrofuran (0.5 mL). After 2 h at room temperature, no reaction was observed. Pyridine (5.0 μl, 0.061 mmol), DMAP (0.5 mg, 4.09 μmol) and additional butyryl chloride (3.5 μl, 0.034 mmol) were added. After 24 h at room temperature, the crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 0.05% TFA; Mobile Phase B: 95:5 acetonitrile:water with 0.05% TFA; Gradient: 15-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 25 minutes, then a 10-minute hold at 55% B; Flow: 20 mL/min. Fractions containing the desired product were combined and dried via centrifugal evaporation to give the title compound (3.9 mg, 22% yield). 1H NMR (500 MHz, 1:1 mixture of chloroform-d/methanol-d4) δ ppm 8.51 (s, 2H), 8.12 (s, 1H), 7.79 (d, J=1.5 Hz, 1H), 7.32 (d, J=1.5 Hz, 1H), 5.54 (t, J=8.4 Hz, 1H), 4.45 (d, J=13.4 Hz, 1H), 4.17 (dd, J=10.2, 3.7 Hz, 1H), 3.95

(td, J=9.7, 2.5 Hz, 1H), 3.87-3.79 (m, 1H), 3.52-3.44 (m, 1H), 3.22 (d, J=13.4 Hz, 1H), 2.80-2.70 (m, 1H), 2.47-2.35 (m, 2H), 2.25-2.15 (m, 2H), 1.87-1.77 (m, 1H), 1.69 (sxt, J=7.3 Hz, 2H), 1.08 (s, 3H), 1.05 (s, 3H), 0.97 (t, J=7.4 Hz, 3H); MS (ES+) m/z: 560.4 (M+H); LC retention time: 1.98 min (analytical LCMS Method I).

Example 123

(S)-1-(3-carbamoyl-4-(((R)-1-(5-cyanopyrimidin-2-yl)-3,3-dimethylpiperidin-4-yl)amino)pyrrolo[1,2-b]pyridazin-6-yl)-2-oxopyrrolidin-3-yl hexanoate

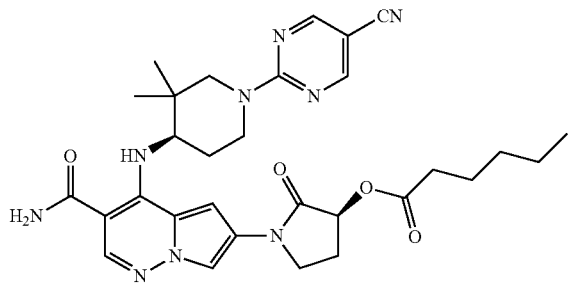 [SMILES: CCCCCC(=O)O[C@H]1CCN(c2cc3c(N[C@@H]4CCN(c5ncc(C#N)cn5)CC4(C)C)c(C(N)=O)cnn3c2)C1=O]

Following conditions used in the synthesis of Example 122, Example 123 was prepared. The crude material was purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 15 minutes, then a 5-minute hold at 100% B; Flow: 20 mL/min. Fractions containing the desired product were combined and dried via centrifugal evaporation to give the title compound (5.1 mg, 28% yield). $^1$H NMR (500 MHz, 1:1 mixture of chloroform-d/methanol-$d_4$) δ ppm 8.52 (s, 2H), 8.13 (s, 1H), 7.81 (d, J=1.5 Hz, 1H), 7.31 (d, J=1.5 Hz, 1H), 5.54 (t, J=8.4 Hz, 1H), 4.69 (d, J=13.4 Hz, 1H), 4.45 (d, J=12.9 Hz, 1H), 4.18 (dd, J=10.2, 3.7 Hz, 1H), 3.95 (td, J=9.7, 2.5 Hz, 1H), 3.87-3.80 (m, 1H), 3.52-3.44 (m, 1H), 3.22 (d, J=13.4 Hz, 1H), 2.75 (dtd, J=13.6, 7.8, 2.5 Hz, 1H), 2.49-2.37 (m, 2H), 2.24-2.14 (m, 2H), 1.88-1.77 (m, 1H), 1.70-1.62 (m, 2H), 1.33 (dq, J=7.2, 3.7 Hz, 4H), 1.08 (s, 3H), 1.05 (s, 3H), 0.92-0.85 (m, 3H); MS (ES+) m/z: 588.4 (M+H); LC retention time: 2.25 min (analytical LCMS Method I).

Example 124

6-((S)-3-amino-2-oxopyrrolidin-1-yl)-4-(((R)-1-(4-cyanophenyl)-3,3-dimethylpiperidin-4-yl)amino)pyrrolo[1,2-b]pyridazine-3-carboxamide

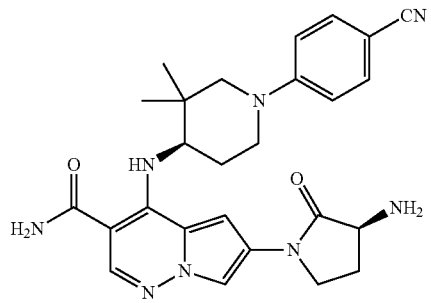 [SMILES: CC1(C)CN(c2ccc(C#N)cc2)CC[C@H]1Nc1c(C(N)=O)cnn2cc(N3CC[C@H](N)C3=O)cc12]

Step 1: tert-butyl ((S)-1-(3-carbamoyl-4-(((R)-1-(4-cyanophenyl)-3,3-dimethylpiperidin-4-yl)amino)pyrrolo[1,2-b]pyridazin-6-yl)-2-oxopyrrolidin-3-yl)carbamate

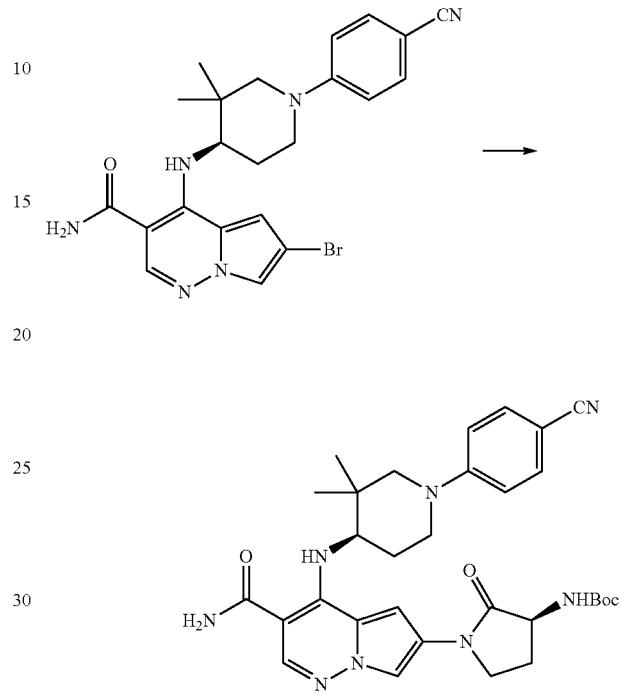

A mixture of (R)-6-bromo-4-((1-(4-cyanophenyl)-3,3-dimethylpiperidin-4-yl)amino)pyrrolo[1,2-b]pyridazine-3-carboxamide (20 mg, 0.039 mmol), (S)-tert-butyl (2-oxopyrrolidin-3-yl)carbamate (21.6 mg, 0.108 mmol), copper(I) iodide (1.5 mg, 7.70 mmol), potassium carbonate (16.0 mg, 0.116 mmol) in dioxane (0.5 mL) was pumped under vacuum and backfilled with nitrogen twice. $N_1,N_2$-dimethylethane-1,2-diamine (8.3 μl, 0.077 mmol) was added. The reaction tube was sealed and heated at 100° C. for 17 h. The mixture was diluted with a 1:1 mixture of methanol-dichloromethane (2 mL) and filtered. The filtrate was concentrated to give crude product (48.3 mg) as brown solid. Part of the material (15.6 mg) was purified via preparative LC/MS with the following conditions: Column: Waters XBridge C18, 19×100 mm, 5-μm particles; Guard Column: Waters XBridge C18, 19×10 mm, 5-μm particles; Mobile Phase A: water; Mobile Phase B: acetonitrile; Buffer: 20-mM ammonium acetate; Gradient: 15-100% B over 10.9 minutes, then a 4.0 minute hold at 100% B; Flow: 25 mL/min. Fractions containing the desired product were combined and dried via centrifugal evaporation to give tert-butyl ((S)-1-(3-carbamoyl-4-(((R)-1-(4-cyanophenyl)-3,3-dimethylpiperidin-4-yl)amino)pyrrolo[1,2-b]pyridazin-6-yl)-2-oxopyrrolidin-3-yl)carbamate (4.4 mg, 20% yield). 1H NMR (500 MHz, 1:1 mixture of chloroform-d/methanol-d4) δ ppm 8.11 (s, 1H), 7.79 (s, 1H), 7.47 (d, J=8.9 Hz, 2H), 7.27 (s, 1H), 6.94 (d, J=8.9 Hz, 2H), 4.41 (t, J=9.4 Hz, 1H), 4.09 (dd, J=10.2, 3.7 Hz, 1H), 3.91-3.72 (m, 3H), 3.57 (d, J=12.9 Hz, 1H), 3.25-3.16 (m, 1H), 2.95 (d, J=13.4 Hz, 1H), 2.66-2.57 (m, 1H), 2.25-2.07 (m, 2H), 1.96-1.84 (m, 1H), 1.44 (s, 9H), 1.16 (s, 3H), 1.08 (s, 3H); MS (ES+) m/z: 587.1 (M+H); LC retention time: 1.78 min (analytical LCMS Method I).

203

Step 2: 6-((S)-3-amino-2-oxopyrrolidin-1-yl)-4-(((R)-1-(4-cyanophenyl)-3,3-dimethylpiperidin-4-yl)amino)pyrrolo[1,2-b]pyridazine-3-carboxamide (Example 124)

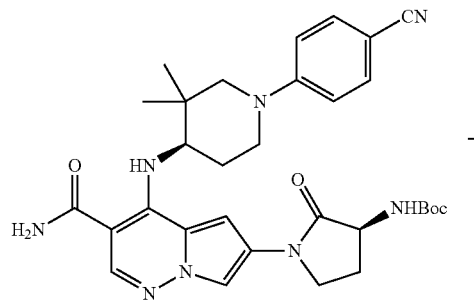

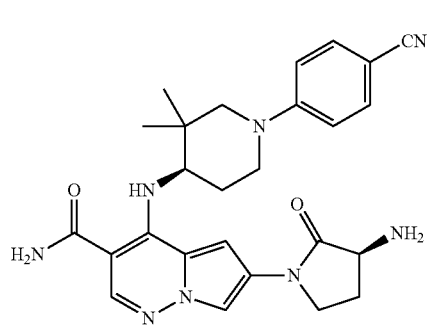

Trifluoroacetic acid (0.4 mL) was added to the rest of the crude material from Step 1 (32.7 mg) in dichloromethane (0.8 mL). After 1.5 h at room temperature, the mixture was concentrated. The crude material was purified via preparative LC/MS with the following conditions: Column: Waters XBridge C18, 19×150 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 0-100% B over 15 minutes, then a 5-minute hold at 100% B; Flow: 20 mL/min. Fractions containing the desired product were combined and dried via centrifugal evaporation to give the title compound (8.1 mg, 43% yield). 1H NMR (500 MHz, 1:1 mixture of chloroform-d/methanol-d4) δ ppm 8.12 (s, 1H), 7.82 (s, 1H), 7.48 (d, J=8.9 Hz, 2H), 7.22 (s, 1H), 6.94 (d, J=9.4 Hz, 2H), 4.30 (br. s., 1H), 4.13-4.05 (m, 1H), 3.94-3.75 (m, 3H), 3.57 (d, J=13.4 Hz, 1H), 3.25-3.15 (m, 1H), 2.96 (d, J=12.9 Hz, 1H), 2.70-2.59 (m, 1H), 2.20 (dd, J=13.4, 3.5 Hz, 1H), 2.11-2.01 (m, 1H), 1.97-1.85 (m, 1H), 1.16 (s, 3H), 1.09 (s, 3H); MS (ES+) m/z: 487.0 (M+H); LC retention time: 1.13 min (analytical LCMS Method I).

204

Example 125

4-((3R,4R)-3-ethyl-1-((S)-2-hydroxybutanoyl)piperidin-4-ylamino)-6-(1-isopropyl-1H-pyrazol-4-yl)pyrrolo[1,2-b]pyridazine-3-carboxamide

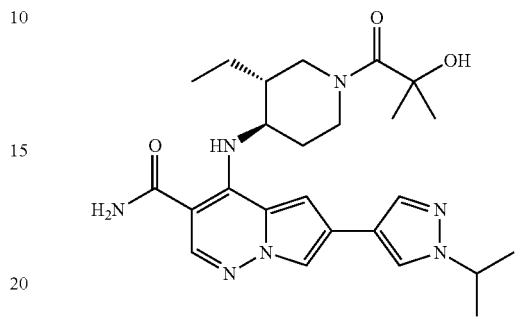

Step 1: (3R,4R)-tert-butyl 4-((6-bromo-3-carbamoylpyrrolo[1,2-b]pyridazin-4-yl)amino)-3-ethylpiperidine-1-carboxylate

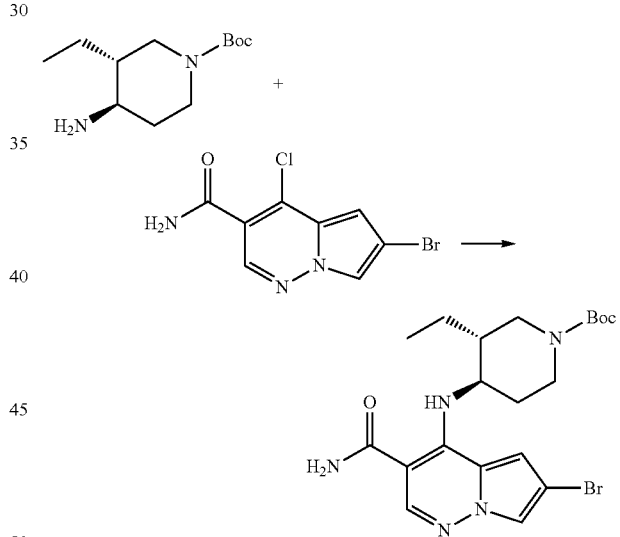

To a solution of 6-bromo-4-chloropyrrolo[1,2-b]pyridazine-3-carboxamide (Intermediate 2, 334 mg, 1.217 mmol) and (3R,4R)-tert-butyl 4-amino-3-ethylpiperidine-1-carboxylate (1.2 eq., Intermediate 8), AcOH (351 mg, 1.217 mmol) in DMF (3.0 ml) was added DIEA (1275 µl, 7.30 mmol). The reaction was heated at 90° C. for 5 hrs. The reaction was diluted with ethyl acetate (100 ml), and washed with water (3×100 ml), dried with sodium sulfate, filtered, and concentrated under reduced pressure. The crude product was purified via medium pressure chromatography (silica gel column, EtOAc/hexanes eluent, 0-100% gradient elution) to afford (3R,4R)-tert-butyl 4-((6-bromo-3-carbamoylpyrrolo[1,2-b]pyridazin-4-yl)amino)-3-ethylpiperidine-1-carboxylate (428.4 mg, 0.919 mmol, 75.0% yield) as a faint yellow solid. LCMS (Method K) m/z 468.2 ([M+H]⁺).

Step 2: 6-bromo-4-((3R,4R)-3-ethylpiperidin-4-ylamino)pyrrolo[1,2-b]pyridazine-3-carboxamide

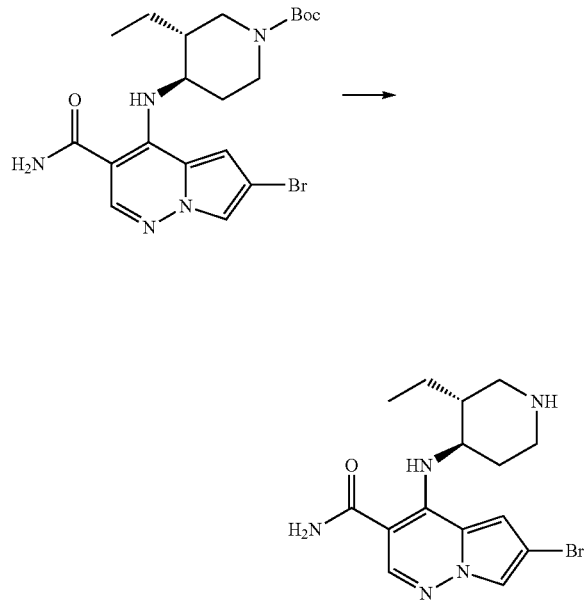

To a solution of (3R,4R)-tert-butyl 4-(((6-bromo-3-carbamoylpyrrolo[1,2-b]pyridazin-4-yl)amino)-3-ethylpiperidine-1-carboxylate (350 mg, 0.750 mmol) in dichloromethane (3.8 ml) cooled to 0° C. was added trifluoroacetic acid (578 µl, 7.50 mmol). The reaction was allowed to warm to room temperature and stirring was continued for 1 hr. After removal of the solvent, the residue was taken into ethyl acetate, washed successively with saturated sodium bicarbonate, water, and brine, dried over sodium sulfate, filtered, and concentrated under reduced pressure, yielding 6-bromo-4-(((3R,4R)-3-ethylpiperidin-4-yl)amino)pyrrolo[1,2-b]pyridazine-3-carboxamide (275 mg, 0.75 mmol, 100% yield) as a yellow solid. LCMS (Method K) m/z 368.3 ([M+H]$^+$). Analytical SFC conditions, Column: CC4 from ES Industries; Mobile phase: 10-50% MeOH (with 0.1% DEA) in $CO_2$ in 8 min, 50% MeOH (with 0.1% DEA) in $CO_2$ for 4 more min; Temperature: 40° C., Flow rate: 3 mL/min, BPR: 140 bars, Detection: UV (254 & 220 nm). Retention Time (min): 8.153 (>98.5% ee).

Step 3: 6-bromo-4-((1R,3 S)-3-carbamoyl-2,2,3-trimethylcyclopentylamino)pyrrolo[1,2-b]pyridazine-3-carboxamide To a solution of 6-bromo-4-(((3R,4R)-3-ethylpiperidin-4-yl)amino)pyrrolo[1,2-b]pyridazine-3-carboxamide (275 mg, 0.75 mmol) and 2-hydroxy-2-methylpropanoic acid (156 mg, 1.501 mmol) in dichloromethane (3.8 ml) were added DIEA (1.3 ml, 7.5 mmol) and HATU (571 mg, 1.501 mmol). The reaction was stirred at room temperature for 14 hrs. The product mixture was partitioned between ethyl acetate and water. The ethyl acetate layer was washed with brine, dried over sodium sulfate, filtered, and concentrated under reduced pressure. The crude product was purified via medium pressure chromatography (silica gel column, EtOAc/hexanes eluent, 0-100% gradient elution) to yield 6-bromo-4-((3R,4R)-3-ethyl-1-(2-hydroxy-2-methylpropanoyl)piperidin-4-yl)amino)pyrrolo-[1,2-b]pyridazine-3-carboxamide (240 mg, 0.531 mmol, 70.7% yield) as a white solid. LCMS (Method K) m/z 454.4 ([M+H]$^+$).

Step 4: 4-((3R,4R)-3-ethyl-1-((S)-2-hydroxybutanoyl)piperidin-4-ylamino)-6-(1-isopropyl-1H-pyrazol-4-yl)pyrrolo[1,2-b]pyridazine-3-carboxamide (Example 125)

To a vial charged with 6-bromo-4-(((3R,4R)-3-ethyl-1-(2-hydroxy-2-methylpropanoyl)-piperidin-4-yl)amino)pyrrolo[1,2-b]pyridazine-3-carboxamide (20 mg, 0.044 mmol), 1-isopropyl-4-(4,4,5,5-tetramethyl-1,3,2-dioxaborolan-2-yl)-1H-pyrazole (20.88 mg, 0.088 mmol), and $PdCl_2(dppf)$-$CH_2Cl_2$ Adduct (3.61 mg, 4.42 µmol) were added 1,4-dioxane (295 µl) and a 2M solution of potassium phosphate (66.3 µl, 0.133 mmol). The suspension was purged with nitrogen for 5 minutes. The vial was sealed and heated at 100° C. for 2 hrs. The reaction was diluted with methanol (10 ml), filtered, and concentrated under reduced pressure. The crude product was purified via preparative HPLC (Column: Waters XBridge C18, 19×200 mm, 5-µm). The collected fractions were combined and dried via centrifugal evaporation, yielding 4-(((3R,4R)-3-ethyl-1-(2-hydroxy-2-methylpropanoyl)piperidin-4-yl)amino)-6-(1-isopropyl-1H-pyrazol-4-yl)pyrrolo[1,2-b]pyridazine-3-carboxamide (14.6 mg, 0.030 mmol, 68.6% yield) as a white solid. $^1$H NMR (500 MHz, 1:1 Chloroform-d/Methanol-$d_4$) δ 8.10 (s, 1H), 7.83 (s, 1H), 7.75-7.72 (m, 2H), 6.92 (d, J=1.5 Hz, 1H), 4.65-4.50 (m, 2H), 4.32 (s, 2H), 4.15 (br. s., 1H), 2.97 (d, J=12.4 Hz, 1H), 2.36 (d, J=11.4 Hz, 1H), 1.79 (br. s., 1H), 1.70-1.61 (m, 2H), 1.57 (d, J=6.4 Hz, 6H), 1.49 (s, 6H), 1.41-1.25 (m, 1H), 1.01 (t, J=7.4 Hz, 3H). HPLC (Method F) Rt: 1.966 min. LCMS (Method K) m/z 482.29 ([M+H]⁺).

Example 126

6-(1-(2-cyanoethyl)-1H-pyrazol-4-yl)-4-((3R,4R)-3-ethyl-1-(methylsulfonyl)piperidin-4-ylamino)pyrrolo[1,2-b]pyridazine-3-carboxamide

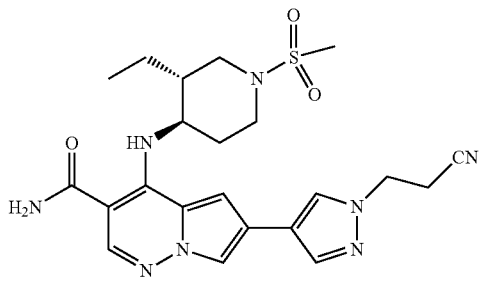 [SMILES: CC[C@@H]1CN(S(C)(=O)=O)CC[C@H]1Nc1c(C(N)=O)cnn2cc(-c3cnn(CCC#N)c3)cc12]

Step 1: 6-bromo-4-((3R,4R)-3-ethyl-1-(methylsulfonyl)piperidin-4-ylamino)pyrrolo[1,2-b]pyridazine-3-carboxamide

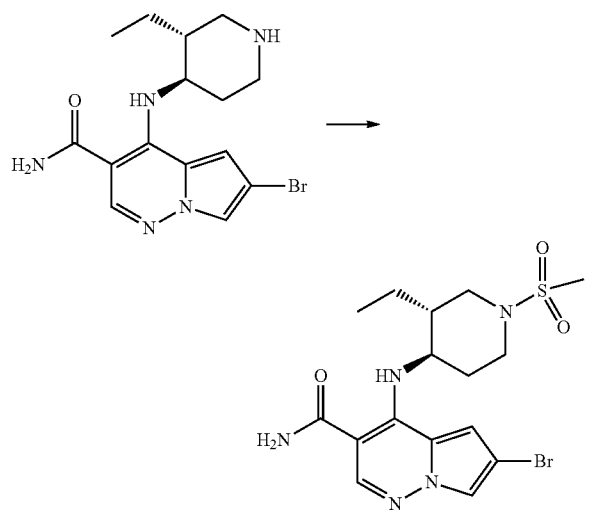

To a solution of 6-bromo-4-(((3R,4R)-3-ethylpiperidin-4-yl)amino)pyrrolo[1,2-b]pyridazine-3-carboxamide from Step 2 of Example 125 (150 mg, 0.410 mmol) and DIEA (429 µl, 2.457 mmol) in DMF (2.7 ml) was added methanesulfonyl chloride (47.5 µl, 0.614 mmol). The reaction was stirred at room temperature for 2 hrs. After removal of the solvent, the residue was dissolved in ethyl acetate, washed successively with saturated ammonium chloride, water, and brine; dried with sodium sulfate, filtered, and concentrated under reduced pressure. The crude product was purified via medium pressure chromatography (silica gel column, EtOAc/hexanes eluent, 0-100% gradient elution) to yield 6-bromo-4-(((3R,4R)-3-ethyl-1-(methylsulfonyl)piperidin-4-yl)amino)pyrrolo[1,2-b]pyridazine-3-carboxamide (95 mg, 0.214 mmol, 52.2% yield) as a yellow solid. LCMS (Method K) m/z 446.0 ([M+H]⁺).

Step 2: 6-(1-(2-cyanoethyl)-1H-pyrazol-4-yl)-4-((3R,4R)-3-ethyl-1-(methylsulfonyl)piperidin-4-ylamino)pyrrolo[1,2-b]pyridazine-3-carboxamide (Example 126)

To a vial charged with 6-bromo-4-(((3R,4R)-3-ethyl-1-(methylsulfonyl)piperidin-4-yl)amino) pyrrolo[1,2-b]pyridazine-3-carboxamide (15 mg, 0.034 mmol), 3-(4-(4,4,5,5-tetramethyl-1,3,2-dioxaborolan-2-yl)-1H-pyrazol-1-yl) propanenitrile (16.68 mg, 0.068 mmol) and PdCl₂(dppf)-CH₂Cl₂ Adduct (3.61 mg, 4.42 µmol) were added 1,4-dioxane (225 µl) and a 2M solution of potassium phosphate (50.6 µl, 0.101 mmol). The suspension was purged with nitrogen for 5 minutes. The vial was sealed and heated at 100° C. for 2 hrs. The reaction mixture was diluted with methanol (10 ml), filtered, and concentrated under reduced pressure. The crude product was purified via preparative HPLC (Column: Waters XBridge C18, 19×200 mm, 5-µm). The collected fractions were combined and dried via centrifugal evaporation, yielding 6-(1-(2-cyanoethyl)-1H-pyrazol-4-yl)-4-(((3R,4R)-3-ethyl-1-(methylsulfonyl)piperidin-4-yl)amino)pyrrolo[1,2-b]pyridazine-3-carboxamide (9.3 mg, 0.019 mmol, 56.9% yield) as a white solid. ¹H NMR (500 MHz, 1:1 Chloroform-d/Methanol-d₄) δ 8.12 (s, 1H), 7.93 (s, 1H), 7.82 (s, 1H), 7.75 (d, J=1.5 Hz, 1H), 6.91 (d, J=1.0 Hz, 1H), 4.48 (t, J=6.4 Hz, 2H), 4.11 (td, J=8.4, 4.0 Hz, 1H), 3.79-3.61 (m, 2H), 3.25-3.17 (m, 1H), 3.05 (t, J=6.4 Hz, 2H), 2.97-2.85 (m, 4H), 2.43-2.34 (m, 1H), 1.88-1.76 (m, 3H), 1.51-1.40 (m, 1H), 1.04-0.97 (m, 3H). LCMS (Method K) m/z 485.0 ([M+H]⁺). HPLC (Method F) Rt: 1.14 min.

Example 127

4-(((3R,4R)-3-ethyl-1-((S)-2-hydroxybutanoyl)piperidin-4-yl)amino)-6-(1-methyl-1H-pyrazol-4-yl)pyrrolo[1,2-b]pyridazine-3-carboxamide

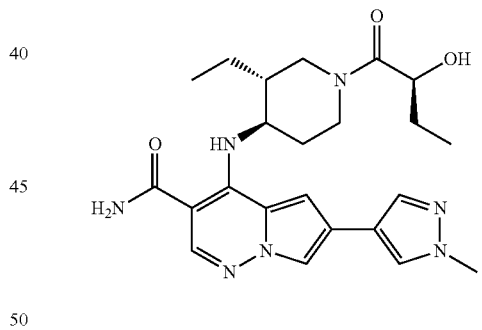

Step 1: (3R,4R)-tert-butyl 4-(3-carbamoyl-6-(1-methyl-1H-pyrazol-4-yl)pyrrolo[1,2-b]pyridazin-4-ylamino)-3-ethylpiperidine-1-carboxylate

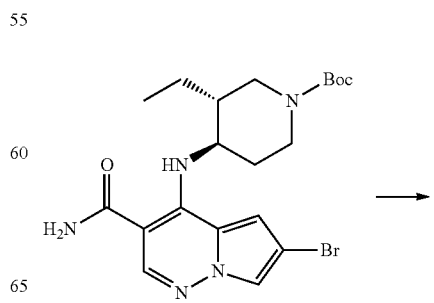

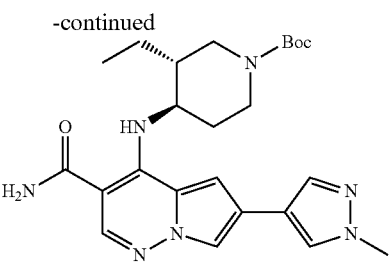

To a vial charged with (3R,4R)-tert-butyl 4-((6-bromo-3-carbamoylpyrrolo[1,2-b]pyridazin-4-yl)amino)-3-ethylpiperidine-1-carboxylate from Step 1 of Example 125 (349 mg, 0.748 mmol), 1-methyl-4-(4,4,5,5-tetramethyl-1,3,2-dioxaborolan-2-yl)-1H-pyrazole (467 mg, 2.245 mmol) and PdCl$_2$(dppf)-CH$_2$Cl$_2$ Adduct (61.1 mg, 0.075 mmol) were added dioxane (5.0 ml) and a 2M solution of potassium phosphate (1.1 ml, 2.245 mmol). The suspension was purged with nitrogen for 5 minutes. The vial was sealed and heated at 100° C. for 1 hr. The reaction mixture was diluted with methanol (10 ml), filtered, and concentrated. The residue was partitioned between ethyl acetate (50 ml) and water. The organic layer was washed with brine, dried over sodium sulfate, filtered, and concentrated under reduced pressure. The crude product was purified via medium pressure chromatography (silica gel column, EtOAc/hexanes eluent, 0-100% gradient elution) to yield (3R,4R)-tert-butyl 4-((3-carbamoyl-6-(1-methyl-1H-pyrazol-4-yl)pyrrolo[1,2-b]pyridazin-4-yl)amino)-3-ethylpiperidine-1-carboxylate (288 mg, 0.618 mmol, 83% yield) as a white solid. LCMS (Method K) m/z 468.4 ([M+H]$^+$).

Step 2: 4-((3R,4R)-3-ethylpiperidin-4-ylamino)-6-(1-methyl-1H-pyrazol-4-yl)pyrrolo[1,2-b]pyridazine-3-carboxamide

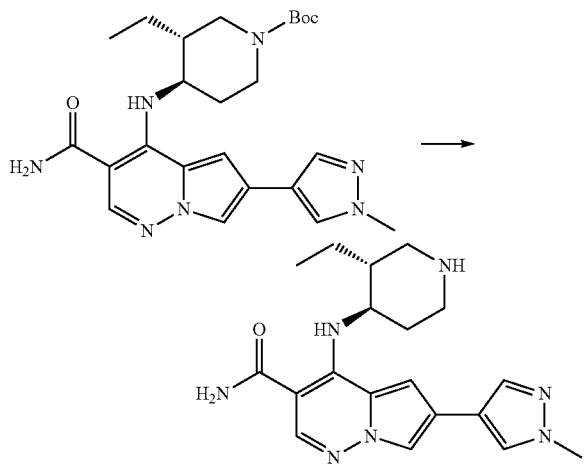

To a solution of (3R,4R)-tert-butyl 4-((3-carbamoyl-6-(1-methyl-1H-pyrazol-4-yl)pyrrolo[1,2-b]pyridazin-4-yl)amino)-3-ethylpiperidine-1-carboxylate (288 mg, 0.618 mmol) in dichloromethane (5.0 ml) cooled to 0° C. was added trifluoroacetic acid (288 µl, 3.74 mmol). The reaction was allowed to warm to room temperature and stirring was continued for 1 hr. After removal of the solvent in vacuo, the residue was diluted with ethyl acetate, washed successively with saturated sodium bicarbonate, water, and brine; dried with sodium sulfate, filtered, and concentrated under reduced pressure, yielding 4-(((3R,4R)-3-ethylpiperidin-4-yl)amino)-6-(1-methyl-1H-pyrazol-4-yl)pyrrolo[1,2-b]pyridazine-3-carboxamide (227 mg, 0.618 mmol, 99% yield) as a white solid. LCMS (Method K) m/z 368.4 ([M+H]$^+$).

Step 3: 4-(((3R,4R)-3-ethyl-1-((S)-2-hydroxybutanoyl)piperidin-4-yl)amino)-6-(1-methyl-1H-pyrazol-4-yl)pyrrolo[1,2-b]pyridazine-3-carboxamide (Example 127)

To a solution of (S)-2-hydroxybutanoic acid (3.54 mg, 0.034 mmol) in DMF (181 µl) were added DIEA (28.5 µl, 0.163 mmol) and HATU (25.9 mg, 0.068 mmol). After 15 minutes, 4-(((3R,4R)-3-ethylpiperidin-4-yl)amino)-6-(1-methyl-1H-pyrazol-4-yl)pyrrolo[1,2-b]pyridazine-3-carboxamide (10 mg, 0.027 mmol) was added. The reaction was stirred at room temperature for 3 hrs. The product mixture was partitioned between ethyl acetate and water. The organic layer was washed with brine, dried with sodium sulfate, filtered, and concentrated under reduced pressure. The crude product was purified via preparative HPLC (Column: Waters XBridge C18, 19×200 mm, 5-µm). The collected fractions were combined and dried via centrifugal evaporation to yield the title compound (7.9 mg, 0.017 mmol, 64.0% yield) as a white solid. $^1$H NMR (500 MHz, 1:1 Chloroform-d/Methanol-d$_4$) δ 8.12-8.09 (m, 1H), 7.77 (d, J=2.5 Hz, 1H), 7.72 (d, J=3.5 Hz, 2H), 6.92-6.88 (m, 1H), 4.42-4.34 (m, 2H), 4.24-4.13 (m, 1H), 3.95 (s, 3H), 3.12-3.03 (m, 1H), 2.41-2.34 (m, 1H), 1.84-1.73 (m, 2H), 1.70-1.58 (m, 3H), 1.43-1.32 (m, 1H), 1.06-0.97 (m, 7H). LCMS (Method K) m/z 454.249 ([M+H]$^+$). HPLC (Method F) Rt: 1.12 min.

Examples 128-156

According to the procedure described in Step 4 for Example 125, Examples 128-133 were prepared by Suzuki coupling of 6-bromo-4-((1R,3S)-3-carbamoyl-2,2,3-trimethylcyclopentylamino)pyrrolo[1,2-b]pyridazine-3-carboxamide (from Step 3 of Example 125) with appropriate boronic acids or boronic acid esters, which were commercially available. Examples 134-146 were prepared following conditions described in Example 125, where 2-hydroxy-2-methylpropanoic acid was replaced with (S)-2-hydroxypropanoic acid, (R)-2-hydroxypropanoic acid, 2-cyanoacetic acid or 1-cyanocyclopropanecarboxylic acid in the amidation of 6-bromo-4-((3R,4R)-3-ethylpiperidin-4-ylamino)pyrrolo[1,2-b]pyridazine-3-carboxamide (from Step 3 of Example 125), followed by Suzuki coupling with appropriate boronic acids or boronic acid esters, which were commercially available. According to the procedure described for Example 126, Examples 147-150 were prepared by Suzuki coupling of 6-bromo-4-((3R,4R)-3-ethyl-1-(methylsulfonyl)piperidin-4-ylamino)pyrrolo[1,2-b]pyridazine-3-carboxamide (from Step 1 of Example 126) with appropriate boronic acids or boronic acid esters, which were commercially available. According to the procedure described in Step 3 of Example 127, Examples 151 and 152 were prepared by amidation of 4-((3R,4R)-3-ethylpiperidin-4-ylamino)-6-(1-methyl-1H-pyrazol-4-yl)pyrrolo[1,2-b]pyridazine-3-carboxamide (from Step 2 of Example 127) with 3,3,3-trifluoropropanoic acid and (R)-2-hydroxypropanoic acid respectively. Examples 153-156 were prepared following conditions described in Example 127, where 1-methyl-4-(4,4,5,5-tetramethyl-1,3,2-dioxaborolan-2-yl)-1H-pyrazole was replaced by pyridin-4- ylboronic acid or 2-methoxypyridin-4-ylboronic acid in the Suzuki coupling with (3R,4R)-tert-butyl-4-(6-bromo-3-carbamoylpyrrolo[1,2-b]pyridazin-4-ylamino)-3-ethylpiperidine-1-carboxylate (from Step 3 of Example 125), followed by N-Boc deprotection by TFA and amidation with appropriate acids, which were commercially available. Examples 128, 129, 134, 135, 138, 139, 147, 151 and 156 were analyzed using HPLC Method H. Examples 130-133, 136, 137, 140-146, 148-150 and 153-155 were analyzed using HPLC Method F.

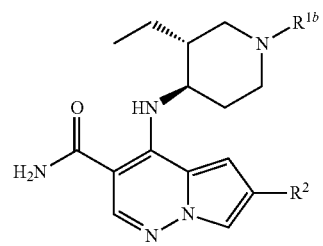

| Ex # | Name | —R$^{1b}$ | —R$^2$ | HPLC Rt (minute) | LCMS [m/z (M + H)] |
|---|---|---|---|---|---|
| 128 | 4-((3R,4R)-3-ethyl-1-(2-hydroxy-2-methylpropanoyl)piperidin-4-ylamino)-6-(2-methoxypyridin-4-yl)pyrrolo[1,2-b]pyridazine-3-carboxamide | | | 1.13 | 481.24 |
| 129 | 4-((3R,4R)-3-ethyl-1-(2-hydroxy-2-methylpropanoyl)piperidin-4-ylamino)-6-(1-propyl-1H-pyrazol-4-yl)pyrrolo[1,2-b]pyridazine-3-carboxamide | | | 1.35 | 482.28 |
| 130 | 4-((3R,4R)-3-ethyl-1-(2-hydroxy-2-methylpropanoyl)piperidin-4-ylamino)-6-(1-methyl-1H-pyrazol-4-yl)pyrrolo[1,2-b]pyridazine-3-carboxamide | | | 1.62 | 454.20 |
| 131 | 4-((3R,4R)-3-ethyl-1-(2-hydroxy-2-methylpropanoyl)piperidin-4-ylamino)-6-(2-methylpyridin-4-yl)pyrrolo[1,2-b]pyridazine-3-carboxamide | | | 1.82 | 465.20 |
| 132 | 4-((3R,4R)-3-ethyl-1-(2-hydroxy-2-methylpropanoyl)piperidin-4-ylamino)-6-(6-methylpyridin-3-yl)pyrrolo[1,2-b]pyridazine-3-carboxamide | | | 1.29 | 465.09 |
| 133 | 4-((3R,4R)-3-ethyl-1-(2-hydroxy-2-methylpropanoyl)piperidin-4-ylamino)-6-(6-(methylcarbamoyl)pyridin-3-yl)pyrrolo[1,2-b]pyridazine-3-carboxamide | | | 1.18 | 508.09 |
| 134 | 4-((3R,4R)-3-ethyl-1-((S)-2-hydroxypropanoyl)piperidin-4-ylamino)-6-(2-methoxypyridin-4-yl)pyrrolo[1,2-b]pyridazine-3-carboxamide | | | 1.63 | 467.24 |
| 135 | 4-((3R,4R)-3-ethyl-1-((S)-2-hydroxypropanoyl)piperidin-4-ylamino)-6-(1-methyl-1H-pyrazol-4-yl)pyrrolo[1,2-b]pyridazine-3-carboxamide | | | 1.45 | 440.54 |

-continued

| Ex # | Name | —R$^{1b}$ | —R$^2$ | HPLC Rt (minute) | LCMS [m/z (M + H)] |
|---|---|---|---|---|---|
| 136 | 4-((3R,4R)-3-ethyl-1-((S)-2-hydroxypropanoyl)piperidin-4-ylamino)-6-(1-isopropyl-1H-pyrazol-4-yl)pyrrolo[1,2-b]pyridazine-3-carboxamide | 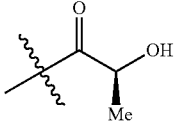 [SMILES: *C(=O)[C@H](C)O] | 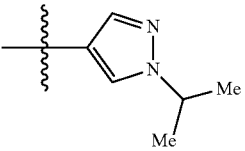 [SMILES: *c1cnn(C(C)C)c1] | 1.26 | 468.14 |
| 137 | 4-((3R,4R)-3-ethyl-1-((S)-2-hydroxypropanoyl)piperidin-4-ylamino)-6-(1-isobutyl-1H-pyrazol-4-yl)pyrrolo[1,2-b]pyridazine-3-carboxamide | 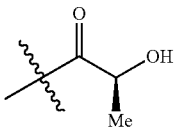 [SMILES: *C(=O)[C@H](C)O] | 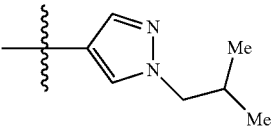 [SMILES: *c1cnn(CC(C)C)c1] | 1.39 | 482.15 |
| 138 | 4-((3R,4R)-3-ethyl-1-((R)-2-hydroxypropanoyl)piperidin-4-ylamino)-6-(1-isopropyl-1H-pyrazol-4-yl)pyrrolo[1,2-b]pyridazine-3-carboxamide | 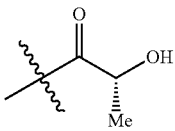 [SMILES: *C(=O)[C@@H](C)O] | 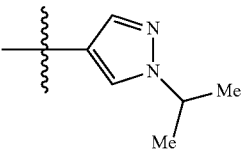 [SMILES: *c1cnn(C(C)C)c1] | 1.74 | 468.00 |
| 139 | 4-((3R,4R)-3-ethyl-1-((R)-2-hydroxypropanoyl)piperidin-4-ylamino)-6-(1-propyl-1H-pyrazol-4-yl)pyrrolo[1,2-b]pyridazine-3-carboxamide | 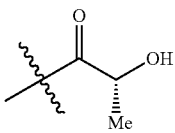 [SMILES: *C(=O)[C@@H](C)O] | 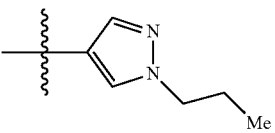 [SMILES: *c1cnn(CCC)c1] | 1.76 | 468.00 |
| 140 | 4-((3R,4R)-3-ethyl-1-((R)-2-hydroxypropanoyl)piperidin-4-ylamino)-6-(1-ethyl-1H-pyrazol-4-yl)pyrrolo[1,2-b]pyridazine-3-carboxamide | 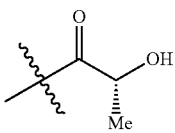 [SMILES: *C(=O)[C@@H](C)O] | 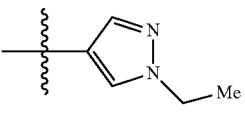 [SMILES: *c1cnn(CC)c1] | 1.72 | 454.25 |
| 141 | 4-((3R,4R)-1-(2-cyanoacetyl)-3-ethylpiperidin-4-ylamino)-6-(1,3-dimethyl-1H-pyrazol-4-yl)pyrrolo[1,2-b]pyridazine-3-carboxamide | 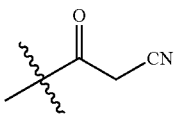 [SMILES: *C(=O)CC#N] | 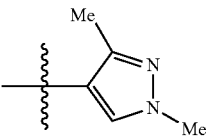 [SMILES: *c1cn(C)nc1C] | 1.45 | 449.10 |
| 142 | 4-((3R,4R)-1-(2-cyanoacetyl)-3-ethylpiperidin-4-ylamino)-6-(1-isopropyl-1H-pyrazol-4-yl)pyrrolo[1,2-b]pyridazine-3-carboxamide | 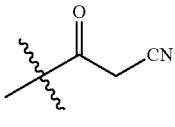 [SMILES: *C(=O)CC#N] | 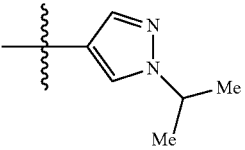 [SMILES: *c1cnn(C(C)C)c1] | 1.69 | 463.10 |
| 143 | 4-((3R,4R)-1-(2-cyanoacetyl)-3-ethylpiperidin-4-ylamino)-6-(1-ethyl-1H-pyrazol-4-yl)pyrrolo[1,2-b]pyridazine-3-carboxamide | 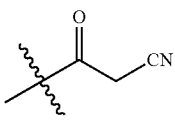 [SMILES: *C(=O)CC#N] | 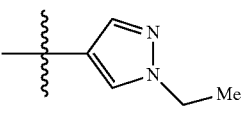 [SMILES: *c1cnn(CC)c1] | 1.83 | 449.20 |
| 144 | 4-((3R,4R)-1-(2-cyanoacetyl)-3-ethylpiperidin-4-ylamino)-6-(1-isobutyl-1H-pyrazol-4-yl)pyrrolo[1,2-b]pyridazine-3-carboxamide | 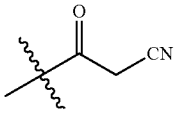 [SMILES: *C(=O)CC#N] | 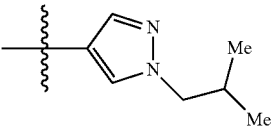 [SMILES: *c1cnn(CC(C)C)c1] | 1.97 | 477.20 |
| 145 | 4-((3R,4R)-1-(1-cyanocyclopropanecarbonyl)-3-ethylpiperidin-4-ylamino)-6-(2-fluoropyridin-4-yl)pyrrolo[1,2-b]pyridazine-3-carboxamide | 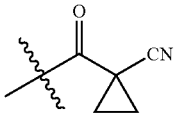 | 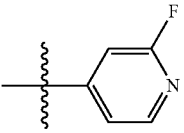 [SMILES: *c1ccnc(F)c1] | 1.48 | 476.07 |

-continued

| Ex # | Name | —R$^{1b}$ | —R$^2$ | HPLC Rt (minute) | LCMS [m/z (M + H)] |
|---|---|---|---|---|---|
| 146 | 4-((3R,4R)-1-(1-cyanocyclopropanecarbonyl)-3-ethylpiperidin-4-ylamino)-6-(1-methyl-1H-pyrazol-4-yl)pyrrolo[1,2-b]pyridazine-3-carboxamide | cyclopropyl-C(O)- with CN | 1-methyl-1H-pyrazol-4-yl | 1.17 | 461.10 |
| 147 | 4-((3R,4R)-3-ethyl-1-(methylsulfonyl)piperidin-4-ylamino)-6-(6-methylpyridazin-4-yl)pyrrolo[1,2-b]pyridazine-3-carboxamide | -S(O)$_2$Me | 6-methylpyridazin-4-yl | 0.92 | 458.19 |
| 148 | 4-((3R,4R)-3-ethyl-1-(methylsulfonyl)piperidin-4-ylamino)-6-(2-methoxypyrimidin-5-yl)pyrrolo[1,2-b]pyridazine-3-carboxamide | -S(O)$_2$Me | 2-methoxypyrimidin-5-yl | 1.67 | 474.15 |
| 149 | 4-((3R,4R)-3-ethyl-1-(methylsulfonyl)piperidin-4-ylamino)-6-(pyridin-4-yl)pyrrolo[1,2-b]pyridazine-3-carboxamide | -S(O)$_2$Me | pyridin-4-yl | 1.60 | 443.15 |
| 150 | 6-(6-cyanopyridin-3-yl)-4-((3R,4R)-3-ethyl-1-(methylsulfonyl)piperidin-4-ylamino)pyrrolo[1,2-b]pyridazine-3-carboxamide | -S(O)$_2$Me | 6-cyanopyridin-3-yl | 1.79 | 468.15 |
| 151 | 4-((3R,4R)-3-ethyl-1-(3,3,3-trifluoropropanoyl)piperidin-4-ylamino)-6-(1-methyl-1H-pyrazol-4-yl)pyrrolo[1,2-b]pyridazine-3-carboxamide | -C(O)CH$_2$CF$_3$ | 1-methyl-1H-pyrazol-4-yl | 1.87 | 479.00 |
| 152 | 4-((3R,4R)-3-ethyl-1-((R)-2-hydroxypropanoyl)piperidin-4-ylamino)-6-(1-methyl-1H-pyrazol-4-yl)pyrrolo[1,2-b]pyridazine-3-carboxamide | -C(O)CH(OH)Me (R) | 1-methyl-1H-pyrazol-4-yl | 0.98 | 440.10 |
| 153 | 4-((3R,4R)-3-ethyl-1-((S)-2-hydroxypropanoyl)piperidin-4-ylamino)-6-(pyridin-4-yl)pyrrolo[1,2-b]pyridazine-3-carboxamide | -C(O)CH(OH)Me (S) | pyridin-4-yl | 1.07 | 437.19 |
| 154 | 4-((3R,4R)-3-ethyl-1-((R)-2-hydroxypropanoyl)piperidin-4-ylamino)-6-(pyridin-4-yl)pyrrolo[1,2-b]pyridazine-3-carboxamide | -C(O)CH(OH)Me (R) | pyridin-4-yl | 1.07 | 437.20 |
| 155 | 4-((3R,4R)-1-(1-cyanocyclopropanecarbonyl)-3-ethylpiperidin-4-ylamino)-6-(pyridin-4-yl)pyrrolo[1,2-b]pyridazine-3-carboxamide | cyclopropyl-C(O)- with CN | pyridin-4-yl | 0.96 | 458.16 |
| 156 | 4-((3R,4R)-1-(2-cyanoacetyl)-3-ethylpiperidin-4-ylamino)-6-(6-methoxypyridin-3-yl)pyrrolo[1,2-b]pyridazine-3-carboxamide | -C(O)CH$_2$CN | 6-methoxypyridin-3-yl | 2.72 | 462.2 |

Example 157

4-(((3R,4R)-1-(5-cyanopyridin-2-yl)-3-ethylpiperidin-4-yl)amino)-6-(2-methoxypyrimidin-5-yl)pyrrolo[1,2-b]pyridazine-3-carboxamide

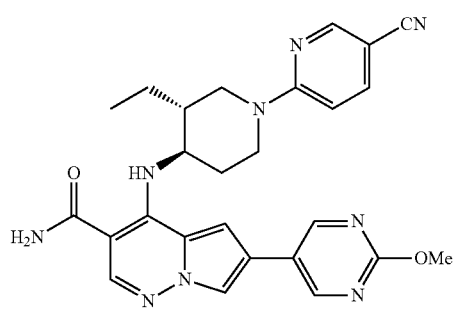 [SMILES: CC[C@@H]1CN(c2ccc(C#N)cn2)CC[C@H]1Nc1c(C(N)=O)cnn2cc(-c3cnc(OC)nc3)cc12]

Following conditions in the synthesis of Example 1, Example 157 was prepared from 6-bromo-4-chloropyrrolo[1,2-b]pyridazine-3-carboxamide (Intermediate 2) and (3R,4R)-tert-butyl 4-amino-3-ethylpiperidine-1-carboxylate (Intermediate 8). The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation to give the title compound (9.1 mg). 1H NMR (500 MHz, 1:1 mixture of chloroform-d/methanol-d4) δ ppm 8.79 (s, 2H), 8.38 (d, J=2.5 Hz, 1H), 8.13 (s, 1H), 7.90 (d, J=1.5 Hz, 1H), 7.66 (dd, J=9.2, 2.2 Hz, 1H), 7.08 (d, J=1.5 Hz, 1H), 6.77 (d, J=8.9 Hz, 1H), 4.43 (dd, J=13.6, 2.7 Hz, 1H), 4.32-4.19 (m, 2H), 4.04 (s, 3H), 3.44 (ddd, J=13.6, 10.7, 3.0 Hz, 1H), 3.16 (dd, J=13.9, 9.4 Hz, 1H), 2.41-2.30 (m, 1H), 1.84-1.64 (m, 3H), 1.46-1.33 (m, 1H), 1.02 (t, J=7.4 Hz, 3H); MS (ES+) m/z: 498.0 (M+H); LC retention time: 1.61 min (analytical LCMS Method I).

Example 158

4-(((3S,4S)-1-(5-cyanopyridin-2-yl)-4-methylpyrrolidin-3-yl)amino)-6-(1-(2-hydroxy-2-methylpropyl)-1H-pyrazol-4-yl)pyrrolo[1,2-b]pyridazine-3-carboxamide

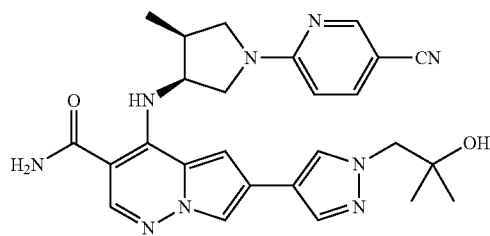 [SMILES: C[C@H]1CN(c2ccc(C#N)cn2)C[C@H]1Nc1c(C(N)=O)cnn2cc(-c3cnn(CC(C)(C)O)c3)cc12]

Step 1: 6-bromo-4-(((3S,4S)-4-methylpyrrolidin-3-yl)amino)pyrrolo[1,2-b]pyridazine-3-carboxamide

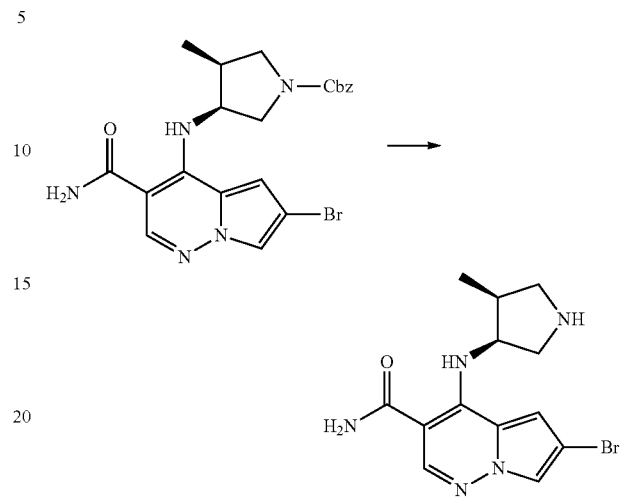

Iodotrimethylsilane (6.23 mL, 45.8 mmol) was added dropwise to a suspension of (3S,4S)-benzyl 3-((6-bromo-3-carbamoylpyrrolo[1,2-b]pyridazin-4-yl)amino)-4-methylpyrrolidine-1-carboxylate (8.65 g, 18.31 mmol, prepared by coupling Intermediate 2 and enantiopure Intermediate 5 as previously described in Example 52) in acetonitrile (60 mL). The resulting mixture turned to a homogeneous solution several minutes after completion of addition and gradually turned to brown suspension. After 2 h at room temperature, the resulting mixture was quenched with methanol (10 mL), stirred for 5 min and concentrated in vacuo. The solid residue was diluted with ether (80 mL) and dichloromethane (80 mL), stirred for 30 min and filtered. The filter cake was washed with ether-dichloromethane (1:1 mixture, 160 mL), and dried under vacuum to give the desired 6-bromo-4-(((3S,4S)-4-methylpyrrolidin-3-yl)amino)pyrrolo[1,2-b]pyridazine-3-carboxamide as yellow powder, assumed as HI salt (10.64 g). 1H NMR (400 MHz, methanol-d4) δ ppm 8.20 (s, 1H), 7.73 (d, J=1.8 Hz, 1H), 7.03 (d, J=1.8 Hz, 1H), 5.03-4.92 (m, 1H), 3.83-3.72 (m, 1H), 3.67 (dd, J=12.0, 7.8 Hz, 1H), 3.49-3.40 (m, J=2.4 Hz, 1H), 3.14 (t, J=11.3 Hz, 1H), 2.85-2.71 (m, J=7.3 Hz, 1H), 1.25 (d, J=7.0 Hz, 3H); MS (ES+) m/z: 338.0 (M+H); LC retention time: 2.485 min (analytical HPLC Method H).

Step 2: 6-bromo-4-(((3S,4S)-1-(5-cyanopyridin-2-yl)-4-methylpyrrolidin-3-yl)amino)pyrrolo[1,2-b]pyridazine-3-carboxamide

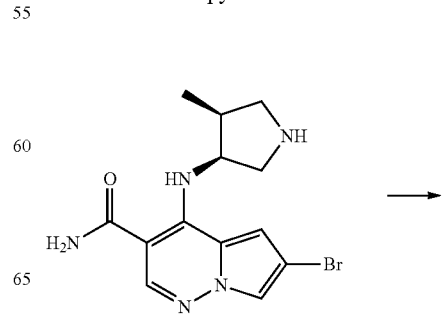

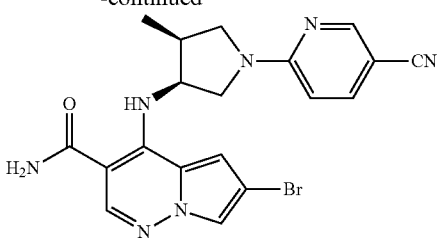

A solution of 6-bromo-4-(((3S,4S)-4-methylpyrrolidin-3-yl)amino)pyrrolo[1,2-b]pyridazine-3-carboxamide hydroiodide (250 mg, 0.536 mmol), 6-bromonicotinonitrile (103 mg, 0.563 mmol) and potassium carbonate (222 mg, 1.609 mmol) in N,N-dimethylformamide (3 mL) was heated at 100° C. in a sealed tube for 90 min. The resulting mixture was cooled to room temperature, triturated with water and filtered. The filter cake was washed with water and dried under vacuum to give 6-bromo-4-(((3S,4S)-1-(5-cyanopyridin-2-yl)-4-methylpyrrolidin-3-yl)amino)pyrrolo[1,2-b]pyridazine-3-carboxamide (0.228 g, 97% yield). 1H NMR (400 MHz, 1:1 mixture of chloroform-d/methanol-d4) δ ppm 8.39-8.27 (m, 1H), 8.08 (s, 1H), 7.69-7.57 (m, 2H), 6.95-6.82 (m, 1H), 6.48 (d, J=9.0 Hz, 1H), 4.83 (br. s., 1H), 4.01-3.69 (m, 3H), 3.39 (t, J=9.6 Hz, 1H), 2.81 (br. s., 1H), 1.27 (d, J=6.8 Hz, 3H); MS (ES+) m/z: 440.2 (M+H); LC retention time: 3.885 min (analytical HPLC Method H).

Step 3: 2-methyl-1-(4-(4,4,5,5-tetramethyl-1,3,2-dioxaborolan-2-yl)-1H-pyrazol-1-yl)propan-2-ol

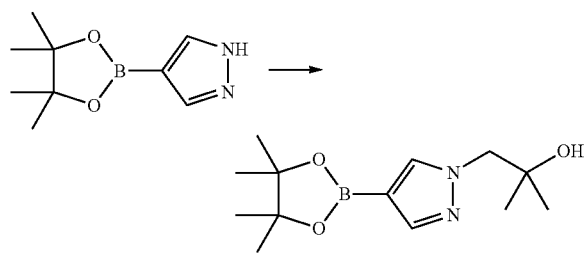

A suspension of 4-(4,4,5,5-tetramethyl-1,3,2-dioxaborolan-2-yl)-1H-pyrazole (514.3 mg, 2.65 mmol), cesium carbonate (1.295 g, 3.98 mmol) and 2,2-dimethyloxirane (0.589 mL, 6.63 mmol) in acetonitrile (5 mL) was heated at 130° C. under microwave for 1 h. The resulting mixture was concentrated. The residue was triturated with dichloromethane, stirred at room temperature for 30 min and filtered. The filtrate was concentrated to give crude 2-methyl-1-(4-(4,4,5,5-tetramethyl-1,3,2-dioxaborolan-2-yl)-1H-pyrazol-1-yl)propan-2-ol (0.4289 g). This material was used in subsequent Suzuki coupling reactions without further purification. 1H NMR (400 MHz, DMSO-d6) δ ppm 7.84 (d, J=0.4 Hz, 1H), 7.55 (d, J=0.7 Hz, 1H), 4.02 (s, 2H), 4.01 (s, 1H), 1.25 (s, 12H), 1.04 (s, 6H).

Step 4: 4-(((3S,4S)-1-(5-cyanopyridin-2-yl)-4-methylpyrrolidin-3-yl)amino)-6-(1-(2-hydroxy-2-methylpropyl)-1H-pyrazol-4-yl)pyrrolo[1,2-b]pyridazine-3-carboxamide (Example 158)

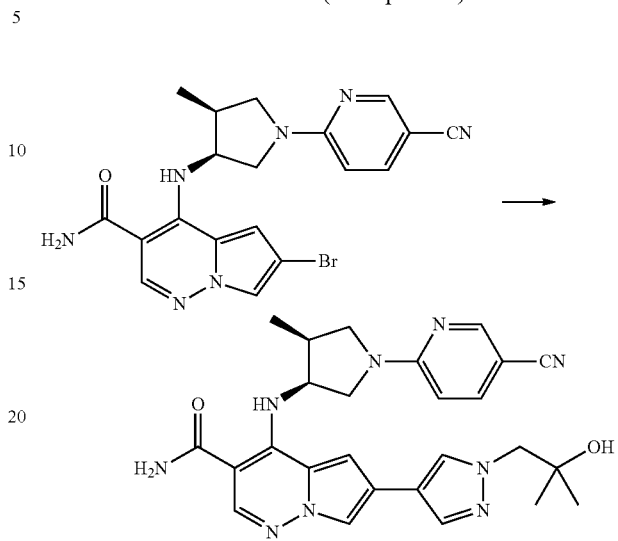

A solution of 6-bromo-4-(((3S,4S)-1-(5-cyanopyridin-2-yl)-4-methylpyrrolidin-3-yl)amino)pyrrolo[1,2-b]pyridazine-3-carboxamide (20 mg, 0.045 mmol, from Step 2), 2-methyl-1-(4-(4,4,5,5-tetramethyl-1,3,2-dioxaborolan-2-yl)-1H-pyrazol-1-yl)propan-2-ol (24.18 mg, 0.091 mmol, from Step 3), potassium phosphate tribasic (28.9 mg, 0.136 mmol), palladium(II) acetate (1 mg, 4.45 µmol) and dicyclohexyl(2',4',6'-triisopropyl-3,6-dimethoxy-[1,1'-biphenyl]-2-yl)phosphine (4.78 mg, 8.90 µmol) in tert-butanol (0.5 mL) was degassed by vacuum-N2 refill cycle twice. The sealed tube was then heated at 110° C. for 2 h. The crude material was diluted with methanol (1.3 mL) and water (0.2 mL) and filtered. The filtrate was purified by preparative RP-HPLC (50-80% solvent B in 30 min, 30 mL/min, Pursuit XRs 10 u C18 30×250 mm) to give the title compound (9.7 mg). $^1$H NMR (500 MHz, 1:1 mixture of chloroform-d/methanol-d$_4$) δ ppm 8.31 (br. s., 1H), 8.07 (s, 1H), 7.85 (s, 1H), 7.74 (s, 2H), 7.63 (dd, J=8.9, 1.5 Hz, 1H), 6.98 (d, J=1.5 Hz, 1H), 6.49 (d, J=8.9 Hz, 1H), 4.97 (br. s., 1H), 4.10 (s, 2H), 3.99-3.75 (m, 3H), 3.46-3.36 (m, 1H), 2.84 (br. s., 1H), 1.29 (d, J=6.9 Hz, 3H), 1.20 (s, 6H); MS (ES+) m/z: 500.2 (M+H); LC retention time: 1.18 min (analytical LCMS Method I).

Example 159

4-(((3S,4S)-1-(5-cyanopyrimidin-2-yl)-4-ethylpyrrolidin-3-yl)amino)-6-(1-methyl-6-oxo-1,6-dihydropyridin-3-yl)pyrrolo[1,2-b]pyridazine-3-carboxamide

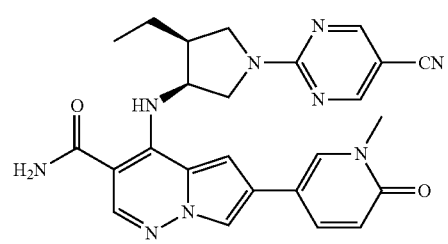 [SMILES: CC[C@H]1CN(c2ncc(C#N)cn2)C[C@H]1Nc1c(C(N)=O)cnn2cc(-c3ccc(=O)n(C)c3)cc12]

Step 1: 6-bromo-4-(((3S,4S)-1-(5-cyanopyrimidin-2-yl)-4-ethylpyrrolidin-3-yl)amino)pyrrolo[1,2-b]pyridazine-3-carboxamide

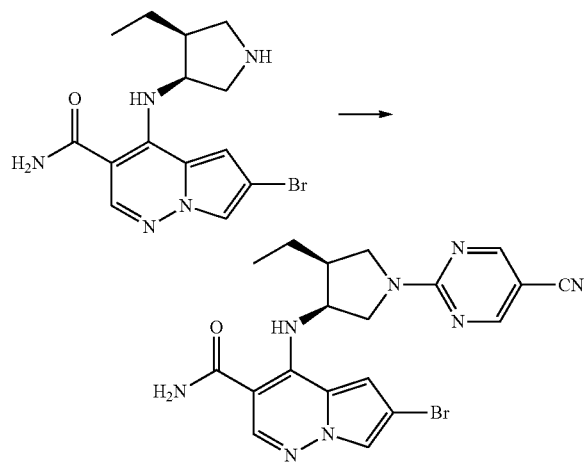

A mixture of 6-bromo-4-(((3S,4S)-4-ethylpyrrolidin-3-yl)amino)pyrrolo[1,2-b]pyridazine-3-carboxamide hydroiodide (0.250 g, 0.521 mmol, prepared from Intermediates 2 and 8 using the methods in Example 52 and Step 1 of Example 158), 2-chloropyrimidine-5-carbonitrile (0.087 g, 0.625 mmol), and potassium carbonate (0.216 g, 1.562 mmol) in a sealed vial was placed in a 90° C. heating block for 3 h. The mixture was triturated with water (5 mL). The resulting suspension was stirred for 10 min and filtered. The solid was washed with water (20 mL) and dried under vacuum to give 6-bromo-4-(((3S,4S)-1-(5-cyanopyrimidin-2-yl)-4-ethylpyrrolidin-3-yl)amino)pyrrolo[1,2-b]pyridazine-3-carboxamide as yellow solid (199 mg, 84% yield). 1H NMR (400 MHz, 1:1 mixture of chloroform-d/methanol-d4) δ ppm 8.57 (d, J=2.9 Hz, 1H), 8.51 (d, J=3.1 Hz, 1H), 8.11 (s, 1H), 7.64 (d, J=1.8 Hz, 1H), 6.92 (d, J=1.8 Hz, 1H), 4.89 (t, J=4.4 Hz, 1H), 4.18-4.01 (m, 2H), 4.00-3.88 (m, 1H), 3.52 (t, J=11.6 Hz, 1H), 2.71-2.50 (m, 1H), 1.85-1.68 (m, 2H), 1.05 (t, J=7.5 Hz, 3H); MS (ES+) m/z: 455.1 (M+H); LC retention time: 4.085 min (analytical HPLC Method H).

Step 2: 1-methyl-5-(4,4,5,5-tetramethyl-1,3,2-dioxaborolan-2-yl)pyridin-2(1H)-one

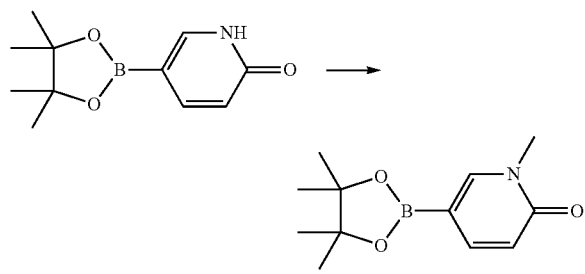

Iodomethane (0.283 mL, 4.52 mmol) was added to a mixture of 5-(4,4,5,5-tetramethyl-1,3,2-dioxaborolan-2-yl)pyridin-2-ol (0.500 g, 2.262 mmol) and potassium carbonate (1.563 g, 11.31 mmol) in acetonitrile (10 mL). The reaction vial was sealed and stirred at 50° C. for 16 h. The resulting mixture was filtered to remove the inorganic salt and the filter cake rinsed with ethyl acetate. The filtrate was concentrated, treated with ethyl acetate (20 mL) and dichloromethane (20 mL), and filtered to remove the residual inorganic salt. The filtrate was concentrated and dried under vacuum to give crude 1-methyl-5-(4,4,5,5-tetramethyl-1,3,2-dioxaborolan-2-yl)pyridin-2(1H)-one as white solid (399.4 mg). This material was used in subsequent Suzuki coupling reactions without further purification. 1H NMR (400 MHz, chloroform-d) δ ppm 7.76 (d, J=2.0 Hz, 1H), 7.60 (dd, J=9.2, 2.0 Hz, 1H), 6.52 (d, J=9.0 Hz, 1H), 3.55 (s, 3H), 1.31 (s, 12H).

Step 3: 4-(((3S,4S)-1-(5-cyanopyrimidin-2-yl)-4-ethylpyrrolidin-3-yl)amino)-6-(1-methyl-6-oxo-1,6-dihydropyridin-3-yl)pyrrolo[1,2-b]pyridazine-3-carboxamide (Example 159)

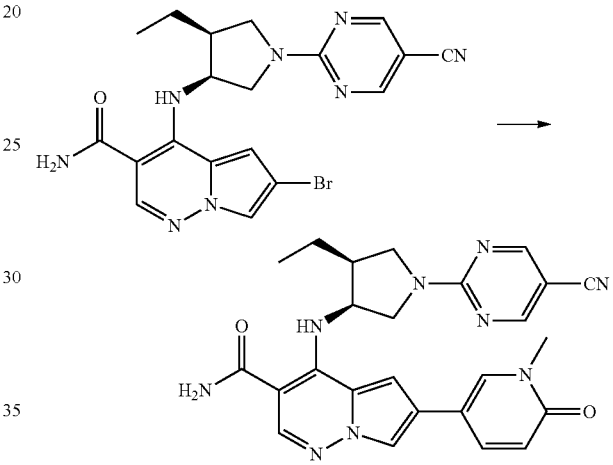

A mixture of 6-bromo-4-(((3S,4S)-1-(5-cyanopyrimidin-2-yl)-4-ethylpyrrolidin-3-yl)amino)pyrrolo[1,2-b]pyridazine-3-carboxamide (20 mg, 0.044 mmol, from Step 1), 1-methyl-5-(4,4,5,5-tetramethyl-1,3,2-dioxaborolan-2-yl)pyridin-2(1H)-one (31.0 mg, 0.132 mmol, from Step 2), and PdCl$_2$(dppf)-CH$_2$Cl$_2$ adduct (7.17 mg, 8.79 μmol) was pumped under vacuum and backfilled with nitrogen three times. A 2 M aqueous solution of potassium phosphate tribasic (0.066 mL, 0.132 mmol) and N,N-dimethylformamide (0.5 mL) were added. The mixture was immediately pumped under vacuum and backfilled with nitrogen three times, sealed and placed in a 90° C. heating block for 3 h, then cooled to room temperature. The mixture was filtered to remove the insoluble material. The filtrate was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-100% B over 25 minutes, then a 5-minute hold at 100% B; Flow: 20 mL/min. Fractions containing the desired product were combined and dried via centrifugal evaporation to give the title compound (9.4 mg, 44% yield). 1H NMR (500 MHz, DMSO-d6) δ ppm 11.16 (d, J=7.4 Hz, 1H), 8.77 (d, J=3.0 Hz, 1H), 8.67 (d, J=3.0 Hz, 1H), 8.28 (d, J=2.5 Hz, 1H), 8.21 (s, 1H), 8.13 (d, J=2.0 Hz, 1H), 8.00-7.90 (m, 1H), 7.25 (d, J=1.5 Hz, 1H), 6.48 (d, J=9.4 Hz, 1H), 5.09-4.91 (m, 1H), 4.09-3.94 (m, 2H), 3.85 (d, J=12.4 Hz, 1H), 3.51 (s, 3H), 2.66-2.55 (m, 1H), 1.64 (quin, J=7.4 Hz, 2H), 0.96 (t, J=7.4 Hz, 3H); MS (ES+) m/z: 484.2 (M+H); LC retention time: 1.19 min (analytical LCMS Method I).

Examples 160-183

According to the procedure described for Example 159, Examples 160-172 were prepared from 6-bromo-4-(((3S,4S)-4-methylpyrrolidin-3-yl)amino)pyrrolo[1,2-b]pyridazine-3-carboxamide (from Step 1 of Example 158), and Examples 173-183 were prepared from 6-bromo-4-(((3S,4S)-4-ethylpyrrolidin-3-yl)amino)pyrrolo[1,2-b]pyridazine-3-carboxamide. The pre-requisite boronic acid esters for the Suzuki coupling reaction for Examples 166, 167, 172, 173, 178 and 181 were prepared following conditions analogous to Step 3 of Example 158. The pre-requisite boronic acid esters for the Suzuki coupling reaction for Examples 160, 173 and 174 were prepared following conditions analogous to Step 2 of Example 159. Retention time for Example 168 was measured using analytical HPLC Method H. Retention times for all other examples were measured using analytical LCMS Method I.

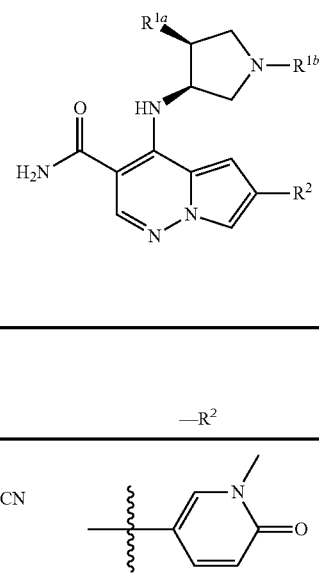

| Ex | Name | —R$^{1a}$ | R$^{1b}$ | —R$^2$ | HPLC or LCMS Rt (minutes) | LCMS [m/z (M + H)] |
|---|---|---|---|---|---|---|
| 160 | 4-((3S,4S)-1-(5-cyanopyridin-2-yl)-4-methylpyrrolidin-3-ylamino)-6-(1-methyl-6-oxo-1,6-dihydropyridin-3-yl)pyrrolo[1,2-b]pyridazine-3-carboxamide | —Me | pyridyl-CN | 1-methyl-pyridinone | 1.07 | 469.2 |
| 161 | 4-((3S,4S)-1-(5-cyanopyridin-2-yl)-4-methylpyrrolidin-3-ylamino)-6-(1-(difluoromethyl)-1H-pyrazol-4-yl)pyrrolo[1,2-b]pyridazine-3-carboxamide | —Me | pyridyl-CN | CHF$_2$-pyrazole | 1.37 | 478.0 |
| 162 | 4-((3S,4S)-1-(5-cyanopyrimidin-2-yl)-4-methylpyrrolidin-3-ylamino)-6-(4-(methylsulfonyl)phenyl)pyrrolo[1,2-b]pyridazine-3-carboxamide | —Me | pyrimidyl-CN | 4-(SO$_2$Me)phenyl | 1.37 | 517.2 |
| 163 | 4-((3S,4S)-1-(5-cyanopyrimidin-2-yl)-4-methylpyrrolidin-3-ylamino)-6-(1-methyl-1H-pyrazol-4-yl)pyrrolo[1,2-b]pyridazine-3-carboxamide | —Me | pyrimidyl-CN | 1-Me-pyrazole | 1.16 | 443.0 |
| 164 | 4-((3S,4S)-1-(5-cyanopyrimidin-2-yl)-4-methylpyrrolidin-3-ylamino)-6-(1-ethyl-1H-pyrazol-4-yl)pyrrolo[1,2-b]pyridazine-3-carboxamide | —Me | pyrimidyl-CN | 1-Et-pyrazole | 1.32 | 457.2 |
| 165 | 4-((3S,4S)-1-(5-cyanopyrimidin-2-yl)-4-methylpyrrolidin-3-ylamino)-6-(1-(1,1,1-trideuteomethyl)-1H-pyrazol-4-yl)pyrrolo[1,2-b]pyridazine-3-carboxamide | —Me | pyrimidyl-CN | 1-CD$_3$-pyrazole | 1.19 | 446.2 |
| 166 | 4-((3S,4S)-1-(5-cyanopyrimidin-2-yl)-4-methylpyrrolidin-3-ylamino)-6-(1-((R)-2-hydroxypropyl)-1H-pyrazol-4-yl)pyrrolo[1,2-b]pyridazine-3-carboxamide | —Me | pyrimidyl-CN | 1-((R)-2-OH-propyl)-pyrazole | 1.14 | 487.1 |
| 167 | 4-((3S,4S)-1-(5-cyanopyrimidin-2-yl)-4-methylpyrrolidin-3-ylamino)-6-(1-((S)-2-hydroxypropyl)-1H-pyrazol-4-yl)pyrrolo[1,2-b]pyridazine-3-carboxamide | —Me | pyrimidyl-CN | 1-((S)-2-OH-propyl)-pyrazole | 1.14 | 487.2 |

| Ex | Name | —R¹ᵃ | R¹ᵇ | —R² | HPLC or LCMS Rt (minutes) | LCMS [m/z (M + H)] |
|---|---|---|---|---|---|---|
| 168 | 4-((3S,4S)-1-(5-bromopyrimidin-2-yl)-4-methylpyrrolidin-3-ylamino)-6-(1-methyl-1H-pyrazol-4-yl)pyrrolo[1,2-b]pyridazine-3-carboxamide | —Me | 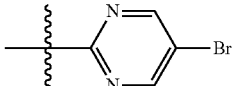 | 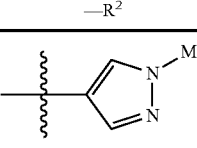 | 3.890 | 496.1 |
| 169 | 4-((3S,4S)-1-(6-cyanopyridazin-3-yl)-4-methylpyrrolidin-3-ylamino)-6-(1-methyl-1H-pyrazol-4-yl)pyrrolo[1,2-b]pyridazine-3-carboxamide | —Me | 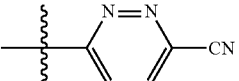 | 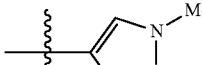 | 1.10 | 443.2 |
| 170 | 4-((3S,4S)-4-methyl-1-(6-(trifluoromethyl)pyridazin-3-yl)pyrrolidin-3-ylamino)-6-(1-methyl-1H-pyrazol-4-yl)pyrrolo[1,2-b]pyridazine-3-carboxamide | —Me | 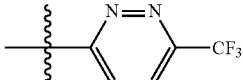 | 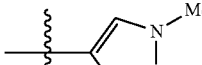 | 1.27 | 486.1 |
| 171 | 4-((3S,4S)-1-(4-carbamoylpyrimidin-2-yl)-4-methylpyrrolidin-3-ylamino)-6-(1-methyl-1H-pyrazol-4-yl)pyrrolo[1,2-b]pyridazine-3-carboxamide | —Me | 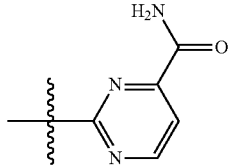 [SMILES: *c1nccc(C(N)=O)n1] | 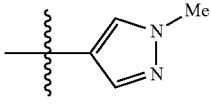 | 1.05 | 461.2 |
| 172 | 6-(1-(2-hydroxy-2-methylpropyl)-1H-pyrazol-4-yl)-4-((3S,4S)-4-methyl-1-(5-(trifluoromethyl)pyrazin-2-yl)pyrrolidin-3-ylamino)pyrrolo[1,2-b]pyridazine-3-carboxamide | —Me | 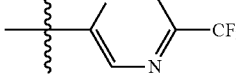 | 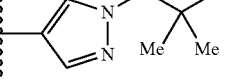 | 1.49 | 544.2 |
| 173 | 4-((3S,4S)-1-(5-cyanopyridin-2-yl)-4-ethylpyrrolidin-3-ylamino)-6-(1-methyl-6-oxo-1,6-dihydropyridin-3-yl)pyrrolo[1,2-b]pyridazine-3-carboxamide | —Et | 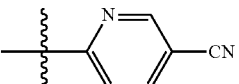 | 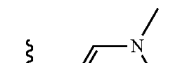 | 1.17 | 483.1 |
| 174 | 4-((3S,4S)-1-(5-cyanopyridin-2-yl)-4-ethylpyrrolidin-3-ylamino)-6-(1-ethyl-6-oxo-1,6-dihydropyridin-3-yl)pyrrolo[1,2-b]pyridazine-3-carboxamide | —Et | 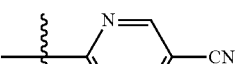 | 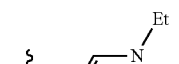 | 1.27 | 497.2 |
| 175 | 4-((3S,4S)-1-(5-cyanopyridin-2-yl)-4-ethylpyrrolidin-3-ylamino)-6-(1-methyl-1H-pyrazol-4-yl)pyrrolo[1,2-b]pyridazine-3-carboxamide | —Et | 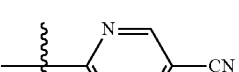 | 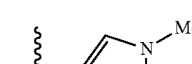 | 1.24 | 456.0 |
| 176 | 4-((3S,4S)-1-(5-cyanopyridin-2-yl)-4-ethylpyrrolidin-3-ylamino)-6-(1-ethyl-1H-pyrazol-4-yl)pyrrolo[1,2-b]pyridazine-3-carboxamide | —Et | 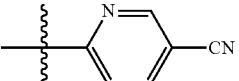 | 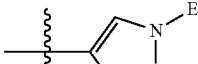 | 1.40 | 470.1 |
| 177 | 4-((3S,4S)-1-(5-cyanopyrimidin-2-yl)-4-ethylpyrrolidin-3-ylamino)-6-(1-(2-hydroxy-2-methylpropyl)-1H-pyrazol-4-yl)pyrrolo[1,2-b]pyridazine-3-carboxamide | —Et | 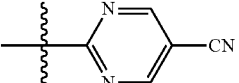 | 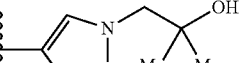 | 1.32 | 515.2 |
| 178 | 4-((3S,4S)-1-(5-cyanopyrimidin-2-yl)-4-ethylpyrrolidin-3-ylamino)-6-(1-((R)-2-hydroxypropyl)-1H-pyrazol-4-yl)pyrrolo[1,2-b]pyridazine-3-carboxamide | —Et | 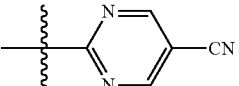 | 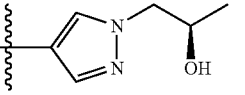 | 1.24 | 501.1 |

| Ex | Name | —R$^{1a}$ | R$^{1b}$ | —R$^2$ | HPLC or LCMS Rt (minutes) | LCMS [m/z] (M + H)] |
|---|---|---|---|---|---|---|
| 179 | 4-((3S,4S)-1-(5-cyanopyrimidin-2-yl)-4-ethylpyrrolidin-3-ylamino)-6-(4-(2-hydroxypropan-2-yl)phenyl)pyrrolo[1,2-b]pyridazine-3-carboxamide | —Et | pyrimidine-CN | phenyl-C(Me)(Me)OH | 1.61 | 511.2 |
| 180 | 6-(6-aminopyridin-3-yl)-4-((3S,4S)-1-(5-cyanopyrimidin-2-yl)-4-ethylpyrrolidin-3-ylamino)pyrrolo[1,2-b]pyridazine-3-carboxamide | —Et | pyrimidine-CN | pyridine-NH$_2$ | 1.05 | 469.1 |
| 181 | 4-((3S,4S)-4-ethyl-1-(5-(trifluoromethyl)pyrazin-2-yl)pyrrolidin-3-ylamino)-6-(1-((R)-2-hydroxypropyl)-1H-pyrazol-4-yl)pyrrolo[1,2-b]pyridazine-3-carboxamide | —Et | pyrazine-CF$_3$ | pyrazole-CH$_2$CH(OH)Me | 1.77 | 544.1 |
| 182 | 4-((3S,4S)-1-(5-cyanothiazol-2-yl)-4-ethylpyrrolin-3-ylamino)-6-(1-methyl-1H-pyrazol-4-yl)pyrrolo[1,2-b]pyridazine-3-carboxamide | —Et | thiazole-CN | pyrazole-Me | 1.33 | 462.1 |
| 183 | 4-((3S,4S)-1-(5-cyanothiazol-2-yl)-4-ethylpyrrolin-3-ylamino)-6-(1-isobutyl-1H-pyrazol-4-yl)pyrrolo[1,2-b]pyridazine-3-carboxamide | —Et | thiazole-CN | pyrazole-CH$_2$CH(Me)Me | 1.71 | 504.1 |

Example 184

4-(((3S,4S)-1-(5-cyanopyridin-2-yl)-4-methylpyrrolidin-3-yl)amino)-6-(1-(2-(3,3-difluoroazetidin-1-yl)-2-oxoethyl)-1H-pyrazol-4-yl)pyrrolo[1,2-b]pyridazine-3-carboxamide

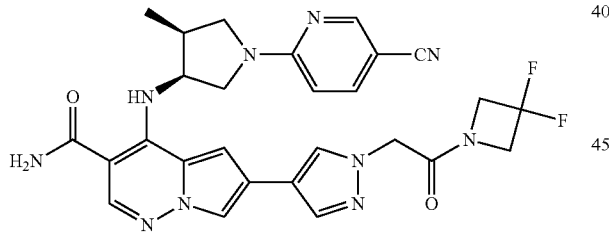

Step 1: ethyl 2-(4-(3-carbamoyl-4-(((3S,4S)-1-(5-cyanopyridin-2-yl)-4-methylpyrrolidin-3-yl)amino)pyrrolo[1,2-b]pyridazin-6-yl)-1H-pyrazol-1-yl)acetate

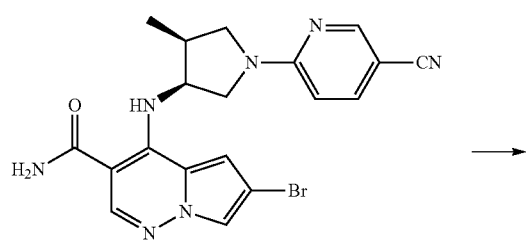

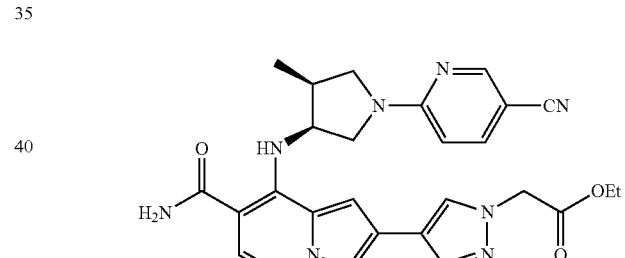

A stirred solution of 6-bromo-4-(((3S,4S)-1-(5-cyanopyridin-2-yl)-4-methylpyrrolidin-3-yl)amino)pyrrolo[1,2-b]pyridazine-3-carboxamide (55 mg, 0.125 mmol, from Step 1 of Example 158), ethyl 2-(4-(4,4,5,5-tetramethyl-1,3,2-dioxaborolan-2-yl)-1H-pyrazol-1-yl)acetate (70.0 mg, 0.250 mmol), potassium phosphate tribasic (80 mg, 0.375 mmol), palladium(II) acetate (5.61 mg, 0.025 mmol) and 1,1'-bis(di-tert-butylphosphino)ferrocene (12.00 mg, 0.025 mmol) in N,N-dimethylformamide (1 mL) was degassed by vacuum-N2 refill cycle twice. The sealed tube was then heated at 100° C. for 40 min. The reaction mixture was diluted with water and filtered. The filter cake was washed with water and dried under vacuum to give crude ethyl 2-(4-(3-carbamoyl-4-(((3S,4S)-1-(5-cyanopyridin-2-yl)-4-methylpyrrolidin-3-yl)amino)pyrrolo[1,2-b]pyridazin-6-yl)-1H-pyrazol-1-yl)acetate (76.8 mg), which was used in the next step without purification.

Step 2: 2-(4-(3-carbamoyl-4-(((3S,4S)-1-(5-cyanopyridin-2-yl)-4-methylpyrrolidin-3-yl)amino)pyrrolo[1,2-b]pyridazin-6-yl)-1H-pyrazol-1-yl)acetic acid

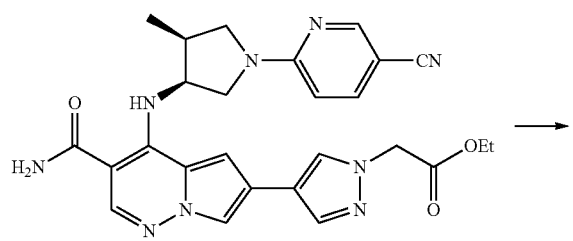 [SMILES: C[C@H]1CN(c2ccc(C#N)cn2)C[C@H]1Nc1c(C(N)=O)cnn2cc(-c3cnn(CC(=O)N4CC(F)(F)C4)c3)cc12]

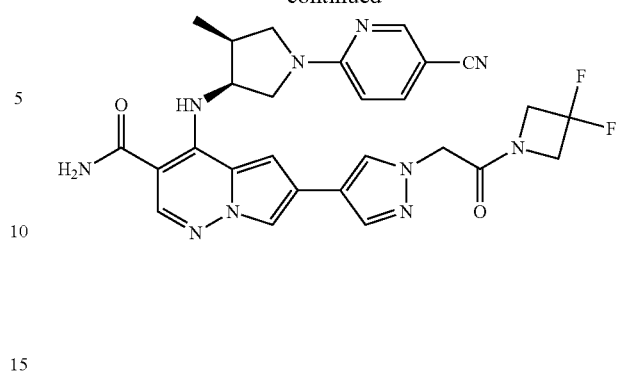

A mixture of the crude ethyl 2-(4-(3-carbamoyl-4-(((3S,4S)-1-(5-cyanopyridin-2-yl)-4-methylpyrrolidin-3-yl)amino)pyrrolo[1,2-b]pyridazin-6-yl)-1H-pyrazol-1-yl)acetate from Step 1, a 2 N aqueous solution of NaOH (0.5 mL), methanol (0.5 mL) and tetrahydrofuran (0.5 mL) was stirred at room temperature for 1 h. The organic solvents were evaporated in vacuo. The aqueous residue was treated with 1 N HCl (1 mL) and water (1 mL) and filtered. The filter cake was washed with water and dried under vacuum to give crude 2-(4-(3-carbamoyl-4-(((3S,4S)-1-(5-cyanopyridin-2-yl)-4-methylpyrrolidin-3-yl)amino)pyrrolo[1,2-b]pyridazin-6-yl)-1H-pyrazol-1-yl)acetic acid as dark brown solid (66.3 mg). This material was used in the next step without further purification. MS (ES+) m/z: 486.1 (M+H).

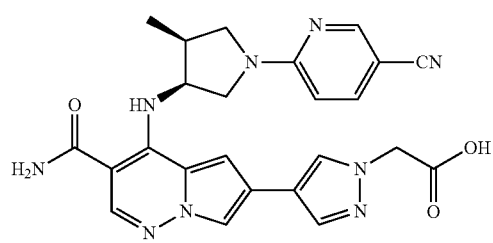

Hunig's base (0.014 mL, 0.079 mmol) was added to a stirred solution of crude 2-(4-(3-carbamoyl-4-(((3S,4S)-1-(5-cyanopyridin-2-yl)-4-methylpyrrolidin-3-yl)amino)pyrrolo[1,2-b]pyridazin-6-yl)-1H-pyrazol-1-yl)acetic acid (20 mg, from Step 2) and HATU (20.05 mg, 0.053 mmol). After 2.5 h at room temperature, 3,3-difluoroazetidine hydrochloride (6.83 mg, 0.053 mmol) was added. After 40 min at room temperature, the reaction was complete. The crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 15 minutes, then a 7-minute hold at 100% B; Flow: 25 mL/min. Fractions containing the desired product were combined and dried via centrifugal evaporation to give the title compound (4.1 mg). 1H NMR (500 MHz, chloroform-d/methanol-d4) δ ppm 8.31 (br. s., 1H), 8.07 (s, 1H), 7.89 (s, 1H), 7.82 (s, 1H), 7.75 (d, J=1.5 Hz, 1H), 7.63 (dd, J=8.9, 1.5 Hz, 1H), 6.99 (d, J=1.5 Hz, 1H), 6.49 (d, J=8.9 Hz, 1H), 4.99-4.91 (m, 3H), 4.46 (t, J=11.9 Hz, 2H), 4.39 (t, J=11.9 Hz, 2H), 3.94 (br. s., 2H), 3.41 (br. s., 1H), 2.84 (br. s., 1H), 1.29 (d, J=6.9 Hz, 3H); MS (ES+) m/z: 561.1 (M+H); LC retention time: 1.24 min (analytical LCMS Method I).

Examples 185-189

According to the procedures described in Step 2 of Example 158 and Example 184, Examples 185-189 were prepared from 6-bromo-4-(((3S,4S)-4-methylpyrrolidin-3-yl)amino)pyrrolo[1,2-b]pyridazine-3-carboxamide (from Step 1 of Example 158). Retention times for all examples were measured using analytical LCMS Method I.

Step 3: 4-(((3S,4S)-1-(5-cyanopyridin-2-yl)-4-methylpyrrolidin-3-yl)amino)-6-(1-(2-(3,3-difluoroazetidin-1-yl)-2-oxoethyl)-1H-pyrazol-4-yl)pyrrolo[1,2-b]pyridazine-3-carboxamide (Example 184)

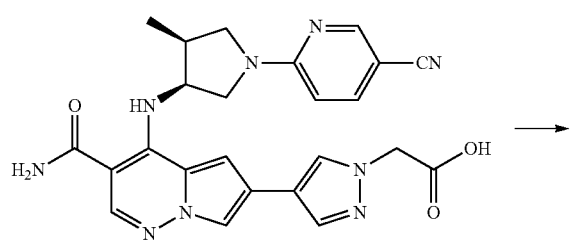

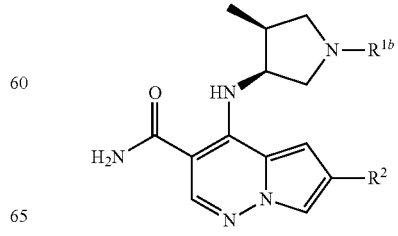

| Ex # | NAME | —R[1b] | —R[2] | HPLC or LCMS Rt (minutes) | LCMS [m/z (M + H)] |
|---|---|---|---|---|---|
| 185 | 4-(((3S,4S)-1-(5-cyanopyridin-2-yl)-4-methylpyrrolidin-3-yl)amino)-6-(1-(2-(3,3-difluoropyrrolidin-1-yl)-2-oxoethyl)-1H-pyrazol-4-yl)pyrrolo[1,2-b]pyridazine-3-carboxamide | 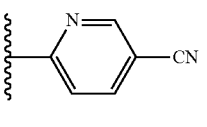 | 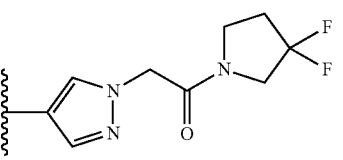 [SMILES: *c1cnn(CC(=O)N2CCC(F)(F)C2)c1] | 1.36 | 575.3 |
| 186 | 4-(((3S,4S)-1-(5-cyanopyridin-2-yl)-4-methylpyrrolidin-3-yl)amino)-6-(1-(2-(dimethylamino)-2-oxoethyl)-1H-pyrazol-4-yl)pyrrolo[1,2-b]pyridazine-3-carboxamide | 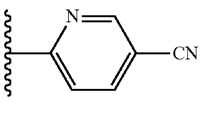 | 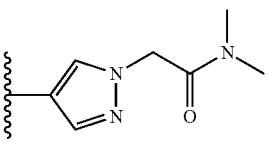 [SMILES: *c1cnn(CC(=O)N(C)C)c1] | 1.10 | 513.2 |
| 187 | 4-(((3S,4S)-1-(5-cyanopyrimidin-2-yl)-4-methylpyrrolidin-3-yl)amino)-6-(1-(2-(dimethylamino)-2-oxoethyl)-1H-pyrazol-4-yl)pyrrolo[1,2-b]pyridazine-3-carboxamide | 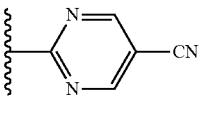 | 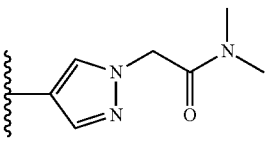 [SMILES: *c1cnn(CC(=O)N(C)C)c1] | 1.12 | 514.2 |
| 188 | 4-(((3S,4S)-1-(5-chloropyridin-2-yl)-4-methylpyrroldin-3-yl)amino)-6-(1-(2-(methylamino)-2-oxoethyl)-1H-pyrazol-4-yl)pyrrolo[1,2-b]pyridazine-3-carboxamide | 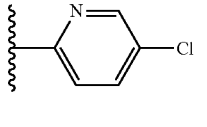 | 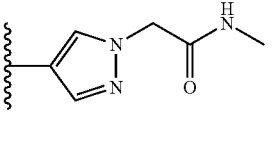 [SMILES: *c1cnn(CC(=O)NC)c1] | 0.91 | 508.0 |
| 189 | 4-(((3S,4S)-1-(5-chloropyridin-2-yl)-4-methylpyrrolidin-3-yl)amino)-6-(1-(2-morpholino-2-oxoethyl)-1H-pyrazol-4-yl)pyrrolo[1,2-b]pyridazine-3-carboxamide | 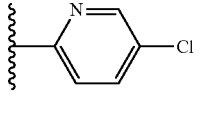 | 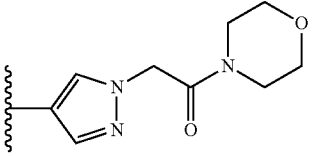 [SMILES: *c1cnn(CC(=O)N2CCOCC2)c1] | 0.97 | 564.1 |

Example 190

4-(((3S,4S)-1-(5-cyanopyrimidin-2-yl)-4-ethylpyrrolidin-3-yl)amino)-6-(1-(difluoromethyl)-6-oxo-1,6-dihydropyridin-3-yl)pyrrolo[1,2-b]pyridazine-3-carboxamide

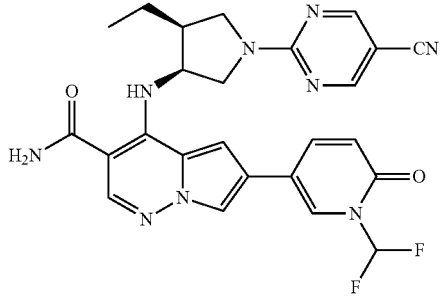 [SMILES: CC[C@H]1CN(c2ncc(C#N)cn2)C[C@H]1Nc1c(C(N)=O)cnn2cc(-c3ccc(=O)n(C(F)F)c3)cc12]

Step 1: 1-(difluoromethyl)-5-(4,4,5,5-tetramethyl-1,3,2-dioxaborolan-2-yl)pyridin-2(1H)-one

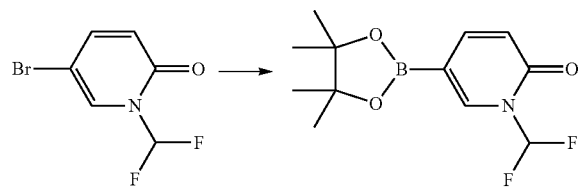 [SMILES: O=c1ccc(Br)cn1C(F)F ; CC1(C)OB(c2ccc(=O)n(C(F)F)c2)OC1(C)C]

A reaction vial was charged with 5-bromo-1-(difluoromethyl)pyridin-2(1H)-one (250 mg, 1.116 mmol, reference M. Ando et al., Organic Letters 2009, 8, 3805), potassium acetate (219 mg, 2.232 mmol) and 4,4,4',4',5,5,5',5'-octamethyl-2,2'-bi(1,3,2-dioxaborolane) (340 mg, 1.339 mmol) in dioxane (3 mL) and methyl sulfoxide (0.150 mL). The resulting mixture was deoxygenated by bubbling nitrogen through the mixture for 5 min. $PdCl_2(dppf)$ (82 mg, 0.112 mmol) was added and the mixture was heated at 95° C. for 3 h. The reaction mixture was cooled to room temperature and partitioned between ethyl acetate and water. The organic layer was washed with water twice, brine, dried (MgSO4) and concentrated. Silica gel chromatography, eluting with 0 to 60% ethyl acetate in hexanes, gave 1-(difluoromethyl)-5-(4,4,5,5-tetramethyl-1,3,2-dioxaborolan-2-yl)pyridin-2(1H)-one (260 mg, 86% yield). NMR (400 MHz, chloroform-d) δ ppm 7.91 (d, J=1.1 Hz, 1H), 7.84-7.15 (m, 2H), 6.51 (d, J=9.5 Hz, 1H), 1.41-1.27 (m, 12H); MS (ES+) m/z: 272.1 (M+H).

Step 2: 4-(((3S,4S)-1-(5-cyanopyrimidin-2-yl)-4-ethylpyrrolidin-3-yl)amino)-6-(1-(difluoromethyl)-6-oxo-1,6-dihydropyridin-3-yl)pyrrolo[1,2-b]pyridazine-3-carboxamide (Example 190)

A mixture of 4-(((3S,4S)-1-(5-cyanopyrimidin-2-yl)-4-ethylpyrrolidin-3-yl)amino)-6-(1-(difluoromethyl)-6-oxo-1,6-dihydropyridin-3-yl)pyrrolo[1,2-b]pyridazine-3-carboxamide (16 mg, 0.035 mmol, from Step 1 of Example 159), 1-(difluoromethyl)-5-(4,4,5,5-tetramethyl-1,3,2-dioxaborolan-2-yl)pyridin-2(1H)-one (19.05 mg, 0.070 mmol, from Step 1), $PdCl_2(dppf)$ (2.57 mg, 3.51 mmol) and 2.0 M aqueous solution of potassium phosphate tribasic (0.070 mL, 0.141 mmol) in N,N-dimethylformamide (1 mL) was deoxygenated by bubbling N2 through the mixture for 5 min and heated to 90° C. under N2 for 1 h. The crude material was filtered and purified via preparative LC/MS with the following conditions: Column: Waters XBridge Shield RP18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 5-45% B over 25 minutes, then a 15-minute hold at 45% B; Flow: 20 mL/min. Fractions containing the desired product were combined and dried via centrifugal evaporation to give the title compound (4.9 mg, 27% yield). 1H NMR (500 MHz, DMSO-d6) δ ppm 11.19 (d, J=7.8 Hz, 1H), 8.77 (d, J=3.1 Hz, 1H), 8.67 (d, J=3.1 Hz, 1H), 8.38-8.22 (m, 3H), 8.16 (dd, J=9.7, 2.5 Hz, 1H), 8.01-7.84 (m, 1H), 7.40 (d, J=1.7 Hz, 1H), 6.65 (d, J=9.7 Hz, 1H), 5.08 (dt, J=7.8, 4.2 Hz, 1H), 4.18-3.78 (m, 4H), 2.64-2.58 (m, 1H), 1.65 (quin, J=7.4 Hz, 2H), 0.98 (t, J=7.5 Hz, 3H); MS (ES+) m/z: 520.2 (M+H); LC retention time: 1.48 min (analytical LCMS Method I).

Example 191

4-((3S,4S)-1-(2-cyanoacetyl)-4-methylpyrrolidin-3-ylamino)-6-(4-methoxyphenyl)pyrrolo[1,2-b]pyridazine-3-carboxamide

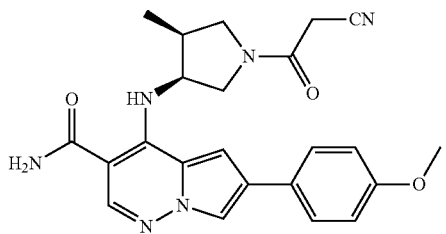 [SMILES: COc1ccc(-c2cc3c(N[C@@H]4CN(C(=O)CC#N)C[C@@H]4C)c(C(N)=O)cnn3c2)cc1]

Step 1: 6-bromo-4-((3S,4S)-1-(2-cyanoacetyl)-4-methylpyrrolidin-3-ylamino)pyrrolo[1,2-b]pyridazine-3-carboxamide

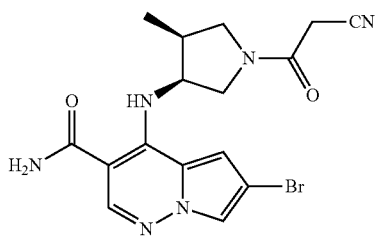 [SMILES: C[C@H]1CN(C(=O)CC#N)C[C@H]1Nc1c(C(N)=O)cnn2cc(Br)cc12]

To solution of 6-bromo-4-((3S,4S)-4-methylpyrrolidin-3-ylamino)pyrrolo[1,2-b]pyridazine-3-carboxamide hydrogen iodide salt prepared as previously described in Step 1 of Example 158 (200 mg, 0.429 mmol), 2-cyanoacetic acid (43.8 mg, 0.515 mmol) and BOP (285 mg, 0.644 mmol) in DMF (2 mL) was added DIPEA (0.225 mL, 1.288 mmol) and the resulting mixture was stirred at rt for 4 h. The reaction mixture was added to water (~5 volumes) and the pH was adjusted to ~7 with 1 N HCl and the resulting cloudy mixture was extracted with EtOAc (150 mL×2). The combined organic extracts were washed with water, brine, dried over anhyd. magnesium sulfate, filtered and concentrated to afford the title compound which was used directly in the next transformation. HPLC (method B) retention time=2.55 min. LCMS (m+1)=405.

Step 2: 4-((3S,4S)-1-(2-cyanoacetyl)-4-methylpyrrolidin-3-ylamino)-6-(4-methoxyphenyl)pyrrolo[1,2-b]pyridazine-3-carboxamide (Example 191)

A mixture of 6-bromo-4-((3S,4S)-1-(2-cyanoacetyl)-4-methylpyrrolidin-3-ylamino)pyrrolo[1,2-b]pyridazine-3-carboxamide (0.020 g, 0.049 mmol), 2-(4-methoxyphenyl)-4,4,5,5-tetramethyl-1,3,2-dioxaborolane (0.015 g, 0.064 mmol), palladium acetate (0.554 mg, 2.468 µmol) and 2-(dicyclohexylphosphino)-2',4',6'-triisopropylbiphenyl (2.353 mg, 4.94 µmol) in dioxane (0.3 mL) was sparged with argon for 3 min. then 2M aq. K$_3$PO$_4$ (0.074 mL, 0.148 mmol) was added and the reaction vial was sealed and heated at 95° C. for 3 h. After cooling to rt, the mixture was extracted with EtOAc (4 mL×3) and the combined organic extracts were dried over anhyd sodium sulfate, filtered and concentrated to afford a yellow solid which was purified via preparative reverse-phase HPLC (method A) to afford 8 mg (27%) of the TFA salt of the title compound as a tan solid. HPLC (method B) retention time=3.06 min. LCMS (m+1)=433.3. $^1$H NMR (400 MHz, DMSO-d$_6$) δ 11.06 (t, J=7.5 Hz, 1H), 8.23 (s, 1H), 8.17-8.11 (m, 1H), 7.74 (d, J=8.8 Hz, 1H), 7.22 (s, 1H), 6.97 (d, J=8.4 Hz, 1H), 5.09-4.82 (m, 1H), 4.06-3.86 (m, 2H), 3.79 (s, 2H), 3.65-3.46 (m, 1H), 3.27-3.05 (m, 1H), 1.10 (t, J=7.6 Hz, 3H).

Example 192

4-((3S,4S)-1-(1-cyanocyclopropanecarbonyl)-4-methylpyrrolidin-3-ylamino)-6-(6-(dimethylcarbamoyl)pyridin-3-yl)pyrrolo[1,2-b]pyridazine-3-carboxamide

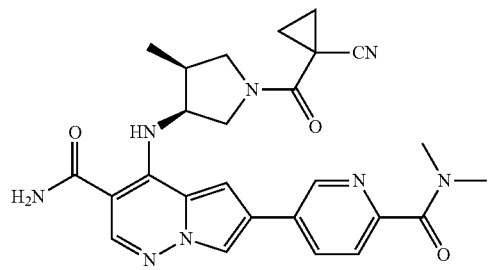 [SMILES: C[C@H]1CN(C(=O)C2(C#N)CC2)C[C@H]1Nc1c(C(N)=O)cnn2cc(-c3ccc(C(=O)N(C)C)nc3)cc12]

Step 1: tert-butyl 5-(4,4,5,5-tetramethyl-1,3,2-dioxaborolan-2-yl)picolinate

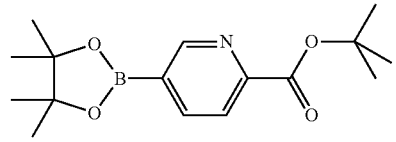 [SMILES: CC(C)(C)OC(=O)c1ccc(B2OC(C)(C)C(C)(C)O2)cn1]

A reaction vial was charged with tert-butyl 5-bromopicolinate (0.50 g, 1.937 mmol), potassium acetate (0.380 g, 3.87 mmol) and 4,4,4',4',5,5,5',5'-octamethyl-2,2'-bi(1,3,2-dioxaborolane) (0.590 g, 2.325 mmol) in dioxane (3.69 mL) and DMSO (0.184 mL). The resulting mixture was sparged with argon for ~5 min. then PdCl$_2$(dppf)-CH$_2$Cl$_2$ adduct (0.079 g, 0.097 mmol) was added and the resulting mixture was heated at 90° C. for 3 h. After cooling to rt, the mixture was partitioned between EtOAc (300 mL) and water (80 mL) and the layers were separated. The organic portion was washed with water (100 mL×2), brine, then dried over MgSO4, filtered and concentrated to afford dark oil as the crude product mixture. This material was purified via ISCO column chromatography (Hex/EtOAc; 24 g silica column) to afford after isoaltion and concentration of the desired fractions 0.60 g (~quant.) of a near white solid as the title compound. HPLC (method B) retention time=2.07 min. $^1$H NMR (400 MHz, CHLORO- FORM-d) δ 9.05 (s, 1H), 8.17 (dd, J=7.8, 1.7 Hz, 1H), 7.99 (dd, J=7.7, 0.9 Hz, 1H), 1.28 (s, 9H), 1.25 (s, 12H).

Step 2: 6-tert-butyl 5-(3-carbamoyl-4-((3S,4S)-1-(1-cyanocyclopropanecarbonyl)-4-methylpyrrolidin-3-ylamino)pyrrolo[1,2-b]pyridazin-6-yl)picolinate

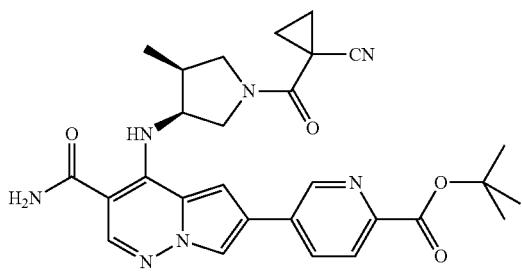 [SMILES: C[C@H]1CN(C(=O)C2(C#N)CC2)C[C@H]1Nc1c(C(N)=O)cnn2cc(-c3ccc(C(=O)OC(C)(C)C)nc3)cc12]

The title compound was prepared from 6-bromo-4-((3S, 4S)-4-methylpyrrolidin-3-ylamino)pyrrolo[1,2-b]pyridazine-3-carboxamide from Step 1 of Example 158 using the methods previously described in Step 1 of Example 191 by replacing cyanoacetic acid with cyclopropylcyanoacetic acid and in Step 2 of Example 191 and by replacing 2-(4-methoxyphenyl)-4,4,5,5-tetramethyl-1,3,2-dioxaborolane with tert-butyl 5-(4,4,5,5-tetramethyl-1,3,2-dioxaborolan-2-yl)picolinate. HPLC (method B) retention time=3.39 min. LCMS (m+1)=530.

Step 3: 5-(3-carbamoyl-4-((3S,4S)-1-(1-cyanocyclopropanecarbonyl)-4-methylpyrrolidin-3-ylamino)pyrrolo[1,2-b]pyridazin-6-yl)picolinic acid

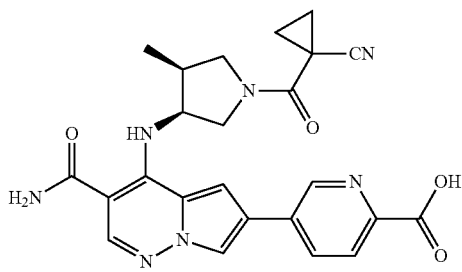 [SMILES: C[C@H]1CN(C(=O)C2(C#N)CC2)C[C@H]1Nc1c(C(N)=O)cnn2cc(-c3ccc(C(=O)O)nc3)cc12]

A solution of 6-tert-butyl 5-(3-carbamoyl-4-((3S,4S)-1-(1-cyanocyclopropanecarbonyl)-4-methylpyrrolidin-3-ylamino)pyrrolo[1,2-b]pyridazin-6-yl)picolinate (85 mg, 0.161 mmol) in dichloromethane (0.5 mL) was stirred with TFA (0.618 mL, 8.03 mmol) at rt for 3 h. The resulting mixture was concentrated to remove excess TFA and DCM, co-evaporated with additional dichloromethane (3x) to remove any residual TFA and the resulting residue obtained was triturated with diethyl ether. The solid formed was collected and rinsed with additional diethyl ether and was dried under vacuum to afford 74 mg of the title compound as a dark solid. HPLC (method B) retention time=2.44 min. LCMS (m+1)=474.1.

Step 4: 4-((3S,4S)-1-(1-cyanocyclopropanecarbonyl)-4-methylpyrrolidin-3-ylamino)-6-(6-(dimethylcarbamoyl)pyridin-3-yl)pyrrolo[1,2-b]pyridazine-3-carboxamide (Example 192)

To solution of 5-(3-carbamoyl-4-((3S,4S)-1-(1-cyanocyclopropanecarbonyl)-4-methylpyrrolidin-3-ylamino)pyrrolo[1,2-b]pyridazin-6-yl)picolinic acid (15 mg, 0.026 mmol), DIPEA (0.018 mL, 0.102 mmol) and BOP (16.94 mg, 0.038 mmol) in DMF (0.3 mL) was added a 2 M solution of dimethylamine in THF (0.026 mL, 0.051 mmol) and the resulting mixture was stirred for 1 h. The mixture was concentrated to remove the THF and was purified by preparative LC/MS with the following conditions: column: Waters XBridge C18, 19×200 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-100% B over 15 minutes, then a 7-minute hold at 100% B; Flow: 25 mL/min. Fractions containing the desired product were combined and dried via centrifugal evaporation to afford 7.2 mg of the title compound. LCMS (method H) retention time=1.78 min. (MH+501.2). $^1$H NMR (500 MHz, METHANOL-$d_4$, appeared as rotomers) δ 9.06 (dd, J=7.9, 1.5 Hz, 1H), 8.40-8.29 (m, 2H), 8.22 (dd, J=11.1, 1.7 Hz, 1H), 7.80 (d, J=7.9 Hz, 1H), 7.47-7.34 (m, 1H), 5.28-5.04 (m, 1H), 4.58-4.42 (m, 2H), 4.13-3.87 (m, 2H), 3.64-3.52 (m, 1H), 3.34-3.26 (m, 6H), 3.09-2.89 (m, 1H), 2.01-1.83 (m, 1H), 1.80-1.59 (m, 3H), 1.51-1.35 (m, 3H).

Example 193

4-((3S,4S)-4-methyl-1-(methylsulfonyl)pyrrolidin-3-ylamino)-6-(6-(methylcarbamoyl)pyridin-3-yl)pyrrolo[1,2-b]pyridazine-3-carboxamide

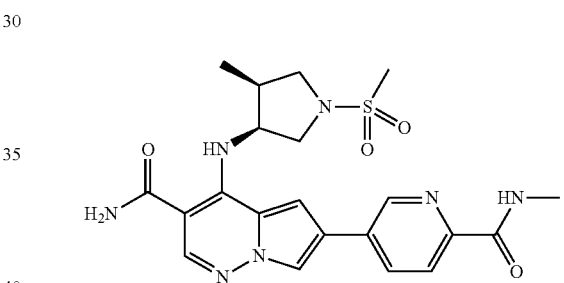

Step 1: 6-bromo-4-((3S,4S)-4-methyl-1-(methylsulfonyl)pyrrolidin-3-ylamino)pyrrolo[1,2-b]pyridazine-3-carboxamide

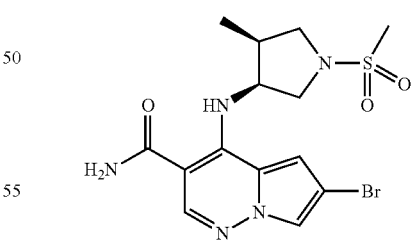

To a slurry of 6-bromo-4-((3S,4S)-4-methylpyrrolidin-3-ylamino)pyrrolo[1,2-b]pyridazine-3-carboxamide hydroiodide salt from Step 1 of Example 158 (500 mg, 1.073 mmol) and DIPEA (0.562 mL, 3.22 mmol) in DCM (5 mL) at 0° C. was added a solution of methanesulfonyl chloride (160 mg, 1.395 mmol) in 1 mL of DCM dropwise and the resulting mixture was stirred at rt for 1 h. The reaction was quenched by addition of MeOH (~1 mL) and was then concentrated to afford a solid which was suspended in water, stirred for 30 min. and collected by vacuum filtration and dried under vacuum to afford 380 mg (85%) of the title compound. HPLC (method B) retention time 2.75 min. LCMS (m+1)=416/418 (1:1).

Step 2: 4-((3S,4S)-4-methyl-1-(methylsulfonyl)pyrrolidin-3-ylamino)-6-(6-(methylcarbamoyl)pyridin-3-yl)pyrrolo[1,2-b]pyridazine-3-carboxamide (Example 193)

The title compound was prepared from 6-bromo-4-((3S,4S)-4-methyl-1-(methylsulfonyl)pyrrolidin-3-ylamino)pyrrolo[1,2-b]pyridazine-3-carboxamide using the method previously described in Step 2 of Example 191 and by replacing 2-(4-methoxyphenyl)-4,4,5,5-tetramethyl-1,3,2-dioxaborolane with N-methyl-5-(4,4,5,5-tetramethyl-1,3,2-dioxaborolan-2-yl)picolinamide. LCMS (method H) retention time=1.09 min. (MH+472.2). $^1$H NMR (500 MHz, DMSO-$d_6$, appeared as rotomers) δ 11.19 (d, J=7.9 Hz, 1H), 9.11 (d, J=2.0 Hz, 1H), 8.70 (q, J=4.5 Hz, 1H), 8.51 (d, J=1.5 Hz, 1H), 8.41 (dd, J=8.2, 2.2 Hz, 1H), 8.31 (s, 1H), 8.03 (d, J=8.4 Hz, 1H), 7.87 (br. s., 1H), 7.48 (d, J=1.5 Hz, 1H), 7.23 (br. s., 1H), 5.04-4.92 (m, 1H), 3.86-3.63 (m, 2H), 3.38 (d, J=1.5 Hz, 1H), 3.03 (t, J=9.9 Hz, 1H), 2.89 (s, 3H), 2.84 (d, J=5.0 Hz, 3H), 2.72-2.64 (m, 1H), 1.09 (d, J=6.9 Hz, 3H).

Examples 194-213

According to the procedures described for the preparation of Example 191, Examples 194-207 in the table below were prepared using commercially available acids for similar amide couplings as described in Step 1 of Example 191 and commercially available boronic acids or esters for similar coupling reactions as described in Step 2 of Example 191. Example 208 was prepared using the methods previously described for the preparation of Example 192 by replacing dimethylamine with isopropylamine in Step 4 of Example 192. According to the procedures described for the preparation of Example 193, Examples 209-213 were prepared using the appropriate commercially available boronic acids or esters. Example 211 utilized commerically available N-Boc-pyrazole-4-boronic acid pinacol ester in which the Boc protecting group was removed under the reaction conditions to afford the final compound. Examples 212 and 213 were prepared by replacing methanesulfonyl chloride with ethanesulfonyl chloride and methyl chloroformate respectively using the procedure in Step 1 of Example 193. Examples 194 and 198 were analyzed using HPLC Method B. Examples 195-197 and 199-205 were analyzed using HPLC Method F. Example 206 was analyzed using HPLC Method M. Example 207 was analyzed using LCMS Method H. Examples 208-210, 212 and 213 were analyzed using HPLC Method F. Example 211 was analyzed using HPLC Method B.

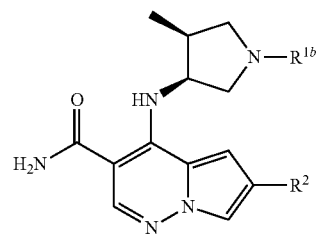

| Ex # | Name | —R$^{1b}$ | —R$^2$ | HPLC Rt (minutes) | LCMS [m/z (M + H)] |
|---|---|---|---|---|---|
| 194 | 4-(((3S,4S)-1-(2-cyanoacetyl)-4-methylpyrrolidin-3-yl)amino)-6-(6-fluoropyridin-3-yl)pyrrolo[1,2-b]pyridazine-3-carboxamide | -C(O)CH₂CN | 6-fluoropyridin-3-yl | 2.64 | 421.3 |
| 195 | 4-(((3S,4S)-1-(2-cyanoacetyl)-4-methylpyrrolidin-3-yl)amino)-6-(6-methylpyridin-3-yl)pyrrolo[1,2-b]pyridazine-3-carboxamide | -C(O)CH₂CN | 6-methylpyridin-3-yl | 0.71 | 418.2 |
| 196 | 4-(((3S,4S)-1-(2-cyanoacetyl)-4-methylpyrrolidin-3-yl)amino)-6-(2-methoxypyridin-4-yl)pyrrolo[1,2-b]pyridazine-3-carboxamide | -C(O)CH₂CN | 2-methoxypyridin-4-yl | 0.92 | 434.2 |
| 197 | 4-(((3S,4S)-1-(2-cyanoacetyl)-4-methylpyrrolidin-3-yl)amino)-6-(6-(trifluoromethyl)pyridin-3-yl)pyrrolo[1,2-b]pyridazine-3-carboxamide | -C(O)CH₂CN | 6-(trifluoromethyl)pyridin-3-yl | 1.44 | 472.2 |

-continued

| Ex # | Name | —R^{1b} | —R^2 | HPLC Rt (minutes) | LCMS [m/z (M + H)] |
|---|---|---|---|---|---|
| 198 | 4-(((3S,4S)-1-(2-cyanoacetyl)-4-methylpyrrolidin-3-yl)amino)-6-(5-fluoropyridin-3-yl)pyrrolo[1,2-b]pyridazine-3-carboxamide | | | 2.58 | 422.2 |
| 199 | 4-(((3S,4S)-1-(2-cyanoacetyl)-4-methylpyrrolidin-3-yl)amino)-6-(6-ethoxypyridin-3-yl)pyrrolo[1,2-b]pyridazine-3-carboxamide | | | 1.27 | 448.2 |
| 200 | 4-(((3S,4S)-1-(2-cyanoacetyl)-4-methylpyrrolidin-3-yl)amino)-6-(6-fluoro-5-methylpyridin-3-yl)pyrrolo[1,2-b]pyridazine-3-carboxamide | | | 1.31 | 436.2 |
| 201 | 4-(((3S,4S)-1-(2-cyanoacetyl)-4-methylpyrrolidin-3-yl)amino)-6-(2-fluoropyridin-4-yl)pyrrolo[1,2-b]pyridazine-3-carboxamide | | | 1.20 | 422.2 |
| 202 | 4-(((3S,4S)-1-(2-cyanoacetyl)-4-methylpyrrolidin-3-yl)amino)-6-(2-methylpyridin-4-yl)pyrrolo[1,2-b]pyridazine-3-carboxamide | | | 0.76 | 418.2 |
| 203 | 4-(((3S,4S)-1-(1-cyanocyclopropanecarbonyl)-4-methylpyrrolidin-3-yl)amino)-6-(2-methoxypyrimidin-5-yl)pyrrolo[1,2-b]pyridazine-3-carboxamide | | | 1.46 | 461.2 |
| 204 | 4-(((3S,4S)-1-(1-cyanocyclopropanecarbonyl)-4-methylpyrrolidin-3-yl)amino)-6-(2-ethoxypyrimidin-5-yl)pyrrolo[1,2-b]pyridazine-3-carboxamide | | | 1.27 | 475.2 |
| 205 | 4-(((3S,4S)-1-(1-cyanocyclopropanecarbonyl)-4-methylpyrrolidin-3-yl)amino)-6-(2-methylpyrimidin-5-yl)pyrrolo[1,2-b]pyridazine-3-carboxamide | | | 1.03 | 445.2 |
| 206 | 4-(((3S,4S)-1-(1-cyanocyclopropanecarbonyl)-4-methylpyrrolidin-3-yl)amino)-6-(2-(difluoromethoxy)pyrimidin-5-yl)pyrrolo[1,2-b]pyridazine-3-carboxamide | | | 1.45 | 497.2 |

-continued

| Ex # | Name | —R¹ᵇ | —R² | HPLC Rt (minutes) | LCMS [m/z (M + H)] |
|---|---|---|---|---|---|
| 207 | 4-(((3S,4S)-1-(1-cyanocyclobutanecarbonyl)-4-methylpyrrolidin-3-yl)amino)-6-(2-methoxypyrimidin-5-yl)pyrrolo[1,2-b]pyridazine-3-carboxamide | | | 1.28 | 475.2 |
| 208 | 4-(((3S,4S)-1-(1-cyanocyclopropanecarbonyl)-4-methylpyrrolidin-3-yl)amino)-6-(6-(isopropylcarbamoyl)pyridin-3-yl)pyrrolo[1,2-b]pyridazine-3-carboxamide | | | 1.09 | 472.2 |
| 209 | 6-(5-fluoro-2-methoxypyridin-4-yl)-4-(((3S,4S)-4-methyl-1-(methylsulfonyl)pyrrolidin-3-yl)amino)pyrrolo[1,2-b]pyridazine-3-carboxamide | | | 1.46 | 463.2 |
| 210 | 6-(5-fluoro-6-methoxypyridin-3-yl)-4-(((3S,4S)-4-methyl-1-(methylsulfonyl)pyrrolidin-3-yl)amino)pyrrolo[1,2-b]pyridazine-3-carboxamide | | | 1.46 | 463.2 |
| 211 | 4-(((3S,4S)-4-methyl-1-(methylsulfonyl)pyrrolidin-3-yl)amino)-6-(1H-pyrazol-4-yl)pyrrolo[1,2-b]pyridazine-3-carboxamide | | | 2.28 | 404.2 |
| 212 | 4-(((3S,4S)-1-(ethylsulfonyl)-4-methylpyrrolidin-3-yl)amino)-6-(6-(methylcarbamoyl)pyridin-3-yl)pyrrolo[1,2-b]pyridazine-3-carboxamide | | | 1.19 | 486.2 |
| 213 | (3S,4S)-methyl 3-((3-carbamoyl-6-(6-(methylcarbamoyl)pyridin-3-yl)pyrrolo[1,2-b]pyridazin-4-yl)amino)-4-methylpyrrolidine-1-carboxylate | | | 1.12 | 452.2 |

Example 214

6-(1-(2-hydroxy-2-methylpropyl)-1H-pyrazol-4-yl)-4-((3S,4S)-4-methyl-1-(methylsulfonyl)pyrrolidin-3-ylamino)pyrrolo[1,2-b]pyridazine-3-carboxamide

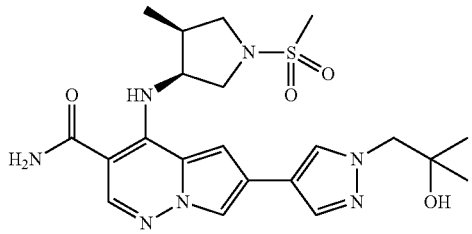 [SMILES: C[C@H]1CN(S(C)(=O)=O)C[C@H]1Nc1c(C(N)=O)cnn2cc(-c3cnn(CC(C)(C)O)c3)cc12]

To slurry of 4-((3S,4S)-4-methyl-1-(methylsulfonyl)pyrrolidin-3-ylamino)-6-(1H-pyrazol-4-yl)pyrrolo[1,2-b]pyridazine-3-carboxamide (Example 211, 40 mg, 0.099 mmol) in acetonitrile (0.3 mL) was added DBU (0.060 mL, 0.397 mmol) and 2,2-dimethyloxirane (25.02 mg, 0.347 mmol) and the resulting mixture was heated at 60° C. for ~16 h. The mixture was cooled, diluted with MeOH, and was purified via preparative reverse-phase HPLC (method B). Fractions which contained the major product were combined and concentrated to give an aqueous solution which was lyophilized to afford a near white solid. This solid was triturated with 1 mL of aq sat. NaHCO3, sonicated, and the resulting solid was collected, rinsed with water and dried on the filter to afford 15 mg (30%) of the title compound as an off-white solid. HPLC (method B) retention time=2.57 min. LCMS (M+1)=476.2. $^1$HNMR (400 MHz, METHANOL-$d_4$) δ 8.18 (s, 1H), 7.99 (s, 1H), 7.88 (d, J=1.5 Hz, 1H), 7.85 (s, 1H), 7.10 (d, J=1.5 Hz, 1H), 4.98-4.93 (m, 1H), 4.15 (s, 2H), 3.85 (dd, J=10.8, 4.4 Hz, 1H), 3.75 (dd, J=9.8, 7.8 Hz, 1H), 3.58 (dd, J=10.9, 1.7 Hz, 1H), 3.25 (t, J=10.1 Hz, 1H), 2.88 (s, 3H), 2.86-2.77 (m, 1H), 1.27-1.22 (m, 9H).

Example 215

4-((3S,4S)-1-(2-cyanoacetyl)-4-ethylpyrrolidin-3-ylamino)-6-(2-methoxypyridin-4-yl)pyrrolo[1,2-b]pyridazine-3-carboxamide

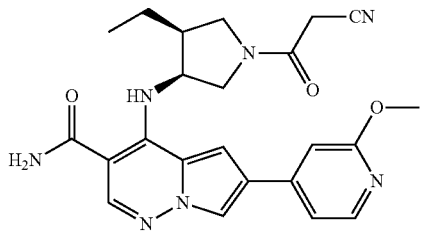 [SMILES: CC[C@H]1CN(C(=O)CC#N)C[C@H]1Nc1c(C(N)=O)cnn2cc(-c3ccnc(OC)c3)cc12]

Step 1: 6-bromo-4-((3S,4S)-1-(2-cyanoacetyl)-4-ethylpyrrolidin-3-ylamino)pyrrolo[1,2-b]pyridazine-3-carboxamide

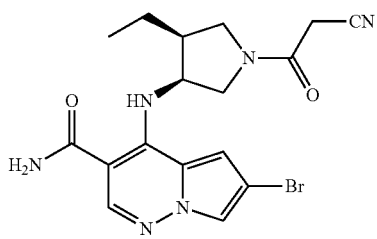 [SMILES: CC[C@H]1CN(C(=O)CC#N)C[C@H]1Nc1c(C(N)=O)cnn2cc(Br)cc12]

Prepared from 6-bromo-4-((3S,4S)-4-ethylpyrrolidin-3-ylamino)pyrrolo[1,2-b]pyridazine-3-carboxamide using the method described in Step 1 of Example 191. HPLC (method B) retention time=2.79 min. LCMS (m+1)=419/421 (1:1).

Step 2: 4-((3S,4S)-1-(2-cyanoacetyl)-4-ethylpyrrolidin-3-ylamino)-6-(2-methoxypyridin-4-yl)pyrrolo[1,2-b]pyridazine-3-carboxamide (Example 215)

Prepared from 6-bromo-4-((3S,4S)-1-(2-cyanoacetyl)-4-ethylpyrrolidin-3-ylamino)pyrrolo[1,2-b]pyridazine-3-carboxamide using the method described in Step 2 of Example 191. LCMS (method H) retention time=1.39 min. LCMS (m+1)=448.2. $^1$H NMR (500 MHz, METHANOL-$d_4$, appeared as rotomers) δ 8.38-8.34 (m, 1H), 8.32-8.27 (m, 1H), 8.25-8.18 (m, 1H), 7.46-7.39 (m, 1H), 7.37-7.33 (m, 1H), 7.29-7.22 (m, 1H), 5.25-5.07 (m, 1H), 4.23-4.16 (m, 2H), 4.15 (s, 3H), 4.10-3.90 (m, 2H), 3.69-3.60 (m, 1H), 2.88-2.75 (m, 1H), 2.74-2.65 (m, 1H), 1.98-1.82 (m, 2H), 1.25-1.16 (m, 3H).

Examples 216-263

According to the procedures described for the preparation of Example 215, Examples 216-232 and Examples 247-263 in the following table were similarly prepared using commercially available acids for amide couplings as described in Step 1 of Example 191 and commercially available boronic acids or esters for similar coupling reactions as described in Step 2 of Example 191. Examples 230, 252 and 253 were prepared as previously described for Example 192. Examples 233-246 were prepared using the appropriate commercially available sulfonyl chlorides using the method previously described for Example 193. Examples 238, 239, 243 and 244 were prepared using a similar method as previously described for Example 214. Example 254 utilized commercially available N-Boc-pyrazole-4-boronic acid pinacol ester in which the Boc protecting group was removed under the reaction conditions. Examples 217 and 250 were analyzed using HPLC Method B. Example 245 was analyzed using HPLC Method M. Examples 216 and 218-244, 246-249 and 251-254, 259-262 were analyzed using HPLC Method F. Examples 255-258, 262 and 263 were analyzed by LCMS conditions H

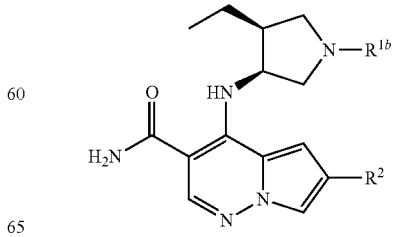

| Ex # | Name | —R$^{1b}$ | —R$^2$ | HPLC Rt (minutes) | LCMS [m/z (M + H)] |
|---|---|---|---|---|---|
| 216 | 4-((3S,4S)-1-(2-cyanoacetyl)-4-ethylpyrrolidin-3-ylamino)-6-(6-methylpyridin-3-yl)pyrrolo[1,2-b]pyridazine-3-carboxamide | 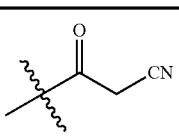 | 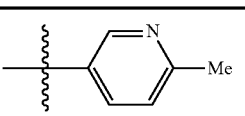 | 0.85 | 432.2 |
| 217 | 4-((3S,4S)-1-(2-cyanoacetyl)-4-ethylpyrrolidin-3-ylamino)-6-(6-methoxypyridin-3-yl)pyrrolo[1,2-b]pyridazine-3-carboxamide | 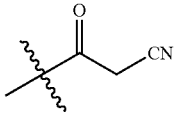 [SMILES: *C(=O)CC#N] | 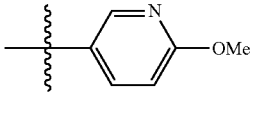 | 2.90 | 448.2 |
| 218 | 4-((3S,4S)-1-(1-cyanocyclopropanecarbonyl)-4-ethylpyrrolidin-3-ylamino)-6-(6-methoxypyridin-3-yl)pyrrolo[1,2-b]pyridazine-3-carboxamide | 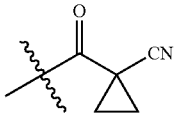 [SMILES: *C(=O)C1(C#N)CC1] | 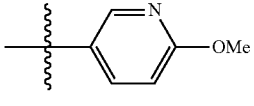 | 1.76 | 474.2 |
| 219 | 4-((3S,4S)-1-(1-cyanocyclopropanecarbonyl)-4-ethylpyrrolidin-3-ylamino)-6-(1-methyl-1H-pyrazol-4-yl)pyrrolo[1,2-b]pyridazine-3-carboxamide | 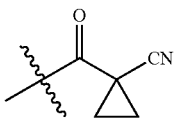 | 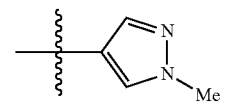 [SMILES: *c1cnn(C)c1] | 1.49 | 447.2 |
| 220 | 4-((3S,4S)-1-(1-cyanocyclopropanecarbonyl)-4-ethylpyrrolidin-3-ylamino)-6-(1,3-dimethyl-1H-pyrazol-4-yl)pyrrolo[1,2-b]pyridazine-3-carboxamide | 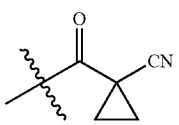 | 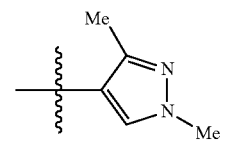 [SMILES: *c1cn(C)nc1C] | 1.14 | 461.2 |
| 221 | 4-((3S,4S)-1-(1-cyanocyclopropanecarbonyl)-4-ethylpyrrolidin-3-ylamino)-6-(6-methylpyridin-3-yl)pyrrolo[1,2-b]pyridazine-3-carboxamide | 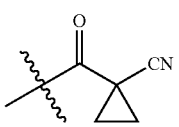 | 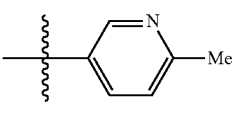 | 0.88 | 458.2 |
| 222 | 4-((3S,4S)-1-(1-cyanocyclopropanecarbonyl)-4-ethylpyrrolidin-3-ylamino)-6-(2-methylpyridin-4-yl)pyrrolo[1,2-b]pyridazine-3-carboxamide | 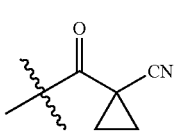 [SMILES: *C(=O)C1(C#N)CC1] | 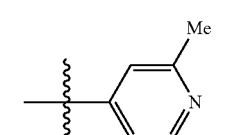 | 0.90 | 458.2 |
| 223 | 4-((3S,4S)-1-(1-cyanocyclopropanecarbonyl)-4-ethylpyrrolidin-3-ylamino)-6-(1-(difluoromethyl)-1H-pyrazol-4-yl)pyrrolo[1,2-b]pyridazine-3-carboxamide | 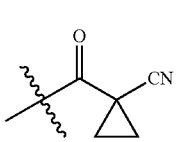 [SMILES: *C(=O)C1(C#N)CC1] | 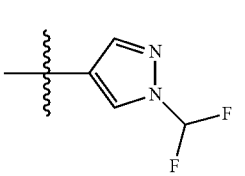 [SMILES: *c1cnn(C(F)F)c1] | 1.35 | 483.2 |
| 224 | 4-((3S,4S)-1-(1-cyanocyclopropanecarbonyl)-4-ethylpyrrolidin-3-ylamino)-6-(6-fluoropyridin-3-yl)pyrrolo[1,2-b]pyridazine-3-carboxamide | 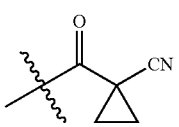 [SMILES: *C(=O)C1(C#N)CC1] | 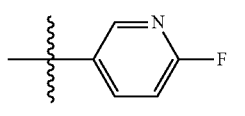 | 1.79 | 462.2 |
| 225 | 4-((3S,4S)-1-(1-cyanocyclopropanecarbonyl)-4-ethylpyrrolidin-3-ylamino)-6-(2-methoxypyrimidin-5-yl)pyrrolo[1,2-b]pyridazine-3-carboxamide | 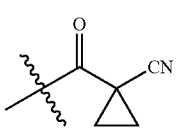 | 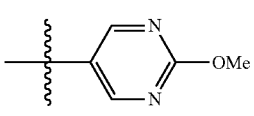 | 1.66 | 475.2 |
| 226 | 4-((3S,4S)-1-(1-cyanocyclopropanecarbonyl)-4-ethylpyrrolidin-3-ylamino)-6-(1-ethyl-1H-pyrazol-4-yl)pyrrolo[1,2-b]pyridazine-3-carboxamide | 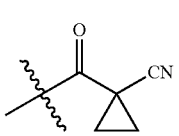 [SMILES: *C(=O)C1(C#N)CC1] | 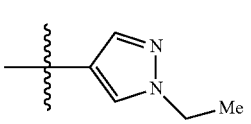 | 1.66 | 461.2 |

-continued

| Ex # | Name | —R$^{1b}$ | —R$^2$ | HPLC Rt (minutes) | LCMS [m/z (M + H)] |
|---|---|---|---|---|---|
| 227 | 4-((3S,4S)-1-(1-cyanocyclopropanecarbonyl)-4-ethylpyrrolidin-3-ylamino)-6-(4-(methylcarbamoyl)phenyl)pyrrolo[1,2-b]pyridazine-3-carboxamide | 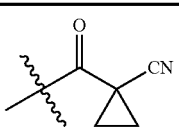 | 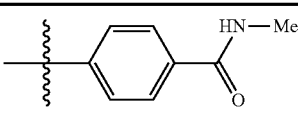 | 1.62 | 500.1 |
| 228 | 4-((3S,4S)-1-(1-cyanocyclopropanecarbonyl)-4-ethylpyrrolidin-3-ylamino)-6-(6-(methylcarbamoyl)pyridin-3-yl)pyrrolo[1,2-b]pyridazine-3-carboxamide | 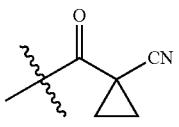 [SMILES: *C(=O)C1(C#N)CC1] | 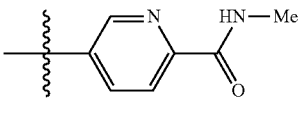 [SMILES: *c1ccc(C(=O)NC)nc1] | 1.83 | 501.2 |
| 229 | 4-((3S,4S)-1-(1-cyanocyclopropanecarbonyl)-4-ethylpyrrolidin-3-ylamino)-6-(2-methylpyrimidin-5-yl)pyrrolo[1,2-b]pyridazine-3-carboxamide | 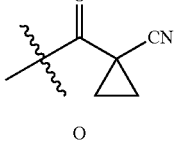 | 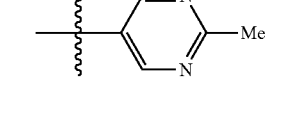 | 1.13 | 459.2 |
| 230 | 4-((3S,4S)-1-(1-cyanocyclopropanecarbonyl)-4-ethylpyrrolidin-3-ylamino)-6-(6-(isopropylcarbamoyl)pyridin-3-yl)pyrrolo[1,2-b]pyridazine-3-carboxamide | 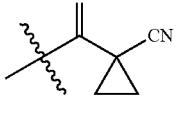 | 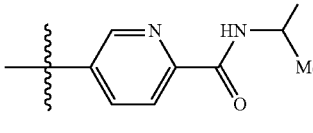 | 1.50 | 511.2 |
| 231 | 4-((3S,4S)-1-(1-cyanocyclopropanecarbonyl)-4-ethylpyrrolidin-3-ylamino)-6-(6-(trifluoromethyl)pyridin-3-yl)pyrrolo[1,2-b]pyridazine-3-carboxamide | 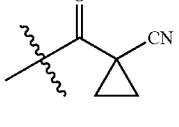 | 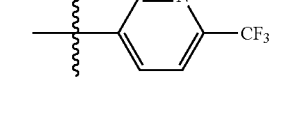 | 1.54 | 511.2 |
| 232 | 4-((3S,4S)-1-(1-cyanocyclopropanecarbonyl)-4-ethylpyrrolidin-3-ylamino)-6-(2-methoxypyridin-4-yl)pyrrolo[1,2-b]pyridazine-3-carboxamide | 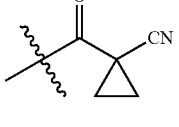 | 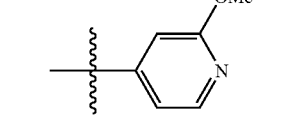 | 1.71 | 512.2 |
| 233 | 4-((3S,4S)-4-ethyl-1-(methylsulfonyl)pyrrolidin-3-ylamino)-6-(1-methyl-1H-pyrazol-5-yl)pyrrolo[1,2-b]pyridazine-3-carboxamide | 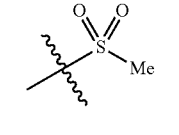 | 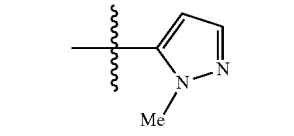 | 1.19 | 432.2 |
| 234 | 4-((3S,4S)-4-ethyl-1-(methylsulfonyl)pyrrolidin-3-ylamino)-6-(1-methyl-1H-pyrazol-4-yl)pyrrolo[1,2-b]pyridazine-3-carboxamide | 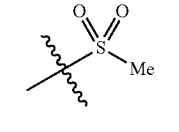 | 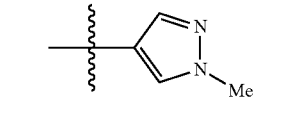 [SMILES: *c1cnn(C)c1] | 1.17 | 432.2 |
| 235 | 6-(1,3-dimethyl-1H-pyrazol-4-yl)-4-((3S,4S)-4-ethyl-1-(methylsulfonyl)pyrrolidin-3-ylamino)pyrrolo[1,2-b]pyridazine-3-carboxamide | 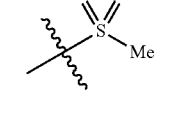 | 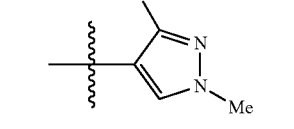 | 1.22 | 446.2 |
| 236 | 6-(1,5-dimethyl-1H-pyrazol-4-yl)-4-((3S,4S)-4-ethyl-1-(methylsulfonyl)pyrrolidin-3-ylamino)pyrrolo[1,2-b]pyridazine-3-carboxamide | 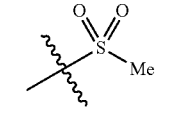 [SMILES: *S(C)(=O)=O] | 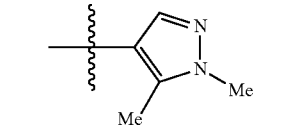 [SMILES: *c1cnn(C)c1C] | 1.24 | 446.2 |
| 237 | 4-((3S,4S)-4-ethyl-1-(methylsulfonyl)pyrrolidin-3-ylamino)-6-(1-ethyl-1H-pyrazol-4-yl)pyrrolo[1,2-b]pyridazine-3-carboxamide | 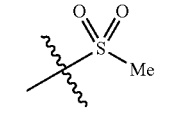 [SMILES: *S(C)(=O)=O] | 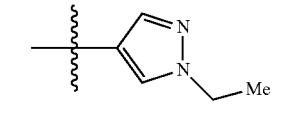 [SMILES: *c1cnn(CC)c1] | 1.34 | 446.2 |

-continued

| Ex # | Name | —R^{1b} | —R^2 | HPLC Rt (minutes) | LCMS [m/z] (M + H] |
|---|---|---|---|---|---|
| 238 | 4-((3S,4S)-4-ethyl-1-(methylsulfonyl)pyrrolidin-3-ylamino)-6-(1-(2-hydroxy-2-methylpropyl)-1H-pyrazol-4-yl)pyrrolo[1,2-b]pyridazine-3-carboxamide | S(O)(O)Me | pyrazole-CH2-C(Me)(Me)OH | 1.26 | 490.2 |
| 239 | 4-((3S,4S)-4-ethyl-1-(methylsulfonyl)pyrrolidin-3-ylamino)-6-(1-isobutyl-1H-pyrazol-4-yl)pyrrolo[1,2-b]pyridazine-3-carboxamide | S(O)(O)Me | pyrazole-CH2-CH(Me)Me | 1.70 | 474.2 |
| 240 | 4-((3S,4S)-4-ethyl-1-(methylsulfonyl)pyrrolidin-3-ylamino)-6-(4-(methylcarbamoyl)phenyl)pyrrolo[1,2-b]pyridazine-3-carboxamide | S(O)(O)Me | 4-(C(O)NHMe)phenyl | 1.36 | 485.2 |
| 241 | 6-(2,4-dimethoxyphenyl)-4-((3S,4S)-4-ethyl-1-(methylsulfonyl)pyrrolidin-3-ylamino)pyrrolo[1,2-b]pyridazine-3-carboxamide | S(O)(O)Me | 2,4-(OMe)2-phenyl | 1.89 | 488.2 |
| 242 | 4-((3S,4S)-4-ethyl-1-(methylsulfonyl)pyrrolidin-3-ylamino)-6-(3-fluoro-4-(methylcarbamoyl)phenyl)pyrrolo[1,2-b]pyridazine-3-carboxamide | S(O)(O)Me | 3-F-4-(C(O)NHMe)phenyl | 1.27 | 503.2 |
| 243 | 4-((3S,4S)-4-ethyl-1-(methylsulfonyl)pyrrolidin-3-ylamino)-6-(1-(2-methoxyethyl)-1H-pyrazol-4-yl)pyrrolo[1,2-b]pyridazine-3-carboxamide | S(O)(O)Me | pyrazole-CH2CH2-OMe | 1.44 | 476.2 |
| 244 | 4-((3S,4S)-4-ethyl-1-(methylsulfonyl)pyrrolidin-3-ylamino)-6-(1-(2-morpholinoethyl)-1H-pyrazol-4-yl)pyrrolo[1,2-b]pyridazine-3-carboxamide | S(O)(O)Me | pyrazole-CH2CH2-morpholine | 0.97 | 531.2 |
| 245 | 4-((3S,4S)-4-ethyl-1-(methylsulfonyl)pyrrolidin-3-ylamino)-6-(6-methoxypyridin-3-yl)pyrrolo[1,2-b]pyridazine-3-carboxamide | S(O)(O)Me | 6-methoxypyridin-3-yl | 1.77 | 459.2 |
| 246 | 4-((3S,4S)-4-ethyl-1-(methylsulfonyl)pyrrolidin-3-ylamino)-6-(6-methylpyridin-3-yl)pyrrolo[1,2-b]pyridazine-3-carboxamide | S(O)(O)Me | 6-methylpyridin-3-yl | 0.92 | 443.2 |
| 247 | 4-((3S,4S)-1-(2-cyano-2-methylpropanoyl)-4-ethylpyrrolidin-3-ylamino)-6-(1-methyl-1H-pyrazol-4-yl)pyrrolo[1,2-b]pyridazine-3-carboxamide | C(O)C(Me)(Me)CN | 1-methyl-1H-pyrazol-4-yl | 1.61 | 449.2 |
| 248 | 4-((3S,4S)-1-(2-cyano-2-methylpropanoyl)-4-ethylpyrrolidin-3-ylamino)-6-(1,3-dimethyl-1H-pyrazol-4-yl)pyrrolo[1,2-b]pyridazine-3-carboxamide | C(O)C(Me)(Me)CN | 1,3-dimethyl-1H-pyrazol-4-yl | 1.30 | 463.2 |

-continued

| Ex # | Name | —R$^{1b}$ | —R$^2$ | HPLC Rt (minutes) | LCMS [m/z (M + H)] |
|---|---|---|---|---|---|
| 249 | 4-((3S,4S)-1-(2-cyano-2-methylpropanoyl)-4-ethylpyrrolidin-3-ylamino)-6-(1-ethyl-1H-pyrazol-4-yl)pyrrolo[1,2-b]pyridazine-3-carboxamide | | | 1.40 | 463.2 |
| 250 | 4-((3S,4S)-1-(2-cyano-2-methylpropanoyl)-4-ethylpyrrolidin-3-ylamino)-6-(1-(1,1,1-trideutero)methyl-1H-pyrazol-4-yl)pyrrolo[1,2-b]pyridazine-3-carboxamide | | | 2.84 | 452.3 |
| 251 | 4-((3S,4S)-1-(2-cyano-2-methylpropanoyl)-4-ethylpyrrolidin-3-ylamino)-6-(3-fluoro-4-(methylcarbamoyl)phenyl)pyrrolo[1,2-b]pyridazine-3-carboxamide | | | 1.35 | 520.2 |
| 252 | 4-((3S,4S)-1-(2-cyano-2-methylpropanoyl)-4-ethylpyrrolidin-3-ylamino)-6-(6-(ethylcarbamoyl)pyridin-3-yl)pyrrolo[1,2-b]pyridazine-3-carboxamide | | | 1.43 | 517.3 |
| 253 | 4-((3S,4S)-1-(2-cyano-2-methylpropanoyl)-4-ethylpyrrolidin-3-ylamino)-6-(6-(dimethylcarbamoyl)pyridin-3-yl)pyrrolo[1,2-b]pyridazine-3-carboxamide | | | 1.22 | 517.3 |
| 254 | 4-((3S,4S)-1-(2-cyano-2-methylpropanoyl)-4-ethylpyrrolidin-3-ylamino)-6-(1H-pyrazol-4-yl)pyrrolo[1,2-b]pyridazine-3-carboxamide | | | 1.06 | 435.2 |
| 255 | 4-((3S,4S)-1-(1-cyanocyclobutanecarbonyl)-4-ethylpyrrolidin-3-ylamino)-6-(1-methyl-1H-pyrazol-4-yl)pyrrolo[1,2-b]pyridazine-3-carboxamide | | | 1.25 | 461.2 |
| 256 | 4-((3S,4S)-1-(1-cyanocyclobutanecarbonyl)-4-ethylpyrrolidin-3-ylamino)-6-(3-fluoro-4-(methylcarbamoyl)phenyl)pyrrolo[1,2-b]pyridazine-3-carboxamide | | | 1.38 | 532.2 |
| 257 | 6-(2-chloropyridin-4-yl)-4-((3S,4S)-1-(1-cyanocyclobutanecarbonyl)-4-ethylpyrrolidin-3-ylamino)pyrrolo[1,2-b]pyridazine-3-carboxamide | | | 1.58 | 492.2 |
| 258 | 4-((3S,4S)-1-(3-oxabicyclo[3.1.0]hexane-6-carbonyl)-4-ethylpyrrolidin-3-ylamino)-6-(1-methyl-1H-pyrazol-4-yl)pyrrolo[1,2-b]pyridazine-3-carboxamide | | | 1.09 | 464.3 |

-continued

| Ex # | Name | —R$^{1b}$ | —R$^2$ | HPLC Rt (minutes) | LCMS [m/z (M + H)] |
|---|---|---|---|---|---|
| 259 | 4-((3S,4S)-4-ethyl-1-(2-methylcyclopropanecarbonyl)pyrrolidin-3-ylamino)-6-(1-methyl-1H-pyrazol-4-yl)pyrrolo[1,2-b]pyridazine-3-carboxamide | | | 1.23 | 436.2 |
| 260 | 4-((3S,4S)-1-(2,2-difluoroacetyl)-4-ethylpyrrolidin-3-ylamino)-6-(6-fluoropyridin-3-yl)pyrrolo[1,2-b]pyridazine-3-carboxamide | | | 1.41 | 447.2 |
| 261 | 4-((3S,4S)-1-(2,2-difluoroacetyl)-4-ethylpyrrolidin-3-ylamino)-6-(3-fluoro-4-(methylcarbamoyl)phenyl)pyrrolo[1,2-b]pyridazine-3-carboxamide | | | 1.25 | 503.2 |
| 262 | 4-((3S,4S)-1-(2,2-difluoroacetyl)-4-ethylpyrrolidin-3-ylamino)-6-(6-methylpyridin-3-yl)pyrrolo[1,2-b]pyridazine-3-carboxamide | | | 1.31 | 443.2 |
| 263 | 4-((3S,4S)-1-(2,2-difluoroacetyl)-4-ethylpyrrolidin-3-ylamino)-6-(4-methoxyphenyl)pyrrolo[1,2-b]pyridazine-3-carboxamide | | | 1.63 | 458.2 |

Example 264

4-((3S,4S)-1-(1-cyanocyclopropanecarbonyl)-4-ethylpyrrolidin-3-ylamino)-6-(2-(difluoromethoxy)pyrimidin-5-yl)pyrrolo[1,2-b]pyridazine-3-carboxamide

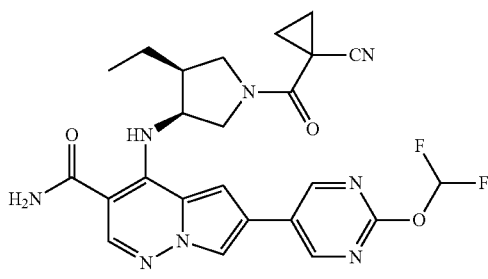 [SMILES: CC[C@H]1CN(C(=O)C2(C#N)CC2)C[C@H]1Nc1c(C(N)=O)cnn2cc(-c3cnc(OC(F)F)nc3)cc12]

Step 1: 5-bromo-2-(difluoromethoxy)pyrimidine

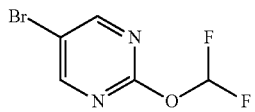

A reaction vial was charged with 5-bromopyrimidin-2-ol (1.50 g, 8.57 mmol), sodium 2-chloro-2,2-difluoroacetate (2.61 g, 17.14 mmol), potassium carbonate (2.1 equiv.) and DMF (10 mL). The resulting mixture was sparged with nitrogen for ~5 min., then heated to 65° C. and stirred overnight (~15 h). After cooling to rt, the resulting mixture was partitioned between EtOAc (300 mL) and water (100 mL). The layers were separated and the organic portion was washed with water (50 mL×2) then 80 mL of hexanes was added and washed again with water (50 mL×2), brine, then dried over sodium sulfate. The resulting solution was filtered and concentrated to remove solvent which afforded a colorless oil as the crude product mixture. This material was purified by ISCO silica gel chromatography (gradient Hex/EtOAc mixtures as eluant; 40 g column) Fractions containing the desired product were collected, combined and concentrated under vacuum to afford 186 mg (10%) of a colorless oil as the title compound. $^1$H NMR (400 MHz, METHANOL-d$_4$) δ 8.95-8.71 (m, 2H), 7.83-7.27 (m, 1H).

Step 2: 2-(difluoromethoxy)-5-(4,4,5,5-tetramethyl-1,3,2-dioxaborolan-2-yl)pyrimidine

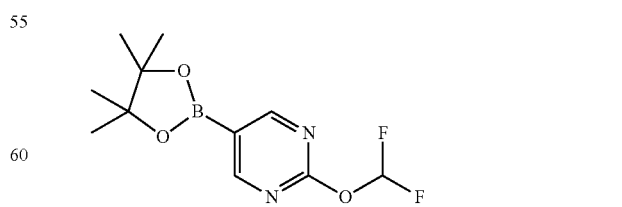

A reaction vial was charged with 5-bromo-2-(difluoromethoxy)pyrimidine (120 mg, 0.533 mmol), potassium acetate (105 mg, 1.067 mmol) and 4,4,4',4',5,5,5',5'-octamethyl-2,2'-bi(1,3,2-dioxaborolane) (163 mg, 0.640 mmol) in dioxane (1.0 mL) and DMSO (0.050 mL). The resulting mixture was sparged with argon for ~5 min. then PdCl2(dppf)-CH2Cl2 adduct (21.78 mg, 0.027 mmol) was added and the mixture was heated at 90° C. for 3 h. After cooling to rt, the reation mixture was partitioned between EtOAc (100 mL) and water (40 mL) and the organic portion was washed with water (2×), brine, dried over MgSO4, filtered and concentrated to afford dark oil as the crude product mixture. This material was purified via ISCO silica gel chromatography (gradient elution of a mixture of Hexanes/EtOAc; 24 g column). Fractions containing the major product were combined and concentrated under vacuum to afford 140 mg (96%) of the title compound as a near colorless oil. HPLC (method B) retention time=1.13 min. LCMS (m+1)=273.

Step 3: 4-((3S,4S)-1-(1-cyanocyclopropanecarbonyl)-4-ethylpyrrolidin-3-ylamino)-6-(2-(difluoromethoxy)pyrimidin-5-yl)pyrrolo[1,2-b]pyridazine-3-carboxamide (Example 264)

Prepared from 6-bromo-4-((3S,4S)-4-ethylpyrrolidin-3-ylamino)pyrrolo[1,2-b]pyridazine-3-carboxamide and 2-(difluoromethoxy)-5-(4,4,5,5-tetramethyl-1,3,2-dioxaborolan-2-yl)pyrimidine using the method described in Step 2 of Example 191. LCMS (method H) retention time=1.54 min. LCMS (m+1)=511.2.

Example 265

4-(((3S,4S)-1-(1-cyanocyclopropanecarbonyl)-4-ethylpyrrolidin-3-yl)amino)-6-(6-((2-methoxyacetamido)methyl)pyridin-3-yl)pyrrolo[1,2-b]pyridazine-3-carboxamide

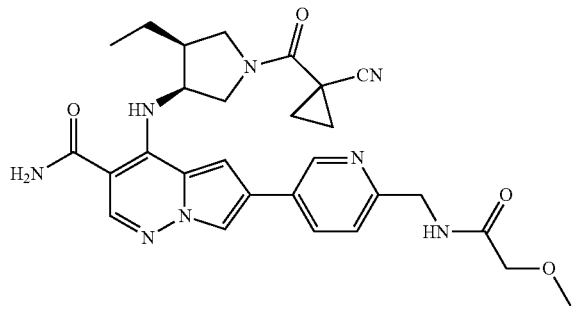 [SMILES: CC[C@H]1CN(C(=O)C2(C#N)CC2)C[C@H]1Nc1c(C(N)=O)cnn2cc(-c3ccc(CNC(=O)COC)nc3)cc12]

Step 1: 2-((5-bromopyridin-2-yl)methyl)isoindoline-1,3-dione.

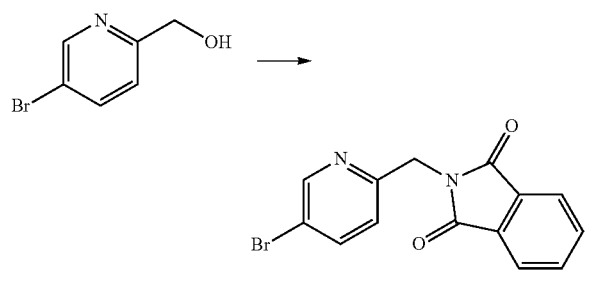

A mixture of (5-bromopyridin-2-yl)methanol (1.2 g, 6.38 mmol), 1,1'-(azodicarbonyl)-dipiperidine (2.093 g, 8.30 mmol), triphenylphosphine (2.176 g, 8.30 mmol) and phthalimide (1.221 g, 8.30 mmol) in THF (60 mL) at rt was stirred over the weekend. The reaction mixture was filtered and the filtrate was concentrated to a yellow solid that was triturated with methanol. Filtration and drying afforded 2-((5-bromopyridin-2-yl)methyl)isoindoline-1,3-dione (1.295 g, 4.08 mmol, 64.0% yield) as a colorless crystalline solid. $^1$H NMR (400 MHz, DMSO-$d_6$) δ 8.57 (d, J=2.0 Hz, 1H), 8.03 (dd, J=8.4, 2.2 Hz, 1H), 7.90 (d, J=9.0 Hz, 4H), 7.44 (d, J=8.4 Hz, 1H), 4.89 (s, 2H). MS (ES+) m/z: 316.95, 318.96 (M+H); LC retention time: 2.297 min (analytical HPLC Method O).

Step 2: (6-((1,3-dioxoisoindolin-2-yl)methyl)pyridin-3-yl)boronic acid

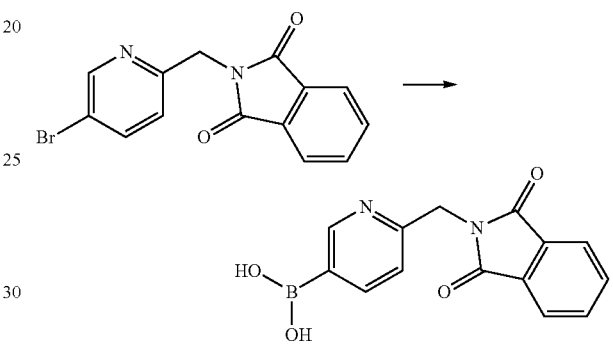

To a mixture of 2-((5-bromopyridin-2-yl)methyl)isoindoline-1,3-dione (317 mg, 1.000 mmol) and 4,4,4',4',5,5,5',5'-octamethyl-2,2'-bi(1,3,2-dioxaborolane) (381 mg, 1.499 mmol) in dioxane (10 mL) at rt under nitrogen was added potassium acetate (294 mg, 3.00 mmol), followed by PdCl$_2$(dppf)-CH$_2$Cl$_2$Adduct (82 mg, 0.100 mmol). At this time, the reaction mixture was heated to 70° C. under nitrogen for 5 hr. After cooling to rt, the solvent was removed on the rotovap and the residue was taken up in EtOAc (30 ml). The mixture was filtered through celite and the filter cake was thoroughly washed with EtOAc. The EtOAc filtrate was concentrated to afford (6-((1,3-dioxoisoindolin-2-yl)methyl)pyridin-3-yl)boronic acid (280 mg, 0.993 mmol, 99% yield) as a brown oil. This material was used as is in the next step. MS (ES+) m/z: 283.1 (M+H); LC retention time: 0.54 min (analytical LCMS Method B).

Step 3: (3S,4S)-benzyl 3-((3-carbamoyl-6-(6-((1,3-dioxoisoindolin-2-yl)methyl)pyridin-3-yl)pyrrolo[1,2-b]pyridazin-4-yl)amino)-4-ethylpyrrolidine-1-carboxylate

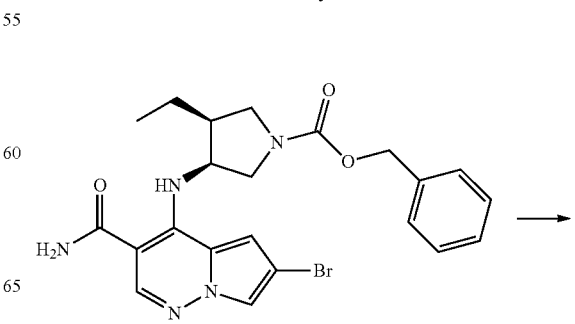

259

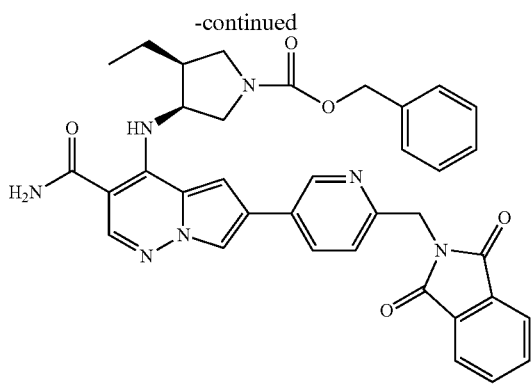

A mixture of 100 mg (0.206 mmol) of (3S,4S)-benzyl 3-((6-bromo-3-carbamoylpyrrolo[1,2-b]pyridazin-4-yl)amino)-4-ethylpyrrolidine-1-carboxylate (prepared by coupling Intermediate 2 and Intermediate 9 using the method described in Step 1 of Example 52), (6-((1,3-dioxoisoindolin-2-yl)methyl)pyridin-3-yl)boronic acid (174 mg, 0.617 mmol), potassium phosphate, tribasic, 2M (0.514 mL, 1.028 mmol) and PdCl$_2$(dppf) (30.1 mg, 0.041 mmol) in DMA (2 mL) was stirred at 90° C. for 1 hr. After cooling to rt, the reaction mixture was filtered through celite and the filtrate was partitioned between EtOAc (30 ml) and water (30 ml). The organic layer was washed with 10% LiCl solution (2×30 ml) and brine (30 ml). After drying (MgSO$_4$) and filtration, the organic layer was concentrated to a brown oil that was chromatographed on a 40 gm ISCO silica gel cartridge, eluting with a 0-100% EtOAc/Hex gradient. The pure fractions were concentrated to afford (3S,4S)-benzyl 3-((3-carbamoyl-6-(6-((1,3-dioxoisoindolin-2-yl)methyl)pyridin-3-yl)pyrrolo[1,2-b]pyridazin-4-yl)amino)-4-ethylpyrrolidine-1-carboxylate (59 mg, 0.092 mmol, 44.6% yield) as a tan solid. The material was used as is in the next step. MS (ES+) m/z: 644.3 (M+H); LC retention time: 2.916 min (analytical HPLC Method O).

Step 4: (3S,4S)-benzyl 3-((6-(6-(aminomethyl)pyridin-3-yl)-3-carbamoylpyrrolo[1,2-b]pyridazin-4-yl)amino)-4-ethylpyrrolidine-1-carboxylate

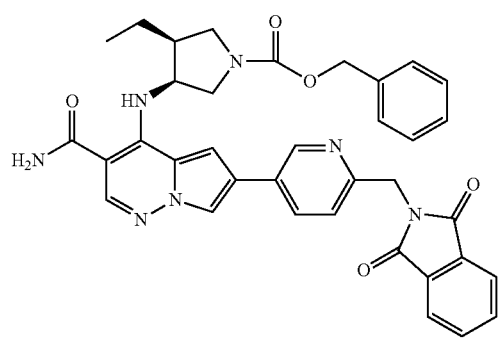

260

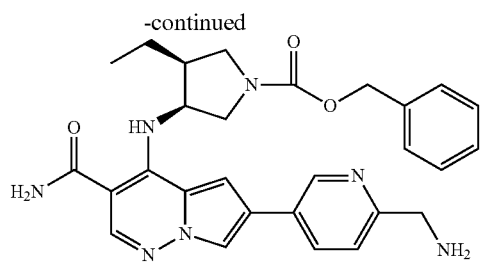

A mixture of (3S,4S)-benzyl 3-((3-carbamoyl-6-(6-((1,3-dioxoisoindolin-2-yl)methyl)pyridin-3-yl)pyrrolo[1,2-b]pyridazin-4-yl)amino)-4-ethylpyrrolidine-1-carboxylate (57 mg, 0.089 mmol) and hydrazine, hydrate (8.29 µl, 0.266 mmol) in EtOH (2 mL) was heated to 70° C. for 10 minutes. THF (0.5 ml) was added to obtain homogeneity and heating was continued for 1.5 hr. Additional hydrazine, hydrate (8.29 µl, 0.266 mmol) (times 4; total of 12 equivalents) was added and heating was continued for 1.5 hr. A precipitation was observed. After cooling to rt, the reaction mixture was filtered and the filtrate was concentrated to a residue that was triturated with EtOAc. Filtration and drying afforded (3S,4S)-benzyl 3-((6-(6-(aminomethyl)pyridin-3-yl)-3-carbamoylpyrrolo[1,2-b]pyridazin-4-yl)amino)-4-ethylpyrrolidine-1-carboxylate (30 mg, 0.058 mmol, 66.0% yield) as a tan solid. The material is contaminated with the hydrazide by-product and will be used as is in the next step. MS (ES+) m/z: 514.4 (M+H); LC retention time: 2.303 min (analytical HPLC Method O).

Step 5: (3S,4S)-benzyl 3-((3-carbamoyl-6-(6-((2-methoxyacetamido)methyl)pyridin-3-yl)pyrrolo[1,2-b]pyridazin-4-yl)amino)-4-ethylpyrrolidine-1-carboxylate

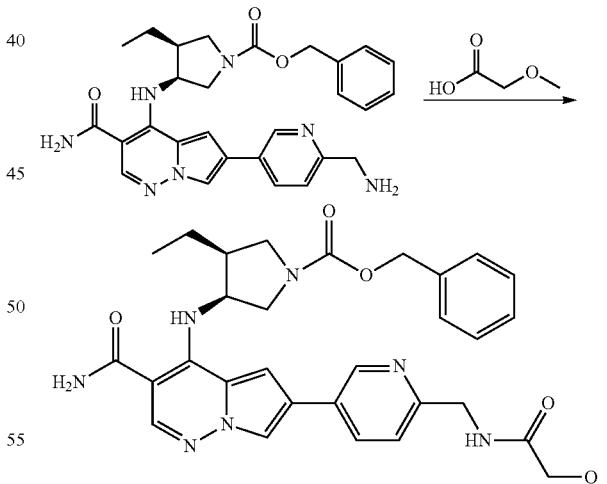

A mixture of (3S,4S)-benzyl 3-((6-(6-(aminomethyl)pyridin-3-yl)-3-carbamoylpyrrolo[1,2-b]pyridazin-4-yl)amino)-4-ethylpyrrolidine-1-carboxylate (29 mg, 0.056 mmol), 2-methoxyacetic acid (9.56 µl, 0.124 mmol), BOP (54.9 mg, 0.124 mmol) and diisopropylethylamine (0.039 mL, 0.226 mmol) in DMF (0.5 mL) was stirred at rt overnight. The reaction mixture was partitioned between EtOAc (20 ml) and 10% LiCl solution (20 ml). The organic layer was washed with 10% LiCl solution (2×20 ml) and brine (20 ml). After drying (MgSO$_4$) and filtration, the organic layer was concentrated to afford (3S,4S)-benzyl 3-((3-carbamoyl-6-(6-((2-methoxyacetamido)methyl)pyridin-3-yl)pyrrolo[1,2-b]pyridazin-4-yl)amino)-4-ethylpyrrolidine-1-carboxylate (22 mg, 0.038 mmol, 66.5% yield) as a yellow semisolid. The material will be used as is in the next step. MS (ES+) m/z: 586.22 (M+H); LC retention time: 2.370 min (analytical HPLC Method O).

Step 6: 4-(((3S,4S)-4-ethylpyrrolidin-3-yl)amino)-6-(6-((2-methoxyacetamido)methyl)pyridin-3-yl)pyrrolo[1,2-b]pyridazine-3-carboxamide, 2 hydroiodide

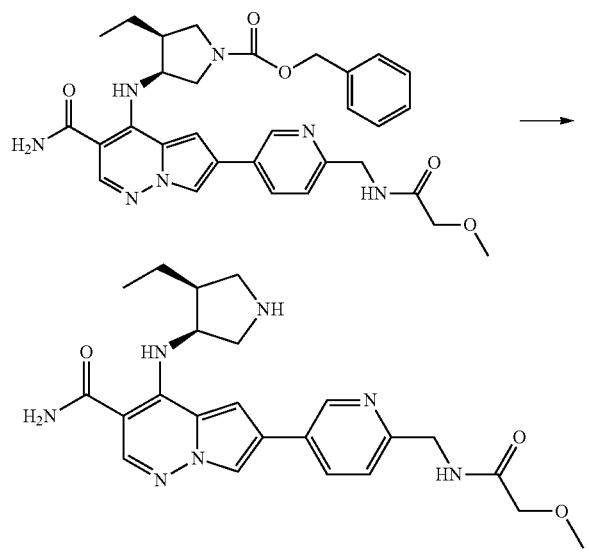

To a suspension of (3S,4S)-benzyl 3-((3-carbamoyl-6-((2-methoxyacetamido)methyl)pyridin-3-yl)pyrrolo[1,2-b]pyridazin-4-yl)amino)-4-ethylpyrrolidine-1-carboxylate (22 mg, 0.038 mmol) in Acetonitrile (1 mL) at 0° C. was added TMS-I (0.013 mL, 0.094 mmol) and after stirring 15 minutes at 0° C., the cooling bath was removed. At 3.5 hr, SM remained by HPLC. The reaction mixture was recooled to 0° C. and additional TMS-I (0.013 mL, 0.094 mmol) was added. After stirring 15 minutes at 0° C., the cooling bath was removed and the reaction mixture was stirred 2 hr at rt. The reaction mixture was recooled to 0° C. and 0.5 ml of MeOH was added. Stirring at 0° C. was continued for 30 minutes. At this time, the volatiles were removed in vacuo to afford crude 4-(((3S,4S)-4-ethylpyrrolidin-3-yl)amino)-6-(6-((2-methoxyacetamido)methyl)pyridin-3-yl)pyrrolo[1,2-b]pyridazine-3-carboxamide, dihydroiodide (26 mg, 0.037 mmol, 98% yield) as a brown solid. The material was used as is in the next step.

Step 7: 4-(((3S,4S)-1-(1-cyanocyclopropanecarbonyl)-4-ethylpyrrolidin-3-yl)amino)-6-(6-((2-methoxyacetamido)methyl)pyridin-3-yl)pyrrolo[1,2-b]pyridazine-3-carboxamide (Example 265).

A mixture of 4-(((3S,4S)-4-ethylpyrrolidin-3-yl)amino)-6-(6-((2-methoxyacetamido)methyl)pyridin-3-yl)pyrrolo[1,2-b]pyridazine-3-carboxamide, 2hydroiodide (26 mg, 0.037 mmol), 1-cyanocyclopropanecarboxylic acid (12.25 mg, 0.110 mmol), BOP-reagent (48.8 mg, 0.110 mmol) and Hunig's Base (0.045 mL, 0.257 mmol) in DMF (1 mL) was stirred at rt overnight. The reaction mixture was purified via preparative LC/MS with the following conditions: Column: Waters XBridge C18, 19×200 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 15 minutes, then a 7-minute hold at 100% B; Flow: 25 mL/min. Fractions containing the desired product were combined and dried via centrifugal evaporation to afford the title compound (6 mg, 0.011 mmol, 30% yield). $^1$H NMR (500 MHz, METHANOL-d$_4$) δ 8.78 (dd, J=11.9, 2.0 Hz, 1H), 8.19-8.10 (m, 1H), 8.07-7.90 (m, 2H), 7.38 (dd, J=8.2, 3.7 Hz, 1H), 7.20-7.06 (m, 1H), 5.05 (t, J=4.2 Hz, 0.5H), 4.91 (t, J=4.5 Hz, 0.5H), 4.57 (s, 2H), 4.37-4.25 (m, 1.5H), 4.18 (d, J=11.4 Hz, 0.5H), 3.97 (s, 2H), 3.94-3.75 (m, 1.5H), 3.49-3.37 (m, 3.5H), 2.69-2.59 (m, 0.5H), 2.58-2.46 (m, 0.5H), 1.83-1.32 (m, 6H), 1.08-0.96 (m, 3H) fractional peaks are due to the presence of amide rotamers. MS (ES+) m/z: 545.1 (M+H); LC retention time: 1.15 min (analytical LCMS Method H).

Example 266

4-(((3S,4S)-1-(2-cyano-2-methylpropanoyl)-4-ethylpyrrolidin-3-yl)amino)-6-(6-((2-methoxyacetamido)methyl)pyridin-3-yl)pyrrolo[1,2-b]pyridazine-3-carboxamide

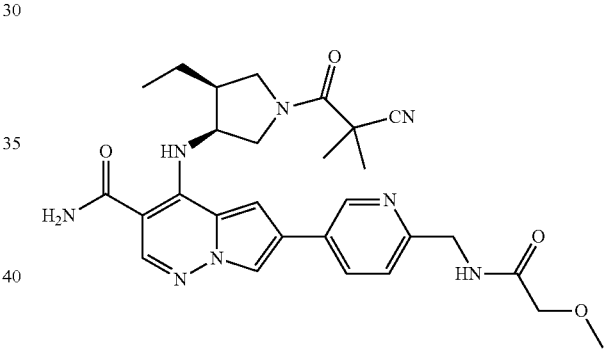

Step 1: (5-bromopyridin-2-yl)methanamine

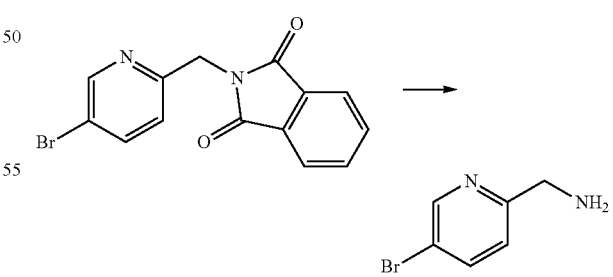

A mixture of 2-((5-bromopyridin-2-yl)methyl)isoindoline-1,3-dione from Step 1 of Example 265 (630 mg, 1.987 mmol) and hydrazine monohydrate (0.484 mL, 9.93 mmol) was heated to 70° C. for 1.5 hr. A thick suspension formed. after cooling to rt, the reaction mixture was diluted with 20 ml of EtOH, filtered and the filter cake was washed with EtOH. The filtrate was concentrated to ⅓ volume and was refiltered.

Concentration of that filtrate afforded (5-bromopyridin-2-yl)methanamine (364 mg, 1.946 mmol, 98% yield) as a colorless semisolid. $^1$H NMR (400 MHz, DMSO-$d_6$) δ 8.58 (d, J=2.2 Hz, 1H), 7.99 (dd, J=8.4, 2.4 Hz, 1H), 7.45 (dd, J=8.4, 0.4 Hz, 1H), 3.77 (s, 2H). MS (ES+) m/z: 187.12, 189.07 (M+H); LC retention time: 0.298 min (analytical HPLC Method O).

Step 2:
N-((5-bromopyridin-2-yl)methyl)-2-methoxyacetamide

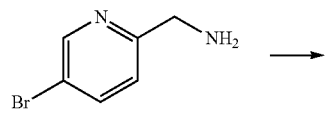

A mixture of (5-bromopyridin-2-yl)methanamine (358 mg, 1.914 mmol), 2-methoxyacetic acid (0.191 mL, 2.488 mmol), BOP-reagent (1101 mg, 2.488 mmol) and diisopropylethylamine (1.003 mL, 5.74 mmol) in DMF (8 mL) was stirred at rt for 2 hr. The reaction mixture was partitioned between EtOAc (60 ml) and saturated NaHCO$_3$ solution (60 ml). The organic layer was washed with 10% LiCl solution (2×50 ml) and brine (50 ml). After drying (MgSO$_4$) and filtration, the organic layer was concentrated to afford an orange oil that was chromatographed on a 24 gm ISCO silica gel cartridge, eluting with a 0-100% EtOAc/Hex gradient. The pure fractions were concentrated to afford N-((5-bromopyridin-2-yl)methyl)-2-methoxyacetamide (337 mg, 1.301 mmol, 68.0% yield) as an orange oil. $^1$H NMR (400 MHz, CHLOROFORM-d) δ 8.62 (d, J=2.2 Hz, 1H), 7.79 (dd, J=8.4, 2.4 Hz, 1H), 7.44 (d, J=4.8 Hz, 1H), 7.20 (d, J=8.4 Hz, 1H), 4.56 (d, J=5.5 Hz, 2H), 3.97 (s, 2H), 3.45 (s, 3H). MS (ES+) m/z: 259.0, 261.0 (M+H); LC retention time: 0.907 min (analytical HPLC Method O).

Step 3: (6-((2-methoxyacetamido)methyl)pyridin-3-yl)boronic acid

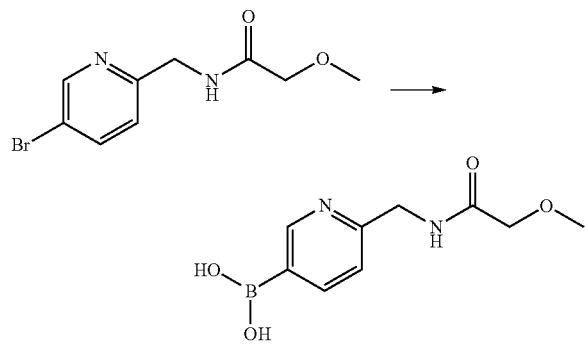

A mixture N-((5-bromopyridin-2-yl)methyl)-2-methoxyacetamide (387 mg, 1.494 mmol), 4,4,4',4',5,5,5',5'-octamethyl-2,2'-bi(1,3,2-dioxaborolane) (493 mg, 1.942 mmol), PdCl$_2$(dppf)-CH$_2$Cl$_2$Adduct (122 mg, 0.149 mmol) and potassium acetate (366 mg, 3.73 mmol) in dioxane (10 mL) was heated to 70° C. for 3 hr. LCMS indicated that the major product was boronic acid. After cooling to rt, the reaction mixture was filtered through celite and the filtrate was concentrated to afford (6-((2-methoxyacetamido)methyl)-pyridin-3-yl)boronic acid (335 mg, 1.495 mmol, 100% yield) as a brown oil. The material was used as is in the next step. MS (ES+) m/z: 225.0 (M+H); LC retention time: 0.38 min (analytical LCMS Method B).

Step 4: (3S,4S)-benzyl 3-((3-carbamoyl-6-(6-((2-methoxyacetamido)methyl)pyridin-3-yl)pyrrolo[1,2-b]pyridazin-4-yl)amino)-4-ethylpyrrolidine-1-carboxylate

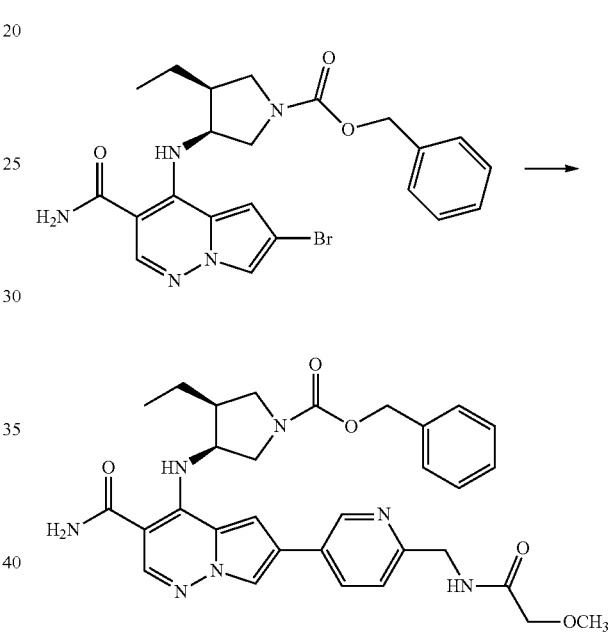

A mixture of 180 mg (0.370 mmol) of (3S,4S)-benzyl 3-((6-bromo-3-carbamoylpyrrolo[1,2-b]pyridazin-4-yl)amino)-4-ethylpyrrolidine-1-carboxylate (prepared by coupling Intermediate 2 and Intermediate 9 using the method described in Step 1 of Example 52), (6-((2-methoxyacetamido)methyl)pyridin-3-yl)boronic acid (332 mg, 1.480 mmol), potassium phosphate, tribasic, 2M (0.925 mL, 1.850 mmol) and PdCl$_2$(dppf) (54.2 mg, 0.074 mmol) in DMA (2.5 mL) was stirred at 90° C. for 45 minutes. After cooling to rt, the reaction mixture was diluted with ~40 ml of EtOAc. The resulting dark mixture was filtered through celite and the filtrate was washed with water (40 ml), 10% LiCl solution (2×40 ml) and brine (40 ml). After drying (MgSO$_4$) and filtration, the organic layer was concentrated to a brown oil that was chromatographed on a 4 gm ISCO silica gel cartridge, eluting with a 0-100% EtOAc/Hex gradient, followed by a 0-10% MeOH/CH$_2$Cl$_2$ gradient. The pure fractions were concentrated to afford a brown oil that was triturated with ethyl ether. Filtration and drying afforded (3S,4S)-benzyl 3-((3-carbamoyl-6-(6-((2-methoxyacetamido)methyl)pyridin-3-yl)pyrrolo[1,2-b]pyridazin-4-yl)amino)-4-ethylpyrrolidine-1-carboxylate (203 mg, 0.347 mmol, 94% yield) as a tan solid. The material will be used as is in the next step. MS (ES+) m/z: 586.3 (M+H); LC retention time: 2.388 min (analytical HPLC Method O).

Step 5: 4-(((3S,4S)-4-ethylpyrrolidin-3-yl)amino)-6-(6-((2-methoxyacetamido)methyl)pyridin-3-yl)pyrrolo[1,2-b]pyridazine-3-carboxamide, 2hydroiodide

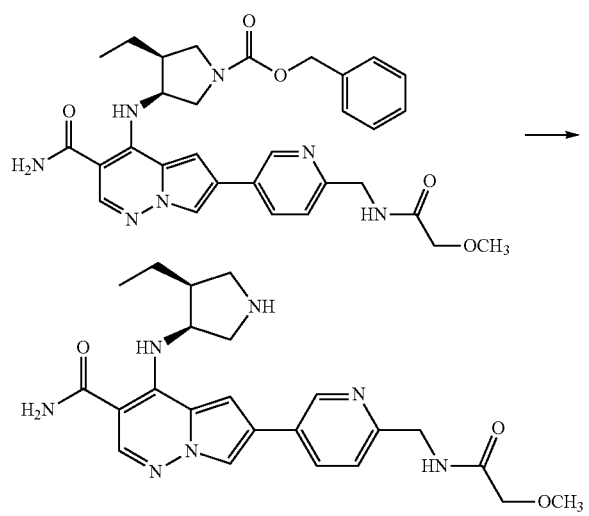

To a suspension of (3S,4S)-benzyl 3-((3-carbamoyl-6-(6-((2-methoxyacetamido)methyl)pyridin-3-yl)pyrrolo[1,2-b]pyridazin-4-yl)amino)-4-ethylpyrrolidine-1-carboxylate (203 mg, 0.347 mmol) in acetonitrile (8 mL) at 0° C. was added TMS-I (0.189 mL, 1.386 mmol) and after stirring 15 minutes at 0° C., the cooling bath was removed. After stirring 4 hr at rt, the reaction mixture was re-cooled to 0° C. and 2 ml of MeOH were added. The mixture was allowed to warm to rt with stirring over 2 hr. At this time, the volatiles were removed in vacuo and the residue was triturated with ethyl ether. Filtration afforded a dark brown solid. Attempts to triturate with EtOAc were unsuccessful, so the mother liquor from the EtOAc trituration was recombined with the filter cake. The material was taken up in MeOH and was filtered. The filtrate was concentrated and was triturated with DCM. Filtration and drying afforded 4-(((3S,4S)-4-ethylpyrrolidin-3-yl)amino)-6-(6-((2-methoxyacetamido)methyl)pyridin-3-yl)pyrrolo[1,2-b]pyridazine-3-carboxamide, 2hydroiodide (277 mg, 0.392 mmol, 113% yield) as a dark brown solid. The material will be used as is in the next step. MS (ES+) m/z: 452.4 (M+H); LC retention time: 1.453 min (analytical HPLC Method O).

Step 6: 4-(((3S,4S)-1-(2-cyano-2-methylpropanoyl)-4-ethylpyrrolidin-3-yl)amino)-6-(6-((2-methoxyacetamido)methyl)pyridin-3-yl)pyrrolo[1,2-b]pyridazine-3-carboxamide (Example 266).

A mixture of 4-(((3S,4S)-4-ethylpyrrolidin-3-yl)amino)-6-(6-((2-methoxyacetamido)methyl)pyridin-3-yl)pyrrolo[1,2-b]pyridazine-3-carboxamide, 2hydroiodide (30 mg, 0.042 mmol), 2-cyano-2-methylpropanoic acid (14.39 mg, 0.127 mmol), BOP (56.3 mg, 0.127 mmol) and Hunig's Base (0.052 mL, 0.297 mmol) in DMF (0.25 mL) was stirred at rt for 2 hr. The reaction mixture was purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 15 minutes, then a 5-minute hold at 100% B; Flow: 20 mL/min. Fractions containing the desired product were combined and dried via centrifugal evaporation to afford the title compound (6 mg, 0.011 mmol, 26% yield). $^1$H NMR (500 MHz, METHANOL-$d_4$) δ 8.79 (dd, J=9.4, 2.0 Hz, 1H), 8.14 (d, J=5.0 Hz, 1H), 8.06-7.93 (m, 2H), 7.38 (dd, J=8.2, 3.2 Hz, 1H), 7.20-7.10 (m, 1H), 5.07-4.87 (m, 1H), 4.57 (s, 2H), 4.36-4.14 (m, 2H), 3.97 (s, 2H), 3.95-3.68 (m, 2H), 3.46 (s, 3H), 2.68-2.44 (m, 1H), 1.83-1.39 (m, 8H), 1.07-0.95 (m, 3H). MS (ES+) m/z: 547.1 (M+H); LC retention time: 1.19 min (analytical LCMS Method H).

Example 267

4-(((3S,4S)-1-(1-cyanocyclopropanecarbonyl)-4-methylpyrrolidin-3-yl)amino)-6-(6-((2-methoxyacetamido)methyl)pyridin-3-yl)pyrrolo[1,2-b]pyridazine-3-carboxamide

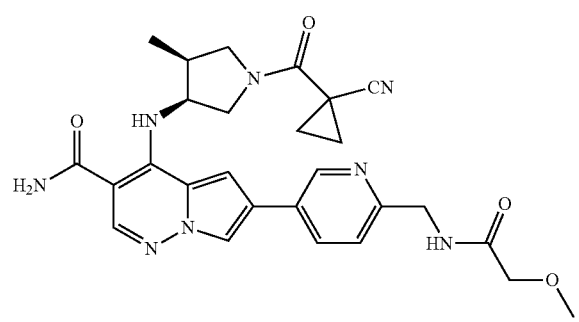 [SMILES: COCC(=O)NCc1ccc(-c2cc3c(N[C@@H]4CN(C(=O)C5(C#N)CC5)C[C@@H]4C)c(C(N)=O)cnn3c2)cn1]

Step 1: (3S,4S)-tert-butyl 3-((6-bromo-3-carbamoylpyrrolo[1,2-b]pyridazin-4-yl)amino)-4-methylpyrrolidine-1-carboxylate

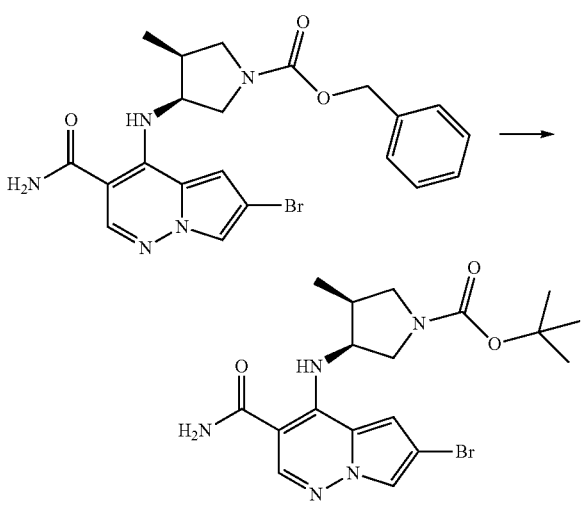

A suspension of 5.8 g (12.28 mmol) of (3S,4S)-benzyl 3-((6-bromo-3-carbamoylpyrrolo[1,2-b]pyridazin-4-yl)

amino)-4-methylpyrrolidine-1-carboxylate (prepared by coupling Intermediate 2 and enantiopure intermediate 5 as described in Step 1 of Example 52) in acetonitrile (75 mL) was cooled to 0° C. in an ice-water bath. Iodotrimethylsilane (6.99 mL, 49.1 mmol) was then added dropwise and the reaction mixture was stirred while the ice bath was allowed to slowly warm to room temperature. After 90 minutes, the deprotection step is complete. The reaction mixture was recooled to 0° C. and was quenched by slowly adding 35 mL MeOH. After stirring 45 minutes to ensure that the quench was complete, the volatiles were removed in vacuo to afford a solid. After drying for 1 hour under high vacuum, di-t-butyldicarbonate (4.02 g, 18.42 mmol) was weighed into the flask containing the solid. DCM (100 mL) and N,N-Di-iso-propylethylamine (10.69 mL, 61.4 mmol) were then added and the solution was stirred at room temperature. Within 15 minutes the reaction is complete and the product began to precipitate out of solution. The reaction mixture was diluted with 150 mL DCM and the resulting suspension was filtered. The filter cake was washed with 1:1 hexanes:ethyl ether and dried to afford 3.44 gm of title compound as a white solid. The DCM mother liquor was washed 2× with water and 1× brine. After drying over sodium sulfate and concentration, the residue was loaded onto a 120 gm ISCO column for purification by flash chromatography, eluting with 0-10% MeOH in DCM. Concentration of the pure fractions afforded an additional 1.13 gm of the titile compound as a light yellow solid. Concentration gave (3S,4S)-tert-butyl 3-((6-bromo-3-carbamoylpyrrolo[1,2-b]pyridazin-4-yl)amino)-4-methylpyrrolidine-1-carboxylate (4.57 gm; 9.90 mmol; 81% yield). MS (ES+) m/z: 438.0, 440.0 (M+H); LC retention time: 3.103 min (analytical HPLC Method O).

Step 2: (3S,4S)-tert-butyl 3-((3-carbamoyl-6-(6-((2-methoxyacetamido)methyl)pyridin-3-yl)pyrrolo[1,2-b]pyridazin-4-yl)amino)-4-methylpyrrolidine-1-carboxylate

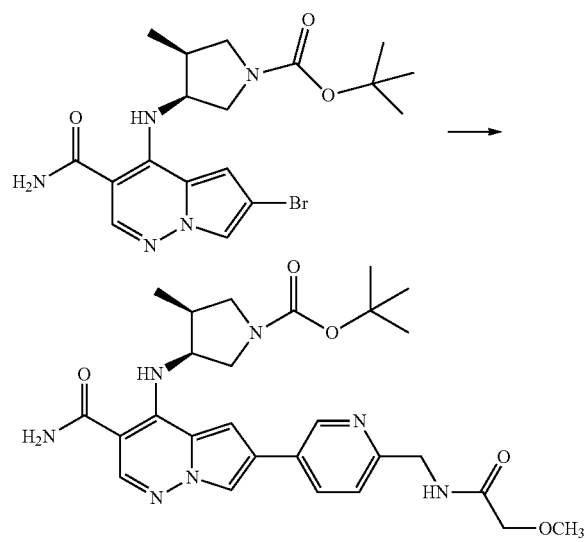

A mixture of (3S,4S)-tert-butyl 3-((6-bromo-3-carbamoylpyrrolo[1,2-b]pyridazin-4-yl)amino)-4-methylpyrrolidine-1-carboxylate (120 mg, 0.274 mmol), (6-((2-methoxyacetamido)methyl)pyridin-3-yl)boronic acid from Step 3 of Example 266 (184 mg, 0.821 mmol), potassium phosphate, tribasic, 2M (0.684 mL, 1.369 mmol) and $PdCl_2$(dppf)-DCM adduct (40.1 mg, 0.055 mmol) in DMA (2.5 mL) was stirred at 90° C. for 45 minutes. After cooling to rt, the reaction mixture was diluted with ~40 ml of EtOAc. The resulting dark mixture was filtered through celite and the filtrate was washed with water (40 ml), 10% LiCl solution (2×40 ml) and brine (40 ml). After drying ($MgSO_4$) and filtration, the organic layer was concentrated to a brown oil that was chromatographed on a chromatographed on a 12 gm ISCO silica gel cartridge, eluting with a 0-9% MeOH/$CH_2Cl_2$ gradient. The pure fractions were concentrated to afford (3S,4S)-tert-butyl 3-((3-carbamoyl-6-(6-((2-methoxyacetamido)methyl)pyridin-3-yl)pynolo[1,2-b]pyridazin-4-yl)amino)-4-methylpyrrolidine-1-carboxylate as a brown solid. The material was used as is in the next step. MS (ES+) m/z: 538.2 (M+H); LC retention time: 2.213 min (analytical HPLC Method O).

Step 2: 6-(6-((2-methoxyacetamido)methyl)pyridin-3-yl)-4-(((3S,4S)-4-methylpyrrolidin-3-yl)amino)pyrrolo[1,2-b]pyridazine-3-carboxamide, 2 HCl

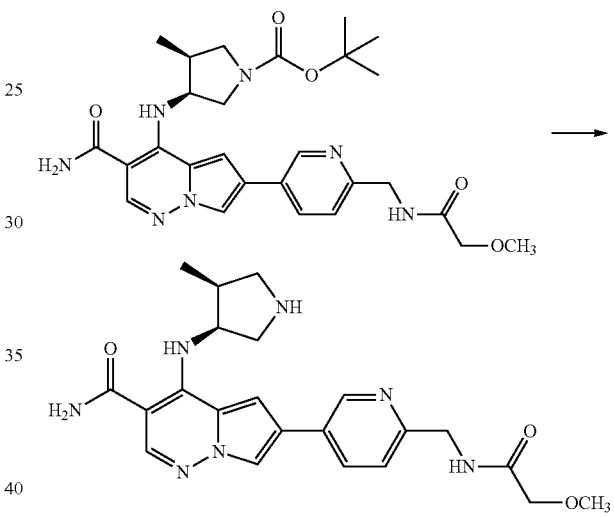

A mixture of (3S,4S)-tert-butyl 3-((3-carbamoyl-6-(6-((2-methoxyacetamido)methyl)pyridin-3-yl)pyrrolo[1,2-b]pyridazin-4-yl)amino)-4-methylpyrrolidine-1-carboxylate (105 mg, 0.195 mmol) and HCl, 4N in dioxane (0.488 mL, 1.953 mmol) in DCM (2 mL) was allowed to stand at rt for 4 hr. The volatiles were removed in vacuo and the residue was triturated with DCM. Filtration and drying afforded 6-(6-((2-methoxyacetamido)methyl)pyridin-3-yl)-4-(((3S,4S)-4-methylpyrrolidin-3-yl)amino)pyrrolo[1,2-b]pyridazine-3-carboxamide, 2 HCl (69 mg, 0.135 mmol, 49% yield over 2 steps) as a brown solid. $^1$H NMR (400 MHz, METHANOL-$d_4$) δ 9.30 (s, 1H), 8.99 (d, J=8.4 Hz, 1H), 8.35 (s, 1H), 8.26 (s, 1H), 7.98 (d, J=8.4 Hz, 1H), 7.62 (s, 1H), 5.21 (d, J=3.3 Hz, 1H), 4.77 (s, 2H), 4.03 (s, 2H), 3.95 (dd, J=12.3, 5.3 Hz, 1H), 3.73 (dd, J=11.9, 7.5 Hz, 1H), 3.48 (s, 4H), 3.17 (t, J=11.0 Hz, 1H), 2.94-2.78 (m, 1H), 1.28 (d, J=6.8 Hz, 3H). MS (ES+) m/z: 438.3 (M+H); LC retention time: 1.383 min (analytical HPLC Method O).

Step 3: 4-(((3S,4S)-1-(1-cyanocyclopropanecarbonyl)-4-methylpyrrolidin-3-yl)amino)-6-(6-((2-methoxyacetamido)methyl)pyridin-3-yl)pyrrolo[1,2-b]pyridazine-3-carboxamide (Example 267).

A mixture of 6-(6-((2-methoxyacetamido)methyl)pyridin-3-yl)-4-(((3S,4S)-4-methylpyrrolidin-3-yl)amino)pyrrolo[1, 2-b]pyridazine-3-carboxamide, 2 HCl (15 mg, 0.029 mmol), 1-cyanocyclopropanecarboxylic acid (9.79 mg, 0.088 mmol), BOP-reagent (39.0 mg, 0.088 mmol) and diisopropylethylamine (0.036 mL, 0.206 mmol) in DMF (0.25 mL) was stirred at rt for 2 hr. The reaction mixture was purified via preparative LC/MS with the following conditions: Column: Waters XBridge C18, 19×150 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 0-100% B over 15 minutes, then a 5-minute hold at 100% B; Flow: 20 mL/min. Fractions containing the desired product were combined and dried via centrifugal evaporation to afford the title compound (9.4 mg, 0.017 mmol, 57.9% yield). MS (ES+) m/z: 531.2 (M+H); LC retention time: 1.06 min (analytical LCMS Method H).

Example 268

(3S,4S)-tert-butyl 3-((3-carbamoyl-6-(6-(isobutyramidomethyl)pyridin-3-yl)pyrrolo[1,2-b]pyridazin-4-yl)amino)-4-ethylpyrrolidine-1-carboxylate

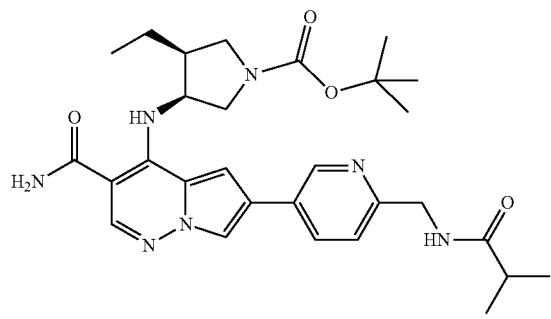 [SMILES: CC[C@H]1CN(C(=O)OC(C)(C)C)C[C@H]1Nc1c(C(N)=O)cnn2cc(-c3ccc(CNC(=O)C(C)C)nc3)cc12]

Step 1:
N-((5-bromopyridin-2-yl)methyl)isobutyramide

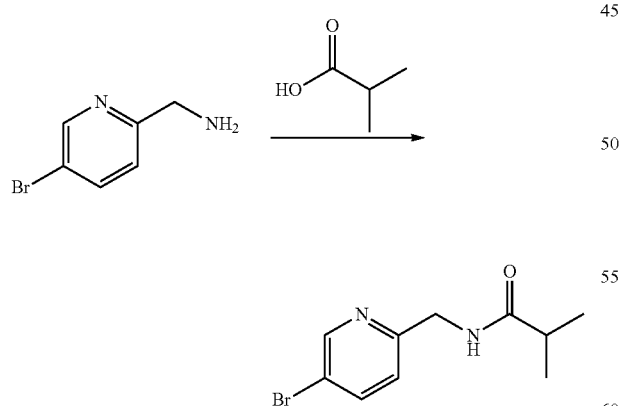

A mixture of (5-bromopyridin-2-yl)methanamine (200 mg, 1.069 mmol), isobutyric acid (0.159 mL, 1.711 mmol), BOP-reagent (757 mg, 1.711 mmol) and diisopropylethylamine (0.747 mL, 4.28 mmol) in DMF (6 mL) was stirred at rt for 2 hr. The reaction mixture was partitioned between EtOAc (60 ml) and saturated NaHCO$_3$ solution (60 ml). The organic layer was washed with 10% LiCl solution (2×50 ml) and brine (50 ml). After drying (MgSO$_4$) and filtration, the organic layer was concentrated to afford an orange oil that was chromatographed on a 24 gm ISCO silica gel cartridge, eluting with a 0-100% EtOAc/Hex gradient. The pure fractions were concentrated to afford N-((5-bromopyridin-2-yl)methyl)isobutyramide (230 mg, 0.894 mmol, 84% yield) as an orange oil. $^1$H NMR (400 MHz, METHANOL-d$_4$) δ 8.57 (d, J=2.2 Hz, 1H), 7.95 (dd, J=8.4, 2.4 Hz, 1H), 7.26 (d, J=8.4 Hz, 1H), 4.42 (s, 2H), 2.53 (dt, J=13.8, 6.8 Hz, 1H), 1.15 (d, J=6.8 Hz, 6H). MS (ES+) m/z: 257.0, 259.0 (M+H); LC retention time: 1.200 min (analytical HPLC Method O).

Step 2:
(6-(isobutyramidomethyl)pyridin-3-yl)boronic acid

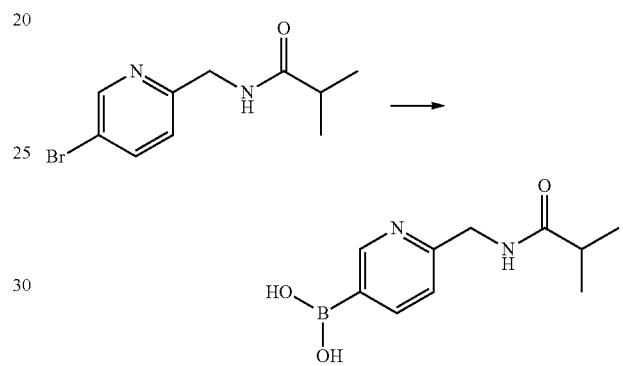

A mixture N-((5-bromopyridin-2-yl)methyl)isobutyramide (228 mg, 0.887 mmol), 4,4,4',4',5,5,5',5'-octamethyl-2,2'-bi(1,3,2-dioxaborolane) (293 mg, 1.153 mmol), PdCl$_2$(dppf)-CH$_2$Cl$_2$Adduct (72.4 mg, 0.089 mmol) and potassium acetate (218 mg, 2.217 mmol) in Dioxane (6 mL) was heated to 70° C. for 3 hr. LCMS indicated that the major product was boronic acid. After cooling to rt, the reaction mixture was filtered through celite and the filtrate was concentrated to afford (6-(isobutyramidomethyl)pyridin-3-yl)boronic acid (195 mg, 0.878 mmol, 99% yield) as a brown oil. The material was used as is in the next step. The yield is assumed to be quantitative. MS (ES+) m/z: 223.1 (M+H); LC retention time: 0.43 min (analytical LCMS Method B).

Step 3: (3 S,4S)-tert-butyl 3-((3-carbamoyl-6-(6-(isobutyramidomethyl)pyridin-3-yl)pynolo[1,2-b]pyridazin-4-yl)amino)-4-ethylpyrrolidine-1-carboxylate (Example 268)

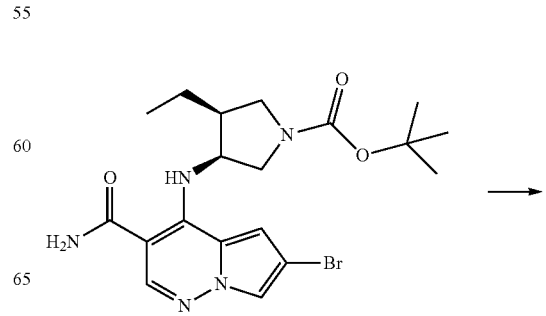

-continued

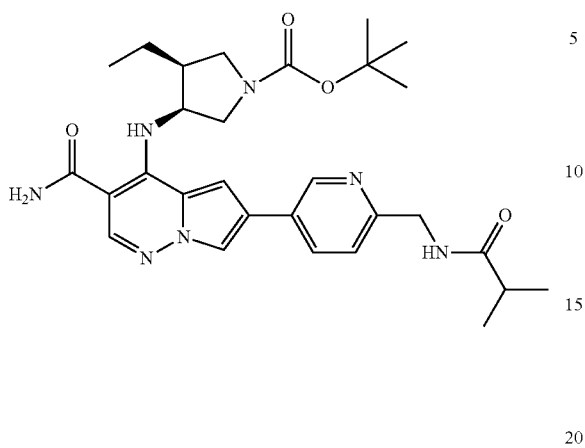

A mixture of 125 mg (0.276 mmol) of (3S,4S)-tert-butyl 3-((6-bromo-3-carbamoylpyrrolo[1,2-b]pyridazin-4-yl)amino)-4-ethylpyrrolidine-1-carboxylate [prepared from Intermediate 2 and Intermediate 9 using the methods described in Step 1 of Example 52 and Step 1 of Example 267], (6-(isobutyramidomethyl)pyridin-3-yl)boronic acid (184 mg, 0.829 mmol), potassium phosphate, tribasic, 2M (0.691 mL, 1.382 mmol) and PdCl$_2$(dppf)-DCM Adduct (40.4 mg, 0.055 mmol) in DMA (2.5 mL) was stirred at 90° C. for 4 hr. After cooling to rt, additional PdCl2(dppf)-DCM Adduct (40.4 mg, 0.055 mmol) was added and heating was continued for 2 hr. The reaction mixture was diluted with ~40 ml of EtOAc. The resulting dark mixture was filtered through celite and the filtrate was washed with water (40 ml), 10% LiCl solution (2×40 ml) and brine (40 ml). After drying (MgSO$_4$) and filtration, the organic layer was concentrated to a brown oil. The oil was chromatographed on a 24 gm ISCO silica gel cartridge, eluting with a 0-10% MeOH/CH$_2$Cl$_2$ gradient. The product containing fractions were concentrated to afford (3S,4S)-tert-butyl 3-((3-carbamoyl-6-(6-(isobutyramidomethyl)pyridin-3-yl)pyrrolo[1,2-b]pyridazin-4-yl)amino)-4-ethylpyrrolidine-1-carboxylate (94 mg, 0.171 mmol, 61.9% yield) as a tan solid. A 12 mg sample was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation to afford (4.3 mg, 0.008 mmol, 35.5% yield based on the 12 mg sample) of the title compound. $^1$H NMR (500 MHz, METHANOL-d$_4$) δ 8.77-8.71 (m, 1H), 8.18-8.10 (m, 1H), 8.02-7.97 (m, 1H), 7.97-7.92 (m, 1H), 7.35 (dd, J=7.7, 5.7 Hz, 1H), 7.07 (d, J=5.0 Hz, 1H), 4.94-4.79 (m, 1H), 4.53-4.44 (m, 2H), 3.82-3.53 (m, 3H), 3.28-3.21 (m, 1H), 2.58-2.37 (m, 2H), 1.73-1.57 (m, 2H), 1.42 (d, J=18.8 Hz, 9H), 1.17 (d, J=6.9 Hz, 6H), 0.97 (q, J=7.1 Hz, 3H). MS (ES+) m/z: 550.2 (M+H); LC retention time: 1.57 min (analytical LCMS Method H).

Example 269

4-(((3S,4S)-1-(1-cyanocyclopropanecarbonyl)-4-methylpyrrolidin-3-yl)amino)-6-(3-methyl-1,2,4-oxadiazol-5-yl)pyrrolo[1,2-b]pyridazine-3-carboxamide

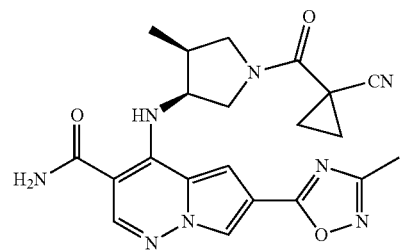 [SMILES: Cc1noc(-c2cc3c(N[C@@H]4CN(C(=O)C5(C#N)CC5)C[C@@H]4C)c(C(N)=O)cnn3c2)n1]

Step 1: ethyl 4-(((3S,4S)-1-((benzyloxy)carbonyl)-4-methylpyrrolidin-3-yl)amino)-3-carbamoylpyrrolo[1,2-b]pyridazine-6-carboxylate

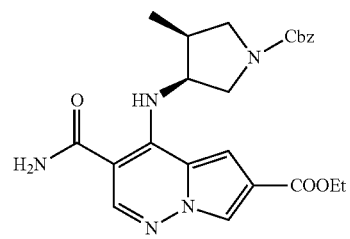

A mixture of ethyl 3-carbamoyl-4-chloropyrrolo[1,2-b]pyridazine-6-carboxylate (Intermediate 1, 375 mg, 1.401 mmol), (3S,4S)-benzyl 3-amino-4-methylpyrrolidine-1-carboxylate (Intermediate 5, 361 mg, 1.541 mmol) and diisopropylethylamine (0.734 mL, 4.20 mmol) in DMA (5 mL) was heated to 100° C. for 3 hr. After cooling, the volatiles were removed in vacuo and the residue was triturated with water. Filtration and drying afforded a tan solid that was rinsed with hexane and redried to afford ethyl 4-(((3S,4S)-1-((benzyloxy)carbonyl)-4-methylpyrrolidin-3-yl)amino)-3-carbamoylpyrrolo[1,2-b]pyridazine-6-carboxylate (650 mg, 1.396 mmol, 100% yield) as a tan solid. $^1$H NMR (400 MHz, DMSO-d$_6$) δ 11.29 (d, J=7.3 Hz, 1H), 8.34 (s, 1H), 8.13 (d, J=2.4 Hz, 1H), 7.50-7.06 (m, 7H), 5.15-4.96 (m, 2H), 4.81 (d, J=4.8 Hz, 1H), 4.35-4.20 (m, 2H), 3.85-3.63 (m, 2H), 3.45 (dd, J=10.9, 3.4 Hz, 1H), 3.09 (dt, J=16.1, 10.2 Hz, 1H), 2.72-2.58 (m, 1H), 1.34-1.27 (m, 3H), 1.07 (d, J=6.8 Hz, 3H). MS (ES+) m/z: 466.3 (M+H); LC retention time: 3.095 min (analytical HPLC Method O).

Step 2: ethyl 4-(((3S,4S)-1-(tert-butoxycarbonyl)-4-methylpyrrolidin-3-yl)amino)-3-carbamoylpyrrolo[1,2-b]pyridazine-6-carboxylate

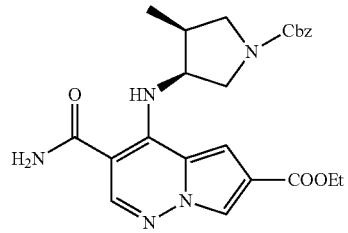 [SMILES: CCOC(=O)c1cc2c(N[C@@H]3CN(C(=O)OCc4ccccc4)C[C@@H]3C)c(C(N)=O)cnn2c1]

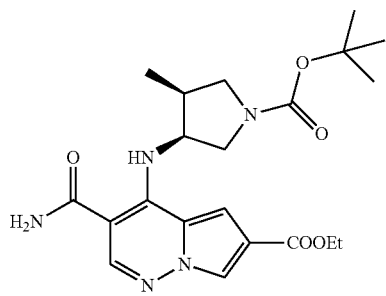

A mixture of ethyl 4-(((3S,4S)-1-((benzyloxy)carbonyl)-4-methylpyrrolidin-3-yl)amino)-3-carbamoylpyrrolo[1,2-b]pyridazine-6-carboxylate (650 mg, 1.396 mmol), di-t-butyl-dicarbonate (0.486 mL, 2.095 mmol) and Pd/C, 10% (74.3 mg, 0.070 mmol) in ethanol (14 mL) was stirred briskly under an atmosphere of hydrogen for 18 hr. Filtration through celite and concentration of the filtrate afforded a yellow oil that was chromatographed on a 40 gm ISCO silica gel cartridge, eluting with a 0-100% EtOAc/Hex gradient. The pure fractions were concentrated to afford ethyl 4-(((3S,4S)-1-(tert-butoxycarbonyl)-4-methylpyrrolidin-3-yl)amino)-3-carbamoylpyrrolo[1,2-b]pyridazine-6-carboxylate (590 mg, 1.367 mmol, 98% yield) as a light yellow foam. MS (ES+) m/z: 332.2 (M+H-Boc); LC retention time: 3.045 min (analytical HPLC Method O).

Step 3: 4-(((3S,4S)-1-(tert-butoxycarbonyl)-4-methylpyrrolidin-3-yl)amino)-3-carbamoylpyrrolo[1,2-b]pyridazine-6-carboxylic acid

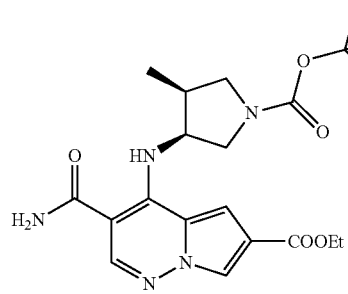

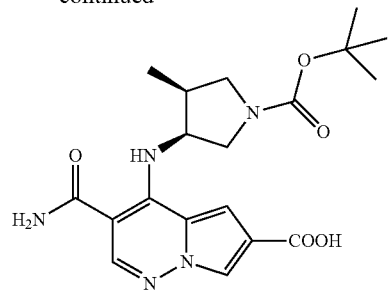

A mixture of ethyl 4-(((3S,4S)-1-(tert-butoxycarbonyl)-4-methylpyrrolidin-3-yl)amino)-3-carbamoylpyrrolo[1,2-b]pyridazine-6-carboxylate (585 mg, 1.356 mmol) and NaOH, 1N (3.39 mL, 3.39 mmol) in THF (14 mL) was stirred at rt for 4 days. At the end of each day, additional NaOH, 1N (3.39 mL, 3.39 mmol) was added, for a total of three additions. The reaction mixture was partitioned between ~70 ml of EtOAc and 50 ml of water. While stirring the biphasic mixture, the pH was adjusted to ~2 with saturated $KHSO_4$ solution. The layers were separated and the aqueous layer was extracted with DCM (50 ml). A precipitate began to form in the combined organic layer. The solid was very fine and the suspension was dried over $Na_2SO_4$. The supernate was decanted off and the sodium sulfate was thoroughly rinsed with hot EtOAc and hot MeOH. The decanted supernates were concentrated to afford 4-(((3S,4S)-1-(tert-butoxycarbonyl)-4-methylpyrrolidin-3-yl)amino)-3-carbamoylpyrrolo[1,2-b]pyridazine-6-carboxylic acid (545 mg, 1.351 mmol, 100% yield) as a tan solid. $^1$H NMR (400 MHz, DMSO-$d_6$) δ 12.51 (br. s., 1H), 11.23 (br. s., 1H), 8.32 (s, 1H), 8.07 (d, J=1.3 Hz, 1H), 7.19 (d, J=1.3 Hz, 1H), 4.76 (d, J=15.0 Hz, 1H), 3.83-3.51 (m, 2H), 3.40-3.34 (m, 1H), 3.09-2.87 (m, 1H), 2.58 (d, J=7.5 Hz, 1H), 1.37 (d, J=13.2 Hz, 9H), 1.13-0.86 (m, 3H). MS (ES+) m/z: 304.2 (M+H-Boc); LC retention time: 2.533 min (analytical HPLC Method O).

Step 4: (Z)—N'-hydroxyacetimidamide

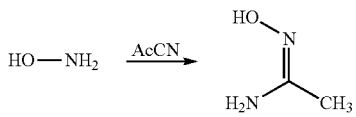

A mixture of hydroxylamine, 50% in water (3.70 g, 56 mmol) and acetonitrile (30 mL) was refluxed for 7.5 hr. After cooling to rt, the reaction mixture was allowed to stand in the refridgerator for 7 days. No crystals precipitated. The solution was placed on the rotovap under vacuum with no warming bath. After ~5 ml of solvent was removed, crystals formed. Filtration, washing with acetonitrile and drying afforded (Z)—N'-hydroxyacetimidamide (1.48 g, 19.98 mmol, 35.7% yield) as a colorless crystalline solid. ¹H NMR (400 MHz, CHLOROFORM-d) δ 4.53 (br. s., 2H), 1.85 (s, 3H).

Step 5: (3S,4S)-tert-butyl 3-((3-carbamoyl-6-(3-methyl-1,2,4-oxadiazol-5-yl)pyrrolo[1,2-b]pyridazin-4-yl)amino)-4-methylpyrrolidine-1-carboxylate

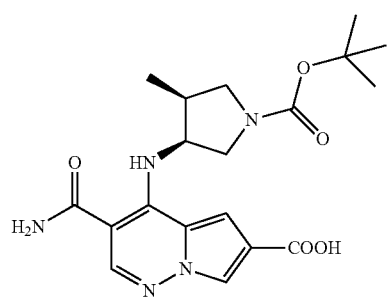

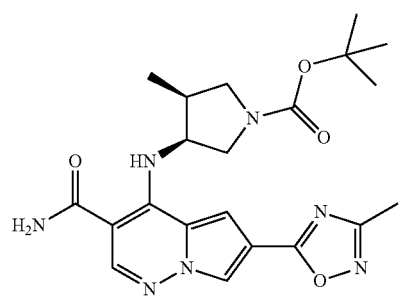

A mixture of 4-(((3S,4S)-1-(tert-butoxycarbonyl)-4-methylpyrrolidin-3-yl)amino)-3-carbamoylpyrrolo[1,2-b]pyridazine-6-carboxylic acid (120 mg, 0.297 mmol), EDC (68.4 mg, 0.357 mmol) and 1-hydroxybenzotriazole (54.7 mg, 0.357 mmol) in DMF (2 mL) was stirred at rt for 30 minutes. (Z)—N'-hydroxyacetimidamide (48.5 mg, 0.654 mmol) was added and the reaction mixture was stirred for 30 min at rt and 3 hr at 125° C. for 5 hr. After cooling to rt, The reaction mixture was partitioned between EtOAc (30 ml) and saturated NaHCO₃ solution (30 ml). The organic layer was washed with saturated NaHCO₃ solution (30 ml), 10% LiCl solution (2×30 ml) and brine (30 ml). After drying (MgSO₄) and filtration, the organic layer was concentrated to a yellow oil that was chromatographed on a 12 gm ISCO silica gel cartridge, eluting with a 0-100% EtOAc/Hex gradient. The pure fractions were concentrated to afford (3S,4S)-tert-butyl 3-((3-carbamoyl-6-(3-methyl-1,2,4-oxadiazol-5-yl)pyrrolo[1,2-b]pyridazin-4-yl)amino)-4-methylpyrrolidine-1-carboxylate (50 mg, 0.110 mmol, 36.9% yield) as an off-white solid. ¹H NMR (400 MHz, METHANOL-d₄) δ 8.27 (s, 2H), 7.48 (s, 1H), 3.88-3.50 (m, 4H), 3.21 (td, J=10.3, 4.4 Hz, 1H), 2.72 (d, J=6.4 Hz, 1H), 2.43 (s, 3H), 1.45 (d, J=13.6 Hz, 9H), 1.18 (d, J=6.8 Hz, 3H). MS (ES+) m/z: 442.2 (M+H); LC retention time: 2.991 min (analytical HPLC Method O).

Step 6: 6-(3-methyl-1,2,4-oxadiazol-5-yl)-4-(3S,4S)-4-methylpyrrolidin-3-yl)amino)pyrrolo[1,2-b]pyridazine-3-carboxamide, HCl

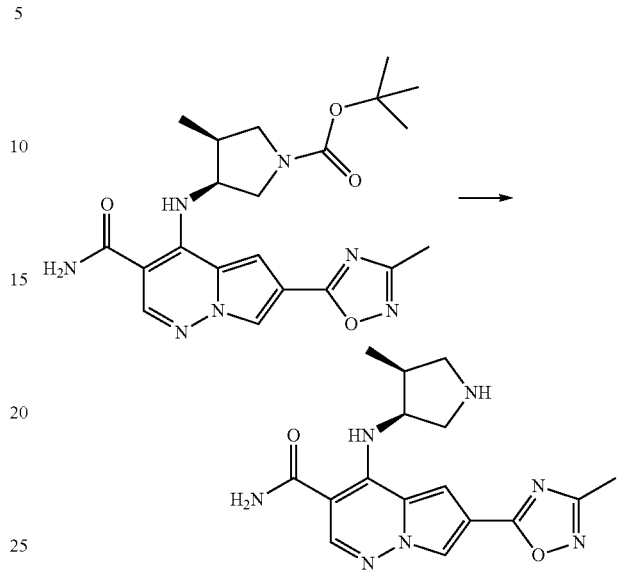

A mixture of (3S,4S)-tert-butyl 3-((3-carbamoyl-6-(3-methyl-1,2,4-oxadiazol-5-yl)pyrrolo[1,2-b]pyridazin-4-yl)amino)-4-methylpyrrolidine-1-carboxylate (46 mg, 0.104 mmol) and HCl, 4N in dioxane (0.521 mL, 2.084 mmol) in DCM (1 mL) was allowed to stand at rt overnight. The volatiles were removed in vacuo to afford 6-(3-methyl-1,2,4-oxadiazol-5-yl)-4-(((3S,4S)-4-methylpyrrolidin-3-yl)amino)pyrrolo[1,2-b]pyridazine-3-carboxamide, HCl (39 mg, 0.103 mmol, 99% yield) as an off-white solid. MS (ES+) m/z: 342.1 (M+H); LC retention time: 1.835 min (analytical HPLC Method O).

Step 7: 4-(((3S,4S)-1-(1-cyanocyclopropanecarbonyl)-4-methylpyrrolidin-3-yl)amino)-6-(3-methyl-1,2,4-oxadiazol-5-yl)pyrrolo[1,2-b]pyridazine-3-carboxamide (Example 269)

A mixture of 6-(3-methyl-1,2,4-oxadiazol-5-yl)-4-(((3S,4S)-4-methylpyrrolidin-3-yl)amino)pyrrolo[1,2-b]pyridazine-3-carboxamide, HCl (12 mg, 0.032 mmol), 1-cyanocyclopropanecarboxylic acid (5.29 mg, 0.048 mmol), BOP-reagent (21.07 mg, 0.048 mmol) and diisopropylethylamine (0.039 mL, 0.222 mmol) in DMF (0.25 mL) was stirred at rt for 2 hr. The reaction mixture was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 5-100% B over 15 minutes, then a 5-minute hold at 100% B; Flow: 20 mL/min. Fractions containing the desired product were combined and dried via centrifugal evaporation to afford the title compound (10.5 mg, 0.024 mmol, 75% yield). ¹H NMR (500 MHz, METHANOL-d₄) δ 8.27-8.19 (m, 2H), 7.50-7.38 (m, 1H), 4.99 (d, J=3.0 Hz, 0.5H), 4.85 (d, J=1.5 Hz, 0.5H), 4.32-4.22 (m, 1.5H), 4.09 (dd, J=11.4, 2.5 Hz, 0.5H), 3.95-3.74 (m, 1.5H), 3.37 (dd, J=12.4, 9.4 Hz, 0.5H), 2.90-2.81 (m, 0.5H), 2.80-2.71 (m, 0.5H), 2.44 (s, 3H), 1.79-1.48 (m, 4H), 1.30-1.17 (m, 3H) fractional peaks are due to the presence of amide rotomers. MS (ES+) m/z: 435.1 (M+H); LC retention time: 1.21 min (analytical LCMS Method H).

Example 270

4-(((3S,4S)-1-(5-cyanothiazol-2-yl)-4-ethylpyrrolidin-3-yl)amino)-6-(6-((2-methoxyacetamido)methyl)pyridin-3-yl)pyrrolo[1,2-b]pyridazine-3-carboxamide

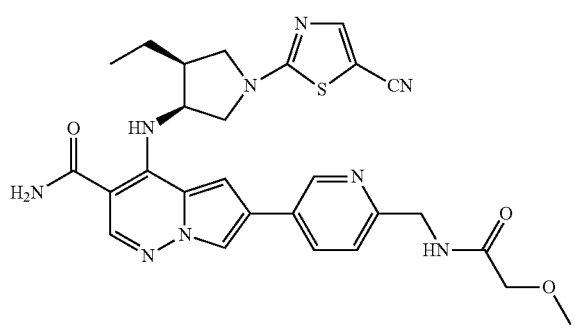 [SMILES: CC[C@H]1CN(c2ncc(C#N)s2)C[C@H]1Nc1c(C(N)=O)cnn2cc(-c3ccc(CNC(=O)COC)nc3)cc12]

A mixture of 4-(((3S,4S)-4-ethylpyrrolidin-3-yl)amino)-6-(6-((2-methoxyacetamido)methyl)pyridin-3-yl)pyrrolo[1,2-b]pyridazine-3-carboxamide, 2hydroiodide from Step 5 of Example 266 (30 mg, 0.042 mmol), 2-chlorothiazole-5-carbonitrile (7.36 mg, 0.051 mmol) and diisopropylethylamine (0.052 mL, 0.297 mmol) in DMA (0.25 mL) was heated to 100° C. for 2 hr. The reaction mixture was purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 15 minutes, then a 5-minute hold at 100% B; Flow: 20 mL/min. Fractions containing the desired product were combined and dried via centrifugal evaporation to afford the title compound (5.3 mg, 0.024 mmol, 22% yield). $^1$H NMR (500 MHz, METHANOL-d$_4$) δ 8.80 (d, J=2.0 Hz, 1H), 8.14 (s, 1H), 8.02 (dd, J=8.2, 2.2 Hz, 1H), 7.98 (d, J=1.5 Hz, 1H), 7.69 (s, 1H), 7.39 (d, J=7.9 Hz, 1H), 7.14 (d, J=1.5 Hz, 1H), 5.07 (t, J=4.5 Hz, 1H), 4.58 (s, 2H), 4.01 (dd, J=10.9, 4.0 Hz, 1H), 3.97 (s, 2H), 3.83 (d, J=7.9 Hz, 2H), 3.46 (s, 4H), 2.79-2.66 (m, 1H), 1.77 (tq, J=14.6, 7.1 Hz, 2H), 1.04 (t, J=7.4 Hz, 3H). MS (ES+) m/z: 560.1 (M+H); LC retention time: 1.31 min (analytical LCMS Method H).

Example 271

4-((3S,4S)-1-(1-cyanocyclopropanecarbonyl)-4-methylpyrrolidin-3-ylamino)-6-(4-methyl-1H-pyrazol-1-yl)pyrrolo[1,2-b]pyridazine-3-carboxamide

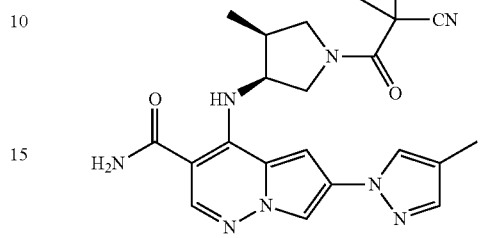

The title compound was prepared from 20 mg (0.046 mmol) of 6-bromo-4-((3S,4S)-1-(1-cyanocyclopropanecarbonyl)-4-methylpyrrolidin-3-ylamino)pyrrolo[1,2-b]pyridazine-3-carboxamide (prepared from the product of Step 1 of Example 158 using the methods previously described in Step 1 of Example 191 by replacing cyanoacetic acid with cyclopropylcyanoacetic acid), potassium carbonate (32.0 mg, 0.232 mmol), 4-methyl-1H-pyrazole (15.2 mg, 0.18 mmol), (1S,2S)—N1,N2-dimethylcyclohexane-1,2-diamine (13.2 mg, 0.09 mmol) and dioxane (0.30 mL). The resulting mixture was sparged with argon for ~5 min. then copper iodide (17.7 mg, 0.09 mmol) was added and the mixture was heated at 100° C. for 3 h. After cooling to rt, the mixture was purified by preparative LC/MS using the following conditions: (column: Waters XBridge C18, 19×250 mm, 5-μm particles; guard column: Waters XBridge C18, 19×10 mm, 5-μm particles; mobile phase A: 5:95 acetonitrile:water with 10-mM ammonium acetate; mobile phase B: 95:5 acetonitrile:water with 10-mM ammonium acetate; gradient: 10-100% B over 25 minutes, then a 5-minute hold at 100% B; Flow: 20 mL/min.). Fractions containing the desired product were combined and dried via centrifugal evaporation to afford 6.8 mg of the title compound. Analytical LCMS (method H) retention time=1.98 min. (MH+ 433.2). $^1$H NMR (500 MHz, METHANOL-d$_4$, appeared as rotomers) δ 8.39-8.32 (m, 1H), 8.14 (s, 1H), 8.07 (dd, J=12.4, 1.5 Hz, 1H), 7.98 (d, J=7.4 Hz, 1H), 7.69-7.64 (m, 1H), 7.34-7.24 (m, 1H), 5.20-5.00 (m, 2H), 4.55-4.41 (m, 3H), 4.13-3.90 (m, 3H), 3.04-2.80 (m, 1H), 2.34 (s, 3H), 1.99-1.65 (m, 4H), 1.49-1.38 (m, 4H).

Example 272

6-(1-ethyl-1H-pyrazol-4-yl)-4-(3S,4S)-4-(fluoromethyl)-1-(methylsulfonyl)pyrrolidin-3-yl)amino)pyrrolo[1,2-b]pyridazine-3-carboxamide

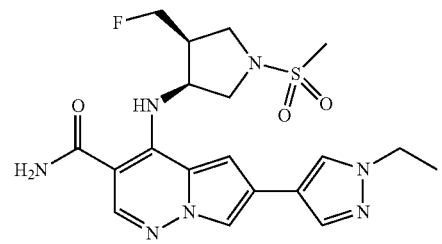 [SMILES: CCn1cc(-c2cc3c(N[C@@H]4CN(S(C)(=O)=O)C[C@@H]4CF)c(C(N)=O)cnn3c2)cn1]

Step 1: (3S,4S)-benzyl 3-((6-bromo-3-carbamoylpyr-rolo[1,2-b]pyridazin-4-yl)amino)-4-(fluoromethyl)pyrrolidine-1-carboxylate

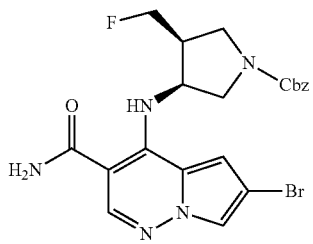 [SMILES: NC(=O)c1cnn2cc(Br)cc2c1N[C@@H]1CN(C(=O)OCc2ccccc2)C[C@@H]1CF]

A solution of 6-bromo-4-chloropyrrolo[1,2-b]pyridazine-3-carboxamide (Intermediate 2, 740 mg, 2.70 mmol), (3S, 4S)-benzyl 3-amino-4-(fluoromethyl)pyrrolidine-1-carboxylate (Intermediate 10, 714 mg, 2.83 mmol) and DIPEA (0.989 mL, 5.66 mmol) in DMF (8 mL) was heated to 80° C. for 16 hrs. The reaction mixture was concentrated and purified on silica gel column with Hexanes/EtOAc (1/1) to give the title compound (1.06 g, 80% yield). $^1$H NMR (500 MHz, DMSO-$d_6$) δ 8.30 (s, 1H), 7.94 (br. s., 1H), 7.42-7.27 (m, 5H), 7.15 (s, 1H), 5.16-4.94 (m, 3H), 4.70-4.54 (m, 2H), 3.90-3.41 (m, 4H), 3.02-2.84 (m, 1H), MS (ES+) m/z: 490.1, 492.1 (M+H); LC retention time: 3.261 min (analytical HPLC Method H).

Step 2: 6-bromo-4-(((3S,4S)-4-(fluoromethyl)pyrro-lidin-3-yl)amino)pyrrolo[1,2-b]pyridazine-3-carboxamide

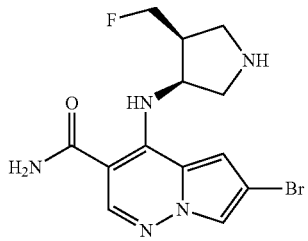 [SMILES: NC(=O)c1cnn2cc(Br)cc2c1N[C@@H]1CNC[C@@H]1CF]

A solution of (3S,4S)-benzyl 3-((6-bromo-3-carbamoylpyrrolo[1,2-b]pyridazin-4-yl)amino)-4-(fluoromethyl)pyrrolidine-1-carboxylate (1.15 g, 2.345 mmol) in Acetonitrile (15 mL) at 0° C. was added TMS-I (1.277 mL, 9.38 mmol) dropwise and the resulting mixture was stirred for 10 min. and then allowed to warm to RT and stir for 1 hr. The reaction was quenched with 1.5 mL of MeOH and stirred for 10 minutes. The solid was collected as a hydroiodide salt of the title compound (1.07 g, 94% yield). MS (ES+) m/z: 356.1, 358.0 (M+H); HPLC: 96.7%, retention time: 1.525 min (analytical HPLC Method H).

Step 3: 6-bromo-4-(((3S,4S)-4-(fluoromethyl)-1-(methylsulfonyl)pyrrolidin-3-yl)amino)pyrrolo[1,2-b]pyridazine-3-carboxamide A solution of 6-bromo-4-(((3S,4S)-4-(fluoromethyl)pyr-rolidin-3-yl)amino) pyrrolo[1,2-b]pyridazine-3-carboxamide hydroiodide salt (894 mg, 2.846 mmol) and Et3N (1.399 mL, 10.04 mmol) in DMF (10 mL) was added METHANESULFONYL CHLORIDE (0.293 mL, 3.76 mmol) and the resulting mixture was stirred at RT for 30 minutes. To the reaction mixture was then added 150 mL of EtOAc and the mixture was washed with 50 mL×2 of 10% LiCl solution, 50 mL of brine and then dried over Na2SO4. Filtration and concentration afforded a crude product which was triturated with MeOH and the resulting solid collected and dried under vacuum to afford the title compound (0.719 g, 90% yield). MS (ES+) m/z: 434.1, 436.1 (M+H); HPLC: 89.6%, retention time: 2.348 min (analytical HPLC Method H).

Step 4: 6-(1-ethyl-1H-pyrazol-4-yl)-4-(((3S,4S)-4-(fluoromethyl)-1-(methylsulfonyl)pyrrolidin-3-yl)amino)pyrrolo[1,2-b]pyridazine-3-carboxamide (Example 272)

A degassed solution of 6-bromo-4-(((3S,4S)-4-(fluoromethyl)-1-(methylsulfonyl)pyrrolidin-3-yl)amino)pyrrolo[1,2-b]pyridazine-3-carboxamide (50 mg, 0.115 mmol), 1-ethyl-4-(4,4,5,5-tetramethyl-1,3,2-dioxaborolan-2-yl)-1H-pyrazole (38.4 mg, 0.173 mmol), 2-(Dicyclohexylphosphino)-2',4',6'-triisopropylbiphenyl (5.49 mg, 0.012 mmol), Pd(OAc)$_2$ (1.292 mg, 5.76 µmol) and 2 M aq. potassium phosphate solution (0.173 mL, 0.345 mmol) in DMF (0.5 mL) was heated to 105° C. for 2 hrs. The crude reaction mixture was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min. Fractions containing the desired product were combined and dried via centrifugal evaporation to give the title compound (25.2 mg, 48% yield). $^1$H NMR (500 MHz, 1:1, Chloroform-$d_3$ & METHANOL-$d_4$) δ 8.14 (s, 1H), 7.87 (s, 1H), 7.79 (d, J=1.5 Hz, 1H), 7.76 (s, 1H), 7.00 (d, J=1.5 Hz, 1H), 5.17-5.10 (m, 1H), 4.71-4.64 (m, 1H), 4.42 (s, 1H), 4.22 (q, J=7.1 Hz, 2H), 3.90-3.74 (m, 2H), 3.59-3.45 (m, 2H), 3.13-3.02 (m, 1H), 2.90 (s, 3H), 1.52 (t, J=7.4 Hz, 3H). MS (ES+) m/z: 450.2 (M+H); HPLC: 99%, retention time: 1.739 min (analytical HPLC Method F).

Examples 274-291

All examples listed in the following table were prepared enantiopure unless otherwise noted. Using the methods described for the preparation of Example 272, Examples 274-278 were prepared from racemic 6-bromo-4-((4-(fluoromethyl)-1-(methylsulfonyl)pyrrolidin-3-yl)amino)pyrrolo[1,2-b]pyridazine-3-carboxamide or enantiopure 6-bromo-4-(((3S,4S)-4-(fluoromethyl)-1-(methylsulfonyl)pyrrolidin-3-yl)amino)pyrrolo[1,2-b]pyridazine-3-carboxamide with appropriate boronic acids or boronic acid esters, which were commercially available. Examples 279 was prepared as similar to Example 192. Examples 280-285 were prepared similar to Example 191. Examples 286-289 were prepared similar to Example 159. Example 290 was prepared similar to Example 266. Example 274-277, 279-281, 283, 284, 286, 287, 290, and 291 were analyzed using HPLC Method F. Example 278, 282, 285, 288 and 289 were analyzed using HPLC Method P.

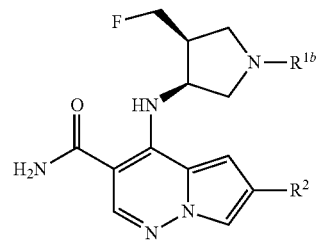

| Ex # | Name | —$R^{1b}$ | —$R^2$ | HPLC Rt (minutes) | LCMS [m/z (M + H)] |
|---|---|---|---|---|---|
| 274 | (+/−)-Cis-4-((-4-(fluoromethyl)-1-(methylsulfonyl)pyrrolidin-3-yl)amino)-6-(2-methoxypyridin-4-yl)pyrrolo[1,2-b]pyridazine-3-carboxamide | S(O)(O)Me | 2-methoxypyridin-4-yl | 1.01 | 463.2 |
| 275 | (+/−)-Cis-4-((-4-(fluoromethyl)-1-(methylsulfonyl)pyrrolidin-3-yl)amino)-6-(6-(trifluoromethyl)pyridin-3-yl)pyrrolo[1,2-b]pyridazine-3-carboxamide | S(O)(O)Me | 6-(trifluoromethyl)pyridin-3-yl | 1.55 | 501.2 |
| 276 | 4-((3S,4S)-4-(fluoromethyl)-1-(methylsulfonyl)pyrrolidin-3-ylamino)-6-(1-methyl-1H-pyrazol-4-yl)pyrrolo[1,2-b]pyridazine-3-carboxamide | S(O)(O)Me | 1-methyl-1H-pyrazol-4-yl | 0.94 | 436.1 |
| 277 | 4-((3S,4S)-4-(fluoromethyl)-1-(methylsulfonyl)pyrrolidin-3-ylamino)-6-(6-fluoropyridin-3-yl)pyrrolo[1,2-b]pyridazine-3-carboxamide | S(O)(O)Me | 6-fluoropyridin-3-yl | 1.25 | 450.9 |
| 278 | 4-((3S,4S)-4-(fluoromethyl)-1-(methylsulfonyl)pyrrolidin-3-ylamino)-6-(2-fluoropyridin-4-yl)pyrrolo[1,2-b]pyridazine-3-carboxamide | S(O)(O)Me | 2-fluoropyridin-4-yl | 1.19 | 450.9 |
| 279 | 4-((3S,4S)-1-(1-cyanocyclopropanecarbonyl)-4-(fluoromethyl)pyrrolidin-3-ylamino)-6-(6-(cyclopropylcarbamoyl)pyridin-3-yl)pyrrolo[1,2-b]pyridazine-3-carboxamide | C(O)-C(CN)(cyclopropane) | 6-(cyclopropylcarbamoyl)pyridin-3-yl | 1.25 | 531.2 |
| 280 | 4-((3S,4S)-1-(1-cyanocyclopropanecarbonyl)-4-(fluoromethyl)pyrrolidin-3-ylamino)-6-(2-methoxypyrimidin-5-yl)pyrrolo[1,2-b]pyridazine-3-carboxamide | C(O)-C(CN)(cyclopropane) | 2-methoxypyrimidin-5-yl | 1.17 | 479.1 |
| 281 | 4-((3S,4S)-1-(1-cyanocyclopropanecarbonyl)-4-(fluoromethyl)pyrrolidin-3-ylamino)-6-(2-ethoxypyrimidin-5-yl)pyrrolo[1,2-b]pyridazine-3-carboxamide | C(O)-C(CN)(cyclopropane) | 2-ethoxypyrimidin-5-yl | 1.33 | 493.1 |

| Ex # | Name | —R¹ᵇ | —R² | HPLC Rt (minutes) | LCMS [m/z] (M + H) |
|---|---|---|---|---|---|
| 282 | 4-((3S,4S)-1-(1-cyanocyclopropanecarbonyl)-4-(fluoromethyl)pyrrolidin-3-ylamino)-6-(6-fluoropyridin-3-yl)pyrrolo[1,2-b]pyridazine-3-carboxamide | cyclopropyl-C(=O)- with CN | 6-fluoropyridin-3-yl | 1.29 | 466.2 |
| 283 | 4-((3S,4S)-1-(2-cyano-2-methylpropanoyl)-4-(fluoromethyl)pyrrolidin-3-ylamino)-6-(1-methyl-1H-pyrazol-4-yl)pyrrolo[1,2-b]pyridazine-3-carboxamide | C(=O)-C(Me)(Me)CN | 1-methyl-1H-pyrazol-4-yl | 1.07 | 453.2 |
| 284 | 6-(1-ethyl-1H-pyrazol-4-yl)-4-((3S,4S)-4-(fluoromethyl)-1-(1-hydroxycyclopropanecarbonyl)pyrrolidin-3-ylamino)pyrrolo[1,2-b]pyridazine-3-carboxamide | cyclopropyl-C(=O)- with OH | 1-ethyl-1H-pyrazol-4-yl | 1.00 | 456.2 |
| 285 | 4-((3S,4S)-4-(fluoromethyl)-1-(1-hydroxycyclopropanecarbonyl)pyrrolidin-3-ylamino)-6-(6-methoxypyridin-3-yl)pyrrolo[1,2-b]pyridazine-3-carboxamide | cyclopropyl-C(=O)- with OH | 6-methoxypyridin-3-yl | 1.11 | 469.2 |
| 286 | 4-((3S,4S)-1-(5-cyanopyrimidin-2-yl)-4-(fluoromethyl)pyrrolidin-3-ylamino)-6-(1-methyl-1H-pyrazol-4-yl)pyrrolo[1,2-b]pyridazine-3-carboxamide | 5-cyanopyrimidin-2-yl | 1-methyl-1H-pyrazol-4-yl | 1.15 | 461.2 |
| 287 | 4-((3S,4S)-1-(6-cyanopyridazin-3-yl)-4-(fluoromethyl)pyrrolidin-3-ylamino)-6-(1-ethyl-1H-pyrazol-4-yl)pyrrolo[1,2-b]pyridazine-3-carboxamide | 6-cyanopyridazin-3-yl | 1-ethyl-1H-pyrazol-4-yl | 1.19 | 475.2 |
| 288 | 4-((3S,4S)-1-(5-chloropyrimidin-2-yl)-4-(fluoromethyl)pyrrolidin-3-ylamino)-6-(1-ethyl-1H-pyrazol-4-yl)pyrrolo[1,2-b]pyridazine-3-carboxamide | 5-chloropyrimidin-2-yl | 1-ethyl-1H-pyrazol-4-yl | 1.47 | 484.1 |
| 289 | 4-((3S,4S)-1-(5-chloropyrimidin-2-yl)-4-(fluoromethyl)pyrrolidin-3-ylamino)-6-(1-methyl-1H-pyrazol-4-yl)pyrrolo-[1,2-b]pyridazine-3-carboxamide | 5-chloropyrimidin-2-yl | 1-methyl-1H-pyrazol-4-yl | 1.35 | 470.1 |
| 290 | 4-((3S,4S)-1-(1-cyanocyclopropanecarbonyl)-4-(fluoromethyl)pyrrolidin-3-ylamino)-6-(6-((2-methoxyacetamido)methyl)-pyridin-3-yl)pyrrolo[1,2-b]pyridazine-3-carboxamide | cyclopropyl-C(=O)- with CN | 6-((2-methoxyacetamido)methyl)pyridin-3-yl | 0.83 | 549.2 |

Example 292

4-(((3S,4S)-1-(1-cyanocyclopropanecarbonyl)-4-ethylpyrrolidin-3-yl)amino)-6-(3-methylisoxazol-5-yl)pyrrolo[1,2-b]pyridazine-3-carboxamide

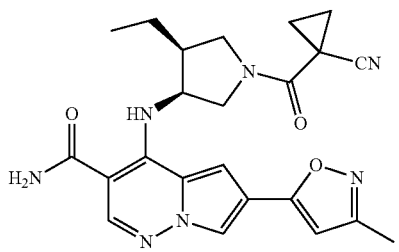 [SMILES: CC[C@H]1CN(C(=O)C2(C#N)CC2)C[C@H]1Nc1c(C(N)=O)cnn2cc(-c3cc(C)no3)cc12]

Step 1: (3S,4S)-tert-butyl 3-((6-bromo-3-carbamoylpyrrolo[1,2-b]pyridazin-4-yl)amino)-4-ethylpyrrolidine-1-carboxylate

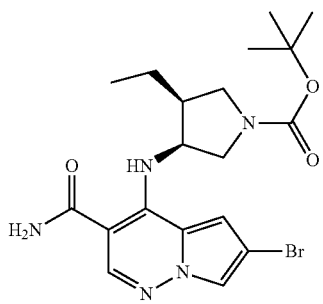 [SMILES: CC[C@H]1CN(C(=O)OC(C)(C)C)C[C@H]1Nc1c(C(N)=O)cnn2cc(Br)cc12]

A mixture of 3 mmol of 6-bromo-4-((3S,4S)-4-ethylpyrrolidin-3-ylamino)pyrrolo[1,2-b]pyridazine-3-carboxamide hydroiodide (prepared from Intermediate 2 and Intermediate 9 using the methods described in Step 1 of Example 52 and Step 2 of Example 272), di-t-butyldicarbonate (0.992 g, 4.55 mmol), and N,N-diisopropylethylamine (2.64 mL, 15.15 mmol) in dichloromethane (25 mL) was stirred at rt for 15 minutes. The resulting mixture was diluted with 100 mL of dichloromethane, washed twice with water, once with brine, and then dried over sodium sulfate. The organic layer was then filtered and concentrated and the crude material was purified by silica gel chromatography, eluting with 0-10% methanol in dichloromethane, to give a tan solid as the title compound (1.23 g, 84% yield). MS (ES+) m/z: 452.1, 454.1 (M+H); LC retention time: 3.215 min (analytical HPLC Method O).

Step 2: (3S,4S)-tert-butyl 3-((3-carbamoyl-6-ethynylpyrrolo[1,2-b]pyridazin-4-yl)amino)-4-ethylpyrrolidine-1-carboxylate

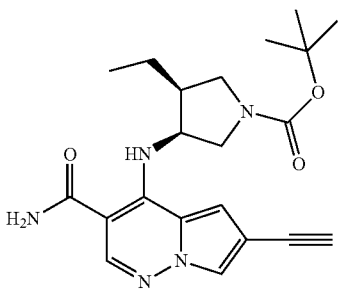 [SMILES: C#Cc1cc2c(N[C@@H]3CN(C(=O)OC(C)(C)C)C[C@@H]3CC)c(C(N)=O)cnn2c1]

A mixture of (3S,4S)-tert-butyl 3-((6-bromo-3-carbamoylpyrrolo[1,2-b]pyridazin-4-yl)amino)-4-ethylpyrrolidine-1-carboxylate (330 mg, 0.730 mmol), bis(triphenylphosphine)-palladium(II) chloride (154 mg, 0.219 mmol) and copper(I) iodide (41.7 mg, 0.219 mmol) in DMF (4 mL) was stirred and degassed by bubbling nitrogen through for 15 minutes. While maintaining positive nitrogen pressure, bis(isopropyl)amine (2.58 mL, 18.24 mmol) and ethynyltrimethylsilane (0.515 mL, 3.65 mmol) were added. The flask was immediately placed in a hot oil bath at 90° C. After stirring overnight at 90° C., the reaction was complete. The reaction was then cooled to room temperature and diluted with ethyl acetate (50 mL). This mixture was filtered through Celite, and was concentrated to an oil. This crude material was suspended in MeOH (5 mL) and potassium carbonate (121 mg, 0.876 mmol) was added. After stirring the mixture at room temperature for 1 h, the insoluble solids were removed by filtration, and the resulting solution was concentrated to an oil. This crude material was purified by flash chromatography, eluting with 0-100% EtOAc in hexanes. Concentration of the pure fractions afforded a brown solid as the title compound (168 mg, 56.7% yield). $^1$H NMR (400 MHz, DMSO-$d_6$) δ 11.14 (t, J=9.0 Hz, 1H), 8.27 (s, 1H), 7.96 (d, J=1.3 Hz, 1H), 7.06 (s, 1H), 4.85-4.65 (m, 1H), 4.10 (d, J=1.8 Hz, 1H), 3.73-3.54 (m, 2H), 3.43-3.24 (m, 1H), 3.08-2.92 (m, 1H), 2.44-2.26 (m, 1H), 1.55-1.43 (m, 2H), 1.36 (d, J=15.4 Hz, 9H), 0.86 (t, J=7.4 Hz, 3H). MS (ES+) m/z: 398.2 (M+H); LC retention time: 2.993 min (analytical HPLC Method O).

Step 3: (Z)—N-hydroxyacetimidoyl chloride

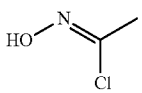

A solution of (E)-acetaldehyde oxime (0.277 g, 4.69 mmol) and N-chlorosuccinimide (0.626 g, 4.69 mmol) in DMF (15 mL) was stirred at 50° C. After 90 minutes, the reaction mixture was partitioned between ethyl acetate and water. The aqueous layer was washed once with ethyl acetate. The combined ethyl acetate layers were dried over sodium sulfate, then filtered and concentrated to afford (Z)—N-hydroxyacetimidoyl chloride (0.44 g, 4.47 mmol, 95% yield) as a colorless oil. This material was used without any further purification in the next step.

Step 4: (3S,4S)-tert-butyl 3-((3-carbamoyl-6-(3-methylisoxazol-5-yl)pyrrolo[1,2-b]pyridazin-4-yl)amino)-4-ethylpyrrolidine-1-carboxylate

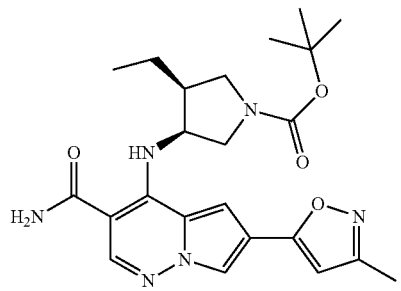 [SMILES: CC[C@H]1CN(C(=O)OC(C)(C)C)C[C@H]1Nc1c(C(N)=O)cnn2cc(-c3cc(C)no3)cc12]

To a solution of (3S,4S)-tert-butyl 3-((3-carbamoyl-6-ethynylpyrrolo[1,2-b]pyridazin-4-yl)amino)-4-ethylpyrrolidine-1-carboxylate from Step 2 (88 mg, 0.221 mmol) in dichloromethane (2 mL) and triethylamine (0.046 mL, 0.332 mmol) was added (Z)—N-hydroxyacetimidoyl chloride (25.9 mg, 0.277 mmol). The solution was stirred at 40° C. overnight. After stirring overnight, the reaction was cooled to room temperature and diluted with dichloromethane. This solution was washed once with aqueous potassium carbonate, and once with water. It was then dried over sodium sulfate, filtered and concentrated. The crude material was purified by flash chromatography, eluting with 0-100% ethyl acetate in hexanes. Concentration of the pure fractions afforded the title compound (64 mg, 60.4% yield) as an off-white solid. $^1$H NMR (400 MHz, DMSO-d$_6$) δ 11.20 (t, J=9.1 Hz, 1H), 8.31 (s, 1H), 8.24 (d, J=1.3 Hz, 1H), 7.30 (br. s., 1H), 6.72 (s, 1H), 5.01-4.74 (m, 1H), 3.81-3.58 (m, 2H), 3.48-3.34 (m, 1H), 3.10-2.96 (m, 1H), 2.42 (d, J=12.8 Hz, 1H), 2.28 (s, 3H), 1.60-1.46 (m, 2H), 1.37 (d, J=19.1 Hz, 9H), 0.96-0.75 (m, 3H). MS (ES+) m/z: 455.2 (M+H); LC retention time: 3.038 min (analytical HPLC Method O).

Step 5: 4-(((3S,4S)-4-ethylpyrrolidin-3-yl)amino)-6-(3-methylisoxazol-5-yl)pyrrolo[1,2-b]pyridazine-3-carboxamide

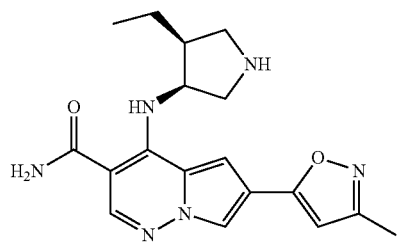 [SMILES: CC[C@H]1CNC[C@H]1Nc1c(C(N)=O)cnn2cc(-c3cc(C)no3)cc12]

To a solution of (3S,4S)-tert-butyl 3-((3-carbamoyl-6-(3-methylisoxazol-5-yl)pyrrolo[1,2-b]pyridazin-4-yl)amino)-4-ethylpyrrolidine-1-carboxylate (62 mg, 0.136 mmol) in dichloromethane (1 mL) was added 4N HCl in 1,4-dioxane (0.512 mL, 2.046 mmol). After stirring at room temperature overnight, the deprotection was complete. The volatile were removed in vacuo to afford the hydrochloride salt of the title compound (52 mg, 98% yield) as an off-white solid. MS (ES+) m/z: 355.1 (M+H).

Step 6: (3S,4S)-tert-butyl 3-((3-carbamoyl-6-(3-methylisoxazol-5-yl)pyrrolo[1,2-b]pyridazin-4-yl)amino)-4-ethylpyrrolidine-1-carboxylate (Example 292)

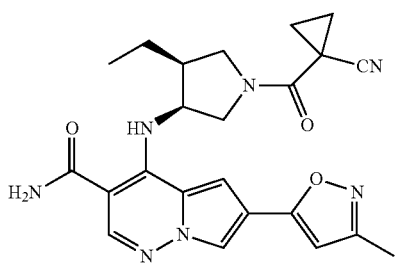 [SMILES: CC[C@H]1CN(C(=O)C2(C#N)CC2)C[C@H]1Nc1c(C(N)=O)cnn2cc(-c3cc(C)no3)cc12]

4-(((3S,4S)-4-ethylpyrrolidin-3-yl)amino)-6-(3-methylisoxazol-5-yl)pyrrolo[1,2-b]pyridazine-3-carboxamide (14 mg, 0.040 mmol), 1-cyanocyclopropanecarboxylic acid (6.58 mg, 0.059 mmol), and O-(7-azabenzotriazol-1-yl)-N,N,N',N'-tetramethyluronium hexafluorophosphate (22.53 mg, 0.059 mmol) were weighed into a vial. DMF (0.25 mL) and N,N-diisopropylethylamine (0.034 mL, 0.198 mmol) were added and the solution was stirred at room temperature. After stirring 45 minutes, the reaction was complete. The reaction mixture was diluted with DMF and this crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min. Fractions containing the desired product were combined and dried via centrifugal evaporation to give the title compound (5.3 mg, 28.2% yield) as an off-white solid. $^1$H NMR (500 MHz, METHANOL-d$_4$) δ 8.22-8.09 (m, 1H), 7.98 (dd, J=15.9, 1.5 Hz, 1H), 7.19-7.05 (m, 1H), 6.45-6.33 (m, 1H), 5.00 (t, J=4.0 Hz, 0.5H), 4.86 (t, J=4.2 Hz, 0.5H), 4.35-4.23 (m, 1.5H), 4.13 (d, J=10.9 Hz, 0.5H), 3.96-3.75 (m, 1.5H), 3.47-3.37 (m, 0.5H), 2.64 (s, 0.5H), 2.54 (s, 0.5H), 2.32 (s, 3H), 1.84-1.34 (m, 6H), 1.11-0.89 (m, 3H) fractional protons are due to the presence of amide rotamers; MS (ES+) m/z: 448.2 (M+H); LC retention time: 1.64 min (analytical LCMS Method H).

Example 293

4-(((3S,4S)-1-(1-cyanocyclopropanecarbonyl)-4-ethylpyrrolidin-3-yl)amino)-6-(1-phenyl-1H-1,2,3-triazol-4-yl)pyrrolo[1,2-b]pyridazine-3-carboxamide

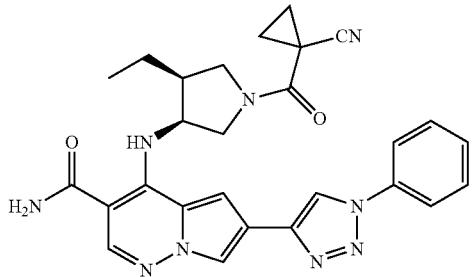 [SMILES: CC[C@H]1CN(C(=O)C2(C#N)CC2)C[C@H]1Nc1c(C(N)=O)cnn2cc(-c3cn(-c4ccccc4)nn3)cc12]

Step 1: (3S,4S)-tert-butyl 3-((3-carbamoyl-6-(1-phenyl-1H-1,2,3-triazol-4-yl)pyrrolo[1,2-b]pyridazin-4-yl)amino)-4-ethylpyrrolidine-1-carboxylate

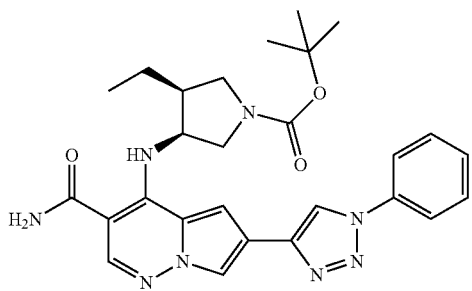 [SMILES: CC[C@H]1CN(C(=O)OC(C)(C)C)C[C@H]1Nc1c(C(N)=O)cnn2cc(-c3cn(-c4ccccc4)nn3)cc12]

To a solution of (3S,4S)-tert-butyl 3-((3-carbamoyl-6-ethynylpyrrolo[1,2-b]pyridazin-4-yl)amino)-4-ethylpyrrolidine-1-carboxylate from Step 2 of Example 292 (71 mg, 0.179 mmol) in toluene (2 mL) and DMF (0.2 mL) was added azidobenzene (149 mg, 1.250 mmol). The flask was purged with nitrogen, and the reaction solution was stirred at room temperature for 1 hour, then warmed to 95° C. After stirring over two nights, the reaction was cooled to room temperature. The volatiles were removed in vacuo and the residue was diluted with 3 mL DMF and purified by via preparative HPLC with the following conditions: Column: Phenomenex Luna C18, 21.5×250 mm, 5-μm particles; Mobile Phase A: 10:90 methanol:water with 0.1% trifluoroacetic acid; Mobile Phase B: 90:10 methanol:water with 0.1% trifluoroacetic acid; Gradient: 30-100% B over 14 minutes, then a 2-minute hold at 100% B; Flow: 25 mL/min. Fractions containing the desired product were combined and concentrated via centrifugal evaporation to remove the methanol. The solution was neutralized with 1N NaOH, and was then partitioned between ethyl acetate and saturated aqueous sodium bicarbonate. The organic layer was dried over sodium sulfate. Filtration and evaporation afforded the title compound (41 mg, 42% yield). MS (ES+) m/z: 517.1 (M+H); LC retention time: 3.385 min (analytical LCMS Method J).

Step 2: 4-(((3S,4S)-4-ethylpyrrolidin-3-yl)amino)-6-(1-phenyl-1H-1,2,3-triazol-4-yl)pyrrolo[1,2-b]pyridazine-3-carboxamide

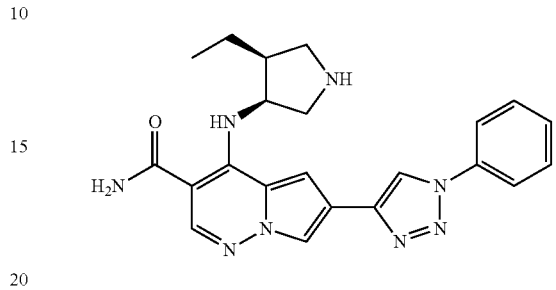

To a solution of (3S,4S)-tert-butyl 3-((3-carbamoyl-6-(1-phenyl-1H-1,2,3-triazol-4-yl)pyrrolo[1,2-b]pyridazin-4-yl)amino)-4-ethylpyrrolidine-1-carboxylate (41 mg, 0.079 mmol) in dichloromethane (1 mL) was added 4N HCl in 1,4-dioxane (0.198 mL, 0.794 mmol). The solution was stirred at room temperature. After stirring 2 h, the reaction is complete. Concentration afforded a tan solid as the hydrochloride salt of the title compound (35 mg, 99% yield). MS (ES+) m/z: 417.1 (M+H). LC retention time: 2.776 min (analytical LCMS Method J).

Step 3: 4-(((3S,4S)-1-(1-cyanocyclopropanecarbonyl)-4-ethylpyrrolidin-3-yl)amino)-6-(1-phenyl-1H-1,2,3-triazol-4-yl)pyrrolo[1,2-b]pyridazine-3-carboxamide (Example 293)

4-(((3S,4S)-4-ethylpyrrolidin-3-yl)amino)-6-(1-phenyl-1H-1,2,3-triazol-4-yl)pyrrolo[1,2-b]pyridazine-3-carboxamide, HCl (16 mg, 0.035 mmol), 1-cyanocyclopropanecarboxylic acid (5.89 mg, 0.053 mmol) and O-(7-azabenzotriazol-1-yl)-N,N,N',N'-tetramethyluronium hexafluorophosphate (20.15 mg, 0.053 mmol) were weighed into a 1 dram vial. DMF (0.25 mL) and N,N-diisopropylethylamine (0.037 mL, 0.212 mmol) were added and the reaction solution was stirred at room temperature. After stirring 2 h, the reaction was complete. The reaction was then diluted with 1.5 mL DMF, and this crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 15 minutes, then a 5-minute hold at 100% B; Flow: 20 mL/min. Fractions containing the desired product were combined and dried via centrifugal evaporation to give the title compound (5.3 mg, 28.2% yield) as an off-white solid. $^1$H NMR (500 MHz, METHANOL-$d_4$) δ 8.57 (d, J=1.9 Hz, 1H), 8.17-8.11 (m, 1H), 8.06 (d, J=17.5 Hz, 1H), 7.83 (d, J=7.8 Hz, 2H), 7.60-7.52 (m, 2H), 7.51-7.45 (m, 1H), 7.33 (d, J=17.5 Hz, 1H), 5.07 (br. s., 0.5H), 4.93 (br. s., 0.5H), 4.38-4.10 (m, 1.5H), 3.98-3.71 (m, 2H), 3.53-3.37 (m, 0.5H), 2.71-2.59 (m, 0.5H), 2.52 (br. s., 0.5H), 1.85-1.33 (m, 6H), 1.11-0.91 (m, 3H) fractional protons are due to the presence of amide rotomers; MS (ES+) m/z: 510.2 (M+H); LC retention time: 1.57 min (analytical LC/MS Method H).

Example 294

(+/−)-4-(1-(2-cyanoacetyl)-4,4-dimethylpyrrolidin-3-ylamino)-6-(2-methoxypyridin-4-yl)pyrrolo[1,2-b]pyridazine-3-carboxamide

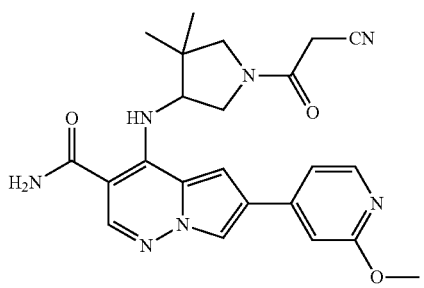 [SMILES: COc1cc(-c2cc3c(NC4CN(C(=O)CC#N)CC4(C)C)c(C(N)=O)cnn3c2)ccn1]

Step 1: Benzyl 4-(6-bromo-3-carbamoylpyrrolo[1,2-b]pyridazin-4-ylamino)-3,3-dimethylpyrrolidine-1-carboxylate

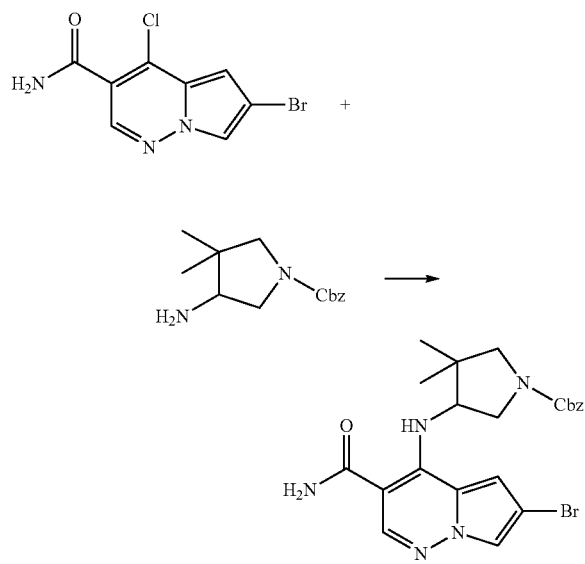

A solution of 6-bromo-4-chloropyrrolo[1,2-b]pyridazine-3-carboxamide (Intermediate 2, 63.0 mg, 0.230 mmol) in N,N-dimethylformamide (0.5 mL), was added benzyl 4-amino-3,3-dimethylpyrrolidine-1-carboxylate (Intermediate 11, 57 mg, 0.230 mmol) and N,N-diiosopropylethylamine (0.121 mL), and heated at 90° C. for 16 h. The reaction was added water, stirred at rt for a 3 hours and filtered. The solid was rinsed with water and dried under vacuum to give benzyl 4-((6-bromo-3-carbamoylpyrrolo[1,2-b]pyridazin-4-yl)amino)-3,3-dimethylpyrrolidine-1-carboxylate (72 mg, 64.5% yield) as a yellow solid. $^1$H NMR (400 MHz, METHANOL-d$_4$) δ 10.83-10.77 (m, 1H), 8.16 (s, 1H), 7.67 (s, 1H), 7.41-7.27 (m, 7H), 7.09-7.04 (m, 1H), 5.18-5.08 (m, 2H), 4.56-4.45 (m, 1H), 4.16-3.95 (m, 1H), 3.42 (d, J=2.2 Hz, 3H), 1.20 (d, J=13.9 Hz, 6H); MS (ES+) m/z: 486.4, 487.9 (M+H); LC retention time: 4.02 min (analytical HPLC Method I).

Step 2: 4-(4,4-dimethylpyrrolidin-3-ylamino)-6-(2-methoxypyridin-4-yl)pyrrolo[1,2-b]pyridazine-3-carboxamide hydroiodide

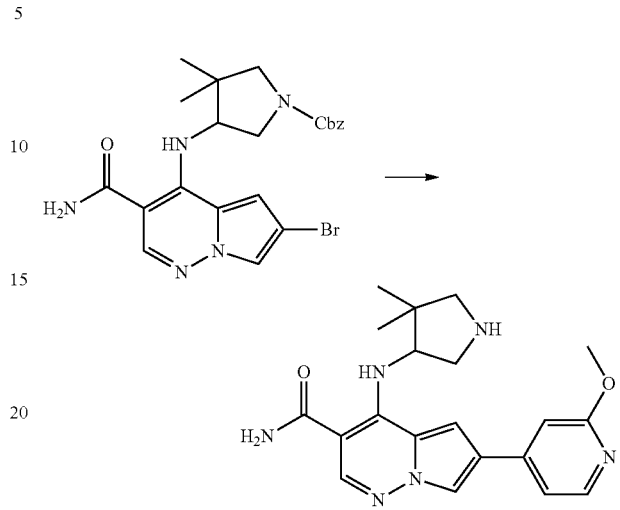

A solution of benzyl 4-((6-bromo-3-carbamoylpyrrolo[1,2-b]pyridazin-4-yl)amino)-3,3-dimethylpyrrolidine-1-carboxylate (35 mg, 0.07 mmol) in 1,4-dioxane (0.3 mL), was added (2-methoxypyridin-4-yl)boronic acid (14.3 mg, 0.094 mmol), X-Phos (3.4 mg, 7.2 μmol) and potassium phosphate (2M, 0.115 mL, 0.23 mmol). The reaction vial was purged with nitrogen, sealed and heated at 100° C. for 16 h. The mixture was diluted with ethyl acetate (30 mL), washed with aq. sodium bicarbonate, dried and concentrated. The residue was dissolved in acetonitrile (5 mL), added trimethylsilane iodide (36 mg, 0.180 mmol) at 0° C. and stirred at rt for 1 h. The suspension was added ether (25 mL), stirred for additional 2 h, filtered and rinsed with ether to give the hydroiodide salt of 4-((4,4-dimethylpyrrolidin-3-yl)amno)-6-(2-methoxypyridin-4-yl)pyrrolo[1,2-b]pyridazine-3-carboxamide (15 mg, 0.030 mmol, 41% yield) as a yellow solid. $^1$H NMR (500 MHz, METHANOL-d$_4$) δ 8.15 (s, 1H), 8.09 (d, J=5.4 Hz, 1H), 8.01 (d, J=1.5 Hz, 1H), 7.58 (s, 3H), 7.31 (d, J=1.5 Hz, 1H), 7.25 (dd, J=5.4, 1.5 Hz, 1H), 7.09 (d, J=1.0 Hz, 1H), 4.61-4.54 (m, 1H), 4.30 (br. s., 1H), 3.94 (s, 3H), 3.73 (dd, J=11.9, 6.9 Hz, 1H), 3.12-3.04 (m, 2H), 1.97 (s, 2H), 1.24 (d, J=14.4 Hz, 6H), MS (ES+) m/z: 380.2, 381.3 (M+H); LC retention time: 0.84 min (analytical HPLC Method I).

Step 3: 4-(1-(2-cyanoacetyl)-4,4-dimethylpyrrolidin-3-ylamino)-6-(2-methoxypyridin-4-yl)pyrrolo[1,2-b]pyridazine-3-carboxamide (Example 294)

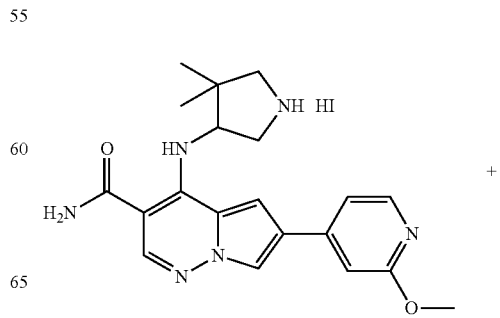

-continued

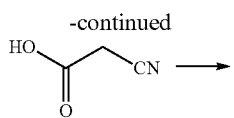

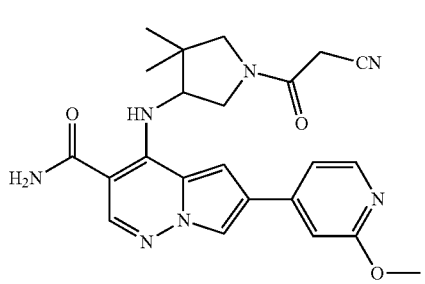

A solution of 4-((4,4-dimethylpyrrolidin-3-yl)amino)-6-(2-methoxypyridin-4-yl)pyrrolo[1,2-b]pyridazine-3-carboxamide hydroiodide (12 mg, 0.024 mmol) in N,N-dimethylformamide (0.5 mL), was added BOP (10.2 mg, 0.024 mmol) and N,N-diisopropylethylamine (0.012 mL, 0.071 mmol) was stirred at rt for 6 h. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Fractions containing the desired product were combined and dried via centrifugal evaporation to give the TFA salt of 4-((1-(2-cyanoacetyl)-4,4-dimethylpyrrolidin-3-yl)amino)-6-(2-methoxypyridin-4-yl)pyrrolo[1,2-b]pyridazine-3-carboxamide (7 mg, 52% yield). $^1$H NMR (400 MHz, METHANOL-$d_4$) δ 8.32 (s, 1H), 8.23 (d, J=3.7 Hz, 1H), 8.18-8.14 (m, 1H), 7.60 (s, 1H), 7.55 (d, J=1.8 Hz, 1H), 7.52-7.50 (m, 1H), 7.50-7.47 (m, 2H), 4.23-4.14 (m, 1H), 4.11 (d, J=6.4 Hz, 3H), 3.85 (d, J=3.5 Hz, 1H), 3.81 (s, 1H), 3.62-3.42 (m, 4H), 1.30-1.21 (m, 6H). MS (ES+) m/z: 448.17 (M+H); LC retention time: 2.86 min (analytical HPLC Method I).

Example 295

(S)-4-(1-(2-cyanoacetyl)-4,4-dimethylpyrrolidin-3-ylamino)-6-(2-methoxypyridin-4-yl)pyrrolo[1,2-b]pyridazine-3-carboxamide

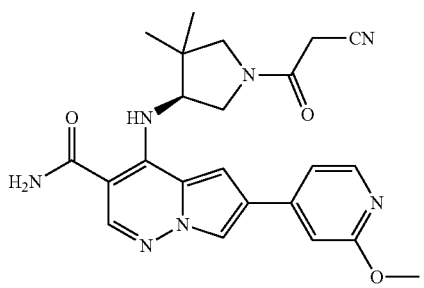 [SMILES: COc1cc(-c2cc3c(N[C@@H]4CN(C(=O)CC#N)CC4(C)C)c(C(N)=O)cnn3c2)ccn1]

Step 1: (S)-benzyl 4-(6-bromo-3-carbamoylpyrrolo[1,2-b]pyridazin-4-ylamino)-3,3-dimethylpyrrolidine-1-carboxylate

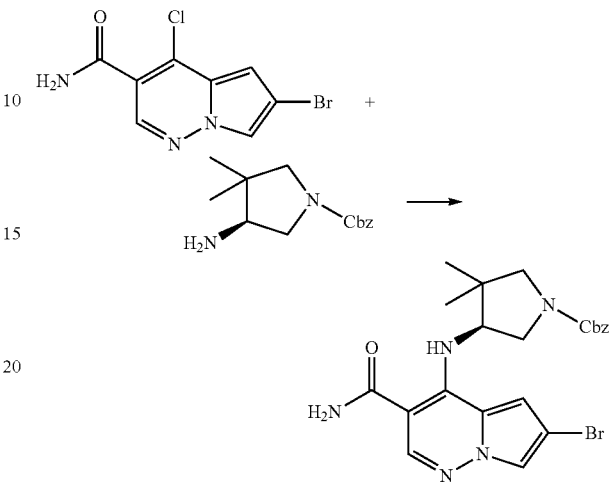

According to the procedure described for Step 1 of Example 294, the title compound was prepared by coupling enantiopure Intermediate 11 with Intermediate 2.

Step 2: (S)-4-(4,4-dimethylpyrrolidin-3-ylamino)-6-(2-methoxypyridin-4-yl)pyrrolo[1,2-b]pyridazine-3-carboxamide

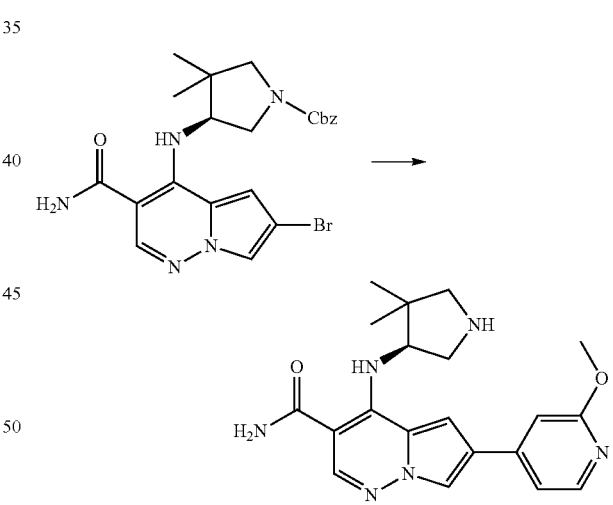

A solution of benzyl 4-((6-bromo-3-carbamoylpyrrolo[1,2-b]pyridazin-4-yl)amino)-3,3-dimethylpyrrolidine-1-carboxylate (35 mg, 0.072 mmol) in 1,4-dioxane (0.3 mL), was added (2-methoxypyridin-4-yl)boronic acid (14.3 mg, 0.094 mmol), X-Phos (3.43 mg, 7.2 μmol) and potassium phosphate (2 M, 0.115 mL, 0.23 mmol). The reaction vial was purged with nitrogen, sealed and heated at 100° C. for 18 h. The reaction was diluted with ethyl acetate (50 mL), washed with aq. sodium bicarbonate and brine. The organic layer was dried and concentrated. The residue was suspended in acetonitrile (5 mL), was added iodotrimethylsilane (36.0 mg, 0.180 mmol) at 0° C., stirred at rt for 1 h. To the suspension was added ether (30 mL), stirred for additional 2 h, filtered and rinsed the collected solid with ether and dried to give the hydroiodide salt of the title compound (15 mg, 0.030 mmol, 41.0% yield) as a yellow solid. $^1$H NMR (500 MHz, METHANOL-$d_4$) δ 8.15 (s, 1H), 8.09 (d, J=5.4 Hz, 1H), 8.01 (d, J=1.5 Hz, 1H), 7.58 (s, 3H), 7.31 (d, J=1.5 Hz, 1H), 7.25 (dd, J=5.4, 1.5 Hz, 1H), 7.09 (d, J=1.0 Hz, 1H), 4.61-4.54 (m, 1H), 4.30 (br. s., 1H), 3.94 (s, 3H), 3.73 (dd, J=11.9, 6.9 Hz, 1H), 3.12-3.04 (m, 2H), 1.97 (s, 2H), 1.24 (d, J=14.4 Hz, 6H), MS (ES+) m/z: 380.2, 381.3 (M+H); LC retention time: 0.84 min (analytical HPLC Method I).

Step 3: (S)-4-((1-(2-cyanoacetyl)-4,4-dimethylpyrrolidin-3-yl)amino)-6-(2-methoxypyridin-4-yl)pyrrolo[1,2-b]pyridazine-3-carboxamide (Example 295)

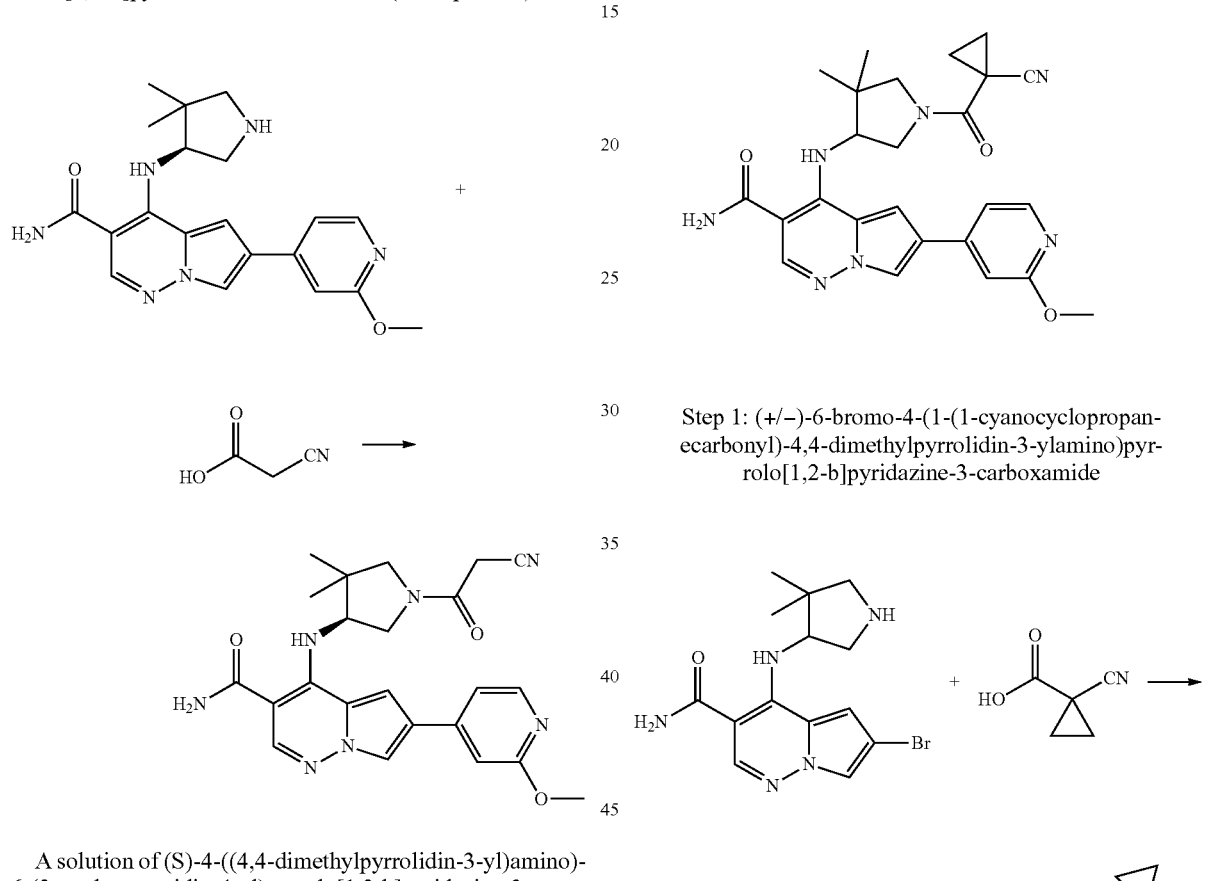

A solution of (S)-4-((4,4-dimethylpyrrolidin-3-yl)amino)-6-(2-methoxypyridin-4-yl)pyrrolo[1,2-b]pyridazine-3-carboxamide hydroiodide (12 mg, 0.024 mmol) in N,N-dimethylformamide (1 mL), was added BOP (10.2 mg, 0.024 mmol) and N,N-diisopropylethylamine (0.012 mL, 0.07 mmol). The mixture was stirred for 2 h. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min. Fractions containing the desired product were combined and dried via centrifugal evaporation to give the title compound (7 mg, 52% yield). $^1$H NMR (400 MHz, METHANOL-$d_4$, Rotamer) δ 8.36 (s, 1H), 8.27 (d, J=3.7 Hz, 1H), 8.20 (d, J=5.9 Hz, 1H), 7.67-7.62 (m, 1H), 7.57 (dd, J=16.5, 1.8 Hz, 1H), 7.53 (d, J=3.1 Hz, 1H), 4.73 (t, J=5.9 Hz, 1H), 4.28-4.17 (m, 1H), 4.15 (d, J=6.4 Hz, 3H), 3.89 (d, J=3.5 Hz, 1H), 3.86-3.83 (m, 1H), 3.65-3.46 (m, 4H), 1.36-1.25 (m, 6H). MS (ES+) m/z: 448.2, 448.2 (M+H); LC retention time: 2.86 min (analytical HPLC Method I).

Example 296

(+/−)-4-(1-(1-cyanocyclopropanecarbonyl)-4,4-dimethylpyrrolidin-3-ylamino)-6-(2-methoxypyridin-4-yl)pyrrolo[1,2-b]pyridazine-3-carboxamide Step 1: (+/−)-6-bromo-4-(1-(1-cyanocyclopropanecarbonyl)-4,4-dimethylpyrrolidin-3-ylamino)pyrrolo[1,2-b]pyridazine-3-carboxamide

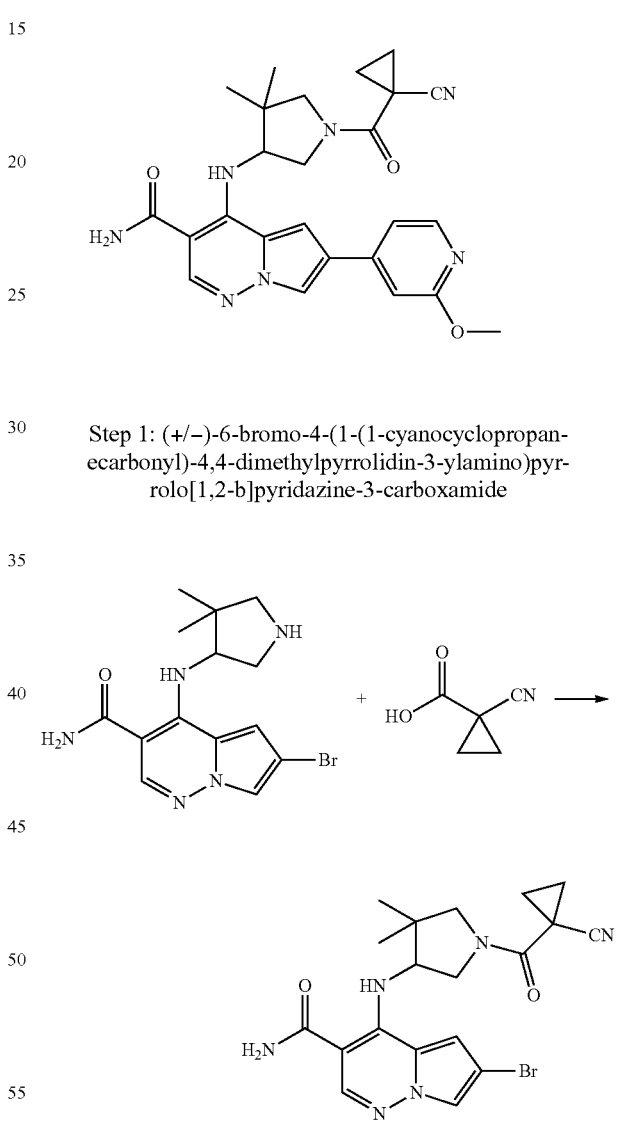

A solution of (+/−)-6-bromo-4-((4,4-dimethylpyrrolidin-3-yl)amino)pyrrolo[1,2-b]pyridazine-3-carboxamide hydroiodide (50 mg, 0.104 mmol) in DMF (0.3 mL), was added 1-cyanocyclopropanecarboxylic acid (13.9 mg, 0.13 mmol), BOP (55.4 mg, 0.13 mmol), DIPEA (0.046 mL, 0.26 mmol). The mixture was stirred at rt for 3 h, quenched with water then filtered. The solid was rinsed with water, dried under vacuum to give 6-bromo-4-((1-(1-cyanocyclopropanecarbonyl)-4,4-dimethylpyrrolidin-3-yl)amino)pyrrolo[1,2- b]pyridazine-3-carboxamide (36 mg, 78% yield) was obtained as a brown solid. MS (ES+) m/z: 444.1, 445.2 (M+H).

Step 2: (+/−)-4-(1-(1-cyanocyclopropanecarbonyl)-4,4-dimethylpyrrolidin-3-ylamino)-6-(2-methoxypyridin-4-yl)pyrrolo[1,2-b]pyridazine-3-carboxamide (Example 296)

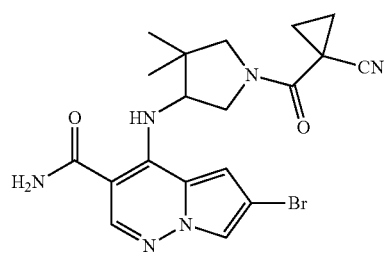

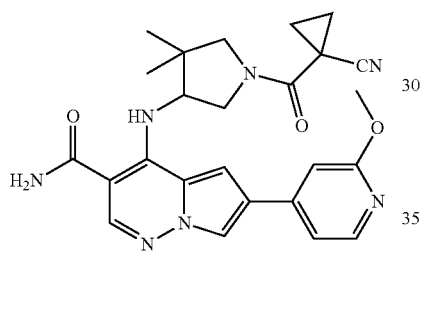

A solution of (S)-6-bromo-4-(1-(1-cyanocyclopropanecarbonyl)-4,4-dimethylpyrrolidin-3-ylamino)pyrrolo[1,2-b]pyridazine-3-carboxamide (10 mg, 0.022 mmol) in 1,4-Dioxane (0.5 mL), was added (2-methoxypyridin-4-yl)boronic acid (4.12 mg, 0.027 mmol), palladium (II) acetate (0.25 mg, 1.123 mmol), X-Phos (1.07 mg, 2.25 mmol) and potassium phosphate (2M, 0.04 mL, 0.08 mmol). The reaction vial was purged with nitrogen, sealed and heated at 100° C. overnight. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min. Fractions containing the desired product were combined and dried via centrifugal evaporation to give the title compound (2.2 mg, 17% yield). $^1$H NMR (500 MHz, METHANOL-$d_4$) δ 8.43 (dd, J=5.4, 2.5 Hz, 1H), 8.23-8.09 (m, 1H), 7.99-7.93 (m, 1H), 7.90 (dd, J=10.4, 1.5 Hz, 1H), 7.61 (s, 2H), 7.17-7.08 (m, 1H), 6.86 (d, J=8.4 Hz, 1H), 4.12 (dd, J=12.9, 6.4 Hz, 1H), 3.96 (s, 3H), 3.95-3.87 (m, 1H), 3.64-3.55 (m, 1H), 3.50-3.44 (m, 1H), 3.01 (s, 1H), 2.88 (s, 1H), 1.75-1.53 (m, 4H), 1.35-1.24 (m, 6H). MS (ES+) m/z: 474.2 (M+H); LC retention time: 1.41 min (analytical HPLC Method I).

Example 297

(+/−)-4-(4,4-dimethyl-1-(methylsulfonyl)pyrrolidin-3-ylamino)-6-(1,5-dimethyl-1H-pyrazol-4-yl)pyrrolo[1,2-b]pyridazine-3-carboxamide

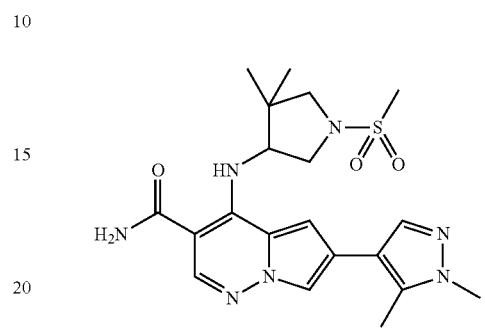

Step 1: (+/−)-6-bromo-4-(4,4-dimethyl-1-(methylsulfonyl)pyrrolidin-3-ylamino)pyrrolo[1,2-b]pyridazine-3-carboxamide

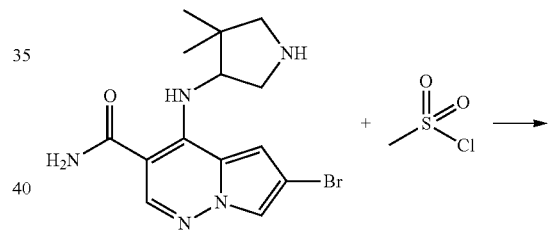

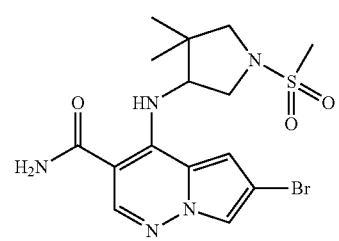

A suspension of 6-bromo-4-((4,4-dimethylpyrrolidin-3-yl)amino)pyrrolo[1,2-b]pyridazine-3-carboxamide hydroiodide (97 mg, 0.25 mmol) in DCM (3 mL), was added DIPEA (0.16 mL, 0.87 mmol) and methanesulfonyl chloride (0.04 mL, 0.5 mmol). The mixture was stirred at rt overnight. The reaction was quenched with water, extracted by dichloromethane, washed with hydrochloride (0.5N), aq. sodium bicarbonate and brine. The organic layer was dried over sodium sulfate and concentrated. The residue was triturated in ether then filtered to give (+/−)-6-bromo-4-(4,4-dimethyl-1-(methylsulfonyl)pyrrolidin-3-ylamino)pyrrolo[1,2-b]pyridazine-3-carboxamide (92 mg, 86%). MS (ES+) m/z: 431.99 (M+H).

Step 2: (+/−)-4-(4,4-dimethyl-1-(methylsulfonyl) pyrrolidin-3-ylamino)-6-(1,5-dimethyl-1H-pyrazol-4-yl)pyrrolo[1,2-b]pyridazine-3-carboxamide (Example 297)

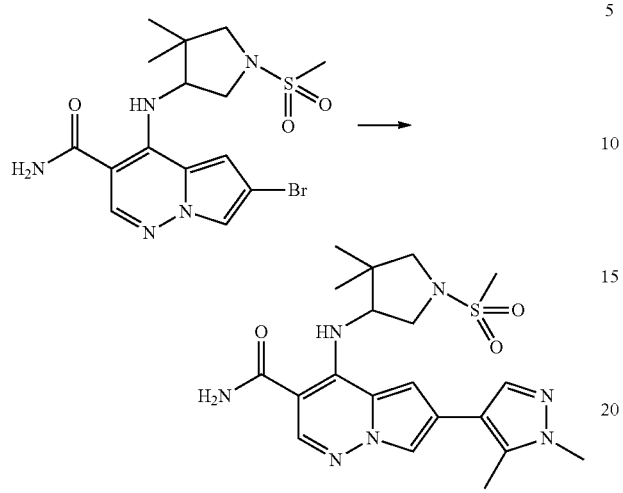

A solution of (+/−)-6-bromo-4-((4,4-dimethyl-1-(methylsulfonyl)pyrrolidin-3-yl)amino)pyrrolo[1,2-b]pyridazine-3-carboxamide (10 mg, 0.023 mmol) in 1,4-dioxane (0.5 mL), was added (1,5-dimethyl-1H-pyrazol-4-yl)boronic acid (3.25 mg, 0.023 mmol), palladium (II) acetate (0.52 mg, 2.32 μmol), X-Phos (2.22 mg, 4.7 μmol), potassium phosphate (0.04 mL, 0.08 mmol. The reaction vial was purged with nitrogen, sealed and heated at 90° C. overnight. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min. Fractions containing the desired product were combined and dried via centrifugal evaporation to give the title compound (3.6 mg, 35% yield). $^1$H NMR (500 MHz, METHANOL-d$_4$) δ 8.12 (s, 1H), 7.67 (d, J=1.5 Hz, 1H), 7.63-7.56 (m, 3H), 6.84 (d, J=1.5 Hz, 1H), 4.50 (t, J=5.0 Hz, 1H), 4.32 (br. s., 1H), 3.97 (dd, J=10.9, 5.9 Hz, 1H), 3.83 (s, 3H), 3.44 (dd, J=10.9, 4.5 Hz, 1H), 3.39-3.33 (m, 2H), 2.97-2.80 (m, 3H), 2.43 (s, 3H), 1.27 (d, J=5.4 Hz, 6H). MS (ES+) m/z: 446.2 (M+H); LC retention time: 1.25 min (analytical HPLC Method I).

Example 298

(+/−)-4-(4,4-dimethyl-1-(methylsulfonyl)pyrrolidin-3-ylamino)-6-(1-methyl-1H-pyrazol-4-yl)pyrrolo[1,2-b]pyridazine-3-carboxamide

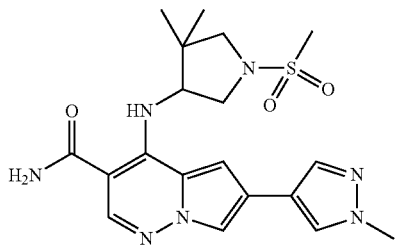 [SMILES: Cn1cc(-c2cc3c(NC4CN(S(C)(=O)=O)CC4(C)C)c(C(N)=O)cnn3c2)cn1]

The title compound was prepared according to the procedure described for Example 297 by Suzuki coupling with (+/−)-6-bromo-4-(4,4-dimethyl-1-(methylsulfonyl)pyrrolidin-3-ylamino)pyrrolo[1,2-b]pyridazine-3-carboxamide (from Step 1 of Example 297) with 1-methyl-4-(4,4,5,5-tetramethyl-1,3,2-dioxaborolan-2-yl)-1H-pyrazole.

Example 299

(+/−)-4-(1-(5-cyanopyridin-2-yl)-4,4-dimethylpyrrolidin-3-ylamino)-6-(1-ethyl-1H-pyrazol-3-yl)pyrrolo[1,2-b]pyridazine-3-carboxamide

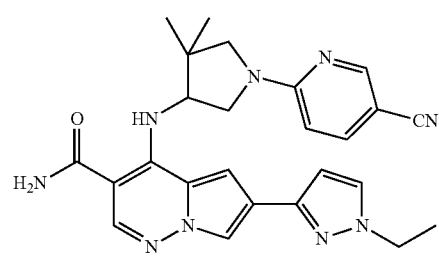 [SMILES: CCn1ccc(-c2cc3c(NC4CN(c5ccc(C#N)cn5)CC4(C)C)c(C(N)=O)cnn3c2)n1]

Step 1: (+/−)-4-(4,4-dimethylpyrrolidin-3-ylamino)-6-(1-ethyl-1H-pyrazol-4-yl)pyrrolo[1,2-b]pyridazine-3-carboxamide

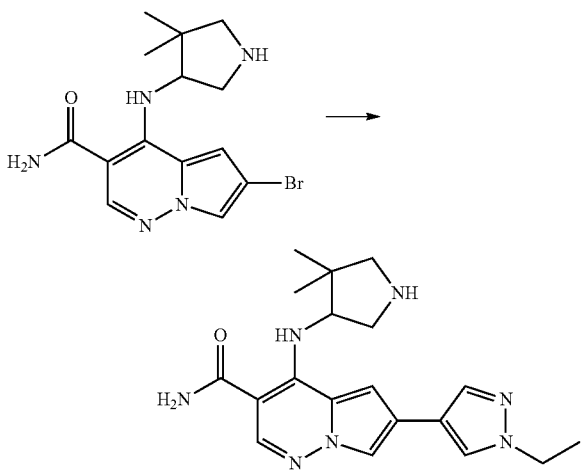

A solution of (+/−)-6-bromo-4-(4,4-dimethylpyrrolidin-3-yl)pyrrolo[1,2-b]pyridazine-3-carboxamide hydroiodide (50 mg, 0.104 mmol) in 1,4-dioxane (1 mL) was added 1-ethyl-1H-pyrazol-4-ylboronic acid (21.9 mg, 0.156 mmol), palladium (II) acetate (1.2 mg, 0.005 mmol), X-Phos (5 mg, 0.01 mmol) and potassium phosphate (2M, 184 mL, 0.364 mmol). The reaction vial was purged with nitrogen, sealed and heated at 100° C. overnight. The reaction was added water (5 mL), extracted with ethyl acetate (30 mL) and washed with brine. The organic layer was dried, filtered, and concentrated to give

Step 2: 4-(1-(5-cyanopyridin-2-yl)-4,4-dimethylpyrrolidin-3-ylamino)-6-(1-ethyl-1H-pyrazol-3-yl)pyrrolo[1,2-b]pyridazine-3-carboxamide (Example 299)

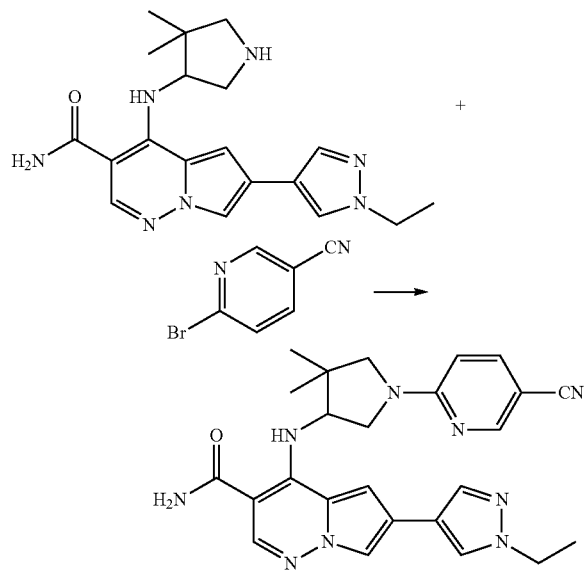

To a solution of 4-((4,4-dimethylpyrrolidin-3-yl)amino)-6-(1-ethyl-1H-pyrazol-4-yl)pyrrolo[1,2-b]pyridazine-3-carboxamide (38 mg, 0.103 mmol) in DMF (0.3 mL), was added 6-bromonicotinonitrile (20.8 mg, 0.114 mmol), DIPEA (0.06 mL, 0.31 mmol), The mixture was heated at 100° C. overnight. The reaction was cooled to rt, and purified via preparative HPLC to afford 15 mg of the. The product was subjected to chiral SFC chromatography to afford the title compound (1.1 mg, 2% yield) as a single enantiomer. $^1$H NMR (400 MHz, METHANOL-$d_4$) δ 8.40 (d, J=1.8 Hz, 1H), 8.16 (s, 1H), 8.02 (s, 1H), 7.87-7.83 (m, 2H), 7.76 (dd, J=8.9, 2.3 Hz, 1H), 7.21 (d, J=1.8 Hz, 1H), 6.65 (d, J=8.8 Hz, 1H), 4.22 (q, J=7.3 Hz, 2H), 3.70-3.54 (m, 3H), 3.51-3.49 (m, 1H), 3.18-3.14 (m, 1H), 1.51 (t, J=7.3 Hz, 3H), 1.32 (d, J=9.7 Hz, 6H). MS (ES+) m/z: 470.32 (M+H); LC retention time: 3.50 min (analytical HPLC Method H).

Example 300

Cis-(±)-4-1-(1-cyanocyclopropanecarbonyl)-4-methoxypyrrolidin-3-ylamino)-6-(4-methoxyphenyl)pyrrolo[1,2-b]pyridazine-3-carboxamide

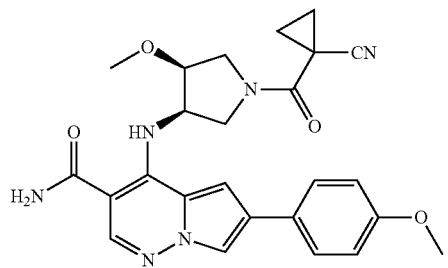 [SMILES: COc1ccc(-c2cc3c(N[C@@H]4CN(C(=O)C5(C#N)CC5)C[C@@H]4OC)c(C(N)=O)cnn3c2)cc1]

Step 1: 6-bromo-4-((cis-4-methoxypyrrolidin-3-yl)amino)pyrrolo[1,2-b]pyridazine-3-carboxamide

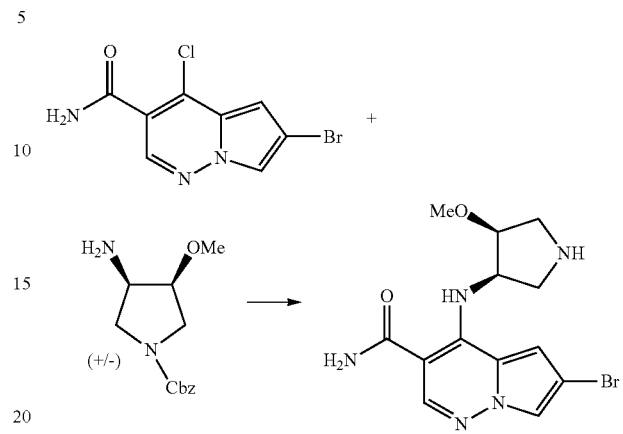

To a solution of 6-bromo-4-chloropyrrolo[1,2-b]pyridazine-3-carboxamide (Intermediate 2, 0.27 g, 0.99 mmol) in DMF (1 mL) was added (±)-cis-benzyl 3-amino-4-methoxypyrrolidine-1-carboxylate (Intermediate 12, 0.3 g, 1.18 mmol) and DIPEA (0.37 mL, 2.1 mmol). The mixture was heated at 80° C. overnight. The mixture was then poured into water, stirred for 1 h, and filtered. The solid was rinsed with water, dried under vacuum. The solid was dissolved in acetonitrile (5 mL) and iodotrimethylsilane (0.590 g, 2.95 mmol) was added at 0° C., then the mixture was stirred at rt for 3 h, diluted with ether and stirred at rt for 1 h. The solids were filtered and rinsed with ether and dried to afford the hydroiodide salt of 6-bromo-4-((cis-4-methoxypyrrolidin-3-yl)amino)pyrrolo[1,2-b]pyridazine-3-carboxamide (0.4 g, 84% yield) as brown solid. $^1$H NMR (400 MHz, METHANOL-$d_4$) δ 8.17 (s, 1H), 7.70 (d, J=1.5 Hz, 1H), 7.07 (s, 1H), 4.97-4.88 (m, 2H), 4.56 (br. s., 1H), 4.16-4.09 (m, 1H), 3.67 (dd, J=11.4, 7.7 Hz, 1H), 3.53-3.50 (m, 3H), 3.50-3.45 (m, 1H), 3.40-3.34 (m, 1H), 3.11 (dd, J=11.6, 8.5 Hz, 1H); MS (ES+) m/z: 353.1, 354.0 (M+H); LC retention time: 2.01 min (analytical HPLC Method J).

Step 2: (±)-6-bromo-4-((cis-1-(1-cyanocyclopropanecarbonyl)-4-methoxypyrrolidin-3-yl)amino)pyrrolo[1,2-b]pyridazine-3-carboxamide

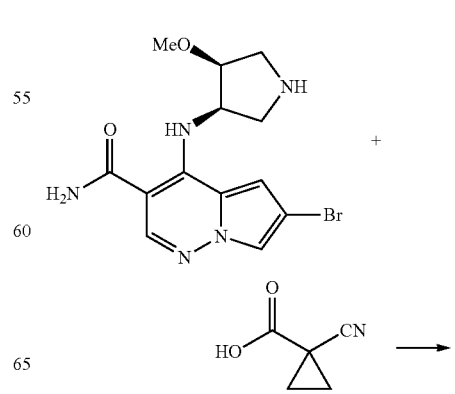

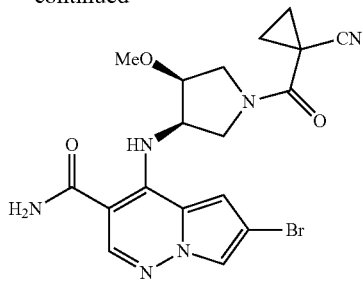

A solution of (±)-6-bromo-4-((cis-4-methoxypyrrolidin-3-yl)amino)pyrrolo[1,2-b]pyridazine-3-carboxamide hydroiodide (0.30 g, 0.62 mmol) in DMF (0.5 mL), was added 1-cyanocyclopropanecarboxylic acid (0.073 g, 0.65 mmol), BOP (0.30 g, 0.68 mmol) and DIPEA (0.23 mL, 1.31 mmol). The mixture was stirred at rt for 2 h, quenched with water, stirred, filtered and rinsed with water. The brown solid was dried under vacuum to afford (±)-6-bromo-4-((cis-1-(1-cyanocyclopropanecarbonyl)-4-methoxypyrrolidin-3-yl)amino)pyrrolo[1,2-b]pyridazine-3-carboxamide (250 mg, 90% yield) as a brown solid. ¹H NMR (400 MHz, METHANOL-d₄) δ 8.17 (d, J=6.6 Hz, 1H), 7.68 (d, J=7.0 Hz, 1H), 7.11 (d, J=17.8 Hz, 1H), 5.09-4.92 (m, 2H), 4.55 (br. s., 2H), 4.46-3.93 (m, 3H), 3.88-3.59 (m, 2H), 3.50 (d, J=14.1 Hz, 3H), 1.75-1.46 (m, 4H); MS (ES+) m/z: 446.1, 447.2 (M+H); LC retention time: 3.1 min (analytical HPLC Method J).

Step 3: (±)-4-1-(1-cyanocyclopropanecarbonyl)-4-methoxypyrrolidin-3-ylamino)-6-(4-methoxyphenyl)pyrrolo[1,2-b]pyridazine-3-carboxamide (Example 300)

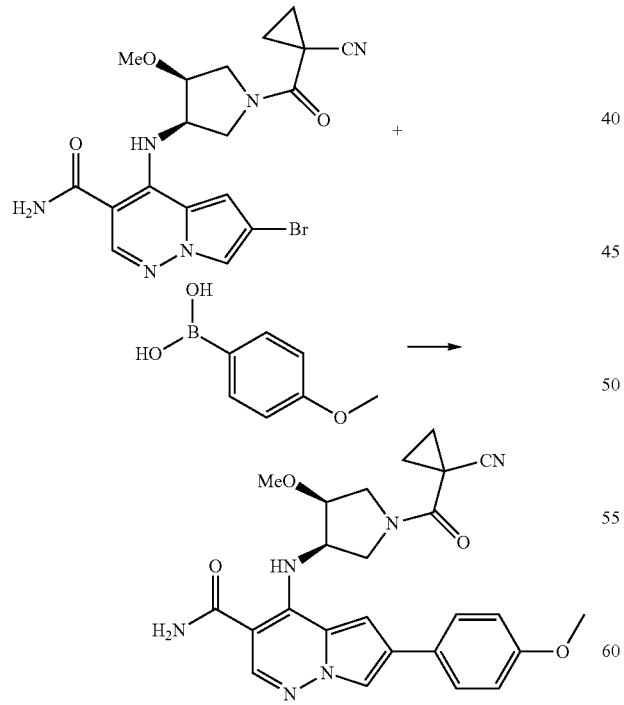

To a solution of (±)-6-bromo-4-((cis-1-(1-cyanocyclopropanecarbonyl)-4-methoxypyrrolidin-3-yl)amino)pyrrolo[1,2-b]pyridazine-3-carboxamide (15 mg, 0.034 mmol) in 1,4-Dioxane (0.3 mL), was added (4-methoxyphenyl)boronic acid, palladium (II) acetate (0.38 mg, 1.68 µmol), X-Phos (1.6 mg, 3.4 µmol) and potassium acetate (2M, 0.06 mL, 0.12 mmol). The reaction vial was purged with nitrogen, sealed and heated at 85° C. overnight. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min. Fractions containing the desired product were combined and dried via centrifugal evaporation to give the title compound (3.8 mg 19% yield). ¹H NMR (500 MHz, METHANOL-d₄, Rotamer) δ 8.10 (d, J=9.4 Hz, 1H), 7.89-7.77 (m, 1H), 7.57 (t, J=8.2 Hz, 4H), 7.14-7.00 (m, 1H), 6.96-6.91 (m, 2H), 5.09-4.95 (m, 1H), 4.55-4.50 (m, 0.5H), 4.32-4.25 (m, 1H), 4.24-4.18 (m, 0.5H), 4.17-4.12 (m, 1H), 4.13-4.01 (m, 1H), 3.95-3.86 (m, 0.5H), 3.84 (s, 3H), 3.73.9s, 0.5H), 3.70-3.56 (m, 1H), 3.52 (d, J=17.8 Hz, 3H), 1.81-1.48 (m, 4H); MS (ES+) m/z: 475.3 (M+H); LC retention time: 1.93 min (analytical HPLC Method J).

Example 301

(+/−)-Cis-44-1-(1-cyanocyclopropanecarbonyl)-4-methoxypyrrolidin-3-yl)amino)-6-(4-fluorophenyl)pyrrolo[1,2-b]pyridazine-3-carboxamide

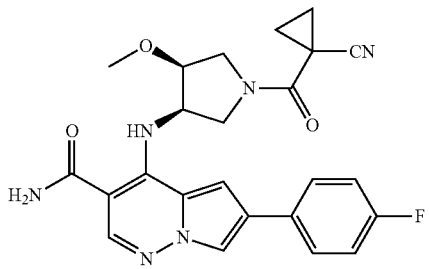 [SMILES: CO[C@H]1CN(C(=O)C2(C#N)CC2)C[C@H]1Nc1c(C(N)=O)cnn2cc(-c3ccc(F)cc3)cc12]

Example 301 was prepared by Suzuki coupling with 6-bromo-4-((cis-1-(1-cyanocyclopropanecarbonyl)-4-methoxypyrrolidin-3-yl)amino)pyrrolo[1,2-b]pyridazine-3-carboxamide (from Step 2 of Example 300) with (4-fluorophenyl)boronic according to the procedure described for Step 3 of Example 300. MS (ES+) m/z: 463.4 (M+H); LC retention time: 1.427 min (analytical HPLC Method J).

Example 302

4-((3R,4S)-1-(1-cyanocyclopropanecarbonyl)-4-methoxypyrrolidin-3-ylamino)-6-(4-methoxyphenyl)pyrrolo[1,2-b]pyridazine-3-carboxamide

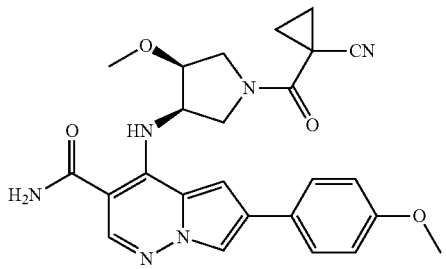 [SMILES: COc1ccc(-c2cc3c(N[C@@H]4CN(C(=O)C5(C#N)CC5)C[C@@H]4OC)c(C(N)=O)cnn3c2)cc1]

Step 1: (3R,4S)-benzyl 3-((6-bromo-3-carbamoylpyrrolo[1,2-b]pyridazin-4-yl)amino)-4-methoxypyrrolidine-1-carboxylate

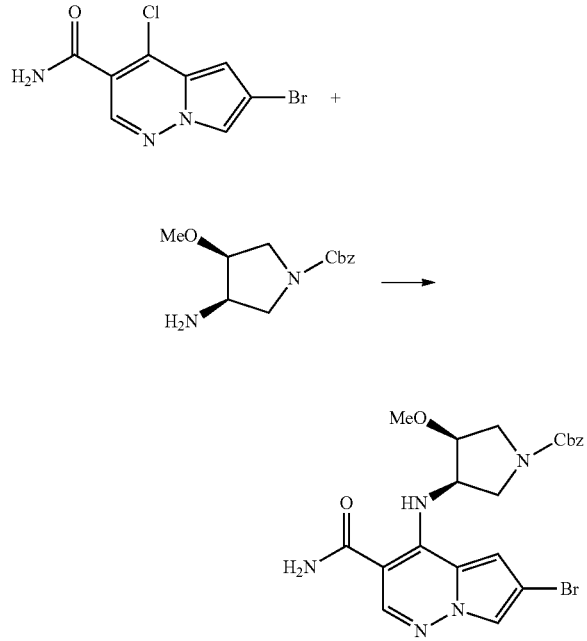

A solution of 6-bromo-4-chloropyrrolo[1,2-b]pyridazine-3-carboxamide (Intermediate 2, 0.4 g, 1.46 mmol) in DMF (2 mL), was added (3R,4S)-benzyl 3-amino-4-methoxypyrrolidine-1-carboxylate (enantiopure Intermediate 12, 0.40 g, 1.60 mmol) and N,N-diisopropylethylamine (0.3 mL, 3.1 mmol). The mixture was heated at 85° C. overnight. After cooling, the mixture was added water, stirred for 3 h, filtered, rinsed with water, and dried to give (3R,4S)-benzyl 3-((6-bromo-3-carbamoylpyrrolo[1,2-b]pyridazin-4-yl)amino)-4-methoxypyrrolidine-1-carboxylate (0.62 g, 87% yield) as a brown solid. MS (ES+) m/z: 487.1, 488.3 (M+H); LC retention time: 3.82 min (analytical HPLC Method).

Step 2: 6-bromo-4-(((3R,4S)-4-methoxypyrrolidin-3-yl)amino)pyrrolo[1,2-b]pyridazine-3-carboxamide

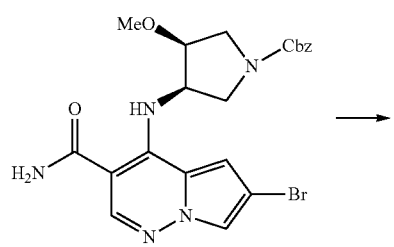

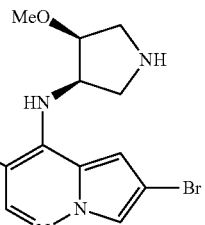

A solution of (3R,4S)-benzyl 3-((6-bromo-3-carbamoylpyrrolo[1,2-b]pyridazin-4-yl)amino)-4-methoxypyrrolidine-1-carboxylate (300 mg, 0.61 mmol) in acetonitrile (5 mL), was added iodotrimethylsilane (123 mg, 0.614 mmol) at 0° C., the mixture was then stirred at rt for 2 h. The mixture was diluted with ether (30 mL), stirred for 1 h, filtered and rinsed with ether to give the hydroiodide salt of 6-bromo-4-(((3R,4S)-4-methoxypyrrolidin-3-yl)amino)pyrrolo[1,2-b]pyridazine-3-carboxamide (292 mg, 99% yield) as a brown solid. $^1$H NMR (400 MHz, METHANOL-$d_4$) δ 8.17 (s, 1H), 7.70 (d, J=1.5 Hz, 1H), 7.07 (s, 1H), 4.97-4.88 (m, 2H), 4.56 (br. s., 1H), 4.16-4.09 (m, 1H), 3.67 (dd, J=11.4, 7.7 Hz, 1H), 3.53-3.50 (m, 3H), 3.50-3.45 (m, 1H), 3.40-3.34 (m, 1H), 3.11 (dd, J=11.6, 8.5 Hz, 1H); MS (ES+) m/z: 353.1, 354.0 (M+H); LC retention time: 2.01 min (analytical HPLC Method B).

Step 3: 6-bromo-4-(((3R,4S)-1-(1-cyanocyclopropanecarbonyl)-4-methoxypyrrolidin-3-yl)amino)pyrrolo[1,2-b]pyridazine-3-carboxamide

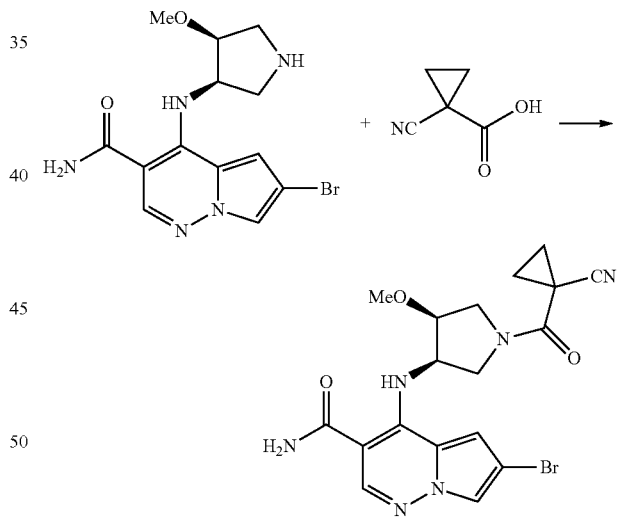

A solution of 6-bromo-4-(((3R,4S)-4-methoxypyrrolidin-3-yl)amino)pyrrolo[1,2-b]pyridazine-3-carboxamide hydroiodide (260 mg, 0.54 mmol) in DMF (1 mL) at rt, was added 1-cyanocyclopropanecarboxylic acid (66 mg, 0.6 mmol), BOP (287 mg, 0.65 mmol) and DIPEA (0.3 mL, 1.7 mmol). The mixture was stirred for 2 h. The reaction was added water, stirred at rt for 2 h, filtered and rinsed with water to give 6-bromo-4-(((3R,4S)-1-(1-cyanocyclopropanecarbonyl)-4-methoxypyrrolidin-3-yl)amino)pyrrolo[1,2-b]pyridazine-3-carboxamide (192 mg, 80% yield) as a brown solid. $^1$H NMR (400 MHz, METHANOL-$d_4$) δ 8.17 (d, J=6.6 Hz, 1H), 7.68 (d, J=7.0 Hz, 1H), 7.11 (d, J=17.8 Hz, 1H), 5.09-4.92 (m, 2H), 4.55 (br. s., 2H), 4.46-3.93 (m, 3H), 3.88-

3.59 (m, 2H), 3.50 (d, J=14.1 Hz, 3H), 1.75-1.46 (m, 4H); MS (ES+) m/z: 446.1, 447.2 (M+H); LC retention time: 3.49 min (analytical HPLC Method B).

Step 4: 4-((3R,4S)-1-(1-cyanocyclopropanecarbonyl)-4-methoxypyrrolidin-3-ylamino)-6-(4-methoxyphenyl)pyrrolo[1,2-b]pyridazine-3-carboxamide (Example 302)

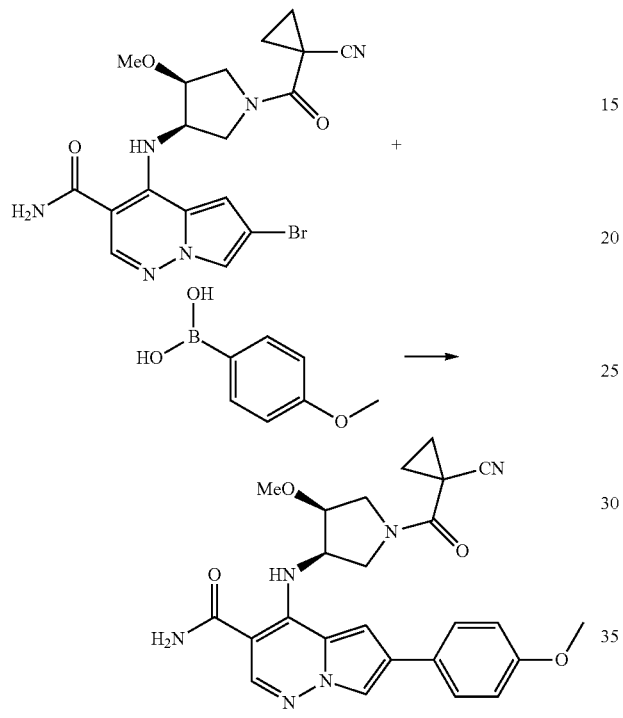

A solution of 6-bromo-4-(((3R,4S)-1-(1-cyanocyclopropanecarbonyl)-4-methoxypyrrolidin-3-yl)amino)pyrrolo[1,2-b]pyridazine-3-carboxamide (20 mg, 0.045 mmol) in 1,4-dioxane (0.3 mL), was added (4-methoxyphenyl)boronic acid (10.2 mg, 0.07 mmol), [1,1'-(diphenylphosphino)ferrocene]-dichloropalladium (II) (3.27 mg, 4.5 µmol), potassium phosphate (0.08 mL, 0.16 mmol). The reaction vial was purged with N$_2$, sealed and heated at 85° C. overnight. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min. Fractions containing the desired product were combined and dried via centrifugal evaporation to give the title compound (9 mg 42% yield). $^1$H NMR (400 MHz, METHANOL-d$_4$) δ 8.19 (d, J=7.0 Hz, 1H), 7.95 (d, J=7.0 Hz, 1H), 7.72-7.65 (m, 2H), 7.28 (d, J=14.5 Hz, 1H), 7.02-6.95 (m, 2H), 5.23-5.11 (m, 1H), 4.57 (dd, J=10.1, 7.0 Hz, 1H), 4.32-4.24 (m, 1H), 4.24-4.16 (m, 1H), 4.14-4.06 (m, 1H), 3.94-3.88 (m, 1H), 3.86 (s, 3H), 3.78-3.71 (m, 1H), 3.60-3.53 (m, 2H), 3.40 (s, 3H), 1.79-1.52 (m, 3H), 1.45-1.35 (m, 1H); MS (ES+) m/z: 475.2 (M+H); LC retention time: 3.49 min (analytical HPLC Method B).

Examples 303-314

Examples 303-314 were prepared by Suzuki coupling of 6-bromo-4-(((3R,4S)-1-(1-cyanocyclopropanecarbonyl)-4-methoxypyrrolidin-3-yl)amino)pyrrolo[1,2-b]pyridazine-3-carboxamide (from Step 3 of Example 302) with appropriate boronic acids or boronic acid esters, which were commercially available, according to the procedure described for Step 4 of Example 302. All Examples were analyzed using HPLC Method I.

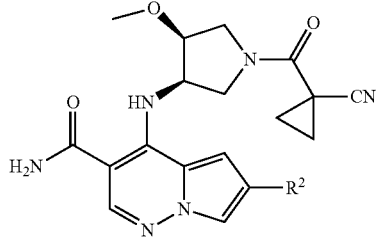

| Ex # | NAME | —R² | HPLC Rt (minutes) | LCMS [m/z (M + H)] |
|---|---|---|---|---|
| 303 | 4-(((3R,4S)-1-(1-cyanocyclopropanecarbonyl)-4-methoxypyrrolidin-3-yl)amino)-6-(3-(methylcarbamoyl)phenyl)pyrrolo[1,2-b]pyridazine-3-carboxamide | 3-(methylcarbamoyl)phenyl | 1.11 | 502.17 |
| 304 | 4-(((3R,4S)-1-(1-cyanocyclopropanecarbonyl)-4-methoxypyrrolidin-3-yl)amino)-6-(4-(ethylcarbamoyl)phenyl)pyrrolo[1,2-b]pyridazine-3-carboxamide | 4-(ethylcarbamoyl)phenyl | 1.18 | 516.17 |
| 305 | 4-(((3R,4S)-1-(1-cyanocyclopropanecarbonyl)-4-methoxypyrrolidin-3-yl)amino)-6-(4-fluorophenyl)pyrrolo[1,2-b]pyridazine-3-carboxamide | 4-fluorophenyl | 1.43 | 463.21 |

-continued

| Ex # | NAME | —R² | HPLC Rt (minutes) | LCMS [m/z (M + H)] |
|---|---|---|---|---|
| 306 | 4-(((3R,4S)-1-(1-cyanocyclopropanecarbonyl)-4-methoxypyrrolidin-3-yl)amino)-6-(6-methoxypyridin-3-yl)pyrrolo[1,2-b]pyridazine-3-carboxamide | | 1.30 | 476.13 |
| 307 | 4-(((3R,4S)-1-(1-cyanocyclopropanecarbonyl)-4-methoxypyrrolidin-3-yl)amino)-6-(4-morpholinophenyl)pyrrolo[1,2-b]pyridazine-3-carboxamide | | 1.18 | 530.12 |
| 308 | 4-(((3R,4S)-1-(1-cyanocyclopropanecarbonyl)-4-methoxypyrrolidin-3-yl)amino)-6-(4-cyanophenyl)pyrrolo[1,2-b]pyridazine-3-carboxamide | | 1.37 | 470.2 |
| 309 | 4-(((3R,4S)-1-(1-cyanocyclopropanecarbonyl)-4-methoxypyrrolidin-3-yl)amino)-6-(4-(2-hydroxypropan-2-yl)phenyl)pyrrolo[1,2-b]pyridazine-3-carboxamide | | 1.28 | 503.24 |
| 310 | 4-(((3R,4S)-1-(1-cyanocyclopropanecarbonyl)-4-methoxypyrrolidin-3-yl)amino)-6-(4-(difluoromethoxy)phenyl)pyrrolo[1,2-b]pyridazine-3-carboxamide | | 1.58 | 511.13 |
| 311 | 4-(((3R,4S)-1-(1-cyanocyclopropanecarbonyl)-4-methoxypyrrolidin-3-yl)amino)-6-(3-fluoro-4-(methylcarbamoyl)phenyl)pyrrolo[1,2-b]pyridazine-3-carboxamide | | 1.14 | 520.12 |
| 312 | 6-(4-(1H-pyrazol-1-yl)phenyl)-4-(((3R,4S)-1-(1-cyanocyclopropanecarbonyl)-4-methoxypyrrolidin-3-yl)amino)pyrrolo[1,2-b]pyridazine-3-carboxamide | | 1.45 | 511.12 |
| 313 | 4-(((3R,4S)-1-(1-cyanocyclopropanecarbonyl)-4-methoxypyrrolidin-3-yl)amino)-6-(3-fluoro-4-methoxyphenyl)pyrrolo[1,2-b]pyridazine-3-carboxamide | | 1.48 | 493.21 |
| 314 | 4-(((3R,4S)-1-(1-cyanocyclopropanecarbonyl)-4-methoxypyrrolidin-3-yl)amino)-6-(4-methyl-3,4-dihydro-2H-benzo[b][1,4]oxazin-7-yl)pyrrolo[1,2-b]pyridazine-3-carboxamide | | 1.42 | 516.23 |

Example 315

4-((3R,4S)-4-methoxy-1-(methylsulfonyl)pyrrolidin-3-ylamino)-6-(6-methoxypyridin-3-yl)pyrrolo[1,2-b]pyridazine-3-carboxamide

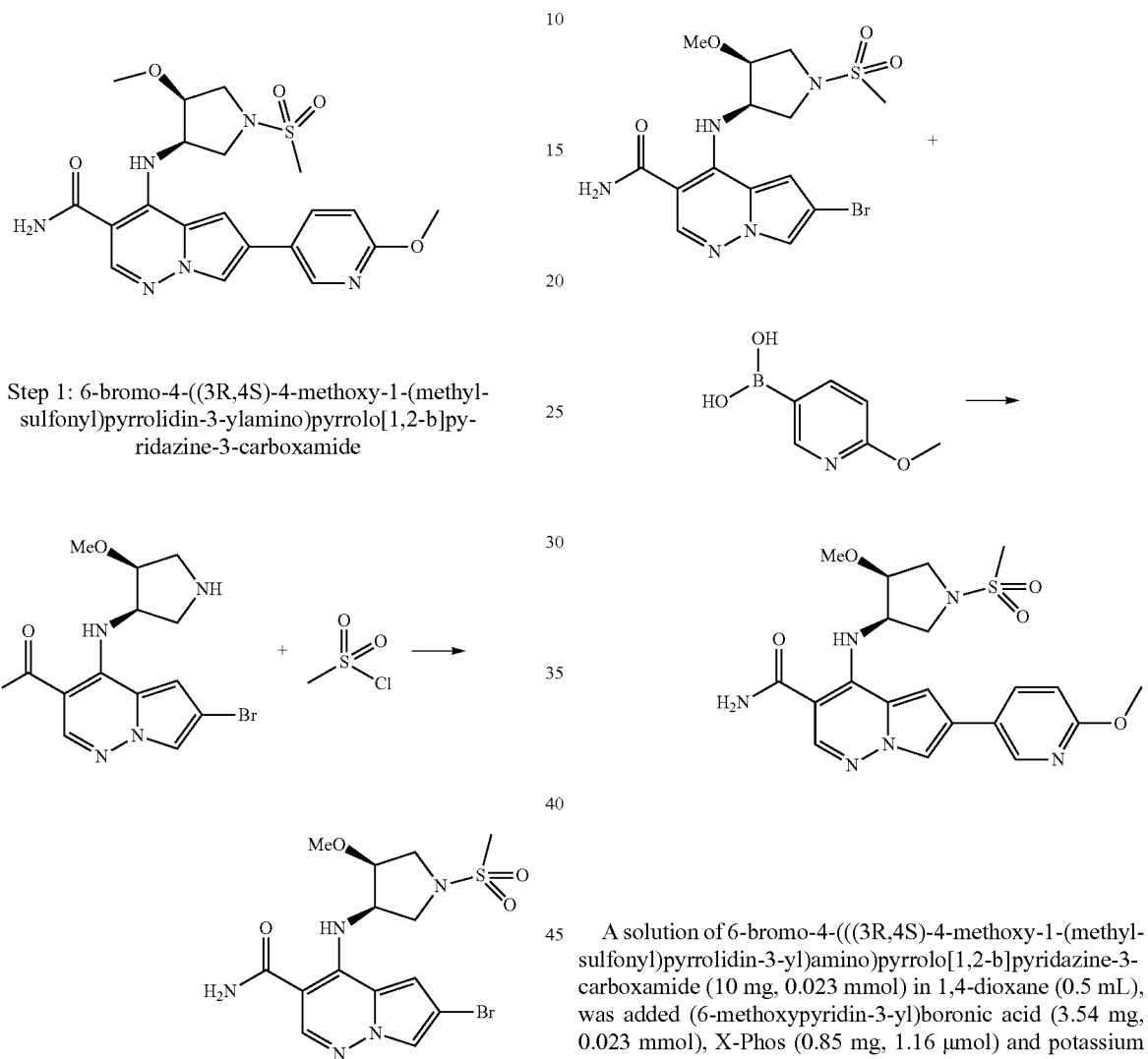

Step 1: 6-bromo-4-((3R,4S)-4-methoxy-1-(methylsulfonyl)pyrrolidin-3-ylamino)pyrrolo[1,2-b]pyridazine-3-carboxamide A solution of 6-bromo-4-(((3R,4S)-4-methoxypyrrolidin-3-yl)amino)pyrrolo[1,2-b]pyridazine-3-carboxamide hydroiodide (from Step 2 of Example 202, 210 mg, 0.436 mmol) in dichloromethane (2 mL), was added N,N-diisopropylethylamine (0.23 mL, 1.31 mmol) and methanesulfonyl chloride (0.043 mL, 0.52 mmol) at rt. The mixture was stirred at rt for 2 h. The reaction was then quenched with water, diluted with dichloromethane, washed with aq. sodium bicarbonate and brine. The organic layer was dried and concentrated. The crude was tritrated in ether and filtered to give 6-bromo-4-(((3R,4S)-4-methoxy-1-(methylsulfonyl)pyrrolidin-3-yl)amino)pyrrolo[1,2-b]pyridazine-3-carboxamide (136 mg, 72% yield) as a yellow solid. MS (ES+) m/z: 432.3, 463.1 (M+H); LC retention time: 2.31 min (analytical HPLC Method H).

Step 2: 4-((3R,4S)-4-methoxy-1-(methylsulfonyl)pyrrolidin-3-ylamino)-6-(6-methoxypyridin-3-yl)pyrrolo[1,2-b]pyridazine-3-carboxamide (Example 315)

A solution of 6-bromo-4-(((3R,4S)-4-methoxy-1-(methylsulfonyl)pyrrolidin-3-yl)amino)pyrrolo[1,2-b]pyridazine-3-carboxamide (10 mg, 0.023 mmol) in 1,4-dioxane (0.5 mL), was added (6-methoxypyridin-3-yl)boronic acid (3.54 mg, 0.023 mmol), X-Phos (0.85 mg, 1.16 μmol) and potassium phosphate (2M, 0.040 mL, 0.081 mmol). The mixture was heated at 100° C. for 3 h. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min. Fractions containing the desired product were combined and dried via centrifugal evaporation to give the title compound (4.0 mg, 37% yield). $^1$H NMR (500 MHz, METHANOL-$d_4$) δ 8.41 (d, J=2.0 Hz, 1H), 8.21-8.10 (m, 1H), 7.96-7.90 (m, 1H), 7.89-7.85 (m, 1H), 7.59 (s, 2H), 7.16-6.99 (m, 1H), 6.88-6.79 (m, 1H), 5.13-4.90 (m, 1H), 4.12 (br. s., 1H), 4.00-3.90 (m, 4H), 3.74-3.67 (m, 1H), 3.58 (dd, J=11.6, 2.2 Hz, 1H), 3.50 (br. s., 3H), 3.42-3.34 (m, 1H), 2.90 (s, 3H), 2.64 (s, 1H); MS (ES+) m/z: 461.2 (M+H); LC retention time: 2.09 min (analytical HPLC Method H).

Example 316

4-((3R,4S)-1-(5-cyanopyrimidin-2-yl)-4-methoxypyrrolidin-3-ylamino)-6-(4-(cyclopropylcarbamoyl)phenyl)pyrrolo[1,2-b]pyridazine-3-carboxamide

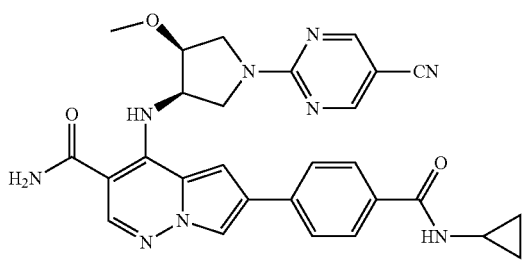 [SMILES: CO[C@H]1CN(c2ncc(C#N)cn2)C[C@H]1Nc1c(C(N)=O)cnn2cc(-c3ccc(C(=O)NC4CC4)cc3)cc12]

Step 1: 6-bromo-4-((3R,4S)-1-(5-cyanopyrimidin-2-yl)-4-methoxypyrrolidin-3-ylamino)pyrrolo[1,2-b]pyridazine-3-carboxamide

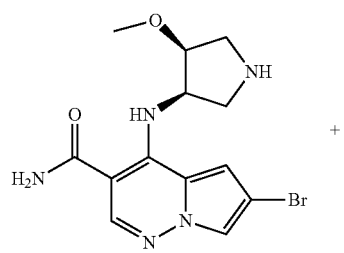

+

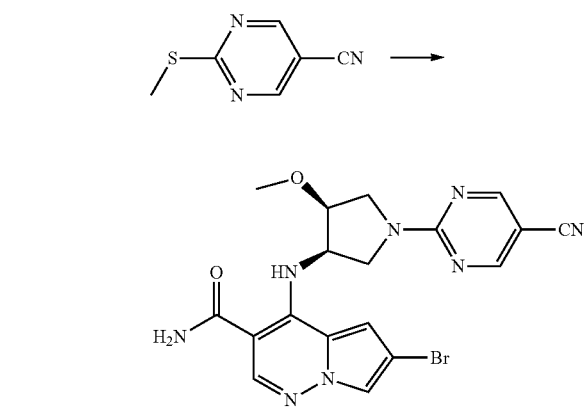

A solution of 6-bromo-4-(((3R,4S)-4-methoxypyrrolidin-3-yl)amino)pyrrolo[1,2-b]pyridazine-3-carboxamide hydroiodide (from Step 2 of Example 302, 200 mg, 0.415 mmol) in N,N-dimethylformamide (1 mL), was added 2-(methylthio)pyrimidine-5-carbonitrile (75 mg, 0.5 mmol) and N,N-diisopropylethylamine (0.22 mL, 1.25 mmol). The mixture was heated at 80° C. for 5 h. The mixture was added water, stirred at rt for 2 h, filtered and rinsed with water to give 6-bromo-4-((3R,4S)-1-(5-cyanopyrimidin-2-yl)-4-methoxypyrrolidin-3-ylamino)pyrrolo[1,2-b]pyridazine-3-carboxamide (162 mg, 80% yield). $^1$H NMR (400 MHz, METHANOL-$d_4$) δ 8.38 (d, J=2.0 Hz, 1H), 8.17 (s, 1H), 7.73 (dd, J=8.9, 2.3 Hz, 1H), 7.10 (s, 1H), 6.59 (s, 1H), 5.10-5.01 (m, 1H), 4.25 (d, J=3.7 Hz, 1H), 4.09 (br. s., 1H), 3.85-3.74 (m, 2H), 3.61-3.46 (m, 5H), 1.28 (d, J=6.4 Hz, 2H); MS (ES+) m/z: 372.26 (M+H); LC retention time: 1.92 min (analytical HPLC Method H).

Step 2: 4-((3R,4S)-1-(5-cyanopyrimidin-2-yl)-4-methoxypyrrolidin-3-ylamino)-6-(4-(cyclopropylcarbamoyl)phenyl)pyrrolo[1,2-b]pyridazine-3-carboxamide (Example 316)

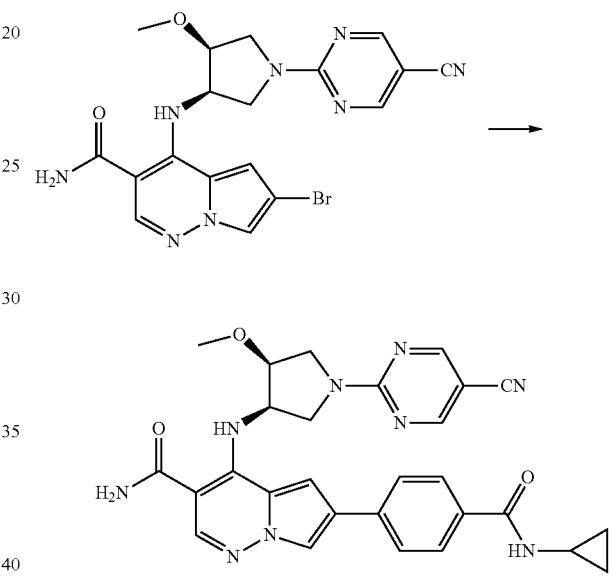

A solution of 6-bromo-4-(((3R,4S)-1-(5-cyanopyrimidin-2-yl)-4-methoxypyrrolidin-3-yl)amino)pyrrolo[1,2-b]pyridazine-3-carboxamide (10 mg, 0.022 mmol) in 1,4-dioxane (0.5 mL), was added [1,1'-[bis(diphenylphosphino)ferrocene]-dicholorpalladium (II) (1.601 mg, 2.187 μmol), [4-(cyclopropylcarbamoyl)phenyl]-boronic acid (6.73 mg, 0.033 mmol) and potassium phosphate (2M, 0.033 mL, 0.066 mmol). The reaction vial was purged with nitrogen, sealed and heated at 140° C. for 1 h. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min. Fractions containing the desired product were combined and dried via centrifugal evaporation to give the title compound (4.2 mg, 35% yield). $^1$H NMR (500 MHz, METHANOL-$d_4$) δ 8.57 (br. s., 1H), 8.51 (d, J=3.0 Hz, 1H), 8.13 (d, J=3.5 Hz, 1H), 7.95 (br. s., 1H), 7.87-7.75 (m, 2H), 7.73-7.66 (m, 2H), 7.62-7.55 (m, 2H), 7.18 (br. s., 1H), 5.09 (br. s., 1H), 4.33-4.22 (m, 2H), 4.02-3.94 (m, 1H), 3.93-3.84 (m, 1H), 3.77-3.69 (m, 1H), 3.52 (d, J=3.5 Hz, 3H), 2.89-2.80

(m, 1H), 0.80 (m, 4H). MS (ES+) m/z: 538.22 (M+H); LC retention time: 1.31 min (analytical HPLC Method I).

Example 317

4-(((3R,4S)-1-(1-cyanocyclopropanecarbonyl)-4-fluoro-4-methylpyrrolidin-3-yl)amino)-6-(1-methyl-1H-pyrazol-4-yl)pyrrolo[1,2-b]pyridazine-3-carboxamide

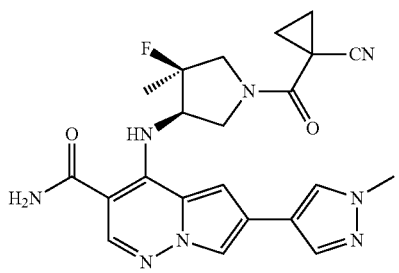 [SMILES: Cn1cc(-c2cc3c(N[C@@H]4CN(C(=O)C5(C#N)CC5)C[C@]4(C)F)c(C(N)=O)cnn3c2)cn1]

Step 1: benzyl allyl(2-methylallyl)carbamate

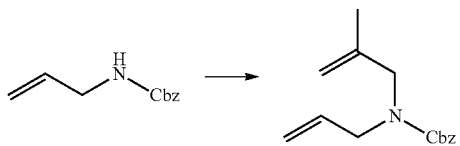 [SMILES: C=CCNC(=O)OCc1ccccc1 ; C=CCN(CC(=C)C)C(=O)OCc1ccccc1]

A solution of benzyl allyl carbamate (24.86 g, 130 mmol) in DME (20 mL) was added over 20 min to a slurry of sodium hydride (6.24 g, 156 mmol, 60% in mineral oil) in DME (60 mL) at room temperature under nitrogen. After 1.5 h at room temperature, 3-bromo-2-methylprop-1-ene (13.11 mL, 130 mmol) was added. After another 6 h at room temperature, the mixture was carefully quenched with water (100 mL), 1 N aqueous HCl (100 mL), and extracted with ethyl acetate (2×200 mL). The combined organic extracts were washed with brine, dried (MgSO4) and concentrated. Silica gel chromatography, eluting with 0-10% ethyl acetate in hexanes, gave benzyl allyl(2-methylallyl)carbamate (23.3 g, 73% yield). 1H NMR (400 MHz, chloroform-d) δ ppm 7.44-7.29 (m, 5H), 5.33-5.01 (m, 4H), 4.92-4.71 (m, 2H), 3.97-3.51 (m, 4H), 1.78-1.59 (m, 3H); MS (ES+) m/z: 246.2 (M+H).

Step 2: benzyl 3-methyl-2,5-dihydro-1H-pyrrole-1-carboxylate

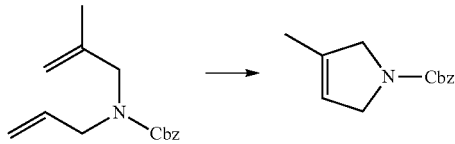 [SMILES: C=CCN(CC(=C)C)C(=O)OCc1ccccc1 ; CC1=CCN(C(=O)OCc2ccccc2)C1]

A solution of benzyl allyl(2-methylallyl)carbamate (20.2 g, 82 mmol) in dichloromethane (500 mL) was purged with argon for 5 min. Grubbs I catalyst (1.694 g, 2.059 mmol) was added and the resulting purple solution was warmed to a gentle reflux under argon for 24 h. The mixture was concentrated and purified by silica gel chromatography, eluting with 0-20% ethyl acetate in hexanes, to give benzyl 3-methyl-2,5-dihydro-1H-pyrrole-1-carboxylate (16.2 g, 91% yield). 1H NMR (400 MHz, chloroform-d) δ ppm 7.65-7.28 (m, 5H), 5.69-5.27 (m, 2H), 4.30-3.91 (m, 5H), 1.84-1.68 (m, 3H); MS (ES+) m/z: 218.2 (M+H).

Step 3: benzyl 1-methyl-6-oxa-3-azabicyclo[3.1.0]hexane-3-carboxylate

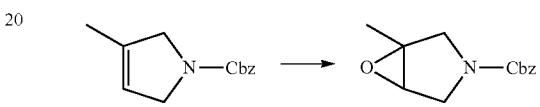

A 0.004 M aqueous solution of EDTA disodium salt dihydrate (354 mL, 0.142 mmol) and 1,1,1-trifluoroacetone (49.6 mL, 567 mmol) was added sequentially to a solution of benzyl 3-methyl-2,5-dihydro-1H-pyrrole-1-carboxylate (15.4 g, 70.9 mmol) in acetonitrile (700 mL) at 0° C. A mixture of oxone (153 g, 248 mmol) and sodium bicarbonate (35.7 g, 425 mmol) was added in 5 portions over 1 h. After additions were complete, the mixture was stirred for another hour at 0° C. and filtered. The filtrate was extracted with dichloromethane (3×300 mL). The combined organic extracts were washed with brine, dried (MgSO4) and concentrated. Silica gel chromatography, eluting with 10-40% ethyl acetate in hexanes, gave benzyl 1-methyl-6-oxa-3-azabicyclo[3.1.0]hexane-3-carboxylate (12.5 g, 76% yield). 1H NMR (400 MHz, chloroform-d) δ ppm 7.73-7.30 (m, 5H), 5.21-4.94 (m, 2H), 4.33-4.05 (m, 1H), 3.93-3.70 (m, 2H), 3.56-3.13 (m, 2H), 1.58-1.44 (m, 3H).

Step 4: (1R,5S)-benzyl 1-methyl-6-oxa-3-azabicyclo[3.1.0]hexane-3-carboxylate

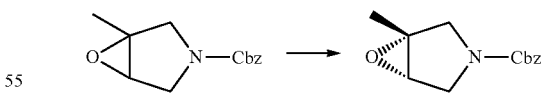

A racemic mixture of benzyl 1-methyl-6-oxa-3-azabicyclo[3.1.0]hexane-3-carboxylate (12 g) was resolved under the following conditions: Column: Chiralpak AD-H (5×25 cm, 5 µm), BPR pressure: 100 bars; temperature: 40° C.; flow rate: 290 mL/min; mobile Phase: CO2/MeOH (90/10); Detector Wavelength: 215 nm; injection: 0.83 mL with cycle time 2.6 min; sample preparation: 12.0 g/400 mL MeOH, 30.0 mg/mL. The desired (1R,5S)-benzyl 1-methyl-6-oxa-3-azabicyclo[3.1.0]hexane-3-carboxylate was obtained as the slower eluting peak (4.5 g).

Step 5: (3R,4R)-benzyl 4-amino-3-hydroxy-3-methylpyrrolidine-1-carboxylate

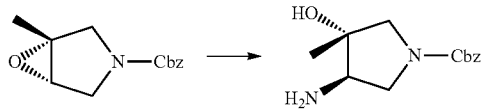 [SMILES: C[C@@]12CN(C(=O)OCc3ccccc3)C[C@@H]1O2 ; C[C@@]1(O)CN(C(=O)OCc2ccccc2)C[C@H]1N]

A mixture of (1R,5S)-benzyl 1-methyl-6-oxa-3-azabicyclo[3.1.0]hexane-3-carboxylate (4.50 g, 19.29 mmol) and concentrated ammonium hydroxide (16 mL, 411 mmol) in dioxane (8 mL) in a sealed vessel was heated to 100° C. for 15 h. The resulting mixture was concentrated to afford (3R,4R)-benzyl 4-amino-3-hydroxy-3-methylpyrrolidine-1-carboxylate along with its regioisomer (4.8 g, 85:15 ratio), which was used in the next step without purification. MS (ES+) m/z: 218.2 (M+H).

Step 6: (3R,4R)-benzyl 4-((6-bromo-3-cyanopyrrolo[1,2-b]pyridazin-4-yl)amino)-3-hydroxy-3-methylpyrrolidine-1-carboxylate

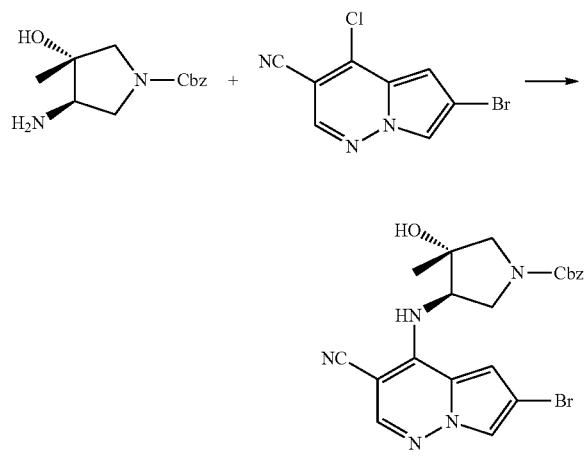

Hunig's base (0.279 mL, 1.599 mmol) was added to a solution of 205 mg (0.80 mmol) of 6-bromo-4-chloropyrrolo[1,2-b]pyridazine-3-carbonitrile (from Step 5 of Intermediate 2 preparation) and (3R,4R)-benzyl 4-amino-3-hydroxy-3-methylpyrrolidine-1-carboxylate (260 mg, 1.039 mmol) in 1-methyl-2-pyrrolidinone (4 mL). The resulting mixture was heated to 90° C. for 2 h, cooled to room temperature, diluted with ethyl acetate (80 mL), washed with water, brine, dried (MgSO4) and concentrated. The residue was purified by silica gel chromatography, eluting with 20 to 80% ethyl acetate in hexanes, to give (3R,4R)-benzyl 4-((6-bromo-3-cyanopyrrolo[1,2-b]pyridazin-4-yl)amino)-3-hydroxy-3-methylpyrrolidine-1-carboxylate (310 mg, 82% yield). 1H NMR (400 MHz, chloroform-d) δ ppm 7.81 (s, 1H), 7.67 (d, J=1.5 Hz, 1H), 7.44-7.31 (m, 5H), 6.91 (d, J=1.5 Hz, 1H), 5.58-5.40 (m, 1H), 5.13 (br. s., 2H), 4.84 (ddd, J=9.1, 6.2, 2.3 Hz, 1H), 4.12 (dd, J=11.8, 5.8 Hz, 1H), 3.63-3.50 (m, 2H), 1.49 (s, 3H); MS (ES+) m/z: 470.3 (M+H).

Step 7: (3S,4R)-benzyl 4-((6-bromo-3-cyanopyrrolo[1,2-b]pyridazin-4-yl)amino)-3-fluoro-3-methylpyrrolidine-1-carboxylate

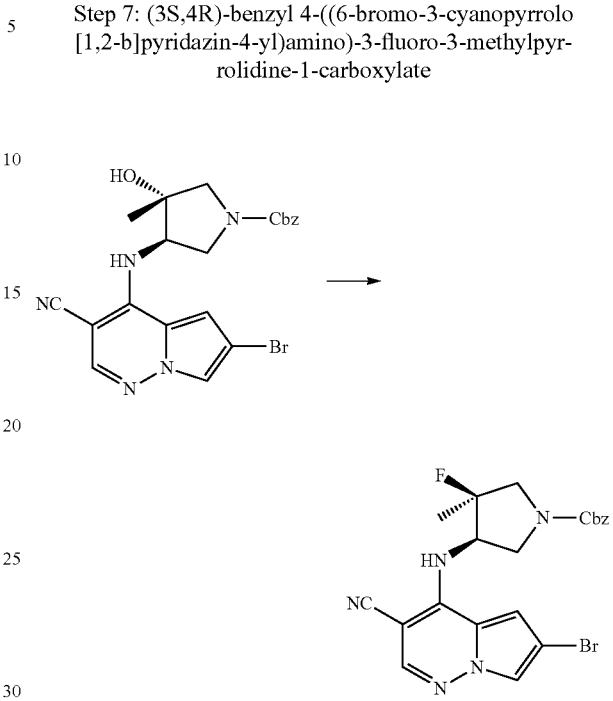

DAST (0.697 mL, 5.27 mmol) was added to a solution of (3R,4R)-benzyl 4-((6-bromo-3-cyanopyrrolo[1,2-b]pyridazin-4-yl)amino)-3-hydroxy-3-methylpyrrolidine-1-carboxylate (310 mg, 0.659 mmol) in dichloromethane (10 mL) at 0° C. After 5 min at 0° C., the mixture was carefully quenched with saturated NaHCO3 (5 mL), diluted with dichloromethane (80 mL), washed with water, brine, dried (MgSO4) and concentrated. The residue was purified by silica gel chromatography, eluting with 0 to 30% ethyl acetate in hexanes, to give (3S,4R)-benzyl 4-((6-bromo-3-cyanopyrrolo[1,2-b]pyridazin-4-yl)amino)-3-fluoro-3-methylpyrrolidine-1-carboxylate (120 mg, 39% yield). 1H NMR (400 MHz, chloroform-d) δ ppm 7.84 (s, 1H), 7.69 (s, 1H), 7.48-7.31 (m, 5H), 6.77 (d, J=8.8 Hz, 1H), 5.25-5.06 (m, 2H), 4.91-4.70 (m, 1H), 4.37-4.21 (m, 1H), 3.99-3.82 (m, 1H), 3.69-3.35 (m, 2H), 1.73-1.55 (m, 3H); MS (ES+) m/z: 472.2 (M+H).

Step 8: (3S,4R)-benzyl 4-((6-bromo-3-carbamoylpyrrolo[1,2-b]pyridazin-4-yl)amino)-3-fluoro-3-methylpyrrolidine-1-carboxylate

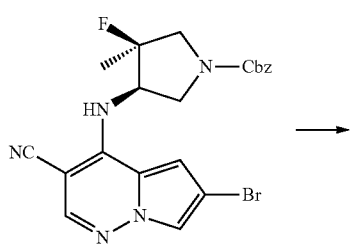

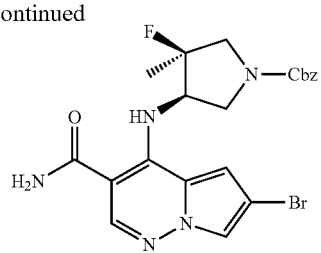

A 2.0 M aqueous NaOH (0.6 mL, 1.200 mmol) was added dropwise to a solution of (3S,4R)-benzyl 4-((6-bromo-3-cyanopyrrolo[1,2-b]pyridazin-4-yl)amino)-3-fluoro-3-methylpyrrolidine-1-carboxylate (120 mg, 0.254 mmol) in methyl sulfoxide (2 mL), methanol (2 mL) and hydrogen peroxide (0.3 mL, 2.94 mmol) at 0° C. After 1 h at 0° C., the mixture was quenched with saturated NaHCO3 (5 mL), diluted with ethyl acetate (80 mL), washed with water, brine, dried (MgSO4) and concentrated. The residue was purified by silica gel chromatography, eluting with 20 to 80% ethyl acetate in hexanes, to give (3S,4R)-benzyl 4-((6-bromo-3-carbamoylpyrrolo[1,2-b]pyridazin-4-yl)amino)-3-fluoro-3-methylpyrrolidine-1-carboxylate (115 mg, 92% yield). 1H NMR (400 MHz, chloroform-d) δ ppm 10.71 (d, J=8.4 Hz, 1H), 7.98-7.85 (m, 1H), 7.73-7.59 (m, 1H), 7.51-7.30 (m, 5H), 6.79 (d, J=7.5 Hz, 1H), 5.79-5.54 (m, 2H), 4.69-4.33 (m, 1H), 4.32-4.08 (m, 1H), 4.00-3.74 (m, 1H), 3.59-3.42 (m, 2H), 1.61-1.43 (m, 3H); MS (ES+) m/z: 490.1 (M+H).

Step 9: 6-bromo-4-(((3R,4S)-4-fluoro-4-methylpyrrolidin-3-yl)amino)pyrrolo[1,2-b]pyridazine-3-carboxamide

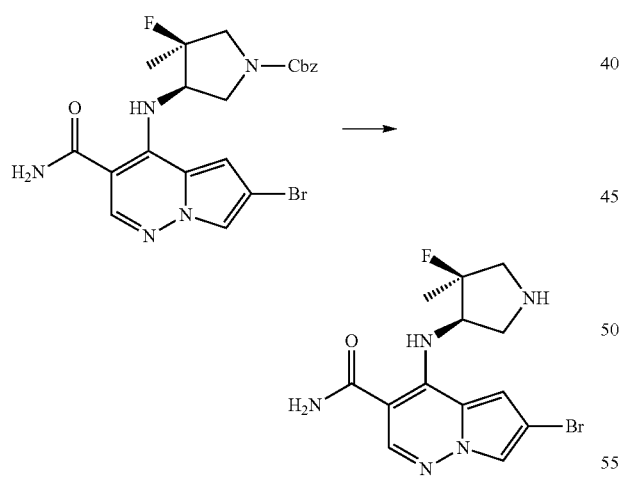

Iodotrimethylsilane (0.134 mL, 0.938 mmol) was added dropwise to a solution of (3S,4R)-benzyl 4-((6-bromo-3-carbamoylpyrrolo[1,2-b]pyridazin-4-yl)amino)-3-fluoro-3-methylpyrrolidine-1-carboxylate (115 mg, 0.235 mmol) in acetonitrile (3 mL). After 1 h at room temperature, the mixture was quenched with methanol (1 mL) and concentrated in vacuo. The solid residue was triturated with diethyl ether (3 mL) and filtered. The filter cake was rinsed with diethyl ether and dried under vacuum to give crude 6-bromo-4-(((3R,4S)-4-fluoro-4-methylpyrrolidin-3-yl)amino)pyrrolo[1,2-b]pyridazine-3-carboxamide hydroiodide (120 mg), which was used in the next step without further purification. MS (ES+) m/z: 356.0 (M+H).

Step 10: 6-bromo-4-(((3R,4S)-1-(1-cyanocyclopropanecarbonyl)-4-fluoro-4-methylpyrrolidin-3-yl)amino)pyrrolo[1,2-b]pyridazine-3-carboxamide

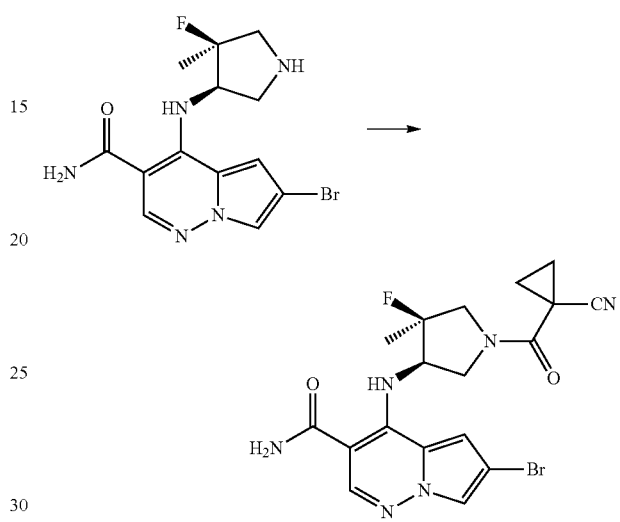

A mixture of 6-bromo-4-(((3R,4S)-4-fluoro-4-methylpyrrolidin-3-yl)amino)pyrrolo[1,2-b]pyridazine-3-carboxamide hydroiodide (100 mg, 0.207 mmol), 1-cyanocyclopropanecarboxylic acid (27.5 mg, 0.248 mmol), Hunig's base (0.144 mL, 0.826 mmol) and BOP (110 mg, 0.248 mmol) in N,N-dimethylformamide (2 mL) was stirred at room temperature for 2 h. The resulting mixture was diluted with ethyl acetate (80 mL) and washed with saturated NaHCO3, water, brine, dried (MgSO4) and concentrated to give crude 6-bromo-4-(((3R,4S)-1-(1-cyanocyclopropanecarbonyl)-4-fluoro-4-methylpyrrolidin-3-yl)amino)pyrrolo[1,2-b]pyridazine-3-carboxamide (70 mg), which was taken to the next step without purification. MS (ES+) m/z: 449.0 (M+H).

Step 11: 4-(((3R,4S)-1-(1-cyanocyclopropanecarbonyl)-4-fluoro-4-methylpyrrolidin-3-yl)amino)-6-(1-methyl-1H-pyrazol-4-yl)pyrrolo[1,2-b]pyridazine-3-carboxamide (Example 317)

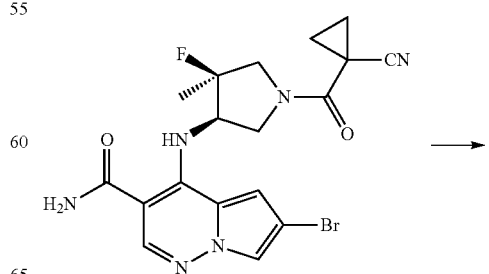

-continued

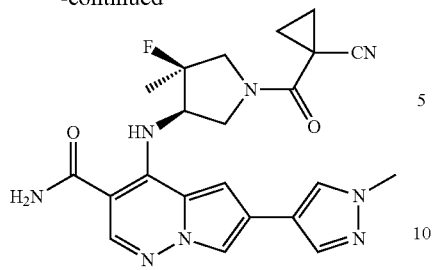

A mixture of 6-bromo-4-(((3R,4S)-1-(1-cyanocyclopropanecarbonyl)-4-fluoro-4-methylpyrrolidin-3-yl)amino)pyrrolo[1,2-b]pyridazine-3-carboxamide (16 mg, 0.036 mmol), 1-methyl-4-(4,4,5,5-tetramethyl-1,3,2-dioxaborolan-2-yl)-1H-pyrazole (14.82 mg, 0.071 mmol), PdCl2(dppf) (2.61 mg, 3.56 mmol) and 2.0 M aqueous solution of potassium phosphate tribasic (0.071 mL, 0.142 mmol) in N,N-dimethylformamide (1 mL) was deoxygenated by bubbling N2 through the mixture for 5 min and heated to 90° C. under N2 for 1 h. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 25 minutes, then a 5-minute hold at 100% B; Flow: 20 mL/min. Fractions containing the desired product were combined and dried via centrifugal evaporation to give the title compound (8.3 mg, 51% yield). 1H NMR (500 MHz, 1:1 mixture of chloroform-d/methanol-d4) δ ppm 8.16 (d, J=8.4 Hz, 1H), 7.90-7.74 (m, 3H), 7.06 (d, J=19.3 Hz, 1H), 5.03-4.87 (m, 1H), 4.38-4.20 (m, 2H), 4.01-3.93 (m, 3H), 3.88-3.54 (m, 2H), 1.99-1.47 (m, 7H); MS (ES+) m/z: 451.2 (M+H); LC retention time: 1.09 min (analytical LCMS Method I).

Example 318

(+/−)-6-(1-methyl-1H-pyrazol-4-yl)-4-(6-methylsulfonyl)-6-azaspiro[3.4]octan-8-ylamino(pyrrolo[1,2-b]pyridazine-3-carboxamide

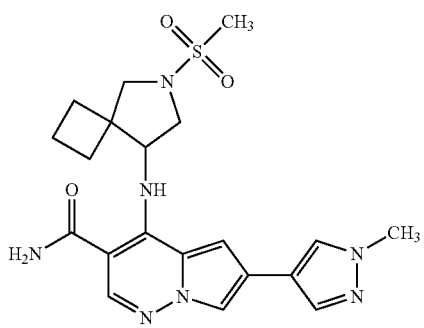 [SMILES: Cn1cc(-c2cc3c(NC4CN(S(C)(=O)=O)CC45CCC5)c(C(N)=O)cnn3c2)cn1]

Step 1: (+/−)-tert-Butyl 6-azaspiro[3.4]octan-8-ylcarbamate

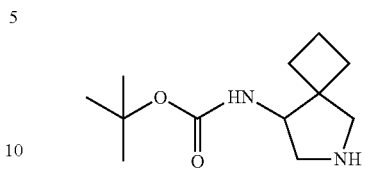

A stirred solution of (+/−)-tert-butyl (6-benzyl-6-azaspiro[3.4]octan-8-yl)carbamate (Intermediate 13, 0.523 g, 1.653 mmol) in ethanol (31.2 mL) with Pd/C (10% b/w) (0.418 g, 3.14 mmol) was hydrogenated for 3 hrs 15 min @ 45 psi. +/−MS after 2 hrs 20 min indicated that the reaction was essentially complete (m/e 227.3, M+H for desired product), 171.1 (M+H-isobutylene); no starting material was detected. The catalyst was removed by filtration through a pad of Celite followed by filtration through VWR 0.45 micron Nylon filter disc. The filtrate was concentrated under vacuum, co-evaporated with CH2Cl2, to yield 0.365 g of the title compound as a viscous yellow oil which became a pale yellow solid on standing under vacuum (0.354 g). +/−MS: m/e 227.3 (M+H). 1H NMR (400 MHz, CHLOROFORM-d) δ 4.59 (br. s., 1H), 3.94 (br. s., 1H), 3.23 (dd, J=11.4, 6.2 Hz, 1H), 3.02 (d, J=11.0 Hz, 1H), 2.86 (d, J=11.0 Hz, 1H), 2.68 (dd, J=11.4, 3.7 Hz, 1H), 2.16-2.06 (m, 1H), 2.02-1.80 (m, 5H), 1.77 (d, J=2.9 Hz, 1H), 1.46 (s, 9H).

Step 2: (+/−)-tert-butyl (6-(methylsulfonyl)-6-azaspiro[3.4]octan-8-yl)carbamate

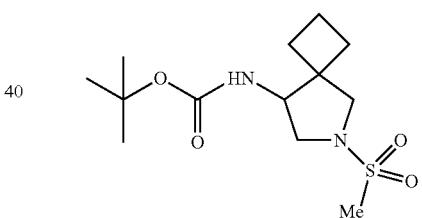

Methanesulfonyl chloride (0.073 ml, 0.939 mmol) was added dropwise to a stirred solution of (+/−)-tert-butyl 6-azaspiro[3.4]octan-8-ylcarbamate (0.177 g, 0.783 mmol) in and triethylamine (0.436 ml, 3.13 mmol) in THF (9.78 mL) @ 0° C. under N2. Stirring @ 0° C. was continued for 1.5 hr. +/−MS after 1 hr 15 min looked the same as for 40 min, mostly desired product with a trace of sm. Additional methanesulfonyl chloride (0.073 ml, 0.939 mmol) was added and stirring was continued for 50 minutes. +/−MS after 40 m indicated that the reaction had proceeded essentially to completion and no starting material was detected by mass spectrum analysis (m/e 303.4, M-H for desired product). The volatile solvents were removed under vacuum. Ethyl acetate and water were added, the organic layer was washed twice with water, followed by washing with brine, and the organic layer was separated, dried (Na2SO4), and concentrated under vacuum to yield 0.231 g of the crude product as a yellow viscous semi-solid. Flash chromatography on silica gel (Teledyne-Isco RediSep Rf 4 g column), eluting with 100 mL of 1:1 hexane:EtOAc yielded 0.197 g of the title compoud as a white solid. +/−MS: m/e 303.4 (M-H). 1H NMR (400 MHz, CHLOROFORM-d) δ 4.61 (br. s., 1H), 4.10 (br. s., 1H), 3.49 (dd, J=10.6, 5.3 Hz, 1H), 3.43-3.36 (m, 2H), 3.29 (dd, J=10.6, 3.1 Hz, 1H), 2.84 (s, 3H), 2.18-2.08 (m, 1H), 2.05-1.86 (m, 5H), 1.47 (s, 9H).

Step 3: (+/−)-6-(Methylsulfonyl)-6-azaspiro[3.4]octan-8-amine

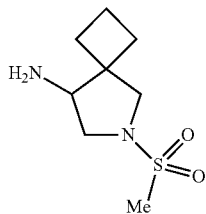

(+/−)-tert-butyl-(6-(methylsulfonyl)-6-azaspiro[3.4]octan-8-yl)carbamate (0.195 g, 0.641 mmol) was dissolved in 4.0 M HCl in dioxane (3.0 mL, 12.00 mmol) and stirred at r. t. for 1 hr 5 min. +/−MS analysis after 50 min. indicated a the reaction had essentially proceeded to completion (m/e 205.2, M+H for desired product; no sm was detected). HCl/dioxane was removed under vacuum, and the residue co-evaporated with ether. The initially obtained oil was dried under vacuum over $P_2O_5$ to yield 0.153 g of the HCl salt of the title compound as a pale tan solid. +/−MS: m/e 205.2 (M+H). $^1$H NMR (400 MHz, DMSO-$d_6$) δ 8.44 (br. s., 2H), 3.74 (br. s., 1H), 3.58-3.49 (m, 1H), 3.45-3.34 (m, 2H), 2.95 (s, 3H), 2.36-2.22 (m, 1H), 2.09-1.92 (m, 2H), 1.91-1.81 (m, 3H).

Step 4: (+/−)-6-Bromo-4-(6-(methylsulfonyl)-6-azaspiro[3.4]octan-8-ylamino[1,2-b]pyridazine-3-carboxamide

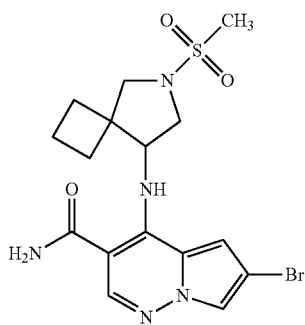 [SMILES: CS(=O)(=O)N1CC(Nc2c(C(N)=O)cnn3cc(Br)cc23)C2(CCC2)C1]

A solution of (+/−)-6-(methylsulfonyl)-6-azaspiro[3.4]octan-8-amine HCl salt (143 mg, 0.594 mmol) in DMA (5.83 mL) was stirred under N2 with 50 mg of 4 A activated molecular sieves for 30 minutes. 6-bromo-4-chloropyrrolo[1,2-b]pyridazine-3-carboxamide (Intermediate 2, 196 mg, 0.713 mmol) and Hunig's Base (0.519 mL, 2.97 mmol) were added, and after 5 minutes, the reaction solution was heated @ 110° C. for 16 hrs. LC/MS and +/−MS analysis after 16 hrs indicated that the reaction had essentially proceeded to completion (m/e 444.10, M+H for desired product with Br-pattern), 427.08 (M+H-ammonia). The volatiles were removed under high vacuum. EtOAc, THF, and 10% aq LiCl were added. The layers were separated, the organic layer was washed twice with 10% aq LiCl solution, and once with brine, dried over $Na_2SO_4$, and concentrated under vacuum to yield 0.322 g of an tan solid. The crude product was suspended in ether, sonicated briefly, collected by filtration, rinsed with ether, and dried under vacuum to yield 188.0 mg of the title compound as a pale tan solid. LC/MS: m/e 444.1 (one of 2 Bromine-pattern peaks, M+H), 425.07 (one of 2 Br-pattern peaks, M+H-ammonia). This material was used in the next step without further purification.

Step 5: (+/−)-6-(1-methyl-1H-pyrazol-4-yl)-4-(6-methylsulfonyl)-6-azaspiro[3.4]octan-8-ylamino(pyrrolo[1,2-b]pyridazine-3-carboxamide (Example 318)

A solution of (+/−)-6-bromo-4-((6-(methylsulfonyl)-6-azaspiro[3.4]octan-8-yl)amino)pyrrolo[1,2-b]pyridazine-3-carboxamide (14.60 mg, 0.033 mmol) and 1-Methyl-4-(4,4,5,5-tetramethyl-1,3,2-dioxaborolan-2-yl)-1H-pyrazole (13.73 mg, 0.066 mmol) in 1,4-dioxane (440 μL) and potassium phosphate (2.0M) (49.5 μL, 0.099 mmol) was degassed for several minutes with N2 gas. 1,1'-Bis(diphenylphosphino)-ferrocenepalladium(II) dichloride, dichloromethane complex (2.71 mg, 3.30 mmol) was added, degassing was continued for 1 more minute. The vial was sealed and the contents were heated @ 110° C. for 1.5 hr. HPLC and LC/MS analysis indicated the reaction had proceeded essentially to completion (m/e 444.21, M+H for desired product, no sm was detected). After cooling to r. t., the reaction was diluted with methanol, filtered and concentrated under vacuum. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-100% B over 25 minutes, then a 5-minute hold at 100% B; Flow: 20 mL/min. Fractions containing the desired product were combined and dried via centrifugal evaporation to afford 8.2 mg of the title compound. LC/MS: m/e 444.0 (M+H), 887.3 (2M+H). $^1$H NMR (500 MHz, METHANOL-$d_4$/CDCl$_3$) δ 8.13 (s, 1H), 7.84 (s, 1H), 7.79 (d, J=2.0 Hz, 1H), 7.76 (s, 1H), 6.93 (d, J=2.0 Hz, 1H), 4.72 (d, J=3.0 Hz, 1H), 3.95 (s, 3H), 3.82 (dd, J=11.1, 4.2 Hz, 1H), 3.71 (d, J=10.4 Hz, 1H), 3.60-3.53 (m, 2H), 2.81 (s, 3H), 2.42-2.30 (m, 1H), 2.28-2.20 (m, 1H), 2.19-2.11 (m, 2H), 2.08-2.00 (m, 2H).

Example 319

(S)-6-(1-methyl-1H-pyrazol-4-yl)-4-(6-methylsulfonyl)-6-azaspiro[3.4]octan-8-ylamino(pyrrolo[1,2-b]pyridazine-3-carboxamide

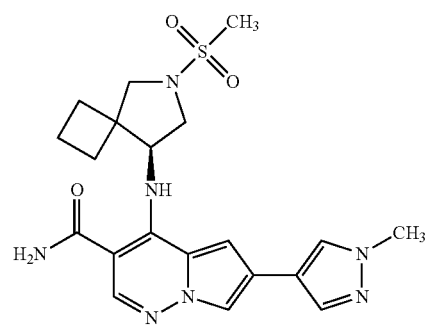 [SMILES: Cn1cc(-c2cc3c(N[C@@H]4CN(S(C)(=O)=O)CC45CCC5)c(C(N)=O)cnn3c2)cn1]

(+/−)-6-(1-methyl-1H-pyrazol-4-yl)-4-(6-methylsulfonyl)-6-azaspiro[3.4]octan-8-ylamino(pyrrolo[1,2-b]pyridazine-3-carboxamide (31 mg) was resolved under the following chiral SFC chromatography conditions: Instrument: Berger SFC MGII, Column: Chiral AS-H 25×3 cm ID, 5 nm, Flow rate: δ 0 mL/min, Mobile Phase: 70/30 CO2/MeOH, Detector Wavelength: 220 nm, sample prep and Injection Volume: 3000 µL of 31 mg dissolved in 7.5 mL 3:1 ACN:MeOH. Fractions were collected containing the resolved enantiomers and were designated as "Peak-1" and "Peak-2" according to the order of elution. The enantiomeric purity of each fraction was estimated to be greater than 99.5% ee based on the prep-SFC chromatograms. Methanol was removed under vacuum for the fractions containing "Peak-1" to yield 12.3 mg of the title compound as a yellow solid. LC/MS: m/e 444.2 (M+H). Methanol was removed under vacuum for peak 2 to yield 13.2 mg of a yellow solid which was assigned the (R) absolute stereochemistry. LC/MS: m/e 444.2 (M+H).

Example 320

(+/−)-4-(6-(1-cyanocyclopropanecarbonyl)-6-azaspiro[3.4]octan-8-ylamino)-6-(1-methyl-1H-pyrazol-4-yl)-pyrrolo[1,2-b]pyridazine-3-carboxamide

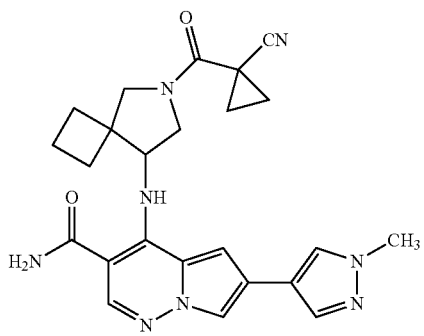 [SMILES: Cn1cc(-c2cc3c(NC4CN(C(=O)C5(C#N)CC5)CC45CCC5)c(C(N)=O)cnn3c2)cn1]

Step 1: (+/−)-tert-Butyl 6-(1-cyanocyclopropanecarbonyl)-6-azaspiro[3.4]octan-8-ylcarbamate

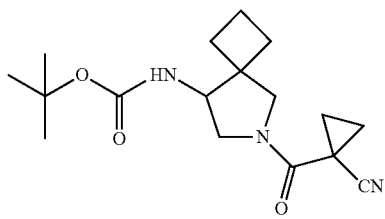 [SMILES: CC(C)(C)OC(=O)NC1CN(C(=O)C2(C#N)CC2)CC12CCC2]

A solution of (+/−)-tert-butyl 6-azaspiro[3.4]octan-8-ylcarbamate (from Step 1 of Example 318, 0.177 g, 0.783 mmol), 1-cyanocyclopropanecarboxylic acid (0.104 g, 0.939 mmol), EDC (0.300 g, 1.565 mmol), HOBT (0.144 g, 0.939 mmol), and Hunig's Base (0.547 mL, 3.13 mmol) in DMA (7.67 mL) was stirred @ r. t. under N2 for 16 hrs. +/−MS analysis after 16 hrs indicated that the reaction had proceeded essentially to completion and no starting material was detected. The volatiles were removed under high vacuum. EtOAc, THF, and 10% aq LiCl solution were added. The layers were separated, the organic layer was washed with 10% aq LiCl solution, 1N HCl (3×), sat. aq NaHCO3 solution (3×), brine, dried over Na2SO4, and concentrated under vacuum to yield 0.223 g of the crude product as an orange viscous semi-solid. Flash chromatography on silica gel (Teledyne-Isco RediSep Rf 4 g column), eluting with 100 mL of 75:25 hexane:EtOAc yielded 0.191 g of the title compound as a pale yellow solid. +/−MS: m/e 320.3 (M+H). 318.5 (M−H), 220.2 (M+H-Boc), 264.2 (M+H-isobutylene). This material was used in the next step without further purification.

Step 2: (+/−)-1-(8-Amino-6-azaspiro[3.4]octan-6-carbonyl)cyclopropanecarbonitrile

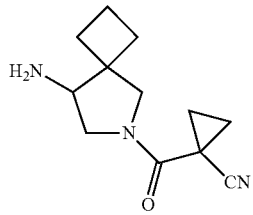 [SMILES: N#CC1(C(=O)N2CC(N)C3(CCC3)C2)CC1]

A solution of (+/−)-tert-butyl (6-(1-cyanocyclopropanecarbonyl)-6-azaspiro[3.4]octan-8-yl)carbamate (0.190 g, 0.595 mmol) in HCl (4.0 M in dioxane) (2.0 mL, 8.00 mmol) was stirred @ r. t. for 50 minutes. +/−MS analysis after 50 min indicated that no starting material could be detected (m/e 220.2, M+H for desired product). The HCl/dioxane was removed under vacuum, and co-evaporated with ether. Additional ether was added to the flask and then decanted off. The ether wash was repeated, and the residual ether was removed under vacuum to afford 0.172 g of the hydrochloride salt of the title compound as a tan, hygroscopic solid. +/−MS: m/e 220.2 (M+H). ¹H NMR (400 MHz, DMSO-d6) δ 8.44 (br. s., 2H), 3.74 (br. s., 1H), 3.58-3.49 (m, 1H), 3.45-3.34 (m, 2H), 2.95 (s, 3H), 2.36-2.22 (m, 1H), 2.09-1.92 (m, 2H), 1.91-1.81 (m, 3H)

Step 3: (+/−)-6-Bromo-4-(6-(1-cyanocyclopropanecarbonyl)-6-azaspiro[3.4]octan-8-ylamino)pyrrolo[1,2-b]pyridazine-3-carboxamide

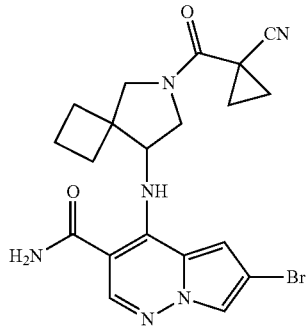 [SMILES: N#CC1(C(=O)N2CC(Nc3c(C(N)=O)cnn4cc(Br)cc34)C3(CCC3)C2)CC1]

A solution of (+/−)-1-(8-amino-6-azaspiro[3.4]octane-6-carbonyl)cyclopropanecarbonitrile, HCl (0.152 g, 0.595 mmol) in DMA (5.83 mL) was stirred under N2 with 100 mg of 4 Å activated molecular sieves for 15 minutes. 6-bromo-4-chloropyrrolo[1,2-b]pyridazine-3-carboxamide (Intermediate 2, 0.196 g, 0.714 mmol) and Hunig's Base (0.520 mL, 2.98 mmol) were added, and after 5 minutes, the reaction solution was heated @ 110° C. for 16 hrs. LC/MS and +/−MS after 16 hrs indicated a complete reaction (m/e 459.14, M+H for desired product with Br-pattern doublet), 440.12 (M+H-ammonia with Br-pattern doublet). The volatiles were removed under high vacuum. EtOAc, THF, and 10% aq LiCl were added. The layers were separated, the organic layer was washed with 10% aq LiCl solution 2×, brine, dried over Na2SO4, and concentrated under vacuum to yield 0.321 g of the crude product as a tan solid. Flash chromatography on silica gel (Teledyne-Isco RediSep Rf), eluting with 200 mL each of 50:50, 30:70, 20:80 hexane:EtOAc, and 100 mL of EtOAc yielded 0.201 g of the title compound as a pale yellow solid. LC/MS: m/e 459.15 (one of 2 Br-pattern peaks, M+H), 442.11 (one of 2 Br-pattern peaks, M+H-ammonia). +/−MS: m/e 455.4 (one of 2 Br-pattern peaks, M−H).

Step 4: (+/−)-4-(6-(1-cyanocyclopropanecarbonyl)-6-azaspiro[3.4]octan-8-ylamino)-6-(1-methyl-1H-pyrazol-4-yl)-pyrrolo[1,2-b]pyridazine-3-carboxamide (Example 320)

A solution of (+/−)-6-bromo-4-((6-(1-cyanocyclopropanecarbonyl)-6-azaspiro[3.4]octan-8-yl)amino)pyrrolo[1,2-b]pyridazine-3-carboxamide (15.09 mg, 0.033 mmol) and 1-Methyl-4-(4,4,5,5-tetramethyl-1,3,2-dioxaborolan-2-yl)-1H-pyrazole (13.73 mg, 0.066 mmol) in 1,4-dioxane (440 µL) and 2M aq. potassium phosphate (49.5 µL, 0.099 mmol) was degassed for several minutes with N2 gas. 1,1'-Bis(diphenylphosphino)ferrocenepalladium(II) dichloride, dichloromethane (2.71 mg, 3.30 µmol) was added and degassing was continued for 1 additional minute. The vial was sealed and the contents were heated @ 110° C. for 1.5 hr. LC/MS and HPLC indicated that no starting material remained (m/e 459.26, no Br pattern, M+H for desired product). After cooling to rt, the reaction was diluted with methanol, filtered and evaporated. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 0-100% B over 25 minutes, then a 5-minute hold at 100% B; Flow: 20 mL/min. Fractions containing the desired product were combined and dried via centrifugal evaporation to afford 8.3 mg of the title compound. ¹H NMR (500 MHz, METHANOL-d₄/CDCl₃) δ 8.13 (d, J=8.9 Hz, 1H), 7.83 (d, J=3.5 Hz, 1H), 7.76 (d, J=5.0 Hz, 2H), 7.06-6.90 (m, 1H), 4.80-4.70 (m, 1H), 4.39-4.34 (m, 0.5 H), 4.29-4.10 (m, 1H), 4.05 (dd, J=11.4, 2.5 Hz, 0.5H), 3.94 (s, 3H), 3.91-3.70 (m, 2H), 2.54-1.99 (m, 6H), 1.83-1.38 (m, 4H).

Example 321

(+/−)-4-(6-(1-cyanocyclopropanecarbonyl)-6-azaspiro[3.4]octan-8-ylamino)-6-(6-methoxypyridin-3yl)pyrrolo[1,2-b]pyridazine-3-carboxamide

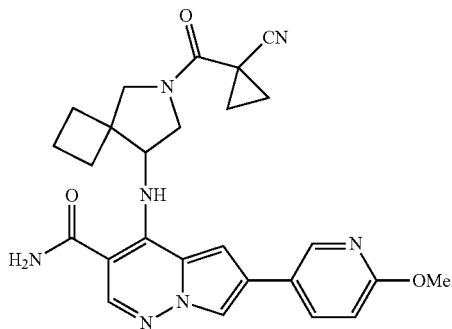 [SMILES: COc1ccc(-c2cc3c(NC4CN(C(=O)C5(C#N)CC5)CC45CCC5)c(C(N)=O)cnn3c2)cn1]

A solution of (+/−)-6-bromo-4-((6-(1-cyanocyclopropanecarbonyl)-6-azaspiro[3.4]octan-8-yl)amino)pyrrolo[1,2-b]pyridazine-3-carboxamide from Step 3 of Example 320 (15.0 mg, 0.033 mmol), 2-Methoxy-5-pyridineboronic acid (10.03 mg, 0.066 mmol) in 1,4-dioxane (437 µl) and potassium phosphate (2.0M) (49.2 µl, 0.098 mmol) was degassed for several minutes with N₂ gas. 1,1'-Bis(diphenylphosphino)ferrocenepalladium(II) dichloride, dichloromethane (2.70 mg, 3.28 µmol) was added, degassing was continued for 1 more minute. The vial was sealed, and the contents were heated @ 105° C. for 50 minutes. HPLC and LC/MS indicated that the reaction had essentially proceeded to completion as no starting material was detected. (m/e 486.24, no Bromine pattern, M+H for desired product). After cooling to room temperature the reaction was diluted with methanol, filtered through a VWR 0.45 micron Nylon filter disc and the crude material was purified via preparative LC/MS with the following conditions: Column: Waters XBridge C18, 19×150 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-100% B over 15 minutes, then a 5-minute hold at 100% B; Flow: 20 mL/min. Fractions containing the desired product were combined and dried via centrifugal evaporation to afford 8.4 mg of the title compound. LC/MS: m/e 486.0 (M+H). 1H NMR (500 MHz, METHANOL-d4/CDCl₃) δ 8.44 (dd, J=7.9, 2.5 Hz, 1H), 8.17 (d, J=9.4 Hz, 1H), 7.96 (ddd, J=8.4, 4.5, 2.5 Hz, 1H), 7.91 (dd, J=12.1, 1.7 Hz, 1H), 7.21-6.99 (m, 1H), 6.86 (d, J=8.4 Hz, 1H), 4.88 (d, J=1.5 Hz, 1H), 4.36 (dd, J=10.9, 5.0 Hz, 0.5H), 4.25 (d, J=10.9 Hz, 1H), 4.11 (d, J=10.9 Hz, 1H), 4.08 (d, J=2.5 Hz, 0.5H), 3.96 (d, J=1.5 Hz, 3H), 3.90 (dd, J=12.9, 4.5 Hz, 0.5H), 3.84-3.71 (m, 0.5H), 2.54-1.96 (m, 6H), 1.84-1.40 (m, 4H)

Example 322

(S)-4-(6-(cyclopropanecarbonyl)-6-azaspiro[3.4]octan-8-ylamino)-6-(1-methyl-1H-pyrazol-4-yl)-pyrrolo[1,2-b]pyridazine-3-carboxamide

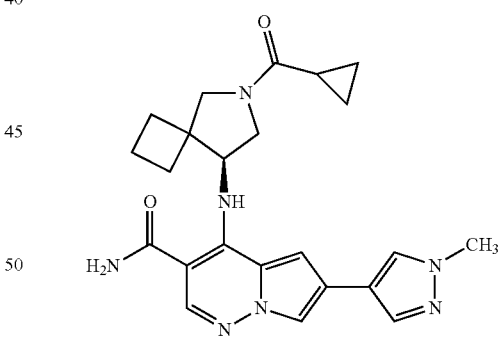

Step 1: (S)-tert-butyl 6-azaspiro[3.4]octan-8-ylcarbamate

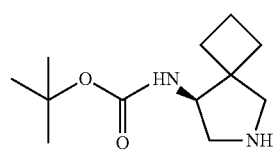 [SMILES: CC(C)(C)OC(=O)N[C@@H]1CNCC12CCC2]

A stirred solution of (S)-tert-butyl (6-benzyl-6-azaspiro [3.4]octan-8-yl)carbamate (enantiopure Intermediate 13, 0.364 g, 1.149 mmol) in Ethanol (21.3 mL) with Pd/C (10% b/w) (0.291 g, 2.73 mmol), was charged with hydrogen gas @ 50 psi in a pressure bottle and agitated for 4 hrs. +/−MS analysis after 3 hrs 15 min indicated that essentially no starting material remained (m/e 227.2, M+H for desired product). The catalyst was removed by filtration, and the filtrate was concentrated under vacuum to yield 0.247 g of the desired product as a tan oil. +/−MS: m/e 227.2 (M+H). $^1$H NMR (400 MHz, CHLOROFORM-d) δ 4.66 (br. s., 1H), 3.96 (br. s., 1H), 3.24 (dd, J=11.3, 6.1 Hz, 1H), 3.05 (d, J=11.0 Hz, 1H), 2.89 (d, J=11.2 Hz, 1H), 2.72 (dd, J=11.6, 3.4 Hz, 1H), 2.13 (dd, J=9.6, 3.4 Hz, 3H), 2.04-1.71 (m, 5H), 1.46 (s, 9H).

Step 2: (S)-Benzyl 8-(tert-butyloxycarbonylamino)-6-azaspiro[3.4]octane-6-carboxylate

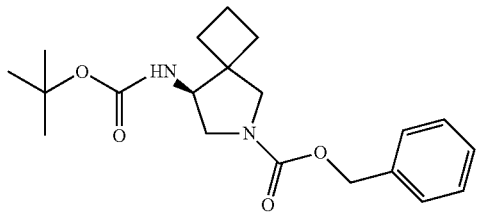 [SMILES: CC(C)(C)OC(=O)N[C@@H]1CN(C(=O)OCc2ccccc2)CC12CCC2]

Benzyl chloroformate (0.224 mL, 1.569 mmol) was added dropwise to a stirred solution of (S)-tert-butyl 6-azaspiro[3.4] octan-8-ylcarbamate (0.2368 g, 1.046 mmol) in dichloromethane (7 mL) and a solution of sodium carbonate (69.1 mg, 0.652 mmol) in Water (1.05 mL) @ 0° C. Stirring of the biphasic reaction was continued @ 0° C. for 45 minutes. +/−MS analysis after 16 hrs indicated that essentially no starting material remained (m/e 361.3, M+H for desired product). A small amount of water was added and the layers were separated. The CH$_2$Cl$_2$ layer was washed with brine, dried over Na$_2$SO$_4$, and concentrated under vacuum to yield 0.433 g of the desired product as a viscous yellow oil. Flash chromatography on silica gel (Teledyne-Isco RediSep Rf 12 g column), eluting with 100 mL ea of 95:5, 90:10, and 200 mL of 80:20 hexane:EtOAc yielded 0.324 g of the title compound as a viscous colorless oil that slowly solidifies upon standing under vacuum to a white solid. +/−MS: m/e 361.3 (M+H), 305.2 (M+H-56 isobutylene), 261.2 (M+H-Boc). $^1$H NMR (400 MHz, CHLOROFORM-d) δ 7.45-7.32 (m, 5H), 5.15 (s, 2H), 4.53 (br. s., 1H), 4.14-4.01 (m, 1H), 3.70-3.50 (m, 2H), 3.47-3.24 (m, 2H), 2.19-2.09 (m, 1H), 2.05-1.83 (m, 5H), 1.49 (s, 9H).

Step 3: (S)-benzyl 8-amino-6-azaspiro[3.4]octane-6-carboxylate

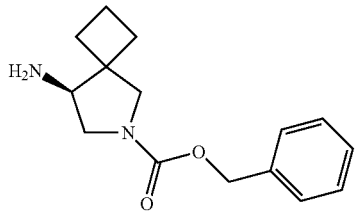 [SMILES: N[C@@H]1CN(C(=O)OCc2ccccc2)CC12CCC2]

A solution of (S)-benzyl 8-((tert-butoxycarbonyl)amino)-6-azaspiro[3.4]octane-6-carboxylate (0.324 g, 0.900 mmol) in HCl (4.0 N in dioxane) (5.0 mL, 20.00 mmol) was stirred for 1 hr 25 min. +/−MS analysis after 1 hr indicated that essentially no starting material remained (m/e 261.3, M+H for desired product). HCl/dioxane was removed under vacuum, co-evaporated with ether, to yield the hydrochloride salt of the title compound as a white, glassy solid (quantitative yield). +/−MS: m/e 261.3 (M+H), 217.2 (M+M-44 CO$_2$). $^1$H NMR (400 MHz, METHANOL-d4) d 7.55-7.20 (m, 5H), 5.20-5.07 (m, 2H), 3.67-3.66 (m, 1H), 3.81-3.64 (m, 2H), 3.62-3.47 (m, 2H), 2.26 (d, J=6.2 Hz, 1H), 2.18-1.87 (m, 5H).

Step 4: (S)-Benzyl 8-(6-bromo-3-carbamoylpyrrolo [1,2-b]pyridazin-4-ylamino)-6-azaspiro[3.4]octane-6-carboxylate

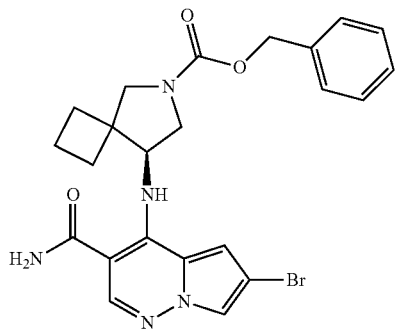 [SMILES: NC(=O)c1cnn2cc(Br)cc2c1N[C@@H]1CN(C(=O)OCc2ccccc2)CC12CCC2]

A solution of (S)-benzyl 8-amino-6-azaspiro[3.4]octane-6-carboxylate, HCl (0.267 g, 0.900 mmol) in DMA (7.0 mL) was stirred under N2 with 100 mg of 4 A activated molecular sieves for 10 minutes. 6-bromo-4-chloropyrrolo[1,2-b]pyridazine-3-carboxamide (Intermediate 2, 0.272 g, 0.990 mmol) and Hunig's Base (0.786 mL, 4.50 mmol) were added and the reaction solution was heated @ 110° C. for 16 hrs. LC/MS after 16 hrs indicated that the reaction had essentially proceeded to completion (m/e 500.2 with Br pattern, M+H for desired product), 997.3 (2M+H). After cooling to r. t., the reaction was diluted with EtOAc and the molecular sieves were removed by filtration. 10% aq LiCl solution was added, the layers were separated, the organic layer was washed twice with 10% aq LiCl solution, once with brine, dried over Na$_2$SO$_4$, and concentrated under vacuum to yield 0.564 g of the a tan-brown oil. Flash chromatography on silica gel (Teledyne-Isco RediSep Rf 24 g column), eluting with 200 mL of 70:30, 400 mL of 50:50, and 200 mL of 30:70 hexane:EtOAc yielded 0.374 g of a pale yellow solid. LC/MS: m/e 500.08 (one of 2 Br-pattern peaks, M+H). A brief sonication followed by a 45-minute stirring trituration with 15 mL of 1:1 hexane:ether yielded 0.318 g of the title compound as a pale yellow solid. LC/MS: m/e 500.06 (one of 2 Br-pattern peaks, M+H). $^1$H NMR (400 MHz, CHLOROFORM-d) δ 10.66-10.40 (m, 1H), 7.86 (s, 1H), 7.63 (s, 1H), 7.43-7.31 (m, 5H), 6.75 (d, J=10.8 Hz, 1H), 5.46 (br. s., 2H), 5.26-5.02 (m, 2H), 4.46 (d, J=4.6 Hz, 1H), 3.86-3.62 (m, 4H), 2.28 (br. s., 1H), 2.16-1.92 (m, 5H).

Step 5: (S)-Benzyl 8-(3-carbamoyl-6-(1-methyl-1H-pyrazol-4-yl)pyrrolo[1,2-b]pyridazin-4-ylamino)-6-azaspiro[3.4]octane-6-carboxylate

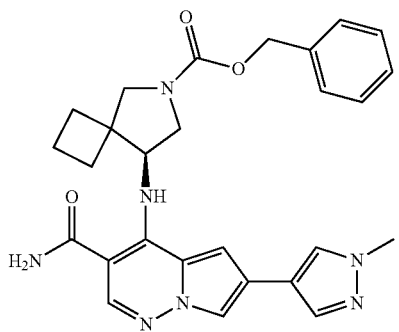 [SMILES: Cn1cc(-c2cc3c(N[C@@H]4CN(C(=O)OCc5ccccc5)CC45CCC5)c(C(N)=O)cnn3c2)cn1]

A solution of (S)-benzyl 8-((6-bromo-3-carbamoylpyrrolo[1,2-b]pyridazin-4-yl)amino)-6-azaspiro[3.4]octane-6-carboxylate (120.0 mg, 0.241 mmol) and 1-methyl-4-(4,4,5,5-tetramethyl-1,3,2-dioxaborolan-2-yl)-1H-pyrazole (100 mg, 0.482 mmol) in 1,4-dioxane (3.20 mL) and potassium phosphate (2.0M) (0.361 mL, 0.722 mmol) was degassed for several minutes with N2 gas. 1,1'-Bis(diphenylphosphino)ferrocenepalladium(II) dichloride dichloromethane complex (19.81 mg, 0.024 mmol) was added, degassing was continued for 1 more minute, vial was sealed, and the contents were heated @ 110° C. for 45 minutes. HPLC and LC/MS after 30 min indicated that the reaction had essentially proceeded to completion (m/e 500.16, M+H for desired product). After cooling to r. t., the reaction was diluted with EtOAc and water. The layers were separated, the EtOAc layer was washed with water, brine, dried over Na$_2$SO$_4$, and concentrated under vacuum to yield a solid. Trituration with ether yielded 124.4 mg of the title compound as a pale mustard-colored solid. LC/MS: m/e 500.15 (M+H). This material was used in the next step without further purification.

Step 6: (S)-4-(6-azaspiro[3.4]octan-8-ylamino)-6-(1-methyl-1H-pyrazol-4-yl)pyrrolo[1,2-b]pyridazine-3-carboxamide

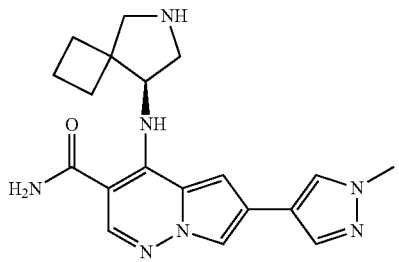 [SMILES: Cn1cc(-c2cc3c(N[C@@H]4CNCC45CCC5)c(C(N)=O)cnn3c2)cn1]

A solution of (S)-benzyl 8-((3-carbamoyl-6-(1-methyl-1H-pyrazol-4-yl)pyrrolo[1,2-b]pyridazin-4-yl)amino)-6-azaspiro[3.4]octane-6-carboxylate (0.120 g, 0.241 mmol) in HBr (33 wt-% in HOAc) (7.42 ml, 45.1 mmol) was stirred @ r. t. for 45 minutes. LC/MS after 23 min. indicated that essentially all of the starting material had been consumed (m/e 366.14, M+H for desired product), 444.1, Br-pattern doublet, M+H for brominated product). HBr in HOAc was removed under vacuum, and the residue co-evaporated twice with toluene. The solvent was removed under reduced pressure and the residue briefly sonicated in the presence of ether to yield 152.3 mg of the HBr salt of the title compound as a tan solid. HPLC and LC/MS indicated the presence of the title compound contaminated with a brominated byproduct. The product mixture was used as is for the next step without further purification.

Step 7: (S)-4-(6-(cyclopropanecarbonyl)-6-azaspiro[3.4]octan-8-ylamino)-6-(1-methyl-1H-pyrazol-4-yl)-pyrrolo[1,2-b]pyridazine-3-carboxamide (Example 322)

A 200 uL aliquot of HATU (23.41 mg, 0.062 mmol) and diisopropylethylamine (21.51 μl, 0.123 mmol) were added to a 200 uL aliquot of 4-(6-azaspiro[3.4]octan-8-ylamino)-6-(1-methyl-1H-pyrazol-4-yl)pyrrolo[1,2-b]pyridazine-3-carboxamide HBr (from Step 6, 15 mg, 0.041 mmol) and cyclopropane carboxylate (1.5 equiv.) in DMF. The reaction was stirred for 3 h at room temperature. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-100% B over 25 minutes, then a 5-minute hold at 100% B; Flow: 20 mL/min. Fractions containing the desired product were combined and dried via centrifugal evaporation to afford the title compound (3.9 mg). $^1$H NMR (500 MHz, METHANOL-d$_4$/CDCl$_3$) δ 8.11 (d, J=11.9 Hz, 1H), 7.80 (d, J=9.9 Hz, 1H), 7.78-7.71 (m, 2H), 6.91 (dd, J=14.1, 1.7 Hz, 1H), 4.83-4.75 (m, 1H), 4.13 (dd, J=10.4, 5.0 Hz, 1H), 4.07-3.99 (m, 1H), 3.96 (s, 1.5H), 3.94 (s, 1.5H), 3.98-3.76 (m, 2H), 2.37 (dd, J=11.1, 7.2 Hz, 1H), 2.28-1.95 (m, 5H), 1.12-0.70 (m, 4H)

Example 323

4-((8S)-6-(2,2-difluorocyclopropanecarbonyl)-6-azaspiro[3.4]octan-8-ylamino)-6-(1-methyl-1H-pyrazol-4-yl)-pyrrolo[1,2-b]pyridazine-3-carboxamide

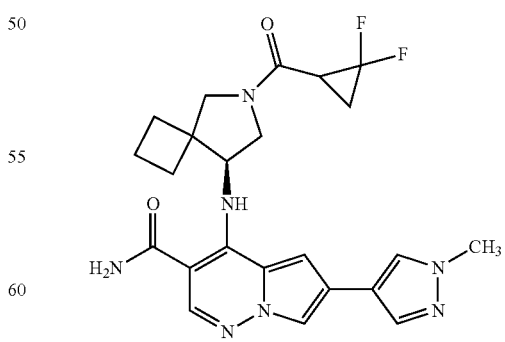

This material was prepared from (S)-4-(6-azaspiro[3.4]octan-8-ylamino)-6-(1-methyl-1H-pyrazol-4-yl)pyrrolo[1,2-b]pyridazine-3-carboxamide HBr (from Step 6 of Example 323), by substituting difluorocyclopropane carboxylate for cyclopropane carboxylate. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-100% B over 25 minutes, then a 5-minute hold at 100% B; Flow: 20 mL/min. Fractions containing the desired product were combined and dried via centrifugal evaporation to afford the title product (2.5 mg). $^1$H NMR (500 MHz, METHANOL-d$_4$/CDCl$_3$) δ 8.14-8.06 (m, 1H), 7.83-7.69 (m, 3H), 6.95-6.85 (m, 1H), 4.85-4.75 (m, 1H), 4.16-4.05 (m, 1H), 3.94 (d, J=1.5 Hz, 3H), 4.01-3.64 (m, 3H), 2.76-2.63 (m, 1H), 2.46-1.95 (m, 6H), 1.83-1.67 (m, 1H).

What is claimed is:

1. A compound having the formula:

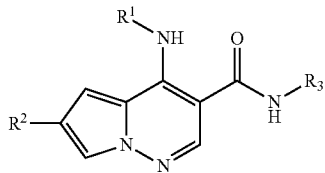

or a stereoisomer or pharmaceutically acceptable salt thereof, wherein $R^1$ is a 4 to 10 membered saturated or partially saturated heterocycle containing one heteroatom selected from O and $NR^{1b}$, substituted with 0-5 $R^{1a}$;

$R^{1a}$ is selected independently at each occurrence from =O, F, Cl, Br, OCF$_3$, CF$_3$, CN, NO$_2$, —(CH$_2$)$_r$OR$^b$, —(CH$_2$)$_r$SR$^b$, —(CH$_2$)$_r$C(O)R$^{1d}$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^{1c}$, —(CH$_2$)$_r$NR$^b$C(O)OR$^c$, —(CH$_2$)$_r$NR$^b$C(O)NR$^{11}$R$^{11}$, —(CH$_2$)$_r$S(O)$_2$NR$^{11}$R$^{11}$, —(CH$_2$)$_r$NR$^b$S(O)$_2$R$^c$, —(CH$_2$)$_r$S(O)R$^c$, —(CH$_2$)$_r$S(O)$_2$R$^c$, C$_{1-6}$ alkyl substituted with 0-2 R$^a$, C$_{1-6}$ haloalkyl, —(CH$_2$)$_r$-3-14 membered carbocycle substituted with 0-2 R$^a$, or —(CH$_2$)$_r$-5-7 membered heterocycle comprising carbon atoms and 1-4 heteroatoms selected from N, O, and S(O)$_p$ substituted with 0-2 R$^a$;

$R^{1b}$ is hydrogen, CF$_3$, —(CH$_2$)$_q$OR$^b$, —(CH$_2$)$_q$SR$^b$, —(CH$_2$)$_q$C(O)R$^{1d}$, —(CH$_2$)$_q$C(O)OR$^b$, —(CH$_2$)$_q$OC(O)R$^b$, —(CH$_2$)$_q$NR$^{11}$R$^{11}$, —(CH$_2$)$_q$C(O)NR$^{11}$R$^{11}$, —(CH$_2$)$_q$NR$^b$C(O)R$^{1c}$, —(CH$_2$)$_q$NR$^b$C(O)OR$^c$, —(CH$_2$)$_q$NR$^b$C(O)NR$^{11}$R$^{11}$, —(CH$_2$)$_q$S(O)$_2$NR$^{11}$R$^{11}$, —S(O)$_2$NR$^{11}$R$^{11}$, —(CH$_2$)$_q$NR$^b$S(O)$_2$R$^c$, —(CH$_2$)$_q$S(O)R$^c$, —(CH$_2$)$_q$S(O)$_2$R$^c$, C$_{1-6}$ alkyl substituted with 0-2 R$^c$, C$_{1-6}$ haloalkyl, —(CH$_2$)$_r$-3-14 membered carbocycle substituted with 0-1 R$^a$, or —(CH$_2$)$_r$-5-7 membered heterocycle comprising carbon atoms and 1-4 heteroatoms selected from N, O, and S(O)$_p$ substituted with 0-2 R$^a$;

$R^{1c}$ is independently at each occurrence hydrogen, C$_{1-6}$ alkyl substituted with 0-3 R$^a$, C$_{2-6}$ alkenyl substituted with 0-3 R$^a$, C$_{3-10}$ cycloalkyl substituted with 0-3 R$^a$, C$_{6-10}$ aryl substituted with 0-3 R$^a$, a 5-10 membered heterocycle containing 1-4 heteroatoms selected from N, O, and S, substituted with 0-3 R$^a$, a 5-10 membered heteroaryl containing 1-4 heteroatoms selected from N, O, and S, substituted with 0-3 R$^a$;

$R^{1d}$ is independently at each occurrence hydrogen, C$_{1-6}$ alkyl substituted with 0-2 R$^d$, C$_{1-6}$ haloalkyl, C(O)NR$^{11}$R$^{11}$, C$_{3-6}$ cycloalkyl substituted with 0-2 R$^d$, or (CH$_2$)$_r$-phenyl substituted with 0-2 R$^a$, a 5-10 membered heterocycle containing 1-4 heteroatoms selected from N, O, and S, substituted with 0-3 R$^a$;

$R^2$ is —NR$^b$C(O)NR$^{11}$R$^{11}$, —NR$^b$C(O)R$^{2b}$, —NR$^b$C(O)OR$^{2d}$, —NR$^b$S(O)$_2$R$^{2b}$, —(—(CH$_2$)$_r$—C$_{6-10}$ aryl substituted with 0-3 R$^{2a}$, or —(CH$_2$)$_r$-4-10 membered heterocycle containing 1-4 heteroatoms selected from N, O, and S substituted with 0-3 R$^{2a}$;

$R^{2a}$ is selected independently at each occurrence from =O, F, Cl, Br, OCF$_3$, CF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^{2b}$, —(CH$_2$)$_r$NR$^b$C(O)OR$^c$, —NR$^b$C(O)NR$^{11}$R$^{11}$, —S(O)$_2$NR$^{11}$R$^{11}$, —NR$^b$S(O)$_2$R$^c$, —S(O)R$^c$, —S(O)$_2$R$^c$, (CH$_2$)$_r$NH(C=NCN)NHR$^{11}$, C$_{1-6}$ alkyl substituted with 0-2 R$^a$, C$_{2-6}$ alkenyl, C$_{1-6}$ haloalkyl, —(CH$_2$)$_r$-3-14 membered carbocycle substituted with 0-1 R$^a$, and —(CH$_2$)$_r$-5-10 membered heterocycle comprising carbon atoms and 1-4 heteroatoms selected from N, O, and S(O)$_p$ substituted with 0-1 R$^a$;

$R^{2b}$ is independently at each occurrence hydrogen, C$_{1-6}$ alkyl substituted with 0-2 R$^a$, C$_{1-6}$ haloalkyl, C$_{3-6}$ cycloalkyl substituted with 0-2 R$^a$, or (CH$_2$)$_r$-phenyl substituted with 0-2 R$^a$, or —(CH$_2$)$_r$-5-10 membered heterocycle comprising carbon atoms and 1-4 heteroatoms selected from N, O, and S(O)p substituted with 0-1 R$^a$;

$R^{2d}$ is independently at each occurrence C$_{1-6}$ alkyl substituted with 0-2 R$^a$, C$_{1-6}$ haloalkyl, C$_{3-6}$ cycloalkyl substituted with 0-2 R$^a$, or (CH$_2$)$_r$-phenyl substituted with 0-2 R$^a$, or —(CH$_2$)$_r$-5-10 membered heterocycle comprising carbon atoms and 1-4 heteroatoms selected from N, O, and S(O)p substituted with 0-1 R$^a$;

$R^3$ is hydrogen, C$_{1-6}$ alkyl substituted with 0-1 R$^a$, phenyl substituted with 0-1 R$^a$, or C$_{3-6}$ cycloalkyl substituted with 0-1 R$^a$;

$R^{11}$ is independently at each occurrence hydrogen or C$_{1-4}$ alkyl substituted with 0-1 R$^a$, C$_{2-4}$ alkenyl substituted with 0-1 R$^a$, —(CH$_2$)$_r$-5-6 membered carbocycle substituted with 0-1 R$^a$, or —(CH$_2$)$_r$-5-7 membered heterocycle comprising carbon atoms and 1-4 heteroatoms selected from N, O, and S(O)$_p$;

$R^a$ is independently at each occurrence hydrogen, =O, F, Cl, Br, OCF$_3$, CF$_3$, CHF2, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^c$R$^c$, —(CH$_2$)$_r$C(O)NR$^c$R$^c$, —(CH$_2$)$_r$NR$^b$C(O)R$^c$, —(CH$_2$)$_r$NR$^b$C(O)OR$^c$, —NR$^b$C(O)NR$^c$R$^c$, —S(O)$_2$NR$^c$R$^c$, —NR$^b$S(O)$_2$R$^c$, —S(O)R$^c$, —S(O)$_2$R$^c$, (CH$_2$)$_r$NH(C=NCN)NHR$^c$, C$_{1-6}$ alkyl substituted with 0-1 R$^f$, C$_{1-6}$ haloalkyl, —(CH$_2$)$_r$-3-14 membered carbocycle substituted with 0-1 R$^d$, or —(CH$_2$)$_r$-5-7 membered heterocycle comprising carbon atoms and 1-4 heteroatoms selected from N, O, and S(O)$_p$ substituted with 0-1 R$^d$, alternatively two R$^a$ on adjacent or the same carbon atom form a cyclic acetal of the formula —O—(CH$_2$)$_n$—O—, or —O—CF$_2$—O—, wherein n is selected from 1 or 2;

$R^b$ is independently at each occurrence hydrogen, C$_{1-6}$ alkyl substituted with 0-2 R$^d$, C$_{1-6}$ haloalkyl, C$_{3-6}$ cycloalkyl substituted with 0-2 R$^d$, or (CH$_2$)$_r$-phenyl substituted with 0-2 R$^d$, or —(CH$_2$)$_r$-5-7 membered heterocycle comprising carbon atoms and 1-4 heteroatoms selected from N, O, and S(O)$_p$ substituted with 0-1 R$^d$, $R^c$ is independently at each occurrence hydrogen, C$_{1-6}$ alkyl substituted with 0-1 R$^f$, C$_{3-6}$ cycloalkyl, or (CH$_2$)$_r$-phenyl substituted with 0-1 R$^f$;

$R^d$ is independently at each occurrence hydrogen, F, Cl, Br, $OCF_3$, $CF_3$, CN, $NO_2$, —$OR^e$, —$(CH_2)_rC(O)R^c$, —$NR^e R^e$, —$NR^eC(O)OR^c$, —$C(O)OR^e$, —$SO_2N(R^e)_2$, $C_{1-6}$ alkyl, or $(CH_2)_r$-phenyl;

$R^e$ is independently at each occurrence hydrogen, $C_{1-6}$ alkyl, $C_{3-6}$ cycloalkyl, or $(CH_2)_r$-phenyl;

$R^f$ is independently at each occurrence hydrogen, halo, CN, $SO_2$-methyl, phenyl, $NH_2$, NHCO methyl, OH, or $OCH_3$;

q is 2 to 5;

r is 0, 1, 2, 3, or 4; and p is 0, 1, or 2.

2. A compound according to claim 1 wherein:

$R^1$ is a 4- to 10-membered saturated or partially saturated heterocycle containing one heteroatom selected from O and $NR^{1b}$, substituted with 0-2 $R^{1a}$, wherein the heterocycle is selected from pyrrolidinyl piperidinyl, octahydrocylopentapyrrolyl, tetrahydrofuranyl, tetrahydropyranyl, oxabicycloheptane, and oxetane;

$R^{1a}$ is independently at each occurrence F, Cl, Br, —$(CH_2)_r OR^b$, $C_{1-6}$ alkyl substituted with 0-2 $R^a$, or —$(CH_2)_r$-3-6 membered carbocycle substituted with 0-2 $R^a$;

$R^{1b}$ is hydrogen, —$(CH_2)_rC(O)R^{1d}$, —$(CH_2)_rC(O)OR^b$, —$(CH_2)_qS(O)_2R^c$, $C_{1-6}$ alkyl substituted with 0-2 $R^a$, or —$(CH_2)_r$-5-7 membered heterocycle comprising carbon atoms and 1-4 heteroatoms selected from N, O, and $S(O)_p$ substituted with 0-2 $R^a$;

$R^{1d}$ is independently at each occurrence hydrogen, $C_{1-6}$ alkyl substituted with 0-2 $R^d$, $C_{1-6}$ haloalkyl, C(O)$NR^{11}R^{11}$, $C_{3-6}$ cycloalkyl substituted with 0-2 $R^d$, or $(CH_2)_r$-phenyl substituted with 0-2 $R^a$, a 5-10 membered heterocycle containing 1-4 heteroatoms selected from N, O, and S, substituted with 0-3 $R^a$; and r is 0, 1, or 2.

3. A compound according to claim 2 wherein $R^3$ is hydrogen.

4. A compound according to claim 3 wherein:

$R^2$ is —$NR^bC(O)R^{2b}$, $C_{6-10}$ aryl substituted with 0-3 $R^{2a}$, or 5-10 membered heterocycle containing 1-4 heteroatoms selected from N, O, and $S(O)_p$ substituted with 0-3 $R^{2a}$;

$R^{2a}$ is independently at each occurrence =O, F, Cl, Br, $CF_3$, CN, —$(CH_2)_rOR^b$, —$(CH_2)_rC(O)R^b$, —$(CH_2)_rC(O)OR^b$, —$(CH_2)_rNR^{11}R^{11}$, —$(CH_2)_rC(O)NR^{11}R^{11}$, —$(CH_2)_rNR^bC(O)R^{2b}$, —$S(O)_2R^c$, $C_{1-6}$ alkyl substituted with 0-2 $R^a$, —$(CH_2)_r$-3-14 membered carbocycle substituted with 0-1 $R^a$, or —$(CH_2)_r$-5-10 membered heterocycle comprising carbon atoms and 1-4 heteroatoms selected from N, O, and $S(O)_p$ substituted with 0-1 $R^a$;

$R^{2b}$ is independently at each occurrence $C_{1-6}$ alkyl substituted with 0-2 $R^a$ or $C_{1-6}$ haloalkyl; and r is 0, 1, or 2.

5. A compound according to claim 1 having the formula:

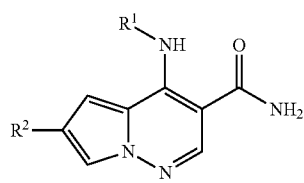

or a stereoisomer or pharmaceutically acceptable salt thereof, wherein:

$R^1$ is a 4- to 10-membered saturated or partially saturated heterocycle containing one heteroatom selected from O and $NR^{1b}$, substituted with 0-2 $R^{1a}$, wherein the heterocycle is selected from pyrrolidinyl piperidinyl, octahydrocylopentapyrrolyl, tetrahydrofuranyl, tetrahydropyranyl, oxabicycloheptane, and oxetane;

$R^{1a}$ is independently at each occurrence F, Cl, Br, —$(CH_2)_r OR^b$, $C_{1-6}$ alkyl substituted with 0-2 $R^a$, —$(CH_2)_r$-3-6 membered carbocycle substituted with 0-2 $R^a$;

$R^{1b}$ is hydrogen, —$(CH_2)_rC(O)R^{1d}$, —$(CH_2)_rC(O)OR^b$, —$(CH_2)_qS(O)_2R^c$, $C_{1-6}$ alkyl substituted with 0-2 $R^a$, or —$(CH_2)_r$-5-7 membered heterocycle comprising carbon atoms and 1-4 heteroatoms selected from N, O, and $S(O)_p$ substituted with 0-2 $R^a$;

$R^{1d}$ is independently at each occurrence hydrogen, $C_{1-6}$ alkyl substituted with 0-2 $R^d$, $C_{1-6}$ haloalkyl, C(O)$NR^{11}R^{11}$, $C_{3-6}$ cycloalkyl substituted with 0-2 $R^d$, or $(CH_2)_r$-phenyl substituted with 0-2 $R^a$, a 5-10 membered heterocycle containing 1-4 heteroatoms selected from N, O, and S, substituted with 0-3 $R^a$;

$R^2$ is —$NR^bC(O)R^{2b}$, $C_{6-10}$ aryl substituted with 0-3 $R^{2a}$, or 4-10 membered heterocycle containing 1-4 heteroatoms selected from N, O, and $S(O)_p$ substituted with 0-3 $R^{2a}$;

$R^{2a}$ is independently at each occurrence =O, F, Cl, Br, $CF_3$, CN, —$(CH_2)_rOR^b$, —$(CH_2)_rC(O)R^b$, —$(CH_2)_rC(O)OR^b$, —$(CH_2)_rNR^{11}R^{11}$, —$(CH_2)_rC(O)NR^{11}R^{11}$, —$(CH_2)_rNR^bC(O)R^{2b}$, —$S(O)_2R^c$, $C_{1-6}$ alkyl substituted with 0-2 $R^a$, —$(CH_2)_r$-3-14 membered carbocycle substituted with 0-1 $R^a$, or —$(CH_2)_p$-5-10 membered heterocycle comprising carbon atoms and 1-4 heteroatoms selected from N, O, and $S(O)_p$ substituted with 0-1 $R^a$;

$R^{2b}$ is independently at each occurrence $C_{1-6}$ alkyl substituted with 0-2 $R^a$ or $C_{1-6}$ haloalkyl;

$R^a$ is independently at each occurrence hydrogen, F, Cl, Br, $CF_3$, CN, —$(CH_2)_rOR^b$, —$(CH_2)_rNR^cR^c$, $C_{1-6}$ alkyl substituted with 0-1 $R^f$, $C_{1-6}$ haloalkyl;

$R^b$ is independently at each occurrence hydrogen, $C_{1-6}$ alkyl substituted with 0-2 $R^d$, $C_{3-6}$ cycloalkyl substituted with 0-2 $R^d$, or —$(CH_2)_r$-5-7 membered heterocycle comprising carbon atoms and 1-4 heteroatoms selected from N, O, and $S(O)_p$ substituted with 0-1 $R^d$;

$R^c$ is independently at each occurrence hydrogen or $C_{1-6}$ alkyl;

$R^d$ is independently at each occurrence hydrogen, F, Cl, Br, $CF_3$, CN, —$OR^e$, or $C_{1-6}$ alkyl;

$R^e$ is independently at each occurrence hydrogen or $C_{1-6}$ alkyl;

q is 2 to 5;

r is 0, 1, 2, 3, or 4; and p is 0, 1, or 2.

6. A compound according to claim 5 wherein $R^1$ is a heterocycle containing a heteroatom, $NR^{1b}$, wherein said heterocycle is pyrrolidinyl, piperidinyl, or octahydrocylopentapyrrolyl, each further substituted with 0-2 $R^{1a}$.

7. A compound according to claim 6 wherein $R^1$ is a pyrrolidinyl having the formula:

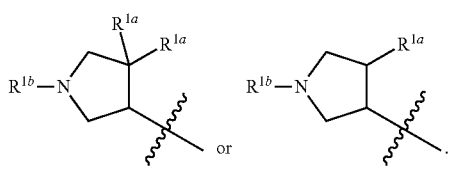
8. A compound according to claim 6 wherein $R^1$ is a piperidinyl having the formula:
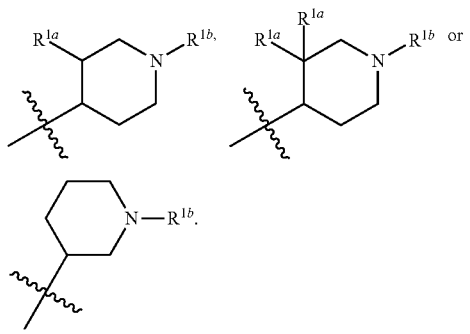
9. A compound according to claim 6 wherein $R^1$ is octahydrocylopentapyrrolyl having the formula
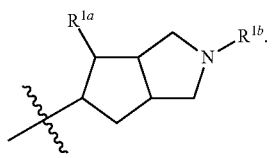
10. A compound according to claim 5 wherein $R^1$ is selected from:
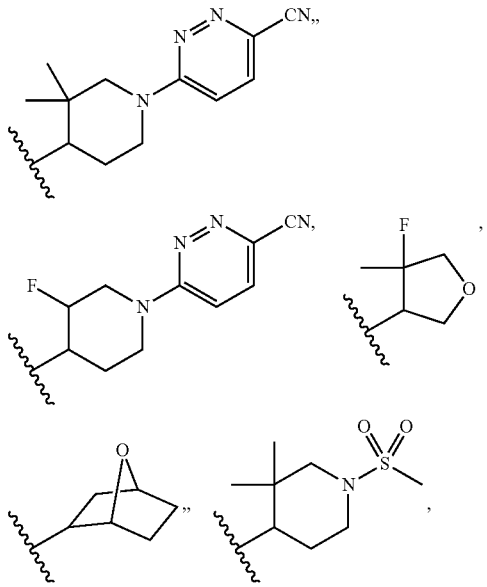
-continued
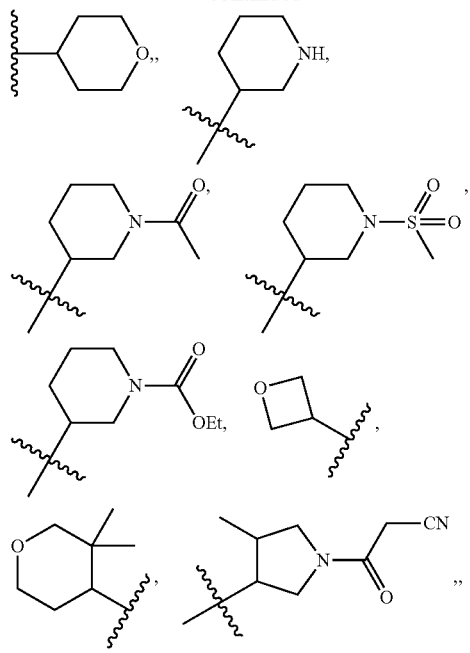
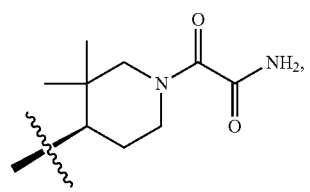
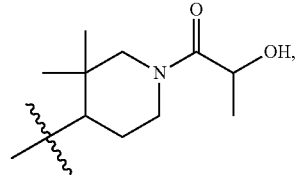
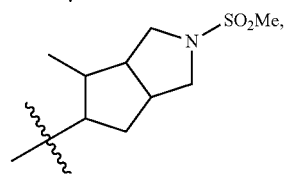
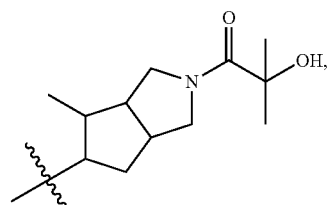
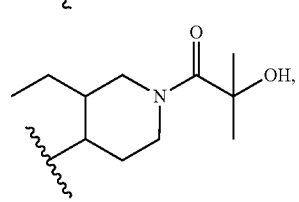

339
-continued
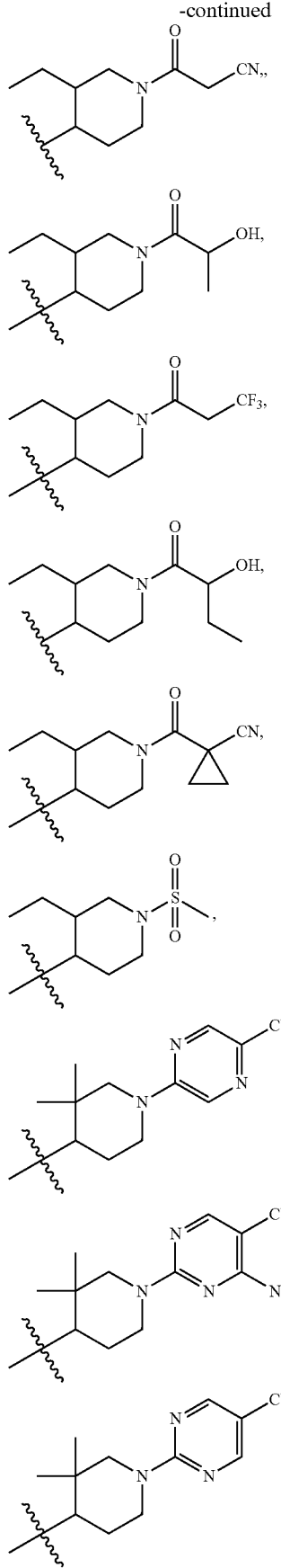
340
-continued
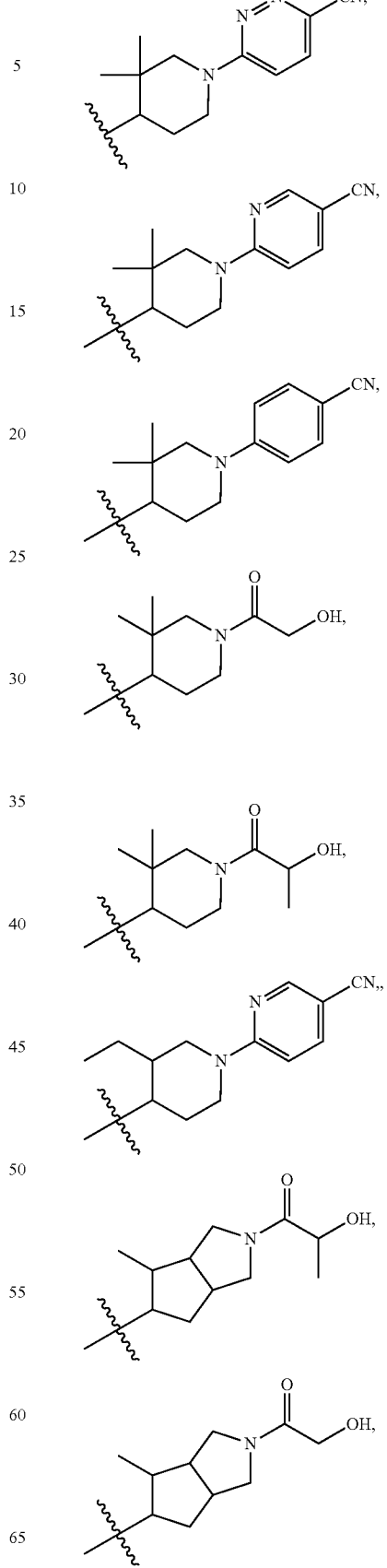

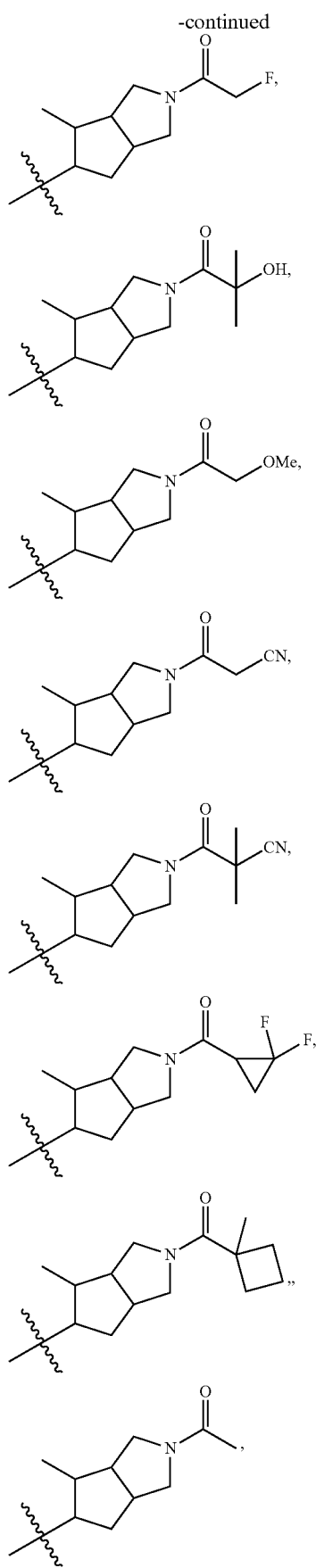
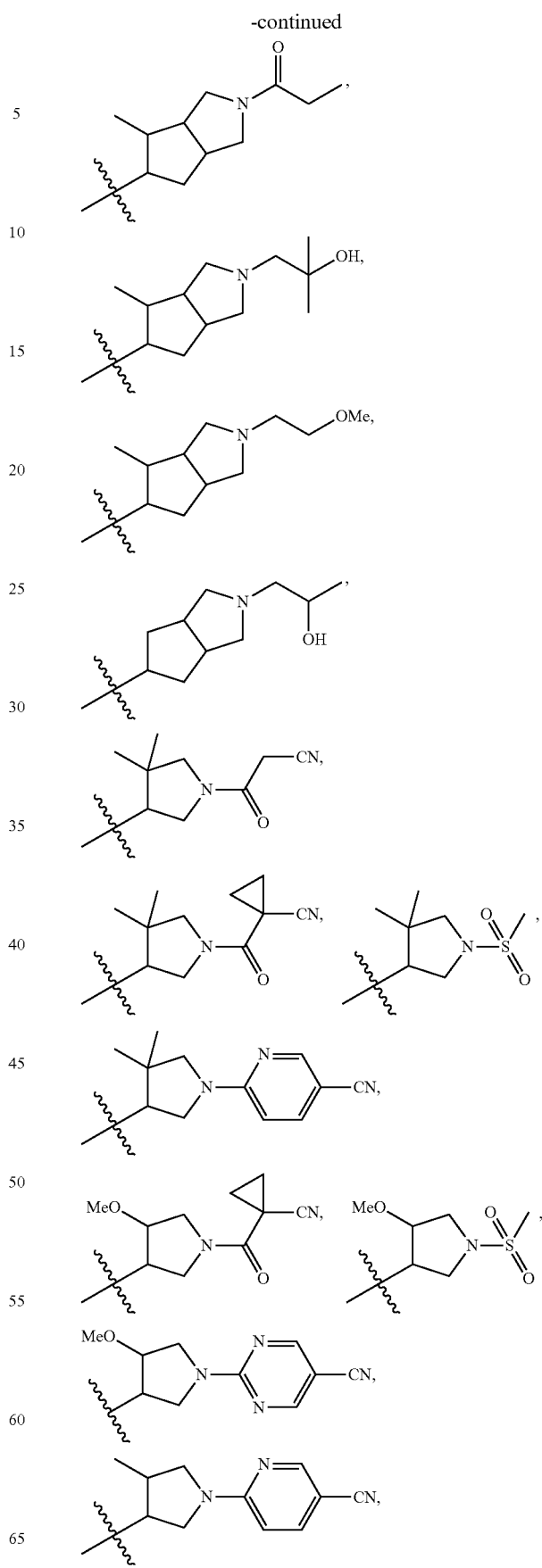

343
-continued
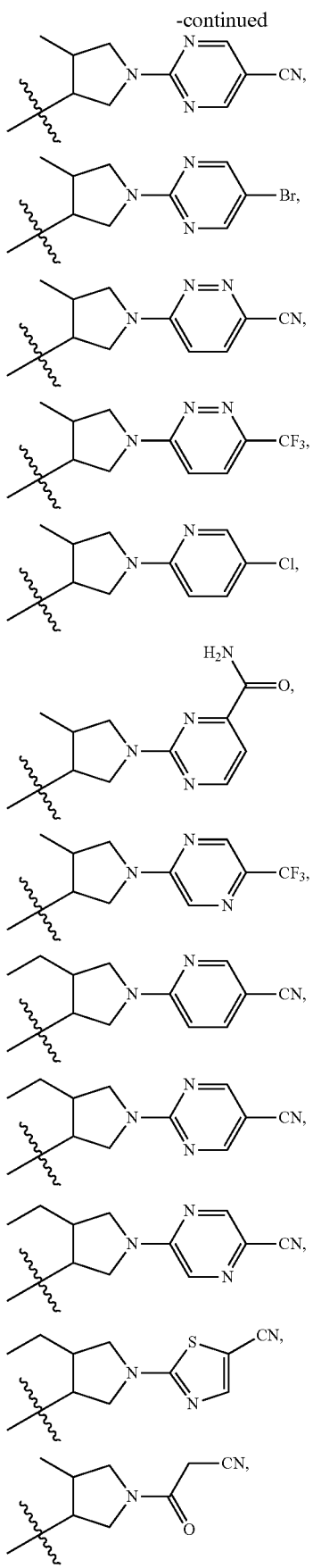
344
-continued
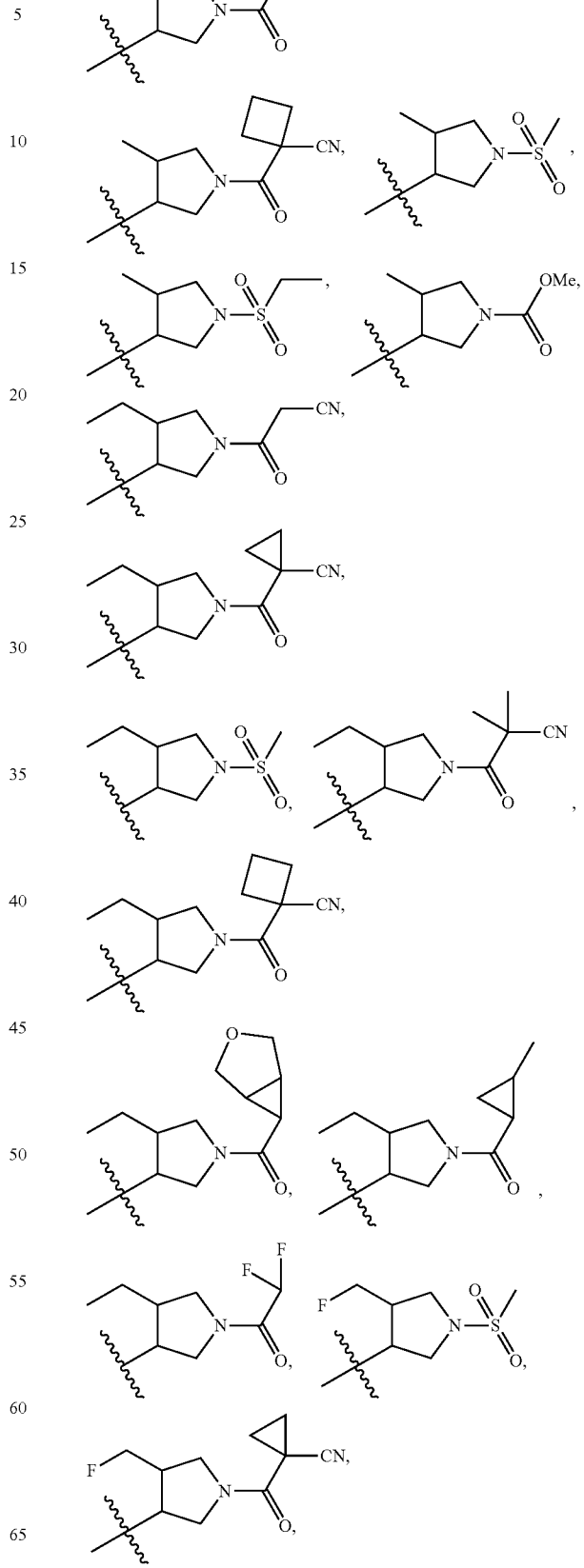

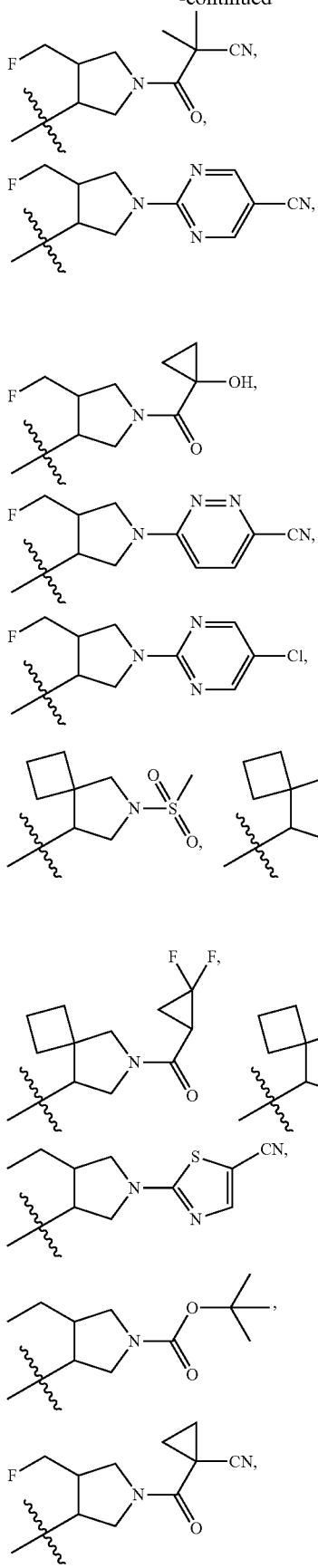

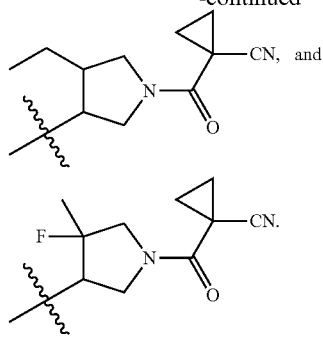

11. A compound according to claim 5 wherein:
R² is selected from NR$^b$C(O)R$^{2b}$ and a group selected from phenyl, pyridyl, morpholinyl, pyridinyl, quinolinyl, pyrrolidinonyl, pyrazolyl, pyrimidinyl, imidazolidinonyl, pyradizinyl, oxadiazolyl, tetrazolyl, dihydrobenzooxazinyl, pyridinonyl, oxadiazolyl, triazolyl and oxazolyl, each group substituted with 0-3 R$^{2a}$; and
R$^{2a}$ is OR$^b$, cyano, CF$_3$, (CH$_2$)$_n$C(O)R$^{b\prime}$, C(O)$_2$R$^b$, fluoro, methyl, (CH$_2$)$_r$C(O)N(R$^{11}$)(R$^{11}$), isopropyl, propyl, ethyl, isobutyl, (CH$_2$)$_2$R$^a$, phenyl, =O, N(R$^{11}$)(R$^{11}$), CH(R$^a$)$_2$, morpholinyl, C(CH$_3$)$_2$R$^a$, S(O)$_2$R$^c$, CD$_3$, CH$_2$CH(R$^a$)(R$^a$), CH$_2$C(CH$_3$)$_2$R$^a$, CH$_2$CH(R$^a$)CH$_3$, CH(R$^a$)$_2$, CH$_2$NR$^b$C(O)R$^{2b}$ or (CH$_2$)$_2$R$^a$.

12. A compound of claim 11 wherein R² is selected from:

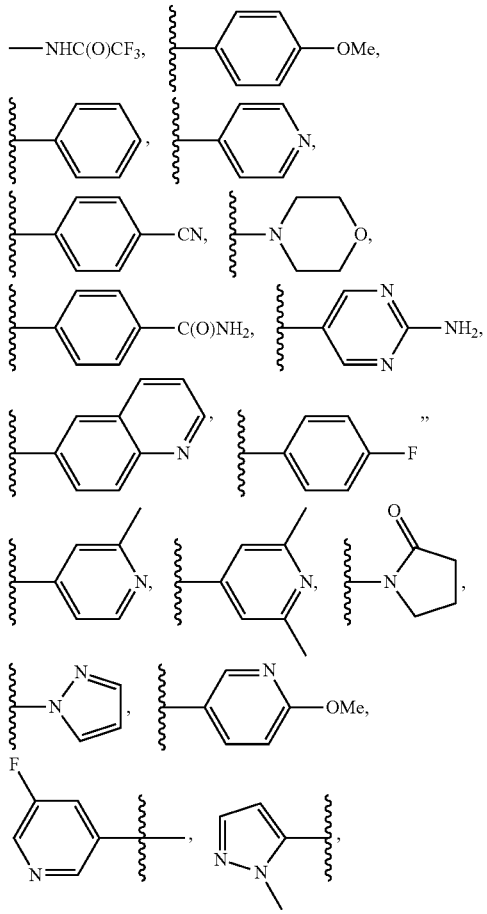

347
-continued
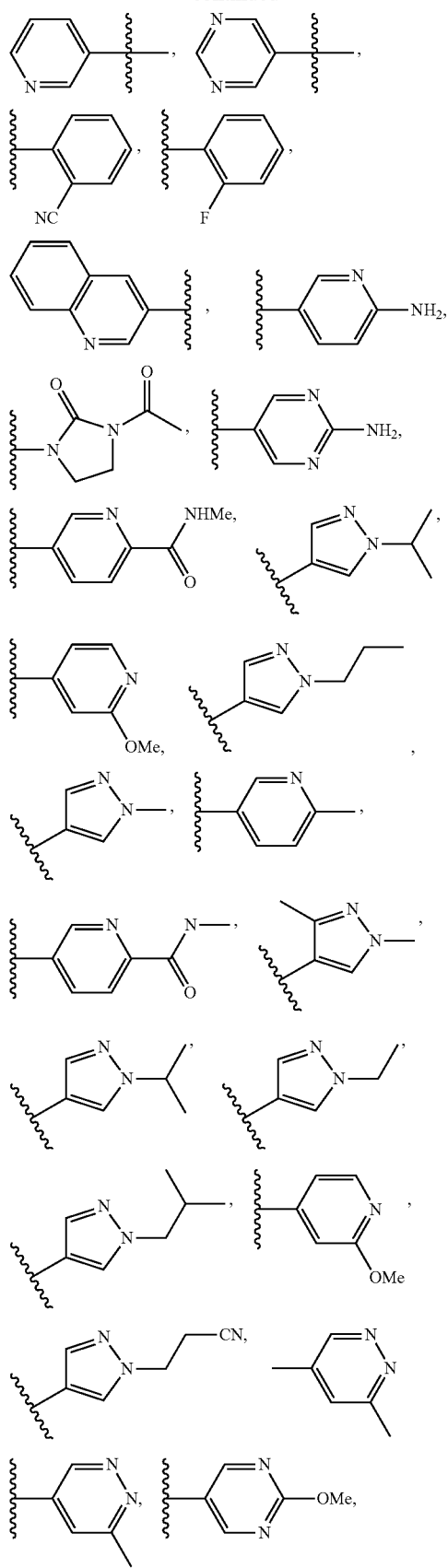
348
-continued
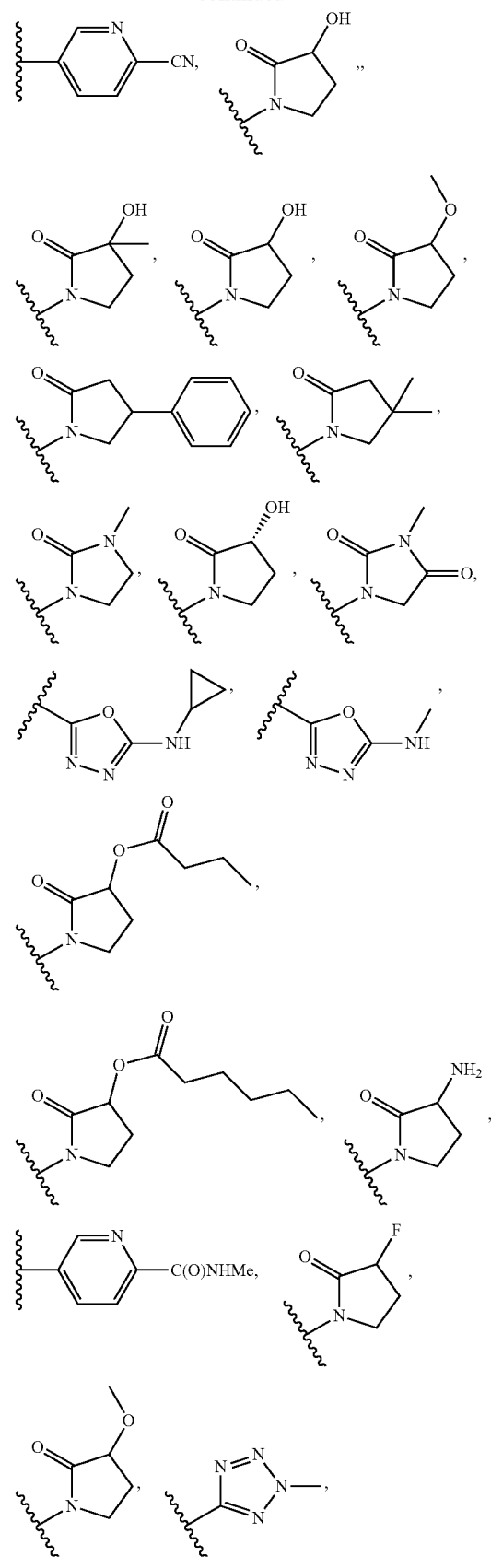

349
-continued
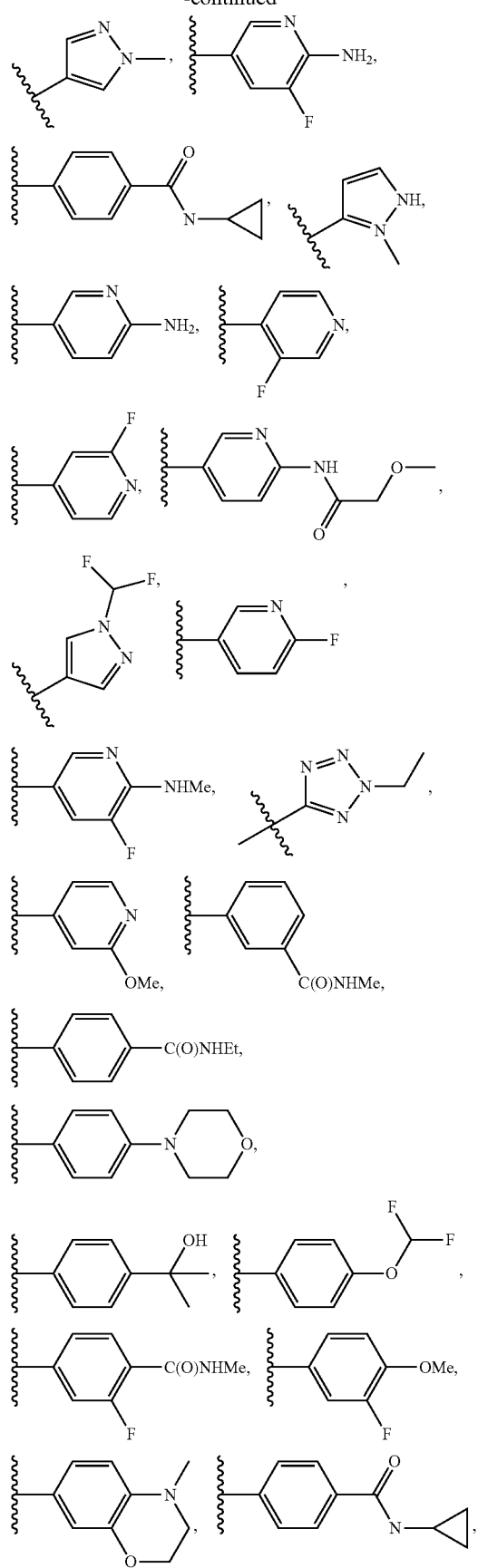
350
-continued
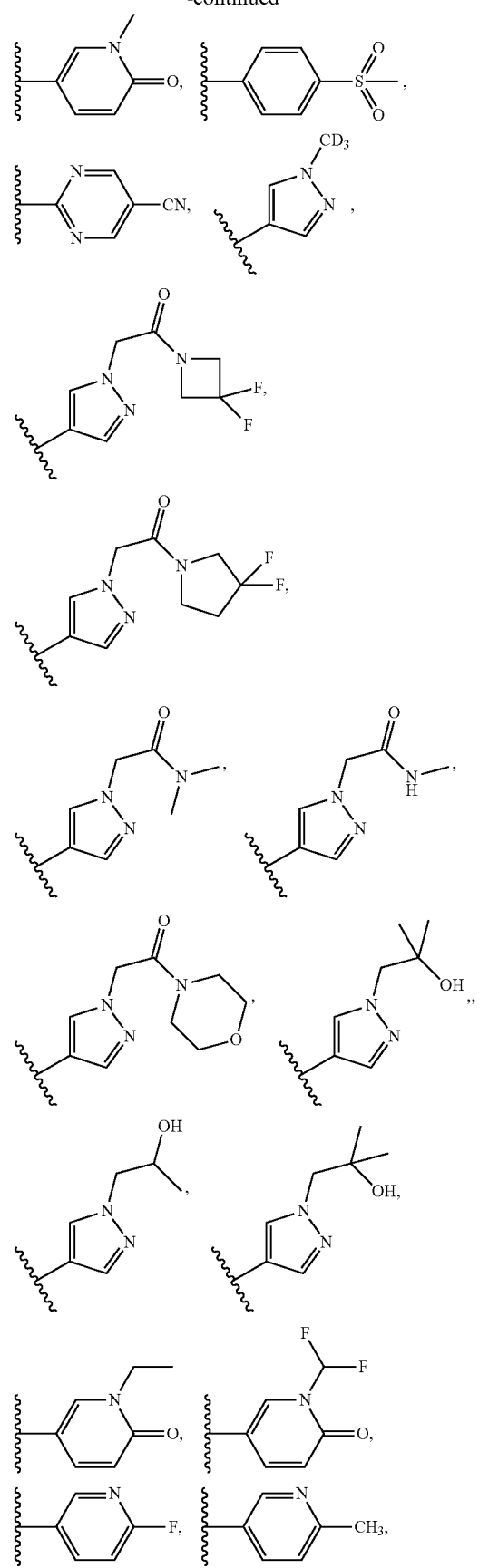

351
-continued
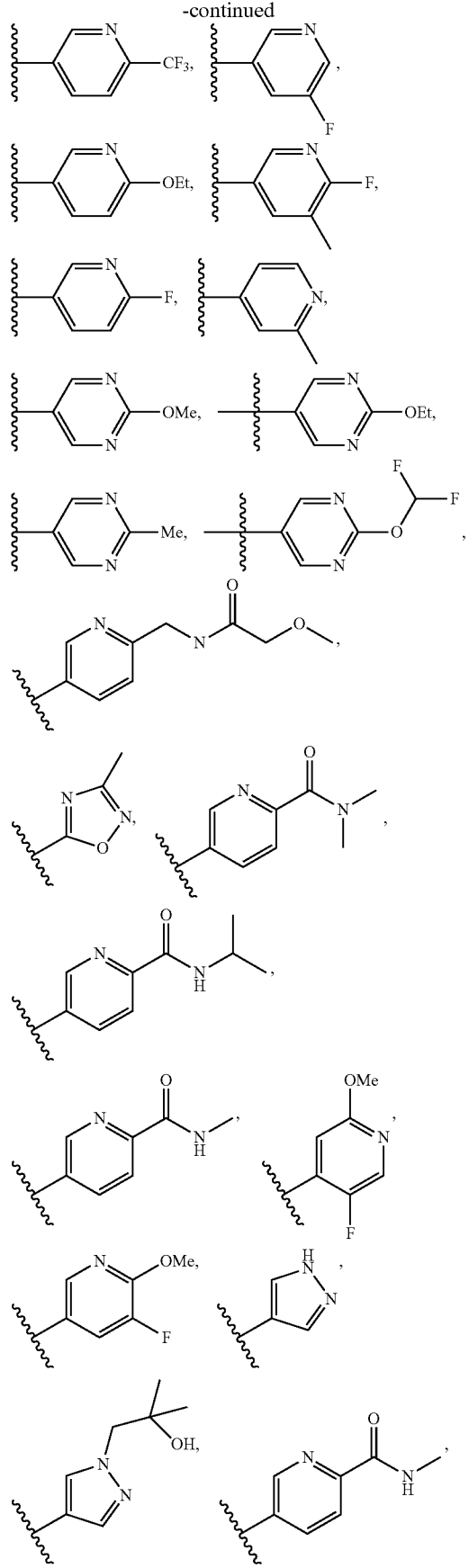
352
-continued
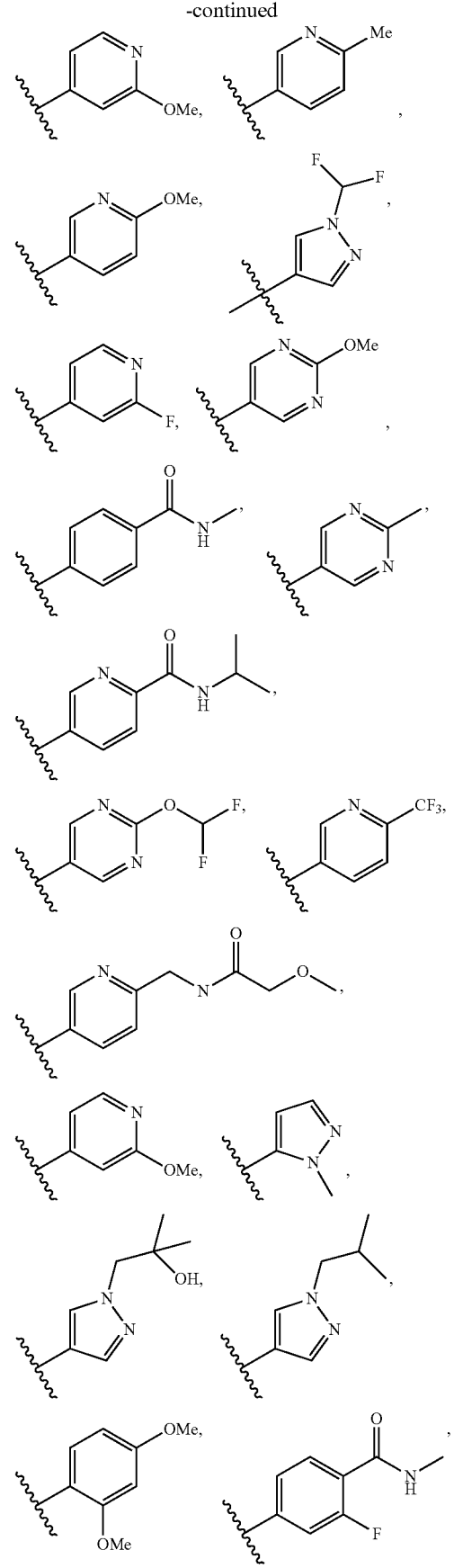

-continued
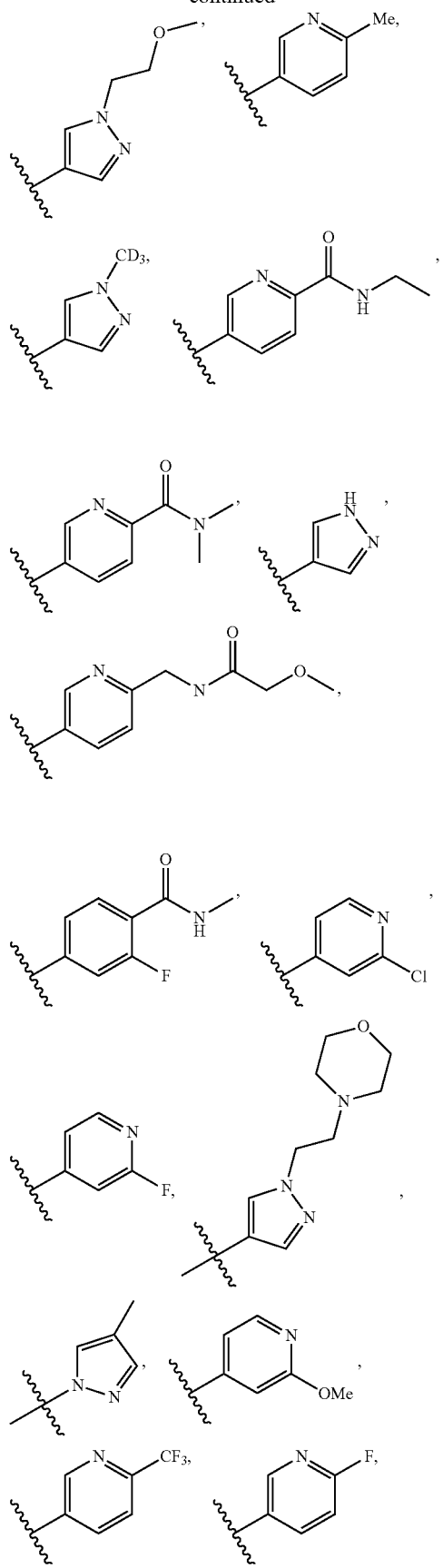
-continued
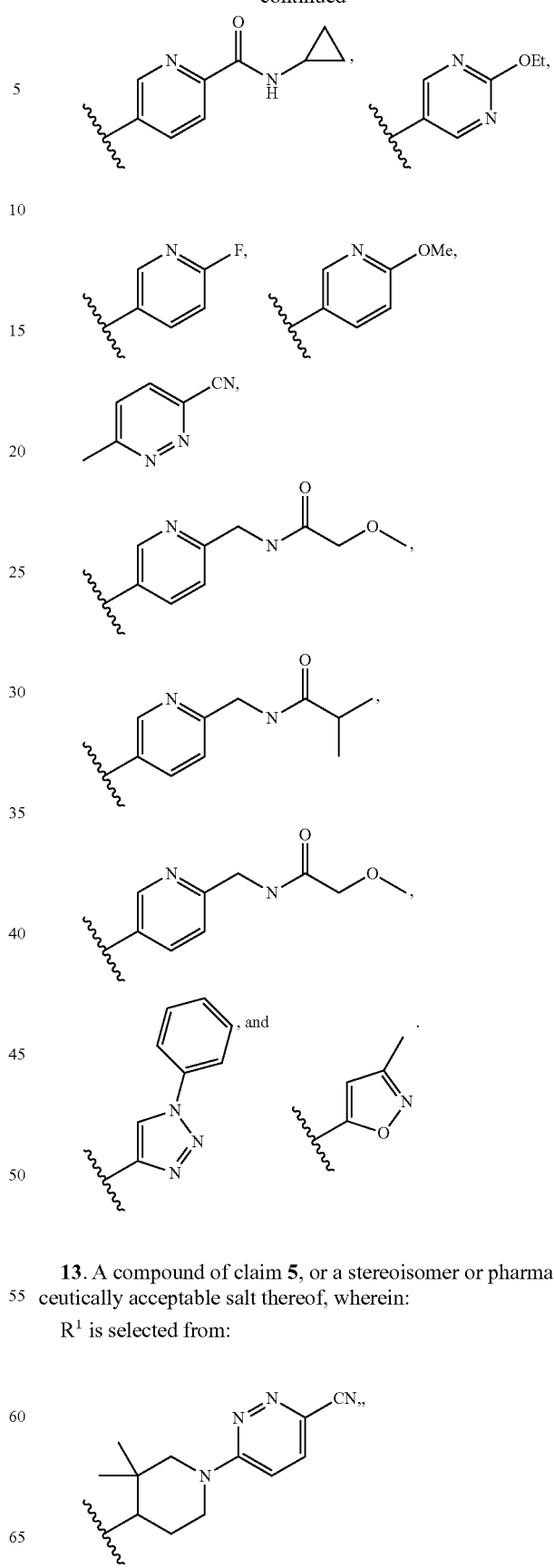
13. A compound of claim 5, or a stereoisomer or pharmaceutically acceptable salt thereof, wherein:
R¹ is selected from:
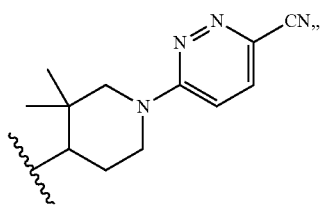

355
-continued
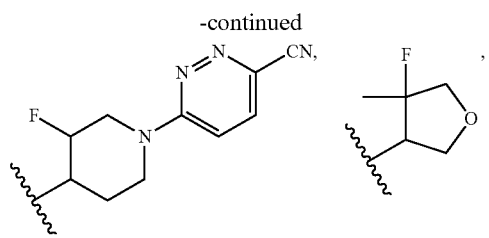
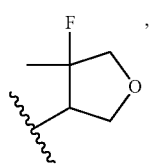
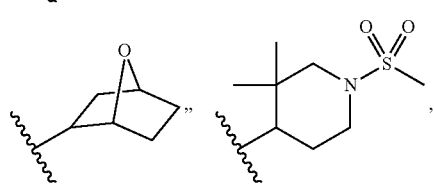
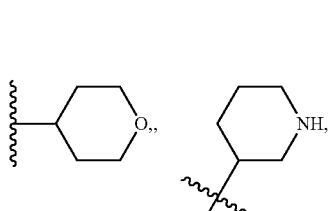
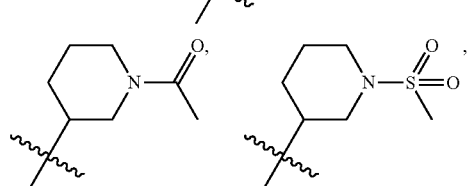
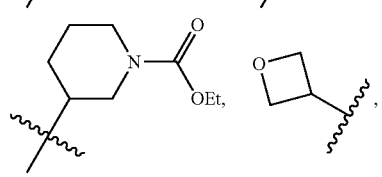
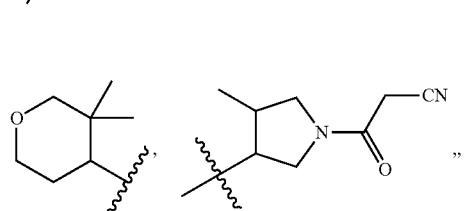
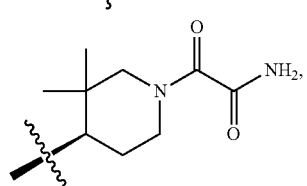
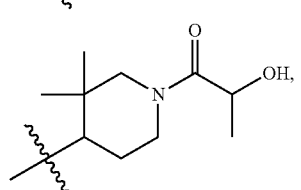
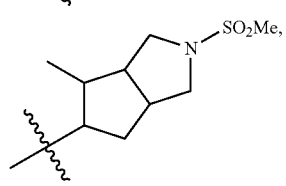
356
-continued
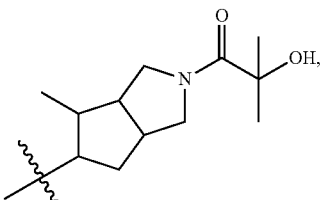
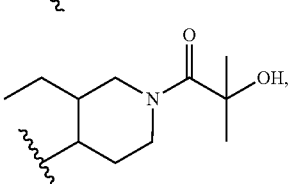
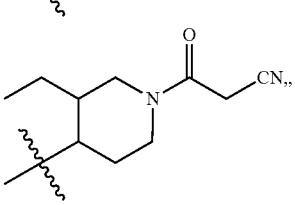
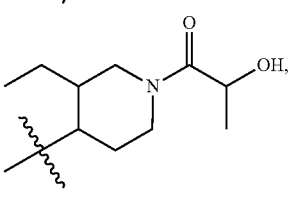
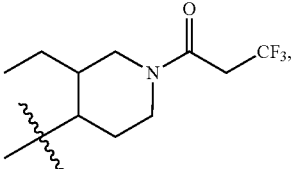
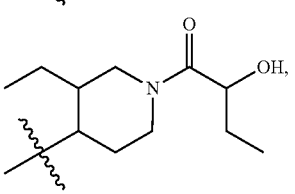
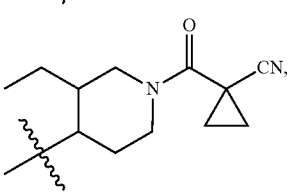
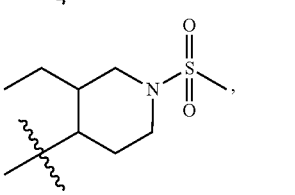
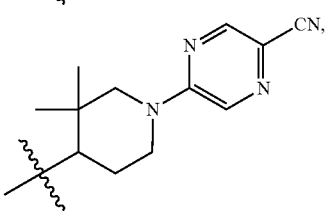

357
-continued
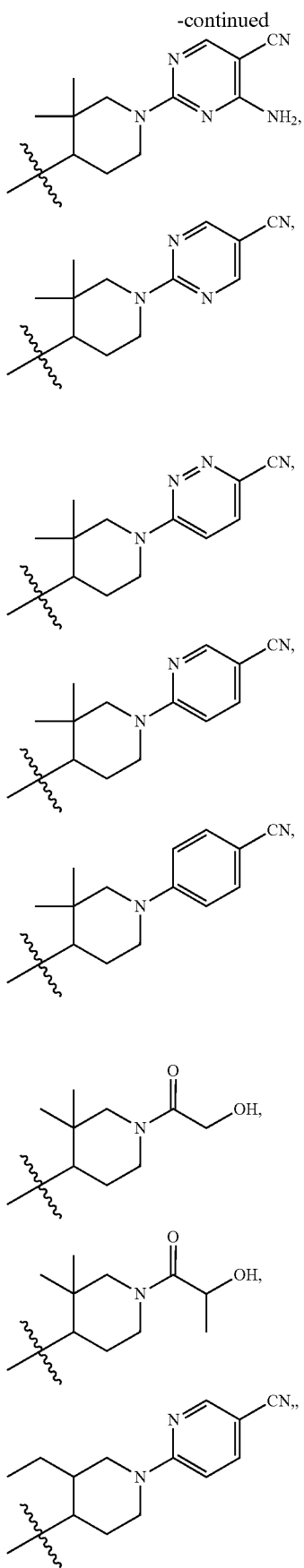
358
-continued
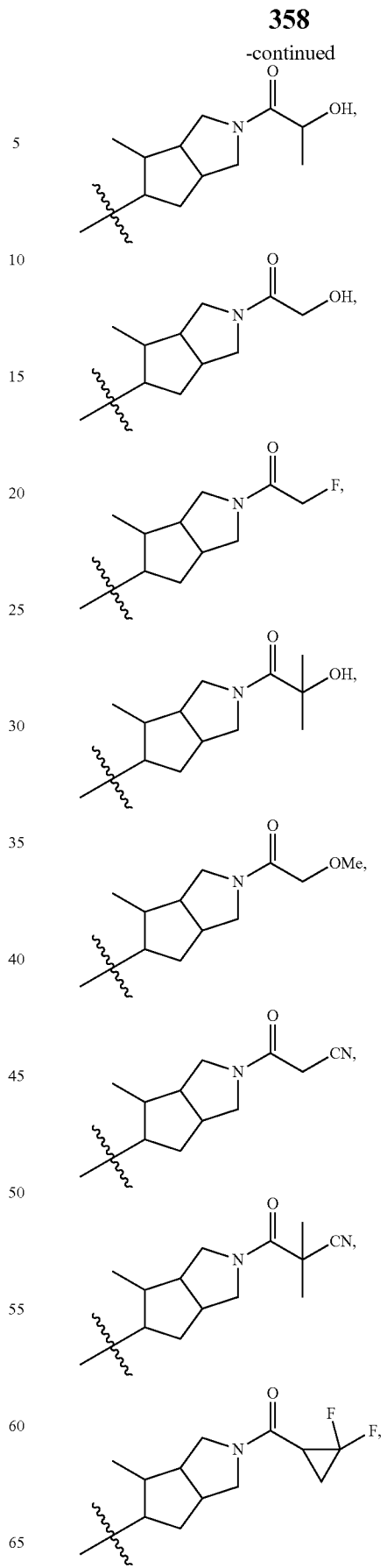

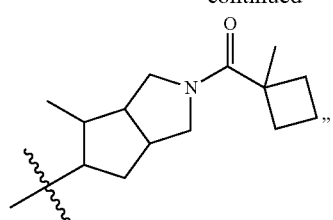
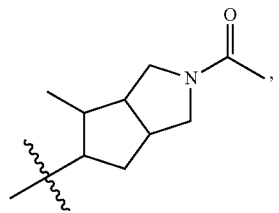
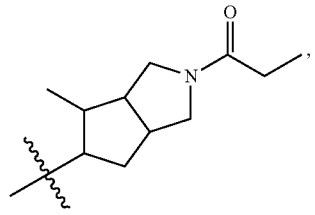
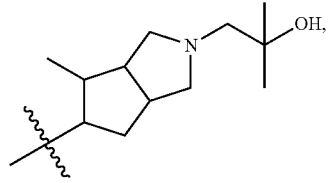
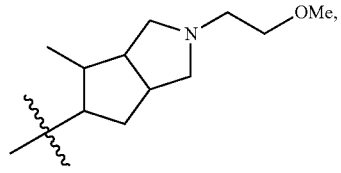
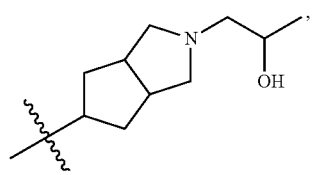
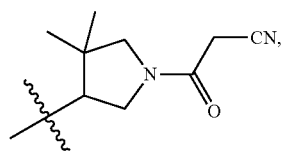
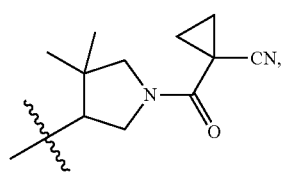
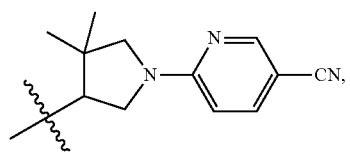
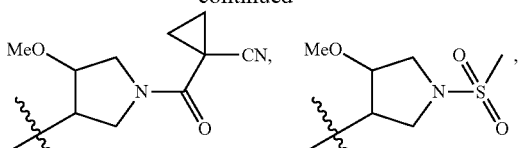
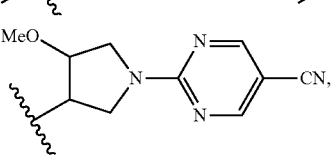
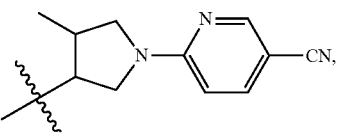
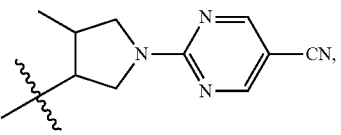
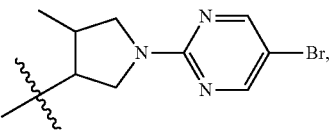
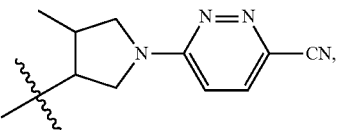
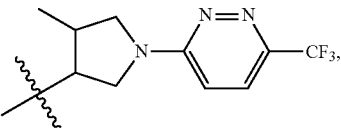
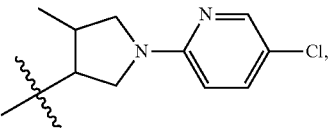
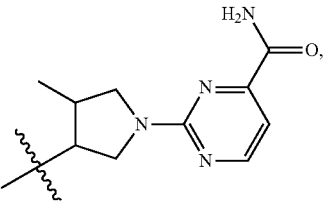
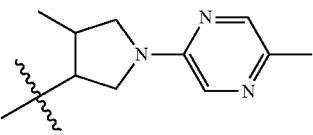
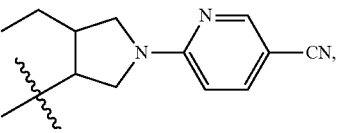
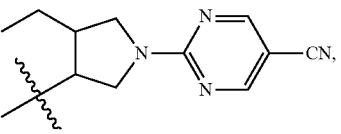

-continued
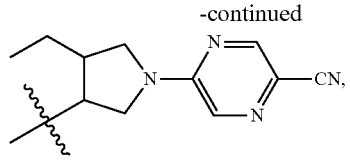
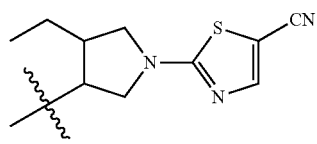
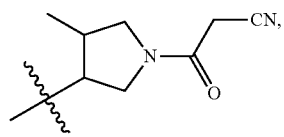
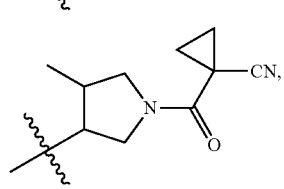
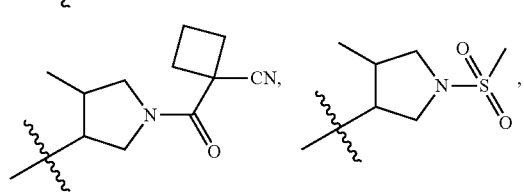
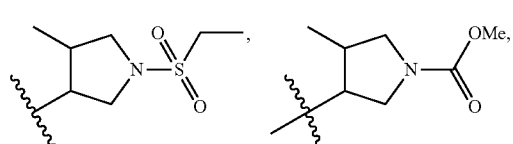
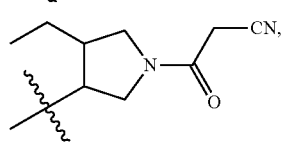
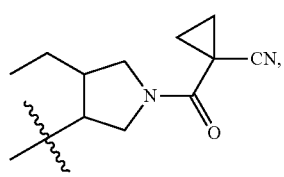
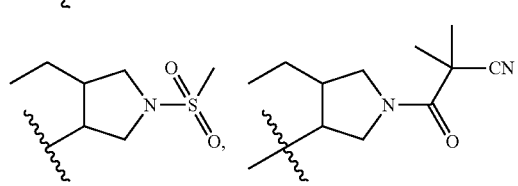
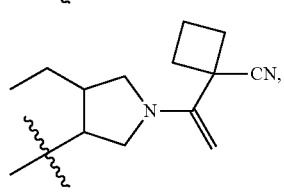
-continued
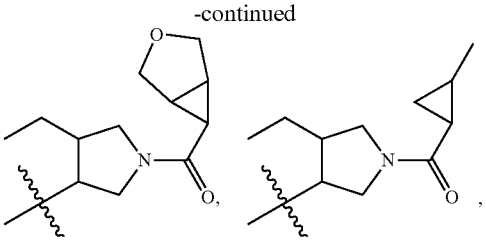
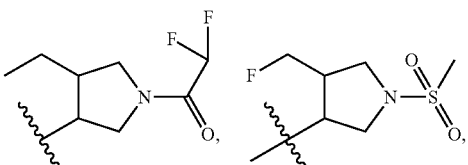
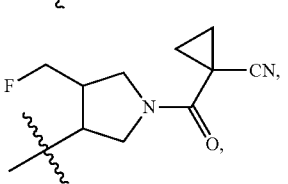
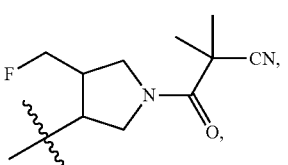
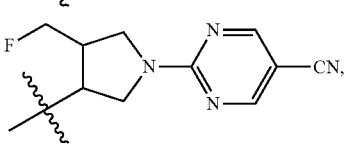
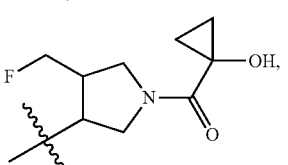
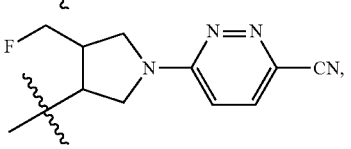
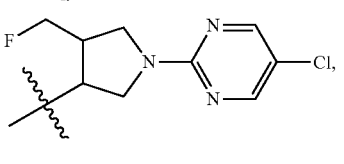
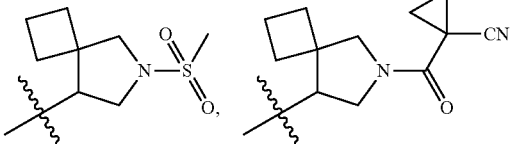
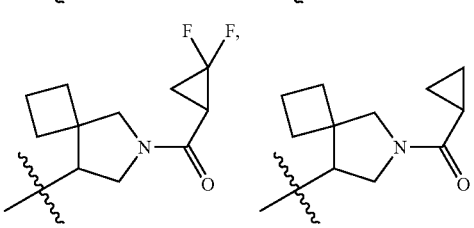

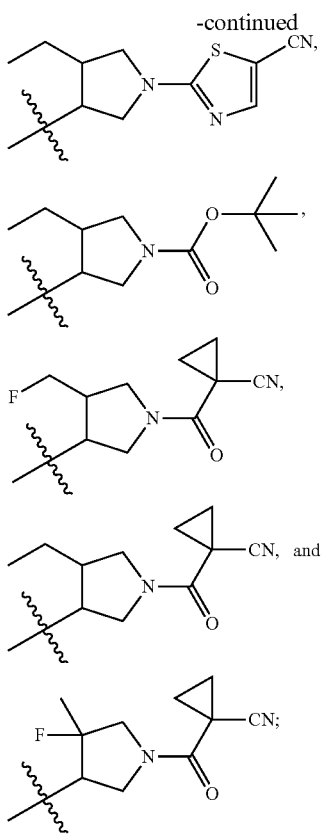
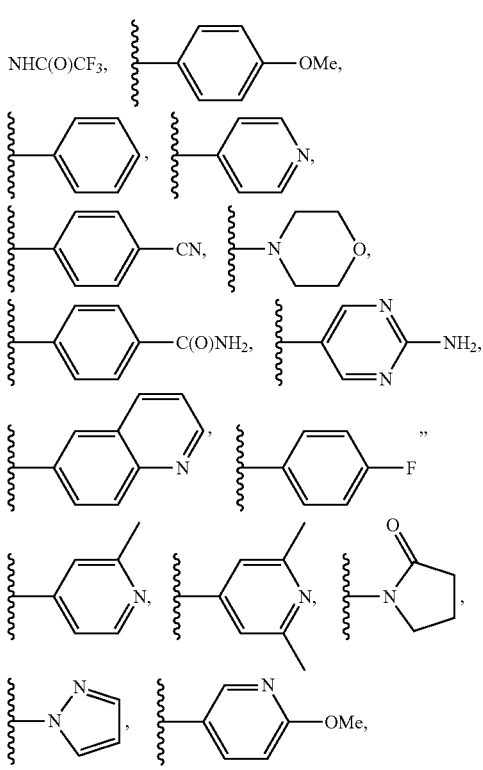
and
R² is selected from:
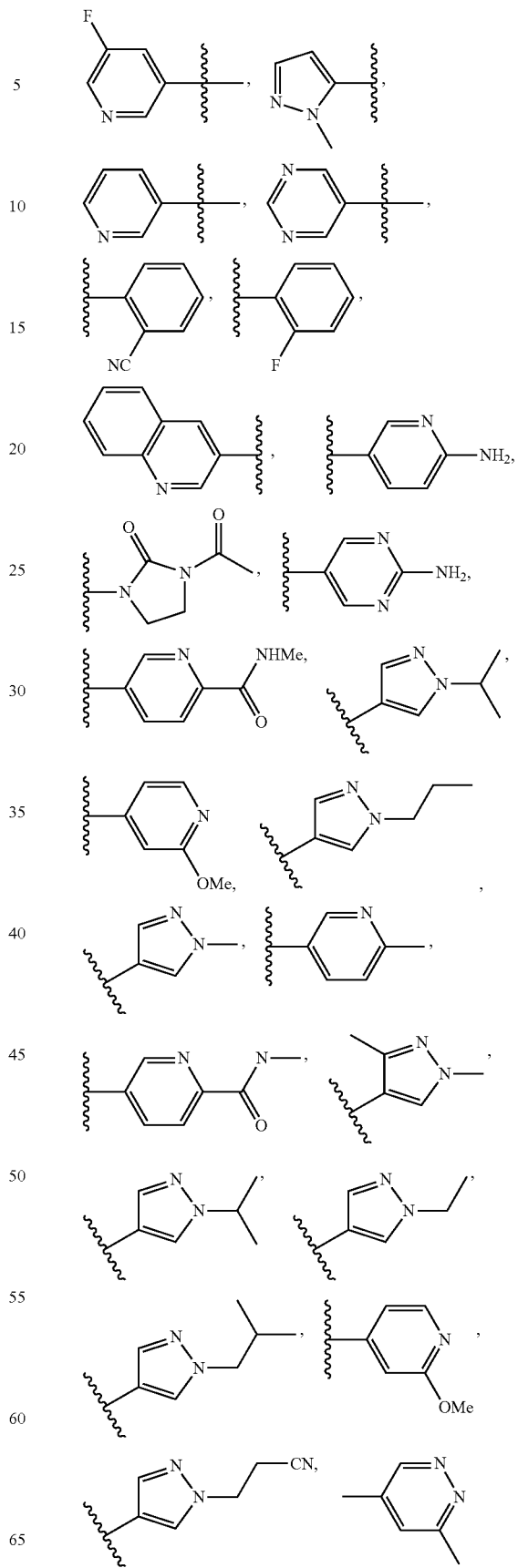

365
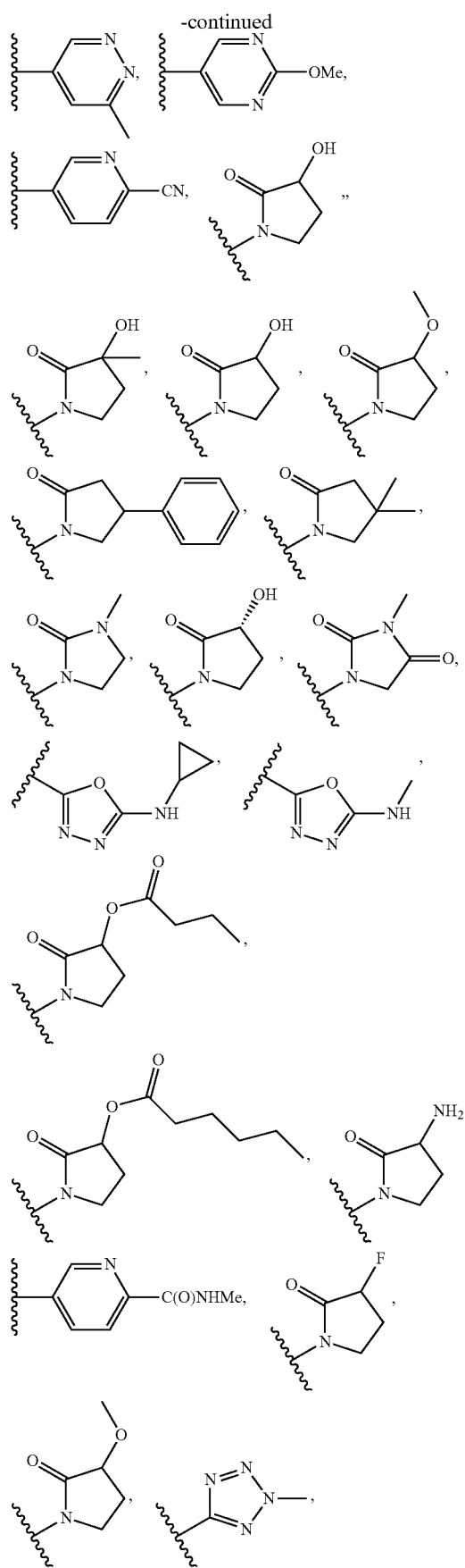
366
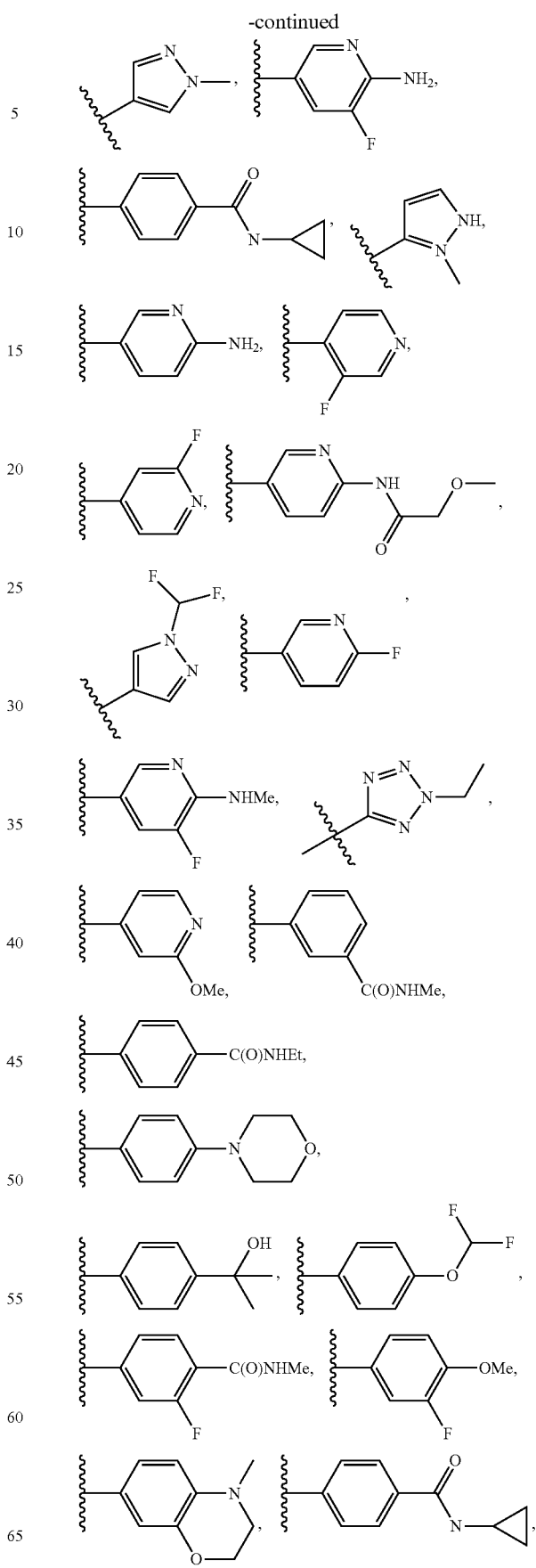

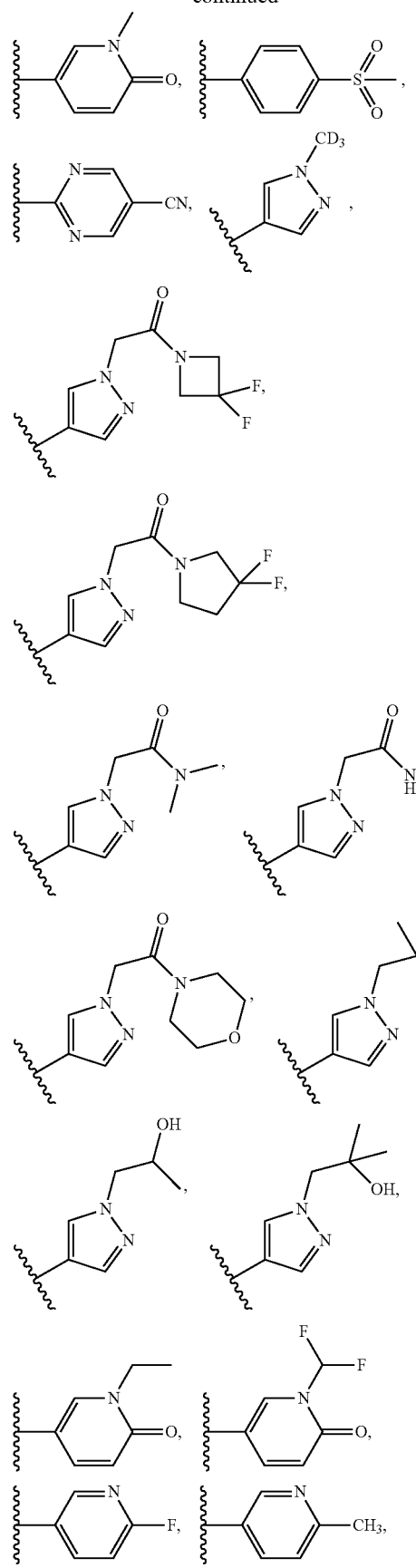
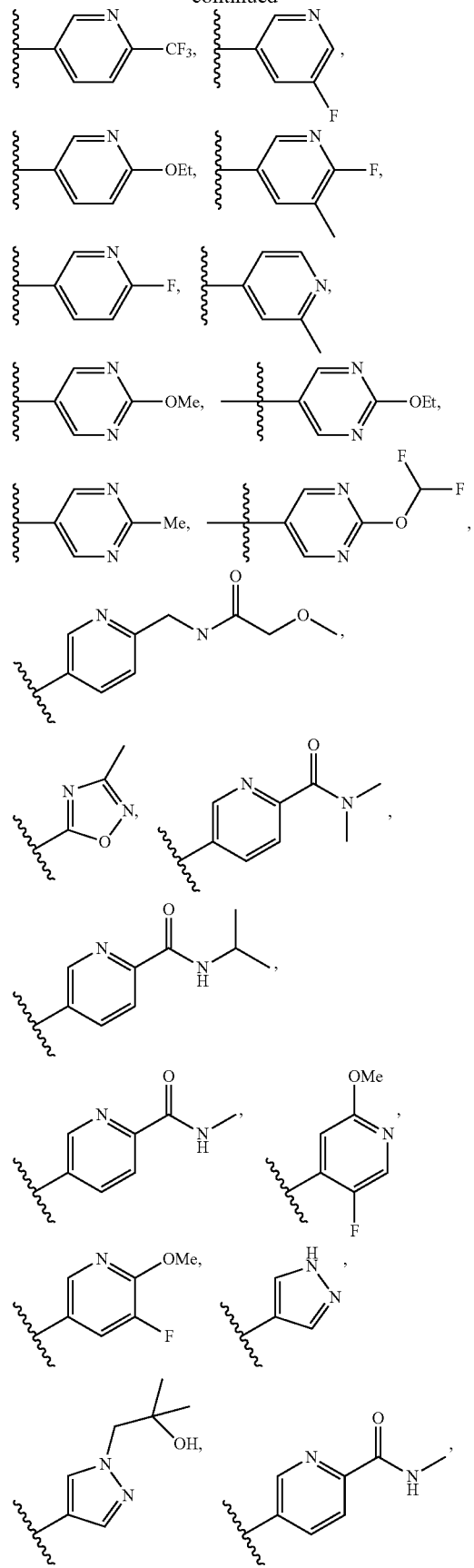

-continued
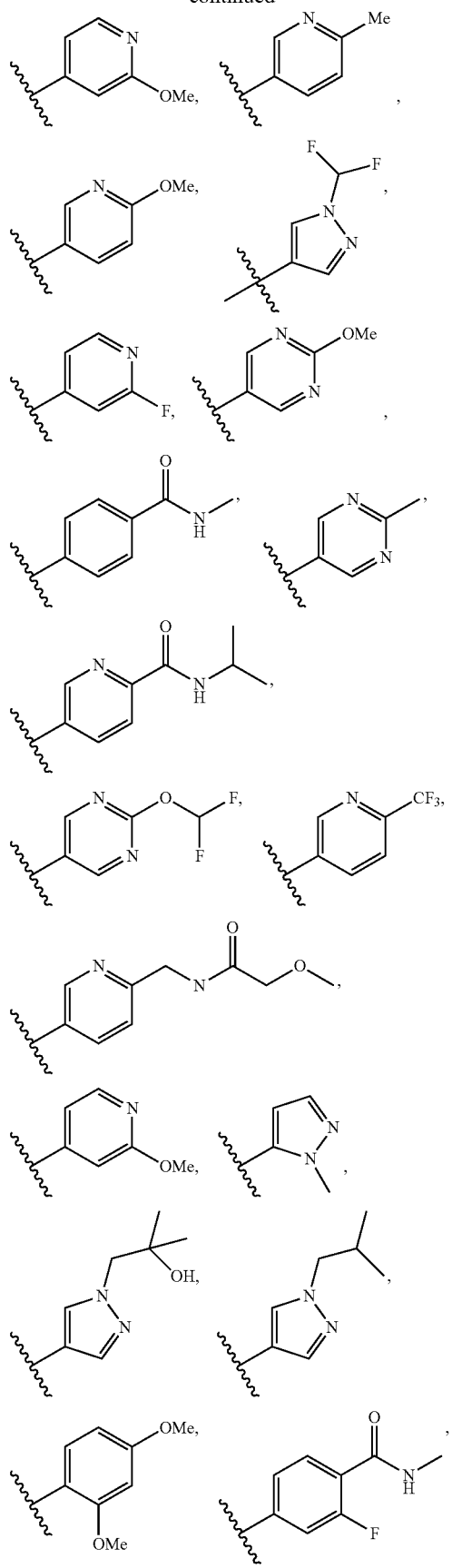
-continued
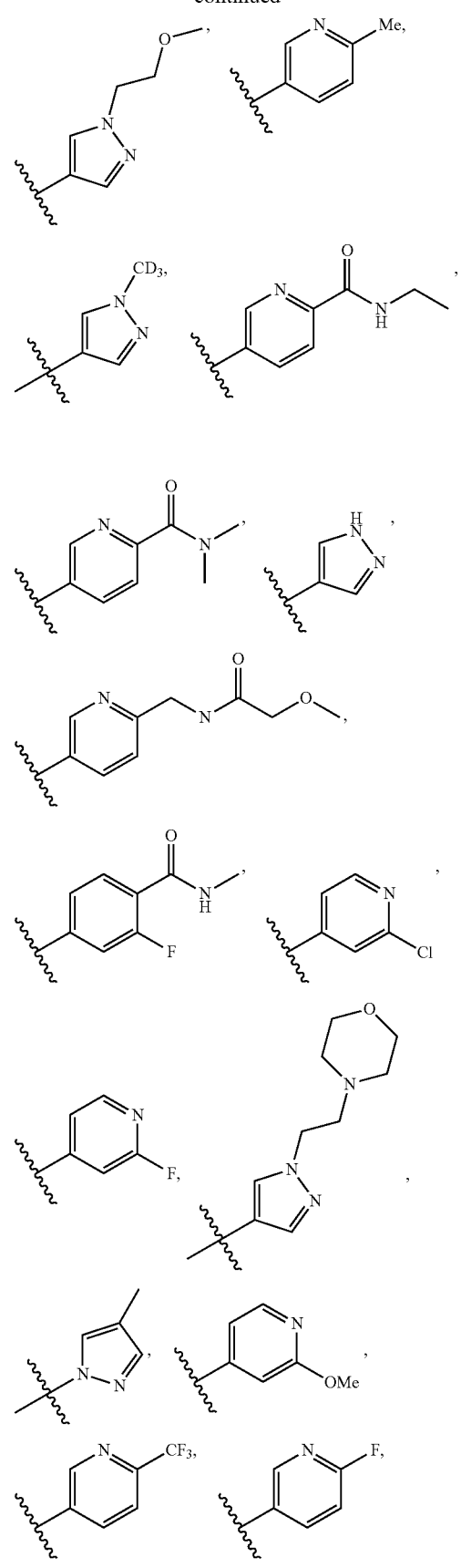

371
-continued
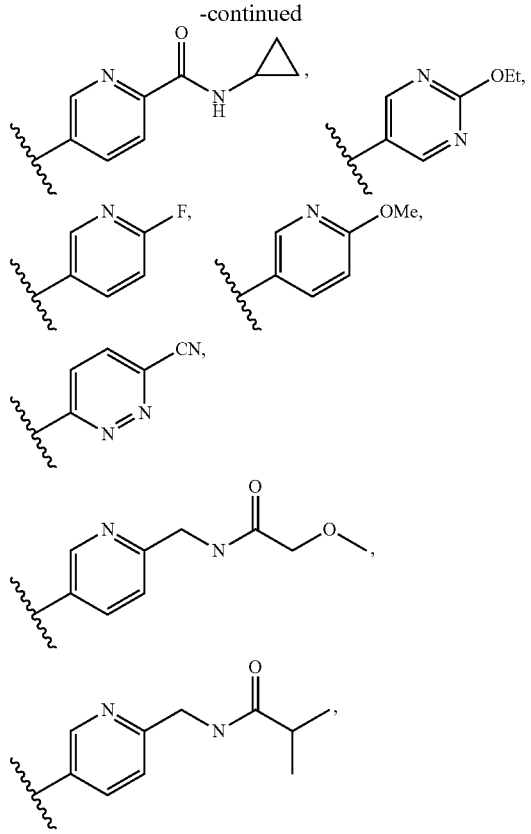
372
-continued
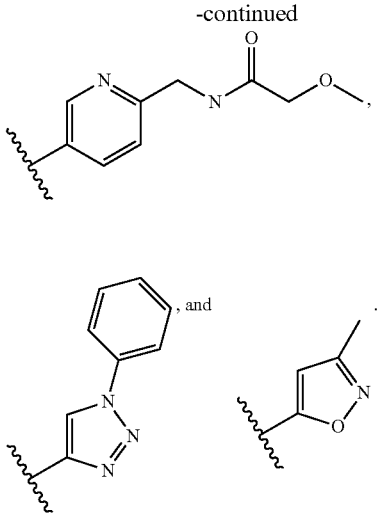
14. A method of treating an inflammatory and/or autoimmune disease comprising administering an effective amount of a compound of claim 1 to a patient in need thereof, wherein said inflammatory and/or autoimmune disease is selected from Crohn's, ulcerative colitis, rheumatoid arthritis, psoriasis, and solid organ transplant rejection.
* * * * *

UNITED STATES PATENT AND TRADEMARK OFFICE
CERTIFICATE OF CORRECTION

PATENT NO. : 8,987,268 B2  
APPLICATION NO. : 14/005568  
DATED : March 24, 2015  
INVENTOR(S) : Stephen Wrobleski et al.

Page 1 of 1

It is certified that error appears in the above-identified patent and that said Letters Patent is hereby corrected as shown below:

In the Claims:

Claim 1, col. 333, line 45, delete "—(CH$_2$)$_r$SR$^b$," and insert -- —(CH$_2$)$_q$SR$^b$, --, Claim 1, col. 333, line 52, delete "R$^c$," and insert -- R$^a$, --, Claim 1, col. 334, line 45, delete "CHF2" and insert -- CHF$_2$ --, Claim 1, col. 335, line 8, delete "NHCO methyl," and insert -- NHCO-methyl, --, Claim 2, col. 335, line 18, delete "pyrrolidinyl" and insert -- pyrrolidinyl, --, Claim 5, col. 336, line 33, delete "—(CH$_2$)$_p$-5-10" and insert -- —(CH$_2$)$_r$-5-10 --, Claim 13, col. 360, lines 52-57, delete " 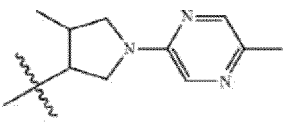 " and insert -- 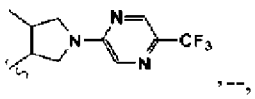 ,--, Claim 13, col. 361, lines 60-65, delete " 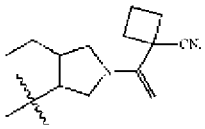 " and insert -- 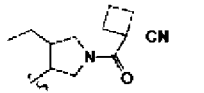 ,--.

Signed and Sealed this  
Twenty-third Day of February, 2016

Michelle K. Lee  
*Director of the United States Patent and Trademark Office*